US011911415B2

(12) United States Patent
Gori et al.

(10) Patent No.: US 11,911,415 B2
(45) Date of Patent: Feb. 27, 2024

(54) CRISPR/CAS-RELATED METHODS AND COMPOSITIONS FOR IMPROVING TRANSPLANTATION

(71) Applicant: EDITAS MEDICINE, INC., Cambridge, MA (US)

(72) Inventors: Jennifer Leah Gori, Jamaica Plain, MA (US); Tongyao Wang, Malden, MA (US); Hariharan Jayaram, Cambridge, MA (US); Penrose ODonnell, Yarmouth, ME (US)

(73) Assignee: Editas Medicine, Inc., Cambridge, MA (US)

( * ) Notice: Subject to any disclaimer, the term of this patent is extended or adjusted under 35 U.S.C. 154(b) by 486 days.

(21) Appl. No.: 15/579,633

(22) PCT Filed: Jun. 9, 2016

(86) PCT No.: PCT/US2016/036602
§ 371 (c)(1),
(2) Date: Dec. 5, 2017

(87) PCT Pub. No.: WO2016/201047
PCT Pub. Date: Dec. 15, 2016

(65) Prior Publication Data

US 2018/0296603 A1 Oct. 18, 2018

Related U.S. Application Data

(60) Provisional application No. 62/294,493, filed on Feb. 12, 2016, provisional application No. 62/173,321, filed on Jun. 9, 2015.

(51) Int. Cl.

| | |
|---|---|
| ***C12N 5/078*** | (2010.01) |
| ***A61K 35/14*** | (2015.01) |
| ***C12N 15/113*** | (2010.01) |
| ***C12N 15/31*** | (2006.01) |
| ***G16B 50/00*** | (2019.01) |
| ***A61K 35/28*** | (2015.01) |
| ***G16B 40/00*** | (2019.01) |
| ***C12N 15/11*** | (2006.01) |
| ***C07K 14/74*** | (2006.01) |
| ***C12N 5/0789*** | (2010.01) |
| ***C12N 9/22*** | (2006.01) |
| ***C12N 15/86*** | (2006.01) |

(52) U.S. Cl.
CPC ........ *A61K 35/28* (2013.01); *C07K 14/70539* (2013.01); *C12N 5/0647* (2013.01); *C12N 9/22* (2013.01); *C12N 15/11* (2013.01); *C12N 15/111* (2013.01); *C12N 15/86* (2013.01); *G16B 40/00* (2019.02); *G16B 50/00* (2019.02); *C12N 2310/20* (2017.05)

(58) Field of Classification Search
None
See application file for complete search history.

(56) References Cited

U.S. PATENT DOCUMENTS

| | | | |
|---|---|---|---|
| 8,546,553 | B2 | 10/2013 | Terns et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,023,649 | B2 | 5/2015 | Mali et al. |
| 9,074,199 | B1 | 7/2015 | Chavez et al. |
| 9,234,213 | B2 | 1/2016 | Wu |
| 9,260,723 | B2 | 2/2016 | Mali et al. |
| 9,260,752 | B1 | 2/2016 | May et al. |
| 9,267,135 | B2 | 2/2016 | Church et al. |
| 9,322,037 | B2 | 4/2016 | Liu et al. |
| 9,388,430 | B2 | 7/2016 | Liu et al. |
| 9,404,098 | B2 | 8/2016 | Terns et al. |
| 9,410,198 | B2 | 8/2016 | May et al. |

(Continued)

FOREIGN PATENT DOCUMENTS

| | | | |
|---|---|---|---|
| WO | WO-2007/025097 | A2 | 3/2007 |
| WO | 2007/047894 | A2 | 4/2007 |

(Continued)

OTHER PUBLICATIONS

US 10,077,445 B2, 09/2018, Doudna et al. (withdrawn)

(Continued)

*Primary Examiner* — Maria Marvich

(74) *Attorney, Agent, or Firm* — McCarter & English, LLP; Maria Laccotripe Zacharakis; Marcie B. Clarke

(57) ABSTRACT

Disclosed herein are compositions and methods for increasing the immunocompatibility of donor cells (e.g., HSCs or T-cells) for transplantation to a recipient subject, as well as database schemes for use in the methods. The methods and compositions described herein result in the allele-specific modification of one or more immunogenicity genes (e.g., an HLA gene) of a cell, resulting in cells that are suitable for transplantation into a recipient subject.

27 Claims, 59 Drawing Sheets

Specification includes a Sequence Listing.

(56) References Cited

U.S. PATENT DOCUMENTS 9,422,553 B2 8/2016 Terns et al.
9,512,446 B1 12/2016 Joung et al.
9,567,603 B2 2/2017 Joung et al.
9,567,604 B2 2/2017 Joung et al.
9,587,252 B2 3/2017 Church et al.
9,616,090 B2 4/2017 Conway et al.
9,637,739 B2 5/2017 Siksnys et al.
9,663,782 B2 5/2017 Yu et al.
9,688,971 B2 6/2017 Doudna et al.
9,725,714 B2 8/2017 May et al.
9,738,908 B2 8/2017 Wu
9,752,132 B2 9/2017 Joung et al.
9,790,490 B2 10/2017 Zhang et al.
9,803,194 B2 10/2017 May et al.
9,809,814 B1 11/2017 May et al.
9,816,074 B2 11/2017 Conway et al.
9,822,370 B2 11/2017 Musunuru et al.
9,822,372 B2 11/2017 Zhang et al.
9,833,479 B2 12/2017 Conway et al.
9,840,713 B2 12/2017 Zhang
9,873,894 B2 1/2018 Conway et al.
9,879,269 B2 1/2018 Barrangou et al.
9,885,026 B2 2/2018 Brouns et al.
9,902,974 B2 2/2018 Conway et al.
9,909,122 B2 3/2018 May et al.
9,926,545 B2 3/2018 Joung et al.
9,926,546 B2 3/2018 Joung et al.
9,944,912 B2 4/2018 Joung et al.
9,957,501 B2 5/2018 Reik et al.
9,957,526 B2 5/2018 Holmes et al.
9,963,689 B2 5/2018 Doudna et al.
9,970,001 B2 5/2018 Miller
9,970,024 B2 5/2018 Church et al.
10,066,233 B2 9/2018 Barrangou et al.
10,077,453 B2 9/2018 Liu et al.
10,093,910 B2 10/2018 Joung et al.
10,100,291 B2 10/2018 Chavez et al.
10,113,167 B2 10/2018 Doudna et al.
10,113,179 B2 10/2018 Begemann et al.
10,113,207 B2 10/2018 Wang
10,119,133 B2 11/2018 Joung et al.
10,125,361 B2 11/2018 May et al.
10,280,402 B2 5/2019 Kim et al.
2009/0156532 A1* 6/2009 Ober .................. C12N 15/1138
514/44 R
2010/0076057 A1 3/2010 Sontheimer et al.
2010/0093617 A1 4/2010 Barrangou et al.
2013/0011828 A1 1/2013 Barrangou et al.
2014/0068797 A1 3/2014 Doudna et al.
2014/0093941 A1 4/2014 Terns et al.
2014/0179770 A1 6/2014 Zhang et al.
2014/0186843 A1 7/2014 Zhang et al.
2014/0186919 A1 7/2014 Zhang et al.
2014/0186958 A1 7/2014 Zhang et al.
2014/0189896 A1 7/2014 Zhang et al.
2014/0199767 A1 7/2014 Barrangou et al.
2014/0242664 A1 8/2014 Zhang et al.
2014/0242699 A1 8/2014 Zhang
2014/0256046 A1 9/2014 Zhang et al.
2014/0273037 A1 9/2014 Wu
2014/0273226 A1 9/2014 Wu
2014/0273230 A1 9/2014 Chen et al.
2014/0273233 A1 9/2014 Chen et al.
2014/0287938 A1 9/2014 Zhang et al.
2014/0294773 A1 10/2014 Brouns et al.
2014/0302563 A1 10/2014 Doudna et al.
2014/0310830 A1 10/2014 Zhang et al.
2014/0315985 A1 10/2014 May et al.
2014/0342456 A1 11/2014 Mali et al.
2014/0342457 A1 11/2014 Mali et al.
2014/0342458 A1 11/2014 Mali et al.
2014/0356956 A1 12/2014 Church et al.
2014/0357523 A1* 12/2014 Zeiner .................. C12Q 1/6806
506/11
2014/0357530 A1 12/2014 Zhang et al.
2014/0377868 A1 12/2014 Joung et al.
2015/0020223 A1 1/2015 Zhang et al.
2015/0024499 A1 1/2015 Brouns et al.
2015/0024500 A1 1/2015 Yu et al.
2015/0031132 A1 1/2015 Church et al.
2015/0031133 A1 1/2015 Church et al.
2015/0031134 A1 1/2015 Zhang et al.
2015/0044772 A1 2/2015 Zhao
2015/0045546 A1 2/2015 Siksnys et al.
2015/0050699 A1 2/2015 Siksnys et al.
2015/0056705 A1 2/2015 Conway et al.
2015/0071889 A1 3/2015 Musunuru et al.
2015/0071898 A1 3/2015 Liu et al.
2015/0071899 A1 3/2015 Liu et al.
2015/0079681 A1 3/2015 Zhang
2015/0152436 A1 6/2015 Musunuru et al.
2015/0166969 A1 6/2015 Takeuchi et al.
2015/0176013 A1 6/2015 Musunuru et al.
2015/0184139 A1 7/2015 Zhang et al.
2015/0203872 A1 7/2015 Zhang
2015/0218253 A1 8/2015 Liu et al.
2015/0232833 A1 8/2015 Mali et al.
2015/0232882 A1 8/2015 Zhang et al.
2015/0240261 A1 8/2015 Siksnys et al.
2015/0247150 A1 9/2015 Zhang et al.
2015/0259684 A1 9/2015 Church et al.
2015/0259704 A1 9/2015 Church et al.
2015/0284727 A1 10/2015 Kim et al.
2015/0291961 A1 10/2015 Siksnys et al.
2015/0291965 A1 10/2015 Zhang et al.
2015/0291966 A1 10/2015 Zhang et al.
2015/0307867 A1 10/2015 Orkin et al.
2015/0322457 A1 11/2015 Kim et al.
2015/0344912 A1 12/2015 Kim et al.
2015/0353905 A1 12/2015 Weiss et al.
2015/0353917 A1 12/2015 Miller
2015/0356239 A1 12/2015 Zhang et al.
2016/0002670 A1 1/2016 Church et al.
2016/0010076 A1 1/2016 Joung et al.
2016/0010154 A1 1/2016 Laganiere et al.
2016/0017366 A1 1/2016 Chen et al.
2016/0024474 A1 1/2016 Conway et al.
2016/0024523 A1 1/2016 Joung et al.
2016/0024524 A1 1/2016 Joung et al.
2016/0030477 A1 2/2016 Conway et al.
2016/0032274 A1 2/2016 Church et al.
2016/0046949 A1 2/2016 May et al.
2016/0046961 A1 2/2016 Jinek et al.
2016/0046962 A1 2/2016 May et al.
2016/0046963 A1 2/2016 May et al.
2016/0046978 A1 2/2016 May et al.
2016/0060653 A1 3/2016 Doudna et al.
2016/0060654 A1 3/2016 Doudna et al.
2016/0068864 A1 3/2016 Doudna et al.
2016/0068887 A1 3/2016 May et al.
2016/0076020 A1 3/2016 May et al.
2016/0090607 A1 3/2016 Conway et al.
2016/0102324 A1 4/2016 Duchateau et al.
2016/0108470 A1 4/2016 May et al.
2016/0115488 A1 4/2016 Zhang et al.
2016/0115489 A1 4/2016 Zhang et al.
2016/0122774 A1 5/2016 Duchateau et al.
2016/0130608 A1 5/2016 Doudna et al.
2016/0130609 A1 5/2016 Doudna et al.
2016/0138008 A1 5/2016 Doudna et al.
2016/0138046 A1 5/2016 Wu
2016/0145646 A1 5/2016 Frendewey et al.
2016/0153003 A1 6/2016 Joung et al.
2016/0153004 A1 6/2016 Zhang et al.
2016/0153006 A1 6/2016 Zhang et al.
2016/0160210 A1 6/2016 Mali et al.
2016/0168592 A1 6/2016 Church et al.
2016/0175462 A1 6/2016 Zhang et al.
2016/0184362 A1 6/2016 Duchateau et al.
2016/0186152 A1 6/2016 Brouns et al.
2016/0186213 A1 6/2016 Zhang et al.
2016/0186214 A1 6/2016 Brouns et al.
2016/0201089 A1 7/2016 Gersbach et al.
2016/0208243 A1 7/2016 Zhang et al.

(56) References Cited

U.S. PATENT DOCUMENTS

2016/0215276 A1 7/2016 Liu et al.
2016/0222416 A1 8/2016 Church et al.
2016/0237455 A1 8/2016 Glucksmann et al.
2016/0237456 A1 8/2016 Church et al.
2016/0251640 A1 9/2016 May et al.
2016/0272965 A1 9/2016 Zhang et al.
2016/0281072 A1 9/2016 Zhang
2016/0298097 A1 10/2016 Chavez et al.
2016/0298125 A1 10/2016 Chen et al.
2016/0298132 A1 10/2016 Chen et al.
2016/0298133 A1 10/2016 Chen et al.
2016/0298134 A1 10/2016 Chen et al.
2016/0298135 A1 10/2016 Chen et al.
2016/0298136 A1 10/2016 Chen et al.
2016/0298137 A1 10/2016 Chen et al.
2016/0298138 A1 10/2016 Chen et al.
2016/0304907 A1 10/2016 Mali et al.
2016/0312198 A1 10/2016 Joung et al.
2016/0312199 A1 10/2016 Joung et al.
2016/0312280 A1 10/2016 May et al.
2016/0319260 A1 11/2016 Joung et al.
2016/0319261 A1 11/2016 Joung et al.
2016/0319281 A1 11/2016 Tsai et al.
2016/0319349 A1 11/2016 May et al.
2016/0340662 A1 11/2016 Zhang et al.
2016/0355796 A1 12/2016 Davidson et al.
2016/0355797 A1 12/2016 Konermann et al.
2016/0355816 A1 12/2016 Terns et al.
2016/0369262 A1 12/2016 Reik et al.
2017/0037416 A1 2/2017 Barrangou et al.
2017/0044569 A9 2/2017 Church et al.
2017/0051276 A1 2/2017 May et al.
2017/0051310 A1 2/2017 Doudna et al.
2017/0051312 A1 2/2017 Jinek et al.
2017/0058271 A1 3/2017 Joung et al.
2017/0073705 A1 3/2017 Chen et al.
2017/0081650 A1 3/2017 Joung et al.
2017/0107536 A1 4/2017 Zhang et al.
2017/0107539 A1 4/2017 Yu et al.
2017/0137845 A1 5/2017 Tan et al.
2017/0152508 A1 6/2017 Joung et al.
2017/0152528 A1 6/2017 Zhang
2017/0166893 A1 6/2017 Doudna et al.
2017/0166903 A1 6/2017 Zhang et al.
2017/0175142 A1 6/2017 Zhang et al.
2017/0175143 A1 6/2017 Tolar et al.
2017/0175144 A1 6/2017 Zhang et al.
2017/0189450 A1 7/2017 Conway et al.
2017/0191078 A1 7/2017 Zhang et al.
2017/0191082 A1 7/2017 Chen et al.
2017/0198269 A1 7/2017 Zhang et al.
2017/0211142 A1 7/2017 Smargon et al.
2017/0215392 A1 8/2017 Haining et al.
2017/0233703 A1 8/2017 Xie et al.
2017/0268022 A1 9/2017 Liu et al.
2017/0298330 A1 10/2017 Sato et al.
2017/0306307 A1 10/2017 Zhang et al.
2017/0306335 A1 10/2017 Zhang et al.
2017/0314015 A1 11/2017 Friedland et al.
2017/0327805 A1 11/2017 Joung et al.
2017/0327806 A1 11/2017 Joung et al.
2017/0327820 A1 11/2017 May et al.
2017/0335300 A1 11/2017 Frisch et al.
2017/0349914 A1 12/2017 Cox et al.
2017/0349915 A1 12/2017 May et al.
2018/0002682 A1 1/2018 Sternberg et al.
2018/0021413 A1 1/2018 Porteus
2018/0021457 A1 1/2018 Kim et al.
2018/0030425 A1 2/2018 Joung et al.
2018/0030438 A1 2/2018 Porteus et al.
2018/0066242 A1 3/2018 Zhang et al.
2018/0071405 A1 3/2018 Kim et al.
2018/0073002 A1 3/2018 Deiters et al.
2018/0080051 A1 3/2018 Sheikh et al.
2018/0100148 A1 4/2018 Vakulskas et al.
2018/0119121 A1 5/2018 Brouns et al.
2018/0119175 A1 5/2018 Conway et al.
2018/0127780 A1 5/2018 Liu et al.
2018/0135073 A1 5/2018 Chen et al.
2018/0135109 A1 5/2018 Jayaram et al.
2018/0148735 A1 5/2018 Begemann et al.
2018/0155708 A1 6/2018 Church et al.
2018/0155716 A1 6/2018 Zhang et al.
2018/0163188 A1 6/2018 Xie et al.
2018/0163213 A1 6/2018 Aneja et al.
2018/0187176 A1 7/2018 Behlke et al.
2018/0187195 A1 7/2018 Siksnys et al.
2018/0200387 A1 7/2018 Porteus
2018/0208931 A1 7/2018 Doudna et al.
2018/0216088 A1 8/2018 Joung et al.
2018/0230495 A1 8/2018 Doudna et al.
2018/0230496 A1 8/2018 Doudna et al.
2018/0230497 A1 8/2018 Doudna et al.
2018/0237801 A1 8/2018 Doudna et al.
2018/0245100 A1 8/2018 Doudna et al.
2018/0245101 A1 8/2018 Doudna et al.
2018/0251791 A1 9/2018 Doudna et al.
2018/0251793 A1 9/2018 Doudna et al.
2018/0251794 A1 9/2018 Doudna et al.
2018/0251795 A1 9/2018 Charpentier et al.
2018/0265864 A1 9/2018 Li et al.
2018/0273609 A1 9/2018 Porteus et al.
2018/0273938 A1 9/2018 Turk et al.
2018/0273981 A1 9/2018 Doudna et al.
2018/0282713 A1 10/2018 Van Der Oost
2018/0282714 A1 10/2018 Joung et al.
2018/0282764 A1 10/2018 Jinek et al.
2018/0291383 A1 10/2018 Musunuru et al.
2018/0296603 A1 10/2018 Gori et al.
2018/0298360 A1 10/2018 Sternberg et al.
2018/0298406 A1 10/2018 Doudna et al.
2018/0298407 A1 10/2018 Doudna et al.
2018/0312824 A1 11/2018 Zhang et al.
2018/0312874 A1 11/2018 Doudna et al.
2018/0312875 A1 11/2018 Doudna et al.
2018/0312876 A1 11/2018 Doudna et al.
2018/0320163 A1 11/2018 Koonin et al.
2018/0320197 A1 11/2018 Gersbach et al.
2018/0320201 A1 11/2018 Vakulskas et al.
2018/0327761 A1 11/2018 Duchateau et al.

FOREIGN PATENT DOCUMENTS

WO WO-2010/011961 A2 1/2010
WO WO-2013/098244 A1 7/2013
WO WO-2013/126794 A1 8/2013
WO WO-2013/141680 A1 9/2013
WO WO-2013/142578 A1 9/2013
WO WO-2013/176772 A1 11/2013
WO WO-2014/018423 A2 1/2014
WO WO 2014/065596 * 5/2014
WO WO-2014/065596 A1 5/2014
WO WO-2014/085593 A1 6/2014
WO WO-2014/089290 A1 6/2014
WO WO-2014/093479 A1 6/2014
WO WO-2014/093595 A1 6/2014
WO WO-2014/093622 A2 6/2014
WO WO-2014/093635 A1 6/2014
WO WO-2014/093655 A2 6/2014
WO WO-2014/093661 A2 6/2014
WO WO-2014/093694 A1 6/2014
WO WO-2014/093701 A1 6/2014
WO WO-2014/093709 A1 6/2014
WO WO-2014/093712 A1 6/2014
WO WO-2014/093718 A1 6/2014
WO WO-2014/099744 A1 6/2014
WO WO-2014/099750 A2 6/2014
WO WO-2014/113493 A1 7/2014
WO WO-2014/144288 A1 9/2014
WO WO-2014/144592 A2 9/2014
WO WO-2014/144761 A2 9/2014
WO WO-2014/145599 A2 9/2014
WO WO-2014/150624 A1 9/2014
WO WO-2014/152432 A2 9/2014

(56) References Cited

FOREIGN PATENT DOCUMENTS

WO 2014/165177 A1 10/2014
WO 2014/165825 A2 10/2014
WO WO 2014/165177 * 10/2014
WO WO-2014/172458 A1 10/2014
WO WO-2014/186585 A2 11/2014
WO WO-2014/191518 A1 12/2014
WO WO-2014/191521 A2 12/2014
WO WO-2014/197568 A2 12/2014
WO WO-2014/197748 A2 12/2014
WO WO-2014/204578 A1 12/2014
WO WO-2014/204724 A1 12/2014
WO WO-2014/204725 A1 12/2014
WO WO-2014/204727 A1 12/2014
WO WO-2014/204728 A1 12/2014
WO WO-2014/204729 A1 12/2014
WO WO-2015/006290 A1 1/2015
WO WO-2015/006294 A2 1/2015
WO WO-2015/006498 A2 1/2015
WO WO-2015/010114 A1 1/2015
WO WO-2015/013583 A2 1/2015
WO WO-2015/021426 A1 2/2015
WO WO-2015/035162 A2 3/2015
WO WO-2015/048577 A2 4/2015
WO WO-2015/057976 A1 4/2015
WO WO-2015/077318 A1 5/2015
WO WO-2015/089351 A1 6/2015
WO WO-2015/089354 A1 6/2015
WO WO-2015/089427 A1 6/2015
WO WO-2015/089486 A2 6/2015
WO WO-2015/117081 A2 8/2015
WO WO-2015/148670 A1 10/2015
WO WO-2015/148716 A1 10/2015
WO WO-2015/148860 A1 10/2015
WO WO-2015/148863 A2 10/2015
WO WO-2015/161276 A2 10/2015
WO WO-2015/168547 A2 11/2015
WO WO-2015/179540 A1 11/2015
WO WO-2015/183885 A1 12/2015
WO WO-2015/188056 A1 12/2015
WO WO-2015/188065 A1 12/2015
WO WO-2016/014794 A1 1/2016
WO 2016/021972 A1 2/2016
WO WO-2016/019144 A2 2/2016
WO WO-2016/022363 A2 2/2016
WO WO-2016/028682 A1 2/2016
WO WO-2016/044416 A1 3/2016
WO WO-2016/057821 A2 4/2016
WO WO-2016/057835 A2 4/2016
WO WO-2016/073433 A1 5/2016
WO WO-2016/081923 A2 5/2016
WO WO-2016/094880 A1 6/2016
WO WO-2016/106236 A1 6/2016
WO WO-2016/106244 A1 6/2016
WO WO-2016/111546 A2 7/2016
WO WO-2016/112242 A1 7/2016
WO WO-2016/114972 A1 7/2016
WO WO-2016/118726 A2 7/2016
WO WO-2016/123578 A1 8/2016
WO WO-2016/124765 A1 8/2016
WO WO-2016/135557 A2 9/2016
WO WO-2016/135558 A2 9/2016
WO WO-2016/135559 A2 9/2016
WO WO-2016/141224 A1 9/2016
WO WO-2016/161207 A1 10/2016
WO WO-2016/164797 A1 10/2016
WO WO-2016/166340 A1 10/2016
WO WO-2016/167300 A1 10/2016
WO WO-2016/172727 A1 10/2016
WO WO-2016/182917 A1 11/2016
WO WO-2016/196655 A1 12/2016
WO WO-2016/201047 A1 12/2016
WO WO-2016/205613 A1 12/2016
WO WO-2016/205680 A1 12/2016
WO WO-2016/205703 A1 12/2016
WO WO-2016/205711 A1 12/2016
WO WO-2016/205749 A1 12/2016
WO WO-2016/205759 A1 12/2016
WO WO-2017/015015 A1 1/2017
WO WO-2017/040348 A1 3/2017
WO WO-2017/048969 A1 3/2017
WO WO-2017/064546 A1 4/2017
WO WO-2017/066588 A2 4/2017
WO WO-2017/066707 A1 4/2017
WO WO-2017/070633 A2 4/2017
WO WO-2017/077394 A2 5/2017
WO WO-2017/099494 A1 6/2017
WO WO-2017/106569 A1 6/2017
WO WO-2017/115268 A1 7/2017
WO WO-2017/127807 A1 7/2017
WO WO-2017/131150 A1 8/2017
WO WO-2017/134529 A1 8/2017
WO WO-2017/136335 A1 8/2017
WO WO-2017/141109 A1 8/2017
WO WO-2017/155407 A1 9/2017
WO WO-2017/155408 A1 9/2017
WO WO-2017/160890 A1 9/2017
WO WO-2017/161068 A1 9/2017
WO WO-2017/181107 A2 10/2017
WO WO-2017/182881 A2 10/2017
WO WO-2017/184768 A1 10/2017
WO WO-2017/189308 A1 11/2017
WO WO-2017/191503 A1 11/2017
WO WO-2017/197238 A1 11/2017
WO WO-2017/219027 A1 12/2017
WO WO-2017/219033 A1 12/2017
WO WO-2017/222773 A1 12/2017
WO WO-2018/022634 A1 2/2018
WO WO-2018/031686 A1 2/2018
WO WO-2018/035387 A1 2/2018
WO WO-2018/035388 A1 2/2018
WO WO-2018/049073 A1 3/2018
WO WO-2018/049077 A1 3/2018
WO WO-2018/049079 A1 3/2018
WO WO-2018/052247 A1 3/2018
WO WO-2018/053053 A1 3/2018
WO WO-2018/058064 A1 3/2018
WO WO-2018/062866 A2 4/2018
WO WO-2018/064352 A1 4/2018
WO WO-2018/064371 A1 4/2018
WO WO-2018/064387 A1 4/2018
WO WO-2018/068053 A2 4/2018
WO WO-2018/069474 A1 4/2018
WO WO-2018/071572 A1 4/2018
WO WO-2018/071868 A1 4/2018
WO WO-2018/071892 A1 4/2018
WO WO-2018/074979 A1 4/2018
WO WO-2018/089664 A1 5/2018
WO WO-2018/098383 A1 5/2018
WO WO-2018/108272 A1 6/2018
WO WO-2018/108338 A1 6/2018
WO WO-2018/108339 A1 6/2018
WO WO-2018/109101 A1 6/2018
WO WO-2018/111947 A1 6/2018
WO WO-2018/112451 A1 6/2018
WO WO-2018/142364 A1 8/2018
WO WO-2018/149888 A1 8/2018
WO WO-2018/170015 A1 9/2018
WO WO-2018/170184 A1 9/2018
WO WO-2018/172556 A1 9/2018
WO WO-2018/188571 A1 10/2018
WO WO-2018/191440 A1 10/2018
WO WO-2018/191715 A2 10/2018
WO WO-2018/192961 A1 10/2018
WO WO-2018/195540 A1 10/2018
WO WO-2018/195545 A2 10/2018
WO WO-2018/197495 A1 11/2018
WO WO-2018/209712 A1 11/2018

(56) References Cited

FOREIGN PATENT DOCUMENTS

WO WO-2018/213351 A1 11/2018
WO WO-2018/218135 A1 11/2018

OTHER PUBLICATIONS

Wilbie et al, Delivery Aspects of CRISPR/Cas for in Vivo Genome Editing, Delivery Aspects of CRISPR/Cas for in Vivo Genome Editing, Acc. Chem. Res. 2019, 52, 1555-1564.*
Mout et al, In Vivo Delivery of CRISPR/Cas9 for Therapeutic Gene Editing: Progress and Challenges, Bioconjugate Chem. 2017, 28 , 880-884.*
Lee et al, Prophylactic reinfusion of T cells for T cell-depleted allogeneic bone marrow transplantation, Biology of Blood and Marrow Transplantation 5:15-27 (1999).*
Masuda et al, Loss or down-regulation of HLA class I expression at the allelic level in freshly isolated leukemic blasts, Cancer Sci, 2007, pp. 102-108.*
Holwera et al, Allelic exclusion of the immunoglobulin heavy chain locus is independent of its nuclear localization in mature B cells, Nucleic Acids Research, 2013, vol. 41, No. 14 6905-6916.*
Porter and June, T-cell reconstitution and expansion after hematopoietic stem cell transplantation: ‘T’ it up!, Bone Marrow Transplantation (2005) 35, 935-942.*
Hacke et al, Suppression of HLA Expression by Lentivirus-mediated Gene Transfer of siRNA Cassettes and In Vivo Chemoselection to Enhance Hematopoietic Stem Cell Transplantation, Immunol Res. 2009 ; 44(1-3): 112-126.*
Yoshimi et al, Allele-specific genome editing and correction of disease-associated phenotypes in rats using the CRISPR-Cas platform Nature, 2014, p. 1-9.*
Cruz-Tapias et al, Chapter 10—Major Histocompatibility Complex: Antigen Processing and Presentation, 2013, from Autoimmunity From Bench to Bedside, editors Anaya et al.*
Furst et al, High-resolution HLA matching in hematopoietic stem cell transplantation: a retrospective collaborative analysis, Blood, Oct. 31, 2013, pp. 3220-3229.*
Feng et al., Scalable generation of universal platelets from human induced pluripotent stem cells. Stem Cell Reports. Nov. 11, 2014;3(5):817-31.
Hoban et al., Evaluation of TALENs and CRISPR/Cas9 Nuclease System to Correct the Sickle Cell Disease Mutation. Molecular Therapy. May 2015;23(Suppl 1):S135, Poster 338.
Torikai et al., Toward eliminating HLA class I expression to generate universal cells from allogeneic donors. Blood. Aug. 22, 2013;122(8):1341-9.
Zhang et al., Designer Platelets: Crispr/Cas-Mediated Conversion of Human Platelet Alloantigen Allotypes. Blood. Dec. 2014;124(21): Poster 573. 1 page.
Ogawa, Basic knowledge of HLA part 2. Major Histocompatibility Complex. 2016;23(3):185-192, abstract only.

* cited by examiner

*Streptococcus thermophilus* a) Structure (See, e.g., Karvelis et al. RNA Biology. 2013; 10(5): 841-851)

Alignment

```
S. pyogenes     5'-NNNNNNNNNNNNNNNNNNNNGUUUUAGAGCUAUGCUGUUUUG-3'     (SEQ ID NO:39)
S. thermophilus 5'-NNNNNNNNNNNNNNNNNNNNGUUUUAGAGCUGUGUUGUUUCG-3'     (SEQ ID NO:45)
                                   *********** ** ***** *
```

```
S. pyogenes     5'-GAACCAUUCAAAACAGCAUAGCAAGUUAAAAUAAGGC-UAGUCCGUUAUCAACUUGAAAAAGUGGCACCGAGUCGGUGCUUUUUUU-3'
S. thermophilus 5'------GGGCGAAACAACACAGCGAGUUAAAAUAAGGCUUAGUCCGUACUCAACUUGAAAAGGUGGCACCGAUUCGGUGUUUUU---3'
                         * ***** ** *** ************** ********  ************ ********** ****** ****
```

S. pyogenes - cont (SEQ ID NO:47)
S. thermophilus - cont (SEQ ID NO:46)

Fig. 1G

```
SM      QRLFQEEFLAVYDNTFENSS------LQEQNVQVEEILTDKISKSAKKDRVLKLFPNEKSN
SP      DKLFIQLVQTYNQLFEENP------INASGVDAKAILSARLSKSRRLENLIAQLPGEKKN
ST      QKNFQDFLDTYNAIFESDL------SLENSKQLEEIVKDKISKLEKKDRILKLFPGEKNS
LI      DGIYKQFIQTYNQVFASGIEDGSLKKLEDNKDVAKILVEKVTRKEKLERILKLYPGEKSA
        :  : ::: .*:  * ..              .. :   *:  ::::  : :.::   *.**.
Motif:  *--*-***--Y*--f-----------------*---I*--****--*-*-**---P-EK--

SM      GRFAEFLKLIVGNQADFKKHFELEEKAPLQFSKDTYEEELEVLLAQIGDNYAELFLSAKK
SP      GLFGNLIALSLGLTPNFKSNFDLAEDAKLQLSKDTYDDDLDNLLAQIGDQYADLFLAAKN
ST      GIFSEFLKLIVGNQADFRKCFNLDEKASLHFSKESYDEDLETLLGYIGDDYSDVFLKAKK
LI      GMFAQFISLIVGSKGNFQKPFDLIEKSDIECAKDSYEEDLESLLALIGDEYAELFVAAKN
        * *.::: * :*   :*:. *:* *.: :. :*::*:::*: **. ***:*:::*: **:
Motif:  G-F-***-L-*G---*F*--F*L-E-*-*--*K**Y***L*-LL--IGD*Y***F*-AK*

SM      LYDSILLSGILTVTDVGTKAPLSASMIQRYNEHQMDLAQLKQFIRQKLSDKYNEVFSDVS
SP      LSDAILLSDILRVNTEITKAPLSASMIKRYDEHHQDLTLLKALVRQQLPEKYKEIFFDQS
ST      LYDAILLSGFLTVTDNETEAPLSSAMIKRYNEHKEDLALLKEYIRNISLKTYNEVFKDDT
LI      AYSAVVLSSIITVAETETNAKLSASMIERFDTHEEDLGELKAFIKLHLPKHYEEIFSNTE
          .:::**.:: *     *:* **::**:*:: *. **   **   ::     . *:*:* :
Motif:  ---***LS-**-V----T*A-LS**MI*R**-H--DL--LK--**-------Y*E*F-*--

SM      KDGYAGYIDGKTNQEAFYKYLKGLLNKIEGSGYFLDKIEREDFLRKQRTFDNGSIPHQIH
SP      KNGYAGYIDGGASQEEFYKFIKPILEKMDGTEELLVKLNREDLLRKQRTFDNGSIPHQIH
ST      KNGYAGYIDGKTNQEDFYVYLKKLLAEFEGADYFLEKIDREDFLRKQRTFDNGSIPYQIH
LI      KHGYAGYIDGKTKQADFYKYMKMTLENIEGADYFIAKIEKENFLRKQRTFDNGAIPHQLH
        *.******** :.*  **  ::*  *  :::*:  :: *:::*::*********:**:*:*
Motif:  K-GYAGYIDG-*-Q--FY-**K--L-***G*--**-K***E**LRKQRTFDNG*IP*Q*H
```

Fig. 2A

```
CLUSTAL format alignment by MAFFT (v7.058b)                    Y

                          *
SM          MKKPYSIGLDIGTNSVGWAVVTDDYKVPAKKMKVLGNTDKSHIEKNLLGALLFDSGNTAED
SP          MDKKYSIGLDIGTNSVGWAVITDEYKVPSKKFKVLGNTDRHSIKKNLIGALLFDSGETAEA
ST          MTKPYSIGLDIGTNSVGWAVTTDNYKVPSKKMKVLGNTSKKYIKKNLLGVLLFDSGITAEG
LI          MKKPYTIGLDIGTNSVGWAVLTDQYDLVKRKMKIAGDSEKKQIKKNFWGVRLFDEGQTAAD
              *  *:***********  **:*.:   :*:*:  *::.:   *:**:  *.  ***.*  **
Motif:      M-K-Y*IGLDIGTNSVGWAV-TD*Y-*---*K*K*-G**-*---I*KN*-G--LFD-G-TA--

SM           RRLKRTARRRYTRRRNRILYLQEIFSEEMGKVDDSFFHRLEDSFLVTEDKRGERHPIFGN
SP           TRLKRTARRRYTRRKNRICYLQEIFSNEMAKVDDSFFHRLEESFLVEEDKKHERHPIFGN
ST           RRLKRTARRRYTRRRNRILYLQEIFSTEMATLDDAFFQRLDDSFLVPDDKRDSKYPIFGN
LI           RRMARTARRRIERRRNRISYLQGIFAEEMSKTDANFFCRLSDSFYVDNEKRNSRHPFFAT
              *: ******  **:*** *** **: **.. *  ** **.:** * ::*: .::*:*..
Motif:       -R*-RTARRR--RR*NRI-YLQ-IF*-EM---D--FF-RL-*SF-V-**K*--**P*F--

SM           LEEEVKYHENFPTIYHLRQYLADNPEKVDLRLVYLALAHIIKFRGHFLIEGKFDTRNNDV
SP           IVDEVAYHEKYPTIYHLRKKLVDSTDKADLRLIYLALAHMIKFRGHFLIEGDLNPDNSDV
ST           LVEEKAYHDEFPTIYHLRKYLADSTKKADLRLVYLALAHMIKYRGHFLIEGEFNSKNNDI
LI           IEEEVEYHKNYPTIYHLREELVNSSEKADLRLVYLALAHIIKYRGNFLIEGALDTQNTSV
             : :*  **.::*******: *.:...*.****:******:**:**:*****  ::. *..:
Motif:       *-*E--YH-**PTIYHLR*-L-*---K-DLRL*YLALAH*IK*RGNFLIEG-**--N--*
```

Fig. 2B

```
SM      LQEMRAIIRRQAEFYPFLADNQDRIEKLLTFRIPYYVGPLARGKSDFAWLSRKSADKITP
SP      LGELHAILRRQEDFYPFLKDNREKIEKILTFRIPYYVGPLARGNSRFAWMTRKSEETITP
ST      LQEMRAILDKQAKFYPFLAKNKERIEKILTFRIPYYVGPLARGNSDFAWSIRKRNEKITP
LI      LEELEAILHQQAKYYPFLKENYDKIKSLVTFRIPYFVGPLANGQSEFAWLTRKADGEIRP
        * *:.**: :*  .:**** .*  ::*:.:;******:*****.*:*  ***   **    * *
Motif:  L-E*-AI*-*Q--*YPFL--N-**I*-**TFRIPY*VGPLA-G*S-FAW--RK----I-P

SM      WNFDEIVDKESSAEAFINRMTNYDLYLPNQKVLPKHSLLYEKFTVYNELTKVKYKTE-QG
SP      WNFEEVVDKGASAQSFIERMTNFDKNLPNEKVLPKHSLLYEYFTVYNELTKVKYVTEGMR
ST      WNFEDVIDKESSAEAFINRMTSFDLYLPEEKVLPKHSLLYETFNVYNELTKVRFIAESMR
LI      WNIEEKVDFGKSAVDFIEKMTNKDTYLPKENVLPKHSLCYQKYLVYNELTKVRYIND-QG
        **:::  :*    **   **::**. *   **:::******* *:  :  ********::   :
Motif:  WN***-*D---SA--FI**MT--D--LP***VLPKHSL-Y*-*-VYNELTKV**---*---

SM      KTAFFDANMKQEIFDGVFKVYRKVTKDKLMDFLEKEFDEFRIVDLTGLDKENKVFNASYG
SP      KPAFLSGEQKKAIVDLLFKTNRKVTVKQLKEDYFKKIECFDSVEISGVEDR---FNASLG
ST      DYQFLDSKQKKDIVRLYFKDKRKVTDKDIIEYL-HAIYGYDGIELKGIEKQ---FNSSLS
LI      KTSYFSGQEKEQIFNDLFKQKRKVKKKDLELFL-RNMSHVESPTIEGLEDS---FNSSYS
        .  ::..: *: *.    **  ***. ..:        : :         : *::.     **:* .
Motif:  ---**--*-K*-I----FK--RKV----*-----*-*-------*-G*-----FN*S--

SM      TYHDLCKIL-DKDFLDNSKNEKILEDIVLTLTLFEDREMIRKRLENYSDLLTKEQVKKLE
SP      TYHDLLKIIKDKDFLDNEENEDILEDIVLTLTLFEDREMIEERLKTYAHLFDDKVMKQLK
ST      TYHDLLNIINDKEFLDDSSNEAIIEEIIHTLTIFEDREMIKQRLSKFENIFDKSVLKKLS
LI      TYHDLLKVGIKQEILDNPVNTEMLENIVKILTVFEDKRMIKEQLQQFSDVLDGVVLKKLE
        *****  ::   .:::**:   *   ::*:*:   **:***:.**.::*.  :  .::    :*:*.
Motif:  TYHDL-**---***LD*--N--**E*I*--LT*FED*-MI-**L--*--**----*K*L-
```

Fig. 2C

```
SM      KLLSAKLITQRKFDNLTKAERGGLTDDDKAGFIKRQLVETRQITKHVARILDERFNTETD
SP      QLLNAKLITQRKFDNLTKAERGGLSELDKAGFIKRQLVETRQITKHVAQILDSRMNTKYD
ST      QLLKSKLISQRKFDNLTKAERGGLSPEDKAGFIQRQLVETRQITKHVARLLDEKFNNKKD
LI      KLYQGNLMSKRKFDYLTKAERGGLTEADKARFIHRQLVETRQITKNVANILHQRFNYEKD
        :*  ..:*:::****  *********;   ***  **;***********:**.:*..::*  :  *
Motif:  *L---*L***RKFD-LTKAERGGL*--DKA-FI*RQLVETRQITK*VA-*L--**N-*-D

                                                         B
SM      ENNKKIRQVKIVTLKSNLVSNFRKEFELYKVREINDYHHAHDAYLNAVIGKALLGVYPQL
SP      ENDKLIREVKVITLKSKLVSDFRKDFQFYKVREINNYHHAHDAYLNAVVGTALIKKYPKL
ST      ENNRAVRTVKIITLKSTLVSQFRKDFELYKVREINDFHHAHDAYLNAVVASALLKKYPKL
LI      DHGNTMKQVRIVTLKSALVSQFRKQFQLYKVRDVNDYHHAHDAYLNGVVANTLLKVYPQL
        ::..  ::  *:::****  ***:***:*::****::*::*********.*:..:*:   **:*
Motif:  **----**-V***TLKS-LVS*FRK*F**LYKV**N**HHAHDAYLN-V*--*L*--YP*L

SM      EPEFVYGDYPHFHGHKE--------NK-ATAKKFFYSNIMNFFKKDDVRTD---------
SP      ESEFVYGDYKVYDVRKMIAKSEQEIGK-ATAKYFFYSNIMNFFKTEITLANGEIRKRPLI
ST      EPEFVYGDYPKYNSFRE--------RKSATEKVYFYSNIMNIFKKSISLADGRVIERPLI
LI      EPEFVYGDYHQFDWFKA--------NK-ATAKKQFYTNIMLFFAQKDRIID---------
        *.*******   :.   :            *  **  *    **:***  :*   .      :
Motif:  E-EFVYGDY--*---*----------K-AT-K--FY*NIM-*F-------*---------

SM      ----KNGEIIWKKDEHISNIKKVLSYPQVNIVKKVEEQTGGFSKE----------SILPK
SP      ETNGETGEIVWDKGRDFATVRKVLSMPQVNIVKKTEVQTGGFSKE----------SILPK
ST      EVNEETGESVWNKESDLATVRRVLSYPQVNVVKKVEEQNHGLDRGKPKGLFNANLSSKPK
LI      ----ENGEILWDK-KYLDTVKKVMSYRQMNIVKKTEIQKGEFSKA----------TIKPK
            :.**  :*.*    :  .:::*:*   *:*:***.* *.   :.:              :   **
Motif:  ----*-GE-*W-K---*--***V*M--Q*N*VKK-E-Q---*-*-----------*--PK
```

Fig. 2E

```
SM       GNSDK-LIPRKTKKFYWDTKKYGGFDSPIVAYSILVIADIEKGKSKKLKTVKALVGVTIM
SP       RNSDK-LIARKKD---WDPKKYGGFDSPTVAYSVLVVAKVEKGKSKKLKSVKELLGITIM
ST       PNSNENLVGAKEY---LDPKKYGGYAGISNSFTVLVKGTIEKGAKKKITNVLEFQGISIL
LI       GNSSK-LIPRKTN---WDPMKYGGLDSPNMAYAVVI--EYAKGKN-KLVFEKKIIRVTIM
          **.: *:  *      *. ****  .    ::::::     ** . *:     :  ::*:
Motif:   -NS-*-L*--K------D--KYGG------******-----KG---K*-----*--**I*

SM       EKMTFERDPVAFLERKGYRNVQEENIIKLPKYSLFKLENGRKRLLAS-------ARELQK
SP       ERSSFEKNPIDFLEAKGYKEVKKDLIIKLPKYSLFELENGRKRMLAS-------AGELQK
ST       DRINYRKDKLNFLLEKGYKDI--ELIIELPKYSLFELSDGSRRMLASILSTNNKRGEIHK
LI       ERKAFEKDEKAFLEEQGYRQP--KVLAKLPKYTLYECEEGRRRMLAS-------ANEAQK
         ::  :.::   **  :**::   . : :****:*:: .:* :*:***          * :*
Motif:   **--*-**---FL--*GY**------*-*LPKY*L**--*G-*R*LAS---------E-*K

SM       GNEIVLPNHLGTLLYHAKNIHKV------DEPKHLDYVDKHKDEFKELLDVVSNFSKKYT
SP       GNELALPSKYVNFLYLASHYEKLKGSPEDNEQKQL-FVEQHKHYLDEIIEQISEFSKRVI
ST       GNQIFLSQKFVKLLYHAKRISNT------INENHRKYVENHKKEFEELFYYILEFNENYV
LI       GNQQVLPNHLVTLLHHAANCEVS-------DGKSLDYIESNREMFAELLAHVSEFAKRYT
         **:  *..:  .:*: * .              : :   :::.::. : *::  : :* :.
Motif:   GN*--L--*---*L*-A-------------*-*---***-**--*-E**--*-*F-*---

SM       LAEGNLEKIKELYAQNNGEDLKELASSFI--------NLLTFTAIGAPATFKFFDKNIDR
SP       LADANLDKVLSAYNKHRDKPIREQAENII--------HLFTLTNLGAPAAFKYFDTTIDR
ST       GAKKNGKLLNSAFQSWQNHSIDELCSSFIGPTGSERKGLFELTSRGSAADFEFLGVKIPR
LI       LAEANLNKINQLFEQNKEGDIKAIAQSFV--------DLMAFNAMGAPASFKFFETTIER
          *. *  . : . : . .   :    ...::         *: :.  *:.* *:::  .* *
Motif:   -A--N---*---*-------*-------**---------L*-*---G*-A-F***---I-R
```

Fig. 2F

```
SM      KR-YTSTTEILNATLIHQSITGLYETRIDLNKLGGD   (SEQ ID NO:1)
SP      KR-YTSTKEVLDATLIHQSITGLYETRIDLSQLGGD   (SEQ ID NO:2)
ST      YRDYTPSSLLKDATLIHQSVTGLYETRIDLAKLGEG   (SEQ ID NO:4)
LI      KR-YNNLKELLNSTIIYQSITGLYESRKRLD----D   (SEQ ID NO:5)
         * *.  . :  ::*:*:**:*****:*  *     .
Motif:  -R-Y-----*-**T*I*QS*TGLYE*R--L------   (SEQ ID NO:14)
```

Fig. 2G

Alignment of the N terminal RuvC-like Domains disclosed in Chylinski et al.
(excluding sequence outliers).
(CLUSTAL format alignment by MAFFT (v7.058b))

| | | |
|---|---|---|
| 1,12 | DIGTNSVGWAVT | (SEQ ID NO:120) |
| 3,20 | DVGTNSVGWAVT | (SEQ ID NO:121) |
| 15 | DMGTNSVGWAVT | (SEQ ID NO:122) |
| 4 | DVGTSSVGWAVT | (SEQ ID NO:123) |
| 7 | DIGTASVGWAVT | (SEQ ID NO:52) |
| 6 | DVGTGSVGWAVT | (SEQ ID NO:53) |
| 9 | DIGTNSVGWAVV | (SEQ ID NO:54) |
| 10 | DIGTNSVGWAVI | (SEQ ID NO:55) |
| 11 | DIGTNSVGWAVL | (SEQ ID NO:56) |
| 42 | DLGTNSIGWAVV | (SEQ ID NO:57) |
| 48 | DLGTNSIGWAI- | (SEQ ID NO:58) |
| 43 | DLGTNSIGWALV | (SEQ ID NO:59) |
| 2 | DIGTNSVGWCVT | (SEQ ID NO:60) |
| 14 | DIGTNSVGYAVT | (SEQ ID NO:61) |
| 5 | DMGTGSLGWAVT | (SEQ ID NO:62) |
| 16 | DIGTSSVGWAAI | (SEQ ID NO:63) |
| 8 | DLGTGSVGWAVV | (SEQ ID NO:64) |
| 22 | DLGVGSVGWAIV | (SEQ ID NO:65) |
| 23 | DLGIASIGWAII | (SEQ ID NO:66) |
| 24 | DLGIASVGWAIV | (SEQ ID NO:67) |
| 25 | DLGVASVGWSIV | (SEQ ID NO:68) |
| 26 | DIGIASVGWAIL | (SEQ ID NO:69) |
| 28 | DLGISSVGWSVI | (SEQ ID NO:70) |
| 32 | DIGIASVGWSVI | (SEQ ID NO:71) |
| 33 | DVGIGSIGWAVI | (SEQ ID NO:72) |
| 39 | DLGVGSIGFAIV | (SEQ ID NO:73) |
| 34 | DIGYASIGWAVI | (SEQ ID NO:74) |
| 47 | DTGTNSLGWAIV | (SEQ ID NO:75) |
| 50 | DLGTNSIGWCLL | (SEQ ID NO:76) |
| 49 | DIGTDSLGWAVF | (SEQ ID NO:77) |
| 18 | DIGSNSIGFAVV | (SEQ ID NO:78) |
| 41 | DLGVGSIGVAVA | (SEQ ID NO:79) |
| 45 | DLGIASCGWGVV | (SEQ ID NO:80) |

Fig. 3A

| | | |
|---|---|---|
| 21 | DLGIASVGWCLT | (SEQ ID NO:81) |
| 27 | DIGIGSVGVGIL | (SEQ ID NO:82) |
| 29 | DIGITSVGYGLI | (SEQ ID NO:83) |
| 30 | DIGITSVGFGII | (SEQ ID NO:84) |
| 31 | DVGITSTGYAVL | (SEQ ID NO:85) |
| 40 | DLGITSFGYAIL | (SEQ ID NO:86) |
| 17 | DIGNASVGWSAF | (SEQ ID NO:87) |
| 19 | DVGTNSCGWVAM | (SEQ ID NO:88) |
| 35 | DVGERSIGLAAV | (SEQ ID NO:89) |
| 36 | DVGLNSVGLAAV | (SEQ ID NO:90) |
| 37 | DVGLMSVGLAAI | (SEQ ID NO:91) |
| 38 | DVGTFSVGLAAI | (SEQ ID NO:92) |
| 13 | DIGTGSVGYACM | (SEQ ID NO:92) |
| 44 | DLGTTSIGFAHI | (SEQ ID NO:94) |
| 46 | DLGTNSIGSSVR | (SEQ ID NO:95) |
| | * * * * | |

Fig. 3B

Alignment of the N terminal RuvC-like Domains disclosed in Chylinski et al.
(CLUSTAL format alignment by MAFFT (v7.058b))

```
1,12        D----IGTNSVGWAVT     (SEQ ID NO:120)
3,20        D----VGTNSVGWAVT     (SEQ ID NO:121)
15          D----MGTNSVGWAVT     (SEQ ID NO:122)
4           D----VGTSSVGWAVT     (SEQ ID NO:123)
7           D----IGTASVGWAVT     (SEQ ID NO:52)
6           D----VGTGSVGWAVT     (SEQ ID NO:53)
9           D----IGTNSVGWAVV     (SEQ ID NO:54)
10          D----IGTNSVGWAVI     (SEQ ID NO:55)
52          D----IGTNSIGWAVI     (SEQ ID NO:96)
11          D----IGTNSVGWAVL     (SEQ ID NO:56)
42          D----LGTNSIGWAVV     (SEQ ID NO:57)
48          D----LGTNSIGWAI-     (SEQ ID NO:58)
43          D----LGTNSIGWALV     (SEQ ID NO:59)
2           D----IGTNSVGWCVT     (SEQ ID NO:60)
14          D----IGTNSVGYAVT     (SEQ ID NO:61)
5           D----MGTGSLGWAVT     (SEQ ID NO:62)
16          D----IGTSSVGWAAI     (SEQ ID NO:63)
8           D----LGTGSVGWAVV     (SEQ ID NO:64)
22          D----LGVGSVGWAIV     (SEQ ID NO:65)
23          D----LGIASIGWAII     (SEQ ID NO:66)
24          D----LGIASVGWAIV     (SEQ ID NO:67)
68          D----LGIASVGWAVV     (SEQ ID NO:97)
25          D----LGVASVGWSIV     (SEQ ID NO:68)
26          D----IGIASVGWAIL     (SEQ ID NO:69)
66          D----IGIASVGWAVL     (SEQ ID NO:98)
59          D----IGIASIGWAVI     (SEQ ID NO:99)
61          D----IGIASVGWAII     (SEQ ID NO:100)
64          D----VGIASVGWAVI     (SEQ ID NO:101)
62          D----IGIASVGWAL-     (SEQ ID NO:102)
67          D----IGIASVGWAMV     (SEQ ID NO:103)
32          D----IGIASVGWSVI     (SEQ ID NO:71)
28          D----LGISSVGWSVI     (SEQ ID NO:70)
63          D----IGITSVGWAVI     (SEQ ID NO:104)
```

Fig. 4A

| | | |
|---|---|---|
| 33 | D----VGIGSIGWAVI | (SEQ ID NO:72) |
| 57 | D----LGISSLGWAIV | (SEQ ID NO:105) |
| 39 | D----LGVGSIGFAIV | (SEQ ID NO:73) |
| 34 | D----IGYASIGWAVI | (SEQ ID NO:74) |
| 50 | D----LGTNSIGWCLL | (SEQ ID NO:76) |
| 54 | D----LGTNSIGWGLL | (SEQ ID NO:106) |
| 47 | D----TGTNSLGWAIV | (SEQ ID NO:75) |
| 49 | D----IGTDSLGWAVF | (SEQ ID NO:77) |
| 51 | D----LGSTSLGWAIF | (SEQ ID NO:107) |
| 58 | D----IGISSIGWAFS | (SEQ ID NO:108) |
| 21 | D----LGIASVGWCLT | (SEQ ID NO:81) |
| 45 | D----LGIASCGWGVV | (SEQ ID NO:80) |
| 18 | D----IGSNSIGFAVV | (SEQ ID NO:78) |
| 65 | D----IGTTSIGFSVI | (SEQ ID NO:109) |
| 29 | D----IGITSVGYGLI | (SEQ ID NO:83) |
| 30 | D----IGITSVGFGII | (SEQ ID NO:84) |
| 44 | D----LGTTSIGFAHI | (SEQ ID NO:94) |
| 27 | D----IGIGSVGVGIL | (SEQ ID NO:82) |
| 41 | D----LGVGSIGVAVA | (SEQ ID NO:79) |
| 31 | D----VGITSTGYAVL | (SEQ ID NO:85) |
| 40 | D----LGITSFGYAIL | (SEQ ID NO:86) |
| 53 | D----IGTSSIGWWLY | (SEQ ID NO:110) |
| 55 | D----LGSNSLGWFVT | (SEQ ID NO:111) |
| 56 | D----LGANSLGWFVV | (SEQ ID NO:112) |
| 17 | D----IGNASVGWSAF | (SEQ ID NO:87) |
| 19 | D----VGTNSCGWVAM | (SEQ ID NO:88) |
| 35 | D----VGERSIGLAAV | (SEQ ID NO:89) |
| 36 | D----VGLNSVGLAAV | (SEQ ID NO:90) |
| 37 | D----VGLMSVGLAAI | (SEQ ID NO:91) |
| 38 | D----VGTFSVGLAAI | (SEQ ID NO:92) |
| 13 | D----IGTGSVGYACM | (SEQ ID NO:93) |
| 46 | D----LGTNSIGSSVR | (SEQ ID NO:95) |
| 60 | DIGLRIGITSCGWSI- | (SEQ ID NO:113) |
| 69 | D----MGAKYTGVFYA | (SEQ ID NO:114) |
| 73 | D----LGGKNTGFFSF | (SEQ ID NO:115) |
| 74 | D----LGVKNTGVFSA | (SEQ ID NO:116) |
| 70 | D----LGAKFTGVALY | (SEQ ID NO:117) |
| 71 | D----LGGKFTGVCLS | (SEQ ID NO:118) |
| 72 | D----LGGTYTGTFIT | (SEQ ID NO:119) |

Fig. 4B

Alignment of the HNH-like Domains disclosed in Chylinski *et al.*
(CLUSTAL format alignment by MAFFT (v7.058b))

```
1     YDIDHIYPRS-LTKD------DSF-DNLVLCERTAN   (SEQ ID NO:196)
2     -DIDHIYPRSKVIKD------DSF-DNLVLVLKNEN   (SEQ ID NO:197)
3     -DRDHIYPQS-KIKD------DSI-DNLVLVNKTYN   (SEQ ID NO:198)
4     -DIDHIYPRS-KIKD------DSI-TNRVLVEKDIN   (SEQ ID NO:195)
6     -DIDHIYPQS-KIKD------DSI-SNRVLVCSSCN   (SEQ ID NO:124)
5     -DIDHIYPQS-KTMD------DSL-NNRVLVKKNYN   (SEQ ID NO:125)
7     -DQDHIYPKS-KIYD------DSL-ENRVLVKKNLN   (SEQ ID NO:126)
8     -QIDHIVPQS-LVKD------DSF-DNRVLVVPSEN   (SEQ ID NO:127)
9     -DIDHIIPQA-FIKD------NSI-DNRVLTSSKEN   (SEQ ID NO:128)
12    -DIDHIIPQA-FLKD------NSI-DNKVLVSSASN   (SEQ ID NO:129)
16    -DIDHIIPQA-YTKD------NSL-DNRVLVSNITN   (SEQ ID NO:130)
11    -DIDHIVPQS-FITD------NSI-DNLVLTSSAGN   (SEQ ID NO:131)
10    -DVDHIVPQS-FLKD------DSI-DNKVLTRSDKN   (SEQ ID NO:132)
14    -NIDHIYPQS-MVKD------DSL-DNKVLVQSEIN   (SEQ ID NO:133)
18    -DIDHILPQS-LIKD------DSL-DNRVLVNATIN   (SEQ ID NO:134)
19    -DIDHILPQS-FIKD------DSL-ENRVLVKKAVN   (SEQ ID NO:135)
13    -EVDHIFPRS-FIKD------DSI-DNKVLVIKKMN   (SEQ ID NO:136)
15    -EVDHIIPRS-YIKD------DSF-ENKVLVYREEN   (SEQ ID NO:137)
17    -DIDHIIPQA-VTQN------DSI-DNRVLVARAEN   (SEQ ID NO:138)
22    -EIDHIIPYS-ISFD------DSS-SNKLLVLAESN   (SEQ ID NO:139)
24    -EIDHIIPYS-LCFD------DSS-ANKVLVHKQSN   (SEQ ID NO:140)
32    -DIDHIIPYS-RSMD------DSY-SNKVLVLSGEN   (SEQ ID NO:141)
63    -DIDHIIPYS-KSMD------DSF-NNKVLCLAEEN   (SEQ ID NO:142)
59    -EIDHIYPYS-RSFD------DSY-MNKVLVFTKQN   (SEQ ID NO:143)
65    -QIDHIYPYS-RSMD------DSY-MNKVLVLTDEN   (SEQ ID NO:144)
64    -EIDHIIPFS-RSFD------DSL-SNKILVLGSEN   (SEQ ID NO:145)
68    -EIDHALPFS-RTWD------DSF-NNKVLVLGSEN   (SEQ ID NO:146)
69    -EIDHALPFS-RTWD------DSF-NNKVLVLASEN   (SEQ ID NO:147)
28    -EIDHIIPIS-ISLD------DSI-NNKVLVLSKAN   (SEQ ID NO:148)
30    -EVDHIIPIS-ISLD------DSI-TNKVLVTHREN   (SEQ ID NO:149)
62    -QVDHALPYS-RSYD------DSK-NNKVLVLTHEN   (SEQ ID NO:150)
27    -EVDHILPLS-ITFD------DSL-ANKVLVYATAN   (SEQ ID NO:151)
26    -EIDHIIPRS-ISFD------DAR-SNKVLVYRSEN   (SEQ ID NO:152)
```

Fig. 5A

| | | |
|---|---|---|
| 29 | -EVDHIIPRS-VSFD------NSY-HNKVLVKQSEN | (SEQ ID NO:153) |
| 67 | -DIDHILPYS-ITFD------DSF-RNKVLVTSQEN | (SEQ ID NO:154) |
| 58 | -EIDHILPRS-RSAD------DSF-ANKVLCLARAN | (SEQ ID NO:155) |
| 51 | -EIEHLLPFS-LTLD------DSM-ANKTVCFRQAN | (SEQ ID NO:156) |
| 55 | -DIDHILPFS-VSLD------DSA-ANKVVCLREAN | (SEQ ID NO:157) |
| 57 | -DIDHLIPPS-ISWD------DSA-ANKVVCMRYAN | (SEQ ID NO:158) |
| 56 | -DIDHILPVA-MTLD------DSP-ANKIICMRYAN | (SEQ ID NO:159) |
| 54 | -DVDHILPYS-RTLD------DSF-PNRTLCLREAN | (SEQ ID NO:160) |
| 52 | -EIEHILPFS-RTLD------DSL-NNRTVAMRRAN | (SEQ ID NO:161) |
| 31 | -EVDHIIPYS-ISWD------DSY-TNKVLTSAKCN | (SEQ ID NO:162) |
| 45 | -QVDHILPWS-RFGD------DSY-LNKTLCTARSN | (SEQ ID NO:163) |
| 53 | -QVDHILPFS-KTLD------DSF-ANKVLAQHDAN | (SEQ ID NO:164) |
| 60 | -QIDHAFPLS-RSLD------DSQ-SNKVLCLTSSN | (SEQ ID NO:165) |
| 21 | -DIDHIVPRS-ISFD------DSF-SNLVIVNKLDN | (SEQ ID NO:166) |
| 23 | -EIEHIIPYS-MSYD------NSQ-ANKILTEKAEN | (SEQ ID NO:167) |
| 25 | -EIDHVIPYS-KSAD------DSW-FNKLLVKKSTN | (SEQ ID NO:168) |
| 49 | -EMDHILPYS-RSLD------NGW-HNRVLVHGKDN | (SEQ ID NO:169) |
| 33 | -EVDHIVPYS-LILD------NTI-NNKALVYAEEN | (SEQ ID NO:170) |
| 42 | -EIEHVIPQS-LYFD------DSF-SNKVICEAEVN | (SEQ ID NO:171) |
| 43 | -DIEHIIPQA-RLFD------DSF-SNKTLEARSVN | (SEQ ID NO:172) |
| 44 | -EIEHIVPKA-RVFD------DSF-SNKTLTFHRIN | (SEQ ID NO:173) |
| 20 | -DKDHIIPQS-MKKD------DSIINNLVLVNKNAN | (SEQ ID NO:174) |
| 66 | -EVEHIWPRS-RSFD------NSP-RNKTLCRKDVN | (SEQ ID NO:175) |
| 61 | -IVNHIIPYN-RSFD------DTY-HNRVLTLTETK | (SEQ ID NO:176) |
| 46 | -DMEHTIPKS-ISFD------NSD-QNLTLCESYYN | (SEQ ID NO:177) |
| 47 | -DIEHTIPRS-AGGD------STK-MNLTLCSSRFN | (SEQ ID NO:178) |
| 48 | -DIEHTIPRS-ISQD------NSQ-MNKTLCSLKFN | (SEQ ID NO:179) |
| 50 | -DIDHVIPLA-RGGR------DSL-DNMVLCQSDAN | (SEQ ID NO:180) |
| 39 | -DIEHLFPIA-ESED------NGR-NNLVISHSACN | (SEQ ID NO:181) |
| 41 | -DVDHIFPRD-DTAD------NSY-GNKVVAHRQCN | (SEQ ID NO:182) |
| 40 | -DIEHIVPQS-LGGL------STD-YNTIVTLKSVN | (SEQ ID NO:183) |
| 35 | -ELDHIVPRT-DGGS------NRH-ENLAITCGACN | (SEQ ID NO:184) |
| 36 | -EMDHIVPRKGVGST------NTR-TNFAAVCAECN | (SEQ ID NO:185) |
| 37 | -EMDHIVPRKGVGST------NTR-VNLAAACAACN | (SEQ ID NO:186) |
| 38 | -EMDHIVPRAGQGST------NTR-ENLVAVCHRCN | (SEQ ID NO:187) |
| 70 | -EIDHILPRS-LIKDARGIVFNAE-PNLIYASSRGN | (SEQ ID NO:188) |
| 71 | -EIDHIIPRS-LTGRTKKTVFNSE-ANLIYCSSKGN | (SEQ ID NO:189) |
| 73 | -EIDHIIPRS-LTLKKSESIYNSE-VNLIFVSAQGN | (SEQ ID NO:190) |

Fig. 5B

```
72    -EIDHIYPRS-LSKKHFGVIFNSE-VNLIYCSSQGN    (SEQ ID NO:191)
74    -EIDHILPRS-HTLKIYGTVFNPE-GNLIYVHQKCN    (SEQ ID NO:192)
75    -ELDHIIPRS-HKKY---GTLNDE-ANLICVTRGDN    (SEQ ID NO:193)
34    -ELEHIVPHS-FRQS-----NAL-SSLVLTWPGVN    (SEQ ID NO:194)
         :*  *             .    .        :
```

Fig. 5C

Alignment of the HNH-like Domains disclosed in Chylinski *et al.* (excluding sequence outliers). (CLUSTAL format alignment by MAFFT (v7.058b))

| | | |
|---|---|---|
| 1 | YDIDHIYPRS-LTKDDS-FDNLVLCERTAN | (SEQ ID NO:196) |
| 2 | -DIDHIYPRSKVIKDDS-FDNLVLVLKNEN | (SEQ ID NO:197) |
| 3 | -DRDHIYPQS-KIKDDS-IDNLVLVNKTYN | (SEQ ID NO:198) |
| 4 | -DIDHIYPRS-KIKDDS-ITNRVLVEKDIN | (SEQ ID NO:195) |
| 6 | -DIDHIYPQS-KIKDDS-ISNRVLVCSSCN | (SEQ ID NO:124) |
| 5 | -DIDHIYPQS-KTMDDS-LNNRVLVKKNYN | (SEQ ID NO:125) |
| 7 | -DQDHIYPKS-KIYDDS-LENRVLVKKNLN | (SEQ ID NO:126) |
| 8 | -QIDHIVPQS-LVKDDS-FDNRVLVVPSEN | (SEQ ID NO:127) |
| 9 | -DIDHIIPQA-FIKDNS-IDNRVLTSSKEN | (SEQ ID NO:128) |
| 12 | -DIDHIIPQA-FLKDNS-IDNKVLVSSASN | (SEQ ID NO:129) |
| 16 | -DIDHIIPQA-YTKDNS-LDNRVLVSNITN | (SEQ ID NO:130) |
| 11 | -DIDHIVPQS-FITDNS-IDNLVLTSSAGN | (SEQ ID NO:131) |
| 10 | -DVDHIVPQS-FLKDDS-IDNKVLTRSDKN | (SEQ ID NO:132) |
| 14 | -NIDHIYPQS-MVKDDS-LDNKVLVQSEIN | (SEQ ID NO:133) |
| 18 | -DIDHILPQS-LIKDDS-LDNRVLVNATIN | (SEQ ID NO:134) |
| 19 | -DIDHILPQS-FIKDDS-LENRVLVKKAVN | (SEQ ID NO:135) |
| 13 | -EVDHIFPRS-FIKDDS-IDNKVLVIKKMN | (SEQ ID NO:136) |
| 15 | -EVDHIIPRS-YIKDDS-FENKVLVYREEN | (SEQ ID NO:137) |
| 17 | -DIDHIIPQA-VTQNDS-IDNRVLVARAEN | (SEQ ID NO:138) |
| 21 | -DIDHIVPRS-ISFDDS-FSNLVIVNKLDN | (SEQ ID NO:166) |
| 22 | -EIDHIIPYS-ISFDDS-SSNKLLVLAESN | (SEQ ID NO:139) |
| 24 | -EIDHIIPYS-LCFDDS-SANKVLVHKQSN | (SEQ ID NO:140) |
| 28 | -EIDHIIPIS-ISLDDS-INNKVLVLSKAN | (SEQ ID NO:148) |
| 30 | -EVDHIIPIS-ISLDDS-ITNKVLVTHREN | (SEQ ID NO:149) |
| 27 | -EVDHILPLS-ITFDDS-LANKVLVYATAN | (SEQ ID NO:151) |
| 26 | -EIDHIIPRS-ISFDDA-RSNKVLVYRSEN | (SEQ ID NO:152) |
| 29 | -EVDHIIPRS-VSFDNS-YHNKVLVKQSEN | (SEQ ID NO:153) |
| 31 | -EVDHIIPYS-ISWDDS-YTNKVLTSAKCN | (SEQ ID NO:162) |
| 32 | -DIDHIIPYS-RSMDDS-YSNKVLVLSGEN | (SEQ ID NO:141) |
| 23 | -EIEHIIPYS-MSYDNS-QANKILTEKAEN | (SEQ ID NO:167) |
| 33 | -EVDHIVPYS-LILDNT-INNKALVYAEEN | (SEQ ID NO:170) |
| 25 | -EIDHVIPYS-KSADDS-WFNKLLVKKSTN | (SEQ ID NO:168) |
| 49 | -EMDHILPYS-RSLDNG-WHNRVLVHGKDN | (SEQ ID NO:169) |
| 42 | -EIEHVIPQS-LYFDDS-FSNKVICEAEVN | (SEQ ID NO:171) |
| 43 | -DIEHIIPQA-RLFDDS-FSNKTLEARSVN | (SEQ ID NO:172) |

Fig. 6A

```
44   -EIEHIVPKA-RVFDDS-FSNKTLTFHRIN     (SEQ ID NO:173)
20   -DKDHIIPQS-MKKDDSIINNLVLVNKNAN     (SEQ ID NO:174)
45   -QVDHILPWS-RFGDDS-YLNKTLCTARSN     (SEQ ID NO:163)
50   -DIDHVIPLA-RGGRDS-LDNMVLCQSDAN     (SEQ ID NO:180)
46   -DMEHTIPKS-ISFDNS-DQNLTLCESYYN     (SEQ ID NO:177)
47   -DIEHTIPRS-AGGDST-KMNLTLCSSRFN     (SEQ ID NO:178)
48   -DIEHTIPRS-ISQDNS-QMNKTLCSLKFN     (SEQ ID NO:179)
39   -DIEHLFPIA-ESEDNG-RNNLVISHSACN     (SEQ ID NO:181)
41   -DVDHIFPRD-DTADNS-YGNKVVAHRQCN     (SEQ ID NO:182)
40   -DIEHIVPQS-LGGLST-DYNTIVTLKSVN     (SEQ ID NO:183)
35   -ELDHIVPRT-DGGSNR-HENLAITCGACN     (SEQ ID NO:184)
36   -EMDHIVPRKGVGSTNT-RTNFAAVCAECN     (SEQ ID NO:185)
37   -EMDHIVPRKGVGSTNT-RVNLAAACAACN     (SEQ ID NO:186)
38   -EMDHIVPRAGQGSTNT-RENLVAVCHRCN     (SEQ ID NO:187)
34   -ELEHIVPHS-FRQSNA-LSSLVLTWPGVN     (SEQ ID NO:194)
```

Fig. 6B

| **Gene →** | **Alleles →** | | |
|---|---|---|---|
| | *HLA-A* | *HLA-B* | *HLA-DRB1* |
| **European American (Caucasian) UCB Donor** | A*29:02:01:01 | B*44:03 | DRB1*07:01 |
| | **A*02:01:01:01** | B*08:01:0 | DRB1*03:01 |
| **African American Recipient** | **A*01:01:01:01** | B*08:01:01 | DRB1*03:01 |
| | A*29:02:01:01 | B*44:03 | DRB1*07:01 |

Fig. 16A

A*01:01:01:01 1098 bp (SEQ ID NO: 362)
ATGGCCGTCATGGCGCCCCGAACCCTCCTCCTGCTACTCTCGGGGGCCCTGGCCCTGACC
CAGACCTGGGCGGGCTCCCACTCCATGAGGTATTTCTTCACATCCGTGTCCCGGCCCGGC
CGCGGGGAGCCCCGCTTCATCGCCGTGGGCTACGTGGACGACACGCAGTTCGTGCGGTTC
GACAGCGACGCCGCGAGCCAGAAGATGGAGCCGCGGGCGCCGTGGATAGAGCAGGAGGGG
CCGGAGTATTGGGACCAGGAGACACGGAATATGAAGGCCCACTCACAGACTGACCGAGCG
AACCTGGGGACCCTGCGCGGCTACTACAACCAGAGCGAGGACGGTTCTCACACCATCCAG
ATAATGTATGGCTGCGACGTGGGGCCGGACGGGCGCTTCCTCCGCGGGTACCGGCAGGAC
GCCTACGACGGCAAGGATTACATCGCCCTGAACGAGGACCTGCGCTCTTGGACCGCGGCG
GACATGGCAGCTCAGATCACCAAGCGCAAGTGGGAGGCGGTCCATGCGGCGGAGCAGCGG
AGAGTCTACCTGGAGGGCCGGTGCGTGGACGGGCTCCGCAGATACCTGGAGAACGGGAAG
GAGACGCTGCAGCGCACGGACCCCCCCAAGACACATATGACCCACCACCCCATCTCTGAC
CATGAGGCCACCCTGAGGTGCTGGGCCCTGGGCTTCTACCCTGCGGAGATCACACTGACC
TGGCAGCGGGATGGGGAGGACCAGACCCAGGACACGGAGCTCGTGGAGACCAGGCCTGCA
GGGGATGGAACCTTCCAGAAGTGGGCGGCTGTGGTGGTGCCTTCTGGAGAGGAGCAGAGA
TACACCTGCCATGTGCAGCATGAGGGTCTGCCCAAGCCCCTCACCCTGAGATGGGAGCTG
TCTTCCCAGCCCACCATCCCCATCGTGGGCATCATTGCTGGCCTGGTTCTCCTTGGAGCT
GTGATCACTGGAGCTGTGGTCGCTGCCGTGATGTGGAGGAGGAAGAGCTCAGATAGAAAA
GGAGGGAGTTACACTCAGGCTGCAAGCAGTGACAGTGCCCAGGGCTCTGATGTGTCTCTC
ACAGCTTGTAAAGTGTGA

Fig. 16B

| Gene → | Alleles ↓ | | |
|---|---|---|---|
| | HLA-A | HLA-B | HLA-DRB1 |
| European American (Caucasian) UCB Donor | A*29:02:01:01 | B*44:03 | DRB1*07:01 |
| | A*02:01:01:01 | B*08:01:01 | DRB1*03:01 |
| Hispanic (Latino) Recipient | A*01:01:01:01 | B*08:01:01 | DRB1*03:01 |
| | A*23:01:01 | B*44:03 | DRB1*07:01 |

Fig. 17A

A*23:01:01 1098 bp (SEQ ID NO: 363)

ATGGCCGTCATGGCGCCCCGAACCCTCGTCCTGCTACTCTCGGGGGCCCTGGCCCTGACC
CAGACCTGGGCAGGCTCCCACTCCATGAGGTATTTCTCCACATCCGTGTCCCGGCCCGGC
CGCGGGGAGCCCCGCTTCATCGCCGTGGGCTACGTGGACGACACGCAGTTCGTGCGGTTC
GACAGCGACGCCGCGAGCCAGAGGATGGAGCCGCGGGCGCCGTGGATAGAGCAGGAGGGG
CCGGAGTATTGGGACGAGGAGACAGGGAAAGTGAAGGCCCACTCACAGACTGACCGAGAG
AACCTGCGGATCGCGCTCCGCTACTACAACCAGAGCGAGGCCGGTTCTCACACCCTCCAG
ATGATGTTTGGCTGCGACGTGGGGTCGGACGGGCGCTTCCTCCGCGGGTACCACCAGTAC
GCCTACGACGGCAAGGATTACATCGCCCTGAAAGAGGACCTGCGCTCTTGGACCGCGGCG
GACATGGCGGCTCAGATCACCCAGCGCAAGTGGGAGGCGGCCCGTGTGGCGGAGCAGTTG
AGAGCCTACCTGGAGGGCACGTGCGTGGACGGGCTCCGCAGATACCTGGAGAACGGGAAG
GAGACGCTGCAGCGCACGGACCCCCCCAAGACACATATGACCCACCACCCCATCTCTGAC
CATGAGGCCACTCTGAGATGCTGGGCCCTGGGCTTCTACCCTGCGGAGATCACACTGACC
TGGCAGCGGGATGGGGAGGACCAGACCCAGGACACGGAGCTTGTGGAGACCAGGCCTGCA
GGGGATGGAACCTTCCAGAAGTGGGCAGCTGTGGTGGTACCTTCTGGAGAGGAGCAGAGA
TACACCTGCCATGTGCAGCATGAGGGTCTGCCCAAGCCCCTCACCCTGAGATGGGAGCCA
TCTTCCCAGCCCACCGTCCACATCGTGGGCATCATTGCTGGCCTGGTTCTCCTTGGAGCT
GTGATCACTGGAGCTGTGGTCGCTGCTGTGATGTGGAGGAGGAACAGCTCAGATAGAAAA
GGAGGGAGCTACTCTCAGGCTGCAAGCAGTGACAGTGCCCAGGGCTCTGATGTGTCTCTC
ACAGCTTGTAAAGTGTGA

Fig. 17B

| Gene → | Alleles ↓ | | |
|---|---|---|---|
| | *HLA-A* | *HLA-B* | *HLA-DRB1* |
| **European American (Caucasian) UCB Donor** | A*29:02:01:01 | B*44:03 | DRB1*07:01 |
| | **A*02:01:01:01** | **B*08:01:01** | **DRB1*03:01:01:01** |
| **Hispanic (Latino) Recipient** | A*29:02:01:01 | B*44:03 | DRB1*03:01 |
| | **A*03:01:01:01** | **B*07:02:01** | **DRB1*15:01:01:01** |

Fig. 18A

A*03:01:01:01 1098 bp (SEQ ID NO: 364)
ATGGCCGTCATGGCGCCCCGAACCCTCCTCCTGCTACTCTCGGGGGCCCTGGCCCTGACCCAGACCTGGGCGGGCTCCCACTCCATGAGGTATTTCTTCACAT
CCGTGTCCCGGCCCGGCCGCGGGGAGCCCCGCTTCATCGCCGTGGGCTACGTGGACGACACGCAGTTCGTGCGGTTCGACAGCGACGCCGCGAGCCAGAGGAT
GGAGCCGCGGGCGCCGTGGATAGAGCAGGAGGGGCCGGAGTATTGGGACCAGGAGACACGGAATGTGAAGGCCCAGTCACAGACTGACCGAGTGGACCTGGGG
ACCCTGCGCGGCTACTACAACCAGAGCGAGGCCGGTTCTCACACCATCCAGATAATGTATGGCTGCGACGTGGGGTCGGACGGGCGCTTCCTCCGCGGGTACC
GGCAGGACGCCTACGACGGCAAGGATTACATCGCCCTGAACGAGGACCTGCGCTCTTGGACCGCGGCGGACATGGCGGCTCAGATCACCAAGCGCAAGTGGGA
GGCGGCCCATGAGGCGGAGCAGTTGAGAGCCTACCTGGATGGCACGTGCGTGGAGTGGCTCCGCAGATACCTGGAGAACGGGAAGGAGACGCTGCAGCGCACG
GACCCCCCCAAGACACATATGACCCACCACCCCATCTCTGACCATGAGGCCACCCTGAGGTGCTGGGCCCTGGGCTTCTACCCTGCGGAGATCACACTGACCT
GGCAGCGGGATGGGGAGGACCAGACCCAGGACACGGAGCTCGTGGAGACCAGGCCTGCAGGGGATGGAACCTTCCAGAAGTGGGCGGCTGTGGTGGTGCCTTC
TGGAGAGGAGCAGAGATACACCTGCCATGTGCAGCATGAGGGTCTGCCCAAGCCCCTCACCCTGAGATGGGAGCTGTCTTCCCAGCCCACCATCCCCATCGTG
GGCATCATTGCTGGCCTGGTTCTCCTTGGAGCTGTGATCACTGGAGCTGTGGTCGCTGCCGTGATGTGGAGGAGGAAGAGCTCAGATAGAAAAGGAGGGAGTT
ACACTCAGGCTGCAAGCAGTGACAGTGCCCAGGGCTCTGATGTGTCCCTCACAGCTTGTAAAGTGTGA

B*07:02:01 1089 bp (SEQ ID NO: 365)
ATGCTGGTCATGGCGCCCCGAACCGTCCTCCTGCTGCTCTCGGCGGCCCTGGCCCTGACCGAGACCTGGGCCGGCTCCCACTCCATGAGGTATTTCTACACCT
CCGTGTCCCGGCCCGGCCGCGGGGAGCCCCGCTTCATCTCAGTGGGCTACGTGGACGACACCCAGTTCGTGAGGTTCGACAGCGACGCCGCGAGTCCGAGAGA
GGAGCCGCGGGCGCCGTGGATAGAGCAGGAGGGGCCGGAGTATTGGGACCGGAACACACAGATCTACAAGGCCCAGGCACAGACTGACCGAGAGAGCCTGCGG
AACCTGCGCGGCTACTACAACCAGAGCGAGGCCGGGTCTCACACCCTCCAGAGCATGTACGGCTGCGACGTGGGGCCGGACGGGCGCCTCCTCCGCGGGCATG
ACCAGTACGCCTACGACGGCAAGGATTACATCGCCCTGAACGAGGACCTGCGCTCCTGGACCGCCGCGGACACGGCGGCTCAGATCACCCAGCGCAAGTGGGA
GGCGGCCCGTGAGGCGGAGCAGCGGAGAGCCTACCTGGAGGGCGAGTGCGTGGAGTGGCTCCGCAGATACCTGGAGAACGGGAAGGACAAGCTGGAGCGCGCT
GACCCCCCAAAGACACACGTGACCCACCACCCCATCTCTGACCATGAGGCCACCCTGAGGTGCTGGGCCCTGGGTTTCTACCCTGCGGAGATCACACTGACCT
GGCAGCGGGATGGCGAGGACCAAACTCAGGACACTGAGCTTGTGGAGACCAGACCAGCAGGAGATAGAACCTTCCAGAAGTGGGCAGCTGTGGTGGTGCCTTC
TGGAGAAGAGCAGAGATACACATGCCATGTACAGCATGAGGGGCTGCCGAAGCCCCTCACCCTGAGATGGGAGCCGTCTTCCCAGTCCACCGTCCCCATCGTG
GGCATTGTTGCTGGCCTGGCTGTCCTAGCAGTTGTGGTCATCGGAGCTGTGGTCGCTGCTGTGATGTGTAGGAGGAAGAGTTCAGGTGGAAAAGGAGGGAGCT
ACTCTCAGGCTGCGTGCAGCGACAGTGCCCAGGGCTCTGATGTGTCTCTCACAGCTTGA

DRB1*15:01:01:01 801 bp (SEQ ID NO: 366)
ATGGTGTGTCTGAAGCTCCCTGGAGGCTCCTGCATGACAGCGCTGACAGTGACACTGATGGTGCTGAGCTCCCCACTGGCTTTGTCTGGGGACACCCGACCAC
GTTTCCTGTGGCAGCCTAAGAGGGAGTGTCATTTCTTCAATGGGACGGAGCGGGTGCGGTTCCTGGACAGATACTTCTATAACCAGGAGGAGTCCGTGCGCTT
CGACAGCGACGTGGGGGAGTTCCGGGCGGTGACGGAGCTGGGGCGGCCTGACGCTGAGTACTGGAACAGCCAGAAGGACATCCTGGAGCAGGCGCGGGCCGCG
GTGGACACCTACTGCAGACACAACTACGGGGTTGTGGAGAGCTTCACAGTGCAGCGGCGAGTCCAACCTAAGGTGACTGTATATCCTTCAAAGACCCAGCCCC
TGCAGCACCACAACCTCCTGGTCTGCTCTGTGAGTGGTTTCTATCCAGGCAGCATTGAAGTCAGGTGGTTCCTGAACGGCCAGGAAGAGAAGGCTGGGATGGT
GTCCACAGGCCTGATCCAGAATGGAGACTGGACCTTCCAGACCCTGGTGATGCTGGAAACAGTTCCTCGAAGTGGAGAGGTTTACACCTGCCAAGTGGAGCAC
CCAAGCGTGACAAGCCCTCTCACAGTGGAATGGAGAGCACGGTCTGAATCTGCACAGAGCAAGATGCTGAGTGGAGTCGGGGGCTTTGTGCTGGGCCTGCTCT
TCCTTGGGGCCGGGCTGTTCATCTACTTCAGGAATCAGAAAGGACACTCTGGACTTCAGCCAACAGGATTCCTGAGCTGA

Example Query/Input:

Donor: **A*02:01:01:01** - B*08:01:01 - DRB1*03:01:01:01,
**A*29:02:01:01** - B*44:03:01 - DRB1*07:01:01:01

Patient: A*01:01:01:01 - B*08:01:01 - DRB1*03:01:01:01,
A*23:01:01 - B*44:03:01 - DRB1*07:01:01:01

2950

| | | | | |
|---|---|---|---|---|
| Target: **A*02:01:01:01, A*29:02:01:01** | | | | |
| Exclude: B*44:03:01, B*08:01:01, DRB1*03:01:01:01, DRB1*07:01:01:01 | | | | |
| | | | | |
| gRNA ID | gRNA sequence | type | strand | OT-Score |
| 5313 | GAGAGTAGCTCCCTCCTTTTCTAT | sa24 | - | 49.39 |
| 10721 | CAGGCTGCAAGCAGTGACAGTGCC | sa24 | + | 215.18 |
| 84971 | GGCTCCCATCTCAGGGTGAGGGGC | sa24 | - | 1343.83 |
| 22084 | AGGAAGAGCTCAGATAGAAAAGGA | sa24 | + | 2806.08 |
| 85367 | GCACTGTCACTGCTTGCAGC | sa20 | - | 19300 |
| 23351 | TGTGAGAACCGGCCTCGCTC | spy20 | - | 112250 |
| 59952 | CTGCAAGCAGTGACAGTGCC | sa20 | + | 146450 |
| 8253 | TGCAAGCAGTGACAGTGCCC | spy20 | + | 167650 |
| 36332 | GAAGAGCTCAGATAGAAAAG | sa20 | + | 296400 |
| 22286 | AGGAAGAGCTCAGATAGAAA | sa20 | + | 424800 |
| 51658 | GAGCCCGCCCAGGTCTGGGT | sa20 | - | 546350 |
| 30580 | AAGAGCTCAGATAGAAAAGG | spy20 | + | 852200 |
| 100025 | GCAAGCAGTGACAGTGCCCA | spy20 | + | 1281550 |
| 38840 | GAGAACCGGCCTCGCTC | spy17 | - | 7263000 |
| 83009 | GCCCGCCCAGGTCTGGGTCA | spy20 | - | 43085400 |

| Allele ID | Allele | Gene | Allele cDNA sequence |
|---|---|---|---|
| 1 | A*01:01:01:01 | HLA-A | ATGGCCGTCATGGCGCCCCGAACCCTCCTCCTGCTACTCTCGGGGGCCCTGGCCCTGACCCA<br>GACCTGGGCGGGCTCCCACTCCATGAGGTATTTCTTCACATCCGTGTCCCGGCCCGGCCGCG<br>GGGAGCCCCGCTTCATCGCCGTGGGCTACGTGGACGACACGCAGTTCGTGCGGTTCGACAG<br>CGACGCCGCGAGCCAGAAGATGGAGCCGCGGGCGCCGTGGATAGAGCAGGAGGGGCCGG<br>AGTATTGGGACCAGGAGACACGGAATATGAAGGCCCACTCACAGACTGACCGAGCGAACCT<br>GGGGACCCTGCGCGGCTACTACAACCAGAGCGAGGACGGTTCTCACACCATCCAGATAATGT<br>ATGGCTGCGACGTGGGGCCGGACGGGCGCTTCCTCCGCGGGTACCGGCAGGACGCCTACGA<br>CGGCAAGGATTACATCGCCCTGAACGAGGACCTGCGCTCTTGGACCGCGGCGGACATGGCA<br>GCTCAGATCACCAAGCGCAAGTGGGAGGCGGTCCATGCGGCGGAGCAGCGGAGAGTCTAC<br>CTGGAGGGCCGGTGCGTGGACGGGCTCCGCAGATACCTGGAGAACGGGAAGGAGACGCTG<br>CAGCGCACGGACCCCCCCAAGACACATATGACCCACCACCCCATCTCTGACCATGAGGCCAC<br>CCTGAGGTGCTGGGCCCTGGGCTTCTACCCTGCGGAGATCACACTGACCTGGCAGCGGGAT<br>GGGGAGGACCAGACCCAGGACACGGAGCTCGTGGAGACCAGGCCTGCAGGGGATGGAACC<br>TTCCAGAAGTGGGCGGCTGTGGTGGTGCCTTCTGGAGAGGAGCAGAGATACACCTGCCATG<br>TGCAGCATGAGGGTCTGCCCAAGCCCCTCACCCTGAGATGGGAGCTGTCTTCCCAGCCCACC<br>ATCCCCATCGTGGGCATCATTGCTGGCCTGGTTCTCCTTGGAGCTGTGATCACTGGAGCTGTG<br>GTCGCTGCCGTGATGTGGAGGAGGAAGAGCTCAGATAGAAAAGGAGGGAGTTACACTCAG<br>GCTGCAAGCAGTGACAGTGCCCAGGGCTCTGATGTGTCTCTCACAGCTTGTAAAGTGTGA |
| 248 | A*02:01:01:01 | HLA-A | ATGGCCGTCATGGCGCCCCGAACCCTCGTCCTGCTACTCTCGGGGGCTCTGGCCCTGACCCA<br>GACCTGGGCGGGCTCTCACTCCATGAGGTATTTCTTCACATCCGTGTCCCGGCCCGGCCGCG<br>GGGAGCCCCGCTTCATCGCAGTGGGCTACGTGGACGACACGCAGTTCGTGCGGTTCGACAG<br>CGACGCCGCGAGCCAGAGGATGGAGCCGCGGGCGCCGTGGATAGAGCAGGAGGGTCCGG<br>AGTATTGGGACGGGGAGACACGGAAAGTGAAGGCCCACTCACAGACTCACCGAGTGGACCT<br>GGGGACCCTGCGCGGCTACTACAACCAGAGCGAGGCCGGTTCTCACACCGTCCAGAGGATG<br>TATGGCTGCGACGTGGGGTCGGACTGGCGCTTCCTCCGCGGGTACCACCAGTACGCCTACGA<br>CGGCAAGGATTACATCGCCCTGAAAGAGGACCTGCGCTCTTGGACCGCGGCGGACATGGCA<br>GCTCAGACCACCAAGCACAAGTGGGAGGCGGCCCATGTGGCGGAGCAGTTGAGAGCCTACC<br>TGGAGGGCACGTGCGTGGAGTGGCTCCGCAGATACCTGGAGAACGGGAAGGAGACGCTGC<br>AGCGCACGGACGCCCCCAAAACGCATATGACTCACCACGCTGTCTCTGACCATGAAGCCACC<br>CTGAGGTGCTGGGCCCTGAGCTTCTACCCTGCGGAGATCACACTGACCTGGCAGCGGGATG<br>GGGAGGACCAGACCCAGGACACGGAGCTCGTGGAGACCAGGCCTGCAGGGGATGGAACCT<br>TCCAGAAGTGGGCGGCTGTGGTGGTGCCTTCTGGACAGGAGCAGAGATACACCTGCCATGT<br>GCAGCATGAGGGTTTGCCCAAGCCCCTCACCCTGAGATGGGAGCCGTCTTCCCAGCCCACCA<br>TCCCCATCGTGGGCATCATTGCTGGCCTGGTTCTCTTTGGAGCTGTGATCACTGGAGCTGTGG<br>TCGCTGCTGTGATGTGGAGGAGGAAGAGCTCAGATAGAAAAGGAGGGAGCTACTCTCAGG<br>CTGCAAGCAGTGACAGTGCCCAGGGCTCTGATGTGTCTCTCACAGCTTGTAAAGTGTGA |

| A | B | DRB1 | EUR_freq | EUR_rank | AFA_freq | AFA_rank | API_freq | API_rank | HIS_freq | HIS_rank |
|---|---|---|---|---|---|---|---|---|---|---|
| 0201g | 4403 | 0301 | 0.00029 | 542 | 0.00000 | NA | 0.00000 | NA | 0.00000 | NA |
| 2902 | 4403 | 0301 | 0.00007 | 1405 | 0.00000 | NA | 0.00000 | NA | 0.00078 | 232 |

| Allele | EUR_freq | EUR_rank | AFA_freq | AFA_rank | API_freq | API_rank | HIS_freq | HIS_rank |
|---|---|---|---|---|---|---|---|---|
| A*0201g | 0.29604 | 1 | 0.12458 | 1 | 0.09458 | 3 | 0.19403 | 1 |
| A*2902 | 0.03279 | 6 | 0.03640 | 12 | 0.00141 | 30 | 0.04167 | 8 |
| B*4403 | 0.04963 | 7 | 0.05373 | 6 | 0.04244 | 6 | 0.06078 | 2 |
| DRB1*0301 | 0.12916 | 3 | 0.07069 | 4 | 0.05373 | 7 | 0.07329 | 2 |

| HLA restriction | Minor H antigen |
|---|---|
| HLA-A*01 | HA-3 |
| HLA-A*02 | HA-1/A2 |
| HLA-A*02 | HA-2 |
| HLA-A*02 | HA-8 |
| HLA-A*02 | HER2 |
| HLA-A*02 | LB-ADIR-1 |
| HLA-A*02 | LB-NISCH-A1 |
| HLA-A*02 | LB-PRCP-1Db |
| HLA-A*02 | LB-SSR1-1S |
| HLA-A*02 | LB-WNK1-1I |
| HLA-A*02 | T4A |
| HLA-A*02 | TRIM22c |
| HLA-A*02 | UGT2B17d |
| HLA-A*02 | UTA2-1 |
| HLA-A*23 | NA |
| HLA-A*29 | P2RX7 |
| HLA-A*29 | UGT2B17d |

FIG. 32

SEQUENCE LISTING

<160> NUMBER OF SEQ ID NOS: 366

<210> SEQ ID NO 1
<211> LENGTH: 1345
<212> TYPE: PRT
<213> ORGANISM: Streptococcus mutans
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 1

Met Lys Lys Pro Tyr Ser Ile Gly Leu Asp Ile Gly Thr Asn Ser Val
1 5 10 15

Gly Trp Ala Val Val Thr Asp Asp Tyr Lys Val Pro Ala Lys Lys Met
20 25 30

Lys Val Leu Gly Asn Thr Asp Lys Ser His Ile Glu Lys Asn Leu Leu
35 40 45

Gly Ala Leu Leu Phe Asp Ser Gly Asn Thr Ala Glu Asp Arg Arg Leu
50 55 60

Lys Arg Thr Ala Arg Arg Arg Tyr Thr Arg Arg Arg Asn Arg Ile Leu
65 70 75 80

Tyr Leu Gln Glu Ile Phe Ser Glu Glu Met Gly Lys Val Asp Asp Ser
85 90 95

Phe Phe His Arg Leu Glu Asp Ser Phe Leu Val Thr Glu Asp Lys Arg
100 105 110

-continued

```
Gly Glu Arg His Pro Ile Phe Gly Asn Leu Glu Glu Glu Val Lys Tyr
        115                 120                 125

His Glu Asn Phe Pro Thr Ile Tyr His Leu Arg Gln Tyr Leu Ala Asp
    130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
        275                 280                 285

Leu Phe Leu Ser Ala Lys Lys Leu Tyr Asp Ser Ile Leu Leu Ser Gly
    290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350

Asp Val Ser Lys Asp Gly Tyr Ala Gly Tyr Ile Asp Gly Lys Thr Asn
        355                 360                 365

Gln Glu Ala Phe Tyr Lys Tyr Leu Lys Gly Leu Leu Asn Lys Ile Glu
    370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
        435                 440                 445

Pro Tyr Tyr Val Gly Pro Leu Ala Arg Gly Lys Ser Asp Phe Ala Trp
    450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
        515                 520                 525
```

```
Tyr Lys Thr Glu Gln Gly Lys Thr Ala Phe Phe Asp Ala Asn Met Lys
    530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
        595                 600                 605

Asp Asn Ser Lys Asn Glu Lys Ile Leu Glu Asp Ile Val Leu Thr Leu
    610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
        675                 680                 685

Asn Ser Asn Arg Asn Phe Met Gln Leu Ile Asn Asp Asp Ala Leu Ser
    690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
        755                 760                 765

Phe Thr Asn Gln Gly Arg Arg Asn Ser Gln Gln Arg Leu Lys Gly Leu
    770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
        835                 840                 845

Asp Asn Ser Ile Asp Asn Arg Val Leu Thr Ser Ser Lys Glu Asn Arg
    850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
        915                 920                 925

Lys His Val Ala Arg Ile Leu Asp Glu Arg Phe Asn Thr Glu Thr Asp
    930                 935                 940

Glu Asn Asn Lys Lys Ile Arg Gln Val Lys Ile Val Thr Leu Lys Ser
```

-continued 945 950 955 960

Asn Leu Val Ser Asn Phe Arg Lys Glu Phe Glu Leu Tyr Lys Val Arg
965 970 975

Glu Ile Asn Asp Tyr His His Ala His Asp Ala Tyr Leu Asn Ala Val
980 985 990

Ile Gly Lys Ala Leu Leu Gly Val Tyr Pro Gln Leu Glu Pro Glu Phe
995 1000 1005

Val Tyr Gly Asp Tyr Pro His Phe His Gly His Lys Glu Asn Lys
1010 1015 1020

Ala Thr Ala Lys Lys Phe Phe Tyr Ser Asn Ile Met Asn Phe Phe
1025 1030 1035

Lys Lys Asp Asp Val Arg Thr Asp Lys Asn Gly Glu Ile Ile Trp
1040 1045 1050

Lys Lys Asp Glu His Ile Ser Asn Ile Lys Lys Val Leu Ser Tyr
1055 1060 1065

Pro Gln Val Asn Ile Val Lys Lys Val Glu Glu Gln Thr Gly Gly
1070 1075 1080

Phe Ser Lys Glu Ser Ile Leu Pro Lys Gly Asn Ser Asp Lys Leu
1085 1090 1095

Ile Pro Arg Lys Thr Lys Lys Phe Tyr Trp Asp Thr Lys Lys Tyr
1100 1105 1110

Gly Gly Phe Asp Ser Pro Ile Val Ala Tyr Ser Ile Leu Val Ile
1115 1120 1125

Ala Asp Ile Glu Lys Gly Lys Ser Lys Lys Leu Lys Thr Val Lys
1130 1135 1140

Ala Leu Val Gly Val Thr Ile Met Glu Lys Met Thr Phe Glu Arg
1145 1150 1155

Asp Pro Val Ala Phe Leu Glu Arg Lys Gly Tyr Arg Asn Val Gln
1160 1165 1170

Glu Glu Asn Ile Ile Lys Leu Pro Lys Tyr Ser Leu Phe Lys Leu
1175 1180 1185

Glu Asn Gly Arg Lys Arg Leu Leu Ala Ser Ala Arg Glu Leu Gln
1190 1195 1200

Lys Gly Asn Glu Ile Val Leu Pro Asn His Leu Gly Thr Leu Leu
1205 1210 1215

Tyr His Ala Lys Asn Ile His Lys Val Asp Glu Pro Lys His Leu
1220 1225 1230

Asp Tyr Val Asp Lys His Lys Asp Glu Phe Lys Glu Leu Leu Asp
1235 1240 1245

Val Val Ser Asn Phe Ser Lys Lys Tyr Thr Leu Ala Glu Gly Asn
1250 1255 1260

Leu Glu Lys Ile Lys Glu Leu Tyr Ala Gln Asn Asn Gly Glu Asp
1265 1270 1275

Leu Lys Glu Leu Ala Ser Ser Phe Ile Asn Leu Leu Thr Phe Thr
1280 1285 1290

Ala Ile Gly Ala Pro Ala Thr Phe Lys Phe Phe Asp Lys Asn Ile
1295 1300 1305

Asp Arg Lys Arg Tyr Thr Ser Thr Thr Glu Ile Leu Asn Ala Thr
1310 1315 1320

Leu Ile His Gln Ser Ile Thr Gly Leu Tyr Glu Thr Arg Ile Asp
1325 1330 1335

Leu Asn Lys Leu Gly Gly Asp
1340 1345

<210> SEQ ID NO 2
<211> LENGTH: 1368
<212> TYPE: PRT
<213> ORGANISM: Streptococcus pyogenes
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
```

-continued

```
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125
```

```
Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 3
<211> LENGTH: 4107
<212> TYPE: DNA
<213> ORGANISM: Streptococcus pyogenes

<400> SEQUENCE: 3

```
atggataaaa agtacagcat cgggctggac atcggtacaa actcagtggg gtgggccgtg     60

attacggacg agtacaaggt accctccaaa aaatttaaag tgctgggtaa cacggacaga    120

cactctataa agaaaaatct tattggagcc ttgctgttcg actcaggcga gacagccgaa    180

gccacaaggt tgaagcggac cgccaggagg cggtatacca ggagaaagaa ccgcatatgc    240

tacctgcaag aaatcttcag taacgagatg gcaaaggttg acgatagctt tttccatcgc    300

ctggaagaat cctttcttgt tgaggaagac aagaagcacg aacggcaccc catctttggc    360

aatattgtcg acgaagtggc atatcacgaa aagtacccga ctatctacca cctcaggaag    420

aagctggtgg actctaccga taaggcggac ctcagactta tttatttggc actcgcccac    480

atgattaaat ttagaggaca tttcttgatc gagggcgacc tgaacccgga caacagtgac    540

gtcgataagc tgttcatcca acttgtgcag acctacaatc aactgttcga agaaaaccct    600

ataaatgctt caggagtcga cgctaaagca atcctgtccg cgcgcctctc aaaatctaga    660
```

agacttgaga atctgattgc tcagttgccc ggggaaaaga aaaatggatt gtttggcaac 720
ctgatcgccc tcagtctcgg actgacccca aatttcaaaa gtaacttcga cctggccgaa 780
gacgctaagc tccagctgtc caaggacaca tacgatgacg acctcgacaa tctgctggcc 840
cagattgggg atcagtacgc cgatctcttt ttggcagcaa agaacctgtc cgacgccatc 900
ctgttgagcg atatcttgag agtgaacacc gaaattacta aagcacccct tagcgcatct 960
atgatcaagc ggtacgacga gcatcatcag gatctgaccc tgctgaaggc tcttgtgagg 1020
caacagctcc ccgaaaaata caaggaaatc ttctttgacc agagcaaaaa cggctacgct 1080
ggctatatag atggtggggc cagtcaggag gaattctata aattcatcaa gcccattctc 1140
gagaaaatgg acggcacaga ggagttgctg gtcaaactta acagggagga cctgctgcgg 1200
aagcagcgga cctttgacaa cggtctatc ccccaccaga ttcatctggg cgaactgcac 1260
gcaatcctga ggaggcagga ggatttttat ccttttctta aagataaccg cgagaaaata 1320
gaaaagattc ttacattcag gatcccgtac tacgtgggac ctctcgcccg gggcaattca 1380
cggtttgcct ggatgacaag gaagtcagag gagactatta caccttggaa cttcgaagaa 1440
gtggtggaca agggtgcatc tgcccagtct ttcatcgagc ggatgacaaa ttttgacaag 1500
aacctcccta atgagaaggt gctgcccaaa cattctctgc tctacgagta ctttaccgtc 1560
tacaatgaac tgactaaagt caagtacgtc accgagggaa tgaggaagcc ggcattcctt 1620
agtggagaac agaagaaggc gattgtagac ctgttgttca agaccaacag gaaggtgact 1680
gtgaagcaac ttaaagaaga ctactttaag aagatcgaat gttttgacag tgtggaaatt 1740
tcaggggttg aagaccgctt caatgcgtca ttggggactt accatgatct tctcaagatc 1800
ataaaggaca aagacttcct ggacaacgaa gaaaatgagg atattctcga agacatcgtc 1860
ctcaccctga ccctgttcga agacagggaa atgatagaag agcgcttgaa aacctatgcc 1920
cacctcttcg acgataaagt tatgaagcag ctgaagcgca ggagatacac aggatgggga 1980
agattgtcaa ggaagctgat caatggaatt agggataaac agagtggcaa gaccatactg 2040
gatttcctca aatctgatgg cttcgccaat aggaacttca tgcaactgat tcacgatgac 2100
tctcttacct tcaaggagga cattcaaaag gctcaggtga gcgggcaggg agactccctt 2160
catgaacaca tcgcgaattt ggcaggttcc cccgctatta aaaagggcat ccttcaaact 2220
gtcaaggtgg tggatgaatt ggtcaaggta atgggcagac ataagccaga aaatattgtg 2280
atcgagatgg cccgcgaaaa ccagaccaca cagaagggcc agaaaaatag tagagagcgg 2340
atgaagagga tcgaggaggg catcaaagag ctgggatctc agattctcaa agaacacccc 2400
gtagaaaaca cacagctgca gaacgaaaaa ttgtacttgt actatctgca gaacggcaga 2460
gacatgtacg tcgaccaaga acttgatatt aatagactgt ccgactatga cgtagaccat 2520
atcgtgcccc agtccttcct gaaggacgac tccattgata acaaagtctt gacaagaagc 2580
gacaagaaca ggggtaaaag tgataatgtg cctagcgagg aggtggtgaa aaaaatgaag 2640
aactactggc gacagctgct taatgcaaag ctcattacac aacggaagtt cgataatctg 2700
acgaaagcag agagaggtgg cttgtctgag ttggacaagg cagggtttat taagcggcag 2760
ctggtggaaa ctaggcagat cacaaagcac gtggcgcaga ttttggacag ccggatgaac 2820
acaaaatacg acgaaaatga taaactgata cgagaggtca aagttatcac gctgaaaagc 2880
aagctggtgt ccgattttcg gaaagacttc cagttctaca aagttcgcga gattaataac 2940
taccatcatg ctcacgatgc gtacctgaac gctgttgtcg ggaccgcctt gataaagaag 3000
tacccaaagc tggaatccga gttcgtatac ggggattaca aagtgtacga tgtgaggaaa 3060

```
atgatagcca agtccgagca ggagattgga aaggccacag ctaagtactt cttttattct   3120

aacatcatga attttttaa gacggaaatt accctggcca acggagagat cagaaagcgg   3180

cccttatag agacaaatgg tgaaacaggt gaaatcgtct gggataaggg cagggatttc   3240

gctactgtga ggaaggtgct gagtatgcca caggtaaata tcgtgaaaaa aaccgaagta   3300

cagaccggag gattttccaa ggaaagcatt ttgcctaaaa gaaactcaga caagctcatc   3360

gcccgcaaga aagattggga ccctaagaaa tacgggggat ttgactcacc caccgtagcc   3420

tattctgtgc tggtggtagc taaggtggaa aaaggaaagt ctaagaagct gaagtccgtg   3480

aaggaactct tgggaatcac tatcatggaa agatcatcct ttgaaaagaa ccctatcgat   3540

ttcctggagg ctaagggtta caaggaggtc aagaaagacc tcatcattaa actgccaaaa   3600

tactctctct tcgagctgga aaatggcagg aagagaatgt tggccagcgc cggagagctg   3660

caaaagggaa acgagcttgc tctgccctcc aaatatgtta attttctcta tctcgcttcc   3720

cactatgaaa agctgaaagg gtctcccgaa gataacgagc agaagcagct gttcgtcgaa   3780

cagcacaagc actatctgga tgaaataatc gaacaaataa gcgagttcag caaaagggtt   3840

atcctggcgg atgctaattt ggacaaagta ctgtctgctt ataacaagca ccgggataag   3900

cctattaggg aacaagccga gaatataatt cacctcttta cactcacgaa tctcggagcc   3960

cccgccgcct tcaaatactt tgatacgact atcgaccgga aacggtatac cagtaccaaa   4020

gaggtcctcg atgccaccct catccaccag tcaattactg gcctgtacga aacacggatc   4080

gacctctctc aactgggcgg cgactag                                       4107
```

<210> SEQ ID NO 4
<211> LENGTH: 1388
<212> TYPE: PRT
<213> ORGANISM: Streptococcus thermophilus
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (760)..(767)
<223> OTHER INFORMATION: RuvC-like domain
<220> FEATURE:
<221> NAME/KEY: misc_feature
<222> LOCATION: (844)..(870)
<223> OTHER INFORMATION: HNH-like domain
<220> FEATURE:
<221> NAME/KEY: misc_feature
<222> LOCATION: (989)..(996)
<223> OTHER INFORMATION: RuvC-like domain

<400> SEQUENCE: 4

```
Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95
```

-continued

```
Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
```

-continued 515 520 525

Phe Ile Ala Glu Ser Met Arg Asp Tyr Gln Phe Leu Asp Ser Lys Gln
530 535 540

Lys Lys Asp Ile Val Arg Leu Tyr Phe Lys Asp Lys Arg Lys Val Thr
545 550 555 560

Asp Lys Asp Ile Ile Glu Tyr Leu His Ala Ile Tyr Gly Tyr Asp Gly
565 570 575

Ile Glu Leu Lys Gly Ile Glu Lys Gln Phe Asn Ser Ser Leu Ser Thr
580 585 590

Tyr His Asp Leu Leu Asn Ile Ile Asn Asp Lys Glu Phe Leu Asp Asp
595 600 605

Ser Ser Asn Glu Ala Ile Ile Glu Glu Ile Ile His Thr Leu Thr Ile
610 615 620

Phe Glu Asp Arg Glu Met Ile Lys Gln Arg Leu Ser Lys Phe Glu Asn
625 630 635 640

Ile Phe Asp Lys Ser Val Leu Lys Lys Leu Ser Arg Arg His Tyr Thr
645 650 655

Gly Trp Gly Lys Leu Ser Ala Lys Leu Ile Asn Gly Ile Arg Asp Glu
660 665 670

Lys Ser Gly Asn Thr Ile Leu Asp Tyr Leu Ile Asp Asp Gly Ile Ser
675 680 685

Asn Arg Asn Phe Met Gln Leu Ile His Asp Asp Ala Leu Ser Phe Lys
690 695 700

Lys Lys Ile Gln Lys Ala Gln Ile Ile Gly Asp Glu Asp Lys Gly Asn
705 710 715 720

Ile Lys Glu Val Val Lys Ser Leu Pro Gly Ser Pro Ala Ile Lys Lys
725 730 735

Gly Ile Leu Gln Ser Ile Lys Ile Val Asp Glu Leu Val Lys Val Met
740 745 750

Gly Gly Arg Lys Pro Glu Ser Ile Val Val Glu Met Ala Arg Glu Asn
755 760 765

Gln Tyr Thr Asn Gln Gly Lys Ser Asn Ser Gln Gln Arg Leu Lys Arg
770 775 780

Leu Glu Lys Ser Leu Lys Glu Leu Gly Ser Lys Ile Leu Lys Glu Asn
785 790 795 800

Ile Pro Ala Lys Leu Ser Lys Ile Asp Asn Asn Ala Leu Gln Asn Asp
805 810 815

Arg Leu Tyr Leu Tyr Tyr Leu Gln Asn Gly Lys Asp Met Tyr Thr Gly
820 825 830

Asp Asp Leu Asp Ile Asp Arg Leu Ser Asn Tyr Asp Ile Asp His Ile
835 840 845

Ile Pro Gln Ala Phe Leu Lys Asp Asn Ser Ile Asp Asn Lys Val Leu
850 855 860

Val Ser Ser Ala Ser Asn Arg Gly Lys Ser Asp Asp Val Pro Ser Leu
865 870 875 880

Glu Val Val Lys Lys Arg Lys Thr Phe Trp Tyr Gln Leu Leu Lys Ser
885 890 895

Lys Leu Ile Ser Gln Arg Lys Phe Asp Asn Leu Thr Lys Ala Glu Arg
900 905 910

Gly Gly Leu Ser Pro Glu Asp Lys Ala Gly Phe Ile Gln Arg Gln Leu
915 920 925

Val Glu Thr Arg Gln Ile Thr Lys His Val Ala Arg Leu Leu Asp Glu
930 935 940

Lys Phe Asn Asn Lys Lys Asp Glu Asn Asn Arg Ala Val Arg Thr Val
945 950 955 960

Lys Ile Ile Thr Leu Lys Ser Thr Leu Val Ser Gln Phe Arg Lys Asp
965 970 975

Phe Glu Leu Tyr Lys Val Arg Glu Ile Asn Asp Phe His His Ala His
980 985 990

Asp Ala Tyr Leu Asn Ala Val Val Ala Ser Ala Leu Leu Lys Lys Tyr
995 1000 1005

Pro Lys Leu Glu Pro Glu Phe Val Tyr Gly Asp Tyr Pro Lys Tyr
1010 1015 1020

Asn Ser Phe Arg Glu Arg Lys Ser Ala Thr Glu Lys Val Tyr Phe
1025 1030 1035

Tyr Ser Asn Ile Met Asn Ile Phe Lys Lys Ser Ile Ser Leu Ala
1040 1045 1050

Asp Gly Arg Val Ile Glu Arg Pro Leu Ile Glu Val Asn Glu Glu
1055 1060 1065

Thr Gly Glu Ser Val Trp Asn Lys Glu Ser Asp Leu Ala Thr Val
1070 1075 1080

Arg Arg Val Leu Ser Tyr Pro Gln Val Asn Val Val Lys Lys Val
1085 1090 1095

Glu Glu Gln Asn His Gly Leu Asp Arg Gly Lys Pro Lys Gly Leu
1100 1105 1110

Phe Asn Ala Asn Leu Ser Ser Lys Pro Lys Pro Asn Ser Asn Glu
1115 1120 1125

Asn Leu Val Gly Ala Lys Glu Tyr Leu Asp Pro Lys Lys Tyr Gly
1130 1135 1140

Gly Tyr Ala Gly Ile Ser Asn Ser Phe Thr Val Leu Val Lys Gly
1145 1150 1155

Thr Ile Glu Lys Gly Ala Lys Lys Lys Ile Thr Asn Val Leu Glu
1160 1165 1170

Phe Gln Gly Ile Ser Ile Leu Asp Arg Ile Asn Tyr Arg Lys Asp
1175 1180 1185

Lys Leu Asn Phe Leu Leu Glu Lys Gly Tyr Lys Asp Ile Glu Leu
1190 1195 1200

Ile Ile Glu Leu Pro Lys Tyr Ser Leu Phe Glu Leu Ser Asp Gly
1205 1210 1215

Ser Arg Arg Met Leu Ala Ser Ile Leu Ser Thr Asn Asn Lys Arg
1220 1225 1230

Gly Glu Ile His Lys Gly Asn Gln Ile Phe Leu Ser Gln Lys Phe
1235 1240 1245

Val Lys Leu Leu Tyr His Ala Lys Arg Ile Ser Asn Thr Ile Asn
1250 1255 1260

Glu Asn His Arg Lys Tyr Val Glu Asn His Lys Lys Glu Phe Glu
1265 1270 1275

Glu Leu Phe Tyr Tyr Ile Leu Glu Phe Asn Glu Asn Tyr Val Gly
1280 1285 1290

Ala Lys Lys Asn Gly Lys Leu Leu Asn Ser Ala Phe Gln Ser Trp
1295 1300 1305

Gln Asn His Ser Ile Asp Glu Leu Cys Ser Ser Phe Ile Gly Pro
1310 1315 1320

Thr Gly Ser Glu Arg Lys Gly Leu Phe Glu Leu Thr Ser Arg Gly
1325 1330 1335

```
Ser Ala  Ala Asp Phe Glu Phe  Leu Gly Val Lys Ile  Pro Arg Tyr
    1340                 1345                 1350

Arg Asp  Tyr Thr Pro Ser Ser  Leu Leu Lys Asp Ala  Thr Leu Ile
    1355                 1360                 1365

His Gln  Ser Val Thr Gly Leu  Tyr Glu Thr Arg Ile  Asp Leu Ala
    1370                 1375                 1380

Lys Leu  Gly Glu Gly
    1385


<210> SEQ ID NO 5
<211> LENGTH: 1334
<212> TYPE: PRT
<213> ORGANISM: Listeria innocua
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (762)..(769)
<223> OTHER INFORMATION: RuvC-like domain
<220> FEATURE:
<221> NAME/KEY: misc_feature
<222> LOCATION: (840)..(866)
<223> OTHER INFORMATION: HNH-like domain
<220> FEATURE:
<221> NAME/KEY: misc_feature
<222> LOCATION: (985)..(992)
<223> OTHER INFORMATION: RuvC-like domain

<400> SEQUENCE: 5

Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Lys Gln Ile Lys Lys Asn Phe Trp
        35                  40                  45

Gly Val Arg Leu Phe Asp Glu Gly Gln Thr Ala Ala Asp Arg Arg Met
    50                  55                  60

Ala Arg Thr Ala Arg Arg Arg Ile Glu Arg Arg Arg Asn Arg Ile Ser
65                  70                  75                  80

Tyr Leu Gln Gly Ile Phe Ala Glu Glu Met Ser Lys Thr Asp Ala Asn
                85                  90                  95

Phe Phe Cys Arg Leu Ser Asp Ser Phe Tyr Val Asp Asn Glu Lys Arg
            100                 105                 110

Asn Ser Arg His Pro Phe Phe Ala Thr Ile Glu Glu Glu Val Glu Tyr
        115                 120                 125

His Lys Asn Tyr Pro Thr Ile Tyr His Leu Arg Glu Glu Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
            180                 185                 190

Asn Gln Val Phe Ala Ser Gly Ile Glu Asp Gly Ser Leu Lys Lys Leu
        195                 200                 205

Glu Asp Asn Lys Asp Val Ala Lys Ile Leu Val Glu Lys Val Thr Arg
    210                 215                 220

Lys Glu Lys Leu Glu Arg Ile Leu Lys Leu Tyr Pro Gly Glu Lys Ser
```

```
225                 230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
            260                 265                 270

Ala Lys Asp Ser Tyr Glu Glu Asp Leu Glu Ser Leu Leu Ala Leu Ile
        275                 280                 285

Gly Asp Glu Tyr Ala Glu Leu Phe Val Ala Ala Lys Asn Ala Tyr Ser
    290                 295                 300

Ala Val Val Leu Ser Ser Ile Ile Thr Val Ala Glu Thr Glu Thr Asn
305                 310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
            340                 345                 350

Tyr Glu Glu Ile Phe Ser Asn Thr Glu Lys His Gly Tyr Ala Gly Tyr
        355                 360                 365

Ile Asp Gly Lys Thr Lys Gln Ala Asp Phe Tyr Lys Tyr Met Lys Met
    370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile
                405                 410                 415

Pro His Gln Leu His Leu Glu Glu Leu Glu Ala Ile Leu His Gln Gln
            420                 425                 430

Ala Lys Tyr Tyr Pro Phe Leu Lys Glu Asn Tyr Asp Lys Ile Lys Ser
        435                 440                 445

Leu Val Thr Phe Arg Ile Pro Tyr Phe Val Gly Pro Leu Ala Asn Gly
    450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
            500                 505                 510

Val Leu Pro Lys His Ser Leu Cys Tyr Gln Lys Tyr Leu Val Tyr Asn
        515                 520                 525

Glu Leu Thr Lys Val Arg Tyr Ile Asn Asp Gln Gly Lys Thr Ser Tyr
    530                 535                 540

Phe Ser Gly Gln Glu Lys Glu Gln Ile Phe Asn Asp Leu Phe Lys Gln
545                 550                 555                 560

Lys Arg Lys Val Lys Lys Lys Asp Leu Glu Leu Phe Leu Arg Asn Met
                565                 570                 575

Ser His Val Glu Ser Pro Thr Ile Glu Gly Leu Glu Asp Ser Phe Asn
            580                 585                 590

Ser Ser Tyr Ser Thr Tyr His Asp Leu Leu Lys Val Gly Ile Lys Gln
        595                 600                 605

Glu Ile Leu Asp Asn Pro Val Asn Thr Glu Met Leu Glu Asn Ile Val
    610                 615                 620

Lys Ile Leu Thr Val Phe Glu Asp Lys Arg Met Ile Lys Glu Gln Leu
625                 630                 635                 640

Gln Gln Phe Ser Asp Val Leu Asp Gly Val Val Leu Lys Lys Leu Glu
                645                 650                 655
```

```
Arg Arg His Tyr Thr Gly Trp Gly Arg Leu Ser Ala Lys Leu Leu Met
            660                 665                 670

Gly Ile Arg Asp Lys Gln Ser His Leu Thr Ile Leu Asp Tyr Leu Met
        675                 680                 685

Asn Asp Asp Gly Leu Asn Arg Asn Leu Met Gln Leu Ile Asn Asp Ser
    690                 695                 700

Asn Leu Ser Phe Lys Ser Ile Ile Glu Lys Glu Gln Val Thr Thr Ala
705                 710                 715                 720

Asp Lys Asp Ile Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
            740                 745                 750

Ser Val Met Gly Tyr Pro Pro Gln Thr Ile Val Val Glu Met Ala Arg
        755                 760                 765

Glu Asn Gln Thr Thr Gly Lys Gly Lys Asn Asn Ser Arg Pro Arg Tyr
    770                 775                 780

Lys Ser Leu Glu Lys Ala Ile Lys Glu Phe Gly Ser Gln Ile Leu Lys
785                 790                 795                 800

Glu His Pro Thr Asp Asn Gln Glu Leu Arg Asn Asn Arg Leu Tyr Leu
                805                 810                 815

Tyr Tyr Leu Gln Asn Gly Lys Asp Met Tyr Thr Gly Gln Asp Leu Asp
            820                 825                 830

Ile His Asn Leu Ser Asn Tyr Asp Ile Asp His Ile Val Pro Gln Ser
        835                 840                 845

Phe Ile Thr Asp Asn Ser Ile Asp Asn Leu Val Leu Thr Ser Ser Ala
    850                 855                 860

Gly Asn Arg Glu Lys Gly Asp Asp Val Pro Pro Leu Glu Ile Val Arg
865                 870                 875                 880

Lys Arg Lys Val Phe Trp Glu Lys Leu Tyr Gln Gly Asn Leu Met Ser
                885                 890                 895

Lys Arg Lys Phe Asp Tyr Leu Thr Lys Ala Glu Arg Gly Gly Leu Thr
            900                 905                 910

Glu Ala Asp Lys Ala Arg Phe Ile His Arg Gln Leu Val Glu Thr Arg
        915                 920                 925

Gln Ile Thr Lys Asn Val Ala Asn Ile Leu His Gln Arg Phe Asn Tyr
    930                 935                 940

Glu Lys Asp Asp His Gly Asn Thr Met Lys Gln Val Arg Ile Val Thr
945                 950                 955                 960

Leu Lys Ser Ala Leu Val Ser Gln Phe Arg Lys Gln Phe Gln Leu Tyr
                965                 970                 975

Lys Val Arg Asp Val Asn Asp Tyr His His Ala His Asp Ala Tyr Leu
            980                 985                 990

Asn Gly Val Val Ala Asn Thr Leu  Leu Lys Val Tyr Pro  Gln Leu Glu
        995                 1000                1005

Pro Glu  Phe Val Tyr Gly Asp  Tyr His Gln Phe Asp  Trp Phe Lys
    1010                1015                1020

Ala Asn  Lys Ala Thr Ala Lys  Lys Gln Phe Tyr Thr  Asn Ile Met
    1025                1030                1035

Leu Phe  Phe Ala Gln Lys Asp  Arg Ile Ile Asp Glu  Asn Gly Glu
    1040                1045                1050

Ile Leu  Trp Asp Lys Lys Tyr  Leu Asp Thr Val Lys  Lys Val Met
    1055                1060                1065
```

Ser Tyr Arg Gln Met Asn Ile Val Lys Lys Thr Glu Ile Gln Lys
1070 1075 1080

Gly Glu Phe Ser Lys Ala Thr Ile Lys Pro Lys Gly Asn Ser Ser
1085 1090 1095

Lys Leu Ile Pro Arg Lys Thr Asn Trp Asp Pro Met Lys Tyr Gly
1100 1105 1110

Gly Leu Asp Ser Pro Asn Met Ala Tyr Ala Val Val Ile Glu Tyr
1115 1120 1125

Ala Lys Gly Lys Asn Lys Leu Val Phe Glu Lys Lys Ile Ile Arg
1130 1135 1140

Val Thr Ile Met Glu Arg Lys Ala Phe Glu Lys Asp Glu Lys Ala
1145 1150 1155

Phe Leu Glu Glu Gln Gly Tyr Arg Gln Pro Lys Val Leu Ala Lys
1160 1165 1170

Leu Pro Lys Tyr Thr Leu Tyr Glu Cys Glu Glu Gly Arg Arg Arg
1175 1180 1185

Met Leu Ala Ser Ala Asn Glu Ala Gln Lys Gly Asn Gln Gln Val
1190 1195 1200

Leu Pro Asn His Leu Val Thr Leu Leu His His Ala Ala Asn Cys
1205 1210 1215

Glu Val Ser Asp Gly Lys Ser Leu Asp Tyr Ile Glu Ser Asn Arg
1220 1225 1230

Glu Met Phe Ala Glu Leu Leu Ala His Val Ser Glu Phe Ala Lys
1235 1240 1245

Arg Tyr Thr Leu Ala Glu Ala Asn Leu Asn Lys Ile Asn Gln Leu
1250 1255 1260

Phe Glu Gln Asn Lys Glu Gly Asp Ile Lys Ala Ile Ala Gln Ser
1265 1270 1275

Phe Val Asp Leu Met Ala Phe Asn Ala Met Gly Ala Pro Ala Ser
1280 1285 1290

Phe Lys Phe Phe Glu Thr Thr Ile Glu Arg Lys Arg Tyr Asn Asn
1295 1300 1305

Leu Lys Glu Leu Leu Asn Ser Thr Ile Ile Tyr Gln Ser Ile Thr
1310 1315 1320

Gly Leu Tyr Glu Ser Arg Lys Arg Leu Asp Asp
1325 1330

<210> SEQ ID NO 6
<211> LENGTH: 1053
<212> TYPE: PRT
<213> ORGANISM: Staphylococcus aureus

<400> SEQUENCE: 6

Met Lys Arg Asn Tyr Ile Leu Gly Leu Asp Ile Gly Ile Thr Ser Val
1 5 10 15

Gly Tyr Gly Ile Ile Asp Tyr Glu Thr Arg Asp Val Ile Asp Ala Gly
20 25 30

Val Arg Leu Phe Lys Glu Ala Asn Val Glu Asn Asn Glu Gly Arg Arg
35 40 45

Ser Lys Arg Gly Ala Arg Arg Leu Lys Arg Arg Arg Arg His Arg Ile
50 55 60

Gln Arg Val Lys Lys Leu Leu Phe Asp Tyr Asn Leu Leu Thr Asp His
65 70 75 80

Ser Glu Leu Ser Gly Ile Asn Pro Tyr Glu Ala Arg Val Lys Gly Leu
85 90 95

```
Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510
```

```
Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
```

```
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                 1005

Asn Asp  Lys Arg Pro Pro Arg  Ile Ile Lys Thr Ile  Ala Ser Lys
    1010                 1015                 1020

Thr Gln  Ser Ile Lys Lys Tyr  Ser Thr Asp Ile Leu  Gly Asn Leu
    1025                 1030                 1035

Tyr Glu  Val Lys Ser Lys Lys  His Pro Gln Ile Ile  Lys Lys Gly
    1040                 1045                 1050


<210> SEQ ID NO 7
<211> LENGTH: 3159
<212> TYPE: DNA
<213> ORGANISM: Staphylococcus aureus

<400> SEQUENCE: 7

atgaaaagga actacattct ggggctggac atcgggatta caagcgtggg gtatgggatt     60

attgactatg aaacaaggga cgtgatcgac gcaggcgtca gactgttcaa ggaggccaac    120

gtggaaaaca atgagggacg gagaagcaag aggggagcca ggcgcctgaa acgacggaga    180

aggcacagaa tccagagggt gaagaaactg ctgttcgatt acaacctgct gaccgaccat    240

tctgagctga gtggaattaa tccttatgaa gccagggtga aaggcctgag tcagaagctg    300

tcagaggaag agttttccgc agctctgctg cacctggcta agcgccgagg agtgcataac    360

gtcaatgagg tggaagagga caccggcaac gagctgtcta caaaggaaca gatctcacgc    420

aatagcaaag ctctggaaga gaagtatgtc gcagagctgc agctggaacg gctgaagaaa    480

gatggcgagg tgagagggtc aattaatagg ttcaagacaa gcgactacgt caaagaagcc    540

aagcagctgc tgaaagtgca gaaggcttac caccagctgg atcagagctt catcgatact    600

tatatcgacc tgctggagac tcggagaacc tactatgagg gaccaggaga agggagcccc    660

ttcggatgga aagacatcaa ggaatggtac gagatgctga tgggacattg cacctatttt    720

ccagaagagc tgagaagcgt caagtacgct tataacgcag atctgtacaa cgccctgaat    780

gacctgaaca acctggtcat caccagggat gaaaacgaga aactggaata ctatgagaag    840

ttccagatca tcgaaaacgt gtttaagcag aagaaaaagc ctacactgaa acagattgct    900

aaggagatcc tggtcaacga agaggacatc aagggctacc gggtgacaag cactggaaaa    960

ccagagttca ccaatctgaa agtgtatcac gatattaagg acatcacagc acggaaagaa   1020

atcattgaga acgccgaact gctggatcag attgctaaga tcctgactat ctaccagagc   1080

tccgaggaca tccaggaaga gctgactaac ctgaacagcg agctgaccca ggaagagatc   1140

gaacagatta gtaatctgaa ggggtacacc ggaacacaca acctgtccct gaaagctatc   1200

aatctgattc tggatgagct gtggcataca aacgacaatc agattgcaat ctttaaccgg   1260

ctgaagctgg tcccaaaaaa ggtggacctg agtcagcaga aagagatccc aaccacactg   1320

gtggacgatt tcattctgtc acccgtggtc aagcggagct tcatccagag catcaaagtg   1380

atcaacgcca tcatcaagaa gtacggcctg cccaatgata tcattatcga gctggctagg   1440
```

gagaagaaca gcaaggacgc acagaagatg atcaatgaga tgcagaaacg aaaccggcag 1500
accaatgaac gcattgaaga gattatccga actaccggga aagagaacgc aaagtacctg 1560
attgaaaaaa tcaagctgca cgatatgcag gagggaaagt gtctgtattc tctggaggcc 1620
atccccctgg aggacctgct gaacaatcca ttcaactacg aggtcgatca tattatcccc 1680
agaagcgtgt ccttcgacaa ttcctttaac aacaaggtgc tggtcaagca ggaagagaac 1740
tctaaaaagg gcaataggac tcctttccag tacctgtcta gttcagattc caagatctct 1800
tacgaaacct ttaaaaagca cattctgaat ctggccaaag gaaagggccg catcagcaag 1860
accaaaaagg agtacctgct ggaagagcgg gacatcaaca gattctccgt ccagaaggat 1920
tttattaacc ggaatctggt ggacacaaga tacgctactc gcggcctgat gaatctgctg 1980
cgatcctatt tccgggtgaa caatctggat gtgaaagtca agtccatcaa cggcgggttc 2040
acatcttttc tgaggcgcaa atggaagttt aaaaaggagc gcaacaaagg gtacaagcac 2100
catgccgaag atgctctgat tatcgcaaat gccgacttca tctttaagga gtggaaaaag 2160
ctggacaaag ccaagaaagt gatggagaac cagatgttcg aagagaagca ggccgaatct 2220
atgcccgaaa tcgagacaga acaggagtac aaggagattt tcatcactcc tcaccagatc 2280
aagcatatca aggatttcaa ggactacaag tactctcacc gggtggataa aaagcccaac 2340
agagagctga tcaatgacac cctgtatagt acaagaaaag acgataaggg gaataccctg 2400
attgtgaaca atctgaacgg actgtacgac aaagataatg acaagctgaa aaagctgatc 2460
aacaaaagtc ccgagaagct gctgatgtac caccatgatc ctcagacata tcagaaactg 2520
aagctgatta tggagcagta cggcgacgag aagaacccac tgtataagta ctatgaagag 2580
actgggaact acctgaccaa gtatagcaaa aaggataatg gccccgtgat caagaagatc 2640
aagtactatg ggaacaagct gaatgcccat ctggacatca cagacgatta ccctaacagt 2700
cgcaacaagg tggtcaagct gtcactgaag ccatacagat tcgatgtcta tctggacaac 2760
ggcgtgtata aatttgtgac tgtcaagaat ctggatgtca tcaaaaagga gaactactat 2820
gaagtgaata gcaagtgcta cgaagaggct aaaaagctga aaaagattag caaccaggca 2880
gagttcatcg cctcctttta caacaacgac ctgattaaga tcaatggcga actgtatagg 2940
gtcatcgggg tgaacaatga tctgctgaac cgcattgaag tgaatatgat tgacatcact 3000
taccgagagt atctggaaaa catgaatgat aagcgccccc ctcgaattat caaaacaatt 3060
gcctctaaga ctcagagtat caaaaagtac tcaaccgaca ttctgggaaa cctgtatgag 3120
gtgaagagca aaaagcaccc tcagattatc aaaaagggc 3159

<210> SEQ ID NO 8
<211> LENGTH: 3159
<212> TYPE: DNA
<213> ORGANISM: Staphylococcus aureus

<400> SEQUENCE: 8
atgaagcgga actacatcct gggcctggac atcggcatca ccagcgtggg ctacggcatc 60
atcgactacg agacacggga cgtgatcgat gccggcgtgc ggctgttcaa agaggccaac 120
gtggaaaaca acgagggcag gcggagcaag agaggcgcca gaaggctgaa gcggcggagg 180
cggcatagaa tccagagagt gaagaagctg ctgttcgact acaacctgct gaccgaccac 240
agcgagctga gcggcatcaa cccctacgag gccagagtga agggcctgag ccagaagctg 300
agcgaggaag agttctctgc cgccctgctg cacctggcca agagaagagg cgtgcacaac 360
gtgaacgagg tggaagagga caccggcaac gagctgtcca ccaaagagca gatcagccgg 420
aacagcaagg ccctggaaga gaaatacgtg gccgaactgc agctggaacg gctgaagaaa 480
gacggcgaag tgcggggcag catcaacaga ttcaagacca gcgactacgt gaaagaagcc 540
aaacagctgc tgaaggtgca gaaggcctac caccagctgg accagagctt catcgacacc 600
tacatcgacc tgctggaaac ccggcggacc tactatgagg gacctggcga gggcagcccc 660
ttcggctgga aggacatcaa agaatggtac gagatgctga tgggccactg cacctacttc 720
cccgaggaac tgcggagcgt gaagtacgcc tacaacgccg acctgtacaa cgccctgaac 780
gacctgaaca atctcgtgat caccagggac gagaacgaga agctggaata ttacgagaag 840
ttccagatca tcgagaacgt gttcaagcag aagaagaagc ccaccctgaa gcagatcgcc 900
aaagaaatcc tcgtgaacga agaggatatt aagggctaca gagtgaccag caccggcaag 960
cccgagttca ccaacctgaa ggtgtaccac gacatcaagg acattaccgc ccggaaagag 1020
attattgaga acgccgagct gctggatcag attgccaaga tcctgaccat ctaccagagc 1080
agcgaggaca tccaggaaga actgaccaat ctgaactccg agctgaccca ggaagagatc 1140
gagcagatct ctaatctgaa gggctatacc ggcacccaca acctgagcct gaaggccatc 1200
aacctgatcc tggacgagct gtggcacacc aacgacaacc agatcgctat cttcaaccgg 1260
ctgaagctgg tgcccaagaa ggtggacctg tcccagcaga aagagatccc caccaccctg 1320
gtggacgact tcatcctgag ccccgtcgtg aagagaagct tcatccagag catcaaagtg 1380
atcaacgcca tcatcaagaa gtacggcctg cccaacgaca tcattatcga gctggcccgc 1440
gagaagaact ccaaggacgc ccagaaaatg atcaacgaga tgcagaagcg gaaccggcag 1500
accaacgagc ggatcgagga aatcatccgg accaccggca aagagaacgc caagtacctg 1560
atcgagaaga tcaagctgca cgacatgcag gaaggcaagt gcctgtacag cctggaagcc 1620
atccctctgg aagatctgct gaacaacccc ttcaactatg aggtggacca catcatcccc 1680
agaagcgtgt ccttcgacaa cagcttcaac aacaaggtgc tcgtgaagca ggaagaaaac 1740
agcaagaagg gcaaccggac cccattccag tacctgagca gcagcgacag caagatcagc 1800
tacgaaacct tcaagaagca catcctgaat ctggccaagg gcaagggcag aatcagcaag 1860
accaagaaag agtatctgct ggaagaacgg gacatcaaca ggttctccgt gcagaaagac 1920
ttcatcaacc ggaacctggt ggataccaga tacgccacca gaggcctgat gaacctgctg 1980
cggagctact tcagagtgaa caacctggac gtgaaagtga agtccatcaa tggcggcttc 2040
accagctttc tgcggcggaa gtggaagttt aagaaagagc ggaacaaggg gtacaagcac 2100
cacgccgagg acgccctgat cattgccaac gccgatttca tcttcaaaga gtggaagaaa 2160
ctggacaagg ccaaaaaagt gatggaaaac cagatgttcg aggaaaagca ggccgagagc 2220
atgcccgaga tcgaaaccga gcaggagtac aaagagatct tcatcacccc ccaccagatc 2280
aagcacatta aggacttcaa ggactacaag tacagccacc gggtggacaa gaagcctaat 2340
agagagctga ttaacgacac cctgtactcc acccggaagg acgacaaggg caacaccctg 2400
atcgtgaaca atctgaacgg cctgtacgac aaggacaatg acaagctgaa aaagctgatc 2460
aacaagagcc ccgaaaagct gctgatgtac caccacgacc cccagaccta ccagaaactg 2520
aagctgatta tggaacagta cggcgacgag aagaatcccc tgtacaagta ctacgaggaa 2580
accgggaact acctgaccaa gtactccaaa aaggacaacg gccccgtgat caagaagatt 2640
aagtattacg gcaacaaact gaacgcccat ctggacatca ccgacgacta ccccaacagc 2700
agaaacaagg tcgtgaagct gtccctgaag ccctacagat tcgacgtgta cctggacaat 2760

-continued

```
ggcgtgtaca agttcgtgac cgtgaagaat ctggatgtga tcaaaaaaga aaactactac   2820

gaagtgaata gcaagtgcta tgaggaagct aagaagctga agaagatcag caaccaggcc   2880

gagtttatcg cctccttcta caacaacgat ctgatcaaga tcaacggcga gctgtataga   2940

gtgatcggcg tgaacaacga cctgctgaac cggatcgaag tgaacatgat cgacatcacc   3000

taccgcgagt acctggaaaa catgaacgac aagaggcccc ccaggatcat taagacaatc   3060

gcctccaaga cccagagcat taagaagtac agcacagaca ttctgggcaa cctgtatgaa   3120

gtgaaatcta agaagcaccc tcagatcatc aaaaagggc                          3159


<210> SEQ ID NO 9
<211> LENGTH: 3159
<212> TYPE: DNA
<213> ORGANISM: Staphylococcus aureus

<400> SEQUENCE: 9

atgaagcgca actacatcct cggactggac atcggcatta cctccgtggg atacggcatc     60

atcgattacg aaactaggga tgtgatcgac gctggagtca ggctgttcaa agaggcgaac    120

gtggagaaca acgaggggcg gcgctcaaag agggggggccc gccggctgaa gcgccgccgc    180

agacatagaa tccagcgcgt gaagaagctg ctgttcgact acaaccttct gaccgaccac    240

tccgaacttt ccggcatcaa cccatatgag gctagagtga agggattgtc ccaaaagctg    300

tccgaggaag agttctccgc cgcgttgctc cacctcgcca agcgcagggg agtgcacaat    360

gtgaacgaag tggaagaaga taccggaaac gagctgtcca ccaaggagca gatcagccgg    420

aactccaagg ccctggaaga gaaatacgtg gcggaactgc aactggagcg gctgaagaaa    480

gacggagaag tgcgcggctc gatcaaccgc ttcaagacct cggactacgt gaaggaggcc    540

aagcagctcc tgaaagtgca aaaggcctat caccaacttg accagtcctt tatcgatacc    600

tacatcgatc tgctcgagac tcggcggact tactacgagg gtccagggga gggctcccca    660

tttggttgga aggatattaa ggagtggtac gaaatgctga tgggacactg cacatacttc    720

cctgaggagc tgcggagcgt gaaatacgca tacaacgcag acctgtacaa cgcgctgaac    780

gacctgaaca atctcgtgat cacccgggac gagaacgaaa agctcgagta ttacgaaaag    840

ttccagatta ttgagaacgt gttcaaacag aagaagaagc cgacactgaa gcagattgcc    900

aaggaaatcc tcgtgaacga agaggacatc aagggctatc gagtgacctc aacgggaaag    960

ccggagttca ccaatctgaa ggtctaccac gacatcaaag acattaccgc ccggaaggag   1020

atcattgaga acgcggagct gttggaccag attgcgaaga ttctgaccat ctaccaatcc   1080

tccgaggata ttcaggaaga actcaccaac ctcaacagcg aactgaccca ggaggagata   1140

gagcaaatct ccaacctgaa gggctacacc ggaactcata acctgagcct gaaggccatc   1200

aacttgatcc tggacgagct gtggcacacc aacgataacc agatcgctat tttcaatcgg   1260

ctgaagctgg tccccaagaa agtggacctc tcacaacaaa aggagatccc tactaccctt   1320

gtggacgatt tcattctgtc ccccgtggtc aagagaagct tcatacagtc aatcaaagtg   1380

atcaatgcca ttatcaagaa atacggtctg cccaacgaca ttatcattga gctcgcccgc   1440

gagaagaact cgaaggacgc ccagaagatg attaacgaaa tgcagaagag gaaccgacag   1500

actaacgaac ggatcgaaga aatcatccgg accaccggga aggaaaacgc gaagtacctg   1560

atcgaaaaga tcaagctcca tgacatgcag gaaggaaagt gtctgtactc gctggaggcc   1620

attccgctgg aggacttgct gaacaaccct tttaactacg aagtggatca tatcattccg   1680

aggagcgtgt cattcgacaa ttccttcaac aacaaggtcc tcgtgaagca ggaggaaaac   1740
```

```
tcgaagaagg gaaaccgcac gccgttccag tacctgagca gcagcgactc caagatttcc   1800
tacgaaacct tcaagaagca catcctcaac ctggcaaagg ggaagggtcg catctccaag   1860
accaagaagg aatatctgct ggaagaaaga gacatcaaca gattctccgt gcaaaaggac   1920
ttcatcaacc gcaacctcgt ggatactaga tacgctactc ggggtctgat gaacctcctg   1980
agaagctact ttagagtgaa caatctggac gtgaaggtca agtcgattaa cggaggtttc   2040
acctccttcc tgcggcgcaa gtggaagttc aagaaggaac ggaacaaggg ctacaagcac   2100
cacgccgagg acgccctgat cattgccaac gccgacttca tcttcaaaga atggaagaaa   2160
cttgacaagg ctaagaaggt catggaaaac cagatgttcg aagaaaagca ggccgagtct   2220
atgcctgaaa tcgagactga acaggagtac aaggaaatct ttattacgcc acaccagatc   2280
aaacacatca aggatttcaa ggattacaag tactcacatc gcgtggacaa aaagccgaac   2340
agggaactga tcaacgacac cctctactcc acccggaagg atgacaaagg gaataccctc   2400
atcgtcaaca accttaacgg cctgtacgac aaggacaacg ataagctgaa gaagctcatt   2460
aacaagtcgc ccgaaaagtt gctgatgtac caccacgacc ctcagactta ccagaagctc   2520
aagctgatca tggagcagta tggggacgag aaaaacccgt tgtacaagta ctacgaagaa   2580
actgggaatt atctgactaa gtactccaag aaagataacg gccccgtgat taagaagatt   2640
aagtactacg gcaacaagct gaacgcccat ctggacatca ccgatgacta ccctaattcc   2700
cgcaacaagg tcgtcaagct gagcctcaag ccctaccggt ttgatgtgta ccttgacaat   2760
ggagtgtaca agttcgtgac tgtgaagaac cttgacgtga tcaagaagga gaactactac   2820
gaagtcaact ccaagtgcta cgaggaagca aagaagttga agaagatctc gaaccaggcc   2880
gagttcattg cctccttcta taacaacgac ctgattaaga tcaacggcga actgtaccgc   2940
gtcattggcg tgaacaacga tctcctgaac cgcatcgaag tgaacatgat cgacatcact   3000
taccgggaat acctggagaa tatgaacgac aagcgccccgc cccggatcat taagactatc   3060
gcctcaaaga cccagtcgat caagaagtac agcaccgaca tcctgggcaa cctgtacgag   3120
gtcaaatcga agaagcaccc ccagatcatc aagaaggga                          3159
```

<210> SEQ ID NO 10
<211> LENGTH: 3159
<212> TYPE: DNA
<213> ORGANISM: Staphylococcus aureus

<400> SEQUENCE: 10

```
atgaaaagga actacattct ggggctggcc atcgggatta caagcgtggg gtatgggatt     60
attgactatg aaacaaggga cgtgatcgac gcaggcgtca gactgttcaa ggaggccaac    120
gtggaaaaca atgagggacg gagaagcaag aggggagcca ggcgcctgaa acgacggaga    180
aggcacagaa tccagagggt gaagaaactg ctgttcgatt acaacctgct gaccgaccat    240
tctgagctga gtggaattaa tccttatgaa gccagggtga aaggcctgag tcagaagctg    300
tcagaggaag agttttccgc agctctgctg cacctggcta agcgccgagg agtgcataac    360
gtcaatgagg tggaagagga caccggcaac gagctgtcta caaaggaaca gatctcacgc    420
aatagcaaag ctctggaaga gaagtatgtc gcagagctgc agctggaacg gctgaagaaa    480
gatggcgagg tgagagggtc aattaatagg ttcaagacaa gcgactacgt caaagaagcc    540
aagcagctgc tgaaagtgca gaaggcttac caccagctgg atcagagctt catcgatact    600
tatatcgacc tgctggagac tcggagaacc tactatgagg gaccaggaga agggagcccc    660
```

-continued

```
ttcggatgga aagacatcaa ggaatggtac gagatgctga tgggacattg cacctatttt    720
ccagaagagc tgagaagcgt caagtacgct tataacgcag atctgtacaa cgccctgaat    780
gacctgaaca acctggtcat caccagggat gaaaacgaga aactggaata ctatgagaag    840
ttccagatca tcgaaaacgt gtttaagcag aagaaaaagc ctacactgaa acagattgct    900
aaggagatcc tggtcaacga agaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca aacgacaatc agattgcaat ctttaaccgg   1260
ctgaagctgg tcccaaaaaa ggtggacctg agtcagcaga aagagatccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga aagagaacgc aaagtacctg   1560
attgaaaaaa tcaagctgca cgatatgcag gagggaaagt gtctgtattc tctggaggcc   1620
atccccctgg aggacctgct gaacaatcca ttcaactacg aggtcgatca tattatcccc   1680
agaagcgtgt ccttcgacaa ttcctttaac aacaaggtgc tggtcaagca ggaagagaac   1740
tctaaaaagg gcaataggac tcctttccag tacctgtcta gttcagattc caagatctct   1800
tacgaaacct ttaaaaagca cattctgaat ctggccaaag gaaagggccg catcagcaag   1860
accaaaaagg agtacctgct ggaagagcgg gacatcaaca gattctccgt ccagaaggat   1920
tttattaacc ggaatctggt ggacacaaga tacgctactc gcggcctgat gaatctgctg   1980
cgatcctatt tccgggtgaa caatctggat gtgaaagtca agtccatcaa cggcgggttc   2040
acatcttttc tgaggcgcaa atggaagttt aaaaaggagc gcaacaaagg gtacaagcac   2100
catgccgaag atgctctgat tatcgcaaat gccgacttca tctttaagga gtggaaaaag   2160
ctggacaaag ccaagaaagt gatggagaac cagatgttcg aagagaagca ggccgaatct   2220
atgcccgaaa tcgagacaga acaggagtac aaggagattt tcatcactcc tcaccagatc   2280
aagcatatca aggatttcaa ggactacaag tactctcacc gggtggataa aaagcccaac   2340
agagagctga tcaatgacac cctgtatagt acaagaaaag acgataaggg gaataccctg   2400
attgtgaaca atctgaacgg actgtacgac aaagataatg acaagctgaa aaagctgatc   2460
aacaaaagtc ccgagaagct gctgatgtac caccatgatc ctcagacata tcagaaactg   2520
aagctgatta tggagcagta cggcgacgag aagaacccac tgtataagta ctatgaagag   2580
actgggaact acctgaccaa gtatagcaaa aaggataatg gccccgtgat caagaagatc   2640
aagtactatg ggaacaagct gaatgcccat ctggacatca cagacgatta ccctaacagt   2700
cgcaacaagg tggtcaagct gtcactgaag ccatacagat tcgatgtcta tctggacaac   2760
ggcgtgtata aatttgtgac tgtcaagaat ctggatgtca tcaaaaagga gaactactat   2820
gaagtgaata gcaagtgcta cgaagaggct aaaaagctga aaaagattag caaccaggca   2880
gagttcatcg cctcctttta caacaacgac ctgattaaga tcaatggcga actgtatagg   2940
gtcatcgggg tgaacaatga tctgctgaac cgcattgaag tgaatatgat tgacatcact   3000
taccgagagt atctggaaaa catgaatgat aagcgccccc ctcgaattat caaaacaatt   3060
```

gcctctaaga ctcagagtat caaaaagtac tcaaccgaca ttctgggaaa cctgtatgag 3120
gtgaagagca aaaagcaccc tcagattatc aaaaagggc 3159

<210> SEQ ID NO 11
<211> LENGTH: 3159
<212> TYPE: DNA
<213> ORGANISM: Staphylococcus aureus

<400> SEQUENCE: 11
atgaaaagga actacattct ggggctggac atcgggatta caagcgtggg gtatgggatt 60
attgactatg aaacaaggga cgtgatcgac gcaggcgtca gactgttcaa ggaggccaac 120
gtggaaaaca atgagggacg gagaagcaag aggggagcca ggcgcctgaa acgacggaga 180
aggcacagaa tccagagggt gaagaaactg ctgttcgatt acaacctgct gaccgaccat 240
tctgagctga gtggaattaa tccttatgaa gccagggtga aaggcctgag tcagaagctg 300
tcagaggaag agttttccgc agctctgctg cacctggcta agcgccgagg agtgcataac 360
gtcaatgagg tggaagagga caccggcaac gagctgtcta caaaggaaca gatctcacgc 420
aatagcaaag ctctggaaga gaagtatgtc gcagagctgc agctggaacg gctgaagaaa 480
gatggcgagg tgagagggtc aattaatagg ttcaagacaa gcgactacgt caaagaagcc 540
aagcagctgc tgaaagtgca gaaggcttac caccagctgg atcagagctt catcgatact 600
tatatcgacc tgctggagac tcggagaacc tactatgagg gaccaggaga agggagcccc 660
ttcggatgga aagacatcaa ggaatggtac gagatgctga tgggacattg cacctatttt 720
ccagaagagc tgagaagcgt caagtacgct tataacgcag atctgtacaa cgccctgaat 780
gacctgaaca acctggtcat caccagggat gaaaacgaga aactggaata ctatgagaag 840
ttccagatca tcgaaaacgt gtttaagcag aagaaaaagc ctacactgaa acagattgct 900
aaggagatcc tggtcaacga agaggacatc aagggctacc gggtgacaag cactggaaaa 960
ccagagttca ccaatctgaa agtgtatcac gatattaagg acatcacagc acggaaagaa 1020
atcattgaga acgccgaact gctggatcag attgctaaga tcctgactat ctaccagagc 1080
tccgaggaca tccaggaaga gctgactaac ctgaacagcg agctgaccca ggaagagatc 1140
gaacagatta gtaatctgaa ggggtacacc ggaacacaca acctgtccct gaaagctatc 1200
aatctgattc tggatgagct gtggcataca aacgacaatc agattgcaat ctttaaccgg 1260
ctgaagctgg tcccaaaaaa ggtggacctg agtcagcaga aagagatccc aaccacactg 1320
gtggacgatt tcattctgtc acccgtggtc aagcggagct tcatccagag catcaaagtg 1380
atcaacgcca tcatcaagaa gtacggcctg cccaatgata tcattatcga gctggctagg 1440
gagaagaaca gcaaggacgc acagaagatg atcaatgaga tgcagaaacg aaaccggcag 1500
accaatgaac gcattgaaga gattatccga actaccggga aagagaacgc aaagtacctg 1560
attgaaaaaa tcaagctgca cgatatgcag gagggaaagt gtctgtattc tctggaggcc 1620 atcccccctgg aggacctgct gaacaatcca ttcaactacg aggtcgatca tattatcccc 1680
agaagcgtgt ccttcgacaa ttcctttaac aacaaggtgc tggtcaagca ggaagaggcc 1740
tctaaaaagg gcaataggac tcctttccag tacctgtcta gttcagattc caagatctct 1800
tacgaaacct ttaaaaagca cattctgaat ctggccaaag gaaagggccg catcagcaag 1860
accaaaaagg agtacctgct ggaagagcgg gacatcaaca gattctccgt ccagaaggat 1920
tttattaacc ggaatctggt ggacacaaga tacgctactc gcggcctgat gaatctgctg 1980

-continued

```
cgatcctatt tccgggtgaa caatctggat gtgaaagtca agtccatcaa cggcgggttc   2040

acatcttttc tgaggcgcaa atggaagttt aaaaaggagc gcaacaaagg gtacaagcac   2100

catgccgaag atgctctgat tatcgcaaat gccgacttca tctttaagga gtggaaaaag   2160

ctggacaaag ccaagaaagt gatggagaac cagatgttcg aagagaagca ggccgaatct   2220

atgcccgaaa tcgagacaga acaggagtac aaggagattt tcatcactcc tcaccagatc   2280

aagcatatca aggatttcaa ggactacaag tactctcacc gggtggataa aaagcccaac   2340

agagagctga tcaatgacac cctgtatagt acaagaaaag acgataaggg gaataccctg   2400

attgtgaaca atctgaacgg actgtacgac aaagataatg acaagctgaa aaagctgatc   2460

aacaaaagtc ccgagaagct gctgatgtac caccatgatc ctcagacata tcagaaactg   2520

aagctgatta tggagcagta cggcgacgag aagaacccac tgtataagta ctatgaagag   2580

actgggaact acctgaccaa gtatagcaaa aaggataatg gccccgtgat caagaagatc   2640

aagtactatg ggaacaagct gaatgcccat ctggacatca cagacgatta ccctaacagt   2700

cgcaacaagg tggtcaagct gtcactgaag ccatacagat tcgatgtcta tctggacaac   2760

ggcgtgtata aatttgtgac tgtcaagaat ctggatgtca tcaaaaagga gaactactat   2820

gaagtgaata gcaagtgcta cgaagaggct aaaaagctga aaaagattag caaccaggca   2880

gagttcatcg cctcctttta caacaacgac ctgattaaga tcaatggcga actgtatagg   2940

gtcatcgggg tgaacaatga tctgctgaac cgcattgaag tgaatatgat tgacatcact   3000

taccgagagt atctggaaaa catgaatgat aagcgccccc ctcgaattat caaaacaatt   3060

gcctctaaga ctcagagtat caaaaagtac tcaaccgaca ttctgggaaa cctgtatgag   3120

gtgaagagca aaaagcaccc tcagattatc aaaaagggc                          3159
```

```
<210> SEQ ID NO 12
<211> LENGTH: 1082
<212> TYPE: PRT
<213> ORGANISM: Neisseria meningitidis

<400> SEQUENCE: 12

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
```

```
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590
```

```
Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Thr His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
        835                 840                 845

Ser Ala Lys Arg Leu Asp Glu Gly Val Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser  Leu His Pro Asn Asp  Leu Val Glu
        995                 1000                1005
```

-continued

```
Val Ile  Thr Lys Lys Ala Arg  Met Phe Gly Tyr Phe  Ala Ser Cys
    1010                 1015                 1020

His Arg  Gly Thr Gly Asn Ile  Asn Ile Arg Ile His  Asp Leu Asp
    1025                 1030                 1035

His Lys  Ile Gly Lys Asn Gly  Ile Leu Glu Gly Ile  Gly Val Lys
    1040                 1045                 1050

Thr Ala  Leu Ser Phe Gln Lys  Tyr Gln Ile Asp Glu  Leu Gly Lys
    1055                 1060                 1065

Glu Ile  Arg Pro Cys Arg Leu  Lys Lys Arg Pro Pro  Val Arg
    1070                 1075                 1080
```

<210> SEQ ID NO 13
<211> LENGTH: 3249
<212> TYPE: DNA
<213> ORGANISM: Neisseria meningitidis
<220> FEATURE:
<221> NAME/KEY: misc_feature
<222> LOCATION: (1)..(3249)
<223> OTHER INFORMATION: Exemplary codon optimized Cas9

<400> SEQUENCE: 13

```
atggccgcct tcaagcccaa ccccatcaac tacatcctgg gcctggacat cggcatcgcc     60

agcgtgggct gggccatggt ggagatcgac gaggacgaga accccatctg cctgatcgac    120

ctgggtgtgc gcgtgttcga gcgcgctgag gtgcccaaga ctggtgacag tctggctatg    180

gctcgccggc ttgctcgctc tgttcggcgc cttactcgcc ggcgcgctca ccgccttctg    240

cgcgctcgcc gcctgctgaa gcgcgagggt gtgctgcagg ctgccgactt cgacgagaac    300

ggcctgatca agagcctgcc caacactcct tggcagctgc gcgctgccgc tctggaccgc    360

aagctgactc ctctggagtg gagcgccgtg ctgctgcacc tgatcaagca ccgcggctac    420

ctgagccagc gcaagaacga gggcgagacc gccgacaagg agctgggtgc tctgctgaag    480

ggcgtggccg acaacgccca cgccctgcag actggtgact tccgcactcc tgctgagctg    540

gccctgaaca agttcgagaa ggagagcggc cacatccgca accagcgcgg cgactacagc    600

cacaccttca gccgcaagga cctgcaggcc gagctgatcc tgctgttcga gaagcagaag    660

gagttcggca acccccacgt gagcggcggc ctgaaggagg gcatcgagac cctgctgatg    720

acccagcgcc ccgccctgag cggcgacgcc gtgcagaaga tgctgggcca ctgcaccttc    780

gagccagccg agcccaaggc cgccaagaac acctacaccg ccgagcgctt catctggctg    840

accaagctga acaacctgcg catcctggag cagggcagcg agcgccccct gaccgacacc    900

gagcgcgcca ccctgatgga cgagccctac cgcaagagca agctgaccta cgcccaggcc    960

cgcaagctgc tgggtctgga ggacaccgcc ttcttcaagg gcctgcgcta cggcaaggac   1020

aacgccgagg ccagcaccct gatggagatg aaggcctacc acgccatcag ccgcgccctg   1080

gagaaggagg gcctgaagga caagaagagt cctctgaacc tgagccccga gctgcaggac   1140

gagatcggca ccgccttcag cctgttcaag accgacgagg acatcaccgg ccgcctgaag   1200

gaccgcatcc agcccgagat cctggaggcc ctgctgaagc acatcagctt cgacaagttc   1260

gtgcagatca gcctgaaggc cctgcgccgc atcgtgcccc tgatggagca gggcaagcgc   1320

tacgacgagg cctgcgccga gatctacggc gaccactacg gcaagaagaa caccgaggag   1380

aagatctacc tgcctcctat ccccgccgac gagatccgca accccgtggt gctgcgcgcc   1440

ctgagccagg cccgcaaggt gatcaacggc gtggtgcgcc gctacggcag ccccgcccgc   1500

atccacatcg agaccgcccg cgaggtgggc aagagcttca aggaccgcaa ggagatcgag   1560
```

aagcgccagg aggagaaccg caaggaccgc gagaaggccg ccgccaagtt ccgcgagtac 1620
ttccccaact tcgtgggcga gcccaagagc aaggacatcc tgaagctgcg cctgtacgag 1680
cagcagcacg gcaagtgcct gtacagcggc aaggagatca acctgggccg cctgaacgag 1740
aagggctacg tggagatcga ccacgccctg cccttcagcc gcacctggga cgacagcttc 1800
aacaacaagg tgctggtgct gggcagcgag aaccagaaca agggcaacca gacccccctac 1860 gagtacttca acggcaagga caacagccgc gagtggcagg agttcaaggc ccgcgtggag 1920
accagccgct tcccccgcag caagaagcag cgcatcctgc tgcagaagtt cgacgaggac 1980
ggcttcaagg agcgcaacct gaacgacacc cgctacgtga accgcttcct gtgccagttc 2040
gtggccgacc gcatgcgcct gaccggcaag ggcaagaagc gcgtgttcgc cagcaacggc 2100
cagatcacca acctgctgcg cggcttctgg ggcctgcgca aggtgcgcgc cgagaacgac 2160
cgccaccacg ccctggacgc cgtggtggtg gcctgcagca ccgtggccat gcagcagaag 2220
atcacccgct tcgtgcgcta caaggagatg aacgccttcg acggtaaaac catcgacaag 2280
gagaccggcg aggtgctgca ccagaagacc cacttccccc agccctggga gttcttcgcc 2340
caggaggtga tgatccgcgt gttcggcaag cccgacggca agcccgagtt cgaggaggcc 2400
gacacccccg agaagctgcg caccctgctg gccgagaagc tgagcagccg ccctgaggcc 2460
gtgcacgagt acgtgactcc tctgttcgtg agccgcgccc ccaaccgcaa gatgagcggt 2520
cagggtcaca tggagaccgt gaagagcgcc aagcgcctgg acgagggcgt gagcgtgctg 2580
cgcgtgcccc tgacccagct gaagctgaag gacctggaga agatggtgaa ccgcgagcgc 2640
gagcccaagc tgtacgaggc cctgaaggcc cgcctggagg cccacaagga cgaccccgcc 2700
aaggccttcg ccgagccctt ctacaagtac gacaaggccg gcaaccgcac ccagcaggtg 2760
aaggccgtgc gcgtggagca ggtgcagaag accggcgtgt gggtgcgcaa ccacaacggc 2820
atcgccgaca acgccaccat ggtgcgcgtg gacgtgttcg agaagggcga caagtactac 2880
ctggtgccca tctacagctg gcaggtggcc aagggcatcc tgcccgaccg cgccgtggtg 2940
cagggcaagg acgaggagga ctggcagctg atcgacgaca gcttcaactt caagttcagc 3000 ctgcaccccca acgacctggt ggaggtgatc accaagaagg cccgcatgtt cggctacttc 3060
gccagctgcc accgcggcac cggcaacatc aacatccgca tccacgacct ggaccacaag 3120
atcggcaaga acggcatcct ggagggcatc ggcgtgaaga ccgccctgag cttccagaag 3180
taccagatcg acgagctggg caaggagatc cgcccctgcc gcctgaagaa gcgccctcct 3240
gtgcgctaa 3249

<210> SEQ ID NO 14
<211> LENGTH: 859
<212> TYPE: PRT
<213> ORGANISM: Artificial Sequence
<220> FEATURE:
<223> OTHER INFORMATION: Synthetic Cas9 consensus sequence derived from
Sm, Sp, St, and Li Cas9 sequences
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(18)
<223> OTHER INFORMATION: N-terminal RuvC-like domain
<220> FEATURE:
<221> NAME/KEY: misc_feature
<222> LOCATION: (21)..(21)
<223> OTHER INFORMATION: Xaa can be any naturally occurring amino acid
<220> FEATURE:

<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: Each Xaa can independently be any naturally
occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Each Xaa can independently be any naturally
occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature

```
<222> LOCATION: (100)..(100)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (128)..(133)
<223> OTHER INFORMATION: Each Xaa can independently be any naturally
      occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(147)
<223> OTHER INFORMATION: Each Xaa can independently be any naturally
      occurring amino acid
<220> FEATURE:
<221> NAME/KEY: misc_feature
<222> LOCATION: (153)..(155)
<223> OTHER INFORMATION: Each Xaa can independently be any naturally
      occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(168)
<223> OTHER INFORMATION: Each Xaa can independently be any naturally
      occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (173)..(175)
<223> OTHER INFORMATION: Each Xaa can independently be any naturally
      occurring amino acid
```

<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (185)..(187)
<223> OTHER INFORMATION: Each Xaa can independently be any naturally
occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (192)..(195)
<223> OTHER INFORMATION: Each Xaa can independently be any naturally
occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:

<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (244)..(246)
<223> OTHER INFORMATION: Each Xaa can independently be any naturally
occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (252)..(254)
<223> OTHER INFORMATION: Each Xaa can independently be any naturally
occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (292)..(294)
<223> OTHER INFORMATION: Each Xaa can independently be any naturally
occurring amino acid
<220> FEATURE:

```
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (319)..(322)
<223> OTHER INFORMATION: Each Xaa can independently be any naturally
      occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (335)..(337)
<223> OTHER INFORMATION: Each Xaa can independently be any naturally
      occurring amino acid
<220> FEATURE:
<221> NAME/KEY: misc_feature
<222> LOCATION: (346)..(346)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (356)..(361)
<223> OTHER INFORMATION: Each Xaa can independently be any naturally
      occurring amino acid
<220> FEATURE:
<221> NAME/KEY: misc_feature
<222> LOCATION: (363)..(363)
<223> OTHER INFORMATION: Xaa can be any naturally occurring amino acid
<220> FEATURE:
<221> NAME/KEY: misc_feature
<222> LOCATION: (370)..(373)
<223> OTHER INFORMATION: Each Xaa can independently be any naturally
      occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (376)..(376)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (386)..(390)
<223> OTHER INFORMATION: Each Xaa can independently be any naturally
      occurring amino acid
<220> FEATURE:
<221> NAME/KEY: misc_feature
<222> LOCATION: (393)..(393)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
```

<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid
<220> FEATURE:
<221> NAME/KEY: misc_feature
<222> LOCATION: (403)..(403)
<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (413)..(416)
<223> OTHER INFORMATION: Each Xaa can independently be any naturally
occurring amino acid
<220> FEATURE:
<221> NAME/KEY: misc_feature
<222> LOCATION: (418)..(418)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (433)..(433)
<223> OTHER INFORMATION: Xaa can be any naturally occurring amino acid
<220> FEATURE:
<221> NAME/KEY: misc_feature
<222> LOCATION: (437)..(439)
<223> OTHER INFORMATION: Each Xaa can independently be any naturally
occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (465)..(469)
<223> OTHER INFORMATION: Each Xaa can independently be any naturally
occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (482)..(482)

<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (490)..(490)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (495)..(502)
<223> OTHER INFORMATION: RuvC-like domain
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (513)..(513)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (517)..(517)
<223> OTHER INFORMATION: Xaa can be any naturally occurring amino acid
<220> FEATURE:
<221> NAME/KEY: misc_feature
<222> LOCATION: (520)..(520)
<223> OTHER INFORMATION: Xaa can be any naturally occurring amino acid
<220> FEATURE:
<221> NAME/KEY: misc_feature
<222> LOCATION: (525)..(525)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (529)..(529)
<223> OTHER INFORMATION: Xaa can be any naturally occurring amino acid
<220> FEATURE:
<221> NAME/KEY: misc_feature
<222> LOCATION: (531)..(531)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (546)..(546)
<223> OTHER INFORMATION: Xaa can be any naturally occurring amino acid
<220> FEATURE:
<221> NAME/KEY: misc_feature

```
<222> LOCATION: (547)..(547)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (555)..(575)
<223> OTHER INFORMATION: HNH-like domain
<220> FEATURE:
<221> NAME/KEY: misc_feature
<222> LOCATION: (556)..(556)
<223> OTHER INFORMATION: Xaa can be any naturally occurring amino acid
<220> FEATURE:
<221> NAME/KEY: misc_feature
<222> LOCATION: (560)..(560)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (565)..(565)
<223> OTHER INFORMATION: Xaa can be any naturally occurring amino acid
<220> FEATURE:
<221> NAME/KEY: misc_feature
<222> LOCATION: (567)..(567)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (582)..(582)
<223> OTHER INFORMATION: Xaa can be any naturally occurring amino acid
<220> FEATURE:
<221> NAME/KEY: misc_feature
<222> LOCATION: (583)..(583)
<223> OTHER INFORMATION: Xaa can be any naturally occurring amino acid
<220> FEATURE:
<221> NAME/KEY: misc_feature
<222> LOCATION: (585)..(585)
<223> OTHER INFORMATION: Xaa can be any naturally occurring amino acid
<220> FEATURE:
<221> NAME/KEY: misc_feature
<222> LOCATION: (588)..(588)
<223> OTHER INFORMATION: Xaa can be any naturally occurring amino acid
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (594)..(596)
<223> OTHER INFORMATION: Each Xaa can independently be any naturally
      occurring amino acid
<220> FEATURE:
<221> NAME/KEY: misc_feature
<222> LOCATION: (610)..(610)
<223> OTHER INFORMATION: Xaa can be any naturally occurring amino acid
<220> FEATURE:
<221> NAME/KEY: misc_feature
<222> LOCATION: (616)..(616)
<223> OTHER INFORMATION: Xaa can be any naturally occurring amino acid
<220> FEATURE:
<221> NAME/KEY: misc_feature
<222> LOCATION: (628)..(628)
<223> OTHER INFORMATION: Xaa can be any naturally occurring amino acid
<220> FEATURE:
<221> NAME/KEY: misc_feature
<222> LOCATION: (631)..(631)
<223> OTHER INFORMATION: Xaa can be any naturally occurring amino acid
```

```
<220> FEATURE:
<221> NAME/KEY: misc_feature
<222> LOCATION: (633)..(633)
<223> OTHER INFORMATION: Xaa can be any naturally occurring amino acid
<220> FEATURE:
<221> NAME/KEY: misc_feature
<222> LOCATION: (634)..(634)
<223> OTHER INFORMATION: Xaa can be any naturally occurring amino acid
<220> FEATURE:
<221> NAME/KEY: misc_feature
<222> LOCATION: (636)..(636)
<223> OTHER INFORMATION: Xaa can be any naturally occurring amino acid
<220> FEATURE:
<221> NAME/KEY: misc_feature
<222> LOCATION: (638)..(641)
<223> OTHER INFORMATION: Each Xaa can independently be any naturally
      occurring amino acid
<220> FEATURE:
<221> NAME/KEY: misc_feature
<222> LOCATION: (643)..(645)
<223> OTHER INFORMATION: Each Xaa can independently be any naturally
      occurring amino acid
<220> FEATURE:
<221> NAME/KEY: misc_feature
<222> LOCATION: (653)..(653)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (659)..(659)
<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (665)..(665)
<223> OTHER INFORMATION: Xaa can be any naturally occurring amino acid
<220> FEATURE:
<221> NAME/KEY: misc_feature
<222> LOCATION: (666)..(666)
<223> OTHER INFORMATION: Xaa can be any naturally occurring amino acid
<220> FEATURE:
<221> NAME/KEY: misc_feature
<222> LOCATION: (668)..(668)
<223> OTHER INFORMATION: Xaa can be any naturally occurring amino acid
<220> FEATURE:
<221> NAME/KEY: misc_feature
<222> LOCATION: (669)..(669)
<223> OTHER INFORMATION: Xaa can be any naturally occurring amino acid
<220> FEATURE:
<221> NAME/KEY: misc_feature
<222> LOCATION: (670)..(677)
<223> OTHER INFORMATION: RuvC-like domain
<220> FEATURE:
<221> NAME/KEY: misc_feature
<222> LOCATION: (680)..(680)
<223> OTHER INFORMATION: Xaa can be any naturally occurring amino acid
<220> FEATURE:
<221> NAME/KEY: misc_feature
<222> LOCATION: (681)..(681)
<223> OTHER INFORMATION: Xaa can be any naturally occurring amino acid
<220> FEATURE:
<221> NAME/KEY: misc_feature
<222> LOCATION: (683)..(683)
<223> OTHER INFORMATION: Xaa can be any naturally occurring amino acid
<220> FEATURE:
<221> NAME/KEY: misc_feature
<222> LOCATION: (686)..(686)
<223> OTHER INFORMATION: Xaa can be any naturally occurring amino acid
<220> FEATURE:
<221> NAME/KEY: misc_feature
<222> LOCATION: (696)..(696)
<223> OTHER INFORMATION: Xaa can be any naturally occurring amino acid
<220> FEATURE:
```

<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (704)..(704)
<223> OTHER INFORMATION: Xaa can be any naturally occurring amino acid
<220> FEATURE:
<221> NAME/KEY: misc_feature
<222> LOCATION: (708)..(708)
<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
<221> NAME/KEY: misc_feature
<222> LOCATION: (711)..(711)
<223> OTHER INFORMATION: Xaa can be any naturally occurring amino acid
<220> FEATURE:
<221> NAME/KEY: misc_feature
<222> LOCATION: (714)..(714)
<223> OTHER INFORMATION: Xaa can be any naturally occurring amino acid
<220> FEATURE:
<221> NAME/KEY: misc_feature
<222> LOCATION: (717)..(720)
<223> OTHER INFORMATION: Each Xaa can independently be any naturally occurring amino acid
<220> FEATURE:
<221> NAME/KEY: misc_feature
<222> LOCATION: (722)..(722)
<223> OTHER INFORMATION: Xaa can be any naturally occurring amino acid
<220> FEATURE:
<221> NAME/KEY: misc_feature
<222> LOCATION: (725)..(725)
<223> OTHER INFORMATION: Xaa can be any naturally occurring amino acid
<220> FEATURE:
<221> NAME/KEY: misc_feature
<222> LOCATION: (727)..(727)
<223> OTHER INFORMATION: Xaa can be any naturally occurring amino acid
<220> FEATURE:
<221> NAME/KEY: misc_feature
<222> LOCATION: (733)..(735)
<223> OTHER INFORMATION: Each Xaa can independently be any naturally occurring amino acid
<220> FEATURE:
<221> NAME/KEY: misc_feature
<222> LOCATION: (740)..(740)
<223> OTHER INFORMATION: Xaa can be any naturally occurring amino acid
<220> FEATURE:
<221> NAME/KEY: misc_feature
<222> LOCATION: (742)..(742)
<223> OTHER INFORMATION: Xaa can be any naturally occurring amino acid
<220> FEATURE:
<221> NAME/KEY: misc_feature
<222> LOCATION: (749)..(754)
<223> OTHER INFORMATION: Each Xaa can independently be any naturally occurring amino acid
<220> FEATURE:
<221> NAME/KEY: misc_feature
<222> LOCATION: (758)..(761)
<223> OTHER INFORMATION: Each Xaa can independently be any naturally occurring amino acid
<220> FEATURE:
<221> NAME/KEY: misc_feature
<222> LOCATION: (763)..(768)
<223> OTHER INFORMATION: Each Xaa can independently be any naturally occurring amino acid
<220> FEATURE:
<221> NAME/KEY: misc_feature
<222> LOCATION: (771)..(771)
<223> OTHER INFORMATION: Xaa can be any naturally occurring amino acid
<220> FEATURE:
<221> NAME/KEY: misc_feature
<222> LOCATION: (774)..(777)
<223> OTHER INFORMATION: Each Xaa can independently be any naturally occurring amino acid
<220> FEATURE:
<221> NAME/KEY: misc_feature
<222> LOCATION: (782)..(782)
<223> OTHER INFORMATION: Xaa can be any naturally occurring amino acid
<220> FEATURE:
<221> NAME/KEY: misc_feature
<222> LOCATION: (784)..(786)
<223> OTHER INFORMATION: Each Xaa can independently be any naturally
occurring amino acid
<220> FEATURE:
<221> NAME/KEY: misc_feature
<222> LOCATION: (788)..(788)
<223> OTHER INFORMATION: Xaa can be any naturally occurring amino acid
<220> FEATURE:
<221> NAME/KEY: misc_feature
<222> LOCATION: (790)..(790)
<223> OTHER INFORMATION: Xaa can be any naturally occurring amino acid
<220> FEATURE:
<221> NAME/KEY: misc_feature
<222> LOCATION: (795)..(795)
<223> OTHER INFORMATION: Xaa can be any naturally occurring amino acid
<220> FEATURE:
<221> NAME/KEY: misc_feature
<222> LOCATION: (799)..(799)
<223> OTHER INFORMATION: Xaa can be any naturally occurring amino acid
<220> FEATURE:
<221> NAME/KEY: misc_feature
<222> LOCATION: (801)..(801)
<223> OTHER INFORMATION: Xaa can be any naturally occurring amino acid
<220> FEATURE:
<221> NAME/KEY: misc_feature
<222> LOCATION: (802)..(802)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (806)..(813)
<223> OTHER INFORMATION: Each Xaa can independently be any naturally
occurring amino acid
<220> FEATURE:
<221> NAME/KEY: misc_feature
<222> LOCATION: (815)..(818)
<223> OTHER INFORMATION: Each Xaa can independently be any naturally
occurring amino acid
<220> FEATURE:
<221> NAME/KEY: misc_feature
<222> LOCATION: (820)..(820)
<223> OTHER INFORMATION: Xaa can be any naturally occurring amino acid
<220> FEATURE:
<221> NAME/KEY: misc_feature
<222> LOCATION: (823)..(827)
<223> OTHER INFORMATION: Each Xaa can independently be any naturally
occurring amino acid
<220> FEATURE:
<221> NAME/KEY: misc_feature
<222> LOCATION: (829)..(829)
<223> OTHER INFORMATION: Xaa can be any naturally occurring amino acid
<220> FEATURE:
<221> NAME/KEY: misc_feature
<222> LOCATION: (830)..(830)
<223> OTHER INFORMATION: Xaa can be any naturally occurring amino acid
<220> FEATURE:
<221> NAME/KEY: misc_feature
<222> LOCATION: (832)..(832)
<223> OTHER INFORMATION: Xaa can be any naturally occurring amino acid
<220> FEATURE:
<221> NAME/KEY: misc_feature
<222> LOCATION: (835)..(837)
<223> OTHER INFORMATION: Each Xaa can independently be any naturally
occurring amino acid
<220> FEATURE:
<221> NAME/KEY: misc_feature
<222> LOCATION: (842)..(844)
<223> OTHER INFORMATION: Each Xaa can independently be any naturally
occurring amino acid
<220> FEATURE:
<221> NAME/KEY: misc_feature
<222> LOCATION: (846)..(846)

-continued

<223> OTHER INFORMATION: Xaa can be any naturally occurring amino acid
<220> FEATURE:
<221> NAME/KEY: misc_feature
<222> LOCATION: (848)..(848)
<223> OTHER INFORMATION: Xaa can be any naturally occurring amino acid
<220> FEATURE:
<221> NAME/KEY: misc_feature
<222> LOCATION: (851)..(851)
<223> OTHER INFORMATION: Xaa can be any naturally occurring amino acid
<220> FEATURE:
<221> NAME/KEY: misc_feature
<222> LOCATION: (857)..(857)
<223> OTHER INFORMATION: Xaa can be any naturally occurring amino acid
<220> FEATURE:
<221> NAME/KEY: misc_feature
<222> LOCATION: (857)..(857)
<223> OTHER INFORMATION: Xaa can be any naturally occurring amino acid

<400> SEQUENCE: 14

Met Lys Tyr Xaa Ile Gly Leu Asp Ile Gly Thr Asn Ser Val Gly Trp
1 5 10 15

Ala Val Thr Asp Xaa Tyr Xaa Xaa Lys Xaa Lys Gly Xaa Xaa Xaa Ile
20 25 30

Xaa Lys Asn Xaa Gly Leu Phe Asp Gly Thr Ala Arg Xaa Arg Thr Ala
35 40 45

Arg Arg Arg Arg Arg Xaa Asn Arg Ile Tyr Leu Gln Ile Phe Xaa Glu
50 55 60

Met Asp Phe Phe Arg Leu Xaa Ser Phe Val Xaa Xaa Lys Xaa Xaa Xaa
65 70 75 80

Pro Xaa Phe Xaa Xaa Glu Tyr His Xaa Xaa Pro Thr Ile Tyr His Leu
85 90 95

Arg Xaa Leu Xaa Lys Asp Leu Arg Leu Xaa Tyr Leu Ala Leu Ala His
100 105 110

Xaa Ile Lys Xaa Arg Gly Asn Phe Leu Ile Glu Gly Xaa Xaa Asn Xaa
115 120 125

Xaa Xaa Xaa Xaa Xaa Tyr Xaa Phe Xaa Ile Xaa Xaa Xaa Xaa Xaa Xaa
130 135 140

Xaa Xaa Xaa Pro Glu Lys Gly Phe Xaa Xaa Xaa Leu Xaa Gly Xaa Phe
145 150 155 160

Xaa Phe Xaa Leu Glu Xaa Xaa Xaa Lys Xaa Xaa Tyr Xaa Xaa Xaa Leu
165 170 175

Xaa Leu Leu Ile Gly Asp Xaa Tyr Xaa Xaa Xaa Phe Xaa Ala Lys Xaa
180 185 190

Xaa Xaa Xaa Leu Ser Xaa Xaa Val Thr Xaa Ala Leu Ser Xaa Xaa Met
195 200 205

Ile Xaa Arg Xaa Xaa His Asp Leu Leu Lys Xaa Xaa Tyr Xaa Glu Xaa
210 215 220

Phe Xaa Lys Gly Tyr Ala Gly Tyr Ile Asp Gly Xaa Gln Phe Tyr Xaa
225 230 235 240

Xaa Lys Leu Xaa Xaa Xaa Gly Xaa Xaa Xaa Lys Xaa Xaa Xaa Glu Xaa
245 250 255

Xaa Leu Arg Lys Gln Arg Thr Phe Asp Asn Gly Xaa Ile Pro Xaa Gln
260 265 270

Xaa His Leu Glu Xaa Ala Ile Xaa Xaa Gln Xaa Tyr Pro Phe Leu Asn
275 280 285

Xaa Xaa Ile Xaa Xaa Xaa Thr Phe Arg Ile Pro Tyr Xaa Val Gly Pro
290 295 300

Leu Ala Gly Xaa Ser Phe Ala Trp Arg Lys Ile Pro Trp Asn Xaa Xaa
305 310 315 320

```
Xaa Xaa Asp Ser Ala Phe Ile Xaa Xaa Met Thr Asp Leu Pro Xaa Xaa
                325                 330                 335

Xaa Val Leu Pro Lys His Ser Leu Tyr Xaa Xaa Val Tyr Asn Glu Leu
            340                 345                 350

Thr Lys Val Xaa Xaa Xaa Xaa Xaa Xaa Lys Xaa Ile Phe Lys Arg Lys
        355                 360                 365

Val Xaa Xaa Xaa Xaa Gly Xaa Xaa Phe Asn Xaa Ser Thr Tyr His Asp
    370                 375                 380

Leu Xaa Xaa Xaa Xaa Xaa Leu Asp Xaa Asn Xaa Xaa Glu Xaa Ile Xaa
385                 390                 395                 400

Leu Thr Xaa Phe Glu Asp Xaa Met Ile Xaa Xaa Leu Xaa Xaa Xaa Xaa
                405                 410                 415

Lys Xaa Leu Arg Arg Xaa Tyr Thr Gly Trp Gly Xaa Leu Ser Xaa Leu
            420                 425                 430

Xaa Gly Ile Arg Xaa Xaa Xaa Ser Thr Ile Leu Asp Xaa Leu Asp Asn
        435                 440                 445

Arg Asn Xaa Met Gln Leu Ile Xaa Asp Leu Xaa Phe Lys Ile Lys Gln
    450                 455                 460

Xaa Xaa Xaa Xaa Xaa Gly Ser Pro Ala Ile Lys Lys Gly Ile Leu Gln
465                 470                 475                 480

Xaa Xaa Lys Xaa Val Asp Glu Leu Val Xaa Met Gly Pro Xaa Ile Val
                485                 490                 495

Xaa Glu Met Ala Arg Glu Asn Gln Thr Xaa Gly Asn Ser Xaa Arg Lys
            500                 505                 510

Xaa Xaa Lys Glu Xaa Gly Ser Xaa Ile Leu Lys Glu Xaa Xaa Asn Leu
        515                 520                 525

Xaa Asn Xaa Xaa Leu Xaa Leu Tyr Tyr Leu Gln Asn Gly Xaa Asp Met
    530                 535                 540

Tyr Xaa Xaa Leu Asp Ile Leu Ser Xaa Tyr Asp Xaa Asp His Ile Xaa
545                 550                 555                 560

Pro Gln Xaa Phe Xaa Asp Xaa Ser Ile Asp Asn Val Leu Ser Asn Arg
                565                 570                 575

Lys Asp Xaa Val Pro Xaa Xaa Val Xaa Lys Lys Xaa Trp Xaa Leu Xaa
            580                 585                 590

Leu Xaa Xaa Xaa Arg Lys Phe Asp Leu Thr Lys Ala Glu Arg Gly Gly
        595                 600                 605

Leu Xaa Asp Lys Ala Phe Ile Xaa Arg Gln Leu Val Glu Thr Arg Gln
    610                 615                 620

Ile Thr Lys Xaa Val Ala Xaa Leu Xaa Xaa Asn Xaa Asp Xaa Xaa Xaa
625                 630                 635                 640

Xaa Val Xaa Xaa Xaa Thr Leu Lys Ser Leu Val Ser Xaa Phe Arg Lys
                645                 650                 655

Xaa Phe Xaa Xaa Leu Tyr Lys Val Xaa Xaa Asn Xaa Xaa His His Ala
            660                 665                 670

His Asp Ala Tyr Leu Asn Val Xaa Xaa Leu Xaa Tyr Pro Xaa Leu Glu
        675                 680                 685

Glu Phe Val Tyr Gly Asp Tyr Xaa Xaa Lys Ala Thr Lys Phe Tyr Xaa
    690                 695                 700

Asn Ile Met Xaa Phe Xaa Xaa Gly Glu Xaa Trp Lys Xaa Xaa Xaa Xaa
705                 710                 715                 720

Val Xaa Met Gln Xaa Asn Xaa Val Lys Lys Glu Gln Xaa Xaa Xaa Pro
                725                 730                 735
```

```
Lys Asn Ser Xaa Leu Xaa Lys Asp Lys Tyr Gly Gly Xaa Xaa Xaa Xaa
            740                 745                 750

Xaa Xaa Lys Gly Lys Xaa Xaa Xaa Xaa Ile Xaa Xaa Xaa Xaa Xaa Xaa
        755                 760                 765

Phe Leu Xaa Gly Tyr Xaa Xaa Xaa Xaa Leu Pro Lys Tyr Xaa Leu Xaa
    770                 775                 780

Xaa Xaa Gly Xaa Arg Xaa Leu Ala Ser Glu Xaa Lys Gly Asn Xaa Leu
785                 790                 795                 800

Xaa Xaa Leu Xaa Ala Xaa Xaa Xaa Xaa Xaa Xaa Xaa Xaa Glu Xaa Xaa
                805                 810                 815

Xaa Xaa Phe Xaa Ala Asn Xaa Xaa Xaa Xaa Xaa Leu Xaa Xaa Gly Xaa
            820                 825                 830

Ala Phe Xaa Xaa Xaa Ile Arg Arg Tyr Xaa Xaa Xaa Thr Xaa Ile Xaa
        835                 840                 845

Gln Ser Xaa Thr Gly Leu Tyr Glu Xaa Arg Leu
    850                 855


<210> SEQ ID NO 15
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (2)..(2)
<223> OTHER INFORMATION: Xaa is Val or His
<220> FEATURE:
<221> NAME/KEY: VARIANT
<222> LOCATION: (3)..(3)
<223> OTHER INFORMATION: Xaa is Ile, Leu, or Val
<220> FEATURE:
<221> NAME/KEY: VARIANT
<222> LOCATION: (5)..(5)
<223> OTHER INFORMATION: Xaa is Met or Thr

<400> SEQUENCE: 15

Ile Xaa Xaa Glu Xaa Ala Arg Glu
1               5


<210> SEQ ID NO 16
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (3)..(3)
<223> OTHER INFORMATION: Xaa is Ile, Leu, or Val

<400> SEQUENCE: 16

Ile Val Xaa Glu Met Ala Arg Glu
1               5


<210> SEQ ID NO 17
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (4)..(4)
<223> OTHER INFORMATION: Xaa is His or Leu
<220> FEATURE:
<221> NAME/KEY: VARIANT
```

<222> LOCATION: (7)..(7)
<223> OTHER INFORMATION: Xaa is Arg or Val
<220> FEATURE:
<221> NAME/KEY: VARIANT
<222> LOCATION: (8)..(8)
<223> OTHER INFORMATION: Xaa is Glu or Val

<400> SEQUENCE: 17

His His Ala Xaa Asp Ala Xaa Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: RuvC-like domain

<400> SEQUENCE: 18

His His Ala His Asp Ala Tyr Leu
1               5

<210> SEQ ID NO 19
<211> LENGTH: 30
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Lys or Pro
<220> FEATURE:
<221> NAME/KEY: VARIANT
<222> LOCATION: (4)..(4)
<223> OTHER INFORMATION: Xaa is Val, Leu, Ile, or Phe
<220> FEATURE:
<221> NAME/KEY: VARIANT
<222> LOCATION: (5)..(5)
<223> OTHER INFORMATION: Xaa is Gly, Ala, or Ser
<220> FEATURE:
<221> NAME/KEY: VARIANT
<222> LOCATION: (6)..(6)
<223> OTHER INFORMATION: Xaa is Leu, Ile, Val, or Phe
<220> FEATURE:
<221> NAME/KEY: MOD_RES
<222> LOCATION: (7)..(26)
<223> OTHER INFORMATION: N-terminal RuvC-like domain, each Xaa can be
      any amino acid or absent, region may encompass 5-20 residues
<220> FEATURE:
<221> NAME/KEY: VARIANT
<222> LOCATION: (29)..(29)
<223> OTHER INFORMATION: Xaa is Asp, Glu, Asn, or Gln

<400> SEQUENCE: 19

Lys Xaa Tyr Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Thr Asp Xaa Tyr
            20                  25                  30

<210> SEQ ID NO 20
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met, or Phe
<220> FEATURE:
<221> NAME/KEY: VARIANT
<222> LOCATION: (6)..(6)
<223> OTHER INFORMATION: Xaa is Ser, Tyr, Asn, or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 20

```
Asp Xaa Gly Xaa Xaa Xaa Xaa Gly Xaa Xaa Xaa Xaa
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met, or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 21

Asp Xaa Gly Xaa Xaa Ser Xaa Gly Xaa Xaa Xaa Xaa
1 5 10

<210> SEQ ID NO 22
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met, or Phe
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 22

Asp Ile Gly Xaa Xaa Ser Val Gly Trp Ala Xaa Xaa
1 5 10

<210> SEQ ID NO 23
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: MOD_RES
<222> LOCATION: (12)..(12)
<223> OTHER INFORMATION: Any non-polar alkyl amino acid or a hydroxyl amino acid

<400> SEQUENCE: 23

Asp Ile Gly Thr Asn Ser Val Gly Trp Ala Val Xaa
1 5 10

<210> SEQ ID NO 24
<211> LENGTH: 73
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (8)..(8)
<223> OTHER INFORMATION: Xaa is Lys or Arg
<220> FEATURE:
<221> NAME/KEY: VARIANT
<222> LOCATION: (12)..(12)
<223> OTHER INFORMATION: Xaa is Val or Thr
<220> FEATURE:
<221> NAME/KEY: VARIANT
<222> LOCATION: (13)..(13)
<223> OTHER INFORMATION: Xaa is Gly or Asp
<220> FEATURE:
<221> NAME/KEY: VARIANT
<222> LOCATION: (14)..(14)
<223> OTHER INFORMATION: Xaa is Glu, Gln, or Asp
<220> FEATURE:

```
<221> NAME/KEY: VARIANT
<222> LOCATION: (15)..(15)
<223> OTHER INFORMATION: Xaa is Glu or Asp
<220> FEATURE:
<221> NAME/KEY: VARIANT
<222> LOCATION: (19)..(19)
<223> OTHER INFORMATION: Xaa is Asp, Asn, or His
<220> FEATURE:
<221> NAME/KEY: VARIANT
<222> LOCATION: (20)..(20)
<223> OTHER INFORMATION: Xaa is Tyr, Arg, or Asn
<220> FEATURE:
<221> NAME/KEY: VARIANT
<222> LOCATION: (23)..(23)
<223> OTHER INFORMATION: Xaa is Gln, Asp, or Asn
<220> FEATURE:
<221> NAME/KEY: MOD_RES
<222> LOCATION: (25)..(64)
<223> OTHER INFORMATION: HNH-like domain, each Xaa can be any amino acid
      or absent, region may encompass 15-40 residues
<220> FEATURE:
<221> NAME/KEY: VARIANT
<222> LOCATION: (67)..(67)
<223> OTHER INFORMATION: Xaa is Gly or Glu
<220> FEATURE:
<221> NAME/KEY: VARIANT
<222> LOCATION: (69)..(69)
<223> OTHER INFORMATION: Xaa is Ser or Gly
<220> FEATURE:
<221> NAME/KEY: VARIANT
<222> LOCATION: (71)..(71)
<223> OTHER INFORMATION: Xaa is Asp or Asn

<400> SEQUENCE: 24

Leu Tyr Tyr Leu Gln Asn Gly Xaa Asp Met Tyr Xaa Xaa Xaa Xaa Leu
1               5                   10                  15

Asp Ile Xaa Xaa Leu Ser Xaa Tyr Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Asn Arg Xaa Lys Xaa Asp Xaa Val Pro
65                  70


<210> SEQ ID NO 25
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp, Glu, Gln, or Asn
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
```

<222> LOCATION: (8)..(8)
<223> OTHER INFORMATION: Xaa is Gln, His, Arg, Lys, Tyr, Ile, Leu, Phe, or Trp
<220> FEATURE:
<221> NAME/KEY: VARIANT
<222> LOCATION: (9)..(9)
<223> OTHER INFORMATION: Xaa is Ser, Ala, Asp, Thr, or Lys
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg, Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr, Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met, Ala, Glu, Gly, or Ser
<220> FEATURE:
<221> NAME/KEY: VARIANT
<222> LOCATION: (13)..(13)
<223> OTHER INFORMATION: Xaa is Asp, Ser, Asn, Arg, Leu, or Thr
<220> FEATURE:
<221> NAME/KEY: VARIANT
<222> LOCATION: (14)..(14)
<223> OTHER INFORMATION: Xaa is Asp, Asn, or Ser
<220> FEATURE:
<221> NAME/KEY: VARIANT
<222> LOCATION: (15)..(15)
<223> OTHER INFORMATION: Xaa is Ser, Ala, Thr, Gly, or Arg
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp, Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe, Leu, Gln, Met, Gly, Tyr, or Val
<220> FEATURE:
<221> NAME/KEY: VARIANT
<222> LOCATION: (19)..(19)
<223> OTHER INFORMATION: Xaa is Lys, Leu, Arg, Met, Thr, or Phe
<220> FEATURE:
<221> NAME/KEY: VARIANT
<222> LOCATION: (20)..(20)
<223> OTHER INFORMATION: Xaa is Val, Leu, Ile, Ala, or Thr
<220> FEATURE:
<221> NAME/KEY: VARIANT
<222> LOCATION: (21)..(21)
<223> OTHER INFORMATION: Xaa is Leu, Ile, Val, or Ala
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys, Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln, Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile, Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu,

Ser, Thr, Gly, Lys, Met, Asp, or Phe

<400> SEQUENCE: 25

```
Xaa Xaa Xaa His Xaa Xaa Pro Xaa Xaa Xaa Xaa Xaa Xaa Xaa Xaa Xaa
1               5                   10                  15

Xaa Asn Xaa Xaa Xaa Xaa Xaa Xaa Xaa Xaa Asn
            20                  25
```

<210> SEQ ID NO 26
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, Phe,
or Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg,
Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr,
Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met,
Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
Leu, Gln, Met, Gly, Tyr, or Val
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
Lys, Val, Ser, Gln, Ile, Tyr, His, or Ala
<220> FEATURE:
<221> NAME/KEY: VARIANT
<222> LOCATION: (24)..(24)

<223> OTHER INFORMATION: Xaa is Ser, Pro, Arg, Lys, Asn, Ala, His, Gln, Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile, Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu, Ser, Thr, Gly, Lys, Met, Asp, or Phe

<400> SEQUENCE: 26

```
Xaa Xaa Xaa His Xaa Xaa Pro Xaa Ser Xaa Xaa Xaa Asp Asp Ser Xaa
1               5                   10                  15

Xaa Asn Lys Val Leu Xaa Xaa Xaa Xaa Xaa Asn
            20                  25
```

<210> SEQ ID NO 27
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, or Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg, Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr, Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met, Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp, Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe, Leu, Gln, Met, Gly, Tyr, or Val
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys, Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln, Gly, or Leu
<220> FEATURE:
<221> NAME/KEY: VARIANT
<222> LOCATION: (25)..(25)

```
<223> OTHER INFORMATION: Xaa is Asp, Gly, Thr, Asn, Ser, Lys, Ala, Ile,
      Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu,
      Ser, Thr, Gly, Lys, Met, Asp, or Phe

<400> SEQUENCE: 27

Xaa Val Xaa His Ile Val Pro Xaa Ser Xaa Xaa Xaa Asp Asp Ser Xaa
1               5                   10                  15

Xaa Asn Lys Val Leu Thr Xaa Xaa Xaa Xaa Asn
            20                  25


<210> SEQ ID NO 28
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (2)..(2)
<223> OTHER INFORMATION: Xaa is Ile or Val
<220> FEATURE:
<221> NAME/KEY: VARIANT
<222> LOCATION: (6)..(6)
<223> OTHER INFORMATION: Xaa is Ile or Val
<220> FEATURE:
<221> NAME/KEY: VARIANT
<222> LOCATION: (9)..(9)
<223> OTHER INFORMATION: Xaa is Ala or Ser
<220> FEATURE:
<221> NAME/KEY: VARIANT
<222> LOCATION: (11)..(11)
<223> OTHER INFORMATION: Xaa is Ile or Leu
<220> FEATURE:
<221> NAME/KEY: VARIANT
<222> LOCATION: (12)..(12)
<223> OTHER INFORMATION: Xaa is Lys or Thr
<220> FEATURE:
<221> NAME/KEY: VARIANT
<222> LOCATION: (14)..(14)
<223> OTHER INFORMATION: Xaa is Asp or Asn
<220> FEATURE:
<221> NAME/KEY: VARIANT
<222> LOCATION: (19)..(19)
<223> OTHER INFORMATION: Xaa is Arg, Lys, or Leu
<220> FEATURE:
<221> NAME/KEY: VARIANT
<222> LOCATION: (22)..(22)
<223> OTHER INFORMATION: Xaa is Thr or Val
<220> FEATURE:
<221> NAME/KEY: VARIANT
<222> LOCATION: (23)..(23)
<223> OTHER INFORMATION: Xaa is Ser or Arg
<220> FEATURE:
<221> NAME/KEY: VARIANT
<222> LOCATION: (25)..(25)
<223> OTHER INFORMATION: Xaa is Lys, Asp, or Ala
<220> FEATURE:
<221> NAME/KEY: VARIANT
<222> LOCATION: (26)..(26)
<223> OTHER INFORMATION: Xaa is Glu, Lys, Gly, or Asn

<400> SEQUENCE: 28

Asp Xaa Asp His Ile Xaa Pro Gln Xaa Phe Xaa Xaa Asp Xaa Ser Ile
1               5                   10                  15

Asp Asn Xaa Val Leu Xaa Xaa Ser Xaa Xaa Asn
            20                  25


<210> SEQ ID NO 29
<211> LENGTH: 116
```

<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 29
nnnnnnnnnn nnnnnnnnnn guuuuagagc uaugcuguuu uggaaacaaa acagcauagc 60
aaguuaaaau aaggcuaguc cguuaucaac uugaaaaagu ggcaccgagu cggugc 116

<210> SEQ ID NO 30
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 30
nnnnnnnnnn nnnnnnnnnn guauuagagc uaugcuguau uggaaacaau acagcauagc 60
aaguuaauau aaggcuaguc cguuaucaac uugaaaaagu ggcaccgagu cggugc 116

<210> SEQ ID NO 31
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)

<223> OTHER INFORMATION: targeting domain
<220> FEATURE:
<221> NAME/KEY: misc_feature
<222> LOCATION: (21)..(32)
<223> OTHER INFORMATION: first complementarity domain
<220> FEATURE:
<221> NAME/KEY: misc_feature
<222> LOCATION: (33)..(36)
<223> OTHER INFORMATION: linking domain
<220> FEATURE:
<221> NAME/KEY: misc_feature
<222> LOCATION: (37)..(50)
<223> OTHER INFORMATION: second complementarity domain
<220> FEATURE:
<221> NAME/KEY: misc_feature
<222> LOCATION: (51)..(62)
<223> OTHER INFORMATION: proximal domain

<400> SEQUENCE: 31
nnnnnnnnnn nnnnnnnnnn guuuaagagc uagaaauagc aaguuuaaau aaggcuaguc 60
cguuaucaac uugaaaaagu ggcaccgagu cggugc 96

<210> SEQ ID NO 32
<211> LENGTH: 47
<212> TYPE: RNA
<213> ORGANISM: Artificial Sequence
<220> FEATURE:
<223> OTHER INFORMATION: gRNA proximal and tail domains derived from S. pyogenes

<400> SEQUENCE: 32
aaggcuaguc cguuaucaac uugaaaaagu ggcaccgagu cggugcu 47

<210> SEQ ID NO 33
<211> LENGTH: 49
<212> TYPE: RNA
<213> ORGANISM: Artificial Sequence
<220> FEATURE:
<223> OTHER INFORMATION: gRNA proximal and tail domains

<400> SEQUENCE: 33
aaggcuaguc cguuaucaac uugaaaaagu ggcaccgagu cgguggugc 49

<210> SEQ ID NO 34
<211> LENGTH: 51
<212> TYPE: RNA
<213> ORGANISM: Artificial Sequence
<220> FEATURE:
<223> OTHER INFORMATION: gRNA proximal and tail domains

<400> SEQUENCE: 34
aaggcuaguc cguuaucaac uugaaaaagu ggcaccgagu cggugcggau c 51

<210> SEQ ID NO 35
<211> LENGTH: 31
<212> TYPE: RNA
<213> ORGANISM: Artificial Sequence
<220> FEATURE:
<223> OTHER INFORMATION: gRNA proximal and tail domains

<400> SEQUENCE: 35
aaggcuaguc cguuaucaac uugaaaaagu g 31

<210> SEQ ID NO 36
<211> LENGTH: 18
<212> TYPE: RNA
<213> ORGANISM: Artificial Sequence
<220> FEATURE:

<223> OTHER INFORMATION: gRNA proximal and tail domains

<400> SEQUENCE: 36
aaggcuaguc cguuauca 18

<210> SEQ ID NO 37
<211> LENGTH: 12
<212> TYPE: RNA
<213> ORGANISM: Artificial Sequence
<220> FEATURE:
<223> OTHER INFORMATION: gRNA proximal and tail domains

<400> SEQUENCE: 37
aaggcuaguc cg 12

<210> SEQ ID NO 38
<211> LENGTH: 102
<212> TYPE: RNA
<213> ORGANISM: Artificial Sequence
<220> FEATURE:
<223> OTHER INFORMATION: Unimolecular gRNA derived from S. aureus
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 38
nnnnnnnnnn nnnnnnnnnn guuuuaguac ucuggaaaca gaaucuacua aaacaaggca 60
aaaugccgug uuuaucucgu caacuuguug gcgagauuuu uu 102

<210> SEQ ID NO 39
<211> LENGTH: 42
<212> TYPE: RNA
<213> ORGANISM: Artificial
<220> FEATURE:
<223> OTHER INFORMATION: Modular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 39
nnnnnnnnnn nnnnnnnnnn guuuuagagc uaugcuguuu ug 42

<210> SEQ ID NO 40
<211> LENGTH: 85
<212> TYPE: RNA
<213> ORGANISM: Artificial Sequence
<220> FEATURE:
<223> OTHER INFORMATION: Modular gRNA derived from S. pyogenes
<220> FEATURE:
<221> NAME/KEY: misc_feature
<222> LOCATION: (1)..(9)
<223> OTHER INFORMATION: 5' extension domain
<220> FEATURE:
<221> NAME/KEY: misc_feature
<222> LOCATION: (10)..(33)
<223> OTHER INFORMATION: Second complementarity domain
<220> FEATURE:
<221> NAME/KEY: misc_feature
<222> LOCATION: (34)..(45)
<223> OTHER INFORMATION: Proximal domain
<220> FEATURE:
<221> NAME/KEY: misc_feature
<222> LOCATION: (46)..(85)
<223> OTHER INFORMATION: Tail domain

<400> SEQUENCE: 40
ggaaccauuc aaaacagcau agcaaguuaa aauaaggcua guccguuauc aacuugaaaa 60
aguggcaccg agucggugcu uuuuu 85

<210> SEQ ID NO 41
<211> LENGTH: 62
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 41
nnnnnnnnnn nnnnnnnnnn guuuuagagc uagaaauagc aaguuaaaau aaggcuaguc 60
cg 62

<210> SEQ ID NO 42
<211> LENGTH: 102
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)

<223> OTHER INFORMATION: Second complementarity domain
<220> FEATURE:
<221> NAME/KEY: misc_feature
<222> LOCATION: (51)..(62)
<223> OTHER INFORMATION: Proximal domain
<220> FEATURE:
<221> NAME/KEY: misc_feature
<222> LOCATION: (63)..(102)
<223> OTHER INFORMATION: Tail domain

<400> SEQUENCE: 42
nnnnnnnnnn nnnnnnnnnn guuuuagagc uagaaauagc aaguuaaaau aaggcuaguc 60
cguuaucaac uugaaaaagu ggcaccgagu cggugcuuuu uu 102

<210> SEQ ID NO 43
<211> LENGTH: 75
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain
<220> FEATURE:
<221> NAME/KEY: misc_feature
<222> LOCATION: (59)..(70)
<223> OTHER INFORMATION: Proximal domain
<220> FEATURE:
<221> NAME/KEY: misc_feature
<222> LOCATION: (71)..(75)
<223> OTHER INFORMATION: Tail domain

<400> SEQUENCE: 43
nnnnnnnnnn nnnnnnnnnn guuuuagagc uaugcugaaa agcauagcaa guuaaaauaa 60
ggcuaguccg uuauc 75

<210> SEQ ID NO 44
<211> LENGTH: 87
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (43)..(46)
<223> OTHER INFORMATION: Linking domain
<220> FEATURE:
<221> NAME/KEY: misc_feature
<222> LOCATION: (57)..(70)
<223> OTHER INFORMATION: Second complementarity domain
<220> FEATURE:
<221> NAME/KEY: misc_feature
<222> LOCATION: (71)..(82)
<223> OTHER INFORMATION: Proximal domain
<220> FEATURE:
<221> NAME/KEY: misc_feature
<222> LOCATION: (83)..(87)
<223> OTHER INFORMATION: Tail domain

<400> SEQUENCE: 44
nnnnnnnnnn nnnnnnnnnn guuuuagagc uaugcuguuu uggaaacaaa acagcauagc 60
aaguuaaaau aaggcuaguc cguuauc 87

<210> SEQ ID NO 45
<211> LENGTH: 42
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 45
nnnnnnnnnn nnnnnnnnnn guuuuagagc uguguuguuu cg 42

<210> SEQ ID NO 46
<211> LENGTH: 78
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(3)
<223> OTHER INFORMATION: 5' extension domain
<220> FEATURE:
<221> NAME/KEY: misc_feature
<222> LOCATION: (4)..(27)
<223> OTHER INFORMATION: Second complementarity domain
<220> FEATURE:
<221> NAME/KEY: misc_feature
<222> LOCATION: (28)..(40)
<223> OTHER INFORMATION: Proximal domain
<220> FEATURE:
<221> NAME/KEY: misc_feature
<222> LOCATION: (41)..(78)
<223> OTHER INFORMATION: Tail domain

<400> SEQUENCE: 46
gggcgaaaca acacagcgag uuaaaauaag gcuuaguccg uacucaacuu gaaaaggugg 60
caccgauucg guguuuuu 78

<210> SEQ ID NO 47
<211> LENGTH: 85
<212> TYPE: RNA

<213> ORGANISM: Artificial Sequence
<220> FEATURE:
<223> OTHER INFORMATION: Modular gRNA derived from S. pyogenes

<400> SEQUENCE: 47
gaaccauuca aaacagcaua gcaaguuaaa auaaggcuag uccguuauca acuugaaaaa 60
guggcaccga gucggugcuu uuuuu 85

<210> SEQ ID NO 48
<211> LENGTH: 96
<212> TYPE: RNA
<213> ORGANISM: Artificial Sequence
<220> FEATURE:
<223> OTHER INFORMATION: gRNA from S. pyogenes
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 48
nnnnnnnnnn nnnnnnnnnn guuuuagagc uagaaauagc aaguuaaaau aaggcuaguc 60
cguuaucaac uugaaaaagu ggcaccgagu cggugc 96

<210> SEQ ID NO 49
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 49
nnnnnnnnnn nnnnnnnnnn guauuagagc uagaaauagc aaguuaauau aaggcuaguc 60
cguuaucaac uugaaaaagu ggcaccgagu cggugc 96

<210> SEQ ID NO 50
<211> LENGTH: 104
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain

<400> SEQUENCE: 50
nnnnnnnnnn nnnnnnnnnn guuuuagagc uaugcugaaa agcauagcaa guuaaaauaa 60
ggcuaguccg uuaucaacuu gaaaaagugg caccgagucg gugc 104

<210> SEQ ID NO 51
<211> LENGTH: 106
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(37)
<223> OTHER INFORMATION: First complementarity domain
<220> FEATURE:
<221> NAME/KEY: misc_feature
<222> LOCATION: (38)..(41)
<223> OTHER INFORMATION: Linking domain
<220> FEATURE:
<221> NAME/KEY: misc_feature
<222> LOCATION: (42)..(60)
<223> OTHER INFORMATION: Second complementarity domain

<400> SEQUENCE: 51
nnnnnnnnnn nnnnnnnnnn guuuuagagc uaugcuggaa acagcauagc aaguuaaaau 60
aaggcuaguc cguuaucaac uugaaaaagu ggcaccgagu cggugc 106

<210> SEQ ID NO 52
<211> LENGTH: 12
<212> TYPE: PRT
<213> ORGANISM: Peptoniphilus duerdenii

<400> SEQUENCE: 52

Asp Ile Gly Thr Ala Ser Val Gly Trp Ala Val Thr
1 5 10

<210> SEQ ID NO 53
<211> LENGTH: 12
<212> TYPE: PRT
<213> ORGANISM: Treponema denticola

<400> SEQUENCE: 53

Asp Val Gly Thr Gly Ser Val Gly Trp Ala Val Thr 1 5 10

<210> SEQ ID NO 54
<211> LENGTH: 12
<212> TYPE: PRT
<213> ORGANISM: S. mutans

<400> SEQUENCE: 54

Asp Ile Gly Thr Asn Ser Val Gly Trp Ala Val Val
1 5 10

<210> SEQ ID NO 55
<211> LENGTH: 12
<212> TYPE: PRT
<213> ORGANISM: S. pyogenes

<400> SEQUENCE: 55

Asp Ile Gly Thr Asn Ser Val Gly Trp Ala Val Ile
1 5 10

<210> SEQ ID NO 56
<211> LENGTH: 12
<212> TYPE: PRT
<213> ORGANISM: L. innocua

<400> SEQUENCE: 56

Asp Ile Gly Thr Asn Ser Val Gly Trp Ala Val Leu
1 5 10

<210> SEQ ID NO 57
<211> LENGTH: 12
<212> TYPE: PRT
<213> ORGANISM: Flavobacterium branchiophilum FL-15

<400> SEQUENCE: 57

Asp Leu Gly Thr Asn Ser Ile Gly Trp Ala Val Val
1 5 10

<210> SEQ ID NO 58
<211> LENGTH: 11
<212> TYPE: PRT
<213> ORGANISM: Artificial Sequence
<220> FEATURE:
<223> OTHER INFORMATION: N-terminal RuvC-like domain

<400> SEQUENCE: 58

Asp Leu Gly Thr Asn Ser Ile Gly Trp Ala Ile
1 5 10

<210> SEQ ID NO 59
<211> LENGTH: 12
<212> TYPE: PRT
<213> ORGANISM: Bacteroides fragilis, NCTC 9343

<400> SEQUENCE: 59

Asp Leu Gly Thr Asn Ser Ile Gly Trp Ala Leu Val
1 5 10

<210> SEQ ID NO 60
<211> LENGTH: 12
<212> TYPE: PRT
<213> ORGANISM: Fusobacterium nucleatum

<400> SEQUENCE: 60

Asp Ile Gly Thr Asn Ser Val Gly Trp Cys Val Thr

-continued 1 5 10

<210> SEQ ID NO 61
<211> LENGTH: 12
<212> TYPE: PRT
<213> ORGANISM: Acidaminococcus sp. D21

<400> SEQUENCE: 61

Asp Ile Gly Thr Asn Ser Val Gly Tyr Ala Val Thr
1 5 10

<210> SEQ ID NO 62
<211> LENGTH: 12
<212> TYPE: PRT
<213> ORGANISM: Coprococcus catus GD-7

<400> SEQUENCE: 62

Asp Met Gly Thr Gly Ser Leu Gly Trp Ala Val Thr
1 5 10

<210> SEQ ID NO 63
<211> LENGTH: 12
<212> TYPE: PRT
<213> ORGANISM: Oenococcus kitaharae DSM 17330

<400> SEQUENCE: 63

Asp Ile Gly Thr Ser Ser Val Gly Trp Ala Ala Ile
1 5 10

<210> SEQ ID NO 64
<211> LENGTH: 12
<212> TYPE: PRT
<213> ORGANISM: Catenibacterium mitsuokai DSM 15897

<400> SEQUENCE: 64

Asp Leu Gly Thr Gly Ser Val Gly Trp Ala Val Val
1 5 10

<210> SEQ ID NO 65
<211> LENGTH: 12
<212> TYPE: PRT
<213> ORGANISM: Mycoplasma gallisepticum str. F

<400> SEQUENCE: 65

Asp Leu Gly Val Gly Ser Val Gly Trp Ala Ile Val
1 5 10

<210> SEQ ID NO 66
<211> LENGTH: 12
<212> TYPE: PRT
<213> ORGANISM: Mycoplasma ovipneumoniae SC01

<400> SEQUENCE: 66

Asp Leu Gly Ile Ala Ser Ile Gly Trp Ala Ile Ile
1 5 10

<210> SEQ ID NO 67
<211> LENGTH: 12
<212> TYPE: PRT
<213> ORGANISM: Mycoplasma canis PG 14

<400> SEQUENCE: 67

Asp Leu Gly Ile Ala Ser Val Gly Trp Ala Ile Val
1 5 10

<210> SEQ ID NO 68
<211> LENGTH: 12
<212> TYPE: PRT
<213> ORGANISM: Mycoplasma synoviae 53

<400> SEQUENCE: 68

Asp Leu Gly Val Ala Ser Val Gly Trp Ser Ile Val
1               5                   10

<210> SEQ ID NO 69
<211> LENGTH: 12
<212> TYPE: PRT
<213> ORGANISM: Eubacterium rectale

<400> SEQUENCE: 69

Asp Ile Gly Ile Ala Ser Val Gly Trp Ala Ile Leu
1               5                   10

<210> SEQ ID NO 70
<211> LENGTH: 12
<212> TYPE: PRT
<213> ORGANISM: Enterococcus faecalis TX0012

<400> SEQUENCE: 70

Asp Leu Gly Ile Ser Ser Val Gly Trp Ser Val Ile
1               5                   10

<210> SEQ ID NO 71
<211> LENGTH: 12
<212> TYPE: PRT
<213> ORGANISM: Ilyobacter polytropus DSM 2926

<400> SEQUENCE: 71

Asp Ile Gly Ile Ala Ser Val Gly Trp Ser Val Ile
1               5                   10

<210> SEQ ID NO 72
<211> LENGTH: 12
<212> TYPE: PRT
<213> ORGANISM: Ruminococcus albus 8

<400> SEQUENCE: 72

Asp Val Gly Ile Gly Ser Ile Gly Trp Ala Val Ile
1               5                   10

<210> SEQ ID NO 73
<211> LENGTH: 12
<212> TYPE: PRT
<213> ORGANISM: Elusimicrobium minutum Pei191

<400> SEQUENCE: 73

Asp Leu Gly Val Gly Ser Ile Gly Phe Ala Ile Val
1               5                   10

<210> SEQ ID NO 74
<211> LENGTH: 12
<212> TYPE: PRT
<213> ORGANISM: Akkermansia muciniphila

<400> SEQUENCE: 74

Asp Ile Gly Tyr Ala Ser Ile Gly Trp Ala Val Ile
1               5                   10

<210> SEQ ID NO 75

<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 75

Asp Thr Gly Thr Asn Ser Leu Gly Trp Ala Ile Val
1 5 10

<210> SEQ ID NO 76
<211> LENGTH: 12
<212> TYPE: PRT
<213> ORGANISM: Cand. Puniceispirillum marinum

<400> SEQUENCE: 76

Asp Leu Gly Thr Asn Ser Ile Gly Trp Cys Leu Leu
1 5 10

<210> SEQ ID NO 77
<211> LENGTH: 12
<212> TYPE: PRT
<213> ORGANISM: Rhodospirillum rubrum

<400> SEQUENCE: 77

Asp Ile Gly Thr Asp Ser Leu Gly Trp Ala Val Phe
1 5 10

<210> SEQ ID NO 78
<211> LENGTH: 12
<212> TYPE: PRT
<213> ORGANISM: Lactobacillus rhamnosus GG

<400> SEQUENCE: 78

Asp Ile Gly Ser Asn Ser Ile Gly Phe Ala Val Val
1 5 10

<210> SEQ ID NO 79
<211> LENGTH: 12
<212> TYPE: PRT
<213> ORGANISM: Sphaerochaeta globus str. Buddy

<400> SEQUENCE: 79

Asp Leu Gly Val Gly Ser Ile Gly Val Ala Val Ala
1 5 10

<210> SEQ ID NO 80
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 80

Asp Leu Gly Ile Ala Ser Cys Gly Trp Gly Val Val
1 5 10

<210> SEQ ID NO 81
<211> LENGTH: 12
<212> TYPE: PRT
<213> ORGANISM: Mycoplasma mobile 163K

<400> SEQUENCE: 81

Asp Leu Gly Ile Ala Ser Val Gly Trp Cys Leu Thr
1 5 10

<210> SEQ ID NO 82
<211> LENGTH: 12
<212> TYPE: PRT
<213> ORGANISM: Streptococcus thermophilus LMD-9

<400> SEQUENCE: 82

Asp Ile Gly Ile Gly Ser Val Gly Val Gly Ile Leu
1 5 10

<210> SEQ ID NO 83
<211> LENGTH: 12
<212> TYPE: PRT
<213> ORGANISM: Staphylococcus lugdunensis M23590

<400> SEQUENCE: 83

Asp Ile Gly Ile Thr Ser Val Gly Tyr Gly Leu Ile
1 5 10

<210> SEQ ID NO 84
<211> LENGTH: 12
<212> TYPE: PRT
<213> ORGANISM: Eubacterium dolichum DSM 3991

<400> SEQUENCE: 84

Asp Ile Gly Ile Thr Ser Val Gly Phe Gly Ile Ile
1 5 10

<210> SEQ ID NO 85
<211> LENGTH: 12
<212> TYPE: PRT
<213> ORGANISM: Lactobacillus coryniformis KCTC 3535

<400> SEQUENCE: 85

Asp Val Gly Ile Thr Ser Thr Gly Tyr Ala Val Leu
1 5 10

<210> SEQ ID NO 86
<211> LENGTH: 12
<212> TYPE: PRT
<213> ORGANISM: Nitratifractor salsuginis DSM 16511

<400> SEQUENCE: 86

Asp Leu Gly Ile Thr Ser Phe Gly Tyr Ala Ile Leu
1 5 10

<210> SEQ ID NO 87
<211> LENGTH: 12
<212> TYPE: PRT
<213> ORGANISM: Bifidobacterium bifidum S17

<400> SEQUENCE: 87

Asp Ile Gly Asn Ala Ser Val Gly Trp Ser Ala Phe
1 5 10

<210> SEQ ID NO 88
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 88

Asp Val Gly Thr Asn Ser Cys Gly Trp Val Ala Met
1 5 10

<210> SEQ ID NO 89
<211> LENGTH: 12
<212> TYPE: PRT
<213> ORGANISM: Acidothermus cellulolyticus 11B

<400> SEQUENCE: 89

Asp Val Gly Glu Arg Ser Ile Gly Leu Ala Ala Val
1               5                   10

<210> SEQ ID NO 90
<211> LENGTH: 12
<212> TYPE: PRT
<213> ORGANISM: Bifidobacterium longum DJO10A

<400> SEQUENCE: 90

Asp Val Gly Leu Asn Ser Val Gly Leu Ala Ala Val
1               5                   10

<210> SEQ ID NO 91
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 91

Asp Val Gly Leu Met Ser Val Gly Leu Ala Ala Ile
1               5                   10

<210> SEQ ID NO 92
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 92

Asp Val Gly Thr Phe Ser Val Gly Leu Ala Ala Ile
1               5                   10

<210> SEQ ID NO 93
<211> LENGTH: 12
<212> TYPE: PRT
<213> ORGANISM: Staphylococcus pseudintermedius ED99

<400> SEQUENCE: 93

Asp Ile Gly Thr Gly Ser Val Gly Tyr Ala Cys Met
1               5                   10

<210> SEQ ID NO 94
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 94

Asp Leu Gly Thr Thr Ser Ile Gly Phe Ala His Ile
1               5                   10

<210> SEQ ID NO 95
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 95

Asp Leu Gly Thr Asn Ser Ile Gly Ser Ser Val Arg
1 5 10

<210> SEQ ID NO 96
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 96

Asp Ile Gly Thr Asn Ser Ile Gly Trp Ala Val Ile
1 5 10

<210> SEQ ID NO 97
<211> LENGTH: 12
<212> TYPE: PRT
<213> ORGANISM: Pasteurella multocida str. Pm70

<400> SEQUENCE: 97

Asp Leu Gly Ile Ala Ser Val Gly Trp Ala Val Val
1 5 10

<210> SEQ ID NO 98
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 98

Asp Ile Gly Ile Ala Ser Val Gly Trp Ala Val Leu
1 5 10

<210> SEQ ID NO 99
<211> LENGTH: 12
<212> TYPE: PRT
<213> ORGANISM: Helicobacter mustelae 12198

<400> SEQUENCE: 99

Asp Ile Gly Ile Ala Ser Ile Gly Trp Ala Val Ile
1 5 10

<210> SEQ ID NO 100
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 100

Asp Ile Gly Ile Ala Ser Val Gly Trp Ala Ile Ile
1 5 10

<210> SEQ ID NO 101
<211> LENGTH: 12
<212> TYPE: PRT
<213> ORGANISM: Clostridium cellulolyticum H10

<400> SEQUENCE: 101

Asp Val Gly Ile Ala Ser Val Gly Trp Ala Val Ile
1 5 10

<210> SEQ ID NO 102
<211> LENGTH: 11
<212> TYPE: PRT
<213> ORGANISM: Artificial Sequence
<220> FEATURE:
<223> OTHER INFORMATION: N-terminal RuvC-like domain

<400> SEQUENCE: 102

Asp Ile Gly Ile Ala Ser Val Gly Trp Ala Leu
1 5 10

<210> SEQ ID NO 103
<211> LENGTH: 12
<212> TYPE: PRT
<213> ORGANISM: Neisseria meningitidis

<400> SEQUENCE: 103

Asp Ile Gly Ile Ala Ser Val Gly Trp Ala Met Val
1 5 10

<210> SEQ ID NO 104
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 104

Asp Ile Gly Ile Thr Ser Val Gly Trp Ala Val Ile
1 5 10

<210> SEQ ID NO 105
<211> LENGTH: 12
<212> TYPE: PRT
<213> ORGANISM: Wolinella succinogenes DSM 1740

<400> SEQUENCE: 105

Asp Leu Gly Ile Ser Ser Leu Gly Trp Ala Ile Val
1 5 10

<210> SEQ ID NO 106
<211> LENGTH: 12
<212> TYPE: PRT
<213> ORGANISM: Azospirillum sp. B510

<400> SEQUENCE: 106

Asp Leu Gly Thr Asn Ser Ile Gly Trp Gly Leu Leu
1 5 10

<210> SEQ ID NO 107
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 107

Asp Leu Gly Ser Thr Ser Leu Gly Trp Ala Ile Phe
1 5 10

<210> SEQ ID NO 108
<211> LENGTH: 12
<212> TYPE: PRT
<213> ORGANISM: Campylobacter jejuni, NCTC 11168

<400> SEQUENCE: 108

Asp Ile Gly Ile Ser Ser Ile Gly Trp Ala Phe Ser
1 5 10

<210> SEQ ID NO 109
<211> LENGTH: 12
<212> TYPE: PRT
<213> ORGANISM: Parvibaculum lavamentivorans DS-1

<400> SEQUENCE: 109

Asp Ile Gly Thr Thr Ser Ile Gly Phe Ser Val Ile
1 5 10

<210> SEQ ID NO 110
<211> LENGTH: 12
<212> TYPE: PRT
<213> ORGANISM: Dinoroseobacter shibae DFL 12

<400> SEQUENCE: 110

Asp Ile Gly Thr Ser Ser Ile Gly Trp Trp Leu Tyr
1 5 10

<210> SEQ ID NO 111
<211> LENGTH: 12
<212> TYPE: PRT
<213> ORGANISM: Nitrobacter hamburgensis X14

<400> SEQUENCE: 111

Asp Leu Gly Ser Asn Ser Leu Gly Trp Phe Val Thr
1 5 10

<210> SEQ ID NO 112
<211> LENGTH: 12
<212> TYPE: PRT
<213> ORGANISM: Bradyrhizobium sp. BTAi1

<400> SEQUENCE: 112

Asp Leu Gly Ala Asn Ser Leu Gly Trp Phe Val Val
1 5 10

<210> SEQ ID NO 113
<211> LENGTH: 15
<212> TYPE: PRT
<213> ORGANISM: Artificial Sequence
<220> FEATURE:
<223> OTHER INFORMATION: N-terminal RuvC-like domain

<400> SEQUENCE: 113

Asp Ile Gly Leu Arg Ile Gly Ile Thr Ser Cys Gly Trp Ser Ile
1 5 10 15

<210> SEQ ID NO 114
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 114

Asp Met Gly Ala Lys Tyr Thr Gly Val Phe Tyr Ala
1 5 10

<210> SEQ ID NO 115
<211> LENGTH: 12
<212> TYPE: PRT
<213> ORGANISM: Wolinella succinogenes DSM 1740

<400> SEQUENCE: 115

Asp Leu Gly Gly Lys Asn Thr Gly Phe Phe Ser Phe
1 5 10

<210> SEQ ID NO 116
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 116

Asp Leu Gly Val Lys Asn Thr Gly Val Phe Ser Ala
1 5 10

<210> SEQ ID NO 117
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 117

Asp Leu Gly Ala Lys Phe Thr Gly Val Ala Leu Tyr
1 5 10

<210> SEQ ID NO 118
<211> LENGTH: 12
<212> TYPE: PRT
<213> ORGANISM: Legionella pneumophila str. Paris

<400> SEQUENCE: 118

Asp Leu Gly Gly Lys Phe Thr Gly Val Cys Leu Ser
1 5 10

<210> SEQ ID NO 119
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 119

Asp Leu Gly Gly Thr Tyr Thr Gly Thr Phe Ile Thr
1 5 10

<210> SEQ ID NO 120
<211> LENGTH: 12
<212> TYPE: PRT
<213> ORGANISM: S. thermophilus

<400> SEQUENCE: 120

Asp Ile Gly Thr Asn Ser Val Gly Trp Ala Val Thr
1 5 10

<210> SEQ ID NO 121
<211> LENGTH: 12
<212> TYPE: PRT
<213> ORGANISM: Eubacterium yurii

<400> SEQUENCE: 121

Asp Val Gly Thr Asn Ser Val Gly Trp Ala Val Thr
1 5 10

<210> SEQ ID NO 122

<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 122

Asp Met Gly Thr Asn Ser Val Gly Trp Ala Val Thr
1               5                   10

<210> SEQ ID NO 123
<211> LENGTH: 12
<212> TYPE: PRT
<213> ORGANISM: Solobacterium moorei F0204

<400> SEQUENCE: 123

Asp Val Gly Thr Ser Ser Val Gly Trp Ala Val Thr
1               5                   10

<210> SEQ ID NO 124
<211> LENGTH: 27
<212> TYPE: PRT
<213> ORGANISM: Treponema denticola

<400> SEQUENCE: 124

Asp Ile Asp His Ile Tyr Pro Gln Ser Lys Ile Lys Asp Asp Ser Ile
1               5                   10                  15

Ser Asn Arg Val Leu Val Cys Ser Ser Cys Asn
            20                  25

<210> SEQ ID NO 125
<211> LENGTH: 27
<212> TYPE: PRT
<213> ORGANISM: Coprococcus catus GD-7

<400> SEQUENCE: 125

Asp Ile Asp His Ile Tyr Pro Gln Ser Lys Thr Met Asp Asp Ser Leu
1               5                   10                  15

Asn Asn Arg Val Leu Val Lys Lys Asn Tyr Asn
            20                  25

<210> SEQ ID NO 126
<211> LENGTH: 27
<212> TYPE: PRT
<213> ORGANISM: Peptoniphilus duerdenii

<400> SEQUENCE: 126

Asp Gln Asp His Ile Tyr Pro Lys Ser Lys Ile Tyr Asp Asp Ser Leu
1               5                   10                  15

Glu Asn Arg Val Leu Val Lys Lys Asn Leu Asn
            20                  25

<210> SEQ ID NO 127
<211> LENGTH: 27
<212> TYPE: PRT
<213> ORGANISM: Catenibacterium mitsuokai DSM 15897

<400> SEQUENCE: 127

Gln Ile Asp His Ile Val Pro Gln Ser Leu Val Lys Asp Asp Ser Phe
1               5                   10                  15

Asp Asn Arg Val Leu Val Val Pro Ser Glu Asn
            20                  25

<210> SEQ ID NO 128
<211> LENGTH: 27
<212> TYPE: PRT
<213> ORGANISM: S. mutans

<400> SEQUENCE: 128

```
Asp Ile Asp His Ile Ile Pro Gln Ala Phe Ile Lys Asp Asn Ser Ile
1               5                   10                  15

Asp Asn Arg Val Leu Thr Ser Ser Lys Glu Asn
            20                  25
```

<210> SEQ ID NO 129
<211> LENGTH: 27
<212> TYPE: PRT
<213> ORGANISM: S. thermophilus

<400> SEQUENCE: 129

```
Asp Ile Asp His Ile Ile Pro Gln Ala Phe Leu Lys Asp Asn Ser Ile
1               5                   10                  15

Asp Asn Lys Val Leu Val Ser Ser Ala Ser Asn
            20                  25
```

<210> SEQ ID NO 130
<211> LENGTH: 27
<212> TYPE: PRT
<213> ORGANISM: Oenococcus kitaharae DSM 17330

<400> SEQUENCE: 130

```
Asp Ile Asp His Ile Ile Pro Gln Ala Tyr Thr Lys Asp Asn Ser Leu
1               5                   10                  15

Asp Asn Arg Val Leu Val Ser Asn Ile Thr Asn
            20                  25
```

<210> SEQ ID NO 131
<211> LENGTH: 27
<212> TYPE: PRT
<213> ORGANISM: L. inocua

<400> SEQUENCE: 131

```
Asp Ile Asp His Ile Val Pro Gln Ser Phe Ile Thr Asp Asn Ser Ile
1               5                   10                  15

Asp Asn Leu Val Leu Thr Ser Ser Ala Gly Asn
            20                  25
```

<210> SEQ ID NO 132
<211> LENGTH: 27
<212> TYPE: PRT
<213> ORGANISM: S. pyogenes

<400> SEQUENCE: 132

```
Asp Val Asp His Ile Val Pro Gln Ser Phe Leu Lys Asp Asp Ser Ile
1               5                   10                  15

Asp Asn Lys Val Leu Thr Arg Ser Asp Lys Asn
            20                  25
```

<210> SEQ ID NO 133
<211> LENGTH: 27
<212> TYPE: PRT
<213> ORGANISM: Acidaminococcus sp. D21

<400> SEQUENCE: 133

```
Asn Ile Asp His Ile Tyr Pro Gln Ser Met Val Lys Asp Asp Ser Leu
1               5                   10                  15
```

```
Asp Asn Lys Val Leu Val Gln Ser Glu Ile Asn
            20                  25


<210> SEQ ID NO 134
<211> LENGTH: 27
<212> TYPE: PRT
<213> ORGANISM: Lactobacillus rhamnosus GG

<400> SEQUENCE: 134

Asp Ile Asp His Ile Leu Pro Gln Ser Leu Ile Lys Asp Asp Ser Leu
1               5                   10                  15

Asp Asn Arg Val Leu Val Asn Ala Thr Ile Asn
            20                  25


<210> SEQ ID NO 135
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 135

Asp Ile Asp His Ile Leu Pro Gln Ser Phe Ile Lys Asp Asp Ser Leu
1               5                   10                  15

Glu Asn Arg Val Leu Val Lys Lys Ala Val Asn
            20                  25


<210> SEQ ID NO 136
<211> LENGTH: 27
<212> TYPE: PRT
<213> ORGANISM: Staphylococcus pseudintermedius ED99

<400> SEQUENCE: 136

Glu Val Asp His Ile Phe Pro Arg Ser Phe Ile Lys Asp Asp Ser Ile
1               5                   10                  15

Asp Asn Lys Val Leu Val Ile Lys Lys Met Asn
            20                  25


<210> SEQ ID NO 137
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 137

Glu Val Asp His Ile Ile Pro Arg Ser Tyr Ile Lys Asp Asp Ser Phe
1               5                   10                  15

Glu Asn Lys Val Leu Val Tyr Arg Glu Glu Asn
            20                  25


<210> SEQ ID NO 138
<211> LENGTH: 27
<212> TYPE: PRT
<213> ORGANISM: Bifidobacterium bifidum S17

<400> SEQUENCE: 138

Asp Ile Asp His Ile Ile Pro Gln Ala Val Thr Gln Asn Asp Ser Ile
1               5                   10                  15

Asp Asn Arg Val Leu Val Ala Arg Ala Glu Asn
            20                  25
```

<210> SEQ ID NO 139
<211> LENGTH: 27
<212> TYPE: PRT
<213> ORGANISM: Mycoplasma gallisepticum str. F

<400> SEQUENCE: 139

```
Glu Ile Asp His Ile Ile Pro Tyr Ser Ile Ser Phe Asp Asp Ser Ser
1               5                   10                  15

Ser Asn Lys Leu Leu Val Leu Ala Glu Ser Asn
            20                  25
```

<210> SEQ ID NO 140
<211> LENGTH: 27
<212> TYPE: PRT
<213> ORGANISM: Mycoplasma canis PG 14

<400> SEQUENCE: 140

```
Glu Ile Asp His Ile Ile Pro Tyr Ser Leu Cys Phe Asp Asp Ser Ser
1               5                   10                  15

Ala Asn Lys Val Leu Val His Lys Gln Ser Asn
            20                  25
```

<210> SEQ ID NO 141
<211> LENGTH: 27
<212> TYPE: PRT
<213> ORGANISM: Ilyobacter polytropus DSM 2926

<400> SEQUENCE: 141

```
Asp Ile Asp His Ile Ile Pro Tyr Ser Arg Ser Met Asp Asp Ser Tyr
1               5                   10                  15

Ser Asn Lys Val Leu Val Leu Ser Gly Glu Asn
            20                  25
```

<210> SEQ ID NO 142
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 142

```
Asp Ile Asp His Ile Ile Pro Tyr Ser Lys Ser Met Asp Asp Ser Phe
1               5                   10                  15

Asn Asn Lys Val Leu Cys Leu Ala Glu Glu Asn
            20                  25
```

<210> SEQ ID NO 143
<211> LENGTH: 27
<212> TYPE: PRT
<213> ORGANISM: Campylobacter jejuni

<400> SEQUENCE: 143

```
Glu Ile Asp His Ile Tyr Pro Tyr Ser Arg Ser Phe Asp Asp Ser Tyr
1               5                   10                  15

Met Asn Lys Val Leu Val Phe Thr Lys Gln Asn
            20                  25
```

<210> SEQ ID NO 144
<211> LENGTH: 27
<212> TYPE: PRT
<213> ORGANISM: Clostridium cellulolyticum H10

<400> SEQUENCE: 144

```
Gln Ile Asp His Ile Tyr Pro Tyr Ser Arg Ser Met Asp Asp Ser Tyr
1               5                   10                  15

Met Asn Lys Val Leu Val Leu Thr Asp Glu Asn
            20                  25
```

<210> SEQ ID NO 145
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 145

```
Glu Ile Asp His Ile Ile Pro Phe Ser Arg Ser Phe Asp Asp Ser Leu
1               5                   10                  15

Ser Asn Lys Ile Leu Val Leu Gly Ser Glu Asn
            20                  25
```

<210> SEQ ID NO 146
<211> LENGTH: 27
<212> TYPE: PRT
<213> ORGANISM: N. meningitides

<400> SEQUENCE: 146

```
Glu Ile Asp His Ala Leu Pro Phe Ser Arg Thr Trp Asp Asp Ser Phe
1               5                   10                  15

Asn Asn Lys Val Leu Val Leu Gly Ser Glu Asn
            20                  25
```

<210> SEQ ID NO 147
<211> LENGTH: 27
<212> TYPE: PRT
<213> ORGANISM: Pasteurella multocida str. Pm70

<400> SEQUENCE: 147

```
Glu Ile Asp His Ala Leu Pro Phe Ser Arg Thr Trp Asp Asp Ser Phe
1               5                   10                  15

Asn Asn Lys Val Leu Val Leu Ala Ser Glu Asn
            20                  25
```

<210> SEQ ID NO 148
<211> LENGTH: 27
<212> TYPE: PRT
<213> ORGANISM: Enterococcus faecalis TX0012

<400> SEQUENCE: 148

```
Glu Ile Asp His Ile Ile Pro Ile Ser Ile Ser Leu Asp Asp Ser Ile
1               5                   10                  15

Asn Asn Lys Val Leu Val Leu Ser Lys Ala Asn
            20                  25
```

<210> SEQ ID NO 149
<211> LENGTH: 27
<212> TYPE: PRT
<213> ORGANISM: Eubacterium dolichum DSM 3991

<400> SEQUENCE: 149

```
Glu Val Asp His Ile Ile Pro Ile Ser Ile Ser Leu Asp Asp Ser Ile
1               5                   10                  15

Thr Asn Lys Val Leu Val Thr His Arg Glu Asn
            20                  25
```

<210> SEQ ID NO 150
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 150

Gln Val Asp His Ala Leu Pro Tyr Ser Arg Ser Tyr Asp Asp Ser Lys
1 5 10 15

Asn Asn Lys Val Leu Val Leu Thr His Glu Asn
20 25

<210> SEQ ID NO 151
<211> LENGTH: 27
<212> TYPE: PRT
<213> ORGANISM: Streptococcus thermophilus LMD-9

<400> SEQUENCE: 151

Glu Val Asp His Ile Leu Pro Leu Ser Ile Thr Phe Asp Asp Ser Leu
1 5 10 15

Ala Asn Lys Val Leu Val Tyr Ala Thr Ala Asn
20 25

<210> SEQ ID NO 152
<211> LENGTH: 27
<212> TYPE: PRT
<213> ORGANISM: Eubacterium rectale

<400> SEQUENCE: 152

Glu Ile Asp His Ile Ile Pro Arg Ser Ile Ser Phe Asp Asp Ala Arg
1 5 10 15

Ser Asn Lys Val Leu Val Tyr Arg Ser Glu Asn
20 25

<210> SEQ ID NO 153
<211> LENGTH: 27
<212> TYPE: PRT
<213> ORGANISM: Staphylococcus lugdunensis M23590

<400> SEQUENCE: 153

Glu Val Asp His Ile Ile Pro Arg Ser Val Ser Phe Asp Asn Ser Tyr
1 5 10 15

His Asn Lys Val Leu Val Lys Gln Ser Glu Asn
20 25

<210> SEQ ID NO 154
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 154

Asp Ile Asp His Ile Leu Pro Tyr Ser Ile Thr Phe Asp Asp Ser Phe
1 5 10 15

Arg Asn Lys Val Leu Val Thr Ser Gln Glu Asn
20 25

<210> SEQ ID NO 155
<211> LENGTH: 27
<212> TYPE: PRT
<213> ORGANISM: Wolinella succinogenes DSM 1740

<400> SEQUENCE: 155

Glu Ile Asp His Ile Leu Pro Arg Ser Arg Ser Ala Asp Asp Ser Phe
1 5 10 15

Ala Asn Lys Val Leu Cys Leu Ala Arg Ala Asn
20 25

<210> SEQ ID NO 156
<211> LENGTH: 27
<212> TYPE: PRT
<213> ORGANISM: Cand. Puniceispirillum marinum

<400> SEQUENCE: 156

Glu Ile Glu His Leu Leu Pro Phe Ser Leu Thr Leu Asp Asp Ser Met
1 5 10 15

Ala Asn Lys Thr Val Cys Phe Arg Gln Ala Asn
20 25

<210> SEQ ID NO 157
<211> LENGTH: 27
<212> TYPE: PRT
<213> ORGANISM: Azospirillum sp. B510

<400> SEQUENCE: 157

Asp Ile Asp His Ile Leu Pro Phe Ser Val Ser Leu Asp Asp Ser Ala
1 5 10 15

Ala Asn Lys Val Val Cys Leu Arg Glu Ala Asn
20 25

<210> SEQ ID NO 158
<211> LENGTH: 27
<212> TYPE: PRT
<213> ORGANISM: Bradyrhizobium sp. BTAi1

<400> SEQUENCE: 158

Asp Ile Asp His Leu Ile Pro Phe Ser Ile Ser Trp Asp Asp Ser Ala
1 5 10 15

Ala Asn Lys Val Val Cys Met Arg Tyr Ala Asn
20 25

<210> SEQ ID NO 159
<211> LENGTH: 27
<212> TYPE: PRT
<213> ORGANISM: Nitrobacter hamburgensis X14

<400> SEQUENCE: 159

Asp Ile Asp His Ile Leu Pro Val Ala Met Thr Leu Asp Asp Ser Pro
1 5 10 15

Ala Asn Lys Ile Ile Cys Met Arg Tyr Ala Asn
20 25

<210> SEQ ID NO 160
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 160

Asp Val Asp His Ile Leu Pro Tyr Ser Arg Thr Leu Asp Asp Ser Phe
1 5 10 15

Pro Asn Arg Thr Leu Cys Leu Arg Glu Ala Asn
20 25

<210> SEQ ID NO 161
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 161

Glu Ile Glu His Ile Leu Pro Phe Ser Arg Thr Leu Asp Asp Ser Leu
1               5                   10                  15

Asn Asn Arg Thr Val Ala Met Arg Arg Ala Asn
            20                  25

<210> SEQ ID NO 162
<211> LENGTH: 27
<212> TYPE: PRT
<213> ORGANISM: Lactobacillus coryniformis KCTC 3535

<400> SEQUENCE: 162

Glu Val Asp His Ile Ile Pro Tyr Ser Ile Ser Trp Asp Asp Ser Tyr
1               5                   10                  15

Thr Asn Lys Val Leu Thr Ser Ala Lys Cys Asn
            20                  25

<210> SEQ ID NO 163
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 163

Gln Val Asp His Ile Leu Pro Trp Ser Arg Phe Gly Asp Asp Ser Tyr
1               5                   10                  15

Leu Asn Lys Thr Leu Cys Thr Ala Arg Ser Asn
            20                  25

<210> SEQ ID NO 164
<211> LENGTH: 27
<212> TYPE: PRT
<213> ORGANISM: Ralstonia syzygii R24

<400> SEQUENCE: 164

Gln Val Asp His Ile Leu Pro Phe Ser Lys Thr Leu Asp Asp Ser Phe
1               5                   10                  15

Ala Asn Lys Val Leu Ala Gln His Asp Ala Asn
            20                  25

<210> SEQ ID NO 165
<211> LENGTH: 27
<212> TYPE: PRT
<213> ORGANISM: Helicobacter mustelae 12198

<400> SEQUENCE: 165

Gln Ile Asp His Ala Phe Pro Leu Ser Arg Ser Leu Asp Asp Ser Gln
1               5                   10                  15

Ser Asn Lys Val Leu Cys Leu Thr Ser Ser Asn
            20                  25

<210> SEQ ID NO 166
<211> LENGTH: 27
<212> TYPE: PRT

<213> ORGANISM: Mycoplasma mobile 163K

<400> SEQUENCE: 166

Asp Ile Asp His Ile Val Pro Arg Ser Ile Ser Phe Asp Asp Ser Phe
1               5                   10                  15

Ser Asn Leu Val Ile Val Asn Lys Leu Asp Asn
            20                  25

<210> SEQ ID NO 167
<211> LENGTH: 27
<212> TYPE: PRT
<213> ORGANISM: Mycoplasma ovipneumoniae SC01

<400> SEQUENCE: 167

Glu Ile Glu His Ile Ile Pro Tyr Ser Met Ser Tyr Asp Asn Ser Gln
1               5                   10                  15

Ala Asn Lys Ile Leu Thr Glu Lys Ala Glu Asn
            20                  25

<210> SEQ ID NO 168
<211> LENGTH: 27
<212> TYPE: PRT
<213> ORGANISM: Mycoplasma synoviae 53

<400> SEQUENCE: 168

Glu Ile Asp His Val Ile Pro Tyr Ser Lys Ser Ala Asp Asp Ser Trp
1               5                   10                  15

Phe Asn Lys Leu Leu Val Lys Lys Ser Thr Asn
            20                  25

<210> SEQ ID NO 169
<211> LENGTH: 27
<212> TYPE: PRT
<213> ORGANISM: Aminomonas paucivorans DSM 12260

<400> SEQUENCE: 169

Glu Met Asp His Ile Leu Pro Tyr Ser Arg Ser Leu Asp Asn Gly Trp
1               5                   10                  15

His Asn Arg Val Leu Val His Gly Lys Asp Asn
            20                  25

<210> SEQ ID NO 170
<211> LENGTH: 27
<212> TYPE: PRT
<213> ORGANISM: Ruminococcus albus 8

<400> SEQUENCE: 170

Glu Val Asp His Ile Val Pro Tyr Ser Leu Ile Leu Asp Asn Thr Ile
1               5                   10                  15

Asn Asn Lys Ala Leu Val Tyr Ala Glu Glu Asn
            20                  25

<210> SEQ ID NO 171
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 171

Glu Ile Glu His Val Ile Pro Gln Ser Leu Tyr Phe Asp Asp Ser Phe
1               5                   10                  15

-continued

```
Ser Asn Lys Val Ile Cys Glu Ala Glu Val Asn
            20                  25


<210> SEQ ID NO 172
<211> LENGTH: 27
<212> TYPE: PRT
<213> ORGANISM: Bacteroides fragilis, NCTC 9343

<400> SEQUENCE: 172

Asp Ile Glu His Ile Ile Pro Gln Ala Arg Leu Phe Asp Asp Ser Phe
1               5                   10                  15

Ser Asn Lys Thr Leu Glu Ala Arg Ser Val Asn
            20                  25


<210> SEQ ID NO 173
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 173

Glu Ile Glu His Ile Val Pro Lys Ala Arg Val Phe Asp Asp Ser Phe
1               5                   10                  15

Ser Asn Lys Thr Leu Thr Phe His Arg Ile Asn
            20                  25


<210> SEQ ID NO 174
<211> LENGTH: 28
<212> TYPE: PRT
<213> ORGANISM: Finegoldia magna

<400> SEQUENCE: 174

Asp Lys Asp His Ile Ile Pro Gln Ser Met Lys Lys Asp Asp Ser Ile
1               5                   10                  15

Ile Asn Asn Leu Val Leu Val Asn Lys Asn Ala Asn
            20                  25


<210> SEQ ID NO 175
<211> LENGTH: 27
<212> TYPE: PRT
<213> ORGANISM: Parvibaculum lavamentivorans DS-1

<400> SEQUENCE: 175

Glu Val Glu His Ile Trp Pro Arg Ser Arg Ser Phe Asp Asn Ser Pro
1               5                   10                  15

Arg Asn Lys Thr Leu Cys Arg Lys Asp Val Asn
            20                  25


<210> SEQ ID NO 176
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 176

Ile Val Asn His Ile Ile Pro Tyr Asn Arg Ser Phe Asp Asp Thr Tyr
1               5                   10                  15

His Asn Arg Val Leu Thr Leu Thr Glu Thr Lys
            20                  25


<210> SEQ ID NO 177
```

<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 177

Asp Met Glu His Thr Ile Pro Lys Ser Ile Ser Phe Asp Asn Ser Asp
1 5 10 15

Gln Asn Leu Thr Leu Cys Glu Ser Tyr Tyr Asn
20 25

<210> SEQ ID NO 178
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 178

Asp Ile Glu His Thr Ile Pro Arg Ser Ala Gly Gly Asp Ser Thr Lys
1 5 10 15

Met Asn Leu Thr Leu Cys Ser Ser Arg Phe Asn
20 25

<210> SEQ ID NO 179
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 179

Asp Ile Glu His Thr Ile Pro Arg Ser Ile Ser Gln Asp Asn Ser Gln
1 5 10 15

Met Asn Lys Thr Leu Cys Ser Leu Lys Phe Asn
20 25

<210> SEQ ID NO 180
<211> LENGTH: 27
<212> TYPE: PRT
<213> ORGANISM: Rhodospirillum rubrum

<400> SEQUENCE: 180

Asp Ile Asp His Val Ile Pro Leu Ala Arg Gly Gly Arg Asp Ser Leu
1 5 10 15

Asp Asn Met Val Leu Cys Gln Ser Asp Ala Asn
20 25

<210> SEQ ID NO 181
<211> LENGTH: 27
<212> TYPE: PRT
<213> ORGANISM: Elusimicrobium minutum Pei191

<400> SEQUENCE: 181

Asp Ile Glu His Leu Phe Pro Ile Ala Glu Ser Glu Asp Asn Gly Arg
1 5 10 15

Asn Asn Leu Val Ile Ser His Ser Ala Cys Asn
20 25

<210> SEQ ID NO 182
<211> LENGTH: 27
<212> TYPE: PRT
<213> ORGANISM: Sphaerochaeta globus str. Buddy

<400> SEQUENCE: 182

Asp Val Asp His Ile Phe Pro Arg Asp Asp Thr Ala Asp Asn Ser Tyr
1 5 10 15

Gly Asn Lys Val Val Ala His Arg Gln Cys Asn
20 25

<210> SEQ ID NO 183
<211> LENGTH: 27
<212> TYPE: PRT
<213> ORGANISM: Nitratifractor salsuginis DSM 16511

<400> SEQUENCE: 183

Asp Ile Glu His Ile Val Pro Gln Ser Leu Gly Gly Leu Ser Thr Asp
1 5 10 15

Tyr Asn Thr Ile Val Thr Leu Lys Ser Val Asn
20 25

<210> SEQ ID NO 184
<211> LENGTH: 27
<212> TYPE: PRT
<213> ORGANISM: Acidothermus cellulolyticus 11B

<400> SEQUENCE: 184

Glu Leu Asp His Ile Val Pro Arg Thr Asp Gly Gly Ser Asn Arg His
1 5 10 15

Glu Asn Leu Ala Ile Thr Cys Gly Ala Cys Asn
20 25

<210> SEQ ID NO 185
<211> LENGTH: 28
<212> TYPE: PRT
<213> ORGANISM: Bifidobacterium longum DJO10A

<400> SEQUENCE: 185

Glu Met Asp His Ile Val Pro Arg Lys Gly Val Gly Ser Thr Asn Thr
1 5 10 15

Arg Thr Asn Phe Ala Ala Val Cys Ala Glu Cys Asn
20 25

<210> SEQ ID NO 186
<211> LENGTH: 28
<212> TYPE: PRT
<213> ORGANISM: Artificial Sequence
<220> FEATURE:
<223> OTHER INFORMATION: HNH-LIKE domain

<400> SEQUENCE: 186

Glu Met Asp His Ile Val Pro Arg Lys Gly Val Gly Ser Thr Asn Thr
1 5 10 15

Arg Val Asn Leu Ala Ala Ala Cys Ala Ala Cys Asn
20 25

<210> SEQ ID NO 187
<211> LENGTH: 28
<212> TYPE: PRT
<213> ORGANISM: Artificial Sequence
<220> FEATURE:
<223> OTHER INFORMATION: HNH-LIKE domain

<400> SEQUENCE: 187

Glu Met Asp His Ile Val Pro Arg Ala Gly Gln Gly Ser Thr Asn Thr
1 5 10 15

Arg Glu Asn Leu Val Ala Val Cys His Arg Cys Asn
20 25

<210> SEQ ID NO 188
<211> LENGTH: 33
<212> TYPE: PRT
<213> ORGANISM: Artificial Sequence
<220> FEATURE:
<223> OTHER INFORMATION: HNH-LIKE domain

<400> SEQUENCE: 188

Glu Ile Asp His Ile Leu Pro Arg Ser Leu Ile Lys Asp Ala Arg Gly
1 5 10 15

Ile Val Phe Asn Ala Glu Pro Asn Leu Ile Tyr Ala Ser Ser Arg Gly
20 25 30

Asn

<210> SEQ ID NO 189
<211> LENGTH: 33
<212> TYPE: PRT
<213> ORGANISM: Artificial Sequence
<220> FEATURE:
<223> OTHER INFORMATION: HNH-LIKE domain

<400> SEQUENCE: 189

Glu Ile Asp His Ile Ile Pro Arg Ser Leu Thr Gly Arg Thr Lys Lys
1 5 10 15

Thr Val Phe Asn Ser Glu Ala Asn Leu Ile Tyr Cys Ser Ser Lys Gly
20 25 30

Asn

<210> SEQ ID NO 190
<211> LENGTH: 33
<212> TYPE: PRT
<213> ORGANISM: Artificial Sequence
<220> FEATURE:
<223> OTHER INFORMATION: HNH-LIKE domain

<400> SEQUENCE: 190

Glu Ile Asp His Ile Ile Pro Arg Ser Leu Thr Leu Lys Lys Ser Glu
1 5 10 15

Ser Ile Tyr Asn Ser Glu Val Asn Leu Ile Phe Val Ser Ala Gln Gly
20 25 30

Asn

<210> SEQ ID NO 191
<211> LENGTH: 33
<212> TYPE: PRT
<213> ORGANISM: Legionella pneumophila str. Paris

<400> SEQUENCE: 191

Glu Ile Asp His Ile Tyr Pro Arg Ser Leu Ser Lys Lys His Phe Gly
1 5 10 15

Val Ile Phe Asn Ser Glu Val Asn Leu Ile Tyr Cys Ser Ser Gln Gly
20 25 30

Asn

<210> SEQ ID NO 192
<211> LENGTH: 33
<212> TYPE: PRT
<213> ORGANISM: Wolinella succinogenes DSM 1740

<400> SEQUENCE: 192

Glu Ile Asp His Ile Leu Pro Arg Ser His Thr Leu Lys Ile Tyr Gly
1 5 10 15

Thr Val Phe Asn Pro Glu Gly Asn Leu Ile Tyr Val His Gln Lys Cys
20 25 30

Asn

<210> SEQ ID NO 193
<211> LENGTH: 30
<212> TYPE: PRT
<213> ORGANISM: Artificial Sequence
<220> FEATURE:
<223> OTHER INFORMATION: HNH-LIKE domain

<400> SEQUENCE: 193

Glu Leu Asp His Ile Ile Pro Arg Ser His Lys Lys Tyr Gly Thr Leu
1 5 10 15

Asn Asp Glu Ala Asn Leu Ile Cys Val Thr Arg Gly Asp Asn
20 25 30

<210> SEQ ID NO 194
<211> LENGTH: 27
<212> TYPE: PRT
<213> ORGANISM: Akkermansia muciniphila

<400> SEQUENCE: 194

Glu Leu Glu His Ile Val Pro His Ser Phe Arg Gln Ser Asn Ala Leu
1 5 10 15

Ser Ser Leu Val Leu Thr Trp Pro Gly Val Asn
20 25

<210> SEQ ID NO 195
<211> LENGTH: 27
<212> TYPE: PRT
<213> ORGANISM: Solobacterium moorei F0204

<400> SEQUENCE: 195

Asp Ile Asp His Ile Tyr Pro Arg Ser Lys Ile Lys Asp Asp Ser Ile
1 5 10 15

Thr Asn Arg Val Leu Val Glu Lys Asp Ile Asn
20 25

<210> SEQ ID NO 196
<211> LENGTH: 28
<212> TYPE: PRT
<213> ORGANISM: Veillonella atypica ACS-134-V-Col7a

<400> SEQUENCE: 196

Tyr Asp Ile Asp His Ile Tyr Pro Arg Ser Leu Thr Lys Asp Asp Ser
1 5 10 15

Phe Asp Asn Leu Val Leu Cys Glu Arg Thr Ala Asn
20 25

<210> SEQ ID NO 197
<211> LENGTH: 28
<212> TYPE: PRT
<213> ORGANISM: Fusobacterium nucleatum

<400> SEQUENCE: 197

Asp Ile Asp His Ile Tyr Pro Arg Ser Lys Val Ile Lys Asp Asp Ser
1 5 10 15

```
Phe Asp Asn Leu Val Leu Val Leu Lys Asn Glu Asn
            20                  25


<210> SEQ ID NO 198
<211> LENGTH: 27
<212> TYPE: PRT
<213> ORGANISM: Filifactor alocis

<400> SEQUENCE: 198

Asp Arg Asp His Ile Tyr Pro Gln Ser Lys Ile Lys Asp Asp Ser Ile
1               5                   10                  15

Asp Asn Leu Val Leu Val Asn Lys Thr Tyr Asn
            20                  25


<210> SEQ ID NO 199
<211> LENGTH: 5
<212> TYPE: DNA
<213> ORGANISM: S. thermophilus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 199

nggng                                                                   5


<210> SEQ ID NO 200
<211> LENGTH: 7
<212> TYPE: DNA
<213> ORGANISM: S. thermophilus
<220> FEATURE:
<221> NAME/KEY: misc_feature
<222> LOCATION: (1)..(2)
<223> OTHER INFORMATION: n is a, c, g, or t

<400> SEQUENCE: 200

nnagaaw                                                                 7


<210> SEQ ID NO 201
<211> LENGTH: 4
<212> TYPE: DNA
<213> ORGANISM: S. mutans
<220> FEATURE:
<221> NAME/KEY: misc_feature
<222> LOCATION: (1)..(1)
<223> OTHER INFORMATION: n is a, c, g, or t

<400> SEQUENCE: 201

naar                                                                    4


<210> SEQ ID NO 202
<211> LENGTH: 5
<212> TYPE: DNA
<213> ORGANISM: S. aureus
<220> FEATURE:
<221> NAME/KEY: misc_feature
<222> LOCATION: (1)..(2)
<223> OTHER INFORMATION: n is a, c, g, or t

<400> SEQUENCE: 202

nngrr                                                                   5
```

<210> SEQ ID NO 203
<211> LENGTH: 6
<212> TYPE: DNA
<213> ORGANISM: S. aureus
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 203 nngrrn 6

<210> SEQ ID NO 204
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 204 nngrrt 6

<210> SEQ ID NO 205
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 205 nngrrv 6

<210> SEQ ID NO 206
<211> LENGTH: 20
<212> TYPE: DNA
<213> ORGANISM: Artificial Sequence
<220> FEATURE:
<223> OTHER INFORMATION: Synthetic

<400> SEQUENCE: 206
gtaacggcag acttctcctc 20

<210> SEQ ID NO 207
<211> LENGTH: 65
<212> TYPE: DNA
<213> ORGANISM: Artificial Sequence
<220> FEATURE:
<223> OTHER INFORMATION: Synthetic

<400> SEQUENCE: 207
caccgctagc taatacgact cactatagta acggcagact tctcctcgtt ttagagctag 60
aaata 65

<210> SEQ ID NO 208
<211> LENGTH: 20
<212> TYPE: DNA

<213> ORGANISM: Artificial Sequence
<220> FEATURE:
<223> OTHER INFORMATION: Synthetic

<400> SEQUENCE: 208
aaggtgaacg tggatgaagt 20

<210> SEQ ID NO 209
<211> LENGTH: 19
<212> TYPE: DNA
<213> ORGANISM: Artificial Sequence
<220> FEATURE:
<223> OTHER INFORMATION: Synthetic

<400> SEQUENCE: 209
taatacgact cactatagg 19

<210> SEQ ID NO 210
<211> LENGTH: 18
<212> TYPE: DNA
<213> ORGANISM: Artificial Sequence
<220> FEATURE:
<223> OTHER INFORMATION: Synthetic

<400> SEQUENCE: 210
taatacgact cactatag 18

<210> SEQ ID NO 211
<211> LENGTH: 17
<212> TYPE: DNA
<213> ORGANISM: Artificial Sequence
<220> FEATURE:
<223> OTHER INFORMATION: Synthetic

<400> SEQUENCE: 211
taatacgact cactata 17

<210> SEQ ID NO 212
<211> LENGTH: 8
<212> TYPE: DNA
<213> ORGANISM: N. meningitidis
<220> FEATURE:
<221> NAME/KEY: misc_feature
<223> OTHER INFORMATION: N. meningitidis PAM
<220> FEATURE:
<221> NAME/KEY: misc_feature
<222> LOCATION: (1)..(4)
<223> OTHER INFORMATION: any n is a or g

<400> SEQUENCE: 212 nnnngatt 8

<210> SEQ ID NO 213
<211> LENGTH: 8
<212> TYPE: DNA
<213> ORGANISM: N. meningitidis
<220> FEATURE:
<221> NAME/KEY: misc_feature
<223> OTHER INFORMATION: N. meningitidis PAM
<220> FEATURE:
<221> NAME/KEY: misc_feature
<222> LOCATION: (1)..(4)
<223> OTHER INFORMATION: any n is a or g

<400> SEQUENCE: 213 nnnngctt 8

-continued

<210> SEQ ID NO 214
<211> LENGTH: 17
<212> TYPE: RNA
<213> ORGANISM: Artificial Sequence
<220> FEATURE:
<223> OTHER INFORMATION: Synthetic

<400> SEQUENCE: 214
gcgcuucugg uggcccu 17

<210> SEQ ID NO 215
<211> LENGTH: 22
<212> TYPE: RNA
<213> ORGANISM: Artificial Sequence
<220> FEATURE:
<223> OTHER INFORMATION: Synthetic

<400> SEQUENCE: 215
gcuccaagga aagcauagag ga 22

<210> SEQ ID NO 216
<211> LENGTH: 20
<212> TYPE: RNA
<213> ORGANISM: Artificial Sequence
<220> FEATURE:
<223> OTHER INFORMATION: Synthetic

<400> SEQUENCE: 216
gcugccgccc agugggacuu 20

<210> SEQ ID NO 217
<211> LENGTH: 20
<212> TYPE: RNA
<213> ORGANISM: Artificial Sequence
<220> FEATURE:
<223> OTHER INFORMATION: Synthetic

<400> SEQUENCE: 217
guaacggcag acuucuccuc 20

<210> SEQ ID NO 218
<211> LENGTH: 20
<212> TYPE: RNA
<213> ORGANISM: Artificial Sequence
<220> FEATURE:
<223> OTHER INFORMATION: Synthetic

<400> SEQUENCE: 218
guccccucca ccccacagug 20

<210> SEQ ID NO 219
<211> LENGTH: 20
<212> TYPE: RNA
<213> ORGANISM: Artificial Sequence
<220> FEATURE:
<223> OTHER INFORMATION: Synthetic

<400> SEQUENCE: 219
gagugagagc ccgcccaggu 20

<210> SEQ ID NO 220
<211> LENGTH: 20
<212> TYPE: RNA
<213> ORGANISM: Artificial Sequence
<220> FEATURE:
<223> OTHER INFORMATION: Synthetic

<400> SEQUENCE: 220
gcacugucac ugcuugcagc 20

<210> SEQ ID NO 221
<211> LENGTH: 20
<212> TYPE: RNA
<213> ORGANISM: Artificial Sequence
<220> FEATURE:
<223> OTHER INFORMATION: Synthetic

<400> SEQUENCE: 221
gacggcuccc aucucagggu 20

<210> SEQ ID NO 222
<211> LENGTH: 20
<212> TYPE: RNA
<213> ORGANISM: Artificial Sequence
<220> FEATURE:
<223> OTHER INFORMATION: Synthetic

<400> SEQUENCE: 222
guagcucccu ccuuuucuau 20

<210> SEQ ID NO 223
<211> LENGTH: 20
<212> TYPE: RNA
<213> ORGANISM: Artificial Sequence
<220> FEATURE:
<223> OTHER INFORMATION: Synthetic

<400> SEQUENCE: 223
gaagagcuca gauagaaaag 20

<210> SEQ ID NO 224
<211> LENGTH: 24
<212> TYPE: RNA
<213> ORGANISM: Artificial Sequence
<220> FEATURE:
<223> OTHER INFORMATION: Synthetic

<400> SEQUENCE: 224
gaagacggcu cccaucucag ggug 24

<210> SEQ ID NO 225
<211> LENGTH: 24
<212> TYPE: RNA
<213> ORGANISM: Artificial Sequence
<220> FEATURE:
<223> OTHER INFORMATION: Synthetic

<400> SEQUENCE: 225
gagaguagcu cccuccuuuu cuau 24

<210> SEQ ID NO 226
<211> LENGTH: 24
<212> TYPE: RNA
<213> ORGANISM: Artificial Sequence
<220> FEATURE:
<223> OTHER INFORMATION: Synthetic

<400> SEQUENCE: 226
gugagagccc gcccaggucu gggu 24

<210> SEQ ID NO 227
<211> LENGTH: 24

<212> TYPE: RNA
<213> ORGANISM: Artificial Sequence
<220> FEATURE:
<223> OTHER INFORMATION: Synthetic

<400> SEQUENCE: 227
gggcugggaa gacggcuccc aucu 24

<210> SEQ ID NO 228
<211> LENGTH: 24
<212> TYPE: RNA
<213> ORGANISM: Artificial Sequence
<220> FEATURE:
<223> OTHER INFORMATION: Synthetic

<400> SEQUENCE: 228
ggaagacggc ucccaucuca gggu 24

<210> SEQ ID NO 229
<211> LENGTH: 17
<212> TYPE: RNA
<213> ORGANISM: Artificial Sequence
<220> FEATURE:
<223> OTHER INFORMATION: Synthetic

<400> SEQUENCE: 229
gagaaccggc cucgcuc 17

<210> SEQ ID NO 230
<211> LENGTH: 17
<212> TYPE: RNA
<213> ORGANISM: Artificial Sequence
<220> FEATURE:
<223> OTHER INFORMATION: Synthetic

<400> SEQUENCE: 230
gagagcccgc ccagguc 17

<210> SEQ ID NO 231
<211> LENGTH: 17
<212> TYPE: RNA
<213> ORGANISM: Artificial Sequence
<220> FEATURE:
<223> OTHER INFORMATION: Synthetic

<400> SEQUENCE: 231
ggagugagag cccgccc 17

<210> SEQ ID NO 232
<211> LENGTH: 17
<212> TYPE: RNA
<213> ORGANISM: Artificial Sequence
<220> FEATURE:
<223> OTHER INFORMATION: Synthetic

<400> SEQUENCE: 232
gcucagauag aaaagga 17

<210> SEQ ID NO 233
<211> LENGTH: 17
<212> TYPE: RNA
<213> ORGANISM: Artificial Sequence
<220> FEATURE:
<223> OTHER INFORMATION: Synthetic

<400> SEQUENCE: 233
gcucccaucu cagggug 17

<210> SEQ ID NO 234
<211> LENGTH: 20
<212> TYPE: RNA
<213> ORGANISM: Artificial Sequence
<220> FEATURE:
<223> OTHER INFORMATION: Synthetic

<400> SEQUENCE: 234
gggcgggcuc ucacuccaug 20

<210> SEQ ID NO 235
<211> LENGTH: 20
<212> TYPE: RNA
<213> ORGANISM: Artificial Sequence
<220> FEATURE:
<223> OTHER INFORMATION: Synthetic

<400> SEQUENCE: 235
gugagagccc gcccaggucu 20

<210> SEQ ID NO 236
<211> LENGTH: 20
<212> TYPE: RNA
<213> ORGANISM: Artificial Sequence
<220> FEATURE:
<223> OTHER INFORMATION: Synthetic

<400> SEQUENCE: 236
gggaagacgg cucccaucuc 20

<210> SEQ ID NO 237
<211> LENGTH: 20
<212> TYPE: RNA
<213> ORGANISM: Artificial Sequence
<220> FEATURE:
<223> OTHER INFORMATION: Synthetic

<400> SEQUENCE: 237
ggcucccauc ucagggugag 20

<210> SEQ ID NO 238
<211> LENGTH: 20
<212> TYPE: RNA
<213> ORGANISM: Artificial Sequence
<220> FEATURE:
<223> OTHER INFORMATION: Synthetic

<400> SEQUENCE: 238
ggaagacggc ucccaucuca 20

<210> SEQ ID NO 239
<211> LENGTH: 20
<212> TYPE: RNA
<213> ORGANISM: Artificial Sequence
<220> FEATURE:
<223> OTHER INFORMATION: Synthetic

<400> SEQUENCE: 239
gcacugucac ugcuugcagc 20

<210> SEQ ID NO 240
<211> LENGTH: 20
<212> TYPE: RNA
<213> ORGANISM: Artificial Sequence
<220> FEATURE:
<223> OTHER INFORMATION: Synthetic

<400> SEQUENCE: 240
gacggcuccc aucucagggu 20

<210> SEQ ID NO 241
<211> LENGTH: 20
<212> TYPE: RNA
<213> ORGANISM: Artificial Sequence
<220> FEATURE:
<223> OTHER INFORMATION: Synthetic

<400> SEQUENCE: 241
guagcucccu ccuuuucuau 20

<210> SEQ ID NO 242
<211> LENGTH: 20
<212> TYPE: RNA
<213> ORGANISM: Artificial Sequence
<220> FEATURE:
<223> OTHER INFORMATION: Synthetic

<400> SEQUENCE: 242
gaagagcuca gauagaaaag 20

<210> SEQ ID NO 243
<211> LENGTH: 20
<212> TYPE: RNA
<213> ORGANISM: Artificial Sequence
<220> FEATURE:
<223> OTHER INFORMATION: Synthetic

<400> SEQUENCE: 243
gagcccgccc aggucugggu 20

<210> SEQ ID NO 244
<211> LENGTH: 24
<212> TYPE: RNA
<213> ORGANISM: Artificial Sequence
<220> FEATURE:
<223> OTHER INFORMATION: Synthetic

<400> SEQUENCE: 244
gaagacggcu cccaucucag ggug 24

<210> SEQ ID NO 245
<211> LENGTH: 24
<212> TYPE: RNA
<213> ORGANISM: Artificial Sequence
<220> FEATURE:
<223> OTHER INFORMATION: Synthetic

<400> SEQUENCE: 245
gagaguagcu cccuccuuuu cuau 24

<210> SEQ ID NO 246
<211> LENGTH: 24
<212> TYPE: RNA
<213> ORGANISM: Artificial Sequence
<220> FEATURE:
<223> OTHER INFORMATION: Synthetic

<400> SEQUENCE: 246
gggcugggaa gacggcuccc aucu 24

-continued

<210> SEQ ID NO 247
<211> LENGTH: 24
<212> TYPE: RNA
<213> ORGANISM: Artificial Sequence
<220> FEATURE:
<223> OTHER INFORMATION: Synthetic

<400> SEQUENCE: 247
ggaagacggc ucccaucuca gggu 24

<210> SEQ ID NO 248
<211> LENGTH: 24
<212> TYPE: RNA
<213> ORGANISM: Artificial Sequence
<220> FEATURE:
<223> OTHER INFORMATION: Synthetic

<400> SEQUENCE: 248
gggcacuguc acugcuugca gccu 24

<210> SEQ ID NO 249
<211> LENGTH: 17
<212> TYPE: RNA
<213> ORGANISM: Artificial Sequence
<220> FEATURE:
<223> OTHER INFORMATION: Synthetic

<400> SEQUENCE: 249
aagacggcuc ccaucuc 17

<210> SEQ ID NO 250
<211> LENGTH: 17
<212> TYPE: RNA
<213> ORGANISM: Artificial Sequence
<220> FEATURE:
<223> OTHER INFORMATION: Synthetic

<400> SEQUENCE: 250
gagaaccggc cucgcuc 17

<210> SEQ ID NO 251
<211> LENGTH: 17
<212> TYPE: RNA
<213> ORGANISM: Artificial Sequence
<220> FEATURE:
<223> OTHER INFORMATION: Synthetic

<400> SEQUENCE: 251
agcucagaua gaaaagg 17

<210> SEQ ID NO 252
<211> LENGTH: 17
<212> TYPE: RNA
<213> ORGANISM: Artificial Sequence
<220> FEATURE:
<223> OTHER INFORMATION: Synthetic

<400> SEQUENCE: 252
gcucagauag aaaagga 17

<210> SEQ ID NO 253
<211> LENGTH: 17
<212> TYPE: RNA
<213> ORGANISM: Artificial Sequence
<220> FEATURE:
<223> OTHER INFORMATION: Synthetic

<400> SEQUENCE: 253
gcucccaucu cagggug 17

<210> SEQ ID NO 254
<211> LENGTH: 20
<212> TYPE: RNA
<213> ORGANISM: Artificial Sequence
<220> FEATURE:
<223> OTHER INFORMATION: Synthetic

<400> SEQUENCE: 254
cggcucccau cucaggguga 20

<210> SEQ ID NO 255
<211> LENGTH: 20
<212> TYPE: RNA
<213> ORGANISM: Artificial Sequence
<220> FEATURE:
<223> OTHER INFORMATION: Synthetic

<400> SEQUENCE: 255
gggaagacgg cucccaucuc 20

<210> SEQ ID NO 256
<211> LENGTH: 20
<212> TYPE: RNA
<213> ORGANISM: Artificial Sequence
<220> FEATURE:
<223> OTHER INFORMATION: Synthetic

<400> SEQUENCE: 256
ggcucccauc ucagggugag 20

<210> SEQ ID NO 257
<211> LENGTH: 20
<212> TYPE: RNA
<213> ORGANISM: Artificial Sequence
<220> FEATURE:
<223> OTHER INFORMATION: Synthetic

<400> SEQUENCE: 257
ggaagacggc ucccaucuca 20

<210> SEQ ID NO 258
<211> LENGTH: 20
<212> TYPE: RNA
<213> ORGANISM: Artificial Sequence
<220> FEATURE:
<223> OTHER INFORMATION: Synthetic

<400> SEQUENCE: 258
gcaagcagug acagugccca 20

<210> SEQ ID NO 259
<211> LENGTH: 20
<212> TYPE: RNA
<213> ORGANISM: Artificial Sequence
<220> FEATURE:
<223> OTHER INFORMATION: Synthetic

<400> SEQUENCE: 259
gagugagagc ccgcccaggu 20

<210> SEQ ID NO 260

<211> LENGTH: 20
<212> TYPE: RNA
<213> ORGANISM: Artificial Sequence
<220> FEATURE:
<223> OTHER INFORMATION: Synthetic

<400> SEQUENCE: 260
gcacugucac ugcuugcagc 20

<210> SEQ ID NO 261
<211> LENGTH: 20
<212> TYPE: RNA
<213> ORGANISM: Artificial Sequence
<220> FEATURE:
<223> OTHER INFORMATION: Synthetic

<400> SEQUENCE: 261
gacggcuccc aucucagggu 20

<210> SEQ ID NO 262
<211> LENGTH: 20
<212> TYPE: RNA
<213> ORGANISM: Artificial Sequence
<220> FEATURE:
<223> OTHER INFORMATION: Synthetic

<400> SEQUENCE: 262
guagcucccu ccuuuucuau 20

<210> SEQ ID NO 263
<211> LENGTH: 20
<212> TYPE: RNA
<213> ORGANISM: Artificial Sequence
<220> FEATURE:
<223> OTHER INFORMATION: Synthetic

<400> SEQUENCE: 263
gaagagcuca gauagaaaag 20

<210> SEQ ID NO 264
<211> LENGTH: 24
<212> TYPE: RNA
<213> ORGANISM: Artificial Sequence
<220> FEATURE:
<223> OTHER INFORMATION: Synthetic

<400> SEQUENCE: 264
gaagacggcu cccaucucag ggug 24

<210> SEQ ID NO 265
<211> LENGTH: 24
<212> TYPE: RNA
<213> ORGANISM: Artificial Sequence
<220> FEATURE:
<223> OTHER INFORMATION: Synthetic

<400> SEQUENCE: 265
gagaguagcu cccuccuuuu cuau 24

<210> SEQ ID NO 266
<211> LENGTH: 24
<212> TYPE: RNA
<213> ORGANISM: Artificial Sequence
<220> FEATURE:
<223> OTHER INFORMATION: Synthetic

<400> SEQUENCE: 266
gugagagccc gcccaggucu gggu 24

<210> SEQ ID NO 267
<211> LENGTH: 24
<212> TYPE: RNA
<213> ORGANISM: Artificial Sequence
<220> FEATURE:
<223> OTHER INFORMATION: Synthetic

<400> SEQUENCE: 267
gggcugggaa gacggcuccc aucu 24

<210> SEQ ID NO 268
<211> LENGTH: 24
<212> TYPE: RNA
<213> ORGANISM: Artificial Sequence
<220> FEATURE:
<223> OTHER INFORMATION: Synthetic

<400> SEQUENCE: 268
ggaagacggc ucccaucuca gggu 24

<210> SEQ ID NO 269
<211> LENGTH: 17
<212> TYPE: RNA
<213> ORGANISM: Artificial Sequence
<220> FEATURE:
<223> OTHER INFORMATION: Synthetic

<400> SEQUENCE: 269
gagaaccggc cucgcuc 17

<210> SEQ ID NO 270
<211> LENGTH: 17
<212> TYPE: RNA
<213> ORGANISM: Artificial Sequence
<220> FEATURE:
<223> OTHER INFORMATION: Synthetic

<400> SEQUENCE: 270
gagagcccgc ccagguc 17

<210> SEQ ID NO 271
<211> LENGTH: 17
<212> TYPE: RNA
<213> ORGANISM: Artificial Sequence
<220> FEATURE:
<223> OTHER INFORMATION: Synthetic

<400> SEQUENCE: 271
ggagugagag cccgccc 17

<210> SEQ ID NO 272
<211> LENGTH: 17
<212> TYPE: RNA
<213> ORGANISM: Artificial Sequence
<220> FEATURE:
<223> OTHER INFORMATION: Synthetic

<400> SEQUENCE: 272
gcucagauag aaaagga 17

<210> SEQ ID NO 273
<211> LENGTH: 17
<212> TYPE: RNA

<213> ORGANISM: Artificial Sequence
<220> FEATURE:
<223> OTHER INFORMATION: Synthetic

<400> SEQUENCE: 273
gcucccaucu cagggug 17

<210> SEQ ID NO 274
<211> LENGTH: 20
<212> TYPE: RNA
<213> ORGANISM: Artificial Sequence
<220> FEATURE:
<223> OTHER INFORMATION: Synthetic

<400> SEQUENCE: 274
gggcgggcuc ucacuccaug 20

<210> SEQ ID NO 275
<211> LENGTH: 20
<212> TYPE: RNA
<213> ORGANISM: Artificial Sequence
<220> FEATURE:
<223> OTHER INFORMATION: Synthetic

<400> SEQUENCE: 275
gugagagccc gcccaggucu 20

<210> SEQ ID NO 276
<211> LENGTH: 20
<212> TYPE: RNA
<213> ORGANISM: Artificial Sequence
<220> FEATURE:
<223> OTHER INFORMATION: Synthetic

<400> SEQUENCE: 276
gggaagacgg cucccaucuc 20

<210> SEQ ID NO 277
<211> LENGTH: 20
<212> TYPE: RNA
<213> ORGANISM: Artificial Sequence
<220> FEATURE:
<223> OTHER INFORMATION: Synthetic

<400> SEQUENCE: 277
ggcucccauc ucagggugag 20

<210> SEQ ID NO 278
<211> LENGTH: 20
<212> TYPE: RNA
<213> ORGANISM: Artificial Sequence
<220> FEATURE:
<223> OTHER INFORMATION: Synthetic

<400> SEQUENCE: 278
ggaagacggc ucccaucuca 20

<210> SEQ ID NO 279
<211> LENGTH: 20
<212> TYPE: RNA
<213> ORGANISM: Artificial Sequence
<220> FEATURE:
<223> OTHER INFORMATION: Synthetic

<400> SEQUENCE: 279
gcacugucgc ugcacgcagc 20

<210> SEQ ID NO 280
<211> LENGTH: 20
<212> TYPE: RNA
<213> ORGANISM: Artificial Sequence
<220> FEATURE:
<223> OTHER INFORMATION: Synthetic

<400> SEQUENCE: 280
gacggcuccc aucucagggu 20

<210> SEQ ID NO 281
<211> LENGTH: 20
<212> TYPE: RNA
<213> ORGANISM: Artificial Sequence
<220> FEATURE:
<223> OTHER INFORMATION: Synthetic

<400> SEQUENCE: 281
gagccggccc aggucucggu 20

<210> SEQ ID NO 282
<211> LENGTH: 20
<212> TYPE: RNA
<213> ORGANISM: Artificial Sequence
<220> FEATURE:
<223> OTHER INFORMATION: Synthetic

<400> SEQUENCE: 282
guagcucccu ccuuuuccac 20

<210> SEQ ID NO 283
<211> LENGTH: 20
<212> TYPE: RNA
<213> ORGANISM: Artificial Sequence
<220> FEATURE:
<223> OTHER INFORMATION: Synthetic

<400> SEQUENCE: 283
gaagagcuca gguggaaaag 20

<210> SEQ ID NO 284
<211> LENGTH: 24
<212> TYPE: RNA
<213> ORGANISM: Artificial Sequence
<220> FEATURE:
<223> OTHER INFORMATION: Synthetic

<400> SEQUENCE: 284
gaagacggcu cccaucucag ggug 24

<210> SEQ ID NO 285
<211> LENGTH: 24
<212> TYPE: RNA
<213> ORGANISM: Artificial Sequence
<220> FEATURE:
<223> OTHER INFORMATION: Synthetic

<400> SEQUENCE: 285
gcggcuacua caaccagagc gagg 24

<210> SEQ ID NO 286
<211> LENGTH: 24
<212> TYPE: RNA
<213> ORGANISM: Artificial Sequence
<220> FEATURE:

<223> OTHER INFORMATION: Synthetic

<400> SEQUENCE: 286
gugggagccg gcccaggucu cggu 24

<210> SEQ ID NO 287
<211> LENGTH: 24
<212> TYPE: RNA
<213> ORGANISM: Artificial Sequence
<220> FEATURE:
<223> OTHER INFORMATION: Synthetic

<400> SEQUENCE: 287
ggaagacggc ucccaucuca gggu 24

<210> SEQ ID NO 288
<211> LENGTH: 24
<212> TYPE: RNA
<213> ORGANISM: Artificial Sequence
<220> FEATURE:
<223> OTHER INFORMATION: Synthetic

<400> SEQUENCE: 288
ggacugggaa gacggcuccc aucu 24

<210> SEQ ID NO 289
<211> LENGTH: 17
<212> TYPE: RNA
<213> ORGANISM: Artificial Sequence
<220> FEATURE:
<223> OTHER INFORMATION: Synthetic

<400> SEQUENCE: 289
gagacccggc cucgcuc 17

<210> SEQ ID NO 290
<211> LENGTH: 17
<212> TYPE: RNA
<213> ORGANISM: Artificial Sequence
<220> FEATURE:
<223> OTHER INFORMATION: Synthetic

<400> SEQUENCE: 290
gugcagcgac agugccc 17

<210> SEQ ID NO 291
<211> LENGTH: 17
<212> TYPE: RNA
<213> ORGANISM: Artificial Sequence
<220> FEATURE:
<223> OTHER INFORMATION: Synthetic

<400> SEQUENCE: 291
ggagccggcc caggucu 17

<210> SEQ ID NO 292
<211> LENGTH: 17
<212> TYPE: RNA
<213> ORGANISM: Artificial Sequence
<220> FEATURE:
<223> OTHER INFORMATION: Synthetic

<400> SEQUENCE: 292
gcucccaucu cagggug 17

-continued

<210> SEQ ID NO 293
<211> LENGTH: 17
<212> TYPE: RNA
<213> ORGANISM: Artificial Sequence
<220> FEATURE:
<223> OTHER INFORMATION: Synthetic

<400> SEQUENCE: 293
gcucaggugg aaaagga 17

<210> SEQ ID NO 294
<211> LENGTH: 20
<212> TYPE: RNA
<213> ORGANISM: Artificial Sequence
<220> FEATURE:
<223> OTHER INFORMATION: Synthetic

<400> SEQUENCE: 294
gggaagacgg cucccaucuc 20

<210> SEQ ID NO 295
<211> LENGTH: 20
<212> TYPE: RNA
<213> ORGANISM: Artificial Sequence
<220> FEATURE:
<223> OTHER INFORMATION: Synthetic

<400> SEQUENCE: 295
gcgugcagcg acagugccca 20

<210> SEQ ID NO 296
<211> LENGTH: 20
<212> TYPE: RNA
<213> ORGANISM: Artificial Sequence
<220> FEATURE:
<223> OTHER INFORMATION: Synthetic

<400> SEQUENCE: 296
ggcucccauc ucagggugag 20

<210> SEQ ID NO 297
<211> LENGTH: 20
<212> TYPE: RNA
<213> ORGANISM: Artificial Sequence
<220> FEATURE:
<223> OTHER INFORMATION: Synthetic

<400> SEQUENCE: 297
ggaagacggc ucccaucuca 20

<210> SEQ ID NO 298
<211> LENGTH: 20
<212> TYPE: RNA
<213> ORGANISM: Artificial Sequence
<220> FEATURE:
<223> OTHER INFORMATION: Synthetic

<400> SEQUENCE: 298
gggccggcuc ccacuccaug 20

<210> SEQ ID NO 299
<211> LENGTH: 20
<212> TYPE: RNA
<213> ORGANISM: Artificial Sequence
<220> FEATURE:
<223> OTHER INFORMATION: Synthetic

<400> SEQUENCE: 299
gauggacucg ccgcugcacu 20

<210> SEQ ID NO 300
<211> LENGTH: 20
<212> TYPE: RNA
<213> ORGANISM: Artificial Sequence
<220> FEATURE:
<223> OTHER INFORMATION: Synthetic

<400> SEQUENCE: 300
gggacaccag accacguuuc 20

<210> SEQ ID NO 301
<211> LENGTH: 20
<212> TYPE: RNA
<213> ORGANISM: Artificial Sequence
<220> FEATURE:
<223> OTHER INFORMATION: Synthetic

<400> SEQUENCE: 301
ggacaccaga ccacguuucu 20

<210> SEQ ID NO 302
<211> LENGTH: 20
<212> TYPE: RNA
<213> ORGANISM: Artificial Sequence
<220> FEATURE:
<223> OTHER INFORMATION: Synthetic

<400> SEQUENCE: 302
gacuucagcc aagaggauuc 20

<210> SEQ ID NO 303
<211> LENGTH: 20
<212> TYPE: RNA
<213> ORGANISM: Artificial Sequence
<220> FEATURE:
<223> OTHER INFORMATION: Synthetic

<400> SEQUENCE: 303
gaauccucuu ggcugaaguc 20

<210> SEQ ID NO 304
<211> LENGTH: 24
<212> TYPE: RNA
<213> ORGANISM: Artificial Sequence
<220> FEATURE:
<223> OTHER INFORMATION: Synthetic

<400> SEQUENCE: 304
gcuggggaca ccagaccacg uuuc 24

<210> SEQ ID NO 305
<211> LENGTH: 24
<212> TYPE: RNA
<213> ORGANISM: Artificial Sequence
<220> FEATURE:
<223> OTHER INFORMATION: Synthetic

<400> SEQUENCE: 305
gacaagcccu cucacagugg aaug 24

<210> SEQ ID NO 306
<211> LENGTH: 24

<212> TYPE: RNA
<213> ORGANISM: Artificial Sequence
<220> FEATURE:
<223> OTHER INFORMATION: Synthetic

<400> SEQUENCE: 306
gaaaggacac ucuggacuuc agcc 24

<210> SEQ ID NO 307
<211> LENGTH: 24
<212> TYPE: RNA
<213> ORGANISM: Artificial Sequence
<220> FEATURE:
<223> OTHER INFORMATION: Synthetic

<400> SEQUENCE: 307
uuaggaugga cucgccgcug cacu 24

<210> SEQ ID NO 308
<211> LENGTH: 24
<212> TYPE: RNA
<213> ORGANISM: Artificial Sequence
<220> FEATURE:
<223> OTHER INFORMATION: Synthetic

<400> SEQUENCE: 308
ucaggaaucc ucuuggcuga aguc 24

<210> SEQ ID NO 309
<211> LENGTH: 17
<212> TYPE: RNA
<213> ORGANISM: Artificial Sequence
<220> FEATURE:
<223> OTHER INFORMATION: Synthetic

<400> SEQUENCE: 309
gcggcgaguc cauccua 17

<210> SEQ ID NO 310
<211> LENGTH: 17
<212> TYPE: RNA
<213> ORGANISM: Artificial Sequence
<220> FEATURE:
<223> OTHER INFORMATION: Synthetic

<400> SEQUENCE: 310
gaguacucca agaaacg 17

<210> SEQ ID NO 311
<211> LENGTH: 17
<212> TYPE: RNA
<213> ORGANISM: Artificial Sequence
<220> FEATURE:
<223> OTHER INFORMATION: Synthetic

<400> SEQUENCE: 311
caccagacca cguuucu 17

<210> SEQ ID NO 312
<211> LENGTH: 17
<212> TYPE: RNA
<213> ORGANISM: Artificial Sequence
<220> FEATURE:
<223> OTHER INFORMATION: Synthetic

<400> SEQUENCE: 312
cuccaagaaa cgugguc 17

<210> SEQ ID NO 313
<211> LENGTH: 17
<212> TYPE: RNA
<213> ORGANISM: Artificial Sequence
<220> FEATURE:
<223> OTHER INFORMATION: Synthetic

<400> SEQUENCE: 313
aaucagaaag gacacuc 17

<210> SEQ ID NO 314
<211> LENGTH: 20
<212> TYPE: RNA
<213> ORGANISM: Artificial Sequence
<220> FEATURE:
<223> OTHER INFORMATION: Synthetic

<400> SEQUENCE: 314
guagaguacu ccaagaaacg 20

<210> SEQ ID NO 315
<211> LENGTH: 20
<212> TYPE: RNA
<213> ORGANISM: Artificial Sequence
<220> FEATURE:
<223> OTHER INFORMATION: Synthetic

<400> SEQUENCE: 315
gcagcggcga guccauccua 20

<210> SEQ ID NO 316
<211> LENGTH: 20
<212> TYPE: RNA
<213> ORGANISM: Artificial Sequence
<220> FEATURE:
<223> OTHER INFORMATION: Synthetic

<400> SEQUENCE: 316
guacuccaag aaacgugguc 20

<210> SEQ ID NO 317
<211> LENGTH: 20
<212> TYPE: RNA
<213> ORGANISM: Artificial Sequence
<220> FEATURE:
<223> OTHER INFORMATION: Synthetic

<400> SEQUENCE: 317
ggacaccaga ccacguuucu 20

<210> SEQ ID NO 318
<211> LENGTH: 20
<212> TYPE: RNA
<213> ORGANISM: Artificial Sequence
<220> FEATURE:
<223> OTHER INFORMATION: Synthetic

<400> SEQUENCE: 318
gcucuccauu ccacugugag 20

<210> SEQ ID NO 319
<211> LENGTH: 20
<212> TYPE: DNA
<213> ORGANISM: Artificial Sequence
<220> FEATURE:
<223> OTHER INFORMATION: Synthetic

<400> SEQUENCE: 319
acggttctca caccatccag 20

<210> SEQ ID NO 320
<211> LENGTH: 20
<212> TYPE: DNA
<213> ORGANISM: Artificial Sequence
<220> FEATURE:
<223> OTHER INFORMATION: Synthetic

<400> SEQUENCE: 320
cacaccatcc agaggatgta 20

<210> SEQ ID NO 321
<211> LENGTH: 20
<212> TYPE: DNA
<213> ORGANISM: Artificial Sequence
<220> FEATURE:
<223> OTHER INFORMATION: Synthetic

<400> SEQUENCE: 321
ccggaacaca cggaatgtga 20

<210> SEQ ID NO 322
<211> LENGTH: 20
<212> TYPE: DNA
<213> ORGANISM: Artificial Sequence
<220> FEATURE:
<223> OTHER INFORMATION: Synthetic

<400> SEQUENCE: 322
tgcggagcca ctccacgcac 20

<210> SEQ ID NO 323
<211> LENGTH: 17
<212> TYPE: DNA
<213> ORGANISM: Artificial Sequence
<220> FEATURE:
<223> OTHER INFORMATION: Synthetic

<400> SEQUENCE: 323
accatccaga ggatgta 17

<210> SEQ ID NO 324
<211> LENGTH: 17
<212> TYPE: DNA
<213> ORGANISM: Artificial Sequence
<220> FEATURE:
<223> OTHER INFORMATION: Synthetic

<400> SEQUENCE: 324
gttctcacac catccag 17

<210> SEQ ID NO 325
<211> LENGTH: 17
<212> TYPE: DNA
<213> ORGANISM: Artificial Sequence
<220> FEATURE:
<223> OTHER INFORMATION: Synthetic

<400> SEQUENCE: 325
gaacacacgg aatgtga 17

<210> SEQ ID NO 326
<211> LENGTH: 17
<212> TYPE: DNA
<213> ORGANISM: Artificial Sequence
<220> FEATURE:
<223> OTHER INFORMATION: Synthetic

<400> SEQUENCE: 326
ggagccactc cacgcac 17

<210> SEQ ID NO 327
<211> LENGTH: 20
<212> TYPE: DNA
<213> ORGANISM: Artificial Sequence
<220> FEATURE:
<223> OTHER INFORMATION: Synthetic

<400> SEQUENCE: 327
cctcgctctg gttgtagtag 20

<210> SEQ ID NO 328
<211> LENGTH: 20
<212> TYPE: DNA
<213> ORGANISM: Artificial Sequence
<220> FEATURE:
<223> OTHER INFORMATION: Synthetic

<400> SEQUENCE: 328
cgtctgccaa gtgtgagacc 20

<210> SEQ ID NO 329
<211> LENGTH: 20
<212> TYPE: DNA
<213> ORGANISM: Artificial Sequence
<220> FEATURE:
<223> OTHER INFORMATION: Synthetic

<400> SEQUENCE: 329
ctctcggtaa gtctgtgtgt 20

<210> SEQ ID NO 330
<211> LENGTH: 20
<212> TYPE: DNA
<213> ORGANISM: Artificial Sequence
<220> FEATURE:
<223> OTHER INFORMATION: Synthetic

<400> SEQUENCE: 330
gcgaggccgg gtctcacact 20

<210> SEQ ID NO 331
<211> LENGTH: 17
<212> TYPE: DNA
<213> ORGANISM: Artificial Sequence
<220> FEATURE:
<223> OTHER INFORMATION: Synthetic

<400> SEQUENCE: 331
cgctctggtt gtagtag 17

<210> SEQ ID NO 332
<211> LENGTH: 17
<212> TYPE: DNA
<213> ORGANISM: Artificial Sequence
<220> FEATURE:
<223> OTHER INFORMATION: Synthetic

<400> SEQUENCE: 332
aggccgggtc tcacact 17

<210> SEQ ID NO 333
<211> LENGTH: 17
<212> TYPE: DNA
<213> ORGANISM: Artificial Sequence
<220> FEATURE:
<223> OTHER INFORMATION: Synthetic

<400> SEQUENCE: 333
cttaccgaga gaacctg 17

<210> SEQ ID NO 334
<211> LENGTH: 17
<212> TYPE: DNA
<213> ORGANISM: Artificial Sequence
<220> FEATURE:
<223> OTHER INFORMATION: Synthetic

<400> SEQUENCE: 334
cgatccgcag gttctct 17

<210> SEQ ID NO 335
<211> LENGTH: 20
<212> TYPE: DNA
<213> ORGANISM: Artificial Sequence
<220> FEATURE:
<223> OTHER INFORMATION: Synthetic

<400> SEQUENCE: 335
aggacatcct ggaagacgag 20

<210> SEQ ID NO 336
<211> LENGTH: 20
<212> TYPE: DNA
<213> ORGANISM: Artificial Sequence
<220> FEATURE:
<223> OTHER INFORMATION: Synthetic

<400> SEQUENCE: 336
ggaagacgag cgggccgcgg 20

<210> SEQ ID NO 337
<211> LENGTH: 20
<212> TYPE: DNA
<213> ORGANISM: Artificial Sequence
<220> FEATURE:
<223> OTHER INFORMATION: Synthetic

<400> SEQUENCE: 337
cctggaagac gagcgggccg 20

<210> SEQ ID NO 338
<211> LENGTH: 20
<212> TYPE: DNA
<213> ORGANISM: Artificial Sequence
<220> FEATURE:
<223> OTHER INFORMATION: Synthetic

<400> SEQUENCE: 338
ccgcggcccg ctcgtcttcc 20

<210> SEQ ID NO 339

<211> LENGTH: 17
<212> TYPE: DNA
<213> ORGANISM: Artificial Sequence
<220> FEATURE:
<223> OTHER INFORMATION: Synthetic

<400> SEQUENCE: 339
ggaagacgag cgggccg 17

<210> SEQ ID NO 340
<211> LENGTH: 17
<212> TYPE: DNA
<213> ORGANISM: Artificial Sequence
<220> FEATURE:
<223> OTHER INFORMATION: Synthetic

<400> SEQUENCE: 340
acatcctgga agacgag 17

<210> SEQ ID NO 341
<211> LENGTH: 17
<212> TYPE: DNA
<213> ORGANISM: Artificial Sequence
<220> FEATURE:
<223> OTHER INFORMATION: Synthetic

<400> SEQUENCE: 341
catcctggaa gacgagc 17

<210> SEQ ID NO 342
<211> LENGTH: 17
<212> TYPE: DNA
<213> ORGANISM: Artificial Sequence
<220> FEATURE:
<223> OTHER INFORMATION: Synthetic

<400> SEQUENCE: 342
cggcccgctc gtcttcc 17

<210> SEQ ID NO 343
<211> LENGTH: 20
<212> TYPE: DNA
<213> ORGANISM: Artificial Sequence
<220> FEATURE:
<223> OTHER INFORMATION: Synthetic

<400> SEQUENCE: 343
actccacgca cgtgccctcc 20

<210> SEQ ID NO 344
<211> LENGTH: 20
<212> TYPE: DNA
<213> ORGANISM: Artificial Sequence
<220> FEATURE:
<223> OTHER INFORMATION: Synthetic

<400> SEQUENCE: 344
ctacctggag ggcacgtgcg 20

<210> SEQ ID NO 345
<211> LENGTH: 20
<212> TYPE: DNA
<213> ORGANISM: Artificial Sequence
<220> FEATURE:
<223> OTHER INFORMATION: Synthetic

<400> SEQUENCE: 345
gtggacctgg ggaccctgcg 20

<210> SEQ ID NO 346
<211> LENGTH: 20
<212> TYPE: DNA
<213> ORGANISM: Artificial Sequence
<220> FEATURE:
<223> OTHER INFORMATION: Synthetic

<400> SEQUENCE: 346
ccactcacag actcaccgag 20

<210> SEQ ID NO 347
<211> LENGTH: 17
<212> TYPE: DNA
<213> ORGANISM: Artificial Sequence
<220> FEATURE:
<223> OTHER INFORMATION: Synthetic

<400> SEQUENCE: 347
gcacgtgccc tccaggt 17

<210> SEQ ID NO 348
<211> LENGTH: 17
<212> TYPE: DNA
<213> ORGANISM: Artificial Sequence
<220> FEATURE:
<223> OTHER INFORMATION: Synthetic

<400> SEQUENCE: 348
agggcacgtg cgtggag 17

<210> SEQ ID NO 349
<211> LENGTH: 17
<212> TYPE: DNA
<213> ORGANISM: Artificial Sequence
<220> FEATURE:
<223> OTHER INFORMATION: Synthetic

<400> SEQUENCE: 349
cctggagggc acgtgcg 17

<210> SEQ ID NO 350
<211> LENGTH: 17
<212> TYPE: DNA
<213> ORGANISM: Artificial Sequence
<220> FEATURE:
<223> OTHER INFORMATION: Synthetic

<400> SEQUENCE: 350
ctcacagact caccgag 17

<210> SEQ ID NO 351
<211> LENGTH: 22
<212> TYPE: RNA
<213> ORGANISM: Artificial Sequence
<220> FEATURE:
<223> OTHER INFORMATION: Synthetic

<400> SEQUENCE: 351
gccuauaaaa uagagcccug uc 22

<210> SEQ ID NO 352
<211> LENGTH: 22
<212> TYPE: RNA

```
<213> ORGANISM: Artificial Sequence
<220> FEATURE:
<223> OTHER INFORMATION: Synthetic

<400> SEQUENCE: 352

auacagucag uaucaauucu gg                                              22

<210> SEQ ID NO 353
<211> LENGTH: 20
<212> TYPE: RNA
<213> ORGANISM: Artificial Sequence
<220> FEATURE:
<223> OTHER INFORMATION: Synthetic

<400> SEQUENCE: 353

guggugacaa gugugaucac                                                 20

<210> SEQ ID NO 354
<211> LENGTH: 24
<212> TYPE: RNA
<213> ORGANISM: Artificial Sequence
<220> FEATURE:
<223> OTHER INFORMATION: Synthetic

<400> SEQUENCE: 354

ccauacaguc aguaucaauu cugg                                            24

<210> SEQ ID NO 355
<211> LENGTH: 24
<212> TYPE: RNA
<213> ORGANISM: Artificial Sequence
<220> FEATURE:
<223> OTHER INFORMATION: Synthetic

<400> SEQUENCE: 355

aagccuauaa aauagagccc uguc                                            24

<210> SEQ ID NO 356
<211> LENGTH: 24
<212> TYPE: RNA
<213> ORGANISM: Artificial Sequence
<220> FEATURE:
<223> OTHER INFORMATION: Synthetic

<400> SEQUENCE: 356

ugggguggug acaaguguga ucac                                            24

<210> SEQ ID NO 357
<211> LENGTH: 22
<212> TYPE: RNA
<213> ORGANISM: Artificial Sequence
<220> FEATURE:
<223> OTHER INFORMATION: Synthetic

<400> SEQUENCE: 357

ggguggugac aagugugauc ac                                              22

<210> SEQ ID NO 358
<211> LENGTH: 18
<212> TYPE: RNA
<213> ORGANISM: Artificial Sequence
<220> FEATURE:
<223> OTHER INFORMATION: Synthetic

<400> SEQUENCE: 358

ggugacaagu gugaucac                                                   18
```

<210> SEQ ID NO 359
<211> LENGTH: 22
<212> TYPE: RNA
<213> ORGANISM: Artificial Sequence
<220> FEATURE:
<223> OTHER INFORMATION: Synthetic

<400> SEQUENCE: 359
gccuuuugca guuuaucagg au 22

<210> SEQ ID NO 360
<211> LENGTH: 24
<212> TYPE: RNA
<213> ORGANISM: Artificial Sequence
<220> FEATURE:
<223> OTHER INFORMATION: Synthetic

<400> SEQUENCE: 360
gcucuauuuu auaggcuucu ucuc 24

<210> SEQ ID NO 361
<211> LENGTH: 24
<212> TYPE: RNA
<213> ORGANISM: Artificial Sequence
<220> FEATURE:
<223> OTHER INFORMATION: Synthetic

<400> SEQUENCE: 361
gcucuucagc cuuuugcagu uuau 24

<210> SEQ ID NO 362
<211> LENGTH: 1098
<212> TYPE: DNA
<213> ORGANISM: Artificial Sequence
<220> FEATURE:
<223> OTHER INFORMATION: Synthetic: A*01:01:01:01

<400> SEQUENCE: 362
atggccgtca tggcgccccg aaccctcctc ctgctactct cgggggccct ggccctgacc 60
cagacctggg cgggctccca ctccatgagg tatttcttca catccgtgtc ccggcccggc 120
cgcggggagc cccgcttcat cgccgtgggc tacgtggacg acacgcagtt cgtgcggttc 180
gacagcgacg ccgcgagcca gaagatggag ccgcgggcgc cgtggataga gcaggagggg 240
ccggagtatt gggaccagga gacacggaat atgaaggccc actcacagac tgaccgagcg 300
aacctgggga ccctgcgcgg ctactacaac cagagcgagg acggttctca caccatccag 360
ataatgtatg gctgcgacgt ggggccggac gggcgcttcc tccgcgggta ccggcaggac 420
gcctacgacg gcaaggatta catcgccctg aacgaggacc tgcgctcttg gaccgcggcg 480
gacatggcag ctcagatcac caagcgcaag tgggaggcgg tccatgcggc ggagcagcgg 540
agagtctacc tggagggccg gtgcgtggac gggctccgca gatacctgga gaacgggaag 600
gagacgctgc agcgcacgga cccccccaag acacatatga cccaccaccc catctctgac 660
catgaggcca ccctgaggtg ctgggccctg ggcttctacc ctgcggagat cacactgacc 720
tggcagcggg atggggagga ccagacccag gacacggagc tcgtggagac caggcctgca 780
ggggatggaa ccttccagaa gtgggcggct gtggtggtgc cttctggaga ggagcagaga 840
tacacctgcc atgtgcagca tgagggtctg cccaagcccc tcaccctgag atgggagctg 900
tcttcccagc ccaccatccc catcgtgggc atcattgctg gcctggttct ccttggagct 960

```
gtgatcactg gagctgtggt cgctgccgtg atgtggagga ggaagagctc agatagaaaa    1020

ggagggagtt acactcaggc tgcaagcagt gacagtgccc agggctctga tgtgtctctc    1080

acagcttgta aagtgtga                                                   1098

<210> SEQ ID NO 363
<211> LENGTH: 1098
<212> TYPE: DNA
<213> ORGANISM: Artificial Sequence
<220> FEATURE:
<223> OTHER INFORMATION: Synthetic: A*23:01:01

<400> SEQUENCE: 363

atggccgtca tggcgccccg aaccctcgtc ctgctactct cgggggccct ggccctgacc      60

cagacctggg caggctccca ctccatgagg tatttctcca catccgtgtc ccggcccggc     120

cgcggggagc cccgcttcat cgccgtgggc tacgtggacg acacgcagtt cgtgcggttc     180

gacagcgacg ccgcgagcca gaggatggag ccgcgggcgc cgtggataga gcaggagggg     240

ccggagtatt gggacgagga gacagggaaa gtgaaggccc actcacagac tgaccgagag     300

aacctgcgga tcgcgctccg ctactacaac cagagcgagg ccggttctca caccctccag     360

atgatgtttg gctgcgacgt ggggtcggac gggcgcttcc tccgcgggta ccaccagtac     420

gcctacgacg gcaaggatta catcgccctg aaagaggacc tgcgctcttg gaccgcggcg     480

gacatggcgg ctcagatcac ccagcgcaag tgggaggcgg cccgtgtggc ggagcagttg     540

agagcctacc tggagggcac gtgcgtggac gggctccgca gatacctgga gaacgggaag     600

gagacgctgc agcgcacgga cccccccaag acacatatga cccaccaccc catctctgac     660

catgaggcca ctctgagatg ctgggccctg ggcttctacc ctgcggagat cacactgacc     720

tggcagcggg atggggagga ccagacccag gacacggagc ttgtggagac caggcctgca     780

ggggatggaa ccttccagaa gtgggcagct gtggtggtac cttctggaga ggagcagaga     840

tacacctgcc atgtgcagca tgagggtctg cccaagcccc tcaccctgag atgggagcca     900

tcttcccagc ccaccgtcca catcgtgggc atcattgctg gcctggttct ccttggagct     960

gtgatcactg gagctgtggt cgctgctgtg atgtggagga ggaacagctc agatagaaaa    1020

ggagggagct actctcaggc tgcaagcagt gacagtgccc agggctctga tgtgtctctc    1080

acagcttgta aagtgtga                                                   1098

<210> SEQ ID NO 364
<211> LENGTH: 1098
<212> TYPE: DNA
<213> ORGANISM: Artificial Sequence
<220> FEATURE:
<223> OTHER INFORMATION: Synthetic: A*03:01:01:01

<400> SEQUENCE: 364

atggccgtca tggcgccccg aaccctcctc ctgctactct cgggggccct ggccctgacc      60

cagacctggg cggctccca ctccatgagg tatttcttca catccgtgtc ccggcccggc     120

cgcggggagc cccgcttcat cgccgtgggc tacgtggacg acacgcagtt cgtgcggttc     180

gacagcgacg ccgcgagcca gaggatggag ccgcgggcgc cgtggataga gcaggagggg     240

ccggagtatt gggaccagga gacacggaat gtgaaggccc agtcacagac tgaccgagtg     300

gacctgggga ccctgcgcgg ctactacaac cagagcgagg ccggttctca caccatccag     360

ataatgtatg gctgcgacgt ggggtcggac gggcgcttcc tccgcgggta ccggcaggac     420

gcctacgacg gcaaggatta catcgccctg aacgaggacc tgcgctcttg gaccgcggcg     480
```

gacatggcgg ctcagatcac caagcgcaag tgggaggcgg cccatgaggc ggagcagttg 540
agagcctacc tggatggcac gtgcgtggag tggctccgca gatacctgga gaacgggaag 600
gagacgctgc agcgcacgga cccccccaag acacatatga cccaccaccc catctctgac 660
catgaggcca ccctgaggtg ctgggccctg ggcttctacc ctgcggagat cacactgacc 720
tggcagcggg atggggagga ccagacccag gacacggagc tcgtggagac caggcctgca 780
ggggatggaa ccttccagaa gtgggcggct gtggtggtgc cttctggaga ggagcagaga 840
tacacctgcc atgtgcagca tgagggtctg cccaagcccc tcaccctgag atgggagctg 900
tcttcccagc ccaccatccc catcgtgggc atcattgctg gcctggttct ccttggagct 960
gtgatcactg gagctgtggt cgctgccgtg atgtggagga ggaagagctc agatagaaaa 1020
ggagggagtt acactcaggc tgcaagcagt gacagtgccc agggctctga tgtgtccctc 1080
acagcttgta aagtgtga 1098

<210> SEQ ID NO 365
<211> LENGTH: 1089
<212> TYPE: DNA
<213> ORGANISM: Artificial Sequence
<220> FEATURE:
<223> OTHER INFORMATION: Synthetic: B*07:02:01

<400> SEQUENCE: 365
atgctggtca tggcgccccg aaccgtcctc ctgctgctct cggcggccct ggccctgacc 60
gagacctggg ccggctccca ctccatgagg tatttctaca cctccgtgtc ccggcccggc 120
cgcggggagc cccgcttcat ctcagtgggc tacgtggacg acacccagtt cgtgaggttc 180
gacagcgacg ccgcgagtcc gagagaggag ccgcgggcgc cgtggataga gcaggagggg 240
ccggagtatt gggaccggaa cacacagatc tacaaggccc aggcacagac tgaccgagag 300
agcctgcgga acctgcgcgg ctactacaac cagagcgagg ccgggtctca caccctccag 360
agcatgtacg gctgcgacgt ggggccggac gggcgcctcc tccgcgggca tgaccagtac 420
gcctacgacg gcaaggatta catcgccctg aacgaggacc tgcgctcctg gaccgccgcg 480
gacacggcgg ctcagatcac ccagcgcaag tgggaggcgg cccgtgaggc ggagcagcgg 540
agagcctacc tggagggcga gtgcgtggag tggctccgca gatacctgga gaacgggaag 600
gacaagctgg agcgcgctga ccccccaaag acacacgtga cccaccaccc catctctgac 660
catgaggcca ccctgaggtg ctgggccctg ggtttctacc ctgcggagat cacactgacc 720
tggcagcggg atggcgagga ccaaactcag gacactgagc ttgtggagac cagaccagca 780
ggagatagaa ccttccagaa gtgggcagct gtggtggtgc cttctggaga agagcagaga 840
tacacatgcc atgtacagca tgaggggctg ccgaagcccc tcaccctgag atgggagccg 900
tcttcccagt ccaccgtccc catcgtgggc attgttgctg gcctggctgt cctagcagtt 960
gtggtcatcg gagctgtggt cgctgctgtg atgtgtagga ggaagagttc aggtggaaaa 1020
ggagggagct actctcaggc tgcgtgcagc gacagtgccc agggctctga tgtgtctctc 1080
acagcttga 1089

<210> SEQ ID NO 366
<211> LENGTH: 801
<212> TYPE: DNA
<213> ORGANISM: Artificial Sequence
<220> FEATURE:
<223> OTHER INFORMATION: Synthetic: DRB1*15:01:01:01

-continued

<400> SEQUENCE: 366

```
atggtgtgtc tgaagctccc tggaggctcc tgcatgacag cgctgacagt gacactgatg     60
gtgctgagct ccccactggc tttgtctggg gacacccgac cacgtttcct gtggcagcct    120
aagagggagt gtcatttctt caatgggacg gagcgggtgc ggttcctgga cagatacttc    180
tataaccagg aggagtccgt gcgcttcgac agcgacgtgg gggagttccg ggcggtgacg    240
gagctggggc ggcctgacgc tgagtactgg aacagccaga aggacatcct ggagcaggcg    300
cgggccgcgg tggacaccta ctgcagacac aactacgggg ttgtggagag cttcacagtg    360
cagcggcgag tccaacctaa ggtgactgta tatccttcaa agacccagcc cctgcagcac    420
cacaacctcc tggtctgctc tgtgagtggt ttctatccag gcagcattga agtcaggtgg    480
ttcctgaacg gccaggaaga gaaggctggg atggtgtcca caggcctgat ccagaatgga    540
gactggacct tccagaccct ggtgatgctg gaaacagttc ctcgaagtgg agaggtttac    600
acctgccaag tggagcaccc aagcgtgaca agccctctca cagtggaatg gagagcacgg    660
tctgaatctg cacagagcaa gatgctgagt ggagtcgggg gctttgtgct gggcctgctc    720
ttccttgggg ccgggctgtt catctacttc aggaatcaga aaggacactc tggacttcag    780
ccaacaggat tcctgagctg a                                               801
```

CRISPR/CAS-RELATED METHODS AND COMPOSITIONS FOR IMPROVING TRANSPLANTATION

RELATED APPLICATIONS

This application is a 35 U.S.C. § 371 national stage filing of International Application No. PCT/US2016/036602, filed on Jun. 9, 2016, which in turn claims priority to U.S. Provisional Patent Application No. 62/173,321, filed on Jun. 9, 2015; and U.S. Provisional Patent Application No. 62/294,493, filed on Feb. 12, 2016. The entire contents of each of the foregoing applications are expressly incorporated herein by reference.

SEQUENCE LISTING

The instant application contains a Sequence Listing which has been submitted electronically in ASCII format and is hereby incorporated by reference in its entirety. Said ASCII copy, created on Jun. 9, 2016, is named 2016-06-09_126454-01420_EM052PCT1_ST25.txt and is 227 KB in size.

BACKGROUND

Cell therapy is the administration of live cells or maturation of a specific cell population in a patient for the treatment of a disease. For example, allogeneic hematopoietic stem/progenitor cell transplantation (allo-HSCT) and allogeneic umbilical cord transplantation (allo-UCT) are effective treatments for a variety of acquired, malignant, and genetic hematologic diseases, such as sickle cell disease (SCD) (Bacigalupo A, et al. *Haematologica* 100(5): 696-702 (2015); Kamani N R et al. *Biol. Blood Marrow Transplant* 18(8): 1265-72 (2012)).

With the advent of gene therapy, cell therapy using genetically-altered cells is extraordinarily promising, as a multitude of diseases can now potentially be treated by transplanting cells that have been genetically altered to treat the cause of particular disease states (e.g., hematological disorders). For example, the discovery and application of the CRISPR/Cas9 system in mammalian cells results in effective and precise editing of target genes, e.g., through the non-homologous end joining pathway (NHEJ), homology directed repair (HDR), or other DNA repair pathways. Co-delivery of a Cas9 molecule and a target-specific guide RNA (gRNA) molecule, optionally along with a donor DNA repair template molecule, facilitates gene-editing of a target sequence (e.g., a disease-related mutation) in the genome. Thus, the use of the CRISPR/Cas9 system to modify genes in cells (e.g., stem cells) is a promising strategy for treating multiple genetic disorders.

To achieve successful transplantation of a cell that is not derived from the recipient subject (e.g., hematopoietic stem cells (HSCs or HSPCs) and/or T-cells), a donor must be identified such that the donor cells exhibit a high and/or significant degree of matching of alleles at the genetic loci of one or more immunogenicity genes. Unfortunately, the availability of suitable donor cells with matching alleles at one or more immunogenicity gene loci is limited because of haplotype heterogeneity in human populations. Thus, the inability to identify suitable donor cells may ultimately prevent a patient from receiving a necessary transplantation, or force medical practitioners to utilize mismatched donor cells which may ultimately result in immunorejection. For example, the human leukocyte antigen genes (HLAs) are immunogenicity genes that were first identified during early bone marrow hematopoietic stem/progenitor cell transplantation (HSCT) clinic treatments. Mismatch of HLAs between a bone marrow HSPC donor and a recipient subject can cause immune reactions in which lymphocytes emerging from the donor graft mount an immune response against the host tissues. The donor T cell alloreactivity causing this medical condition, or Graft versus Host Disease (GVHD), is concentrated on the skin, gastrointestinal tract (GI), and liver. GVHD is a major cause of non-relapse related morbidity and mortality, which impacts ~50% of allogeneic HSCT subjects (Bhatia S. *Expert Rev Hematol.* 2011: 4(4): 437-452; Garnett C, et al. *Ther Adv Hematol.* 4(6): 366-78 (2013)). Conversely, recipient T cells can recognize the incoming donor allogenic HSPCs as foreign by recognizing HLA proteins or donor-specific antigens that are expressed or presented on the allogeneic HSPC cell surface, ultimately leading to graft rejection.

Despite advances in the medical field to suppress immune responses against allogeneic transplanted donor cells, there still remains a need for additional methods and compositions that can decrease rejection and/or improve the immunocompatibility of donor cells, including donor cells which have been genetically altered to treat the cause of particular disease states, e.g., using CRISPR/Cas9 systems. Most notably, there remains a need to improve the availability of suitable donor cells that can be successfully transplanted into recipient subjects regardless of immunogenicity gene haplotype differences.

SUMMARY

The methods and compositions described herein increase the immunocompatibility of donor cells (e.g., HSCs and/or T-cells) for transplantation to a recipient subject. The methods and compositions described herein result in the allele-specific modification of one or more immunogenicity genes (e.g., an HLA gene) of a cell, resulting in donor cells that are suitable for transplantation into a recipient subject. Specifically, by contacting the cells described herein with a Cas9 molecule and at least one allele-specific gRNA molecule (e.g., a modified gRNA molecule) that targets an endogenous immunogenicity gene, the allele is altered to generate an immune compatible cell (e.g., an immune compatible blood cell). Cells generated using the methods and compositions described herein are less likely to induce an immune response when transplanted in the recipient subject and/or are less likely to be rejected by the recipient's subject immune system. The ability to improve the immunocompatibility of donor cells that can be customized to be transplanted into any donor subject, regardless of immunogenicity gene haplotype of the donor, is particularly advantageous as it results in a dramatic increase in the pool of donor cells that can be used in the field of cell therapy for a multitude of clinical applications.

Provided herein is a method of producing an immune-compatible blood cell, comprising contacting a blood cell with a first allele-specific modified gRNA molecule and a Cas9 molecule, wherein the first allele-specific modified gRNA molecule and the Cas9 molecule associate with a first allele of an endogenous immunogenicity gene, thereby modifying the first allele of the endogenous immunogenicity gene and producing the immune-compatible blood cell.

A method of modifying an endogenous immunogenicity gene in a blood cell, is also provided herein, comprising selecting a first allele-specific gRNA molecule using a database schema, and contacting the blood cell with the first allele-specific gRNA molecule and a Cas9 molecule, wherein the allele-specific gRNA molecule and the Cas9 molecule associate with a first allele of an endogenous immunogenicity gene, thereby modifying the first allele of the endogenous immunogenicity gene.

Also provided is a method of reducing the cell surface expression of a first allele of an endogenous immunogenicity gene in a blood cell, comprising contacting the blood cell with a first allele-specific gRNA molecule and a Cas9 molecule, wherein the allele-specific gRNA molecule and the Cas9 molecule associate with the first allele of the endogenous immunogenicity gene, thereby reducing the cell surface expression of the first allele of the endogenous immunogenicity gene.

A method of transplanting a haplotype-modified blood cell into a subject, is also provided, wherein the method comprises isolating a blood cell from a first subject having a first haplotype at an endogenous immunogenicity gene, contacting the blood cell with a first allele-specific gRNA molecule and a Cas9 molecule, wherein the first allele-specific gRNA molecule associates with a first allele of the endogenous immunogenicity gene, thereby modifying the first allele of the endogenous immunogenicity gene, and transferring the blood cell to a second subject having a second haplotype at an endogenous immunogenicity gene.

The haplotype-modified blood cell may have a decreased likelihood of rejection by the second subject based on increased matching between donor and recipient cells and reduced immunogenicity as determined by mixed lymphocyte or leukocyte reaction assays.

The haplotype-modified blood cell may not be rejected by the second subject.

An ex vivo method of making a composition comprising a population of cells having an allele-specific gene modification, is also provided, comprising contacting a population of cells with an allele-specific gRNA molecule and a Cas9 molecule, wherein the allele-specific gRNA molecule and the Cas9 molecule associate with a single allele of a gene encoding an identifiable gene product; and enriching for cells that express the identifiable gene product but do not express the first allele.

The step of enriching for cells that express the gene but do not express the first allele in the methods described herein may comprise sorting the cells using flow cytometry.

The step of enriching for cells that express the gene but do not express the first allele may comprise contacting each of the plurality of cells with a first antibody that specifically binds to a first variant of the identifiable gene product encoded by the first allele of the gene and a second antibody that binds to a second variant of the identifiable gene product.

The step of enriching for cells that express the gene but do not express the first allele may comprise detecting, in each cell of the plurality of cells, a substance or signal associated with a functional variant of the identifiable gene product.

The population of cells may be a population of blood cells. The blood cells may be hematopoietic stem/progenitor cells (HSCs).

The population of cells may be selected from the group consisting of a population of circulating blood cells, a population of mobilized blood cells, a population of bone marrow cells, a population of myeloid progenitor cells, a population of lymphoid progenitor cells, a population of lymphoid cells, a population of multipotent progenitor cells, a population of lineage restricted progenitor cells, a population of endothelial cells, or a population of mesenchymal stromal cells, or combinations thereof.

The blood cell may be a stem cell. The stem cell may be a hematopoietic stem/progenitor cell (HSC). The cell may also be selected from the group consisting of a circulating blood cell, a mobilized blood cell, a bone marrow cell, a myeloid progenitor cell, a lymphoid progenitor cell, a lymphoid cell, a multipotent progenitor cell, a lineage restricted progenitor cell, an endothelial cell, a T lymphoid cell, or a mesenchymal stromal cell.

The gRNA molecule may be a modified gRNA molecule.

The gRNA molecule may comprise a targeting domain which is complementary to a target domain in a human leukocyte antigen (HLA) gene. The HLA gene may be selected from the group consisting of HLA-A, HLA-B, HLA-C, HLA-DRB1, HLA-DRB3/4/5, HLA-DQ, and HLA-DP.

The method may further comprise contacting the cell, or population of cells, with a second gRNA molecule, wherein said second gRNA molecule targets a gene described in Table 16.

The second gRNA molecule may be a modified gRNA molecule.

The method may further comprise contacting the cell with a second Cas9 molecule.

The Cas9 molecule may be an enzymatically active Cas9 (eaCas9) molecule. The eaCas9 molecule may generate a single strand break in the endogenous immunogenicity gene. The eaCas9 molecule may generate a double strand break in the endogenous immunogenicity gene.

The Cas9 molecule may be selected from the group consisting of wild-type Cas9, a Cas9 nickase, a dead Cas9 (dCas9), a split Cas9, and an inducible Cas9.

The Cas9 molecule may comprise an N-terminal RuvC-like domain cleavage activity, but have no HNH-like domain cleavage activity. The Cas9 molecule may comprise an amino acid mutation at an amino acid position corresponding to amino acid position N863 of *Streptococcus pyogenes* Cas9.

The Cas9 molecule may comprise an HNH-like domain cleavage activity but have no N-terminal RuvC-like domain cleavage activity. The Cas9 molecule may comprise an amino acid mutation at an amino acid position corresponding to amino acid position D10 of *Streptococcus pyogenes* Cas9.

The Cas9 molecule may be a Cas9 polypeptide. The Cas9 polypeptide may be a *Staphylococcus aureus* Cas9 polypeptide. The Cas9 polypeptide may be a *Streptococcus pyogenes* Cas9 polypeptide. The gRNA molecule and the Cas9 polypeptide may be associated in a pre-formed ribonucleotide complex.

The Cas9 molecule may be a nucleic acid encoding a Cas9 polypeptide.

The modified gRNA molecule may comprise a 5'-end cap structure. The 5'-end cap structure is a 3'-O-Me-m7G(5')ppp(5')G anti reverse cap analog (ARCA). The modified gRNA molecule may comprise a 3'-end poly-A tail.

The methods described herein may further comprise contacting the cell, or the population of cells, with a template nucleic acid. The template nucleic acid may be a single stranded oligodeoxynucleotide (ssODN). The ssODN may comprise a 5' phosphorothioate modification. The ssODN comprises a 3' phosphorothioate modification. The ssODN may comprise a 5' phosphorothioate modification and a 3' phosphorothioate modification.

The template nucleic acid may be delivered to the cell, or population of cells, using an adeno-associated virus (AAV) or an integration deficiency lentivirus (ILDV).

The methods described herein may further comprise contacting the cell, or the population of cells, with a transgene, wherein the contacting occurs under conditions that allow the transgene to integrate into the genome of the cell, or into a cell of the population of cells. The transgene may integrate into a safe harbor site in the genome of the cell.

The transgene may be a gene encoding an immune-identical human leukocyte antigen (HLA), a chemotherapy selection marker, a cell surface antigen, or a suicide gene. The transgene may be a HLA gene or a fragment thereof. The HLA gene may be selected from the group consisting of HLA-A, HLA-B, HLA-C, HLA-DRB1, HLA-DRB3/4/5, HLA-DQ, and HLA-DP.

The methods described herein may further comprise contacting the cell, or the population of cells, with an eiCas9 molecule. The eiCas9 may be fused to a transcriptional repressor or a transcriptional activator.

The cell may comprise a population of cells.

The methods described herein may further comprise selecting a cell expressing a specific allele of a gene by sorting the population of cells using an allele-specific antibody. The population of cells may be sorted by fluorescence activated cell sorting (FACS) or immunomagnetic microbead mediated cell sorting.

The gene may be an immunogenicity gene.

The methods described herein may further comprise isolating the blood cell from a first subject having a first haplotype at the endogenous immunogenicity gene.

The methods described herein may further comprise transferring the blood cell to a second subject having a second haplotype at the endogenous immunogenicity gene, after the contacting step.

The methods described herein may further comprise expanding the cell or population of cells ex vivo after the contacting step.

The methods described herein may further comprise a T cell add-back.

The identifiable gene product may be a cell surface marker. The identifiable gene product may be a human leukocyte antigen (HLA). The identifiable gene product may be a major histocompatibility antigen complex protein or a minor histocompatibility antigen (MiHA) (e.g., a chemokine receptor).

The first allele of the gene may encode a non-functional variant of the identifiable gene product.

The methods described herein may further comprise altering (e.g., inactivating, e.g., by knock-down or knock-out), an additional gene locus using a Cas9 molecule and a gRNA molecule. The additional gene locus may be the gene locus of chemokine receptor, e.g., CCR1, CCR2, CCR4, CCR5, CCR6, CCR10, CXCR1, CXCR2, CXCR3, or CXCR6.

In an embodiment, the method further comprises acquiring a sequence of the cell to confirm modification.

The cell or population of cells may be a primary blood cell or population of primary blood cells. The cell or population of cells may be a $CD34^+$ bone marrow cell, a $CD34^+$ peripheral blood cell, or a $CD34^+$ cell generated from an induced pluripotent stem (iPS) cell, an embryonic stem (ES) cell, an endothelial cell, a lymphoid progenitor cell, a myeloid progenitor cell, a T-lymphoid cell, or a population of any of these cells. The population of cells may be a heterogeneous population of cells or a homogeneous population of cells.

The methods described herein may be used to alter a first, second, third, fourth, fifth sixth, second, eighth, ninth, tenth, or more alleles using one or more allele-specific gRNA molecule(s) and a Cas9 molecule. The alleles altered using the methods described herein may lead to the inactivation of the altered allele (e.g., by insertion of an indel).

A composition made by any of the methods described herein is also provided. The composition may be for use as a medicament. The composition may be for use in transplantation.

A cell or population of cells altered by the methods described herein are also provided.

A pharmaceutical composition comprising the cell or population of cells described herein are also provided.

The cell may comprise an HLA-A allele selected from Table 1, an HLA-B allele selected form Table 2, an HLA-C allele selected from Table 3, an HLA-DRB1 allele, selected from Table 4, or an HLA-DQB1 allele selected from Table 5.

The second subject may comprise a haplotype selected from Tables 6-15. The second subject may have an inherited blood disorder, e.g., an anemia an immunodeficiency, or hemoglobinopathy blood dyscrasia, enzyme storage deficiency or other disease (e.g., inherited or acquired hematologic disease). The second subject may have an acquired disorder, or a disorder characterized by unwanted cell proliferation. The second subject may have leukemia, lymphoma, myeloma, myelodysplastic syndrome, or myeloproliferative disease. The second subject may be infected with HIV or have Acquired Immunodeficiency Syndrome (AIDS).

The first and second subject may be of different genders, e.g., the first subject is male and the second subject is female, or the first subject is female and the second subject is male.

The first subject may be of a different ethnic background or ethnicity than the first subject. The first subject and the second subject may be of the same ethnic background or ethnicity. The ethnic background or ethnicity may be Asian (e.g., Asian-American, e.g., Asian Pacific Islander), African (e.g., a diasporic African, e.g., an African American), Caucasian (e.g, European American). Hispanic (e.g., Latino, e.g, Hispanic American), Jewish, or of the Indian subcontinent (Sub continental). The first subject may be of a different ethnic ancestry than the first subject. The first subject and the second subject may be of the same ethnic ancestry.

A method of treating or preventing a disease in a subject comprising administering to the subject a modified cell or a cell altered by any of the methods provided herein is also provided. The disease may be a disease listed in Table 16.

The methods of treating or preventing a disease may comprise a second administration of the modified cell or a cell altered by any of the methods provided herein to the subject. The second administration of modified cells may be within 3, 6, 9, 12, 1, or 24 months of an initial administration.

The subject may have a condition that contradicts conditioning or immunosuppression. The subject may have multiple co-morbidities, severe co-morbid disease, high risk for GVHD or graft rejection, or an ongoing, chronic, or acute, infection. The subject may be more than 50, 55, 60, 65, 70, or 75 years of age. The subject may be less than 5, 4, 3, 2, or 1 year of age.

The method may further comprises conditioning (e.g., to ablate endogenous HSPCs or create hematopoietic space) the subject prior to administration of the modified cells (e.g., a modified HSPC, HPC, CB-HSPC, $CD34^+$ cell, lymphoid progenitor cell, myeloid progenitor cell, or T lymphoid cell).

The conditioning may be less toxic than the conditioning regimen that would be used during the transplantation of an allogenic cell that is unmatched at one or more of the alleles that have been modified in the modified cell.

The method may comprise administering an immunosuppressive treatment to the subject (e.g., before or after administration of the modified cell). The immunosuppressive may be less toxic than the immunosuppressive treatment that would be used in the transplantation of an allogenic cell that is unmatched at one or more of the loci that have been modified in the modified cell.

The subject may have been pregnant prior to the treatment. The subject may have had a blood transfusion previous to the treatment.

The modified cell may be administered after onset of a disorder to be treated. The modified cell may be administered prior to onset of a disorder to be treated.

A blood cell comprising a modification in a first allele of an endogenous immunogenicity gene, wherein the blood cell has been contacted with a first allele-specific modified gRNA molecule and a Cas9 molecule is also provided. The blood cell may be modified at a first, second, third, fourth, fifth sixth, second, eighth, ninth, tenth, or more alleles using one or more allele-specific gRNA molecule(s) and a Cas9 molecule.

A population of blood cells comprising a modification in a first allele of an endogenous immunogenicity gene, wherein the population of blood cells has been contacted with a first allele-specific modified gRNA molecule and a Cas9 molecule is also provided. The population of blood cells may be modified at a first, second, third, fourth, fifth sixth, second, eighth, ninth, tenth, or more alleles using one or more allele-specific gRNA molecule(s) and a Cas9 molecule.

The immunogenicity gene may be a human leukocyte antigen (HLA) gene.

The methods described herein may further comprise selecting the first allele-specific gRNA molecule using a database schema.

The step of selecting the first allele-specific gRNA molecule using a database schema may comprise receiving, via an interface of the computational system, a listing of a first plurality of alleles of the endogenous immunogenicity gene of a first subject; receiving, via the interface of the computational system, a listing of a second plurality of alleles of the endogenous immunogenicity gene of a second subject; processing the listings of the first and second pluralities of alleles to identify one or more mismatched alleles between the first plurality of alleles and the second plurality of alleles; querying a database to determine whether one or more gRNA molecules are suitable for editing the one or more mismatched alleles of the second plurality of alleles; in response to determining that one or more gRNA molecules from the database are suitable to edit the one or more mismatched alleles, generating a list of gRNA molecules that identifies the one or more gRNA molecules found to be suitable; ranking the list of gRNA molecules; and displaying the ranked list of gRNA molecules.

A non-transitory computer readable storage medium storing instructions for execution by a processing device for implementing a database schema is also provided, the database schema comprising: an allele table storing data related to major HLA alleles; a gRNA table storing data related to gRNAs; an allele-gRNA-relation table storing relationships between records of the allele table and records of the gRNA table, the allele table having a one-to-many relationship with the allele-gRNA-relation table, and the gRNA table having a one-to-many relationship with the allele-gRNA-relation table; a haplotype table storing data related to haplotypes, the allele table having a one-to-many relationship with the haplotype table; a haplotype-frequency table storing data related to frequency of a haplotype occurring within a plurality of ancestries, the haplotype table having a one-to-one relationship with the haplotype-frequency table; an ancestry table storing data related to ancestry; an ancestry-haplotype-relation table storing relationships between records of the haplotype-frequency table and records of the ancestry table, the haplotype-frequency table having a one-to-many relationship with the ancestry-haplotype-relation table, the ancestry table having a one-to-many relationship with the an ancestry-haplotype-relation table; an allele frequency table storing data related to frequency of an allele occurring within a plurality of ancestries, the allele table having a one-to-one relationship with the allele frequency table; and an allele-ancestry-relation table storing relationships between records of the allele frequency table and records of the ancestry table, the allele frequency table having a one-to-many relationship with the allele-ancestry-relation table and the ancestry table having a one-to-many relationship with the allele-ancestry-relation table.

The database schema may further comprise a minor-antigens table storing data related to minor histocompatibility antigens; and a major-minor-restriction table storing data related to HLA restrictions to minor histocompatibility antigens, the minor-antigen table having a one-to-many relationship to the major-minor-restriction table, and the allele table having a one-to-many relationship with the major-minor-restriction table.

The allele table may comprise an allele id key, an allele attribute, a gene name attribute, and an allele sequence attribute.

The gRNA table may comprise a gRNA id key, a Cas variant attribute, a gRNA sequence (with PAM) attribute, a gRNA sequence (without PAM) attribute, a strand attribute, an orthogonality score attribute, and an off-target list information attribute.

The allele-guide-relation table may comprise a relation id key, an allele id attribute that corresponds to an allele id key of the allele table, a gRNA id attribute that correspond to a gRNA id key of the gRNA table.

The haplotype table may comprise a haplotype id key, a HLA-A allele attribute, a HLA-B allele attribute, a HLA-C allele attribute, a HLA-DRB1 locus attribute, a HLA-DRB3/DRB4/DRB5 locus attribute, a HLA-DQB1 allele locus attribute.

The haplotype-frequency table may comprise a haplotype frequency id key, a haplotype id attribute that corresponds to a haplotype id key of the haplotype table, an attribute for frequency of occurrence of a haplotype in European ancestry group, an attribute for rank of a haplotype occurrence in European ancestry group, an attribute for frequency of occurrence of a haplotype in African American ancestry group, an attribute for rank of a haplotype occurrence in African American ancestry group, an attribute for frequency of occurrence of a haplotype in Asian ancestry group, an attribute for rank of a haplotype occurrence in Asian ancestry group, an attribute for frequency of occurrence of a haplotype in Hispanic ancestry group, an attribute for rank of a haplotype occurrence in Hispanic ancestry group, an attribute for frequency of occurrence of a haplotype in Jewish ancestry group, and an attribute for rank of a haplotype occurrence in Jewish ancestry group.

The allele-frequency table may comprise an allele frequency id key, an allele id attribute corresponds to an allele id key of the allele table, an attribute for frequency of occurrence of an allele in European ancestry group, an attribute for rank of an allele occurrence in European ancestry group, an attribute for frequency of occurrence of an allele in African American ancestry group, an attribute for rank of an allele occurrence in African American ancestry group, an attribute for frequency of occurrence of an allele in Asian ancestry group, an attribute for rank of an allele occurrence in Asian ancestry group, an attribute for frequency of occurrence of an allele in Hispanic ancestry group, an attribute for rank of an allele occurrence in Hispanic ancestry group, an attribute for frequency of occurrence of an allele in Jewish ancestry group, and an attribute for rank of an allele occurrence in Jewish ancestry group.

The allele-frequency table may have an identifying relationship with the allele table and is entirely dependent on the allele table.

The haplotype-frequency table may have an identifying relationship with the haplotype table and is entirely dependent on the haplotype table.

The gRNAs may be designed for editing immunogenicity alleles. The gRNAs may be designed for editing HLA alleles.

The haplotypes may be groups of alleles for different HLA genes.

Also provided is a method performed in a computational system for identifying gRNAs for editing one or more alleles comprising: receiving, via an interface of the computational system, a listing of a first plurality of alleles of a targeted transplant recipient; receiving, via the interface of the computational system, a listing of a second plurality of alleles of a targeted transplant donor; processing the listings of the first and second pluralities of alleles to identify one or more mismatched alleles between the first plurality of alleles and the second plurality of alleles; querying a database to determine whether one or more gRNAs are suitable for editing the one or more mismatched alleles of the second plurality of alleles; in response to determining that one or more gRNAs from the database are suitable to edit the one or more mismatched alleles, generating a list of gRNAs that identifies the one or more gRNAs found to be suitable; ranking the list of gRNAs; and displaying the ranked list of gRNAs.

A gRNA from the list of gRNAs may be capable of editing a mismatched allele from the second plurality of alleles of the targeted transplant donor to increase the number of matching alleles between the first plurality of alleles and the second plurality of alleles.

A gRNA from the list of gRNAs may be capable of editing the one or more mismatched alleles to reduce the likelihood of Graft-versus-host disease (GVHD) occurring in the targeted transplant recipient.

The methods described herein may further comprise displaying the DNA sequence for each of the first plurality of alleles.

The database may store a number indicating a likelihood of an allele occurring in a racial group. The database may store a number indicating a likelihood of an allele occurring in a ethnic group.

The methods described herein may further comprise displaying a frequency of occurrence of each of the first plurality of alleles within an ancestry.

The methods described herein may further comprise displaying a restriction relationship between each of the first plurality of alleles and a minor histocompatibility antigen.

The first plurality of alleles is the maternally inherited major HLA haplotype of the targeted transplant recipient, and the second plurality of alleles is the maternally inherited major HLA haplotype of the targeted transplant donor.

The listing of the first plurality of alleles may comprise one allele, two alleles, three alleles, four alleles, five alleles, six alleles, seven alleles, eight alleles, nine alleles or ten alleles. The blood cell may be modified at a first, second, third, fourth, fifth sixth, second, eighth, ninth, tenth, or more loci using one or more allele-specific gRNA molecule(s) and a Cas9 molecule.

The listing of the second plurality of alleles may comprise one allele, two alleles, three alleles, four alleles, five alleles, six alleles, seven alleles, or eight alleles.

The list of gRNAs may identify one gRNA for editing one mismatched allele. The list of gRNAs may identify more than one gRNA for editing more than one mismatched allele.

The list of gRNAs may identify one gRNA for editing more than one mismatched allele.

The database may be implemented using the database schema described herein.

Also provided is a system for implementing a database schema, the system comprising a processor; and a memory storing a database schema, wherein the database schema comprises an allele table storing data related to HLA alleles; a gRNA table storing data related to gRNAs; an allele gRNA relation table storing relationships between records of the allele table and records of the gRNA table, the allele table having a one-to-many relationship with the allele gRNA relation table, and the gRNA table having a one-to-many relationship with the allele gRNA relation table; a haplotype table storing data related to haplotypes, the allele table having a one-to-many relationship with the haplotype table; an ancestry table storing data related to ancestral information; an ancestry haplotype relation table storing relationships between records of the haplotype table and records of the ancestry table, the haplotype table having a one-to-many relationship with the ancestry haplotype relation table, the ancestry table having a one-to-many relationship with the ancestry haplotype relation table; an allele frequency table storing data related to frequency of an allele occurring within a plurality of ancestries, the allele table having a one-to-many relationship with the allele frequency table; and allele ancestry relation table storing relationships between records of the allele frequency table and records of the ancestry table, the allele frequency table having a one-to-many relationship with the allele ancestry relation table and the ancestry table having a one-to-many relationship with the allele ancestry relation table.

Also provided is a system for identifying gRNAs for editing one or more alleles, the system comprising a processor; and a memory storing instructions that when executed causes the processor to receive a listing of a first plurality of alleles of a targeted transplant recipient; receive a listing of a second plurality of alleles of a targeted transplant donor, process the listings of the first and second pluralities of alleles to identify one or more mismatched alleles between the first plurality of alleles and the second plurality of alleles; query a database to determine whether one or more gRNAs are suitable for editing the one or more mismatched alleles of the second plurality of alleles; in response to determining that one or more gRNAs from the database are suitable to edit the one or more mismatched alleles, generate a list of gRNAs that identifies the one or more gRNAs found to be suitable; rank the list of gRNAs; and display the ranked list of gRNAs.

Further, provided is a non-transitory computer readable medium storing instructions for execution by a processing device, execution of the instructions causing the processing device to create a database in accordance with a schema, the schema defining: an allele table storing data related to HLA alleles; a gRNA table storing data related to gRNAs; an allele gRNA relation table storing relationships between records of the allele table and records of the gRNA table, the allele table having a one-to-many relationship with the allele gRNA relation table, and the gRNA table having a one-to-many relationship with the allele gRNA relation table; a haplotype table storing data related to haplotypes, the allele table having a one-to-many relationship with the haplotype table; an ancestry table storing data related to ancestral information; an ancestry haplotype relation table storing relationships between records of the haplotype table and records of the ancestry table, the haplotype table having a one-to-many relationship with the ancestry haplotype relation table, the ancestry table having a one-to-many relationship with the ancestry haplotype relation table; an allele frequency table storing data related to frequency of an allele occurring within a plurality of ancestries, the allele table having a one-to-many relationship with the allele frequency table; and allele ancestry relation table storing relationships between records of the allele frequency table and records of the ancestry table, the allele frequency table having a one-to-many relationship with the allele ancestry relation table and the ancestry table having a one-to-many relationship with the allele ancestry relation table.

BRIEF DESCRIPTION OF THE DRAWINGS

FIGS. 1A-1I are representations of several exemplary gRNAs.

FIG. 1A depicts a modular gRNA molecule derived in part (or modeled on a sequence in part) from *Streptococcus pyogenes* (*S. pyogenes*) as a duplexed structure (SEQ ID NOs: 39 and 40, respectively, in order of appearance);

FIG. 1B depicts a unimolecular gRNA molecule derived in part from *S. pyogenes* as a duplexed structure (SEQ ID NO:41);

FIG. 1C depicts a unimolecular gRNA molecule derived in part from *S. pyogenes* as a duplexed structure (SEQ ID NO:42):

FIG. 1D depicts a unimolecular gRNA molecule derived in part from *S. pyogenes* as a duplexed structure (SEQ ID NO:43);

FIG. 1E depicts a unimolecular gRNA molecule derived in part from *S. pyogenes* as a duplexed structure (SEQ ID NO:44);

FIG. 1F depicts a modular gRNA molecule derived in part from *Streptococcus thermophilus* (*S. thermophilus*) as a duplexed structure (SEQ ID NOs:45 and 46, respectively, in order of appearance);

FIG. 1G depicts an alignment of modular gRNA molecules of *S. pyogenes* and *S. thermophilus* (SEQ ID NOs:39, 45, 47, and 46, respectively, in order of appearance).

FIGS. 1H-1I depict additional exemplary structures of unimolecular gRNA molecules.

FIG. 1H shows an exemplary structure of a unimolecular gRNA molecule derived in part from *S. pyogenes* as a duplexed structure (SEQ ID NO:42).

FIG. 1I shows an exemplary structure of a unimolecular gRNA molecule derived in part from *S. aureus* as a duplexed structure (SEQ ID NO:38).

FIGS. 2A-2G depict an alignment of Cas9 sequences (Chylinski 2013). The N-terminal RuvC-like domain is boxed and indicated with a "Y." The other two RuvC-like domains are boxed and indicated with a "B." The HNH-like domain is boxed and indicated by a "G." Sm: *S. mutans* (SEQ ID NO:1); Sp: *S. pyogenes* (SEQ ID NO:2); St: *S. thermophilus* (SEQ ID NO: 4); and Li: *L. innocua* (SEQ ID NO: 5). "Motif" (SEQ ID NO: 14) is a consensus sequence based on the four sequences. Residues conserved in all four sequences are indicated by single letter amino acid abbreviation; "*" indicates any amino acid found in the corresponding position of any of the four sequences; and "-" indicates absent.

FIGS. 3A-3B show an alignment of the N-terminal RuvC-like domain from the Cas9 molecules disclosed in Chylinski 2013 (SEQ ID NOs:52-95, 120-123). The last line of FIG. 3B identifies 4 highly conserved residues.

FIGS. 4A-4B show an alignment of the N-terminal RuvC-like domain from the Cas9 molecules disclosed in Chylinski 2013 with sequence outliers removed (SEQ ID NOs:52-123). The last line of FIG. 4B identifies 3 highly conserved residues.

FIGS. 5A-5C show an alignment of the HNH-like domain from the Cas9 molecules disclosed in Chylinski 2013 (SEQ ID NOs:124-198). The last line of FIG. 5C identifies conserved residues.

FIGS. 6A-6B show an alignment of the HNH-like domain from the Cas9 molecules disclosed in Chylinski 2013 with sequence outliers removed (SEQ ID NOs:124-141, 148, 149, 151-153, 162, 163, 166-174, 177-187, 194-198). The last line of FIG. 6B identifies 3 highly conserved residues.

FIGS. 16A-16B depict targeting Cas9 and single gRNA to disrupt single HLA-A allele in donor cells and replacement of HLA-A allele with recipient allele.

FIG. 16A shows the donor and recipient HLA alleles at A, B, and DRB1 loci. In this example, an African American recipient subject in need of a hematopoietic stem cell transplant does not have a fully matched donor. An European American donor has been identified in which 5 of 6 alleles are matched. Cas9 and gRNA specific for the HLA-A allele A*02:01:01:01 are delivered to donor HSPCs to eliminate expression of the mismatched allele. Next, the cDNA for the recipient HLA-A allele A*01:01:01:01 is introduced into the donor HSPCs to achieve a 6 out of 6 (full match) with recipient. Mismatched alleles are indicated by shaded boxes. The allele that is targeted for disruption by Cas9/gRNA in the donor is indicated by black box, and recipient cDNA replacement indicated by allele in gray box.

FIG. 16B shows the cDNA sequence (SEQ ID NO: 362) for HLA-A*01:01:01:01 that is encoded in a transgene expression cassette and delivered to HLA-A*02:01:01:01 disrupted cells to replace mismatched donor HLA-A allele with identical recipient HLA-A allele.

FIGS. 17A-17B depict targeting Cas9/gRNA for biallelic disruption of HLA-A locus in donor cells and replacement of HLA-A with recipient alleles.

FIG. 17A shows the donor and recipient HLA alleles at A, B, and DRB1 loci. In this example, a Hispanic recipient subject in need a of a hematopoietic stem cell transplant does not have a fully matched donor. A European American HSPC donor has been identified in which 4 of 6 alleles are matched between the potential donor and the recipient. Cas9 and a single gRNA that simultaneously targets both A*02:01:01:01 and A*29:02:01:01 alleles are delivered to donor HSPCs to eliminate expression of both of these mismatched HLA-A alleles. Next, the cDNAs for the recipient HLA-A alleles A*01:01:01:01 and A*23:01:01 are delivered to the donor HSPCs to achieve a to 6 out of 6 (full match) between donor and recipient. Mismatched alleles are indicated by shaded boxes. The alleles that are targeted for disruption by Cas9/gRNA in the donor are indicated by black boxes, and recipient cDNAs that replace the disrupted alleles are indicated by gray boxes.

FIG. 17B shows the cDNA sequence (SEQ ID NO: 363) for HLA-A*23:01:01:01 that are encoded in transgene expression cassette and delivered to HLA-$A^{-/-}$ disrupted cells to replace mismatched donor HLA-A allele with identical recipient HLA-A allele. HLA-A*01:01:01 sequence (shown in previous example, panel B), is also delivered to HLA-$A^{-/-}$ donor cells.

FIGS. 18A-18B depict targeting Cas9/gRNAs for multiplex editing and targeted disruption of haplotype (HLA-A, -B, -DRB1) in donor cells and replacement with recipient alleles.

FIG. 18A shows the donor and recipient HLA alleles at A, B, and DRB1 loci. In this example, an Hispanic recipient subject in need a of a hematopoietic stem cell transplant does not have a fully matched donor. A haploidentical European American HSPC donor has been identified. Cas9 and three gRNAs that target the alleles at three MHC loci (A*02:01:01:01, B*08:01:01, and DRB1*03:01:01:01 01) are delivered to donor HSPCs to eliminate expression of the unmatched haplotype. Next, the cDNAs for the recipient haplotype A*03:01:01:01, B*07:02:01, DRB1*15:01:01:01 are delivered to the donor HSPCs to achieve a to 6 out of 6 (full match) between donor and recipient. Mismatched alleles are indicated by shaded boxes. The alleles that are targeted for disruption by Cas9/gRNA in the donor are indicated by black boxes, and recipient cDNAs that replace the disrupted alleles are indicated by gray boxes.

FIG. 18B shows the cDNA sequences for replacement of mismatched donor haplotype with identical recipient haplotype (A*03:01:01:01 1098 bp (SEQ ID NO: 364); B*07:02:01 1089 bp (SEQ ID NO: 365); DRB1*15:01:01:01 801 bp (SEQ ID NO: 366)).

FIG. 29 illustrates an exemplary query/input and an exemplary gRNA list as an output of the gRNA identification system, according to an exemplary embodiment.

FIG. 30 illustrates an exemplary allele sequence as an output of the gRNA identification system, according to an exemplary embodiment.

FIG. 31A illustrates an exemplary haplotype and allele frequency of different ancestral groups in US population as an output of the gRNA identification system, according to an exemplary embodiment.

FIG. 31B illustrates an exemplary haplotype and allele frequency of different ancestral groups in US population as an output of the gRNA identification system, according to an exemplary embodiment.

FIG. 32 illustrates an exemplary minor histocompatibility antigens (miHAgs) restriction in view of major histocompatibility complex (MHC);

DETAILED DESCRIPTION

Definitions

Figure 1A:
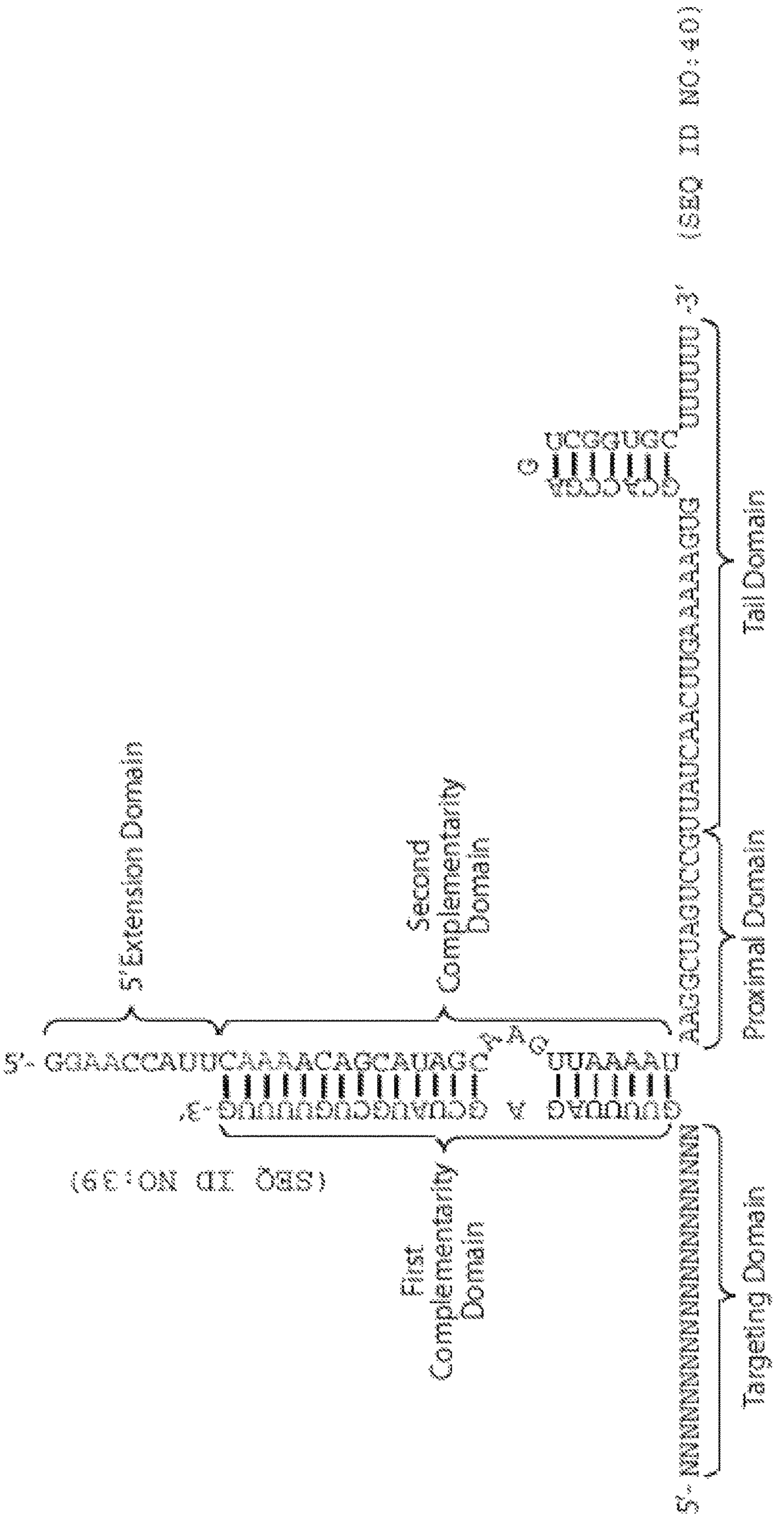
Figure 1B:
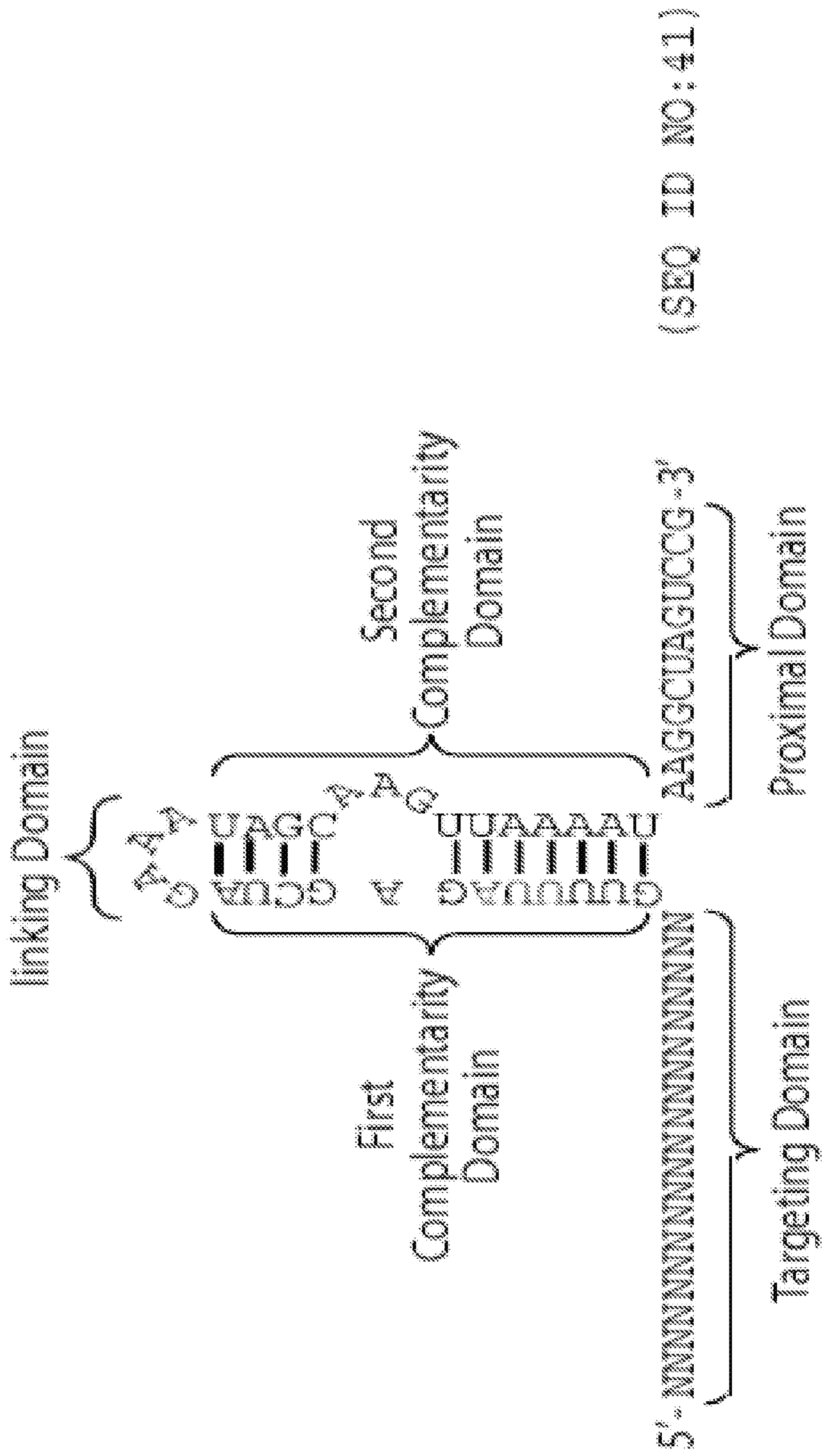
Figure 1C:
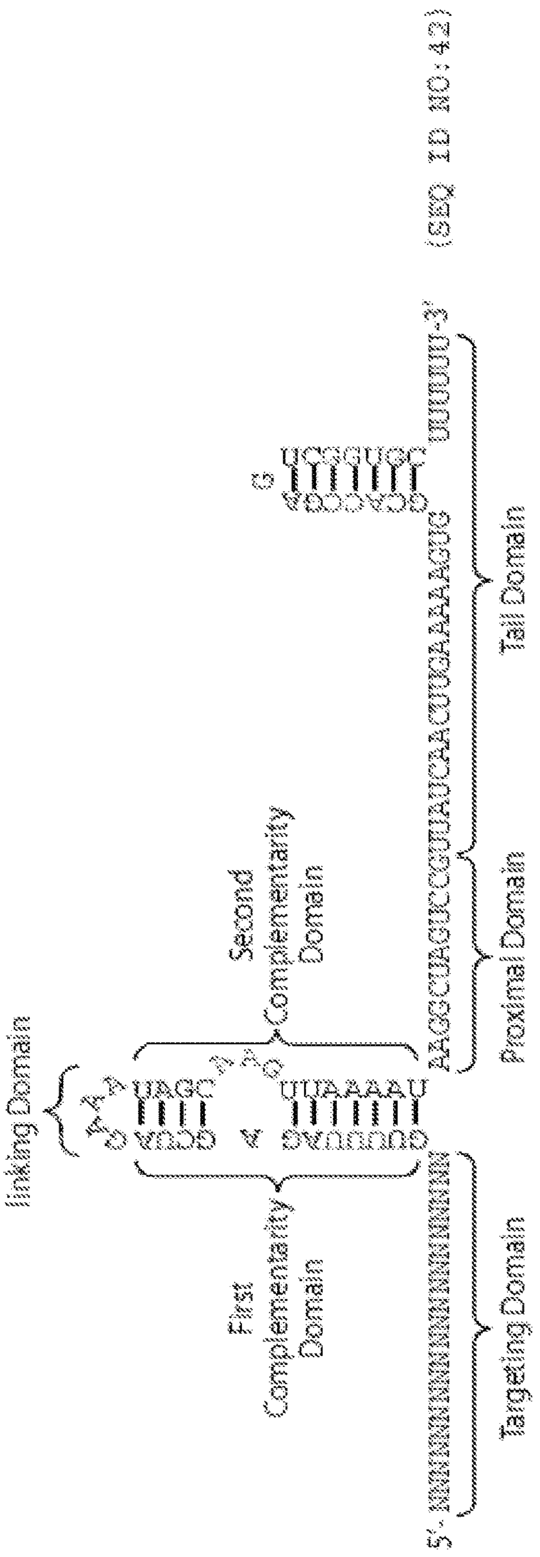
Figure 1D:
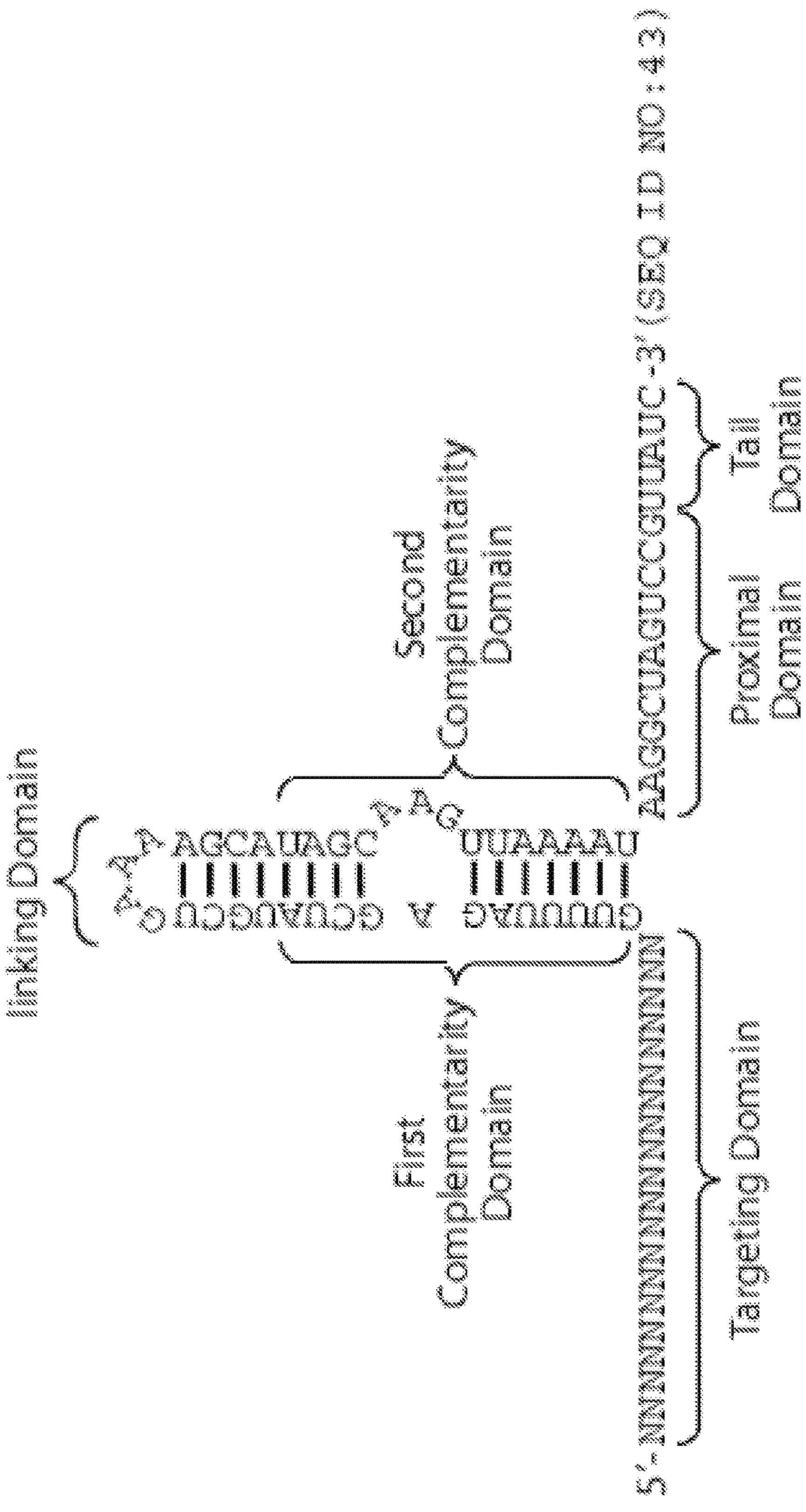
Figure 1E:
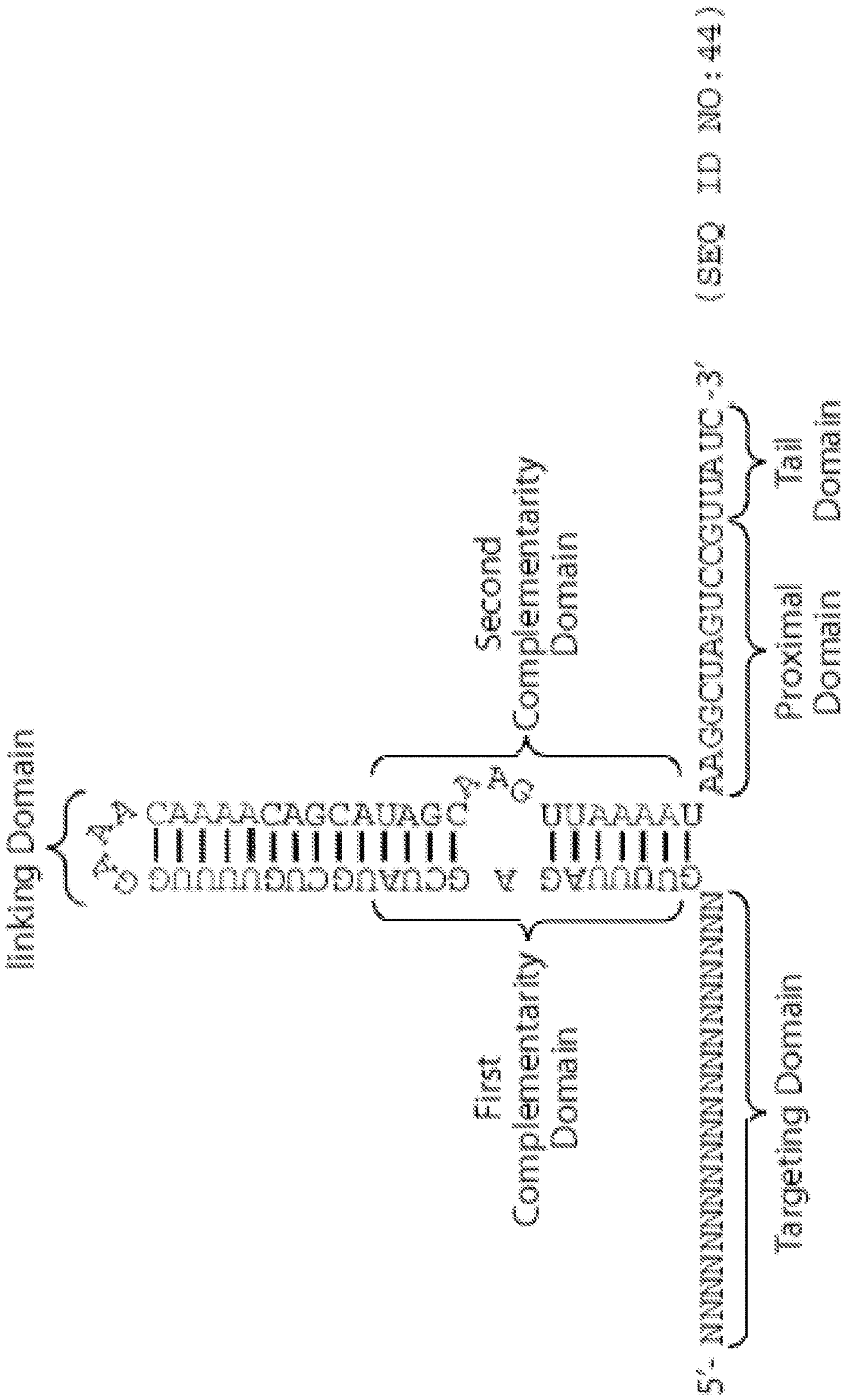
Figure 1F:
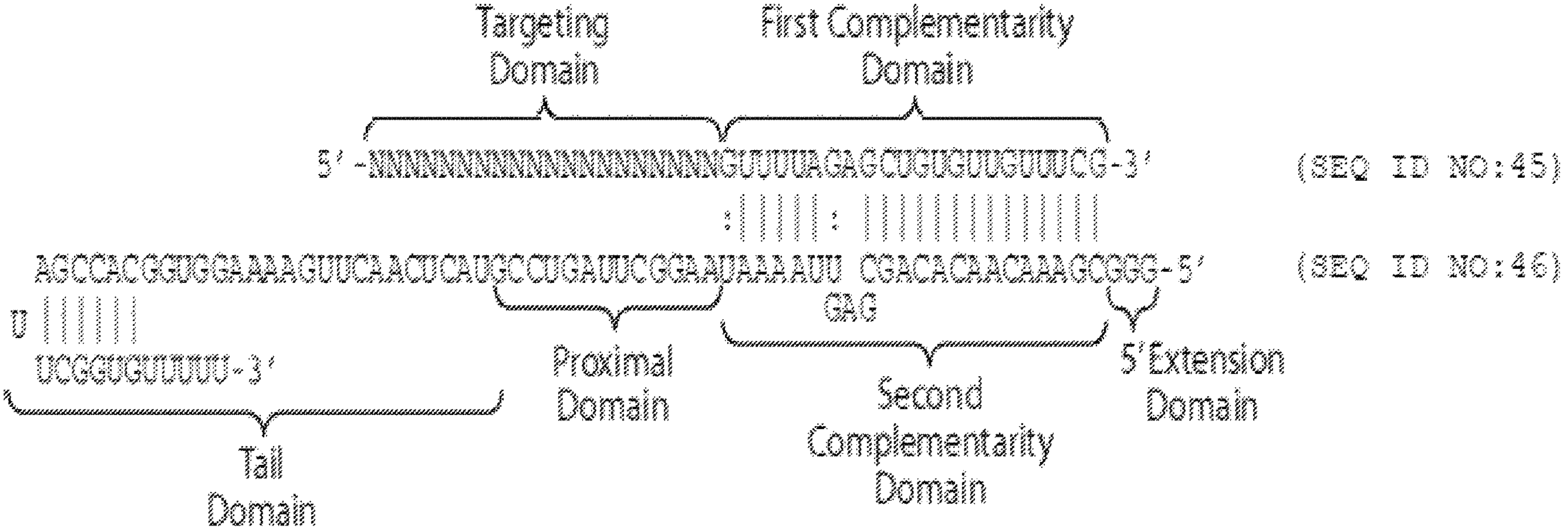

"Target knockout position", as used herein, refers to a position in a gene or locus, e.g., a gene or locus described herein, e.g., a human leukocyte antigen (HLA) gene or locus, which if altered, e.g., by NHEJ-mediated alteration, results in inactivation, e.g., cleavage, of the gene or locus.

"Target knockdown position", as used herein, refers to a position in a gene of locus, e.g., a gene or locus described herein, e.g., a human leukocyte antigen (HLA) gene or locus, which if targeted, e.g., by an eiCas9 molecule or an eiCas9 fusion described herein, results in reduction or elimination of expression of functional gene product from the gene or locus.

"Target knockin position", as used herein, refers to a sequence, which if modified by the insertion of a sequence of a gene or locus, e.g., a gene or locus described herein, e.g., a human leukocyte antigen (HLA) gene or locus, results in expression of functional gene product from the gene or locus.

"Target position", as used herein, refers to any of a target knockout position, a target knockdown position, or a target knockin position, as described herein.

"Canonical HDR", or canonical homology-directed repair, as used herein, refers to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, HDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

"Alt-HDR" or "alternative HDR", or alternative homology-directed repair, as used herein, refers to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Also, alt-HDR uses a single-stranded or nicked homologous nucleic acid for repair of the break.

Unless indicated otherwise, the term "HDR" as used herein encompasses canonical HDR and alt-HDR.

"Non-homologous end joining" or "NHEJ", as used herein, refers to ligation mediated repair and/or non-template mediated repair including canonical NHEJ (cNHEJ), alternative NHEJ (altNHEJ), microhomology-mediated end joining (MMEJ), single-strand annealing (SSA), and synthesis-dependent microhomology-mediated end joining (SD-MMEJ).

"Allele", as used herein, refers to one of several alternate forms of a gene or non-coding regions of DNA that occupy the same position on a chromosome.

"Allele-specific gene modification", as used herein, refers to the process of editing a nucleic acid using a nuclease (e.g., a Cas9 molecule) described herein, wherein a specific allele is targeted for modification via a gRNA molecule that targets a particular allele (i.e., an allele-specific gRNA molecule"). In some embodiments, the gRNA molecule preferentially targets a particular allele.

"Allele-specific gRNA molecule", as used herein, refers to a gRNA molecule which preferentially targets a nuclease (e.g., a Cas9 molecule) to particular allele.

"Cell surface expression" as used herein refers to the availability of a polypeptide in the plasma membrane of a cell. In some embodiments, cell surface expression is regulated by gene expression. In some embodiments, cell surface expression is regulated by post-translational mechanisms.

"Domain", as used herein, is used to describe segments of a protein or nucleic acid. Unless otherwise indicated, a domain is not required to have any specific functional property.

"Donor cell", as used herein, refers to a non-self cell (e.g., a blood cell) that is administered to a subject.

"Recipient cell", as used herein, refers to a cell (e.g., a blood cell) from a subject to whom a donor cell is administered.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

"Governing gRNA molecule", as used herein, refers to a gRNA molecule that comprises a targeting domain that is complementary to a target domain on a nucleic acid that comprises a sequence that encodes a component of the CRISPR/Cas system that is introduced into a cell or subject. A governing gRNA does not target an endogenous cell or subject sequence. In an embodiment, a governing gRNA molecule comprises a targeting domain that is complementary with a target sequence on: (a) a nucleic acid that encodes a Cas9 molecule; (b) a nucleic acid that encodes a gRNA which comprises a targeting domain that targets a gene (a target gene gRNA); or on more than one nucleic acid that encodes a CRISPR/Cas component, e.g., both (a) and (b). In an embodiment, a nucleic acid molecule that encodes a CRISPR/Cas component, e.g., that encodes a Cas9 molecule or a target gene gRNA, comprises more than one target domain that is complementary with a governing gRNA targeting domain. It is believed that a governing gRNA molecule complexes with a Cas9 molecule and results in Cas9 mediated inactivation of the targeted nucleic acid, e.g., by cleavage or by binding to the nucleic acid, and results in cessation or reduction of the production of a CRISPR/Cas system component. In an embodiment, the Cas9 molecule forms two complexes: a complex comprising a Cas9 molecule with a target gene gRNA, which complex will alter the gene; and a complex comprising a Cas9 molecule with a governing gRNA molecule, which complex will act to prevent further production of a CRISPR/Cas system component, e.g., a Cas9 molecule or a target gene gRNA molecule. In an embodiment, a governing gRNA molecule/Cas9 molecule complex binds to or promotes cleavage of a control region sequence, e.g., a promoter, operably linked to a sequence that encodes a Cas9 molecule, a sequence that encodes a transcribed region, an exon, or an intron, for the Cas9 molecule. In an embodiment, a governing gRNA molecule/Cas9 molecule complex binds to or promotes cleavage of a control region sequence, e.g., a promoter, operably linked to a gRNA molecule, or a sequence that encodes the gRNA molecule. In an embodiment, the governing gRNA, e.g., a Cas9-targeting governing gRNA molecule, or a target gene gRNA-targeting governing gRNA molecule, limits the effect of the Cas9 molecule/target gene gRNA molecule complex-mediated gene targeting. In an embodiment, a governing gRNA places temporal, level of expression, or other limits, on activity of the Cas9 molecule/target gene gRNA molecule complex. In an embodiment, a governing gRNA reduces off-target or other unwanted activity. In an embodiment, a governing gRNA molecule inhibits, e.g., entirely or substantially entirely inhibits, the production of a component of the Cas9 system and thereby limits, or governs, its activity.

"Haplotype", as used herein, refers to a haploid genotype, a combination or set of alleles or DNA sequences found at different locations or loci on a chromosome which are typically inherited as a unit and are linked. A haplotype can provide a distinctive genetic pattern of an individual. A haplotype can be determined for one locus, several loci, or an entire chromosome.

"Haplotype-modified blood cell", as used herein, refers to a blood cell that has been genetically-modified at one or more immunogenicity genes to alter the haplotype of the cell.

As used herein, the term "identifiable gene product" refers to a polypeptide or peptide that can be detected using methods known in the art (e.g., FACS, enzyme-linked immunosorbent assay (ELISA), etc.). In some embodiments, the polypeptide or peptide comprises one or more post-translational modifications. In some embodiments, the identifiable gene product is detected on or in an intact cell (e.g., on the surface of the cell or inside a cell).

As used herein, "immunogenicity" refers to property that allows a substance to induce a detectable immune response (humoral or cellular) when introduced into a subject (e.g., a human subject).

As used herein, the term "immunogenicity gene" refers to a gene encoding a major histocompatibility antigen complex protein or a minor histocompatibility antigen (MiHA). In some embodiments, the immunogenicity gene is a gene encoding a protein selected from the group consisting of HLA-A, HLA-B, HLA-C, HLA-DR, HLA-DRB1, HLA-DP, and HLA-DQ.

As used herein, the term "immune-compatible blood cell" refers to a blood cell sharing one or more alleles of a gene encoding a major histocompatibility antigen complex protein and/or minor histocompatibility antigen (MiHA). In some embodiments, an immune-compatible blood cells shares four or more HLA alleles in common with the recipient subject to whom the cells are administered. In some embodiments, the administration of an immune-compatible blood cell to a recipient subject does not induce an immune response in the recipient subject.

As used herein, the term "mixed lymphocyte or leukocyte reaction assay" refers to a cellular immune assay that occurs between two allogenic lymphocyte populations, or any other similar assay which is commonly known to one of ordinary skill in the art. The assay comprises purifying cells from peripheral blood, thymus, lymph nodes, or spleen, and co-culturing with stimulator cell populators. Stimulator cell populations which also contain T-cells are called two way mixed lymphocyte reactions. The stimulator cell population will replicate in the presence of responder cells. For a one way mixed lymphocyte reaction, stimulator cells are prevented from replicated by irradiation or treatment with mitomycin C, a DNA cross-linker which prevents cell replication. Maximum measurable cellular proliferation occurs around five to seven days. Mixed lymphocyte or leukocyte reaction assays provide an in vitro correlate of T cell function. Such assays are well known to one of ordinary skill in the art. For example, see Lindemann, 2014, *Tissue Antigens,* 84:439; Olerup and Zetterquist, 1992, *Tissue Antigens,* 39:225.

"Modified gRNA molecule" or "modified gRNA", as used herein, refers to a gRNA molecule that has an improved half life after being introduced into a cell as compared to a non-modified gRNA molecule after being introduced into a cell. In one embodiment, the modified gRNA molecule does not activate an innate immune response in a cell upon the cell being exposed (e.g., electroporated) to the gRNA molecule. In one embodiment, the modified gRNA molecule activates a reduced innate immune response in a cell upon the cell being exposed to the gRNA molecule, as compared to the innate immune response in the same type of cell upon the cell being exposed to an unmodified gRNA molecule. In another embodiment, the modified gRNA molecule does not activate a programmed cell death pathway (e.g., an apoptotic cell death pathway, a necrosis cell death pathway (e.g., a necroptosis cell death pathway), an autophagic cell death pathway, an aponecrosis cell death pathway, a ferroptosis cell death pathway, an eryptosis cell death pathway, an aponecrosis cell death pathway, or an anoikis cell death pathway) in a cell upon the cell being exposed to the gRNA molecule. In some embodiments, the modified gRNA molecule does not activate a caspase-dependent cell death pathway. In another embodiment, the modified gRNA molecule does not activate a caspase-independent cell death pathway.

In one embodiment, a modified gRNA molecule comprises a 5'-end modification. In one embodiment, the 5'-end modification is a selected from the group consisting of: a G(5')ppp(5')G cap analog, a m7G(5')ppp(5')G cap analog, or a 3'-O-Me-m7G(5')ppp(5')G anti reverse cap analog (ARCA). In one embodiment, the 5'-end modification is a phosphorothioate modification. In one embodiment, the gRNA molecule comprises a 3'-end modification. In one embodiment, the 3'-end modification is a poly adenine tail. In one embodiment, the 3'-end modification is a phosphorothioate modification.

A "template nucleic acid," as the term is used herein, refers to a nucleic acid sequence which can be used in conjunction with a Cas9 molecule and a gRNA molecule to alter the structure of a target position. In an embodiment, the target nucleic acid is modified to have the some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA. In an embodiment, the template nucleic acid is RNA, e.g., double stranded RNA or single stranded RNA. In an embodiment, the template nucleic acid is encoded on the same vector backbone, e.g., AAV genome, plasmid DNA, as the Cas9 and gRNA. In an embodiment, the template nucleic acid is excised from a vector backbone in vivo, e.g., it is flanked by gRNA recognition sequences. In one embodiment, the template DNA is in an ILDV. In one embodiment, the template nucleic acid is an exogenous nucleic acid sequence. In another embodiment, the template nucleic acid sequence is an endogenous nucleic acid sequence, e.g., an endogenous homologous region. In one embodiment, the template nucleic acid is a single stranded oligonucleotide corresponding to a plus strand of a nucleic acid sequence. In another embodiment, the template nucleic acid is a single stranded oligonucleotide corresponding to a minus strand of a nucleic acid sequence.

"Modulator", as used herein, refers to an entity, e.g., a drug, that can alter the activity (e.g., enzymatic activity, transcriptional activity, or translational activity), amount, distribution, or structure of a subject molecule or genetic sequence. In an embodiment, modulation comprises cleavage, e.g., breaking of a covalent or non-covalent bond, or the forming of a covalent or non-covalent bond, e.g., the attachment of a moiety, to the subject molecule. In an embodiment, a modulator alters the, three dimensional, secondary, tertiary, or quaternary structure, of a subject molecule. A modulator can increase, decrease, initiate, or eliminate a subject activity.

"Large molecule", as used herein, refers to a molecule having a molecular weight of at least 2, 3, 5, 10, 20, 30, 40, 50, 60, 70, 80, 90, or 100 kDa. Large molecules include proteins, polypeptides, nucleic acids, biologics, and carbohydrates.

A "polypeptide", as used herein, refers to a polymer of amino acids having less than 100 amino acid residues. In an embodiment, it has less than 50, 20, or 10 amino acid residues.

"Polymorphism", as used herein, refers to al allelic variant. Polymorphisms can include one or more single nucleotide polymorphism(s) as well as sequence length polymorphisms. A polymorphism can be due to one or more nucleotide substitutions at one allele in comparison to another allele or can be due to an insertion or deletion, duplication, inversion and other alterations in a nucleic acid.

A "reference molecule", e.g., a reference Cas9 molecule or reference gRNA, as used herein, refers to a molecule to which a subject molecule, e.g., a subject Cas9 molecule of subject gRNA molecule, e.g., a modified or candidate Cas9 molecule is compared. For example, a Cas9 molecule can be characterized as having no more than 10% of the nuclease activity of a reference Cas9 molecule. Examples of reference Cas9 molecules include naturally occurring unmodified Cas9 molecules, e.g., a naturally occurring Cas9 molecule such as a Cas9 molecule of *S. pyogenes, S. aureus* or *S. thermophilus*. In an embodiment, the reference Cas9 molecule is the naturally occurring Cas9 molecule having the closest sequence identity or homology with the Cas9 molecule to which it is being compared. In an embodiment, the reference Cas9 molecule is a sequence, e.g., a naturally occurring or known sequence, which is the parental form on which a change, e.g., a mutation has been made.

"Replacement", or "replaced", as used herein with reference to a modification of a molecule does not require a process limitation but merely indicates that the replacement entity is present.

"Small molecule", as used herein, refers to a compound having a molecular weight less than about 2 kD, e.g., less than about 2 kD, less than about 1.5 kD, less than about 1 kD, or less than about 0.75 kD.

"Subject", as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In an embodiment, the subject is a human. In another embodiment, the subject is poultry. As used herein, a subject is of a selected ethnicity if the subject self-identifies (or identifies an ancestor) as being of that ethnicity, or if a third party payor, e.g., and insurance company, a government agency, or a health care provider, e.g., a treating physician or genetic counselor, identifies a subject (or an ancestor thereof) of being of the selected ethnicity. In an embodiment the subject is of mixed ancestry, and has a haplotype from a first ethnicity and a haplotype from a second ethnicity.

"Treat", "treating" and "treatment", as used herein, mean the treatment of a disease in a mammal, e.g., in a human, including (a) inhibiting the disease, i.e., arresting or preventing its development; (b) relieving the disease, i.e., causing regression of the disease state; and (c) curing the disease.

"Gene conversion", as used herein, refers to the process of repairing DNA damage by homology directed recombination (HDR) using an endogenous nucleic acid, e.g., a sister chromatid or a plasmid, as a template nucleic acid. BRCA1, BRCA2 and/or RAD51 are believed to be involved in gene conversion. In some embodiments, the endogenous nucleic acid is a nucleic acid sequence having homology, e.g., significant homology, with a fragment of DNA proximal to the site of the DNA lesion or mutation. In some embodiments, the template is not an exogenous nucleic acid.

"Gene correction", as used herein, refers to the process of repairing DNA damage by homology directed recombination using an exogenous nucleic acid, e.g., a donor template nucleic acid. In some embodiments, the exogenous nucleic acid is single-stranded. In some embodiments, the exogenous nucleic acid is double-stranded.

"Gene modification", as used herein, refers to the process of editing a nucleic acid using a CRISPR/Cas9 system described herein. In certain embodiments, the gene modification includes gene correction. In certain embodiments, gene modification includes gene conversion.

"Prevent", "preventing" and "prevention", as used herein, means the prevention of a disease in a mammal, e.g., in a human, including (a) avoiding or precluding the disease, (2) affecting the predisposition toward the disease, e.g., preventing at least one symptom of the disease or to delay onset of at least one symptom of the disease.

"X" as used herein in the context of an amino acid sequence, refers to any amino acid (e.g., any of the twenty natural amino acids) unless otherwise specified.

Manipulation of Cells to Alter HLA Expression Profile

The risk and potential life-threatening complications associated with graft versus host disease (GVHD) have restricted the utility of transplantation (e.g., allo-HSCT) for the treatment of acquired, malignant, and inherited hematologic diseases. Persons of African ancestry are both under-represented in the bone marrow and cord blood HSPC donor registries and have unique haplotypes and differential heterozygosity at the MHC loci that may restrict their access to life-curing allo-HSCT for the treatment of diseases that occur at a higher frequency in their ethnic community (e.g., SCD). As described herein, use of CRISPR/Cas9 related methods and compositions allow for alteration of one or more immunogenicity gene loci (e.g., HLA loci) in donor cells (e.g., HSPCs) to increase immunogenicity gene matching (e.g., HLA matching) such that the donor cells are suitably or fully matched to subject (recipient) HLA loci, thereby creating a suitable donor for transplantation (e.g., allo-HSCT) to treat a disease in a subject who would otherwise not have an HLA matched donor.

Allogeneic T cell activation is induced by presentation of recipient antigens presented on host and donor antigen presenting cells (APCs). Mismatched HLA proteins that are presented to T cells as foreign antigens activate this allo-immune response. HLAs are encoded as part of major histocompatibility complex (MHC) located on human chromosome 6. MHC matching is an important factor that determines the occurrence, intensity, and severity of GVHD. Human HLAs can be subdivided into the major histocompatibility complex (MHC) antigens and minor histocompatibility antigens (MiHA). The degree of mismatched alleles, e.g., at the MHC HLA-A, HLA-B, HLA-C, and HLA-DRB1 loci, is directly related to the occurrence and severity of GVHD. Other factors, such as gender difference between donor and recipient, blood transfusion history (e.g., and generation of alloantibodies through repeated exposure to unmatched HLAs), and MiHA mismatching may also contribute to GVHD pathogenesis.

MHC genes can be further subdivided into Class I and Class II. MHC Class I, which include HLA-A, -B, and —C, are expressed on the surface of all somatic cells. The MHC Class I receptor consists of a constant beta chain ($\beta_2$m, which is encoded on chromosome 11) paired with variable $\alpha$ chains. Class I antigens present intracellular peptides (in non-transplant conditions viral proteins, but in the case of allo-HSCT they present host cell proteins recognized as foreign) to CD8 T cells to induce cytotoxic lymphocyte activation and killing of host cells (causing acute GVHD). In contrast, Class II antigens (e.g., HLA-DR, -DQ, -DP) present extracellular derived antigens to CD4 T cells and are generally expressed on professional antigen presenting cells (APCs, e.g., dendritic cells, macrophages), activating CD4 T cells help to drive a B-cell mediated antibody response to host antigens. Mismatching between other Class II donor and recipient HLAs (DQ, DP) can play a role in GVHD, but to a lesser extent compared to Class I HLA-A, -B, -C, and Class II HLA-DRB1.

The allelic diversity of the MHC locus allows for presentation of a wide range of antigens thereby providing comprehensive immunity against a broad spectrum of potential pathogens. The MHC genes are inherited as a haplotype in a Mendelian manner and both alleles for each gene are expressed in a codominant fashion. Each child has a 25% chance of inheriting the same HLA haplotypes from their parents. In order to protect allo-HSCT subjects from developing GVHD, transplant centers require matching at Class I (HLA-A, -B, -C) and Class II HLA-DRB1 loci. The matching criteria for allo-HSCT in which adult marrow is the cell source is either 7/8, or 9/10 if HLA-DQB1 is included (Dehn J, et al. Biol. Blood Marrow Transplant. 2015; 21(1):137-141). Umbilical cord blood HSCT requires a lesser degree of matching between donor and recipient, with the minimal matching requirement at 4/6 loci (HLA-A, -B, -DRB1).

Effect of Mismatching on Clinical Outcome

Transplantation (e.g., HSCT) from a matched unrelated donor (MUD) may still lead to GVHD, due to reactivity between donor and recipient minor histocompatibility antigens (MiHAs). If the donor and the recipient are mismatched at one out of six HLA antigens (encoded by both alleles of HLA-A, HLA-B, HLA-DR loci), the occurrence of acute GVHD is 65% and mortality in those subjects is 50%. Furthermore, a single mismatch at MHC loci significantly may increase the risk of GVHD. In a study of allo-HSCT in leukemia subjects, the clinical outcome after allo-HSCT (disease-free survival and overall survival) after transplantation with one-antigen mismatched related donor cells (MMRD) was considered to be equivalent to the outcome from matched unrelated donor (MUD) allo-HSCT (Valcárcel D, et al. Biol. Blood Marrow Transplant. 2011; 17(5): 640-648). Subjects transplanted with MUD HSPCs had a higher incidence of chronic (c)GVHD, which has an overall negative impact on quality of life. In another study, recipients of mismatched unrelated donor HSPCs (mismatch at Class I alleles) had higher incidence of GVHD and transplant related mortality (Hauzenberger D, et al. Tissue Antigens. 2008; 72(6): 549-558).

In addition to the higher expressed MHC loci (HEL), mismatches at the lesser expressed loci (LEL), which includes HLA-DRB3/4/5, DQ (e.g., DQB1), and DP, may also have impact on the incidence and severity of GVHD. For subjects matched at HEL, LEL mismatches did not contribute to adverse outcome (Fernandez-Viña M A, et al. Blood. 2013; 121(22): 4603-4610). However, for subjects with 7/8 HEL, a mismatch at HLA-DRB1 was associated with multiple mismatches at LELs. For subjects that were transplanted with donor HSPCs which were matched at 7/8 HELs but for which 3 or more LELs were also detected, the LEL mismatches, those subjects, GVHD in those subjects was associated with a higher degree of mortality compared to subjects transplanted with 7/8 HEL matched donor HSPCs in which 1 LEL mismatch was detected. Together, these findings indicate that a related donor that is fully matched at both HEL and LELs can reduce the risk and severity of transplantation (e.g., allo-HSCT) related GVHD.

Statistics of Finding a Matched Donor

The probability of a subject having a matched sibling donor is around 3% and the probability of a subject having a matched non-sibling matched family member is close to 10% (Ottinger H, et al. Bone Marrow Transplant. 1994; 14 Suppl 4:534-38). Identification of a MUD in the bone marrow and cord blood registries is close to 70%, but the risk of developing GVHD when a MUD is used is 80%, with close to 50% of those subjects developing Grades 111-IV GVHD, which can be fatal. For non-Caucasian subjects, the probability of finding a 7/8 to 8/8 matched donor is lower compared to persons of European American (e.g., Caucasian) ancestry. The National Marrow Donor Program estimates that a MUD may be identified for 90/% of Caucasians, while for subjects of Asian or African ancestry, the probability of finding a 7/8 to 8/8 MUD decreases to 70% and 60%, respectively (Pidala J, et al. Blood. 2013; 122(22): 3651-3658). With respect to subjects of African ancestry (e.g., African American), the hematologic health, disease and unmet medical need is partially due to the reduced probability of identifying a matched donor in the marrow or cord blood registries and then further compounded by the relatively high incidence of sickle cell disease (SCD) in this population. SCD occurs in 1 out of 500 or a total of 1000 African-American births in the U.S. and the disease affects 100,000 Americans (www.cdc.gov). In Central and Western Africa, the incidence of SCD is higher. In Nigeria, for example, SCD occurred in 45,000 to 90,000 births each year (www.SickleCellDisease.org). SCD could be cured with a bone marrow HSCT or UCT from a matched donor (related or unrelated) in which the sickle mutation is absent. Thus, the combination of relatively high incidence of a life-threatening hemoglobinopathy disorder and the challenge of identifying of suitable donor cells (e.g., HSPCs) that would be used to treat this and other blood-based disease underscores the unmet medical need in subjects of African ancestry (Dew A, et al. Biol. Blood Marrow Transplant. 2008; 14(8):938-941).

MHC Allele Differences Between European Americans and African Americans

Given the MHC genes are inherited as haplotypes and given the high degree of polymorphism at the MHC locus, common haplotypes may also vary among persons of disparate ancestry. Historically, European Americans have the highest proportion of 8/8 matched transplants while African Americans have the lowest, according to documented donors in the National Marrow Donor Program (NMDP) registry (Dehn J, et al. Biol. Blood Marrow Transplant. 2015; 21(1):137-141). Of the 8 million people who have registered with the NMDP, only 7% are of African ancestry. Furthermore, people of mixed genetic backgrounds are more difficult to match. For example, a subject of mixed ancestry may carry a paternal haplotype common to African Americans and a maternal haplotype common to European Americans. Finding a matched unrelated donor that has both ancestry-related haplotypes is more challenging. According to NMDP, more education is also needed to inform communities about the donation process in order to encourage enrollment of potential donors from more diverse backgrounds. To date, most studies on HLA polymorphisms have focused on population for which there has been limited genetic mixture. However. HLA diversity is even more pronounced in North America due to continuous migration from other continents. One study sought to characterize the main haplotypes associated with different outbred groups living in the United States including Caucasians (e.g., European Americans), Asians, Native Americans, African Americans, and Latinos (e.g., Hispanics) (Cao K, et al. Hum. Immunol. 2001; 62(9):1009-1030). Among the groups studied. African Americans exhibited maximal heterozygosity at all Class I loci and weaker or nonexistent associations between HLA-A and HLA-B alleles compared to the other populations studies. Furthermore, most common haplotypes associated with African ancestry were distinct from the most common haplotypes associated with Caucasian ancestry. These findings indicate that HLA matching across different ethnicities presents a challenge for identifying suitable matched or haploidentical donor in cases where the subject is non-Caucasian. More recently, the NMDP has provided an updated log of the most frequent alleles and haplotypes that have been detected in different ancestral groups in the United States (bioinformatics.bethematchclinical.org) an extension of the work from Maiers et al., Hum. Immunol. 2007; 68(9):779-788. The groups included: European Americans. African Americans. Asian Pacific Islanders, and Hispanics. Additional common alleles and haplotypes for persons of Jewish ancestry and updates from a previous publication (Klitz et al., 2001, Tissue Antigens, 76(6):442-58) are also available (bioinformatics.bethematchclinical.org).

Table 1 describes the most frequent high-resolution HLA-A alleles detected in the United States Population and in the Jewish Population. For each ancestry shown in the table (e.g, European American, African American, Asian [which includes Pacific Islander], Hispanic [Latino], and persons of Jewish ancestry) the most frequent alleles are ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication (Maiers et al., 2007, *Human Immunology,* 68:779-788). The Jewish high resolution HLA-A frequencies are from the following National Marrow Donor Program Website (US) bioinformatics.bethematchclinical.org. Note that the HLA-A data for the Jewish population are derived from donor samples from the Hadassah Registry—Jerusalem, Israel (Klitz et al., 201, *Tissue Antigens,* 76(6): 442-58. Note that the annotation used (e.g., 0201g for HLA-A indicates is the same as HLA-A*02:01 which indicates the (HLA prefix)-gene*allele group/family: specific HLA protein based on the new nomenclature adopted by the WHO Nomenclature Committee for Factors of the HLA System in 2010). For example, A*0201g becomes A*02:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 1

| | MOST FREQUENT HLA-A ALLELES DETECTED IN THE INDICATED POPULATIONS | | | | |
|---|---|---|---|---|---|
| Rank | European American | African American | Asian Pacific Islander | Hispanic | Jewish |
| 1 | 0201g | 0201g | 2402g | 0201g | 0101 |
| 2 | 0101g | 2301g | 1101g | 2402g | 0201 |
| 3 | 0301g | 0301g | 0201g | 0301g | 2402 |
| 4 | 2402g | 3001 | 3303 | 0101g | 2601 |
| 5 | 1101g | 6802 | 0101g | 3101 | 0301 |
| 6 | 2902 | 3002 | 0206 | 6801g | 1101 |
| 7 | 3201 | 7401g | 0207g | 1101g | 0205 |
| 8 | 2601g | 0101g | 2601g | 2902 | 2301 |
| 9 | 6801g | 3303 | 3101 | 0206 | 3201 |
| 10 | 3101 | 0202 | 0203 | 2301g | 3001 |
| 11 | 2501 | 6801g | 0301g | 2601g | 0302 |
| 12 | 2301g | 2902 | 3001 | 3002 | 2901 |
| 13 | 3001 | 3402 | 6801g | 3201 | 6802 |
| 14 | 3301 | 3601 | 2407 | 6802 | 3301 |
| 15 | 3002 | 2402g | 3401 | 3001 | 6801 |
| 16 | 6802 | 3301 | 1102 | 3301 | 3002 |
| 17 | 0205 | 0205 | 2901g | 0205 | 6901 |
| 18 | 0302 | 1101g | 3201 | 6803 | 6601 |
| 19 | 6601 | 6601 | 0211g | 3303 | 2403 |
| 20 | 2901g | 2601g | 2602 | 2501 | 2902 |
| 21 | 0206 | 3201 | 2403g | 7401g | 3101 |
| 22 | 3303 | 3101 | 0302 | 0202 | 3303 |
| 23 | 2403g | 6602 | 2417 | 6901 | 2501 |
| 24 | 0202 | 8001 | 0205 | 6601 | 0202 |
| 25 | 6901 | 0102 | 3004 | 2901g | 3004 |
| 26 | 3004 | 2501 | 2410 | 6805 | 0103 |
| 27 | 0217 | 6603 | 2301g | 0217 | 7401 |
| 28 | 3402 | 3004 | 2420 | 3402 | 0206 |
| 29 | 2608 | 2901g | 6901 | 0211g | 3402 |
| 30 | 3305 | 2407 | 2902 | 0102 | 2407 |
| 31 | 1104 | 0302 | 2603 | 0204 | 0217 |
| 32 | 7403 | 7409 | 3405 | 3601 | 7403 |
| 33 | 0224 | 0260 | 0216 | 3004 | 8001 |
| 34 | 0230 | 7411 | 7401g | 8001 | 0106 |
| 35 | 0103 | 2608 | 3301 | 2425 | 0222 |
| 36 | 0220 | 2417 | 0210 | 2403g | 0211 |
| 37 | 0213 | 2403g | 2408 | 0222 | 2612 |
| 38 | 1105 | 3401 | 0220 | 0302 | 0214 |
| 39 | 2426 | 2612 | 2501 | 3102 | 2910 |
| 40 | 2609 | 6901 | 3002 | 0220 | 3601 |
| 41 | 6825 | 6805 | 0202 | 3010 | 3010 |
| 42 | 0219 | 6815 | 1103 | 2422 | 0230 |
| 43 | 0116N | 0222 | 0253N | 6602 | 2449 |
| 44 | 3601 | 0214 | 3402 | 2608 | 0220 |
| 45 | 6803 | 2603 | 3112 | 0213 | 0203 |
| 46 | 2458 | 0220 | 6802 | 2426 | 6824 |
| 47 | 2407 | 0103 | 1119 | 2405 | 3401 |
| 48 | 7401g | 0203 | 6601 | 2407 | 2608 |
| 49 | 1102 | 3603 | 0242 | 6807 | 0102 |
| 50 | 0305 | 3403 | 6803 | 3206 | |
| 51 | 0307 | 7403 | | 0212 | |
| 52 | 0102 | 4301 | | 0260 | |
| 53 | 3102 | 0274 | | 2607 | |
| 54 | 2502 | 3104 | | 2305 | |
| 55 | | 0211g | | 3109 | |
| 56 | | 0206 | | 2414 | |
| 57 | | 0213 | | 1104 | |
| 58 | | 0204 | | 1105 | |
| 59 | | 2305 | | 0203 | |
| 60 | | | | 3401 | |
| 61 | | | | 0230 | |
| 62 | | | | 2602 | |

Table 2 describes the most frequent high-resolution HLA-B alleles detected in the United States population and in the Jewish population. For each ancestry shown in the table (e.g, European American, African American, Asian [which includes Pacific Islander], Hispanic [Latino], and persons of Jewish ancestry) the most frequent alleles are indicated and ranked based on their frequency of occurrence with in the ancestral groups indicated in each column (Adapted from The National Marrow Donor Program Website (US) bioinformatics.bethematchclinical.org which represents an update of the high-resolution frequencies from an earlier publication (Maiers et al., 2007, *Human Immunology,*

68:779-788). The Jewish high resolution HLA-A frequencies are from the following National Marrow Donor Program Website (US) URL: bioinformatics.bcthematchclinical.org. Note that the HLA-B data for the Jewish population are derived from donor samples from the Hadassah Registry—Jerusalem, Israel (Klitz et al., 201, *Tissue Antigens,* 76(6):442-58. Note that the annotation used (e.g., 0702g for HLA-B indicates is the same as HLA-B*07:02 which indicates the (HLA prefix)-gene*allele group/family: specific HLA protein based on the new nomenclature adopted by the WHO Nomenclature Committee for Factors of the HLA System in 2010). For example, B*0702g becomes B*07:02. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 2

| | MOST FREQUENT HLA-B ALLELES DETECTED IN THE INDICATED POPULATIONS | | | | |
|---|---|---|---|---|---|
| Rank | European American | African American | Asian Pacific Islander | Hispanic | Jewish |
| 1 | 0702g | 5301 | 4001g | 3501g | 3801 |
| 2 | 0801g | 0702g | 5101g | 4403 | 1801 |
| 3 | 4402g | 3501g | 4601 | 5101g | 5201 |
| 4 | 1501g | 1503g | 5801g | 0702g | 3501 |
| 5 | 3501g | 4201 | 3501g | 4002g | 3502 |
| 6 | 4001g | 4403 | 4403 | 0801g | 1402 |
| 7 | 4403 | 4501g | 4006 | 1402 | 5101 |
| 8 | 1801g | 5802 | 5201g | 1801g | 4101 |
| 9 | 5101g | 0801g | 3802 | 4402g | 4402 |
| 10 | 5701 | 1801g | 1502 | 1501g | 4901 |
| 11 | 2705g | 5801g | 1501g | 5201g | 0801 |
| 12 | 1402 | 5703 | 5401 | 4901 | 5001 |
| 13 | 1302 | 1510 | 1301 | 3905 | 1302 |
| 14 | 3801 | 4901 | 4002g | 4801g | 4403 |
| 15 | 5501 | 1402 | 0702g | 3906 | 0702 |
| 16 | 3503 | 5101g | 3503 | 3801 | 3503 |
| 17 | 3701 | 4402g | 1302 | 3512 | 0705 |
| 18 | 4901 | 8101g | 5701 | 2705g | 3508 |
| 19 | 3502 | 1516 | 4801g | 3517 | 5501 |
| 20 | 4002g | 5201g | 0705g | 1503g | 5801 |
| 21 | 5201g | 4001g | 0801g | 5301 | 1517 |
| 22 | 3901g | 7801 | 5502 | 4501g | 5701 |
| 23 | 1401 | 1501g | 3701 | 5801g | 5301 |
| 24 | 5001 | 1302 | 3901g | 5001 | 4102 |
| 25 | 3906 | 5001 | 1801g | 3503 | 1501 |
| 26 | 5601 | 1401 | 1518 | 4001g | 3701 |
| 27 | 5801g | 0705g | 3505 | 4101 | 1503 |
| 28 | 4501g | 4202 | 2705g | 1302 | 4001 |
| 29 | 3508 | 3910 | 5901 | 5701 | 2702 |
| 30 | 4101 | 4102 | 5601 | 3502 | 5108 |
| 31 | 4102 | 2705g | 1535 | 5501 | 4002 |
| 32 | 5301 | 1517 | 4402g | 3901g | 4405 |
| 33 | 2702 | 3701 | 5001 | 3508 | 4501 |
| 34 | 1517 | 4101 | 2704 | 1401 | 5002 |
| 35 | 4405 | 5701 | 1511 | 3543g | 5702 |
| 36 | 4701 | 5702 | 5102 | 1515 | 3901 |
| 37 | 0705g | 3901g | 1525 | 5703 | 2705 |
| 38 | 1518 | 5501 | 5501 | 1517 | 4006 |
| 39 | 1503g | 4002g | 1527 | 4201 | 5601 |
| 40 | 1507 | 3503 | 1517 | 3701 | 2707 |
| 41 | 4404 | 5704 | 3801 | 4102 | 5703 |
| 42 | 1803 | 1403 | 1521 | 4008 | 5107 |
| 43 | 5108 | 5601 | 1512g | 4005 | 4801 |
| 44 | 4801g | 2703 | 1401 | 5102 | 7301 |
| 45 | 5109 | 3906 | 1507 | 0705g | 1401 |
| 46 | 0704 | 8201 | 1505 | 1510 | 4701 |

TABLE 2-continued

| | MOST FREQUENT HLA-B ALLELES DETECTED IN THE INDICATED POPULATIONS | | | | |
|---|---|---|---|---|---|
| Rank | European American | African American | Asian Pacific Islander | Hispanic | Jewish |
| 47 | 2707 | 3801 | 2706 | 1516 | 3906 |
| 48 | 3924 | 4701 | 5106 | 5802 | 1510 |
| 49 | 5702 | 4410 | 6701 | 3902 | 3910 |
| 50 | 1516 | 4012 | 4003 | 5601 | 1516 |
| 51 | 5703 | 1537 | 3502 | 4701 | 4201 |
| 52 | 3903 | 4103 | 4501g | 1518 | 1518 |
| 53 | 5107 | 1518 | 3508 | 3514 | 3702 |
| 54 | 0710 | 3505 | 1513 | 4006 | 3924 |
| 55 | 7301 | 1502 | 1802 | 2702 | 2703 |
| 56 | 2714 | 5109 | 4803 | 8101g | 1524 |
| 57 | 3512 | 3502 | 1508 | 3908 | 4804 |
| 58 | 1804 | 1531 | 4101 | 4011 | 1529 |
| 59 | 3905 | 0812 | 5604 | 4004 | 2712 |
| 60 | 5002 | 8202 | 5603 | 4202 | 1301 |
| 61 | 5105 | 1547 | 2707 | 1539 | 1508 |
| 62 | 4202 | 3508 | 1529 | 4405 | 1509 |
| 63 | 1510 | 1554 | 4901 | 1530 | 3555 |
| 64 | 0721 | 2706 | 3905 | 1504 | 1805 |
| 65 | 1514 | 1405 | 1402 | 3520 | 1531 |
| 66 | 0805 | 4703 | 5301 | 5108 | 4202 |
| 67 | 5802 | 1301 | 5107 | 7301 | 3704 |
| 68 | 3505 | 4405 | 5108 | 3505 | 1803 |
| 69 | 5119 | 4016 | 4804 | 3911 | 4702 |
| 70 | 5102 | 3543g | 3909 | 7801 | 2709 |
| 71 | 1524 | 5102 | 8101g | 3530 | 3802 |
| 72 | 1545 | 2702 | 1510 | 5002 | 1502 |
| 73 | 2709 | 4801g | 4010 | 5107 | 3505 |
| 74 | 4702 | 1513 | 3915 | 4027 | 0747 |
| 75 | 3517 | 4802 | 2702 | 3522 | 4460 |
| 76 | 4409 | 3909 | 4040 | 2703 | 5137 |
| 77 | 1515 | 4418 | 5512 | 3516 | 5004 |
| 78 | 3809 | 6702 | 5602 | 3510 | 0707 |
| 79 | 0715 | 1561 | 4050 | 4803 | 3809 |
| 80 | 4006 | 7802 | 7301 | 1301 | 0704 |
| 81 | 3527 | 4415 | 1506 | 1540 | 1525 |
| 82 | 2710 | 4404 | 3906 | 3528 | 2708 |
| 83 | 1808 | 5002 | 4701 | 3913 | 5109 |
| 84 | 6701 | 4006 | 4023 | 1547 | 4406 |
| 85 | 2703 | 1507 | 5137 | 3909 | 7801 |
| 86 | | 3528 | 1534 | 1509 | 1403 |
| 87 | | 0709 | 2720 | 1512g | 1513 |
| 88 | | 1525 | 1503g | 1403 | 8202 |
| 89 | | 1552 | | 4020 | |
| 90 | | | | 3504 | |
| 91 | | | | 3521 | |
| 92 | | | | 1507 | |
| 93 | | | | 5114 | |
| 94 | | | | 3523 | |
| 95 | | | | 4016 | |
| 96 | | | | 1806 | |
| 97 | | | | 1802 | |
| 98 | | | | 4404 | |
| 99 | | | | 1502 | |
| 100 | | | | 4703 | |
| 101 | | | | 4410 | |
| 102 | | | | 5702 | |
| 103 | | | | 3910 | |
| 104 | | | | 1803 | |
| 105 | | | | 3903 | |
| 106 | | | | 3506 | |
| 107 | | | | 2712 | |
| 108 | | | | 3912 | |
| 109 | | | | 4802 | |
| 110 | | | | 3924 | |
| 111 | | | | 3914 | |
| 112 | | | | 2704 | |
| 113 | | | | 5106 | |
| 114 | | | | 3511 | |
| 115 | | | | 1406 | |
| 116 | | | | 5401 | |
| 117 | | | | 1535 | |
| 118 | | | | 1508 | |

Table 3 descries the most frequent high-resolution HLA-C alleles in the United States population. For each ancestry shown in the table (e.g. European American, African American, Asian [which includes Pacific Islander], and Hispanic [Latino], the most frequent alleles are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication (Maiers et al., 2007, *Human Immunology,* 68:779-788). Note that the annotation used (e.g., 0701g for HLA-C indicates is the same as HLA-C*07:01 which indicates the (HLA prefix)-gene*allele group/family: specific HLA protein based on the new nomenclature adopted by the WHO Nomenclature Committee for Factors of the HLA System in 2010). For example, C*0702g becomes C*07:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert. L., Klitz, W. High resolution HLA alleles and haplotypes in the US population. 2007". The suffix "N" is used to denote changes in expression (refer to nomenclature link above).

TABLE 3

| | MOST FREQUENT HLA-C ALLELES DETECTED IN THE INDICATED POPULATIONS | | | |
|---|---|---|---|---|
| Rank | European American | African American | Asian Pacific Islander | Hispanic |
| 1 | 0701g | 0401g | 702 | 0401g |
| 2 | 0702 | 0701g | 102 | 702 |
| 3 | 0401g | 1601 | 304 | 0701g |
| 4 | 0602 | 0602 | 0401g | 304 |
| 5 | 0501g | 0202 | 801 | 602 |
| 6 | 0304 | 1701g | 602 | 1601 |
| 7 | 0303g | 0702 | 302 | 102 |
| 8 | 1203 | 0304 | 0303g | 802 |
| 9 | 0802 | 0802 | 1502g | 0501g |
| 10 | 0202 | 0501g | 1402 | 202 |
| 11 | 1601 | 1801g | 1202 | 1203 |
| 12 | 0102 | 1203 | 0701g | 0303g |
| 13 | 1502g | 1505 | 1203 | 1502g |
| 14 | 1402 | 0302 | 403 | 801 |
| 15 | 0704g | 1402 | 1505 | 1701g |
| 16 | 1202 | 0303g | 1403 | 1402 |
| 17 | 1701g | 0804 | 0704g | 1202 |
| 18 | 1602 | 0704g | 0501g | 305 |
| 19 | 1505 | 0102 | 1602 | 0704g |
| 20 | 0302 | 1502g | 803 | 1505 |
| 21 | 1604 | 1403 | 202 | 306 |
| 22 | 1504 | 0407 | 802 | 302 |
| 23 | 0803 | 1202 | 1204 | 1602 |
| 24 | 0505 | 0801 | 103 | 1509 |
| 25 | 1403 | 0735 | 1601 | 1801g |
| 26 | 1801g | 0413 | 1701g | 803 |
| 27 | 1506 | 0705 | 406 | 804 |
| 28 | 1205 | 0403 | 727 | 1604 |
| 29 | 0107 | 0305 | 1504 | 307 |
| 30 | 0707 | 1602 | 410 | 110 |
| 31 | 0710 | 0408 | 404 | 509 |
| 32 | 0309 | 0608 | 105 | 717 |
| 33 | 1511 | 0404 | 337 | 1504 |
| 34 | 0712 | 0609 | 336 | 1403 |
| 35 | 1204 | 1608 | 1508 | 727 |
| 36 | 0610 | 0116 | 118 | 338 |
| 37 | 0319 | 1704 | 615 | 1519 |
| 38 | 0603 | 0214 | 1205 | 812 |

TABLE 3-continued

| | MOST FREQUENT HLA-C ALLELES DETECTED IN THE INDICATED POPULATIONS | | | |
|---|---|---|---|---|
| Rank | European American | African American | Asian Pacific Islander | Hispanic |
| 39 | 1212 | 0813 | 726 | 404 |
| 40 | 0507N | 1803 | 1511 | 403 |
| 41 | 0307 | 0427 | 743 | 308 |
| 42 | 1503 | 0803 | | 811 |
| 43 | 0404 | 1604 | | 1406 |
| 44 | 0709 | | | 705 |
| 45 | 0405 | | | 1520 |
| 46 | 1404 | | | 408 |
| 47 | 0801 | | | 218 |

Table 4 describes the most frequent high-resolution HLA-DRB1 alleles in the United States population and in the Jewish population. For each ancestry shown in the table (e.g., European American. African American, Asian [which includes Pacific Islander], Hispanic [Latino], and persons of Jewish ancestry) the most frequent alleles are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication [Maiers et al., 2007, *Human Immunology,* 68:779-788. The Jewish high resolution HLA-DRB1 frequencies are from the following National Marrow Donor Program Website (US) URL: bioinformatics.bethematchclinical.org. Note that the HLA-DRB1 data for the Jewish population are derived from donor samples from the Hadassah Registry—Jerusalem, Israel (Klitz et al., 201, *Tissue Antigens,* 76(6):442-58. Note that the annotation used (e.g., 1501 for HLA-DRB1 indicates is the same as HLA-DRB1*15:01 which indicates the (HLA prefix)-gene*allele group/family: specific HLA protein based on the new nomenclature adopted by the WHO Nomenclature Committee for Factors of the HLA System in 2010). For example, DRB1*1501 becomes DRB1*15:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 4

| | MOST FREQUENT HLA-DRB1 ALLELES DETECTED IN THE INDICATED POPULATIONS | | | | |
|---|---|---|---|---|---|
| Rank | European American | African American | Asian Pacific Islander | Hispanic | Jewish |
| 1 | 1501 | 1503 | 0901 | 0701 | 1104 |
| 2 | 0701 | 0701 | 0701 | 0301 | 0701 |
| 3 | 0301 | 1101 | 1502 | 0802 | 0402 |
| 4 | 0101 | 0301 | 1501 | 1501 | 0301 |
| 5 | 0401 | 0302 | 1202 | 0407 | 1101 |
| 6 | 1301 | 1302 | 0405 | 0404 | 0102 |
| 7 | 1101 | 1301 | 0301 | 1301 | 1302 |
| 8 | 1302 | 0804 | 0803 | 1101 | 0403 |
| 9 | 0404 | 0102 | 1101 | 0101 | 1301 |

TABLE 4-continued

| | MOST FREQUENT HLA-DRB1 ALLELES DETECTED IN THE INDICATED POPULATIONS | | | | |
|---|---|---|---|---|---|
| Rank | European American | African American | Asian Pacific Islander | Hispanic | Jewish |
| 10 | 1104 | 1201g | 1302 | 1302 | 1401 |
| 11 | 1401g | 1102 | 0403 | 0102 | 1502 |
| 12 | 0801 | 1303 | 1001 | 1406 | 1001 |
| 13 | 0102 | 0901 | 1201g | 1104 | 1501 |
| 14 | 1201g | 1501 | 0101 | 1402 | 1303 |
| 15 | 1601 | 0101 | 1401g | 0411 | 1201 |
| 16 | 1303 | 0401 | 1301 | 1602 | 1601 |
| 17 | 0402 | 1401g | 0406 | 0402 | 1305 |
| 18 | 0407 | 1001 | 1404 | 0405 | 0405 |
| 19 | 0103 | 1602 | 1602 | 0403 | 0404 |
| 20 | 1001 | 1304 | 1405 | 1303 | 0101 |
| 21 | 0901 | 0405 | 0802 | 1001 | 0804 |
| 22 | 1502 | 0404 | 0401 | 0401 | 0401 |
| 23 | 0403 | 1104 | 0404 | 1401g | 0801 |
| 24 | 1103 | 0806 | 1104 | 1502 | 1503 |
| 25 | 0405 | 0801 | 0801 | 1102 | 1103 |
| 26 | 0408 | 0407 | 1312 | 1201g | 0406 |
| 27 | 1305 | 1202 | 1506 | 0804 | 0901 |
| 28 | 1102 | 0403 | 0410 | 1503 | 1404 |
| 29 | 0803 | 0103 | 0402 | 0901 | 1602 |
| 30 | 1602 | 1502 | 1403 | 0801 | 0408 |
| 31 | 0804 | 1110 | 1106 | 0302 | 0103 |
| 32 | 1404 | 0811 | 1406 | 1601 | 1102 |
| 33 | 0406 | 1601 | 1407 | 0103 | 1202 |
| 34 | 0802 | 0802 | 0809 | 1304 | 0407 |
| 35 | 1503 | 0411 | 1418 | 1103 | 0803 |
| 36 | 1304 | 1331 | 0407 | 0410 | 1406 |
| 37 | 0302 | 0410 | 0408 | 0408 | 0808 |
| 38 | 1407 | 1103 | 1111 | 1305 | 1407 |
| 39 | 1139 | 1402 | 1504 | 0406 | 0302 |
| 40 | 0806 | 0408 | 1419 | 0803 | 1111 |
| 41 | 0811 | 0406 | 1503 | 1407 | 0802 |
| 42 | 1406 | 0402 | 1601 | 0806 | 1112 |
| 43 | 1109 | 1404 | 1507 | 1202 | 1203 |
| 44 | 1311 | 1316 | 0703 | 0417 | 1607 |
| 45 | | 0803 | 0103 | 1404 | 1412 |
| 46 | | 1305 | 1422 | 1311 | 0806 |
| 47 | | 0305 | 0805 | 0414 | 0315 |
| 48 | | 0409 | 1350 | 1309 | 1315 |
| 49 | | 1320 | 1408 | 1504 | 1318 |
| 50 | | 1117 | 0102 | 0810 | 1116 |
| 51 | | 1311 | 1208 | 0418 | 1304 |
| 52 | | 0306 | 1303 | 1115 | |
| 53 | | 1336 | 1108 | 1110 | |
| 54 | | | 1402 | 1306 | |
| 55 | | | 1514 | 1340 | |
| 56 | | | 1425 | 1405 | |
| 57 | | | 1412 | 0305 | |

Table 5 describes the most frequent high-resolution HLA-DQB1 alleles detected in the United States population. For each ancestry shown in the table (e.g., European American, African American. Asian [which includes Pacific Islander], and Hispanic [Latino],) the most frequent alleles are indicated and ranked based on their frequency of occurrence with in the ancestral groups indicated in each column (Adapted from The National Marrow Donor Program Website (US): bioinformatics.bethcmatchclinical.org which represents an update of the high-resolution frequencies from an earlier publication (Maiers et al., 2007*, Human Immunology,* 68:779-788). Note that the annotation used (e.g., 0201g for HLA-DQB1 indicates is the same as HLA-DQB1*02:01 which indicates the (HLA prefix)-gene*allele group/family: specific HLA protein based on the new nomenclature adopted by the WHO Nomenclature Committee for Factors of the HLA System in 2010). For example, DQB1*0201g becomes DQB1*02:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert. L., Klitz, W. High resolution HLA alleles and haplotypes in the US population. 2007".

TABLE 5

| | MOST FREQUENT HLA-DQB1 ALLELES DETECTED IN THE INDICATED POPULATIONS | | | |
|---|---|---|---|---|
| Rank | European American | African American | Asian Pacific Islander | Hispanic |
| 1 | 0201g | 0201g | 0301g | 0301g |
| 2 | 0301g | 0602 | 0303 | 0302 |
| 3 | 0602 | 0301g | 0601 | 0201g |
| 4 | 0501 | 0501 | 0201g | 0501 |
| 5 | 0302 | 0402 | 0302 | 0402 |
| 6 | 0603 | 0302 | 0501 | 0602 |
| 7 | 0303 | 0609 | 0502 | 0603 |
| 8 | 0604 | 0502 | 0503 | 0604 |
| 9 | 0402 | 0603 | 0401 | 0303 |
| 10 | 0503 | 0604 | 0602 | 0502 |
| 11 | 0502 | 0303 | 0402 | 0601 |
| 12 | 0609 | 0503 | 0603 | 0503 |
| 13 | 0601 | 0608 | 0609 | 0609 |
| 14 | 0304 | 0203 | 0604 | 0304 |
| 15 | 0504 | 0611 | 0610 | 0608 |
| 16 | 0305 | 0601 | 0305 | 0305 |
| 17 | | 0605 | 0605 | 0611 |
| 18 | | | | 0504 |

Table 6 describes the most frequent high-resolution HLA-A-B haplotypes detected n the United States and Jewish Populations. For each ancestry shown in the table (e.g., European American, African American, Asian [which includes Pacific Islander]. Hispanic [Latino], and persons of Jewish ancestry) the top 50 most frequent HLA-A-B haplotypes are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication [Maiers et al., 2007*, Human Immunology,* 68:779-788. The Jewish high resolution HLA-A-B haplotype frequencies are from the following National Marrow Donor Program Website (US) URL: bioinformatics.bcthematchclinical.org. Note that the HLA-A-B haplotype frequency data for the Jewish population are derived from donor samples from the Hadassah Registry—Jerusalem, Israel (Klitz et al., 201*, Tissue Antigens* 76(6):442-58). Note that the annotation used (e.g., 0201g for HLA-A indicates is the same as HLA-A*02:01 which indicates the (HLA prefix)-gene*allele group/family: specific HLA protein based on the new nomenclature adopted by the WHO Nomenclature Committee for Factors of the HLA System in 2010). For example, A*0201g becomes A*02:05. With the designation shown in this table, the fields that are used to show synonymous DNA substitution in coding region, differences in non-coding regions, and the suffix used to denote changes in expression are not shown (see the following website for more information: hla.allelcs.org). The allele designations in this table with the "g" suffix refer to allele groups defined in table 1 of the publication "Maiers, M., Gragert, L., Klitz. W. High resolution HLA alleles and haplotypes in the US population. 2007".

TABLE 6

MOST FREQUENT HLA-A-B HAPLOTYPES IN THE INDICATED POPULATIONS

| | European American | | African American | | Asian Pacific Islander | | Hispanic | | Jewish | |
|---|---|---|---|---|---|---|---|---|---|---|
| Rank | HLA-A | HLA-B | HLA-A | HLA-B | HLA-A | HLA-B | HLA-A | HLA-B | HLA-A | HLA-B |
| 1 | 0101g | 0801g | 3001 | 4201 | 3303 | 5801g | 2902 | 4403 | 2601 | 3801 |
| 2 | 0301g | 0702g | 0301g | 0702g | 0207g | 4601 | 0101g | 0801g | 2402 | 3502 |
| 3 | 0201g | 4402g | 0201g | 4501g | 3303 | 4403 | 0201g | 5101g | 3301 | 1402 |
| 4 | 0201g | 0702g | 7401g | 1503g | 1101g | 4001g | 0201g | 4402g | 0205 | 5001 |
| 5 | 0201g | 1501g | 3601 | 5301 | 2402g | 4001g | 0301g | 0702g | 2901 | 0705 |
| 6 | 0201g | 4001g | 0101g | 0801g | 1101g | 1502 | 3301 | 1402 | 1101 | 5201 |
| 7 | 2902 | 4403 | 2301g | 1503g | 3001 | 1302 | 2402g | 4002g | 0101 | 0801 |
| 8 | 0101g | 5701 | 6802 | 5301 | 0101g | 5701 | 2402g | 3906 | 0101 | 5201 |
| 9 | 0201g | 5101g | 0201g | 4402g | 2402g | 5101g | 0201g | 1801g | 0201 | 1801 |
| 10 | 0301g | 3501g | 3303 | 5301 | 0201g | 4001g | 0201g | 3501g | 0101 | 5701 |
| 11 | 1101g | 3501g | 2301g | 5301 | 1101g | 1301 | 0201g | 0702g | 0101 | 3502 |
| 12 | 0201g | 2705g | 6802 | 1510 | 2402g | 4006 | 0201g | 3512 | 2402 | 1801 |
| 13 | 2402g | 0702g | 6801g | 5802 | 2402g | 5401 | 0301g | 3501g | 0201 | 3503 |
| 14 | 0201g | 1801g | 0301g | 3501g | 0203 | 3802 | 3002 | 1801g | 3001 | 1302 |
| 15 | 0201g | 5701 | 2902 | 4403 | 2402g | 4002g | 2301g | 4403 | 0201 | 5101 |
| 16 | 2601g | 3801 | 0202 | 5301 | 2901g | 0705g | 0201g | 1501g | 2402 | 3801 |
| 17 | 3001 | 1302 | 2301g | 0702g | 1101g | 5101g | 2601g | 3801 | 0301 | 0702 |
| 18 | 2501 | 1801g | 2301g | 4501g | 2402g | 5201g | 0206 | 4002g | 6802 | 1402 |
| 19 | 0201g | 0801g | 0201g | 3501g | 1101g | 3501g | 2402g | 3501g | 0201 | 4402 |
| 20 | 0101g | 0702g | 0201g | 0702g | 2402g | 4601 | 6801g | 4002g | 0301 | 3801 |
| 21 | 2402g | 1501g | 2301g | 4403 | 1101g | 3802 | 0201g | 5201g | 0201 | 5201 |
| 22 | 3301 | 1402 | 3402 | 4403 | 1101g | 1501g | 0101g | 5701 | 2301 | 4403 |
| 23 | 3101 | 4001g | 0201g | 5301 | 0206 | 5101g | 1101g | 3501g | 2301 | 4901 |
| 24 | 2301g | 4403 | 6802 | 0702g | 2402g | 4801g | 0201g | 3517 | 1101 | 3501 |
| 25 | 0201g | 1302 | 0301g | 5802 | 0201g | 5101g | 6803 | 3905 | 0101 | 3801 |
| 26 | 0101g | 3701 | 0201g | 5101g | 0101g | 3701 | 0201g | 0801g | 0101 | 1517 |
| 27 | 0201g | 3501g | 3001 | 5301 | 2402g | 0702g | 0206 | 3905 | 0302 | 4402 |
| 28 | 0301g | 1402 | 3001 | 4202 | 2402g | 3501g | 2402g | 3502 | 2601 | 3501 |
| 29 | 0201g | 4403 | 0201g | 1801g | 1101g | 5201g | 3101 | 3501g | 6901 | 5501 |
| 30 | 0301g | 1501g | 3002 | 0702g | 0201g | 5401 | 0201g | 4002g | 0301 | 3501 |
| 31 | 0301g | 4402g | 3402 | 3501g | 2402g | 1301 | 2402g | 5101g | 0101 | 4101 |
| 32 | 3002 | 1801g | 3303 | 1516 | 1101g | 5401 | 1101g | 2705g | 0101 | 4901 |
| 33 | 1101g | 5501 | 3002 | 5703 | 1101g | 4601 | 6801g | 4801g | 0205 | 4101 |
| 34 | 6802 | 1402 | 7401g | 5301 | 3101 | 5101g | 6802 | 1402 | 0201 | 0801 |
| 35 | 6801g | 4402g | 3002 | 4403 | 2402g | 1501g | 2402g | 1501g | 0101 | 1302 |
| 36 | 1101g | 0702g | 7401g | 5703 | 0201g | 1301 | 3101 | 4002g | 0101 | 3501 |
| 37 | 0301g | 1801g | 2301g | 4201 | 1101g | 3901g | 0201g | 4403 | 0301 | 1402 |
| 38 | 2402g | 4402g | 0201g | 4001g | 2407 | 3505 | 3001 | 1302 | 2402 | 3508 |
| 39 | 0301g | 5101g | 3301 | 7801 | 0201g | 1501g | 0201g | 4001g | 0301 | 1302 |
| 40 | 3201 | 4402g | 0201g | 4901 | 2402g | 3802 | 0206 | 4801g | 0201 | 3801 |
| 41 | 2402g | 3502 | 0201g | 1501g | 2601g | 0801g | 2402g | 4801g | 2501 | 1801 |
| 42 | 2402g | 1801g | 2301g | 3501g | 0201g | 3501g | 6802 | 5301 | 0101 | 5801 |
| 43 | 2402g | 0801g | 2301g | 5801g | 0301g | 3501g | 0201g | 1515 | 0101 | 4402 |
| 44 | 0101g | 4402g | 3002 | 1402 | 0211g | 4006 | 2501 | 1801g | 6601 | 4102 |
| 45 | 0301g | 0801g | 2301g | 0801g | 2402g | 3503 | 0301g | 1402 | 2402 | 4402 |
| 46 | 0301g | 4001g | 0201g | 1503g | 0101g | 0801g | 2402g | 0801g | 0101 | 3508 |
| 47 | 0201g | 3901g | 3303 | 3501g | 6801g | 5201g | 0301g | 5101g | 0301 | 3503 |
| 48 | 1101g | 5101g | 6601 | 5802 | 2417 | 1502 | 3101 | 5101g | 0301 | 1801 |
| 49 | 0201g | 3503 | 0202 | 0702g | 0101g | 1517 | 2402g | 3905 | 3002 | 1801 |
| 50 | 2402g | 5101g | 3002 | 5301 | 2402g | 5801g | 3001 | 4201 | 0101 | 3701 |

Table 7 describes the most frequent high-resolution HLA-A-B-DRB1 haplotypes detected in the United States and Jewish populations. For each ancestry shown in the table (e.g., European American, African American, Asian [which includes Pacific Islander]. Hispanic [Latino], and persons of Jewish ancestry) top 50 most frequent HLA-A-B-DRB1 haplotypes are indicated and ranked based on their frequency of occurrence with in the ancestral groups indicated in each column (Adapted from The National Marrow Donor Program Website (US): bioinformnatics.bethematchclinical.org which represents an update of the high-resolution frequencies from an earlier publication [Maiers et al., 2007, *Human Immunology,* 68:779-788. The Jewish high resolution HLA-A-B-DRB1 haplotype frequencies are from the following National Marrow Donor Program Website (US) URL: bioinformatics.bethematchclinical.org. Note that the HLA-A-B-DRB1 haplotype frequency data for the Jewish population are derived from donor samples from the Hadassah Registry—Jerusalem, Israel (Klitz et al., 201*, Tissue Antigens,* 76(6):442-58. Note that the annotation used (e.g., 1501 for HLA-DRB1 indicates is the same as HLADRB1*15:01 which indicates the (HLA prefix)—gene*allele group/family: specific HLA protein based on the new nomenclature adopted by the WHO Nomenclature Committee for Factors of the HLA System in 2010). For example, DRB1*1501 becomes DRB1*15:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the “g” suffix refer to allele groups defined in table 1 of the publication “Maiers, M., Gragert, L., Klitz, W. High resolution HLA alleles and haplotypes in the US population. 2007”.

TABLE 7

MOST FREQUENT HLA-A-B-DRB1 HAPLOTYPES IN THE INDICATED POPULATIONS

| Rank | European American HLA-A | European American HLA-B | European American HLA-DRB1 | African American HLA-A | African American HLA-B | African American HLA-DRB1 | Asian Pacific Islander HLA-A | Asian Pacific Islander HLA-B | Asian Pacific Islander HLA-DRB1 |
|---|---|---|---|---|---|---|---|---|---|
| 1 | 0101g | 0801g | 0301 | 3001 | 4201 | 0302 | 3303 | 5801g | 0301 |
| 2 | 0301g | 0702g | 1501 | 0101g | 0801g | 0301 | 0207g | 4601 | 0901 |
| 3 | 0201g | 4402g | 0401 | 6801g | 5802 | 1201g | 3303 | 4403 | 0701 |
| 4 | 0201g | 0702g | 1501 | 6802 | 1510 | 0301 | 3001 | 1302 | 0701 |
| 5 | 2902 | 4403 | 0701 | 3303 | 5301 | 0804 | 3303 | 5801g | 1302 |
| 6 | 0201g | 1501g | 0401 | 3601 | 5301 | 1101 | 1101g | 1502 | 1202 |
| 7 | 0101g | 5701 | 0701 | 0301g | 0702g | 1501 | 2402g | 5201g | 1502 |
| 8 | 0301g | 3501g | 0101 | 3402 | 4403 | 1503 | 0101g | 5701 | 0701 |
| 9 | 0201g | 4001g | 1302 | 2902 | 4403 | 0701 | 3303 | 4403 | 1302 |
| 10 | 3001 | 1302 | 0701 | 0201g | 4402g | 0401 | 0101g | 3701 | 1001 |
| 11 | 0201g | 0801g | 0301 | 2301g | 1503g | 0701 | 2901g | 0705g | 1001 |
| 12 | 0201g | 5701 | 0701 | 7401g | 1503g | 1302 | 2402g | 4001g | 0901 |
| 13 | 2402g | 0702g | 1501 | 6802 | 0702g | 1503 | 1101g | 4601 | 0901 |
| 14 | 1101g | 3501g | 0101 | 3001 | 4201 | 0804 | 2402g | 5401 | 0405 |
| 15 | 3301 | 1402 | 0102 | 3002 | 1402 | 1503 | 2402g | 0702g | 0101 |
| 16 | 2301g | 4403 | 0701 | 6802 | 5301 | 1503 | 1101g | 4001g | 0803 |
| 17 | 0101g | 0702g | 1501 | 7401g | 5703 | 1303 | 2601g | 0801g | 0301 |
| 18 | 0201g | 1501g | 1301 | 2902 | 4901 | 1503 | 1101g | 3802 | 1502 |
| 19 | 0201g | 1302 | 0701 | 2301g | 4403 | 1503 | 0207g | 4601 | 0803 |
| 20 | 3101 | 4001g | 0404 | 0201g | 0801g | 0301 | 1101g | 1301 | 1501 |
| 21 | 2501 | 1801g | 1501 | 0201g | 1501g | 0401 | 1101g | 5401 | 0405 |
| 22 | 0201g | 4403 | 0701 | 6602 | 5801g | 1503 | 0201g | 1301 | 1202 |
| 23 | 0201g | 4402g | 1301 | 0201g | 4501g | 1302 | 1101g | 1501g | 0406 |
| 24 | 0201g | 4402g | 0101 | 6601 | 5802 | 1301 | 2402g | 4001g | 1501 |
| 25 | 0101g | 0801g | 1501 | 2301g | 1503g | 1503 | 2407 | 3505 | 1202 |
| 26 | 0301g | 0702g | 0101 | 0201g | 0702g | 1101 | 2402g | 4601 | 0901 |
| 27 | 0201g | 4402g | 1501 | 2301g | 5301 | 1101 | 2402g | 5101g | 0901 |
| 28 | 0201g | 5101g | 1101 | 0201g | 4501g | 1503 | 1101g | 4001g | 0901 |
| 29 | 2601g | 3801 | 0402 | 6802 | 5301 | 1303 | 0201g | 4001g | 1101 |
| 30 | 0201g | 2705g | 0101 | 7401g | 1503g | 1503 | 0203 | 3802 | 1602 |
| 31 | 0301g | 0801g | 0301 | 2301g | 5301 | 0701 | 2402g | 4001g | 0403 |
| 32 | 3002 | 1801g | 0301 | 2301g | 0702g | 0901 | 1101g | 3501g | 1501 |
| 33 | 0201g | 1801g | 1104 | 0201g | 5101g | 1303 | 2417 | 1502 | 1202 |
| 34 | 2402g | 0801g | 0301 | 2301g | 4201 | 0302 | 1101g | 4001g | 1501 |
| 35 | 2402g | 3502 | 1104 | 6802 | 5301 | 1302 | 2402g | 1301 | 1501 |
| 36 | 0201g | 1501g | 0101 | 0301g | 5802 | 0701 | 1101g | 3901g | 0803 |
| 37 | 1101g | 0702g | 1501 | 2301g | 4403 | 0701 | 2402g | 5901 | 0405 |
| 38 | 6802 | 1402 | 1303 | 2501 | 1801g | 1501 | 1101g | 5201g | 1502 |
| 39 | 0201g | 5101g | 1301 | 2601g | 0801g | 1304 | 0201g | 5101g | 0901 |
| 40 | 0201g | 1501g | 1501 | 6802 | 4201 | 0302 | 0101g | 0801g | 0301 |
| 41 | 3201 | 1401 | 0701 | 0201g | 0702g | 1501 | 2402g | 3501g | 0901 |
| 42 | 0201g | 3501g | 0101 | 2301g | 1503g | 1101 | 1101g | 1502 | 1501 |
| 43 | 0301g | 0702g | 0401 | 0201g | 5301 | 1303 | 2402g | 3802 | 1502 |
| 44 | 0201g | 4402g | 1101 | 3002 | 5703 | 1301 | 2402g | 4601 | 0803 |
| 45 | 0101g | 0801g | 0101 | 0201g | 3501g | 1503 | 1101g | 4403 | 0701 |
| 46 | 0301g | 0702g | 1301 | 0201g | 4501g | 0701 | 2402g | 1301 | 1202 |
| 47 | 0301g | 0702g | 0701 | 0301g | 3501g | 1101 | 0206 | 5901 | 0405 |
| 48 | 0205 | 5001 | 0701 | 3002 | 4403 | 1503 | 3401 | 4002g | 1502 |
| 49 | 0201g | 4001g | 0404 | 3001 | 5301 | 0804 | 1101g | 4001g | 1201g |
| 50 | 0201g | 4001g | 1501 | 0202 | 0702g | 1503 | 1101g | 1301 | 1202 |

| Rank | Hispanic HLA-A | Hispanic HLA-B | Hispanic HLA-DRB1 | Jewish HLA-A | Jewish HLA-B | Jewish HLA-DRB1 |
|---|---|---|---|---|---|---|
| 1 | 2902 | 4403 | 701 | 2601 | 3801 | 0402 |
| 2 | 0101g | 0801g | 301 | 2402 | 3502 | 1104 |
| 3 | 0301g | 0702g | 1501 | 0205 | 5001 | 0701 |
| 4 | 3002 | 1801g | 301 | 0101 | 3502 | 1104 |
| 5 | 3301 | 1402 | 102 | 3301 | 1402 | 0102 |
| 6 | 6803 | 3905 | 407 | 0101 | 0801 | 0301 |
| 7 | 2301g | 4403 | 701 | 2402 | 1801 | 1104 |
| 8 | 2402g | 3906 | 1406 | 1101 | 5201 | 1502 |
| 9 | 0201g | 0702g | 1501 | 0201 | 3503 | 1201 |
| 10 | 206 | 3905 | 407 | 3001 | 1302 | 0701 |
| 11 | 0201g | 3517 | 802 | 2901 | 0705 | 1001 |
| 12 | 2402g | 3502 | 1104 | 6802 | 1402 | 0102 |
| 13 | 0201g | 3512 | 802 | 0101 | 5201 | 1502 |
| 14 | 0201g | 1515 | 802 | 2601 | 3801 | 1401 |
| 15 | 0201g | 4402g | 1301 | 0302 | 4402 | 0402 |
| 16 | 3001 | 1302 | 701 | 0101 | 1517 | 1302 |
| 17 | 6802 | 1402 | 102 | 0201 | 1801 | 1104 |
| 18 | 0201g | 0801g | 301 | 0201 | 5201 | 1502 |
| 19 | 0201g | 4403 | 701 | 0301 | 3801 | 1301 |
| 20 | 1101g | 2705g | 101 | 0101 | 5701 | 1305 |
| 21 | 6801g | 4801g | 404 | 2601 | 3501 | 0402 |
| 22 | 0101g | 5701 | 701 | 2402 | 3801 | 1401 |
| 23 | 0301g | 3501g | 101 | 0201 | 0801 | 0301 |
| 24 | 0301g | 5101g | 701 | 2301 | 4403 | 0701 |
| 25 | 206 | 4002g | 802 | 0301 | 1302 | 0701 |
| 26 | 0201g | 3501g | 407 | 6901 | 5501 | 1101 |
| 27 | 0201g | 5101g | 1101 | 0101 | 1302 | 0701 |
| 28 | 0101g | 0702g | 1501 | 0205 | 4101 | 1305 |
| 29 | 2402g | 4002g | 802 | 0101 | 4101 | 0701 |
| 30 | 0201g | 1402 | 102 | 2601 | 3801 | 1302 |
| 31 | 0201g | 3512 | 407 | 2402 | 1402 | 0102 |
| 32 | 3101 | 3501g | 802 | 0301 | 3502 | 1104 |
| 33 | 2402g | 4002g | 404 | 3201 | 5201 | 1502 |
| 34 | 2501 | 1801g | 1501 | 0301 | 0702 | 1501 |
| 35 | 6801g | 4002g | 407 | 0301 | 1402 | 0102 |
| 36 | 2402g | 3905 | 407 | 2301 | 4101 | 0701 |
| 37 | 1101g | 5201g | 1502 | 0101 | 1801 | 1104 |
| 38 | 2601g | 3801 | 402 | 3002 | 1801 | 0301 |
| 39 | 0201g | 1501g | 401 | 2301 | 4901 | 1104 |
| 40 | 0201g | 1801g | 301 | 2601 | 3801 | 1101 |
| 41 | 2402g | 3543g | 407 | 0101 | 5801 | 0701 |
| 42 | 2402g | 0801g | 301 | 0101 | 3801 | 1301 |
| 43 | 2402g | 4002g | 407 | 0301 | 4101 | 0404 |
| 44 | 0301g | 3501g | 1301 | 0101 | 5201 | 1303 |
| 45 | 2402g | 1402 | 102 | 0101 | 4402 | 1301 |
| 46 | 0201g | 4402g | 401 | 2902 | 1402 | 0701 |
| 47 | 0201g | 5101g | 301 | 0101 | 5701 | 0701 |
| 48 | 0101g | 5201g | 1502 | 2301 | 4901 | 1101 |
| 49 | 6901 | 5501 | 1101 | 0101 | 1501 | 0403 |
| 50 | 3001 | 4201 | 302 | 0302 | 0801 | 0301 |

Table 8 describes the most frequent high-resolution HLA-A-C-B haplotypes detected in the United States population. For each ancestry shown in the table (e.g., European American, African American, Asian [which includes Pacific Islander], and Hispanic [Latino]) the top 50 most frequent HLA-A-C-B haplotypes are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication (Maiers et al., 2007, *Human Immunology,* 68:779-788). Note that the annotation used (e.g., 0201g for HLA-A indicates is the same as HLA-A*02:01 which indicates the (HLA prefix)-gene*allele group/family: specific HLA protein based on the new nomenclature adopted by the WHO Nomenclature Committee for Factors of the HLA System in 2010). For example, A*0201g becomes A*02:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 8

MOST FREQUENT HLA-A-C-B HAPLOTYPES IN THE INDICATED POPULATIONS

| | European American | | | African American | | | Asian Pacific Islander | | | Hispanic | | |
|---|---|---|---|---|---|---|---|---|---|---|---|---|
| Rank | HLA-A | HLA-C | HLA-B | HLA-A | HLA-C | HLA-B | HLA-A | HLA-C | HLA-B | HLA-A | HLA-C | HLA-B |
| 1 | 0101g | 0701g | 0801g | 3001 | 1701g | 4201 | 3303 | 0302 | 5801g | 2902 | 1601 | 4403 |
| 2 | 0301g | 0702 | 0702g | 0201g | 1601 | 4501g | 0207g | 0102 | 4601 | 0101g | 0701g | 0801g |
| 3 | 0201g | 0501g | 4402g | 7401g | 0202 | 1503g | 1101g | 0801 | 1502 | 0301g | 0702 | 0702g |
| 4 | 0201g | 0702 | 0702g | 3601 | 0401g | 5301 | 3001 | 0602 | 1302 | 0201g | 0501g | 4402g |
| 5 | 0201g | 0304 | 4001g | 0101g | 0701g | 0801g | 3303 | 0701g | 4403 | 3301 | 0802 | 1402 |
| 6 | 2902 | 1601 | 4403 | 0301g | 0702 | 0702g | 1101g | 0702 | 4001g | 2402g | 0702 | 3906 |
| 7 | 0101g | 0602 | 5701 | 2301g | 0202 | 1503g | 0101g | 0602 | 5701 | 0201g | 0401g | 3501g |
| 8 | 0301g | 0401g | 3501g | 0201g | 0501g | 4402g | 2901g | 1505 | 0705g | 0201g | 0702 | 0702g |
| 9 | 0201g | 0304 | 1501g | 6802 | 0401g | 5301 | 2402g | 1402 | 5101g | 3002 | 0501g | 1801g |
| 10 | 1101g | 0401g | 3501g | 6801g | 0602 | 5802 | 0203 | 0702 | 3802 | 0201g | 0401g | 3512 |
| 11 | 0201g | 0303g | 1501g | 3303 | 0401g | 5301 | 2402g | 1202 | 5201g | 0301g | 0401g | 3501g |
| 12 | 2402g | 0702 | 0702g | 6802 | 0304 | 1510 | 3303 | 1403 | 4403 | 2301g | 0401g | 4403 |
| 13 | 0201g | 0602 | 5701 | 0301g | 0401g | 3501g | 2402g | 0102 | 5401 | 2601g | 1203 | 3801 |
| 14 | 2601g | 1203 | 3801 | 0202 | 0401g | 5301 | 2402g | 0102 | 4601 | 1101g | 0401g | 3501g |
| 15 | 3001 | 0602 | 1302 | 2301g | 0702 | 0702g | 2402g | 0702 | 0702g | 6803 | 0702 | 3905 |
| 16 | 0201g | 0701g | 0801g | 2301g | 0401g | 5301 | 1101g | 0304 | 1301 | 2402g | 0304 | 4002g |
| 17 | 2501 | 1203 | 1801g | 2902 | 1601 | 4403 | 2402g | 0702 | 4001g | 0201g | 0401g | 3517 |
| 18 | 0101g | 0702 | 0702g | 3402 | 0401g | 4403 | 0201g | 0102 | 5401 | 0206 | 0702 | 3905 |
| 19 | 3301 | 0802 | 1402 | 2301g | 0401g | 4403 | 0101g | 0602 | 3701 | 2402g | 0401g | 3502 |
| 20 | 3101 | 0304 | 4001g | 0201g | 0401g | 5301 | 1101g | 0702 | 3802 | 0201g | 1502g | 5101g |
| 21 | 2301g | 0401g | 4403 | 0201g | 0702 | 0702g | 1101g | 1402 | 5101g | 3101 | 0401g | 3501g |
| 22 | 0201g | 0701g | 1801g | 2301g | 0602 | 4501g | 0206 | 1402 | 5101g | 6801g | 0801 | 4801g |
| 23 | 0201g | 0602 | 1302 | 0201g | 0701g | 4901 | 1101g | 0401g | 1501g | 6801g | 0304 | 4002g |
| 24 | 0101g | 0602 | 3701 | 6802 | 0702 | 0702g | 1101g | 1202 | 5201g | 6802 | 0802 | 1402 |
| 25 | 2402g | 0303g | 1501g | 0301g | 0602 | 5802 | 2402g | 0304 | 1301 | 0201g | 0303g | 5201g |
| 26 | 0201g | 0102 | 2705g | 3001 | 1701g | 4202 | 0201g | 0304 | 1301 | 6802 | 0401g | 5301 |
| 27 | 0301g | 0802 | 1402 | 0201g | 1601 | 3501g | 1101g | 0102 | 5401 | 0201g | 0102 | 1515 |
| 28 | 0201g | 0202 | 2705g | 7401g | 0701g | 5703 | 1101g | 0401g | 3501g | 0206 | 0801 | 4801g |
| 29 | 0201g | 1402 | 5101g | 2301g | 1701g | 4201 | 2402g | 0801 | 4801g | 3001 | 0602 | 1302 |
| 30 | 0201g | 0401g | 3501g | 3303 | 1402 | 1516 | 2407 | 0401g | 3505 | 0101g | 0602 | 5701 |
| 31 | 6802 | 0802 | 1402 | 0201g | 0304 | 4001g | 1101g | 0304 | 4001g | 0201g | 0701g | 0801g |
| 32 | 3002 | 0501g | 1801g | 3301 | 1601 | 7801 | 1101g | 0702 | 3901g | 2402g | 0401g | 3501g |
| 33 | 1101g | 0303g | 5501 | 0201g | 0401g | 3501g | 1101g | 0102 | 4601 | 2501 | 1203 | 1801g |
| 34 | 1101g | 0702 | 0702g | 6601 | 0602 | 5802 | 3101 | 1402 | 5101g | 0201g | 0304 | 4001g |
| 35 | 0201g | 1502g | 5101g | 3002 | 0802 | 1402 | 2402g | 1502g | 4006 | 0206 | 0304 | 4002g |
| 36 | 3201 | 0501g | 4402g | 3303 | 0401g | 3501g | 2601g | 0702 | 0801g | 1101g | 0102 | 2705g |
| 37 | 2402g | 0401g | 3502 | 6802 | 1701g | 4201 | 2402g | 0304 | 4002g | 0301g | 0802 | 1402 |
| 38 | 2402g | 0701g | 0801g | 3001 | 0401g | 5301 | 2402g | 0304 | 4001g | 0201g | 0501g | 1801g |
| 39 | 0301g | 0304 | 4001g | 6602 | 0701g | 5801g | 0201g | 1502g | 4001g | 2402g | 0801 | 4801g |
| 40 | 0201g | 1601 | 4403 | 0201g | 0202 | 1503g | 2402g | 0702 | 3802 | 0201g | 0304 | 4002g |
| 41 | 2402g | 0501g | 4402g | 2301g | 0602 | 5301 | 0301g | 0401g | 3501g | 3001 | 1701g | 4201 |
| 42 | 6801g | 0704g | 4402g | 2902 | 0401g | 5301 | 0211g | 1502g | 4006 | 2301g | 0701g | 4901 |
| 43 | 0301g | 0701g | 0801g | 0101g | 0702 | 0702g | 2417 | 0801 | 1502 | 2402g | 0102 | 3543g |
| 44 | 3201 | 0802 | 1401 | 0205 | 0401g | 5301 | 0101g | 0701g | 1517 | 2402g | 0702 | 0702g |
| 45 | 0301g | 0501g | 4402g | 0205 | 0701g | 5801g | 0206 | 0102 | 5901 | 0201g | 0303g | 1501g |
| 46 | 2301g | 0701g | 4901 | 7401g | 0401g | 5301 | 2402g | 0401g | 3501g | 2402g | 0306 | 4002g |
| 47 | 2402g | 0304 | 4001g | 0102 | 0701g | 4901 | 2402g | 0303g | 3501g | 1101g | 1202 | 5201g |
| 48 | 0205 | 0602 | 5001 | 0202 | 0202 | 1503g | 1101g | 0102 | 5502 | 0201g | 0701g | 1801g |
| 49 | 6801g | 0304 | 4001g | 2902 | 0701g | 4901 | 2402g | 0401g | 4001g | 2402g | 0501g | 4402g |
| 50 | 0101g | 0501g | 4402g | 2301g | 0304 | 0801g | 2402g | 1203 | 3503 | 0201g | 0702 | 3906 |

Table 9 describes the most frequent high-resolution HLA-A-B-DRB1-DQB1 haplotypes detected in the United States population. For each ancestry shown in the table (e.g., European American. African American, Asian [which includes Pacific Islander], and Hispanic [Latino]) the top 50 most frequent HLA-A-B-DRB1-DQB1 haplotypes are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication (Maiers et al., 2007. *Human Immunology,* 68:779-788). Note that the annotation used (e.g., 0201g for HLA-A indicates is the same as HLA-A*02:01 which indicates the (HLA prefix)-gene*allele group/family: specific HLA protein based on the new nomenclature adopted by the WHO Nomenclature Committee for Factors of the HLA System in 2010). For example, A*0201g becomes A*02:01. With the designation shown in this table, the fields that are used to show synonymous DNA substitution in coding region, differences in non-coding regions, and the suffix used to denote changes in expression are not shown (see the following website for more information: hla.allelcs.org). The allele designations in this table with the "g" suffix refer to allele groups defined in table 1 of the publication "Maiers, M., Gragert. L., Klitz, W. High resolution HLA alleles and haplotypes in the US population. 2007".

TABLE 9

MOST FREQUENT HLA-A-B-DRB1-DQB1 HAPLOTYPES IN THE INDICATED POPULATIONS

| | European American | | | | African American | | | |
|---|---|---|---|---|---|---|---|---|
| Rank | HLA-A | HLA-B | DRB1 | DQB1 | HLA-A | HLA-B | DRB1 | DQB1 |
| 1 | 0101g | 0801g | 0301 | 0201g | 3001 | 4201 | 0302 | 0402 |
| 2 | 0301g | 0702g | 1501 | 0602 | 0101g | 0801g | 0301 | 0201g |
| 3 | 0201g | 4402g | 0401 | 0301g | 0301g | 0702g | 1501 | 0602 |
| 4 | 0201g | 0702g | 1501 | 0602 | 3303 | 5301 | 0804 | 0301g |
| 5 | 2902 | 4403 | 0701 | 0201g | 6802 | 1510 | 0301 | 0201g |
| 6 | 0201g | 1501g | 0401 | 0302 | 6801g | 5802 | 1201g | 0501 |
| 7 | 0101g | 5701 | 0701 | 0303 | 3402 | 4403 | 1503 | 0602 |
| 8 | 0301g | 3501g | 0101 | 0501 | 6802 | 0702g | 1503 | 0602 |
| 9 | 0201g | 4001g | 1302 | 0604 | 3601 | 5301 | 1101 | 0602 |
| 10 | 3001 | 1302 | 0701 | 0201g | 2902 | 4403 | 0701 | 0201g |
| 11 | 0201g | 0801g | 0301 | 0201g | 2301g | 4403 | 1503 | 0602 |
| 12 | 0201g | 5701 | 0701 | 0303 | 7401g | 1503g | 1302 | 0609 |
| 13 | 2402g | 0702g | 1501 | 0602 | 0201g | 4402g | 0401 | 0301g |
| 14 | 1101g | 3501g | 0101 | 0501 | 2301g | 5301 | 0701 | 0201g |
| 15 | 3301 | 1402 | 0102 | 0501 | 2301g | 1503g | 0701 | 0201g |
| 16 | 2301g | 4403 | 0701 | 0201g | 6802 | 5301 | 1503 | 0602 |
| 17 | 0201g | 1501g | 1301 | 0603 | 2902 | 4901 | 1503 | 0602 |
| 18 | 0101g | 0702g | 1501 | 0602 | 3001 | 4201 | 0804 | 0301g |
| 19 | 0201g | 1302 | 0701 | 0201g | 6602 | 5801g | 1503 | 0602 |
| 20 | 3101 | 4001g | 0404 | 0302 | 2301g | 1801g | 0701 | 0201g |
| 21 | 2501 | 1801g | 1501 | 0602 | 0201g | 0702g | 1501 | 0602 |
| 22 | 0201g | 4403 | 0701 | 0201g | 0201g | 4501g | 1503 | 0602 |
| 23 | 0201g | 4402g | 1301 | 0603 | 2301g | 5301 | 1503 | 0602 |
| 24 | 0201g | 4402g | 1501 | 0602 | 0202 | 4201 | 0302 | 0402 |
| 25 | 0201g | 4402g | 0101 | 0501 | 2501 | 1801g | 1501 | 0602 |
| 26 | 0101g | 0801g | 1501 | 0602 | 3002 | 1402 | 1503 | 0602 |
| 27 | 0301g | 0702g | 0101 | 0501 | 7401g | 5301 | 1101 | 0602 |
| 28 | 0201g | 5101g | 1101 | 0301g | 2301g | 5301 | 0301 | 0201g |
| 29 | 2601g | 3801 | 0402 | 0302 | 3002 | 0801g | 0301 | 0201g |
| 30 | 0201g | 2705g | 0101 | 0501 | 2902 | 5301 | 0701 | 0201g |
| 31 | 0301g | 0801g | 0301 | 0201g | 0201g | 0801g | 0301 | 0201g |
| 32 | 3002 | 1801g | 0301 | 0201g | 2301g | 4403 | 0701 | 0201g |
| 33 | 0201g | 1801g | 1104 | 0301g | 3002 | 4403 | 1503 | 0602 |
| 34 | 2402g | 0801g | 0301 | 0201g | 6802 | 1510 | 0804 | 0301g |
| 35 | 2402g | 3502 | 1104 | 0301g | 0301g | 0702g | 1503 | 0602 |
| 36 | 0201g | 1501g | 0101 | 0501 | 7401g | 5703 | 1303 | 0201g |
| 37 | 6802 | 1402 | 1303 | 0301g | 0301g | 5802 | 1102 | 0301g |
| 38 | 0201g | 5101g | 1301 | 0603 | 3002 | 7801 | 0701 | 0201g |
| 39 | 0201g | 3501g | 0101 | 0501 | 1101g | 0702g | 1501 | 0602 |
| 40 | 0301g | 0702g | 1301 | 0603 | 0201g | 4901 | 1503 | 0602 |
| 41 | 3201 | 1401 | 0701 | 0201g | 3001 | 4201 | 1503 | 0602 |
| 42 | 0201g | 1501g | 1501 | 0602 | 3303 | 5301 | 1503 | 0602 |
| 43 | 1101g | 0702g | 1501 | 0602 | 2301g | 4201 | 0302 | 0402 |
| 44 | 0101g | 0801g | 0101 | 0501 | 0201g | 5101g | 1303 | 0301g |
| 45 | 0205 | 5001 | 0701 | 0201g | 6802 | 5301 | 1102 | 0301g |
| 46 | 0201g | 4001g | 1501 | 0602 | 0301g | 3501g | 1503 | 0602 |
| 47 | 0201g | 4402g | 1101 | 0301g | 3301 | 1402 | 0102 | 0501 |
| 48 | 0201g | 4001g | 0404 | 0302 | 3002 | 5802 | 1201g | 0501 |
| 49 | 0201g | 4001g | 0801 | 0402 | 0301g | 3501g | 1001 | 0501 |
| 50 | 0301g | 1402 | 1302 | 0609 | 2902 | 3501g | 0701 | 0201g |

| | Asian Pacific Islander | | | | Hispanic | | | |
|---|---|---|---|---|---|---|---|---|
| Rank | HLA-A | HLA-B | DRB1 | DQB1 | HLA-A | HLA-B | DRB1 | DQB1 |
| 1 | 3303 | 5801g | 0301 | 0201g | 2902 | 4403 | 701 | 0201g |
| 2 | 0207g | 4601 | 0901 | 0303 | 0101g | 0801g | 301 | 0201g |
| 3 | 3303 | 4403 | 0701 | 0201g | 0301g | 0702g | 1501 | 602 |
| 4 | 1101g | 1502 | 1202 | 0301g | 3301 | 1402 | 102 | 501 |
| 5 | 3303 | 5801g | 1302 | 0609 | 3002 | 1801g | 301 | 0201g |
| 6 | 2402g | 5201g | 1502 | 0601 | 6803 | 3905 | 407 | 302 |
| 7 | 3001 | 1302 | 0701 | 0201g | 0201g | 0702g | 1501 | 602 |
| 8 | 0101g | 3701 | 1001 | 0501 | 2301g | 4403 | 701 | 0201g |
| 9 | 0101g | 5701 | 0701 | 0303 | 2402g | 3502 | 1104 | 0301g |
| 10 | 1101g | 5401 | 0405 | 0401 | 0201g | 3512 | 407 | 302 |
| 11 | 2901g | 0705g | 1001 | 0501 | 2402g | 4002g | 404 | 302 |
| 12 | 0207g | 4601 | 0803 | 0601 | 0201g | 5101g | 701 | 0201g |
| 13 | 3303 | 4403 | 1302 | 0604 | 2402g | 3906 | 1406 | 0301g |
| 14 | 2402g | 4001g | 0901 | 0303 | 0201g | 4402g | 1301 | 603 |
| 15 | 1101g | 1301 | 1501 | 0601 | 2402g | 3543g | 407 | 302 |
| 16 | 2402g | 0702g | 0101 | 0501 | 206 | 3905 | 407 | 302 |

TABLE 9-continued

MOST FREQUENT HLA-A-B-DRB1-DQB1 HAPLOTYPES IN THE INDICATED POPULATIONS

| | | | | | | | | |
|---|---|---|---|---|---|---|---|---|
| 17 | 2402g | 4601 | 0901 | 0303 | 0201g | 3512 | 802 | 402 |
| 18 | 2407 | 3505 | 1202 | 0301g | 206 | 4002g | 802 | 402 |
| 19 | 0201g | 5101g | 0901 | 0303 | 3001 | 1302 | 701 | 0201g |
| 20 | 0201g | 4001g | 1101 | 0301g | 0101g | 5701 | 701 | 303 |
| 21 | 1101g | 3802 | 1502 | 0502 | 0201g | 0801g | 301 | 0201g |
| 22 | 2402g | 5901 | 0405 | 0401 | 2501 | 1801g | 1501 | 602 |
| 23 | 2601g | 0801g | 0301 | 0201g | 0201g | 1515 | 802 | 402 |
| 24 | 1101g | 4601 | 0901 | 0303 | 0201g | 3501g | 802 | 402 |
| 25 | 2402g | 4001g | 0403 | 0302 | 0201g | 4403 | 701 | 0201g |
| 26 | 0201g | 1301 | 1202 | 0301g | 0201g | 5201g | 1502 | 601 |
| 27 | 0203 | 3802 | 0803 | 0601 | 0201g | 1501g | 401 | 302 |
| 28 | 1101g | 4001g | 0803 | 0601 | 1101g | 2705g | 101 | 501 |
| 29 | 1101g | 5201g | 1502 | 0601 | 1101g | 5201g | 1502 | 601 |
| 30 | 2402g | 5401 | 0405 | 0401 | 204 | 5101g | 411 | 402 |
| 31 | 0203 | 3802 | 1602 | 0502 | 6901 | 5501 | 1101 | 0301g |
| 32 | 2402g | 1501g | 1101 | 0301g | 2402g | 4002g | 407 | 302 |
| 33 | 2402g | 5401 | 0803 | 0601 | 0101g | 0801g | 1301 | 603 |
| 34 | 1101g | 4001g | 0901 | 0303 | 0301g | 3501g | 101 | 501 |
| 35 | 1101g | 1502 | 1501 | 0601 | 6802 | 1402 | 102 | 501 |
| 36 | 3401 | 1535 | 0405 | 0402 | 2402g | 4801g | 404 | 302 |
| 37 | 1101g | 3901g | 0803 | 0601 | 2601g | 3801 | 402 | 302 |
| 38 | 0101g | 0801g | 0301 | 0201g | 0201g | 5601 | 101 | 501 |
| 39 | 0101g | 1517 | 1302 | 0604 | 2402g | 3501g | 407 | 302 |
| 40 | 2402g | 3802 | 0901 | 0303 | 3001 | 4201 | 302 | 402 |
| 41 | 1101g | 1501g | 0406 | 0302 | 1101g | 4901 | 405 | 302 |
| 42 | 1101g | 3501g | 1501 | 0602 | 0201g | 5101g | 1301 | 603 |
| 43 | 0206 | 5101g | 1501 | 0602 | 2402g | 0801g | 301 | 0201g |
| 44 | 2402g | 4006 | 1501 | 0601 | 0301g | 1402 | 102 | 501 |
| 45 | 2402g | 5801g | 0301 | 0201g | 0301g | 5101g | 701 | 0201g |
| 46 | 1102 | 1502 | 1202 | 0301g | 2402g | 1402 | 102 | 501 |
| 47 | 1101g | 1301 | 1202 | 0301g | 0301g | 4403 | 701 | 0201g |
| 48 | 1101g | 5101g | 1404 | 0503 | 1101g | 0702g | 1501 | 602 |
| 49 | 2901g | 0705g | 0803 | 0301g | 3301 | 4403 | 102 | 501 |
| 50 | 2417 | 1502 | 1202 | 0301g | 3201 | 1401 | 701 | 0201g |

Table 10 describes the most frequent high-resolution HLA-A-C-B-DRB1 haplotypes in the United States population. For each ancestry shown in the table (e.g., European American, African American, Asian [which includes Pacific Islander], and Hispanic [Latino]) the top 50 most frequent HLA-A-C-B-DRB1 haplotypes are ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication (Maiers et al., 2007, *Human Immunology,* 68:779-788). Note that the annotation used (e.g., 0201g for HLA-A indicates is the same as HLA-A*02:01 which indicates the (HLA prefix)-gene*allele group/family: specific HLA protein based on the new nomenclature adopted by the WHO Nomenclature Committee for Factors of the HLA System in 2010). For example, A*0201g becomes A*02:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 10

MOST FREQUENT HLA-A-C-B-DRB1 HAPLOTYPES IN THE INDICATED POPULATIONS

| | European American | | | | African American | | | |
|---|---|---|---|---|---|---|---|---|
| Rank | HLA-A | HLA-C | HLA-B | DRB1 | HLA-A | HLA-C | HLA-B | DRB1 |
| 1 | 0101g | 0701g | 0801g | 0301 | 3001 | 1701g | 4201 | 0302 |
| 2 | 0301g | 0702 | 0702g | 1501 | 0101g | 0701g | 0801g | 0301 |
| 3 | 0201g | 0501g | 4402g | 0401 | 6801g | 0602 | 5802 | 1201g |
| 4 | 0201g | 0702 | 0702g | 1501 | 0301g | 0702 | 0702g | 1501 |
| 5 | 2902 | 1601 | 4403 | 0701 | 3601 | 0401g | 5301 | 1101 |
| 6 | 0101g | 0602 | 5701 | 0701 | 3303 | 0401g | 5301 | 0804 |
| 7 | 0301g | 0401g | 3501g | 0101 | 6802 | 0304 | 1510 | 0301 |
| 8 | 0201g | 0304 | 1501g | 0401 | 3402 | 0401g | 4403 | 1503 |
| 9 | 0201g | 0304 | 4001g | 1302 | 2902 | 1601 | 4403 | 0701 |
| 10 | 0201g | 0701g | 0801g | 0301 | 0201g | 0501g | 4402g | 0401 |
| 11 | 3001 | 0602 | 1302 | 0701 | 7401g | 0202 | 1503g | 1302 |
| 12 | 0201g | 0602 | 5701 | 0701 | 2301g | 0202 | 1503g | 0701 |

TABLE 10-continued

MOST FREQUENT HLA-A-C-B-DRB1 HAPLOTYPES IN THE INDICATED POPULATIONS

| | | | | | | | | |
|---|---|---|---|---|---|---|---|---|
| 13 | 2402g | 0702 | 0702g | 1501 | 6802 | 0401g | 5301 | 1503 |
| 14 | 1101g | 0401g | 3501g | 0101 | 3002 | 0802 | 1402 | 1503 |
| 15 | 3301 | 0802 | 1402 | 0102 | 3001 | 1701g | 4201 | 0804 |
| 16 | 2301g | 0401g | 4403 | 0701 | 6802 | 0702 | 0702g | 1503 |
| 17 | 0201g | 0602 | 1302 | 0701 | 2902 | 0701g | 4901 | 1503 |
| 18 | 0101g | 0702 | 0702g | 1501 | 7401g | 0701g | 5703 | 1303 |
| 19 | 0201g | 0303g | 1501g | 1301 | 0201g | 1601 | 4501g | 1302 |
| 20 | 3101 | 0304 | 4001g | 0404 | 2301g | 0401g | 4403 | 1503 |
| 21 | 2501 | 1203 | 1801g | 1501 | 7401g | 0202 | 1503g | 1503 |
| 22 | 0301g | 0702 | 0702g | 0101 | 6601 | 0602 | 5802 | 1301 |
| 23 | 0201g | 0501g | 4402g | 1301 | 2301g | 0401g | 4403 | 0701 |
| 24 | 0101g | 0701g | 0801g | 1501 | 2301g | 1701g | 4201 | 0302 |
| 25 | 0201g | 0501g | 4402g | 1501 | 2301g | 0202 | 1503g | 1503 |
| 26 | 2601g | 1203 | 3801 | 0402 | 2301g | 0202 | 1503g | 1101 |
| 27 | 0201g | 0501g | 4402g | 0101 | 6602 | 0701g | 5801g | 1503 |
| 28 | 3002 | 0501g | 1801g | 0301 | 6802 | 0401g | 5301 | 1303 |
| 29 | 0201g | 1601 | 4403 | 0701 | 0201g | 1601 | 4501g | 1101 |
| 30 | 0301g | 0701g | 0801g | 0301 | 2501 | 1203 | 1801g | 1501 |
| 31 | 2402g | 0401g | 3502 | 1104 | 2601g | 0304 | 0801g | 1304 |
| 32 | 0201g | 0303g | 1501g | 0401 | 0201g | 0401g | 5301 | 1303 |
| 33 | 0201g | 0701g | 1801g | 1104 | 0301g | 0401g | 3501g | 1101 |
| 34 | 2402g | 0701g | 0801g | 0301 | 3001 | 1701g | 4201 | 1302 |
| 35 | 0201g | 0401g | 3501g | 0101 | 0201g | 0702 | 0702g | 1501 |
| 36 | 0201g | 0102 | 2705g | 0101 | 6802 | 0401g | 5301 | 1302 |
| 37 | 6802 | 0802 | 1402 | 1303 | 0201g | 0701g | 0801g | 0301 |
| 38 | 3201 | 0802 | 1401 | 0701 | 0301g | 0602 | 5802 | 0701 |
| 39 | 1101g | 0702 | 0702g | 1501 | 3303 | 0401g | 5301 | 1503 |
| 40 | 0301g | 0702 | 0702g | 0701 | 0201g | 1601 | 4501g | 1301 |
| 41 | 0205 | 0602 | 5001 | 0701 | 3002 | 1801g | 5703 | 1301 |
| 42 | 0101g | 0701g | 0801g | 0101 | 3303 | 1402 | 1516 | 0102 |
| 43 | 0201g | 0304 | 4001g | 1501 | 2301g | 0602 | 4501g | 1101 |
| 44 | 0301g | 0702 | 0702g | 0401 | 0201g | 1601 | 5101g | 1303 |
| 45 | 0301g | 0702 | 0702g | 1301 | 0201g | 1601 | 4501g | 0302 |
| 46 | 0201g | 0702 | 0702g | 0701 | 7401g | 0202 | 1503g | 1101 |
| 47 | 0101g | 0701g | 0801g | 0401 | 0301g | 0602 | 5802 | 1301 |
| 48 | 0301g | 0802 | 1402 | 1302 | 0201g | 1601 | 4501g | 0102 |
| 49 | 0201g | 0304 | 4001g | 0801 | 0101g | 0602 | 5701 | 0701 |
| 50 | 2601g | 1203 | 3801 | 1301 | 2301g | 0702 | 0702g | 0901 |

| | Asian Pacific Islander | | | | Hispanic | | | |
|---|---|---|---|---|---|---|---|---|
| Rank | HLA-A | HLA-C | HLA-B | DRB1 | HLA-A | HLA-C | HLA-B | DRB1 |
| 1 | 3303 | 0302 | 5801g | 0301 | 2902 | 1601 | 4403 | 0701 |
| 2 | 0207g | 0102 | 4601 | 0901 | 0101g | 0701g | 0801g | 0301 |
| 3 | 3001 | 0602 | 1302 | 0701 | 0301g | 0702 | 0702g | 1501 |
| 4 | 3303 | 0701g | 4403 | 0701 | 3002 | 0501g | 1801g | 0301 |
| 5 | 3303 | 0302 | 5801g | 1302 | 3301 | 0802 | 1402 | 0102 |
| 6 | 1101g | 0801 | 1502 | 1202 | 6803 | 0702 | 3905 | 0407 |
| 7 | 2402g | 1202 | 5201g | 1502 | 2301g | 0401g | 4403 | 0701 |
| 8 | 0101g | 0602 | 5701 | 0701 | 2402g | 0702 | 3906 | 1406 |
| 9 | 3303 | 1403 | 4403 | 1302 | 0206 | 0702 | 3905 | 0407 |
| 10 | 0101g | 0602 | 3701 | 1001 | 0201g | 0401g | 3517 | 0802 |
| 11 | 2901g | 1505 | 0705g | 1001 | 0201g | 0702 | 0702g | 1501 |
| 12 | 2402g | 0102 | 5401 | 0405 | 2402g | 0401g | 3502 | 1104 |
| 13 | 2402g | 0702 | 0702g | 0101 | 0201g | 0102 | 1515 | 0802 |
| 14 | 2402g | 0102 | 4601 | 0901 | 0201g | 0401g | 3512 | 0802 |
| 15 | 1101g | 0702 | 3802 | 1502 | 3001 | 0602 | 1302 | 0701 |
| 16 | 2601g | 0702 | 0801g | 0301 | 6802 | 0802 | 1402 | 0102 |
| 17 | 0207g | 0102 | 4601 | 0803 | 6801g | 0801 | 4801g | 0404 |
| 18 | 1101g | 0304 | 1301 | 1501 | 1101g | 0102 | 2705g | 0101 |
| 19 | 1101g | 0102 | 4601 | 0901 | 0301g | 0401g | 3501g | 0101 |
| 20 | 0201g | 0304 | 1301 | 1202 | 0201g | 0501g | 4402g | 1301 |
| 21 | 1101g | 0401g | 1501g | 0406 | 2501 | 1203 | 1801g | 1501 |
| 22 | 2407 | 0401g | 3505 | 1202 | 0201g | 0401g | 3512 | 0407 |
| 23 | 1101g | 0102 | 5401 | 0405 | 0201g | 0501g | 1801g | 0301 |
| 24 | 2402g | 1402 | 5101g | 0901 | 0301g | 0401g | 3501g | 1301 |
| 25 | 0203 | 0702 | 3802 | 1602 | 1101g | 1202 | 5201g | 1502 |
| 26 | 2402g | 0702 | 4001g | 0901 | 2402g | 0102 | 3543g | 0407 |
| 27 | 1101g | 1202 | 5201g | 1502 | 2601g | 1203 | 3801 | 0402 |
| 28 | 2417 | 0801 | 1502 | 1202 | 0201g | 0501g | 4402g | 0401 |
| 29 | 0206 | 0102 | 5901 | 0405 | 3101 | 0401g | 3501g | 0802 |
| 30 | 1101g | 0702 | 3901g | 0803 | 0201g | 0401g | 3501g | 0407 |
| 31 | 2402g | 0702 | 3802 | 1502 | 0101g | 0602 | 5701 | 0701 |
| 32 | 0201g | 1502g | 4001g | 1101 | 0201g | 0802 | 1402 | 0102 |
| 33 | 2402g | 0304 | 1301 | 1202 | 6801g | 0304 | 4002g | 0407 |

TABLE 10-continued

MOST FREQUENT HLA-A-C-B-DRB1 HAPLOTYPES IN THE INDICATED POPULATIONS

| | | | | | | | | |
|---|---|---|---|---|---|---|---|---|
| 34 | 1101g | 0702 | 4001g | 0803 | 2402g | 0304 | 4002g | 0404 |
| 35 | 1101g | 0702 | 4001g | 0901 | 0301g | 0702 | 0702g | 0101 |
| 36 | 2402g | 0102 | 5901 | 0405 | 2402g | 0801 | 4801g | 0404 |
| 37 | 2402g | 0102 | 4601 | 0803 | 3001 | 1701g | 4201 | 0302 |
| 38 | 0201g | 0102 | 5401 | 0405 | 6901 | 0102 | 5501 | 1101 |
| 39 | 0203 | 0702 | 3802 | 0803 | 0204 | 1502g | 5101g | 0411 |
| 40 | 2901g | 1505 | 0705g | 0803 | 0101g | 1202 | 5201g | 1502 |
| 41 | 2402g | 0401g | 4001g | 0403 | 2402g | 0701g | 0801g | 0301 |
| 42 | 0101g | 0701g | 1517 | 1302 | 0201g | 1502g | 5101g | 1101 |
| 43 | 1101g | 0801 | 1502 | 1501 | 2402g | 0802 | 1402 | 0102 |
| 44 | 2402g | 0304 | 1301 | 1501 | 6802 | 0401g | 5301 | 0102 |
| 45 | 0207g | 0102 | 4601 | 0405 | 0201g | 0501g | 4402g | 0701 |
| 46 | 0201g | 0102 | 5401 | 0803 | 2601g | 0802 | 1401 | 0701 |
| 47 | 3401 | 1502g | 4002g | 1502 | 2402g | 0702 | 3906 | 0404 |
| 48 | 1101g | 0401g | 3501g | 0101 | 2601g | 0501g | 4402g | 0402 |
| 49 | 0101g | 0702 | 0801g | 0301 | 0301g | 1601 | 5101g | 0701 |
| 50 | 0201g | 0303g | 1511 | 0901 | 2402g | 0306 | 4002g | 0802 |

Table 11 describes the most frequent high-resolution HLA-A-C-B-DRB1-DQB1 haplotypes in the United States population. For each ancestry shown in the table (e.g., European American, African American, Asian [which includes Pacific Islander], and Hispanic [Latino]) the top 50 most frequent HLA-A-C-B-DRB1-DQB1 haplotypes are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication (Maiers et al., 2007. *Human Immunology,* 68:779-788). Note that the annotation used (e.g., 0201g for HLA-A indicates is the same as HLA-A*02:01 which indicates the (HLA prefix)-gene*allele group/family: specific HLA protein based on the new nomenclature adopted by the WHO Nomenclature Committee for Factors of the HLA System in 2010). For example, A*0201g becomes A*02:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the Vg suffix refer to allele groups defined in table 1 of the publication "Maiers. M., Gragert, L., Klitz, W. High resolution HLA alleles and haplotypes in the US population. 2007".

TABLE 11

MOST FREQUENT HLA-A-C-B-DRB1-DQB1 HAPLOTYPES IN THE INDICATED POPULATIONS

| | European American | | | | | African American | | | | |
|---|---|---|---|---|---|---|---|---|---|---|
| Rank | HLA-A | HLA-C | HLA-B | DRB1 | DQB1 | HLA-A | HLA-C | HLA-B | DRB1 | DQB1 |
| 1 | 0101g | 0701g | 0801g | 0301 | 0201g | 3001 | 1701g | 4201 | 0302 | 0402 |
| 2 | 0301g | 0702 | 0702g | 1501 | 0602 | 0101g | 0701g | 0801g | 0301 | 0201g |
| 3 | 0201g | 0501g | 4402g | 0401 | 0301g | 0301g | 0702 | 0702g | 1501 | 0602 |
| 4 | 0201g | 0702 | 0702g | 1501 | 0602 | 3303 | 0401g | 5301 | 0804 | 0301g |
| 5 | 2902 | 1601 | 4403 | 0701 | 0201g | 6802 | 0304 | 1510 | 0301 | 0201g |
| 6 | 0101g | 0602 | 5701 | 0701 | 0303 | 6801g | 0602 | 5802 | 1201g | 0501 |
| 7 | 0301g | 0401g | 3501g | 0101 | 0501 | 3402 | 0401g | 4403 | 1503 | 0602 |
| 8 | 0201g | 0304 | 1501g | 0401 | 0302 | 2902 | 1601 | 4403 | 0701 | 0201g |
| 9 | 0201g | 0304 | 4001g | 1302 | 0604 | 6802 | 0702 | 0702g | 1503 | 0602 |
| 10 | 0201g | 0701g | 0801g | 0301 | 0201g | 3601 | 0401g | 5301 | 1101 | 0602 |
| 11 | 3001 | 0602 | 1302 | 0701 | 0201g | 0201g | 0501g | 4402g | 0401 | 0301g |
| 12 | 0201g | 0602 | 5701 | 0701 | 0303 | 2301g | 0401g | 4403 | 1503 | 0602 |
| 13 | 2402g | 0702 | 0702g | 1501 | 0602 | 7401g | 0202 | 1503g | 1302 | 0609 |
| 14 | 1101g | 0401g | 3501g | 0101 | 0501 | 2301g | 0401g | 5301 | 0701 | 0201g |
| 15 | 3301 | 0802 | 1402 | 0102 | 0501 | 2902 | 0701g | 4901 | 1503 | 0602 |
| 16 | 2301g | 0401g | 4403 | 0701 | 0201g | 3001 | 1701g | 4201 | 0804 | 0301g |
| 17 | 0201g | 0602 | 1302 | 0701 | 0201g | 6602 | 0701g | 5801g | 1503 | 0602 |
| 18 | 3101 | 0304 | 4001g | 0404 | 0302 | 0201g | 1601 | 4501g | 1503 | 0602 |
| 19 | 0101g | 0702 | 0702g | 1501 | 0602 | 6802 | 0401g | 5301 | 1503 | 0602 |
| 20 | 0201g | 0303g | 1501g | 1301 | 0603 | 2301g | 0202 | 1503g | 0701 | 0201g |
| 21 | 2501 | 1203 | 1801g | 1501 | 0602 | 2501 | 1203 | 1801g | 1501 | 0602 |
| 22 | 0201g | 0501g | 4402g | 1501 | 0602 | 0201g | 0702 | 0702g | 1501 | 0602 |
| 23 | 0301g | 0702 | 0702g | 0101 | 0501 | 2301g | 0202 | 1503g | 1503 | 0602 |
| 24 | 0101g | 0701g | 0801g | 1501 | 0602 | 0202 | 1701g | 4201 | 0302 | 0402 |
| 25 | 0201g | 0501g | 4402g | 1301 | 0603 | 3002 | 0802 | 1402 | 1503 | 0602 |
| 26 | 2601g | 1203 | 3801 | 0402 | 0302 | 7401g | 0701g | 5703 | 1303 | 0201g |
| 27 | 0201g | 0501g | 4402g | 0101 | 0501 | 3002 | 0701g | 0801g | 0301 | 0201g |
| 28 | 3002 | 0501g | 1801g | 0301 | 0201g | 1101g | 0702 | 0702g | 1501 | 0602 |
| 29 | 0301g | 0701g | 0801g | 0301 | 0201g | 2902 | 0401g | 5301 | 0701 | 0201g |

TABLE 11-continued

MOST FREQUENT HLA-A-C-B-DRB1-DQB1 HAPLOTYPES IN THE INDICATED POPULATIONS

| | | | | | | | | | | |
|---|---|---|---|---|---|---|---|---|---|---|
| 30 | 2402g | 0401g | 3502 | 1104 | 0301g | 6802 | 0701g | 5801g | 1503 | 0602 |
| 31 | 0201g | 1601 | 4403 | 0701 | 0201g | 3002 | 1601 | 7801 | 0701 | 0201g |
| 32 | 2402g | 0701g | 0801g | 0301 | 0201g | 3001 | 1701g | 4201 | 1503 | 0602 |
| 33 | 0201g | 0701g | 1801g | 1104 | 0301g | 7401g | 0401g | 5301 | 1101 | 0602 |
| 34 | 0201g | 0401g | 3501g | 0101 | 0501 | 0201g | 0701g | 4901 | 1503 | 0602 |
| 35 | 0201g | 0102 | 2705g | 0101 | 0501 | 2301g | 0401g | 5301 | 0301 | 0201g |
| 36 | 6802 | 0802 | 1402 | 1303 | 0301g | 2301g | 1701g | 4201 | 0302 | 0402 |
| 37 | 3201 | 0802 | 1401 | 0701 | 0201g | 2301g | 0702 | 0702g | 1503 | 0602 |
| 38 | 0301g | 0702 | 0702g | 1301 | 0603 | 2301g | 0401g | 4403 | 0701 | 0201g |
| 39 | 1101g | 0702 | 0702g | 1501 | 0602 | 0201g | 1601 | 5101g | 1303 | 0301g |
| 40 | 0201g | 0303g | 1501g | 0401 | 0302 | 6802 | 0401g | 5301 | 1102 | 0301g |
| 41 | 0201g | 0304 | 4001g | 1501 | 0602 | 0201g | 0501g | 4402g | 1501 | 0602 |
| 42 | 0101g | 0701g | 0801g | 0101 | 0501 | 6601 | 0602 | 5802 | 1301 | 0303 |
| 43 | 0205 | 0602 | 5001 | 0701 | 0201g | 0301g | 0401g | 3501g | 1503 | 0602 |
| 44 | 0201g | 0304 | 4001g | 0801 | 0402 | 3301 | 0802 | 1402 | 0102 | 0501 |
| 45 | 0301g | 0802 | 1402 | 1302 | 0609 | 0201g | 1601 | 4501g | 0901 | 0201g |
| 46 | 2601g | 1203 | 3801 | 1301 | 0603 | 3303 | 0202 | 1503g | 1101 | 0301g |
| 47 | 0201g | 0304 | 4001g | 0404 | 0302 | 0201g | 0701g | 4901 | 0301 | 0201g |
| 48 | 0301g | 0702 | 0702g | 0701 | 0201g | 2601g | 0304 | 0801g | 1304 | 0301g |
| 49 | 0201g | 0702 | 0702g | 0101 | 0501 | 3001 | 0702 | 0702g | 1503 | 0602 |
| 50 | 0101g | 0701g | 0801g | 1301 | 0603 | 2301g | 0202 | 1801g | 0701 | 0201g |

| | Asian Pacific Islander | | | | | Hispanic | | | | |
|---|---|---|---|---|---|---|---|---|---|---|
| Rank | HLA-A | HLA-C | HLA-B | DRB1 | DQB1 | HLA-A | HLA-C | HLA-B | DRB1 | DQB1 |
| 1 | 3303 | 0302 | 5801g | 0301 | 0201g | 0101g | 0701g | 0801g | 0301 | 0201g |
| 2 | 0207g | 0102 | 4601 | 0901 | 0303 | 2902 | 1601 | 4403 | 0701 | 0201g |
| 3 | 3303 | 0701g | 4403 | 0701 | 0201g | 0301g | 0702 | 0702g | 1501 | 0602 |
| 4 | 1101g | 0801 | 1502 | 1202 | 0301g | 3301 | 0802 | 1402 | 0102 | 0501 |
| 5 | 3303 | 0302 | 5801g | 1302 | 0609 | 3002 | 0501g | 1801g | 0301 | 0201g |
| 6 | 3001 | 0602 | 1302 | 0701 | 0201g | 6803 | 0702 | 3905 | 0407 | 0302 |
| 7 | 2402g | 1202 | 5201g | 1502 | 0601 | 2301g | 0401g | 4403 | 0701 | 0201g |
| 8 | 0101g | 0602 | 3701 | 1001 | 0501 | 0201g | 0702 | 0702g | 1501 | 0602 |
| 9 | 0101g | 0602 | 5701 | 0701 | 0303 | 2402g | 0401g | 3502 | 1104 | 0301g |
| 10 | 0207g | 0102 | 4601 | 0803 | 0601 | 2402g | 0702 | 3906 | 1406 | 0301g |
| 11 | 2901g | 1505 | 0705g | 1001 | 0501 | 0201g | 0401g | 3512 | 0407 | 0302 |
| 12 | 3303 | 1403 | 4403 | 1302 | 0604 | 3001 | 0602 | 1302 | 0701 | 0201g |
| 13 | 2402g | 0102 | 4601 | 0901 | 0303 | 2402g | 0102 | 3543g | 0407 | 0302 |
| 14 | 1101g | 0102 | 5401 | 0405 | 0401 | 0206 | 0702 | 3905 | 0407 | 0302 |
| 15 | 2402g | 0702 | 0702g | 0101 | 0501 | 0201g | 0401g | 3517 | 0802 | 0402 |
| 16 | 2407 | 0401g | 3505 | 1202 | 0301g | 0201g | 0102 | 1515 | 0802 | 0402 |
| 17 | 2402g | 0102 | 5901 | 0405 | 0401 | 2402g | 0304 | 4002g | 0404 | 0302 |
| 18 | 2601g | 0702 | 0801g | 0301 | 0201g | 0201g | 1202 | 5201g | 1502 | 0601 |
| 19 | 1101g | 0702 | 3802 | 1502 | 0502 | 2501 | 1203 | 1801g | 1501 | 0602 |
| 20 | 1101g | 0304 | 1301 | 1501 | 0601 | 0201g | 0401g | 3512 | 0802 | 0402 |
| 21 | 0201g | 0304 | 1301 | 1202 | 0301g | 0201g | 0501g | 4402g | 1301 | 0603 |
| 22 | 0203 | 0702 | 3802 | 1602 | 0502 | 6802 | 0802 | 1402 | 0102 | 0501 |
| 23 | 2402g | 0702 | 4001g | 0901 | 0303 | 6901 | 0102 | 5501 | 1101 | 0301g |
| 24 | 1101g | 0102 | 4601 | 0901 | 0303 | 1101g | 0102 | 2705g | 0101 | 0501 |
| 25 | 1101g | 1202 | 5201g | 1502 | 0601 | 0204 | 1502g | 5101g | 0411 | 0402 |
| 26 | 2402g | 0102 | 5401 | 0405 | 0401 | 1101g | 1202 | 5201g | 1502 | 0601 |
| 27 | 0201g | 1502g | 4001g | 1101 | 0301g | 0101g | 0602 | 5701 | 0701 | 0303 |
| 28 | 1101g | 0401g | 1501g | 0406 | 0302 | 0301g | 0401g | 3501g | 0101 | 0501 |
| 29 | 0203 | 0702 | 3802 | 0803 | 0601 | 0101g | 0701g | 0801g | 1301 | 0603 |
| 30 | 2402g | 0102 | 5401 | 0803 | 0601 | 0201g | 0701g | 0801g | 0301 | 0201g |
| 31 | 2402g | 0303g | 3501g | 1501 | 0602 | 2601g | 1203 | 3801 | 0402 | 0302 |
| 32 | 0206 | 1402 | 5101g | 0901 | 0303 | 0201g | 0401g | 4403 | 0701 | 0201g |
| 33 | 2402g | 0401g | 4001g | 0403 | 0302 | 1101g | 0701g | 4901 | 0405 | 0302 |
| 34 | 1101g | 0801 | 1502 | 1501 | 0601 | 3001 | 1701g | 4201 | 0302 | 0402 |
| 35 | 0101g | 0701g | 1517 | 1302 | 0604 | 2402g | 0801 | 4801g | 0404 | 0302 |
| 36 | 1101g | 0702 | 3901g | 0803 | 0601 | 0201g | 0102 | 1501g | 0802 | 0402 |
| 37 | 2402g | 1402 | 5101g | 0901 | 0303 | 0201g | 0102 | 5601 | 0101 | 0501 |
| 38 | 1102 | 0801 | 1502 | 1202 | 0301g | 0201g | 0501g | 4402g | 0401 | 0301g |
| 39 | 2901g | 1505 | 0705g | 0803 | 0301g | 1101g | 0702 | 0702g | 1501 | 0602 |
| 40 | 2417 | 0801 | 1502 | 1202 | 0301g | 0301g | 0802 | 1402 | 0102 | 0501 |
| 41 | 1101g | 0702 | 4001g | 0803 | 0601 | 0301g | 1601 | 5101g | 0701 | 0201g |
| 42 | 2402g | 0702 | 3802 | 0901 | 0303 | 3010 | 0602 | 4101 | 0405 | 0201g |
| 43 | 2402g | 0302 | 5801g | 0301 | 0201g | 6801g | 0801 | 4801g | 0404 | 0302 |
| 44 | 1101g | 0702 | 4001g | 0901 | 0303 | 2402g | 0702 | 3906 | 0404 | 0302 |
| 45 | 0211g | 1502g | 4006 | 1501 | 0601 | 2601g | 0501g | 4402g | 0402 | 0302 |

TABLE 11-continued

| MOST FREQUENT HLA-A-C-B-DRB1-DQB1 HAPLOTYPES IN THE INDICATED POPULATIONS | | | | | | | | | | |
|---|---|---|---|---|---|---|---|---|---|---|
| 46 | 2402g | 1402 | 5101g | 0803 | 0601 | 3201 | 0802 | 1401 | 0701 | 0201g |
| 47 | 3303 | 0302 | 5801g | 1101 | 0301g | 0206 | 0306 | 4002g | 0802 | 0402 |
| 48 | 1101g | 0801 | 1502 | 0901 | 0303 | 3101 | 0304 | 4001g | 0404 | 0302 |
| 49 | 0201g | 0102 | 5401 | 0405 | 0401 | 0301g | 0702 | 0702g | 0101 | 0501 |
| 50 | 0301g | 1202 | 5201g | 1502 | 0601 | 2301g | 0401g | 4403 | 0405 | 0302 |

Table 12 describes the most frequent high-resolution HLA-B-DRB1 Haplotypes in the United States and Jewish populations. For each ancestry shown in the table (e.g., European American. African American, Asian [which includes Pacific Islander], Hispanic [Latino], and persons of Jewish ancestry) top 50 most frequent HLA-B-DRB1 haplotypes are indicated ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication [Maiers et al., 2007, *Human Immunology*, 68:779-788. The Jewish high resolution HLA-B-DRB1 haplotype frequencies are from the following National Marrow Donor Program Website (US) URL: bioinformatics.bethematchclinical.org. Note that the HLA-A-B-DRB1 haplotype frequency data for the Jewish population are derived from donor samples from the Hadassah Registry—Jerusalem, Israel (Klitz et al., 201, *Tissue Antigens*, 76(6):442-58). Note that the annotation used (e.g., 1501 for HLA-DRB1 indicates is the same as HLA-DRB1*15:01 which indicates the (HLA prefix)-gene*allele group/family: specific HLA protein based on the new nomenclature adopted by the WHO Nomenclature Committee for Factors of the HLA System in 2010). For example, DRB1*1501 becomes DRB1*15:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 12

| MOST FREQUENT HLA-B-DRB1 HAPLOTYPES IN THE INDICATED POPULATIONS | | | | | | | | | | |
|---|---|---|---|---|---|---|---|---|---|---|
| | European American | | African American | | Asian Pacific Islander | | Hispanic | | Jewish | |
| Rank | HLA-B | HLA-DRB1 | HLA-B | HLA-DRB1 | HLA-B | HLA-DRB1 | HLA-B | HLA-DRB1 | HLA-B | HLA-DRB1 |
| 1 | 0801g | 0301 | 4201 | 0302 | 4403 | 0701 | 4403 | 0701 | 3502 | 1104 |
| 2 | 0702g | 1501 | 5301 | 0804 | 0702g | 1501 | 0702g | 1501 | 3801 | 0402 |
| 3 | 4403 | 0701 | 0801g | 0301 | 0801g | 0301 | 0801g | 0301 | 5201 | 1502 |
| 4 | 4402g | 0401 | 4403 | 1503 | 1402 | 0102 | 1402 | 0102 | 1402 | 0102 |
| 5 | 3501g | 0101 | 5301 | 1101 | 3905 | 0407 | 3905 | 0407 | 1801 | 1104 |
| 6 | 5701 | 0701 | 5802 | 1201g | 1801g | 0301 | 1801g | 0301 | 0801 | 0301 |
| 7 | 1501g | 0401 | 4403 | 0701 | 4002g | 0407 | 4002g | 0407 | 1302 | 0701 |
| 8 | 1302 | 0701 | 5301 | 1503 | 4801g | 0404 | 4801g | 0404 | 5001 | 0701 |
| 9 | 1402 | 0102 | 0702g | 1501 | 5201g | 1502 | 5201g | 1502 | 3801 | 1401 |
| 10 | 4001g | 0404 | 1510 | 0301 | 3906 | 1406 | 3906 | 1406 | 3801 | 1301 |
| 11 | 4001g | 1302 | 0702g | 1503 | 3501g | 0802 | 3501g | 0802 | 4101 | 0701 |
| 12 | 1501g | 1301 | 1503g | 1101 | 1302 | 0701 | 1302 | 0701 | 4403 | 0701 |
| 13 | 2705g | 0101 | 1503g | 0701 | 3517 | 0802 | 3517 | 0802 | 1517 | 1302 |
| 14 | 1801g | 0301 | 4901 | 1503 | 3512 | 0802 | 3512 | 0802 | 4402 | 0402 |
| 15 | 4402g | 1301 | 5301 | 1303 | 3501g | 0101 | 3501g | 0101 | 3503 | 1201 |
| 16 | 0702g | 0101 | 5301 | 1302 | 4002g | 0802 | 4002g | 0802 | 3501 | 0402 |
| 17 | 1801g | 1104 | 5801g | 1503 | 5101g | 0701 | 5101g | 0701 | 0705 | 1001 |
| 18 | 5101g | 1101 | 5802 | 1301 | 3502 | 1104 | 3502 | 1104 | 3508 | 0403 |
| 19 | 3502 | 1104 | 5703 | 1303 | 4002g | 0404 | 4002g | 0404 | 0702 | 1501 |
| 20 | 1801g | 1501 | 5301 | 0701 | 5701 | 0701 | 5701 | 0701 | 5101 | 1101 |
| 21 | 4402g | 0101 | 3501g | 0302 | 3501g | 0407 | 3501g | 0407 | 3501 | 1104 |
| 22 | 3801 | 1301 | 1503g | 1302 | 2705g | 0101 | 2705g | 0101 | 4901 | 1104 |
| 23 | 4402g | 1501 | 1503g | 1503 | 5001 | 0701 | 5001 | 0701 | 4102 | 1303 |
| 24 | 0702g | 0401 | 1801g | 0701 | 1401 | 0701 | 1401 | 0701 | 4402 | 1104 |
| 25 | 4402g | 1101 | 1516 | 0102 | 5101g | 0411 | 5101g | 0411 | 4402 | 1301 |
| 26 | 5201g | 1502 | 0702g | 0901 | 3512 | 0407 | 3512 | 0407 | 5501 | 1101 |
| 27 | 1401 | 0701 | 3501g | 1302 | 1515 | 0802 | 1515 | 0802 | 1801 | 0301 |
| 28 | 0801g | 1501 | 4402g | 0401 | 4402g | 1301 | 4402g | 1301 | 3801 | 1101 |
| 29 | 0702g | 0701 | 0702g | 1101 | 3543g | 0407 | 3543g | 0407 | 3801 | 1104 |
| 30 | 5101g | 1301 | 3501g | 1503 | 4002g | 0411 | 4002g | 0411 | 1801 | 0701 |
| 31 | 1501g | 0101 | 1801g | 0301 | 5101g | 1101 | 5101g | 1101 | 1402 | 0701 |
| 32 | 3801 | 0402 | 0801g | 1304 | 1801g | 1501 | 1801g | 1501 | 3501 | 1401 |
| 33 | 0702g | 1301 | 4201 | 0804 | 4402g | 0402 | 4402g | 0402 | 5701 | 1305 |
| 34 | 5101g | 0101 | 5703 | 1301 | 5101g | 0802 | 5101g | 0802 | 5201 | 1104 |
| 35 | 4001g | 1501 | 5301 | 0102 | 3501g | 1301 | 3501g | 1301 | 4901 | 1101 |
| 36 | 1501g | 1501 | 5801g | 0701 | 3801 | 0402 | 3801 | 0402 | 3801 | 0701 |
| 37 | 5001 | 0701 | 1402 | 1503 | 4402g | 0401 | 4402g | 0401 | 5301 | 1302 |

TABLE 12-continued

MOST FREQUENT HLA-B-DRB1 HAPLOTYPES IN THE INDICATED POPULATIONS

| | European American | | African American | | Asian Pacific Islander | | Hispanic | | Jewish | |
|---|---|---|---|---|---|---|---|---|---|---|
| Rank | HLA-B | HLA-DRB1 | HLA-B | HLA-DRB1 | HLA-B | HLA-DRB1 | HLA-B | HLA-DRB1 | HLA-B | HLA-DRB1 |
| 38 | 5501 | 1401g | 8101g | 1201g | 3501g | 1402 | 3501g | 1402 | 4101 | 1305 |
| 39 | 4001g | 0401 | 1801g | 1101 | 3801 | 1301 | 3801 | 1301 | 5701 | 0701 |
| 40 | 1801g | 1101 | 4501g | 1503 | 1801g | 1104 | 1801g | 1104 | 5301 | 0301 |
| 41 | 4402g | 1201g | 4501g | 0701 | 1402 | 0301 | 1402 | 0301 | 4101 | 0405 |
| 42 | 5101g | 1501 | 5703 | 1503 | 4901 | 0405 | 4901 | 0405 | 5001 | 0301 |
| 43 | 3701 | 1001 | 4501g | 0102 | 4403 | 1501 | 4403 | 1501 | 3801 | 1302 |
| 44 | 2705g | 0401 | 5301 | 1102 | 5101g | 1301 | 5101g | 1301 | 4102 | 1104 |
| 45 | 0702g | 0404 | 3501g | 1102 | 4002g | 1402 | 4002g | 1402 | 5801 | 1302 |
| 46 | 1402 | 1303 | 5802 | 1102 | 1503g | 0701 | 1503g | 0701 | 4101 | 0301 |
| 47 | 4001g | 0101 | 0702g | 1302 | 4001g | 0404 | 4001g | 0404 | 5801 | 0701 |
| 48 | 1402 | 1302 | 1501g | 0401 | 1501g | 0802 | 1501g | 0802 | 4901 | 0701 |
| 49 | 0702g | 1101 | 4501g | 1101 | 0702g | 0101 | 0702g | 0101 | 3701 | 1104 |

Table 13 describes the most frequent high-resolution HLA-C-B haplotypes in the United States population. For each ancestry shown in the table (e.g., European American. African American, Asian [which includes Pacific Islander], and Hispanic [Latino]) the top 50 most frequent HLA-C-B haplotypes are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication (Maiers et al., 2007, *Human Immunology,* 68:779-788). Note that the annotation used (e.g., 0701g for HLA-C indicates is the same as HLA-C*07:01 which indicates the (HLA prefix)-gene*allele group/family: specific HLA protein based on the new nomenclature adopted by the WHO Nomenclature Committee for Factors of the HLA System in 2010). For example, C*0701g becomes C*07:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers. M., Gragert. L., Klitz, W. High resolution HLA alleles and haplotypes in the US population. 2007". The suffix "N" is used to denote changes in expression (refer to nomenclature link above).

TABLE 13

MOST FREQUENT HLA-C-B HAPLOTYPES IN THE INDICATED POPULATIONS

| | European American | | African American | | Asian Pacific Islander | | Hispanic | |
|---|---|---|---|---|---|---|---|---|
| Rank | HLA-C | HLA-B | HLA-C | HLA-B | HLA-C | HLA-B | HLA-C | HLA-B |
| 1 | 702 | 0702g | 0401g | 5301 | 0102 | 4601 | 0401g | 3501g |
| 2 | 0701g | 0801g | 0202 | 1503g | 0302 | 5801g | 0702 | 0702g |
| 3 | 0501g | 4402g | 0702 | 0702g | 1402 | 5101g | 0802 | 1402 |
| 4 | 304 | 4001g | 1701g | 4201 | 0702 | 3802 | 0701g | 0801g |
| 5 | 0401g | 3501g | 0401g | 3501g | 0801 | 1502 | 1601 | 4403 |
| 6 | 602 | 5701 | 0602 | 5802 | 1202 | 5201g | 0501g | 4402g |
| 7 | 0303g | 1501g | 1601 | 4501g | 0702 | 4001g | 0304 | 4002g |
| 8 | 1601 | 4403 | 0401g | 4403 | 0102 | 5401 | 0701g | 4901 |
| 9 | 802 | 1402 | 0701g | 0801g | 0304 | 1301 | 1502g | 5101g |
| 10 | 602 | 1302 | 0701g | 4901 | 0702 | 0702g | 0702 | 3905 |
| 11 | 304 | 1501g | 0304 | 1510 | 0701g | 4403 | 0702 | 3906 |
| 12 | 1203 | 3801 | 0701g | 5801g | 0304 | 4001g | 1203 | 3801 |
| 13 | 0701g | 1801g | 0802 | 1402 | 0602 | 1302 | 0801 | 4801g |
| 14 | 1502g | 5101g | 0701g | 5703 | 0401g | 3501g | 0401g | 3512 |
| 15 | 202 | 2705g | 0501g | 4402g | 0602 | 5701 | 0401g | 4403 |
| 16 | 1203 | 1801g | 0304 | 4001g | 1502g | 4006 | 0501g | 1801g |
| 17 | 0303g | 5501 | 1601 | 5201g | 0303g | 3501g | 0401g | 3517 |
| 18 | 102 | 2705g | 1601 | 7801 | 0304 | 4002g | 0602 | 5001 |
| 19 | 0401g | 4403 | 1601 | 5101g | 0401g | 3503 | 0401g | 5301 |
| 20 | 602 | 3701 | 1801g | 5703 | 0702 | 0801g | 0202 | 1503g |
| 21 | 0701g | 4901 | 1402 | 1516 | 0801 | 4801g | 0303g | 1501g |
| 22 | 0401g | 3503 | 0501g | 1801g | 0602 | 3701 | 1202 | 5201g |
| 23 | 0501g | 1801g | 1801g | 8101g | 1403 | 4403 | 0304 | 4001g |
| 24 | 1402 | 5101g | 0602 | 5301 | 1505 | 0705g | 1203 | 1801g |
| 25 | 0401g | 3502 | 1505 | 0702g | 0801 | 4006 | 0602 | 1302 |
| 26 | 0704g | 4402g | 1601 | 4403 | 0401g | 1501g | 0401g | 3502 |
| 27 | 1202 | 5201g | 0302 | 5801g | 0702 | 3901g | 0401g | 3503 |
| 28 | 802 | 1401 | 1601 | 3501g | 0303g | 1501g | 0305 | 4002g |
| 29 | 202 | 4002g | 0602 | 4501g | 0401g | 3505 | 0701g | 5801g |

TABLE 13-continued

MOST FREQUENT HLA-C-B HAPLOTYPES IN THE INDICATED POPULATIONS

| | European American | | African American | | Asian Pacific Islander | | Hispanic | |
|---|---|---|---|---|---|---|---|---|
| Rank | HLA-C | HLA-B | HLA-C | HLA-B | HLA-C | HLA-B | HLA-C | HLA-B |
| 30 | 602 | 5001 | 0202 | 1801g | 1502g | 5101g | 0102 | 2705g |
| 31 | 1203 | 3901g | 0304 | 0801g | 1203 | 3503 | 0102 | 1501g |
| 32 | 102 | 5101g | 0804 | 8101g | 0102 | 5901 | 0602 | 5701 |
| 33 | 202 | 5101g | 0602 | 1302 | 0102 | 5502 | 0802 | 1401 |
| 34 | 102 | 5601 | 0602 | 5001 | 1502g | 4002g | 1701g | 4101 |
| 35 | 702 | 3906 | 1701g | 4202 | 0501g | 4402g | 1402 | 5101g |
| 36 | 0401g | 1501g | 0802 | 1401 | 0602 | 5001 | 0701g | 1801g |
| 37 | 602 | 4501g | 1203 | 3910 | 0303g | 1511 | 0102 | 3543g |
| 38 | 1701g | 4102 | 1701g | 4102 | 1602 | 5101g | 0306 | 4002g |
| 39 | 0401g | 3508 | 0702 | 0705g | 1502g | 4001g | 0602 | 4501g |
| 40 | 1203 | 3503 | 0701g | 0702g | 0401g | 4001g | 0102 | 1515 |
| 41 | 0701g | 5801g | 0303g | 1501g | 0702 | 0705g | 0401g | 3508 |
| 42 | 702 | 3901g | 0701g | 4403 | 0702 | 1535 | 0303g | 5201g |
| 43 | 0401g | 5301 | 0501g | 1517 | 1202 | 2704 | 0303g | 5501 |
| 44 | 1701g | 4101 | 0704g | 1801g | 0102 | 5601 | 0202 | 2705g |
| 45 | 0701g | 1517 | 0701g | 1801g | 0102 | 5501 | 1601 | 4501g |
| 46 | 202 | 2702 | 0602 | 5701 | 0102 | 2705g | 1701g | 4201 |
| 47 | 202 | 4405 | 1601 | 1516 | 0701g | 1517 | 0701g | 1517 |
| 48 | 602 | 4701 | 0602 | 3701 | 0704g | 1518 | 1701g | 4102 |
| 49 | 102 | 1501g | 1502g | 5101g | 1203 | 3801 | 0304 | 4008 |
| 50 | 1505 | 0705g | 0303g | 5501 | 0403 | 1525 | 0202 | 5101g |

Table 14 describes the most frequent high-resolution HLA-C-B-DRB1-DQB1 haplotypes in the United States population. For each ancestry shown in the table (e.g., European American, African American, Asian [which includes Pacific Islander], and Hispanic [Latino]) top 50 most frequent HLA-C-B-DRB1-DQB1 haplotypes are indicated and ranked based on their frequency of occurrence with in the ancestral groups indicated in each column (Adapted from The National Marrow Donor Program Website (US): bioinformatics.bethenmatchclinical.org which represents an update of the high-resolution frequencies from an earlier publication [Maiers et al., 2007*, Human Immunology,* 68:779-788. Note that the annotation used (e.g., 1501 for HLA-DRB1 indicates is the same as HLA-DRB1*15:01 which indicates the (HLA prefix)-gene*allele group/family: specific HLA protein based on the new nomenclature adopted by the WHO Nomenclature Committee for Factors of the HLA System in 2010). For example, DRB1*1501 becomes DRB1*15:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 14

MOST FREQUENT HLA-C-B-DRB1-DQB1 HAPLOTYPES IN THE INDICATED POPULATIONS

| | European American | | | | African American | | | | Asian Pacific Islander |
|---|---|---|---|---|---|---|---|---|---|
| Rank | HLA-C | HLA-B | DRB1 | DQB1 | HLA-C | HLA-B | DRB1 | DQB1 | HLA-C |
| 1 | 0701g | 0801g | 0301 | 0201g | 1701g | 4201 | 0302 | 0402 | 0102 |
| 2 | 0702 | 0702g | 1501 | 0602 | 0701g | 0801g | 0301 | 0201g | 0302 |
| 3 | 0501g | 4402g | 0401 | 0301g | 0702 | 0702g | 1501 | 0602 | 0801 |
| 4 | 0401g | 3501g | 0101 | 0501 | 0401g | 5301 | 0804 | 0301g | 1202 |
| 5 | 1601 | 4403 | 0701 | 0201g | 0401g | 4403 | 1503 | 0602 | 0701g |
| 6 | 0602 | 5701 | 0701 | 0303 | 0401g | 5301 | 1503 | 0602 | 0302 |
| 7 | 0602 | 1302 | 0701 | 0201g | 0602 | 5802 | 1201g | 0501 | 0102 |
| 8 | 0304 | 1501g | 0401 | 0302 | 0702 | 0702g | 1503 | 0602 | 0602 |
| 9 | 0802 | 1402 | 0102 | 0501 | 0304 | 1510 | 0301 | 0201g | 0702 |
| 10 | 0304 | 4001g | 0404 | 0302 | 0701g | 4901 | 1503 | 0602 | 0102 |
| 11 | 0304 | 4001g | 1302 | 0604 | 0202 | 1503g | 1101 | 0301g | 0602 |
| 12 | 0401g | 4403 | 0701 | 0201g | 0701g | 5801g | 1503 | 0602 | 0602 |
| 13 | 0303g | 1501g | 1301 | 0603 | 0401g | 5301 | 1101 | 0602 | 0304 |
| 14 | 0702 | 0702g | 0101 | 0501 | 0401g | 3501g | 1503 | 0602 | 0702 |
| 15 | 0501g | 1801g | 0301 | 0201g | 0401g | 4403 | 0701 | 0201g | 1402 |
| 16 | 0501g | 4402g | 1301 | 0603 | 1601 | 4403 | 0701 | 0201g | 0702 |
| 17 | 1203 | 3801 | 1301 | 0603 | 0401g | 5301 | 0301 | 0201g | 1505 |
| 18 | 0102 | 2705g | 0101 | 0501 | 0701g | 5703 | 1503 | 0602 | 0801 |

TABLE 14-continued

MOST FREQUENT HLA-C-B-DRB1-DQB1 HAPLOTYPES IN THE INDICATED POPULATIONS

| | | | | | | | | | |
|---|---|---|---|---|---|---|---|---|---|
| 19 | 0501g | 4402g | 1501 | 0602 | 0202 | 1801g | 0701 | 0201g | 0702 |
| 20 | 1202 | 5201g | 1502 | 0601 | 0202 | 1503g | 1302 | 0609 | 1403 |
| 21 | 0401g | 3502 | 1104 | 0301g | 0202 | 1503g | 0701 | 0201g | 0102 |
| 22 | 0701g | 1801g | 1104 | 0301g | 0501g | 4402g | 0401 | 0301g | 0401g |
| 23 | 0802 | 1401 | 0701 | 0201g | 1701g | 4201 | 0804 | 0301g | 0303g |
| 24 | 0501g | 4402g | 0101 | 0501 | 0702 | 0702g | 0901 | 0201g | 0304 |
| 25 | 1203 | 1801g | 1501 | 0602 | 0401g | 5301 | 0701 | 0201g | 1502g |
| 26 | 0701g | 0801g | 1501 | 0602 | 0804 | 8101g | 1201g | 0501 | 0401g |
| 27 | 0702 | 0702g | 1301 | 0603 | 0304 | 0801g | 1304 | 0301g | 0304 |
| 28 | 1203 | 3801 | 0402 | 0302 | 1601 | 4501g | 1503 | 0602 | 0401g |
| 29 | 0304 | 4001g | 1501 | 0602 | 0202 | 1503g | 1503 | 0602 | 0702 |
| 30 | 0602 | 5001 | 0701 | 0201g | 0401g | 3501g | 1102 | 0301g | 0702 |
| 31 | 0702 | 0702g | 0701 | 0201g | 0701g | 5703 | 1303 | 0201g | 0702 |
| 32 | 0303g | 1501g | 0401 | 0302 | 0602 | 5802 | 1301 | 0303 | 0702 |
| 33 | 0303g | 5501 | 1401g | 0503 | 0802 | 1402 | 0701 | 0201g | 0801 |
| 34 | 0704g | 4402g | 1101 | 0301g | 1601 | 4501g | 0102 | 0501 | 0702 |
| 35 | 0602 | 3701 | 1001 | 0501 | 1801g | 5703 | 1301 | 0501 | 0702 |
| 36 | 0501g | 4402g | 1201g | 0301g | 0802 | 1401 | 0701 | 0201g | 0304 |
| 37 | 0702 | 0702g | 0404 | 0302 | 1601 | 7801 | 0701 | 0201g | 0304 |
| 38 | 0802 | 1402 | 1303 | 0301g | 0802 | 1402 | 1503 | 0602 | 0702 |
| 39 | 0702 | 0702g | 1101 | 0301g | 0602 | 1302 | 0701 | 0201g | 0102 |
| 40 | 0802 | 1402 | 1302 | 0609 | 0501g | 1801g | 0301 | 0201g | 1502g |
| 41 | 0304 | 4001g | 0801 | 0402 | 0401g | 3501g | 0101 | 0501 | 1402 |
| 42 | 0304 | 4001g | 0101 | 0501 | 1601 | 5101g | 1303 | 0301g | 0303g |
| 43 | 0702 | 0702g | 0401 | 0302 | 0401g | 5301 | 1303 | 0201g | 0401g |
| 44 | 0401g | 3501g | 0103 | 0501 | 0401g | 5301 | 0302 | 0402 | 0602 |
| 45 | 0702 | 0702g | 0401 | 0301g | 0702 | 0702g | 1102 | 0301g | 0401g |
| 46 | 0701g | 0801g | 0101 | 0501 | 0202 | 1503g | 0301 | 0201g | 0801 |
| 47 | 0702 | 0702g | 1401g | 0503 | 1601 | 4501g | 0701 | 0201g | 0401g |
| 48 | 0303g | 1501g | 1501 | 0602 | 0401g | 3501g | 0302 | 0402 | 1502g |
| 49 | 0401g | 3501g | 1401g | 0503 | 1402 | 1516 | 0102 | 0501 | 1202 |
| 50 | 0303g | 1501g | 1101 | 0301g | 0602 | 5802 | 1503 | 0602 | 0304 |

| | Asian Pacific Islander | | | Hispanic | | | |
|---|---|---|---|---|---|---|---|
| Rank | HLA-B | DRB1 | DQB1 | HLA-C | HLA-B | DRB1 | DQB1 |
| 1 | 4601 | 0901 | 0303 | 0702 | 0702g | 1501 | 0602 |
| 2 | 5801g | 0301 | 0201g | 0701g | 0801g | 0301 | 0201g |
| 3 | 1502 | 1202 | 0301g | 1601 | 4403 | 0701 | 0201g |
| 4 | 5201g | 1502 | 0601 | 0802 | 1402 | 0102 | 0501 |
| 5 | 4403 | 0701 | 0201g | 0702 | 3905 | 0407 | 0302 |
| 6 | 5801g | 1302 | 0609 | 0401g | 4403 | 0701 | 0201g |
| 7 | 5401 | 0405 | 0401 | 0501g | 1801g | 0301 | 0201g |
| 8 | 1302 | 0701 | 0201g | 1202 | 5201g | 1502 | 0601 |
| 9 | 0801g | 0301 | 0201g | 0602 | 1302 | 0701 | 0201g |
| 10 | 4601 | 0803 | 0601 | 0401g | 3501g | 0101 | 0501 |
| 11 | 5701 | 0701 | 0303 | 0702 | 3906 | 1406 | 0301g |
| 12 | 3701 | 1001 | 0501 | 0801 | 4801g | 0404 | 0302 |
| 13 | 1301 | 1202 | 0301g | 0401g | 3502 | 1104 | 0301g |
| 14 | 3802 | 1502 | 0502 | 0401g | 3512 | 0407 | 0302 |
| 15 | 5101g | 0901 | 0303 | 0304 | 4002g | 0404 | 0302 |
| 16 | 4001g | 0901 | 0303 | 0102 | 3543g | 0407 | 0302 |
| 17 | 0705g | 1001 | 0501 | 0401g | 3517 | 0802 | 0402 |
| 18 | 4006 | 0901 | 0303 | 0802 | 1401 | 0701 | 0201g |
| 19 | 0702g | 0101 | 0501 | 0701g | 4901 | 0405 | 0302 |
| 20 | 4403 | 1302 | 0604 | 0401g | 3512 | 0802 | 0402 |
| 21 | 5901 | 0405 | 0401 | 0501g | 4402g | 1301 | 0603 |
| 22 | 1501g | 0406 | 0302 | 0602 | 5701 | 0701 | 0303 |
| 23 | 3501g | 1501 | 0602 | 0602 | 5001 | 0701 | 0201g |
| 24 | 1301 | 1501 | 0601 | 0501g | 4402g | 0402 | 0302 |
| 25 | 4006 | 1501 | 0601 | 0102 | 1515 | 0802 | 0402 |
| 26 | 3505 | 1202 | 0301g | 0304 | 4002g | 0407 | 0302 |
| 27 | 4001g | 1101 | 0301g | 0401g | 3501g | 0301 | 0201g |
| 28 | 3501g | 0101 | 0501 | 0102 | 1501g | 0802 | 0402 |
| 29 | 3802 | 1502 | 0501 | 0501g | 4402g | 0401 | 0301g |
| 30 | 3802 | 1602 | 0502 | 0102 | 2705g | 0101 | 0501 |
| 31 | 4001g | 0803 | 0601 | 0701g | 1517 | 1302 | 0604 |
| 32 | 3802 | 0803 | 0601 | 1203 | 1801g | 1501 | 0602 |
| 33 | 1502 | 1501 | 0601 | 0701g | 0801g | 1301 | 0603 |
| 34 | 3802 | 0901 | 0303 | 1502g | 5101g | 0411 | 0402 |
| 35 | 3901g | 0803 | 0601 | 1203 | 3801 | 0402 | 0302 |
| 36 | 4002g | 0901 | 0303 | 0401g | 3501g | 0802 | 0402 |
| 37 | 4002g | 1501 | 0602 | 1701g | 4201 | 0302 | 0402 |
| 38 | 0702g | 1501 | 0602 | 0702 | 0702g | 0101 | 0501 |
| 39 | 5401 | 0803 | 0601 | 0102 | 5601 | 0101 | 0501 |

TABLE 14-continued

| MOST FREQUENT HLA-C-B-DRB1-DQB1 HAPLOTYPES IN THE INDICATED POPULATIONS | | | | | | | |
|---|---|---|---|---|---|---|---|
| 40 | 4001g | 1101 | 0301g | 0401g | 5301 | 1302 | 0604 |
| 41 | 5101g | 0405 | 0401 | 0306 | 4002g | 0802 | 0402 |
| 42 | 1501g | 1501 | 0602 | 0305 | 4002g | 0407 | 0302 |
| 43 | 4001g | 0403 | 0302 | 0401g | 3503 | 1101 | 0301g |
| 44 | 5001 | 0701 | 0201g | 0401g | 3501g | 1402 | 0301g |
| 45 | 3503 | 1101 | 0301g | 1203 | 3801 | 1301 | 0603 |
| 46 | 1502 | 0901 | 0303 | 0304 | 4001g | 0404 | 0302 |
| 47 | 1527 | 0406 | 0302 | 0102 | 5501 | 1101 | 0301g |
| 48 | 4002g | 1502 | 0502 | 0304 | 4002g | 0411 | 0302 |
| 49 | 5201g | 0403 | 0302 | 1601 | 5101g | 0701 | 0201g |
| 50 | 4001g | 0803 | 0601 | 0701g | 5703 | 0302 | 0402 |

Table 15 describes the most frequent high-resolution HLA-DRB1-DQB1 haplotypes in the United States population. For each ancestry shown in the table (e.g., European American, African American, Asian [which includes Pacific Islander], and Hispanic [Latino]) top 50 most frequent HLA-C-B-DRB1-DQB1 haplotypes are indicated and ranked based on their frequency of occurrence with in the ancestral groups indicated in each column (Adapted from The National Marrow Donor Program Website (US): bioinformatics.bethematchclinical.org which represents an update of the high-resolution frequencies from an earlier publication [Maiers et al., 2007 *Human Immunology,* 68:779-788]. Note that the annotation used (e.g., 1501 for HLA-DRB1 indicates is the same as HLA-DRB1*15:01 which indicates the (HLA prefix)-gene*allele group/family: specific HLA protein based on the new nomenclature adopted by the WHO Nomenclature Committee for Factors of the HLA System in 2010). For example, DRB1*1501 becomes DRB1*15:01. With the designation shown in this table, the fields that are used to show synonymous DNA substitution in coding region, differences in non-coding regions, and the suffix used to denote changes in expression are not shown (see the following website for more information: hla.alleles.org). The allele designations in this table with the "g" suffix refer to allele groups defined in table 1 of the publication "Maiers, M., Gragert, L., Klitz, W. High resolution HLA alleles and haplotypes in the US population. 2007".

TABLE 15

| | European American | | African American | | Asian Pacific Islander | | Hispanic | |
|---|---|---|---|---|---|---|---|---|
| Rank | HLA-DRB1 | HLA-DQB1 | HLA-DRB1 | HLA-DQB1 | HLA-DRB1 | HLA-DQB1 | HLA-DRB1 | HLA-DQB1 |
| 1 | 1501 | 0602 | 1503 | 0602 | 0901 | 0303 | 0701 | 0201g |
| 2 | 0301 | 0201g | 0701 | 0201g | 1202 | 0301g | 0301 | 0201g |
| 3 | 0701 | 0201g | 0301 | 0201g | 0701 | 0201g | 1501 | 0602 |
| 4 | 0101 | 0501 | 0302 | 0402 | 1101 | 0301g | 0407 | 0302 |
| 5 | 1301 | 0603 | 0804 | 0301g | 0301 | 0201g | 0802 | 0402 |
| 6 | 1101 | 0301g | 0102 | 0501 | 0803 | 0601 | 0404 | 0302 |
| 7 | 0401 | 0301g | 1101 | 0301g | 0405 | 0401 | 0101 | 0501 |
| 8 | 0401 | 0302 | 1101 | 0602 | 1501 | 0602 | 1101 | 0301g |
| 9 | 0701 | 0303 | 1102 | 0301g | 1502 | 0601 | 1301 | 0603 |
| 10 | 0404 | 0302 | 1201g | 0501 | 1501 | 0601 | 0102 | 0501 |
| 11 | 1302 | 0604 | 1501 | 0602 | 0403 | 0302 | 1302 | 0604 |
| 12 | 1104 | 0301g | 0901 | 0201g | 1001 | 0501 | 1104 | 0301g |
| 13 | 1401g | 0503 | 1302 | 0609 | 0101 | 0501 | 1406 | 0301g |
| 14 | 0801 | 0402 | 0101 | 0501 | 1404 | 0503 | 0402 | 0302 |
| 15 | 0102 | 0501 | 1301 | 0603 | 1502 | 0502 | 1402 | 0301g |
| 16 | 1201g | 0301g | 1001 | 0501 | 1301 | 0603 | 0405 | 0302 |
| 17 | 1601 | 0502 | 1303 | 0301g | 1201g | 0301g | 1001 | 0501 |
| 18 | 1303 | 0301g | 1303 | 0201g | 0406 | 0302 | 0403 | 0302 |
| 19 | 0402 | 0302 | 1302 | 0604 | 1502 | 0501 | 0411 | 0302 |
| 20 | 0407 | 0301g | 1401g | 0503 | 1602 | 0502 | 1102 | 0301g |
| 21 | 1001 | 0501 | 1302 | 0501 | 1302 | 0609 | 1602 | 0301g |
| 22 | 0901 | 0303 | 0405 | 0302 | 1405 | 0503 | 0701 | 0303 |
| 23 | 1302 | 0609 | 1602 | 0502 | 0701 | 0303 | 1502 | 0601 |
| 24 | 1502 | 0601 | 1304 | 0301g | 1302 | 0604 | 1503 | 0602 |
| 25 | 0103 | 0501 | 0401 | 0301g | 1401g | 0503 | 1401g | 0503 |
| 26 | 1103 | 0301g | 0401 | 0302 | 1401g | 0502 | 1303 | 0301g |
| 27 | 0403 | 0302 | 1301 | 0501 | 1501 | 0502 | 0401 | 0301g |
| 28 | 0405 | 0302 | 1301 | 0303 | 1201g | 0303 | 1201g | 0301g |
| 29 | 1305 | 0301g | 1201g | 0301g | 0803 | 0301g | 0302 | 0402 |
| 30 | 0103 | 0301g | 0404 | 0302 | 0404 | 0302 | 1601 | 0502 |
| 31 | 0408 | 0301g | 1101 | 0502 | 1104 | 0301g | 0401 | 0302 |
| 32 | 1501 | 0603 | 0701 | 0303 | 0802 | 0302 | 0801 | 0402 |
| 33 | 1102 | 0301g | 1104 | 0301g | 0802 | 0402 | 1103 | 0301g |
| 34 | 0803 | 0301g | 1301 | 0609 | 1312 | 0301g | 1304 | 0301g |
| 35 | 0101 | 0504 | 1401g | 0501 | 0405 | 0402 | 1302 | 0609 |
| 36 | 1104 | 0603 | 1301 | 0608 | 0401 | 0301g | 0901 | 0201g |

TABLE 15-continued

| | European American | | African American | | Asian Pacific Islander | | Hispanic | |
|---|---|---|---|---|---|---|---|---|
| Rank | HLA-DRB1 | HLA-DQB1 | HLA-DRB1 | HLA-DQB1 | HLA-DRB1 | HLA-DQB1 | HLA-DRB1 | HLA-DQB1 |
| 37 | 1602 | 0502 | 1101 | 0501 | 1506 | 0502 | 0103 | 0501 |
| 38 | 0403 | 0305 | 0801 | 0402 | 0801 | 0402 | 0411 | 0402 |
| 39 | 1501 | 0502 | 1401g | 0602 | 1403 | 0301g | 0804 | 0301g |
| 40 | 0403 | 0304 | 0804 | 0402 | 1106 | 0301g | 1101 | 0602 |
| 41 | 0804 | 0402 | 1302 | 0502 | 0402 | 0302 | 1201g | 0501 |
| 42 | 0404 | 0402 | 1104 | 0502 | 1502 | 0503 | 0901 | 0303 |
| 43 | 0407 | 0302 | 0407 | 0302 | 0410 | 0402 | 0407 | 0301g |
| 44 | 0405 | 0201g | 0806 | 0602 | 0401 | 0302 | 1302 | 0501 |
| 45 | 0408 | 0304 | 1301 | 0604 | 1202 | 0502 | 1501 | 0502 |
| 46 | 1101 | 0302 | 0701 | 0302 | 0809 | 0402 | 0410 | 0402 |
| 47 | 1404 | 0503 | 1503 | 0201g | 1406 | 0301g | 1305 | 0301g |
| 48 | 1101 | 0502 | 1202 | 0301g | 0404 | 0402 | 0804 | 0402 |
| 49 | 0701 | 0301g | 1110 | 0602 | 0405 | 0503 | 1303 | 0201g |
| 50 | 0901 | 0201g | 0302 | 0203 | 1201g | 0302 | 0405 | 0201g |

Methods of Improving Donor Cell Transplantation

The methods, compositions, and cells described herein can be used to improve the outcome of transplantation (e.g., hematopoietic stem cell transplantation), e.g., by increasing engraftment, preventing GVHD and graft rejection, reducing requirement for conditioning and immunosuppression, or any combination thereof. For example, the methods, compositions, and cells described herein can provide for a therapy, e.g., a one-time therapy or a multi-dose therapy, that prevents or treats GVHD and/or graft rejection.

In an embodiment, the therapy prevents, inhibits, or reduces the occurrence of GVHD and/or graft rejection in a subject, e.g., a recipient following matched or unmatched transplantation (e.g., allo-HSCT). In another embodiment, the therapy prevents, inhibits, or reduces the severity of GVHD and/or graft rejection in a subject, e.g., a recipient following matched or unmatched transplantation (e.g., allo-HSCT). It is believed that inactivation of one or more donor HLA alleles, e.g., by knocking out or knocking down one or more HLA genes or loci, and providing, e.g., by knocking in, one or more recipient matched HLA alleles, in the donor cells (e.g., the cells described herein, e.g., HSPCs), can prevent, inhibit, or reduce the occurrence or severity of GVHD and/or graft rejection in a subject, e.g., a recipient following matched, partially matched, haploidentical, or mismatched transplantation (e.g., allo-HSCT).

In an embodiment, the therapy prevents, decreases, or eliminates the need, or reduces the intensity, of myeloablative conditioning in a subject, e.g., a recipient of matched or mismatched transplantation (e.g., allo-HSCT).

In an embodiment, the therapy prevents, inhibits, or reduces the occurrence of GVHD and/or graft rejection in a subject, e.g., a recipient following matched or unmatched allo-UCT. In another embodiment, the therapy prevents, inhibits, or reduces the severity of GVHD and/or graft rejection in a subject, e.g., a recipient following matched or unmatched allo-UCT. In an embodiment, it is believed that inactivation of one or more donor HLA alleles, e.g., by knocking out or knocking down one or more HLA genes or loci, and providing, e.g., by knocking in, one or more recipient matched HLA alleles, in the donor cells (e.g., the cells described herein, e.g., HSPCs), can prevent, inhibit, or reduce the occurrence or severity of GVHD and/or graft rejection in a subject, e.g., a recipient following matched, partially matched, haploidentical, or mismatched allo-UCT.

In an embodiment, the subject, e.g., the recipient of matched or mismatched transplantation (e.g., allo-HSCT), is being treated, or has been treated, for a disease, e.g., a disease that would benefit from a transplantation, e.g., HSCT. Exemplary diseases include, but are not limited to, a malignant disorder, hemoglobinopathy, blood dyscrasia, immunodeficiency, a lysosomal storage disorder, or an inherited or acquired hematologic disease. In an embodiment, the subject is receiving, or has received, an anti-cancer therapy, e.g., chemotherapy or radiation therapy.

In an embodiment, the therapy reduces the likelihood of GVHD. In an embodiment, the subject receives reduced dose of pre-transplantation (e.g., pre-HSCT) conditioning regimen that a recipient subject receives prior to transplantation (e.g., HSCT). In an embodiment, treatment with a transplantation (e.g., HSCT) modified according to the methods described herein reduces the requirement for and/or intensity of post transplantation immunosuppression (e.g., tacrolimus, prednisolone, prednisone, and/or other steroids, ATG, CTLA4-Ig, MMF, rapamycin). In an embodiment, treatment with a transplantation (e.g., HSCT) modified according to the methods described herein permits the elimination or partial reduction of conditioning in a recipient subject prior to transplantation.

In an embodiment, the subject has a disease that can be treated with a transplant (e.g., HSCT) and the donor cells are expected to have a survival advantage relative to the recipient. In an embodiment, the subject has a hemoglobinopathy, an immunodeficiency, an inherited or acquired hematologic disease, or a malignant disease. In an embodiment, the subject is receiving or has received an anti-cancer therapy, e.g., chemotherapy or radiation therapy. In any disease in which donor cells (e.g., HSPCs) are expected to have a survival advantage relative to recipient cells and the disease is not a malignancy (e.g., IL2RG-SCID, IL7R-SCID, JAK3-SCID, or Fanconi anemia), treatment with the methods described herein will permit the use of lower dose conditioning or no conditioning in a recipient prior to transplantation. In an embodiment, the subject would not otherwise be eligible for transplantation, e.g., due to the presence of any of the following conditions: multiple co-morbidities, severe co-morbid disease, high risk for GVHD or graft rejection, old age, or presence of ongoing infection.

In an embodiment, the subject is in need of a transplant, e.g., HSCT, for the treatment of a hematologic malignancy. In an embodiment, the subject has acute myeloid leukemia, acute lymphocytic leukemia, non-Hodgkin's lymphoma, Hodgkin's lymphoma, chronic myeloid leukemia, chronic lymphocytic leukemia, chronic myelomonocytic leukemia, or multiple myeloma.

In an embodiment, the subject is in need of a transplant, e.g., HSCT, for the treatment of myelodysplastic syndrome or myeloproliferative neoplasm.

In an embodiment, the subject is in need of a transplant, e.g., HSCT, for the treatment of a solid tumor. In an embodiment, the subject has Ewing's sarcoma, neuroblastoma and glioma, or desmoplastic small round cell tumor.

In an embodiment, the subject is in need of a transplant, e.g., HSCT, for the treatment of a non-malignant condition. In an embodiment, the subject has hemoglobinopathies, blood dyscrasias, thalassemia (e.g., beta-thalassemia or alpha-thalassemia), sickle cell disease (SCD), Fanconi anemia, aplastic anemia, or congenital erythropoietic porphyria.

In an embodiment, the subject is in need of a transplant, e.g., HSCT, for the treatment of an immunodeficiency. In an embodiment, the subject has a severe combined immunodeficiency (SCID) (e.g., Omenn's syndrome, RAG-1 SCID, IL2-RG SCID, CD3-SCID, ADA-SCID, or JAK3-SCID), agammaglobulinemia, Wiskott-Aldrich syndrome. X-linked immunodeficiency with hyperimmunoglobulin M, X-linked Bruton agammaglobulinemia, bare lymphocyte syndrome, Cartilage-hair hypoplasia, Chediak-Higashi syndrome, chronic granulomatous disease, Kostman's syndrome, or leukocyte adhesion deficiency.

In an embodiment, the subject is in need of a transplant, e.g., HSCT, for the treatment of a lysosomal storage disease. In an embodiment, the subject has alpha-mannosidosis, adrenoleukodystrophy, gaucher disease, globoid cell leukodystrophy, metachromatic leukodystrophy, mucopolysaccharidoses (all types), Niemann-Pick disease, or Wolmans disease.

In an embodiment, the subject is in need of a transplant, e.g., HSCT, for the treatment of a disease selected from dyskeratosis congenital, familial hemophagocytic lymphohistiocytosis, hemophilia A, infantile osteopetrosis, osteogenesis imperfect, or Shwachman-Diamond syndrome.

In an embodiment, the subject has an ongoing infection or a co-morbid disease that prevents prior conditioning. In an embodiment, the subject is older than age 50 and cannot tolerate conditioning prior to transplantation.

In an embodiment, the subject has acquired hematologic immunodeficiency HIV/AIDS. In an embodiment, the donor cell has one or more HIV co-receptors (e.g., CCR5 or CXCR4) inactivated, e.g., by Cas9 molecule/gRNA molecule-mediated inactivation (e.g., knockout or knockdown). Inactivation of one or more HIV co-receptors in the HLA modified donor cells can prevent HIV infection of cell progeny after hematopoietic reconstitution.

The methods and compositions described herein focus on modification of donor cells (e.g., HSPCs) to both inactivate incompatible HLAs and to provide recipient matched HLAs to preserve the diversity and complexity in the immune system's recognition and defense against potential pathogens after transplantation with donor cells (e.g., allo-HSPCs). The methods and composition described herein may also include additional non-HLA genetic modifications to donor cells (e.g., allo-HSPCs) in order to further prevent GVHD (e.g., knock out or repression of chemokine receptors in allo-HSPCs to prevent alloreactive T cell migration into GVHD prone tissues), enhance engraftment, and/or correct diseases, both hematologic and nonhematologic in nature (e.g., introduction of genes that and encode secreted proteins for protein replacement therapy, introduction of genes that encode chemotherapy resistance genes to improve engraftment and/or support higher doses of chemotherapy should relapse of malignancy occur in the future). The methods and compositions described herein utilize a bioinformatics system to identify and score target-specific gRNAs for HLA alleles detected and reported to date, such that subject-specific HLA modifications can be allele specific (e.g., monoallelic disruption on one copy at one HLA locus of chromosome 6).

Methods of Altering a Gene or Locus

One or more immunogenicity genes or loci, e.g., HLA genes or loci, e.g., HLA alleles, haplotypes, or loci, can be altered by the methods described herein.

CRISPR/Cas9 Related Approaches to Generate HLA-Matched Cells for Transplantation HLA matched cells (e.g., the cells described herein, e.g., $CD34^+$ HSPCs) for transplantation into a human subject can be generated from unmatched, partially matched, or haploidentical donor cells (e.g., HPSCs) by a multi-step (e.g., two-step) process.

In one step, expression of one or more mismatched HLA alleles, e.g., in partially matched donor cells, is inactivated. For example, the step of inactivation can include one or more of the following steps: 1) performance of high resolution HLA typing, e.g., at the MHC loci, e.g, HLA-A, -B, -C and -DRB1 loci, in the donor and recipient cells. 2) bioinformatic design, tiering, and screening of gRNAs that are specific for a mismatched allele or alleles (e.g., HLA-A*0101) at the target locus or loci (e.g., HLA-A) present in the donor but absent in the recipient subject, 3) delivery of Cas9 and target-specific gRNA(s) to disrupt (e.g., knock out or knock down) expression of the individual mismatched HLA allele (e.g., HLA-A*0101), 4) validation of gene disruption at the targeted locus, and 5) validation loss of HLA expression at the cell surface by flow cytometry and by NK cytolysis assays (NK cells recognize cells down regulate HLA Class I antigens and induce lysis).

In another step, DNA sequence(s) encoding one or more matched recipient subject HLA alleles are introduced into the donor cells. For example, the step of introducing matched recipient HLA alleles can include one or more of the following steps: 1) generation of cDNA from the recipient subject that encodes a recipient subject specific allele of the targeted locus (e.g., for HLA-A locus, the allelic variant HLA-A*301). 2) assembly of a transgene expression cassette in which the recipient's endogenous promoter (e.g., HLA-A promoter) is positioned upstream of the DNA sequence encoding the recipient subject specific HLA allele (e.g., HLA-A*301) for transcriptional regulation of expression, 3) delivery of the transgene expression cassette (e.g., promoter and HLA allele DNA) to the donor cells using a viral vector (e.g., lentivirus vector) or nonviral delivery system. Alternatively, in an embodiment, the recipient HLA recipient subject allele specific transgene expression cassette may be delivered to the donor cells using the CRISPR-Cas9 system to target integration into a "safe harbor" locus (e.g., AAVS1, CCR5) or into the original locus (e.g. HLA-A).

The step of inactivating one or more mismatched donor HLA alleles and the step of introducing one or more matched recipient HLA alleles can be performed in any order. In an embodiment, the step of inactivating one or more mismatched donor HLA alleles is performed prior to the step of introducing one or more matched recipient HLA alleles. In another embodiment, the step of inactivating one or more mismatched donor HLA alleles is performed subsequent to the step of introducing one or more matched recipient HLA alleles. In yet another embodiment, the step of inactivating one or more mismatched donor HLA alleles is performed concurrently with the step of introducing one or more matched recipient HLA alleles.

Before and after gene editing, cells can be cultured in media (e.g., HSPC supportive media) under optimized cell culture conditions to promote cell survival and preservation of cell (e.g., HSPC) phenotype and functionality and to prevent cell immune response from exposure to Cas9 and gRNA components (see examples). Cells (e.g., HSPCs) can be expanded or cultured under optimized conditions to promote cell (e.g., HSPC) maintenance and to prevent differentiation. Optimized cell culturing conditions are described herein. In an embodiment, the cell (e.g., HSPCs) is expanded or cultured under optimized conditions before one or more mismatched donor HLA alleles are inactivated. In an embodiment, the cell (e.g., HSPCs) is expanded or cultured under optimized conditions after one or more mismatched donor HLA alleles are inactivated. In an embodiment, the cell (e.g., HSPCs) is expanded or cultured under optimized conditions before one or more matched recipient HLA alleles are introduced. In an embodiment, the cell (e.g., HSPCs) is expanded or cultured under optimized conditions after one or more matched recipient HLA alleles are introduced. In an embodiment, the cell (HSPCs) is expanded or cultured under optimized conditions after one or more mismatched donor HLA alleles are inactivated and before one or more matched recipient HLA alleles are introduced. In an embodiment, the cell (HSPCs) is expanded or cultured under optimized conditions after one or more matched recipient HLA alleles are introduced and before one or more mismatched recipient HLA alleles are inactivated.

The process of unmatched gene inactivation and matched gene replacement can prevent NK mediated lysis of cells lacking specific HLAs, preserve in vivo immune function after transplantation (e.g., allo-HSCT) by maintaining the diversity of HLA allele expression, and reducing the severity and/or occurrence of GvHD by increasing the HLA matching level between donor and recipient subject cells.

Designing and Screening of gRNAs

Using a publically available data set that includes HLA allelic variants recorded to date (hla.alleles.org), a database was built and established to contain gRNA sequences that are highly specific for individual alleles which have been reported for HLA-A, -B, -C, DRB1, -DRB3/4/5, and -DQB1 loci and cross-references every allele to the ancestry, race, or ethnic background of human subjects within which these individual alleles are represented (Marsh, S. G. E. (2015), Nomenclature for factors of the HLA system, update March 2015. Tissue Antigens. doi: 10.1111/tan.12581; Maiers M, et al. Hum. Immunol. 2007; 68(9):779-788) (see "gRNA" and "example" sections for allele-specific gRNA examples and for detailed database design). The following numbers of allelic variants were included within the database: HLA-A (3094 alleles), HLA-B (3865 alleles), HLA-C (2618), HLA-DRB1 (1719), HLA-DRB3/4/5 (95), HLA-DQB1 (777 alleles). Using the database, gRNAs that are specific to one out of thousands of allelic variants that are represented in the database can be selected. In addition, the database described herein can identify and tier gRNAs that target individual HLA loci without allelic specificity that would allow for bi-allelic disruption with one or more gRNAs. Allelic variants, gRNAs, and ancestry can be linked to current cord blood and bone marrow donor registries for cross-referencing and identifying partially matched donors that could be later modified for matched allo-HSCT in recipient subjects.

Mono-Allelic and Bi-Allelic HLA Targeting

Allele-specific gRNA molecules can be used with the CRISPR-Cas9 system to knock out or knock down expression of the allele-specific gene product, in cases where one allele (either maternal or paternal) at a locus is not matched between donor cells and recipient subject. In addition, in cases where the cell donor and recipient subject are unmatched or are haploidentical, multiplex knockout or knockdown of individual alleles at multiple HLA loci (e.g., HLA-A, -B, -C, and -DRB1) on a single chromosome can be applied by co-delivery of allele specific gRNA molecules targeting the mismatched (unmatched) haplotype in the donor cells followed by providing a recipient matched haplotype. This example of multiplex genome editing would increase matching between donor and recipient from 3/6 or 4/8 to 6/6 or 8/8, respectively, thereby converting a haploidentical matched donor (e.g. HLA-A, -B, -C, -DRB1 mismatched on one copy of chromosome 6, and the second copy matched on chromosome 6) to a fully matched donor. However, in the case where both alleles (maternal and paternal) at a locus are mismatched between donor and recipient (e.g., both alleles at HLA-A), the gene-specific but non-allele specific gRNAs can be used with CRISPSR-Cas9 for biallelic disruption of the locus. In both scenarios, the genes that are knocked out or knocked down can be replaced with recipient specific alleles to increase HLA matching between donor and recipient to preserve HLA diversity in the subject.

For example, after biallelic disruption of HLA-A in the donor cells, two recipient specific HLA-A alleles can be delivered to the allogeneic donor cells in a transgene expression cassette using conventional non-viral or viral delivery methods. Once the HLA replacement has been verified by sequencing, comparative typing of modified donor cells and recipient cells, and expression and functional assays, the HLA edited donor cells can be transplanted into the recipient for hematopoietic reconstitution and the subject is treated according to current standard of care for transplantation subjects. Alternatively, in an embodiment, eiCas9 fused to KRAB and DNMTs targeting the mismatched HLA allele in donor cells (e.g., HSPCs) can be used to permanently repress expression of the mismatched HLA allele.

Next, the donor cells in which one or more mismatched donor HLA alleles have been inactivated can be sorted in order to obtain an enriched, isolated, or purified population of cells (e.g., HSPCs) that lack the mismatched HLA allele(s).

Validation of Inactivation of an Allele at a Targeted HLA Locus

To validate that one or more targeted HLA alleles have been inactivated by CRISPR/Cas9 activity, donor cells before and after targeting can be assayed for alteration of the allele sequence(s) or expression of the allele(s) using conventional methods (e.g., one or more of allele-specific PCR, qRT-PCR, or flow cytometry). In an embodiment, donor cells with or without genome editing can be co-cultured with NK cells and the cytolytic activity directed against the donor cells is quantified to determine the down-regulation of HLA expression. After validation, cells having one or more mismatched donor HLA alleles inactivated and/or one or more matched recipient HLA alleles introduced can be enriched, isolated, or purified from the unmodified cells by conventional sorting methods.

Introduction of a Matched Recipient HLA Allele

A nucleic acid that encodes a matched recipient HLA allele can be introduced into donor cells by conventional viral or nonviral delivery methods. In an embodiment, the nucleic acid is a cDNA, e.g., a cDNA reverse transcribed from recipient mRNA. In another embodiment, the nucleic acid is a genomic DNA sequence. In an embodiment, a nucleic acid that encodes a plurality of matched recipient HLA alleles is introduced. In an embodiment, a plurality of nucleic acids each encoding one or more matched recipient HLA alleles are introduced.

In an embodiment, the nucleic acid is inserted into a viral vector (e.g., lentivirus vector) or nonviral delivery system (e.g., transposon). In an embodiment, the nucleic acid or vector comprises the HLA gene's specific endogenous promoter (e.g., cloned from the recipient genetic locus) to transcriptionally regulate the introduced HLA allele.

In an embodiment, the nucleic acid sequence encoding the recipient matched HLA allele is delivered in a lentivirus vector, e.g., with the recipient endogenous HLA promoter placed proximal to the HLA allele sequence in a transgene expression cassette.

In an embodiment, the nucleic acid is inserted into a SIN lentivirus expression cassette and packaged in lentiviral vector particles. The donor cells can be transduced with the lentivirus vector that contains the recipient HLA transgene. The transduced cells can be sorted based on increased expression of the recipient HLA allele relative to donor cells that were not contacted by the recipient HLA allele specific lentivirus vector. Alternatively, in an embodiment, recipient HLA allele donor templates can be co-delivered to donor cells by alternate methods (e.g., electroporation or lipid transfection) with Cas9 and gRNA molecule(s) for Cas9 mediated targeted integration into a safe harbor locus (e.g., AAVS1 or CCR5), or Cas9 meditated gene replacement into the original locus (e.g., HLA-A).

Alternatively, AAV (e.g., AAV6 or AAVDJ) or nonviral vectors delivering CRISPR-Cas9 components and target specific gRNA molecules, and IDLVs encoding the recipient transgene expression cassette can be delivered to donor cells (e.g., HSPCs).

Introduction of recipient matched HLA alleles to the donor cells can be validated by locus specific PCR, DNA sequencing, or qPCR (e.g., to determine proviral copy number per genome equivalent) where appropriate, and by assaying for increased expression of HLA (e.g., based on conventional methods for detecting mRNA and protein levels). Expression of HLA can also be determined by NK cytolysis assays at various time points, e.g., before or after inactivation of one or more mismatched donor HLA alleles, and before or after introduction of one or more matched recipient HLA alleles. If the donor cells have one or more mismatched donor HLA alleles inactivated and one or more matched recipient HLA alleles introduced, there would be minimal to no NK mediated lysis of cells. HLA typing of donor cells before and after HLA gene editing can be confirmed by conventional methods (e.g., PCR amplification of genetic locus and DNA sequencing. HLA modified donor cells can also be analyzed by qRT-PCR for gene expression analysis.

HLA matched, gene-edited donor cells can then be transplanted into recipient subjects using conventional clinical protocols and regimens. For example, suitable donors can be generated for the subject populations that are underrepresented in national bone marrow and cord blood stem cell registries for whom suitable donors cannot be otherwise identified.

Methods of Altering an HLA Gene or Locus

Disclosed herein are methods for altering a target position (e.g., a target knockout position, a target knockdown position, or a target knockin position) in a gene or locus, e.g., an HLA gene or locus. Altering the target position can be achieved, e.g., by altering one or more locus or allelic variants in the gene. In this approach, mismatched allele(s) are modified such that they match one or more specific allelic variants. For example, donor cells (e.g., HSPCs) can be modified to match one or more HLA alleles associated with a recipient subject. Alteration of an allelic variant of a gene described herein increases the degree of HLA matching between donor and recipient subject cells. The method described herein can be performed in all cell types, e.g., a cell type described herein.

Altering the target position can be achieved, e.g., by:

(1) knocking out a gene:

(a) insertion or deletion (e.g., NHEJ-mediated insertion or deletion) of one or more nucleotides in the gene, or (b) deletion (e.g., NHEJ-mediated deletion) of a genomic sequence including at least a portion of the gene, or (2) knocking down a gene mediated by enzymatically inactive Cas9 (eiCas9) molecule or an eiCas9-fusion protein (e.g., fused to a transcriptional repressor) by targeting the promoter region of the gene, (3) Knocking in a gene (e.g., by HDR).

All approaches give rise to alteration of the gene.

Knocking Out an HLA Allele by Introducing an Indel or a Deletion in an HLA Locus In an embodiment, the method comprises introducing an insertion or deletion of one more nucleotides within a locus, e.g., an HLA locus, e.g., the coding region of an HLA locus (e.g., HLA-A, HLA-B, HLA-C, HLA-DRB1, HLA-DR3/4/5, HLA-DQ, e.g., DQB1, or HLA-DP). As described herein, in one embodiment, the method comprises the introduction of one or more breaks (e.g., single strand breaks or double strand breaks) within an HLA locus, e.g., the coding region of an HLA locus (e.g., HLA-A, HLA-B, HLA-C, HLA-DRB1, HLA-DR3/4/5, HLA-DQ, e.g., DQB1, or HLA-DP). NHEJ-mediated repair of the break(s) allows for the NHEJ-mediated introduction of an indel within an HLA locus, e.g., the coding region of an HLA locus (e.g., HLA-A, HLA-B, HLA-C, HLA-DRB1, HLA-DR3/4/5, HLA-DQ, e.g., DQB1, or HLA-DP).

In an embodiment, the method comprises introducing a deletion of a genomic sequence comprising at least a portion (e.g., a portion within a coding region, e.g., an early coding region, or a portion within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP). As described herein, in an embodiment, the method comprises the introduction of two double stand breaks—one 5' and the other 3' to (i.e., flanking) a position (e.g., within a coding region, e.g., an early coding region, or within a non-coding region, e.g., a non-coding sequence of the HLA locus, e.g., a promoter, an enhancer, an intron, a 3' UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP). In an embodiment, two gRNAs, e.g., unimolecular (or chimeric) or modular gRNA molecules, are configured to position the two double strand breaks on opposite sides of a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP).

In an embodiment, a single strand break is introduced (e.g., positioned by one gRNA molecule) within an HLA locus, e.g., the coding region of an HLA locus (e.g., HLA-A, HLA-B, HLA-C, HLA-DRB1, HLA-DR3/4/5, HLA-DQ, e.g., DQB1, or HLA-DP). In an embodiment, a single gRNA molecule (e.g., with a Cas9 nickase) is used to create a single strand break within an HLA locus, e.g., the coding region of an HLA locus (e.g., HLA-A, HLA-B, HLA-C, HLA-DRB1. HLA-DR3/4/5, HLA-DQ, e.g., DQB1, or HLA-DP or downstream of a position within an HLA locus, e.g., of the coding region of an HLA locus (e.g., HLA-A, HLA-B, HLA-C, HLA-DRB1, HLA-DR3/4/5, HLA-DQ, e.g., DQB1, or HLA-DP). In an embodiment, the break is positioned to avoid unwanted target chromosome elements, such as repeat elements, e.g., an Alu repeat.

In an embodiment, a double strand break is introduced (e.g., positioned by one gRNA molecule) within an HLA locus, e.g., the coding region of an HLA locus (e.g., HLA-A, HLA-B, HLA-C, HLA-DRB1, HLA-DR3/4/5, HLA-DQ, e.g., DQB1, or HLA-DP). In an embodiment, a single gRNA molecule (e.g., with a Cas9 nuclease other than a Cas9 nickase) is used to create a double strand break within an HLA locus, e.g., the coding region of an HLA locus (e.g., HLA-A, HLA-B, HLA-C, HLA-DRB1, HLA-DR3/4/5, HLA-DQ, e.g., DQB1, or HLA-DP), e.g., the gRNA molecule is configured such that the double strand break is positioned either upstream or downstream of a position within an HLA locus, e.g., of the coding region of an HLA locus (e.g., HLA-A, HLA-B, HLA-C, HLA-DRB1, HLA-DR3/4/5, HLA-DQ, e.g., DQB1, or HLA-DP). In an embodiment, the break is positioned to avoid unwanted target chromosome elements, such as repeat elements, e.g., an Alu repeat.

In an embodiment, two single strand breaks are introduced (e.g., positioned by two gRNA molecules) within an HLA locus (e.g., HLA-A, HLA-B, HLA-C, HLA-DRB1, HLA-DR3/4/5, HLA-DQ, e.g., DQB1, or HLA-DP). In an embodiment, two gRNA molecules (e.g., with one or two Cas9 nickases) are used to create two single strand breaks within an HLA locus (e.g., HLA-A, HLA-B, HLA-C, HLA-DRB1, HLA-DR3/4/5, HLA-DQ, e.g., DQB1, or HLA-DP), e.g., the gRNAs molecules are configured such that both of the single strand breaks are positioned e.g., upstream or downstream of a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) an HLA locus (e.g., HLA-A, HLA-B, HLA-C, HLA-DRB1, HLA-DR3/4/5, HLA-DQ, e.g., DQB1, or HLA-DP). In another embodiment, two gRNA molecules (e.g., with two Cas9 nickases) are used to create two single strand breaks within an HLA locus, e.g., the coding region of an HLA locus (e.g., HLA-A, HLA-B, HLA-C, HLA-DRB1, HLA-DR3/4/5, HLA-DQ, e.g., DQB1, or HLA-DP), e.g., the gRNAs molecules are configured such that one single strand break is positioned upstream and a second single strand break is positioned downstream of a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP). In an embodiment, the breaks are positioned to avoid unwanted target chromosome elements, such as repeat elements, e.g., an Alu repeat.

In an embodiment, two double strand breaks are introduced (e.g., positioned by two gRNA molecules) within an HLA locus (e.g., HLA-A, HLA-B, HLA-C, HLA-DRB1, HLA-DR3/4/5, HLA-DQ, e.g., DQB1, or HLA-DP). In an embodiment, two gRNA molecules (e.g., with one or two Cas9 nucleases that are not Cas9 nickases) are used to create two double strand breaks to flank a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP), e.g., the gRNA molecules are configured such that one double strand break is positioned upstream and a second double strand break is positioned downstream of a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP). In an embodiment, the breaks are positioned to avoid unwanted target chromosome elements, such as repeat elements, e.g., an Alu repeat.

In an embodiment, one double strand break and two single strand breaks are introduced (e.g., positioned by three gRNA molecules) within an HLA locus (e.g., HLA-A, HLA-B, HLA-C, HLA-DRB1, HLA-DR3/4/5, HLA-DQ, e.g., DQB1, or HLA-DP). In an embodiment, three gRNA molecules (e.g., with a Cas9 nuclease other than a Cas9 nickase and one or two Cas9 nickases) to create one double strand break and two single strand breaks to flank a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP), e.g., the gRNA molecules are configured such that the double strand break is positioned upstream or downstream of a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP), and the two single strand breaks are positioned at the opposite site, e.g., downstream or upstream of the position within the coding region of an HLA locus (e.g., HLA-A, HLA-B, HLA-C, HLA-DRB1, HLA-DR3/4/5. HLA-DQ, e.g., DQB1, or HLA-DP). In an embodiment, the breaks are positioned to avoid unwanted target chromosome elements, such as repeat elements, e.g., an Alu repeat.

In an embodiment, four single strand breaks are introduced (e.g., positioned by four gRNA molecules) within the coding region of an HLA locus (e.g., HLA-A, HLA-B, HLA-C, HLA-DRB1. HLA-DR3/4/5, HLA-DQ, e.g., DQB1, or HLA-DP). In an embodiment, four gRNA molecule (e.g., with one or more Cas9 nickases are used to create four single strand breaks to flank a position (e.g., within a coding region, e.g., an early coding region, or within a non-coding region, e.g., a non-coding sequence of the HLA locus, e.g., a promoter, an enhancer, an intron, a 3'UTR, and/or a polyadenylation signal) of an HLA locus (e.g., HLA-A, HLA-B, HLA-C, HLA-DRB1, HLA-DR3/4/5, HLA-DQ, e.g., DQB1, or HLA-DP), e.g., the gRNA molecules are configured such that a first and second single strand breaks are positioned upstream of the position within the coding region of an HLA locus (e.g., HLA-A, HLA-B, HLA-C, HLA-DRB1, HLA-DR3/4/5, HLA-DQ, e.g., DQB1, or HLA-DP), and a third and a fourth single stranded breaks are positioned downstream of the position within the coding region of an HLA locus (e.g., HLA-A, HLA-B, HLA-C, HLA-DRB1, HLA-DR3/4/5, HLA-DQ, e.g., DQB1, or HLA-DP). In an embodiment, the breaks are positioned to avoid unwanted target chromosome elements, such as repeat elements, e.g., an Alu repeat.

In an embodiment, two or more (e.g., three or four) gRNA molecules are used with one Cas9 molecule. In another embodiment, when two ore more (e.g., three or four) gRNAs are used with two or more Cas9 molecules, at least one Cas9 molecule is from a different species than the other Cas9 molecule(s). For example, when two gRNA molecules are used with two Cas9 molecules, one Cas9 molecule can be from one species and the other Cas9 molecule can be from a different species. Both Cas9 species are used to generate a single or double-strand break, as desired.

Knocking Down an HLA Allele Mediated by an Enzymatically Inactive Cas9 (eiCas9) Molecule A targeted knockdown approach reduces or eliminates expression of functional gene product, e.g., a functional HLA gene product (e.g., HLA-A, HLA-B, HLA-C, HLA-DRB1, HLA-DR3/4/5, HLA-DQ, e.g., DQB1, or HLA-DP). As described herein, in an embodiment, a targeted knockdown is mediated by targeting an enzymatically inactive Cas9 (eiCas9) molecule or an eiCas9 fused to a transcription repressor domain or chromatin modifying protein to alter transcription, e.g., to block, reduce, or decrease transcription, of an HLA gene.

Methods and compositions discussed herein may be used to alter the expression of the HLA gene (e.g., HLA-A, HLA-B, HLA-C, HLA-DRB1, HLA-DR3/4/5, HLA-DQ, e.g., DQB1, or HLA-DP). In an embodiment, the promoter region is targeted to knock down expression of the HLA gene. A targeted knockdown approach reduces or eliminates expression of functional HLA gene product. As described herein, in an embodiment, a targeted knockdown is mediated by targeting an enzymatically inactive Cas9 (eiCas9) or an eiCas9 fused to a transcription repressor domain or chromatin modifying protein to alter transcription, e.g., to block, reduce, or decrease transcription, of the HLA gene.

In an embodiment, one or more eiCas9s may be used to block binding of one or more endogenous transcription factors. In another embodiment, an eiCas9 can be fused to a chromatin modifying protein. Altering chromatin status can result in decreased expression of the target gene. One or more eiCas9s fused to one or more chromatin modifying proteins may be used to alter chromatin status.

Methods of Knocking in a Gene Sequence

Disclosed herein are methods for altering a target position (e.g., a target knockin position) in a gene or locus, e.g., a gene or locus described herein. In an embodiment, the method includes targeted integration. In an embodiment, the method includes delivery of one or more matched recipient HLA alleles into the original position(s) where the one or more mismatched donor HLA alleles are located. In an embodiment, the method includes inserting one or more matched recipient HLA alleles into a "safe harbor" locus. In an embodiment, the method further includes introducing a chemotherapy resistance gene for in vivo selection in a gene. Altering the target position can be achieved, e.g., by knocking in a gene sequence, e.g., a gene sequence described herein (e.g., a cDNA encoding at least a portion of the gene described herein), e.g., by HDR. Knockin of a gene sequence described herein results in expression of a recipient matched HLA allele.

Multiplexing Alteration of HLA Genes or Loci

The alteration of two or more genes or loci in the same cell or cells is referred to herein as "multiplexing". Multiplexing constitutes the modification of at least two genes or loci (e.g. HLA genes or loci) in the same cell or cells. When two or more genes or loci (e.g., HLA-A, HLA-B, HLA-C, HLA-DRB1, HLA-DRB3/4/5, HLA-DQB1, HLA-DP, MiHAs, and any other MHC Class I or Class II genes or loci) are targeted for alteration, the two or more genes or loci may be altered sequentially or simultaneously. In an embodiment, the alteration of an HLA gene or locus is prior to or subsequent to the alteration of another HLA gene or locus. In an embodiment, the alteration of an HLA gene or locus is concurrent with the alteration of another HLA gene or locus. In an embodiment, the two or more HLA alleles or genes (e.g., HLA-A and HLA-DRB1) are altered sequentially in order reduce the probability of introducing genomic rearrangements (e.g., translocations) involving the two target positions. In an embodiment, the alteration is mono-allelic. In another embodiment, the alteration is bi-allelic. In an embodiment, the effect of the alterations is synergistic. Multiplex alteration of HLA genes or loci can provide a greater likelihood of subjects in need of transplantation (e.g., HSCT) with a suitable donor while reducing the severity and incidence of GVHD.

Optimization of Target Cells

The cells, e.g., target cells, described herein can be optimized or manipulated, e.g., ex vivo or in vivo. Optimization or manipulation of target cells allow for maintenance, expansion, persistence, or regulation of the cells for CRISPR/Cas-mediated gene editing or regulation. For example, optimization or manipulation of the target cells, e.g., hematopoietic stem/progenitor cells (HSPCs), can preserve cell fitness, functionality, self-renewal, or proliferation potential, or prevent cell death through autophagy, apoptosis, necrosis, or cell senescence.

The target cells can be optimized or manipulated before, during, or after contact with a CRISPR/Cas component, e.g., a Cas9 molecule, a gRNA molecule, or both, and optionally, a donor template nucleic acid. In an embodiment, the target cell is optimized or manipulated before and during contact with a CRISPR/Cas component. In an embodiment, the target cell is optimized or manipulated during and after contact with a CRISPR/Cas component. In an embodiment, the target cell is optimized or manipulated before and after contact with a CRISPR/Cas component. In an embodiment, the target cell is optimized or manipulated before, during, and after contact with a CRISPR/Cas component.

Several different optimization or manipulation steps can be applied in sequence, e.g, at specific time intervals relative to contact with a CRISPR/Cas component, e.g., a Cas9 molecule, a gRNA molecule, or both, and optionally a donor template nucleic acid. Several different optimization or manipulation steps can also be applied simultaneously, e.g., at a specific time interval relative to contact with a CRISPR/Cas component, e.g., a Cas9 molecule, a gRNA molecule, or both, and optionally a donor template nucleic acid.

For example, the target cells can be optimized or manipulated to contain one or more transgenes. The transgene can be integrated into a specific locus in the genome of the target cell, e.g., by a CRISPR/Cas related mechanism. Transgenes can provide a safety switch that would allow for regulation of the enrichment and/or purification of modified cells before expansion and transplantation. It is also believed that, in an embodiment, transgenes would allow for expansion of modified cells in vivo if the engrafted cells are not well-detected, or allow for removal of modified cells in vivo in the event that the modified cells are dysfunctional or undergo leukemic transformation. As yet another example, the target cells can be optimized or manipulated by contacting with one or more eiCas9 molecules, e.g., fused to a transcriptional repressor or activator.

Introduction of Truncated Cell Surface Antigens

Purification of modified target cells expressing a cell surface antigen or a selectable marker would provide a means to insure that a CRISPR/Cas component, e.g., a Cas9 molecule, a gRNA molecule, or both, and optionally a donor template nucleic acid, has been delivered to the cells, e.g., ex vivo. Expression of a cell surface antigen by targeted cells would also allow for tracking modified target cells in vivo.

In an embodiment, the target cell comprises, or is contacted with, a gene encoding a cell surface antigen or a selectable marker. In an embodiment, the cell surface antigen or selectable marker is truncated CD19 (tCD19). In another embodiment, the cell surface antigen or selectable marker is truncated CD20 (tCD20). The full-length cell surface receptors CD19 and CD20 are naturally expressed on B-lymphocytes. Truncating CD19 or CD20 prevents intracellular signaling through the receptor since the cytoplasmic domain is removed (Tey e al., 2007, Biol Blood Marrow Transplant, 13(8):913-24). Expression of the extracellular domain of CD19 or CD20 would allow for sorting on the cells and for tracking the cells in vivo (e.g., by taking blood draws and staining the cells with anti-human CD19 or anti-human CD20 antibodies in order to monitor engraftment of the gene-edited cells). In an embodiment, the tCD19 or tCD20 transgene is delivered as a donor template nucleic acid. In an embodiment, the target cell is contacted with one or more gRNA molecules comprising a targeting domain that is complementary to a target domain from the region into which the transgene is integrated. In an embodiment, the tCD19 or tCD20 transgene is integrated into the genome, e.g., at a safe harbor locus, e.g., the AAVS1 safe harbor locus. Introduction or co-introduction (multiplex genome editing) of a truncated CD19 or CD20 cell surface antigen can be used to purify genome edited cells ex vivo or to monitor genome edited cells in vivo.

Introduction of Chemotherapy Resistance Transgenes or Suicide Genes

The methods described herein allow for regulation of target cells in vivo or ex vivo, such that modified target cells with desired properties can be selected or expanded, or modified target cells with undesired properties (e.g., leukemic transformation) can be eliminated.

In an embodiment, the target cell comprises, or is contacted with, a safety switch, which allows for selection of desired target cells, e.g., ex vivo or in vivo, or elimination of undesired target cells, e.g., ex vivo or in vivo. In an embodiment, the safety switch contains a suicide gene and/or a gene encoding a chemotherapy selection marker. For example, the target cells can contain a safety switch that comprises of two components: 1) truncated cell surface antigen (tCD20) and inducible suicide gene that can be used to sort genome edited cells ex vivo, can be used to track cells in vivo, and can also be used to eliminate cells in the event of leukemic transformation in vivo by administration of Rituximab (anti-CD20 monoclonal antibody therapy) to the patient; and 2) a drug-inducible chemotherapy resistance gene (e.g., the P140K variant of methylguanine methyltransferase [P140K MGMT]) which upon treatment of the patient with alkylating chemotherapy (O6-benzylguanin [O6BG] and BCNU) would in vivo select for the genome edited cells by removal of the unedited cells, thereby increasing the in vivo repopulation of the bone marrow with genome edited cells.

In an embodiment, the target cell comprises, or is contacted with, a suicide gene. In an embodiment, the suicide gene encodes an inducible Caspase-9 (iCasp9). In an embodiment, the target cell is further contacted with a chemical inducer of dimerization, e.g., AP1903 or AP2018. Caspase-9 induces apoptosis upon treatment with a chemical inducer of dimerization (Di Stasi et al., 2011, New Eng Journal Med. 365:1673-1683). In another embodiment, the suicide gene encodes a truncated CD20 (tCD20). In an embodiment, the target cell is further contacted with an anti-CD20 antibody, e.g., Rituximab. Anti-CD20 antibody can induce an immune response and lead to death of cells that express CD20 (Redman et al., 2015. Mol Immunol, S0161-5890 (15):00361-2).

In an embodiment, the target cell comprises, is contacted with, a gene encoding a chemotherapy selection marker. In an embodiment, the chemotherapy selection marker is a variant of methylguanine methyltransferase (e.g., the P140K variant of methylguanine methyltransferase). In an embodiment, the target cell is further contacted with a chemotherapeutic agent, e.g., O6BG/BCNU. Use of the P140K variant of methylguanine methyltransferase with O6BG/BCNU chemotherapy is effective in increasing the level of gene-modified hematopoietic stem/progenitor cells in the bone marrow after delivery by lentivirus transduction (Gori et al, 2012, Cancer Gene Therapy, 19(8):1523-9; Beard et al., 2010. J Clin Invest, 120(7):2345-54).

In an embodiment, the transgene is provided on or delivered as a donor template nucleic acid. In an embodiment, the target cell is contacted with one or more gRNA molecules comprising a targeting domain which is complementary with a target domain from a region into which the transgene is integrated. In an embodiment, the transgene is integrated into the genome, e.g., at a safe harbor locus, e.g., the AAVS1 safe harbor locus. In an embodiment, the transgene comprises a tCD20-2A-P140K bicistronic transgene cassette.

Modification of gRNA Molecules

During virus-host co-evolution, viral RNA capping that mimics capping of mRNA evolved to allow viral RNA to escape detection from the cell's innate immune system (Delcroy et al., 2012, Nature Reviews Microbiology, 10:51-65). Toll-like receptors in target cells (e.g., HSPCs) sense the presence of foreign single and double stranded RNA that can lead to innate immune response, cell senescence, and programmed cell death (Kajaste-Rudnitski and Naldini, 2015, Human Gene Therapy, 26:201-209). Results from initial experiments showed that human HSPCs electroporated with unmodified (e.g. gRNAs synthesized without a 5' cap or 3' polyA-tail) gRNA molecules and Cas9 mRNA led to reduced cell survival, proliferation potential, or multipotency (e.g., loss of erythroid differentiation potential and skewed myeloid differentiation potential) compared to cells electroporated with GFP mRNA alone. In order to address this issue, it was hypothesized that cell senescence and apoptosis was due to the target cell sensing of foreign nucleic acid and induction of an innate immune response and subsequent induction of programmed cell death and loss of proliferative and differentiation potential. To evade the cell's innate immune response to foreign nucleic acid, modifying the gRNA molecules to resemble mRNA (e.g., addition of 5' cap and 3' polyA tail) can prevent innate immune response in the cell, interferon response in the cell, cell senescence, or programmed cell death caused by sensing the foreign nucleic acid.

In an embodiment, the target cell is contacted with a capped and tailed gRNA molecule. In an embodiment, the target cell is contacted with a Cas9 molecule/gRNA molecule complex containing a capped and tailed gRNA molecule. Contacting target cells with capped and tailed gRNA molecules can increase survival of modified target cells, preserve target cell multipotency, proliferation potential, or viability, or prevent cell senescence and programmed cell death.

Methods to Treat or Prevent Diseases

Methods and compositions described herein provide for a therapy, e.g., a one-time therapy or a multi-dose therapy that treats or prevents a disease, e.g., a disease described herein. In an embodiment, the method for treating or preventing a disease alter a cell, e.g., a cell described herein, e.g., ex vivo or in vivo. Any type of cell that is associated with the disease can be altered by the methods described herein. For example, the cell is a circulating blood cell, a mobilized blood cell, a bone marrow cell, a myeloid progenitor cell, a lymphoid progenitor cell, a hematopoietic stem/progenitor cell (HSPC), a multipotent progenitor cell, a lineage restricted progenitor cell, an endothelial cell, or a mesenchymal stromal cell. In another embodiment, the method for treating or preventing a disease alters a gene, e.g., a gene described herein, e.g., by CRISPR/Cas-mediated gene editing. Alteration of the cell or gene (e.g., correction, knockout, knockin, knockdown, or activation) can be performed prior to disease onset or after disease onset. Exemplary diseases that can be treated or prevented by the methods described herein include, but are not limited to, the diseases listed in Table 16. Exemplary genes that can be altered by the methods described herein include, but are not limited to, the genes listed in Table 16.

In an embodiment, a gene is knocked into a safe harbor locus (e.g., the AAVS1 safe harbor locus) in a target cell, e.g., an HSPC, using a CRISPR/Cas-mediated method, or any other knockin or gene delivery methods including Sleeping Beauty transposon, lentivirus vector, or adenoassociated viral vector.

In an embodiment, the gene encodes a secreted, soluble protein. Knockin of a gene encoding a secreted, soluble blood protein can be used to treat or cure disease, including diseases listed in Table 16, e.g. a lysosomal storage diseases, glycogen storage diseases, mucopolysaccharidoses, or any disease in which the secretion of a protein will ameliorate the disease.

In an embodiment, the disease is associated with deficiency of a circulating blood protein. Exemplary diseases include, but are not limited to, hemophilia (e.g., hemophilia A or hemophilia B), A1AT deficiency, or lysosomal acid lipase deficiency. Introducing a gene encoding a secreted, soluble blood protein associated with the deficiency can increase the circulating blood levels of the protein and therefore ameliorate or cure the disease. In an embodiment, the disease is hemophelia, e.g., hemophilia A or hemophilia B. In an embodiment, the gene is the F8 gene, coding for clotting factor VIII. In an embodiment, the method includes knocking in the F8 gene, thereby treating or preventing hemophilia A. In another embodiment, the gene is the F9 gene, coding for clotting factor IX. In an embodiment, the method includes knocking in the F9 gene, thereby treating or preventing hemophilia B. In an embodiment, the disease is A1AT deficiency. In an embodiment, the gene is the Sequences of allelic variants of a specific locus, e.g., HLA-A, HLA-B, HLA-C, HLA-DRB1, HLA-DRB3/4/5, or HLA-DQB1, coding for alpha-1-antitrypsin. In an embodiment, the method includes knocking in the sequences of allelic variants of a specific locus, e.g., HLA-A, HLA-B, HLA-C, HLA-DRB1, HLA-DRB3/4/5, or HLA-DQB1, thereby treating or preventing A1AT deficiency. In an embodiment, the disease is lysosomal acid lipase deficiency. In an embodiment, the gene is the LAL gene, coding for lysosomal acid lipase, thereby treating or preventing lysosomal acid lipase deficiency.

In an embodiment, the disease is diabetes. In an embodiment, the gene codes for a secreted, soluble blood protein. Knockin of a gene encoding a secreted, soluble blood protein, e.g., under the control of a druggable, inducible or selectable promoter, can increase the circulating blood levels of this protein and therefore ameliorate or cure the disease. In an embodiment, the gene is the INS gene, coding for the protein insulin. In an embodiment, the gene is the GCG gene, coding for the protein glucagon. In an embodiment, the method includes knocking in the INS gene or GCG gene, e.g., under the control of a druggable, inducible or selectable promoter, thereby treating or preventing diabetes.

In an embodiment, the disease is growth hormone deficiency. In an embodiment, the gene is the GH gene, coding for growth hormone. Knockin of the GH gene, e.g., under the control of a druggable, inducible or selectable promoter, can increase the circulating growth hormone levels and therefore ameliorate or cure the disease. In an embodiment, the method includes knocking in the GH gene, e.g., under the control of a druggable, inducible or selectable promoter, thereby treating or preventing growth hormone deficiency.

In an embodiment, the disease is a cancer, e.g., a hematologic cancer. In an embodiment, the gene is a gene overexpressed in the cancer. Knockdown of the gene, e.g., by an eiCas9 molecule fused to a transcriptional repressor, improves or cures the disease. In an embodiment, the gene is the EGFR gene. In an embodiment, the method includes activating the EGFR gene, thereby treating or preventing cancer progression and metastasis.

In an embodiment, the disease is hereditary angioedema. In an embodiment, the gene is a gene underexpressed in hereditary angioedema. Upregulation or activation of the gene, e.g., by an eiCas9 molecule fused to a transcriptional activator, improves or cures the disease. In an embodiment, the gene is the C1INH gene. In an embodiment, the method includes activating the C1INH gene, thereby treating or preventing hereditary angioedema.

In an embodiment, the disease is Von Willebrand disease. In an embodiment, the gene is underexpressed in Von Willebrand disease. Upregulation or activation of the gene, e.g., by an eiCas9 molecule fused to a transcriptional activator, improves or cures the disease. In an embodiment, the gene is the VWF gene. In an embodiment, the method includes activating the VWF gene, thereby treating or preventing Von Willebrand disease.

In an embodiment, the disease is hereditary or acquired anemia. In an embodiment, the gene is a gene underexpressed in hereditary or acquired anemia. Transient upregulation or activation of the gene, e.g., by an eiCas9 molecule fused to a transcriptional activator, improves or cures the disease. In an embodiment, the gene is the EPO gene. In an embodiment, the method includes activating the EPO gene transiently, thereby treating or preventing the hereditary or acquired anemia.

In an embodiment, the disease is neutropenia. In an embodiment, the gene is a gene underexpressed in neutropenia. WTransient upregulation or activation of the gene, e.g., by an eiCas9 molecule fused to a transcriptional activator, can improve or cure the disease. In an embodiment, the gene is the (CSF2 gene. In an embodiment, the method includes activing the (CSF2 gene transiently, thereby treating or preventing neutropenia.

In an embodiment, the disease is a growth disorder. In an embodiment, the gene is a gene underexpressed in the growth disorder. Transient upregulation or activation of the gene, e.g., by an eiCas9 molecule fused to a transcriptional activator, can improve or cure the disease. In an embodiment, the gene is GH1. In an embodiment, the method includes activating the GH1 gene transiently, thereby treating or preventing the growth disorder.

In an embodiment, the disease is an infectious disease, an autoimmune disease, an inflammatory disease, a rheumatic disease, or an oncologic disease. In an embodiment, the gene encodes a cytokine, a chemokine, an interleukin, or an inflammatory protein. Downregulation or inhibition of a gene encoding a cytokine, a chemokine, an interleukin, or an inflammatory protein, either transiently or permanently, e.g., by an eiCas9 molecule (e.g., an inducible eiCas9 molecule) fused to a transcriptional repressor, can ameliorate or cure disease. In an embodiment, the disease is a hematologic cancer. In an embodiment, the gene is the EPOR gene. In an embodiment, the method includes knocking down the EPOR gene, thereby treating or preventing the hematologic cancer. In an embodiment, the disease is rheumatoid arthritis. In an embodiment, the gene is the TNF gene. In an embodiment, the method includes knocking down the TNF gene, thereby treating or preventing rheumatoid arthritis. In an embodiment, the disease is an inflammatory disease. In an embodiment, the gene is the CS gene. In an embodiment, the method includes knocking down the CS gene, thereby treating or preventing the inflammatory disease.

In an embodiment, the disease is an infectious disease, an autoimmune disease, an inflammatory disease, a rheumatic disease, or an oncologic disease. In an embodiment, the gene encodes a cytokine, a chemokine, an interleukin, or an inflammatory protein. Upregulation or activation of a gene encoding a cytokine, a chemokine, an interleukin, or an inflammatory protein, either transiently or permanently, e.g., by an eiCas9 molecule (e.g., an inducible eiCas9 molecule) fused to a transcriptional activator, can ameliorate or cure disease. In an embodiment, the disease is multiple sclerosis. In an embodiment, the gene is the IFNB1 gene. In an embodiment, the method includes activating the IFNB1 gene, thereby treating or preventing multiple sclerosis.

In an embodiment, the disease is an infectious disease, an autoimmune disease, an inflammatory disease, a rheumatic disease, or an oncologic disease. In an embodiment, the gene encodes a cytokine, a chemokine, an interleukin, or an inflammatory protein receptor. Knockout of a gene encoding a cytokine, a chemokine, an interleukin, or an inflammatory protein, e.g., by an eaCas9 molecule, will ameliorate or cure disease. In an embodiment, the disease is HIV or AIDS. In an embodiment, the gene is CCR5. In another embodiment, the gene is the CXCR4 gene. In an embodiment, the method includes knocking out of the CCR5 gene, the CXCR4 gene, or both, thereby treating or preventing HIV or AIDS.

In an embodiment, the disease is stroke or myocardial infarction. In an embodiment, the gene encodes a soluble blood protein, e.g., a tissue plasminogen activator or a urinary plasminogen activator. Upregulation or activation of the gene, e.g., transiently, e.g., by an eiCas9 molecule fused to a transcriptional, can ameliorate or prevent the disease, e.g., prevents ischemia or dissolves blood clots. In an embodiment, the gene is the PLAT gene. In an embodiment, the method includes activating the PLAT gene, thereby treating or preventing stoke or myocardial infarction.

In an embodiment, the disease is a hemoglobinopathy. In an embodiment, the gene contains a mutation that causes the hemoglobinopathy. In an embodiment, the gene doesn not contain a mutation that causes the hemoglobinopathy. Knockout or correction of the gene can ameliorate or cure the disease. In an embodiment, the gene that contains a mutation is HBB, HBA1, or HBA2. In an embodiment, the method includes correcting a mutated HBB, HBA1, or HBA2 gene, thereby treating or preventing sickle cell disease, alpha thalassemia, or beta thalassemia. In an embodiment, the gene is BCL11A. In an embodiment, the method comprises knocking out the BCL11A gene, thereby treating or preventing sickle cell disease or beta thalassemia.

In an embodiment, the disease is an anemia. In an embodiment, the gene contains a mutation that causes the anemia, e.g., hemolytic anemia, e.g. due to red cell pyruvate kinase deficiency. Knockin or correction of the gene can ameliorate or cure the anemia. In an embodiment, the gene is PKLR. In an embodiment, the method includes correcting knocking in a wild type PKLR gene or correcting a mutated PKLR gene, thereby treating or preventing the anemia, e.g., hemolytic anemia.

In an embodiment, the disease is a clotting factor disease, e.g., hemophilia A. In an embodiment, the gene contains a mutation that causes the clotting factor disease. Correction of the gene can ameliorate or cure the clotting factor disease. In an embodiment, the gene is F8. In an embodiment, the method includes correcting a mutated F8 gene, thereby treating or preventing hemophilia A.

In an embodiment, the disease is a metabolic disease, e.g., mucopolysaccharidosis type I. In an embodiment, the gene contains a mutation that causes the metabolic disease. Knockin or correction of the gene can ameliorate or cure the metabolic disease. In an embodiment, the gene is the IDUA gene. In an embodiment, the method includes knocking in a wild type IDUA gene or correcting a mutated IDUA gene, thereby treating or preventing mucopolysaccharidosis type I.

In an embodiment, the disease is an immunodeficiency, e.g., X-linked severe combined immunodeficiency. In an embodiment, the gene contains a mutation that causes the immunodeficiency. Knockin or correction of the gene can ameliorate or cure the disease. In an embodiment, the gene is the IL2RG gene. In an embodiment, the method includes knocking a wild type IL2RG gene or correcting a mutated IL2RG gene, thereby treating or preventing X-linked severe combined immunodeficiency.

In an embodiment, the disease is a myeloid immunodeficiency, e.g., chronic granulomatous disease. In an embodiment, the gene contains a mutation that causes the myeloid immunodeficiency. Knockin or correction of the gene can ameliorate or cure the disease. In an embodiment, the gene is the NCF1 gene. In an embodiment, the method includes knocking in a wild type NCF1 gene or correcting a mutated NCF1 gene, thereby treating or preventing chronic granulomatous disease.

In an embodiment, the disease a beta-lymphoid or immunoglobulin deficiency, e.g., X-linked agammaglobulinemia. In an embodiment, the gene contains a mutation that is associated with the beta-lymphoid or immunoglobulin deficiency. Knockin or correction of the gene can ameliorate or cure the disease. In an embodiment, the gene is the BTK gene. In an embodiment, the method includes knocking in a wild type BTK gene or correcting a mutated BTK gene, thereby treating or preventing X-linked agammaglobulinemia.

In an embodiment, the disease is a cytopenia disorder, e.g., congenital amegakayoctytic thrombocytopenia type I. In an embodiment, the gene contains a mutation associated with the cytopenia disorder. Knockin or correction of the gene can ameliorate or cure the disease. In an embodiment, the gene is the MPL gene. In an embodiment, the method includes knocking in a wild type MPL gene or correcting a mutated MPL gene, thereby treating or preventing congenital amegakaryoctytic thrombocytopenia type I.

In an embodiment, the disease is a metabolic disease, an enzyme deficiency, a trafficking disorder, or a storage disease, e.g., mucopolysaccharidosis type IIIA. In an embodiment, the gene contains a mutation associated with the metabolic disease, enzyme deficiency, trafficking disorder, or storage disease. Knockin or correction of the gene can ameliorate or cure the disease. In an embodiment, the gene is the SGSH gene. In an embodiment, the method includes knocking in a wild type SGSH gene or correcting a mutated SGSH gene, thereby treating or preventing mucopolysaccharidosis type IIIA.

In an embodiment, the disease is an erythroid disease, e.g., a primary familial and congenital polycythemia. In an embodiment, the gene contains a mutation associated the erythroid disease. Knockin or correction of the gene can ameliorate or cure the disease. In an embodiment, the gene is the EPOR gene. In an embodiment, the method includes knocking down the EPOR gene, either transiently or permanently, thereby treating or preventing the primary familial and congenital polycythemia.

In an embodiment, the disease is an erythroid disease, e.g., a primary familial and congenital polycythemia. In an embodiment, the gene contains a mutation associated the erythroid disease. Knockin or correction of the gene can ameliorate or cure the disease. In an embodiment, the gene is the EPOR gene. In an embodiment, the method includes knocking out or knocking down the EPOR gene, thereby treating or preventing the primary familial and congenital polycythemia.

Table 16 describes exemplary diseases that can be treated or prevented by the methods described herein and exemplary genes that can be altered by the methods described herein.

TABLE 16

| Disease | Gene |
|---|---|
| Hemoglobinopathies | |
| Sickle Cell Disease | HBB |
| Sickle Cell Disease | BCL11a |
| Beta Thalassemia | HBB |
| Beta Thalassemia | BCL11a |
| Alpha Thalassemia | HBA1 |
| Alpha Thalassemia | HBA2 |
| X-linked alpha-thalassemia | ATRX |
| Anemias | |
| Blackfan-Diamond syndrome | RPS19 |
| Fanconi anemia | FANCA, FANCB, FANCC, FANCD1, FANCD2, FANCE, FANCF, FANCG, FANCI, FANCJ, FANCL, FANCM, FANCN, FANCP, RAD51C |
| Hemolytic anemia due to red cell pyruvate kinase deficiency | PKLR |
| Aplastic anemia | IFNG |
| Congenital dyserythropoietic anemia type 2 | SEC23B |
| Hereditary spherocytosis | ANK1 |
| Hereditary spherocytosis | SPTB |
| Hereditary spherocytosis | SPTA |
| Hereditary spherocytosis | SLC4A1 |
| Hereditary spherocytosis | EPB42 |
| Anemia | EPO |
| Neutropenia | CSF2 |
| Neutropenia | CSF3 |
| Disorders of Hemostasis | |
| Von Willebrand Disease | VWF |
| Hemophilia | F7 |
| Hemophilia A | F8 |
| Hemophilia B | F9 |
| Disorder of Hemostasis | F2 |
| Parahemophilia | F5 |
| Bleeding Tendancy | F7 |
| Factor X Deficiency | F10 |
| Disorder of Hemostasis, clotting disorder | F11 |
| Disorder of Hemostasis | F12 |
| Factor XIII deficiency | F13A1 |
| Factor XIII deficiency | F13B |
| Disorder of Hemostasis | PROC |
| Disorder of Hemostasis | PROS1 |
| Thrombosis | SERPINC1 |
| Fibrinogen deficiency/Hypofibrinoginemia | FGA, FGB, FGG |
| Disorder of Hemostasis | PROZ |
| Plasminogen deficiency | PLG |
| Disorder of Hemostasis, cardiovascular disease | PLAT |
| Disorder of Hemostasis, cardiovascular disease | PLAU |
| Disorder of Hemostasis | F3 |

TABLE 16-continued

| Disease | Gene |
|---|---|
| Disorder of Hemostasis | TFPI |
| Disorder of Hemostasis | PAI |
| Thrombophilia due to heparin cofactor II deficiency | HCF2 |
| Metabolic Diseases | |
| Mucopolysaccharidoses | |
| MPS I- Hurler's | IDUA |
| MPS II- Hunter's | IDS |
| MPS-IVA | GALNS |
| MPS-VI | ARSB |
| MPS IIIA | SGSH |
| MPSIIIB- Sanfilippo B Syndrome | NAGLU |
| MPSIIIC | HGSNAT |
| MPS IV | GALNS |
| Severe Immunodeficiencies | |
| X-linked Severe Combined Immunodeficiency | IL2RG |
| ADA Severe Combined Immunodeficiency | ADA |
| IL7-RA Severe Combined Immunodeficiency | IL7R |
| CD3 Severe Combined Immunodeficiency | CD247 |
| RAG1 Severe Combined Immunodeficiency | RAG1 |
| RAG2 Severe Combined Immunodeficiency | RAG2 |
| Artemis Severe Combined Immunodeficiency | DCLRE1C |
| CD45 Severe Combined Immunodeficiency | PTPRC |
| Jak3 Severe Combined Immunodeficiency | JAK3 |
| Cartilage-hair hypoplasia syndrome | RMRP |
| IPEX X-linked Immunodysregulation, polyendocrinopathy, and enteropathy | FOXP3 |
| IPEX-like syndrome | STAT1 |
| Common variable immunodeficiency 1 | ICOS |
| Common variable immunodeficiency 2 | TNFRSF13B |
| Common variable immunodeficiency 3 | CD19 |
| Common variable immunodeficiency 4 | TNFRSF13C |
| Common variable immunodeficiency 5 | CD20 |
| Common variable immunodeficiency 6 | CD81 |
| HIV | CCR5 |
| HIV | CXCR4 |
| Bare lymphocyte Syndrome type II, complementation group E | RFX5 |
| Bare lymphocyte Syndrome type II, complementation group C | RFX5 |
| Bare lymphocyte Syndrome type II, complementation group D | RFXAP |
| Bare lymphocyte Syndrome type II, complementation group A | MHC2TA |
| Bare lymphocyte Syndrome type II | RFXB |
| Bare lymphocyte Syndrome type I | TAP1 |
| Bare lymphocyte Syndrome type I | TAP2 |
| Bare lymphocyte Syndrome type I | TAPBP |
| Myeloid Immunodeficiencies | |
| Congenital agranulocytosis | VPS45 |
| Congenital agranulocytosis | HAX1 |
| Congenital agranulocytosis | ELANE |
| Chronic granulomatous disease | NCF1 |
| Chronic granulomatous disease | CYBB |
| Chronic granulomatous disease | CYBA |
| Chronic granulomatous disease | NCF2 |
| Chronic granulomatous disease | NCF4 |
| Familial hemophagocytic lymphohistiocytosis type 2 | PRF1, HPLH |
| Wiskott-Aldrich syndrome | WAS |
| Chediak-Higashi syndrome | LYST |
| Reticular dysgenesis | AK2 |
| B-lymphoid and Immunoglobulin immunodeficiencies | |
| X-Linked Agammaglobulinemia | BTK |
| X linked hyperimmunoglobulin M | TNFSF5 |
| Hyper IgM type 2 | AICDA |
| Hyper IgM type 3 | CD40 |
| Hyper IgM type 5 | UNG |
| Cytopenia Disorders (with neurologic complications) | |
| Gaucher's disease | GBA |
| Congenital amegakaryocytic thrombocytopenia type I | MPL |
| Metabolic, Enzyme Deficiency, Trafficking, and Storage Diseases | |
| Alpha-mannosidosis | MAN2B1 |
| Lysosomal acid lipase deficiency | LIPA |
| Glycogen Storage Disease 0 | GYS2 |
| Glycogen Storage Disease 1A | G6PC |
| Glycogen Storage Disease 1B | G6PT1/SLC37A4 |
| Glycogen Storage Disease II/Pompe | GAA |
| Glycogen Storage Disease III | AGL |

TABLE 16-continued

| Disease | Gene |
|---|---|
| Glycogen Storage Disease IV | GBE1 |
| Glycogen Storage Disease V | PYGM |
| Glycogen Storage Disease VI | PYGL |
| Glycogen Storage Disease VII | PFKM |
| Glycogen Storage Disease 9a | PHKA2 |
| Glycogen Storage Disease 9b | PHKB |
| Glycogen Storage Disease X | PGAM2 |
| Growth failure, growth abnormalities | GH1 |
| Thyroid disorders | TG |
| Diabetes and disorders of metabolism | INS |
| Diabetes and disorders of metabolism | GCG |
| Friedrich's Ataxia | FXN |
| Metabolic disease; cholesterol disorder | LCAT |
| Metabolic disease; lipoprotein disorder | APOA1 |
| Primary IGF-1 deficiency | IGF1 |
| Aspartylglucosaminuria | AGA |
| Gout | UOX |
| Mucopolysaccharidoses | |
| MPS I- Hurler's | IDUA |
| MPS II- Hunter's | IDS |
| MPS-IVA | GALNS |
| MPS-VI | ARSB |
| MPS IIIA | SGSH |
| MPSIIIB- Sanfilippo B Syndrome | NAGLU |
| Metachromatic leukodystrophy | ARSA |
| Adrenoleukodystrophy | ABCD1 |
| Fabry's disease | GLA |
| Lesch-Nyhan syndrome | HPRT |
| Adenosine deaminase deficiency- ADA | ADA |
| Krabbe Disease | GALC |
| Farber disease | ASAH1 |
| neuronal ceroid lipofuscinosis (NCL) 1 | PPT1 |
| neuronal ceroid lipofuscinosis (NCL) 2 | TPP1 |
| niemann pick type C1 | NPC1 |
| Niemann-Pick type C2 | NPC2 protein |
| Niemann-Pick type A | SMPD1 |
| Niemann-Pick type B | SMPD1 |
| Erythroid Diseases | |
| Polycythemia Vera | JAK2 |
| Polycythemia Vera | TET2 |
| Primary familial and congenital polycythemias (PFCPs) | EPOR |
| Cancer- Metastatic growth | EPOR |
| Paroxysmal nocturnal hemoglobinuria | PIGA |
| Autoimmune disease; inflammatory disease; infectious disease; oncologic disease | |
| Autoimmune disease; inflammatory disease; infectious disease | C5 |
| Autoimmune disease; inflammatory disease; infectious disease | C3 |
| Autoimmune disease; inflammatory disease; GVHD, acute organ rejection | IL6 |
| Autoimmune disease; inflammatory disease; infectious disease, oncologic disease | IL1A, IL1B |
| Autoimmune disease; inflammatory disease; infectious disease, oncologic disease | IL2 |
| Autoimmune disease; inflammatory disease; infectious disease, oncologic disease | IL3 |
| Autoimmune disease; inflammatory disease; infectious disease, oncologic disease | IL7 |
| Autoimmune disease; inflammatory disease; infectious disease, oncologic disease | IL9 |
| Autoimmune disease; inflammatory disease; infectious disease, oncologic disease | IL12 |
| Autoimmune disease; inflammatory disease; infectious disease, oncologic disease | IL17 |
| Autoimmune disease; inflammatory disease; infectious disease, oncologic disease | IL18 |
| Autoimmune disease; inflammatory disease; infectious disease, oncologic disease | IL4 |
| Autoimmune disease; inflammatory disease; infectious disease, oncologic disease | IL10 |
| Autoimmune disease; inflammatory disease; infectious disease, oncologic disease | IL11 |
| Autoimmune disease; inflammatory disease; infectious disease, oncologic disease | IL35 |
| Autoimmune disease; inflammatory disease; infectious disease, oncologic disease | IL26 |
| Autoimmune disease; inflammatory disease; infectious disease, oncologic disease | IL13 |
| Autoimmune disease; inflammatory disease; infectious disease, oncologic disease | IL23 |
| Autoimmune disease; inflammatory disease; infectious disease, oncologic disease | IL27 |
| Autoimmune disease; inflammatory disease; infectious disease, oncologic disease | IFNG |
| Autoimmune disease; inflammatory disease; infectious disease, oncologic disease | CXCL1 |
| Autoimmune disease; inflammatory disease; infectious disease, oncologic disease | CXCL2 |
| Autoimmune disease; inflammatory disease; infectious disease, oncologic disease | CXCL3 |
| Autoimmune disease; inflammatory disease; infectious disease, oncologic disease | CXCL4 |
| Autoimmune disease; inflammatory disease; infectious disease, oncologic disease | CXCL5 |
| Autoimmune disease; inflammatory disease; infectious disease, oncologic disease | CXCL6 |
| Autoimmune disease; inflammatory disease; infectious disease, oncologic disease | CXCL7 |
| Autoimmune disease; inflammatory disease; infectious disease, oncologic disease | CXCL8 |
| Autoimmune disease; inflammatory disease; infectious disease, oncologic disease | CXCL9 |
| Autoimmune disease; inflammatory disease; infectious disease, oncologic disease | CXCL10 |
| Autoimmune disease; inflammatory disease; infectious disease, oncologic disease | CXCL11 |
| Autoimmune disease; inflammatory disease; infectious disease, oncologic disease | CXCL12 |

TABLE 16-continued

| Disease | Gene |
|---|---|
| Autoimmune disease; inflammatory disease; infectious disease, oncologic disease | CXCL13 |
| Autoimmune disease; inflammatory disease; infectious disease, oncologic disease | CXCL14 |
| Autoimmune disease; inflammatory disease; infectious disease, oncologic disease | CXCL15 |
| Autoimmune disease; inflammatory disease; infectious disease, oncologic disease | CXCL16 |
| Autoimmune disease; inflammatory disease; infectious disease, oncologic disease | CCL1 |
| Autoimmune disease; inflammatory disease; infectious disease, oncologic disease | CCL2 |
| Autoimmune disease; inflammatory disease; infectious disease, oncologic disease | CCL3 |
| Autoimmune disease; inflammatory disease; infectious disease, oncologic disease | CCL4 |
| Autoimmune disease; inflammatory disease; infectious disease, oncologic disease | CCL5 |
| Autoimmune disease; inflammatory disease; infectious disease, oncologic disease | CCL6 |
| Autoimmune disease; inflammatory disease; infectious disease, oncologic disease | CCL7 |
| Autoimmune disease; inflammatory disease; infectious disease, oncologic disease | CCL8 |
| Autoimmune disease; inflammatory disease; infectious disease, oncologic disease | CCL9 |
| Autoimmune disease; inflammatory disease; infectious disease, oncologic disease | CCL10 |
| Autoimmune disease; inflammatory disease; infectious disease, oncologic disease | CCL11 |
| Autoimmune disease; inflammatory disease; infectious disease, oncologic disease | CCL12 |
| Autoimmune disease; inflammatory disease; infectious disease, oncologic disease | CCL13 |
| Autoimmune disease; inflammatory disease; infectious disease, oncologic disease | CCL14 |
| Autoimmune disease; inflammatory disease; infectious disease, oncologic disease | CCL15 |
| Autoimmune disease; inflammatory disease; infectious disease, oncologic disease | CCL16 |
| Autoimmune disease; inflammatory disease; infectious disease, oncologic disease | CCL17 |
| Autoimmune disease; inflammatory disease; infectious disease, oncologic disease | CCL18 |
| Autoimmune disease; inflammatory disease; infectious disease, oncologic disease | CCL19 |
| Autoimmune disease; inflammatory disease; infectious disease, oncologic disease | CCL20 |
| Autoimmune disease; inflammatory disease; infectious disease, oncologic disease | CCL21 |
| Autoimmune disease; inflammatory disease; infectious disease, oncologic disease | CCL22 |
| Autoimmune disease; inflammatory disease; infectious disease, oncologic disease | CCL23 |
| Autoimmune disease; inflammatory disease; infectious disease, oncologic disease | CCL24 |
| Autoimmune disease; inflammatory disease; infectious disease, oncologic disease | CCL25 |
| Autoimmune disease; inflammatory disease; infectious disease, oncologic disease | CCL26 |
| Autoimmune disease; inflammatory disease; infectious disease, oncologic disease | CCL27 |
| Autoimmune disease; inflammatory disease; infectious disease, oncologic disease | CCL28 |
| Autoimmune disease; inflammatory disease; infectious disease, oncologic disease | XCL1 |
| Autoimmune disease; inflammatory disease; infectious disease, oncologic disease | XCL2 |
| Autoimmune disease; inflammatory disease; infectious disease, oncologic disease | CX3CL1 |
| Autoimmune disease; inflammatory disease; infectious disease, oncologic disease | CXCR1 |
| Autoimmune disease; inflammatory disease; infectious disease, oncologic disease | CXCR2 |
| Autoimmune disease; inflammatory disease; infectious disease, oncologic disease | CXCR3 |
| Autoimmune disease; inflammatory disease; infectious disease, oncologic disease | CXCR4 |
| Autoimmune disease; inflammatory disease; infectious disease, oncologic disease | CXCR5 |
| Autoimmune disease; inflammatory disease; infectious disease, oncologic disease | CCR1 |
| Autoimmune disease; inflammatory disease; infectious disease, oncologic disease | CCR2 |
| Autoimmune disease; inflammatory disease; infectious disease, oncologic disease | CCR3 |
| Autoimmune disease; inflammatory disease; infectious disease, oncologic disease | CCR4 |
| Autoimmune disease; inflammatory disease; infectious disease, oncologic disease | CCR5 |
| Autoimmune disease; inflammatory disease; infectious disease, oncologic disease | CCR6 |
| Autoimmune disease; inflammatory disease; infectious disease, oncologic disease | CCR7 |
| Autoimmune disease; inflammatory disease; infectious disease, oncologic disease | CCR8 |
| Autoimmune disease; inflammatory disease; infectious disease, oncologic disease | CCR9 |
| Autoimmune disease; inflammatory disease; infectious disease, oncologic disease | CCR10 |
| Autoimmune disease; inflammatory disease; infectious disease, oncologic disease | CCR11 |
| Autoimmune disease; inflammatory disease; infectious disease, oncologic disease | CX3CR1 |
| Autoimmune disease; inflammatory disease; infectious disease, oncologic disease | DARC |
| Hereditary Angioedema | C1INH |
| Inflammatory, Rheumatoid, Oncologic Disease | EGF |
| Inflammatory, Rheumatoid, Oncologic Disease | VEGF |
| Multiple sclerosis | IFNA1, IFNA2, IFNB1 |
| Autoimmune disease; Rheumatoid Arthritis | TNF |
| lymphoma | ABL1 |
| lymphoma | BCL2 |
| lymphoma | BCL11A |
| lymphoma | BCL11B |
| lymphoma | BCR |
| lymphoma | BMI1 |
| lymphoma | BRD2 |
| lymphoma | CCND1 |
| lymphoma | CCND2 |
| lymphoma | CDX2 |
| lymphoma | ETV6 |
| lymphoma | JAK2 |
| lymphoma | JUND |
| lymphoma | KLF6 |
| lymphoma | LCK |
| lymphoma | LMO1 |
| lymphoma | LMO2 |
| lymphoma | LYL1 |
| lymphoma | MLL |

TABLE 16-continued

| Disease | Gene |
|---|---|
| lymphoma | MLLT10 |
| lymphoma | MTCP1 |
| lymphoma | MYC |
| lymphoma | NFKB2 |
| lymphoma | NOTCH1 |
| lymphoma | NUP98 |
| lymphoma | OLIG2 |
| lymphoma | PBX1 |
| lymphoma | PICALM |
| lymphoma | RAP1GDS1 |
| lymphoma | RUNX1 |
| lymphoma | STIL |
| lymphoma | TAL1 |
| lymphoma | TAL2 |
| lymphoma | NKAIN2 |
| lymphoma | TCF3 |
| lymphoma | TCL1A |
| lymphoma | TLX1 |
| lymphoma | TLX3 |
| Oncologic disease/Cancer | FAS |
| Oncologic disease/Cancer | BID |
| Oncologic disease/Cancer | CD152 |
| Oncologic disease/Cancer | PCDCD1 |
| Oncologic disease/Cancer | CBLB |
| Oncologic disease/Cancer | PTPN6 |
| Oncologic disease/Cancer | CD19 |
| Oncologic disease/Cancer | PARP1 |
| Oncologic disease/Cancer | CD223 |
| Oncologic disease/Cancer | CD272 |
| Oncologic disease/Cancer | CD200R1 |
| Oncologic disease/Cancer | TIGIT |
| Oncologic disease/Cancer | LAIR1 |
| Oncologic disease/Cancer | PTGER2 |
| Oncologic disease/Cancer | PTGER4 |
| Oncologic disease/Cancer | CD16 |
| Oncologic disease/Cancer | PDCD1 |
| Oncologic disease/Cancer | HAVCR2 |
| Oncologic disease/Cancer | CD40 |
| Oncologic disease/Cancer | WAS |
| Oncologic disease/Cancer; Leukemia | WT1 |
| Oncologic disease/Cancer; Leukemia | CHK1 |

In an embodiment, the treatment is initiated in a subject after onset of the disease. In an embodiment, the treatment is initiated in a subject after onset of the disease, but early in the course of disease progression (e.g., prior to the development of certain symptoms), e.g., to prevent progression of the disease. In an embodiment, the method comprises initiating treatment of a subject in an advanced stage of disease, e.g., to slow progression of the disease.

In an embodiment, a method described herein is used to treat a subject having a disease described herein. In an embodiment, a method described herein is used to prevent, or delay the onset or progression of, a disease described herein.

In an embodiment, a method described herein results in a selective advantage to survival of one or more of modified cells. In an embodiment, the target cell is modified and has a gene knockout, knockin, knockdown or correction. Diseased cells that are not modified may undergo apoptosis. Thus, in an embodiment, after the treatment described herein, modified cells survive, while unmodified cells die. This selective advantage can drive eventual colonization in cells with at least 50%, e.g., at least 60%, 70%, 80%, 90%, 95%, 99%, or 100% modified cells.

In an embodiment, the method comprises initiating treatment in a subject who undergoes genetic testing which finds a mutation in a gene, e.g., a gene described herein.

In an embodiment, the method comprises initiating treatment in a subject who tests positive for a disease described herein.

In an embodiment, the method comprises initiating treatment in a subject with a family history of the disease who demonstrates any of the symptoms or signs of the disease and/or has been found to have a mutation in a gene associated the disease.

In an embodiment, the method comprises treating a subject at the appearance of a symptom consistent or associated with the disease.

In an embodiment, the method includes isolating a cell from a subject. In an embodiment, a cell is altered ex vivo and returned (e.g., transplanted) to a subject. In an embodiment, the subject is the same subject from whom the cell is isolated. In another embodiment, the subject is different from the subject from whom the cell is isolated. In an embodiment, an autologous stem/progenitor cell is altered ex vivo and returned to the subject. In another embodiment, a heterologous stem/progenitor cell is altered ex vivo and returned into the subject.

In an embodiment, the treatment comprises delivery of a gRNA molecule, a Cas9 molecule, and optionally, a donor template nucleic acid, to a cell described herein. In an embodiment, the gRNA molecule, the Cas9 molecule, or both, and optionally the template nucleic acid, are delivered by a viral vector, e.g., an AAV vector or lentivirus vector, e.g., integration deficient lentivirus (IDLV). In another embodiment, the gRNA molecule and the Cas9 molecule are delivered as a gRNA molecule/Cas9 molecule ribonucleoprotein complex. In another embodiment, the gRNA molecule and the Cas9 molecule are delivered as RNA. In an embodiment, the template nucleic acid comprises at least one exon of the target gene. In an embodiment, the template nucleic acid does not contain the mutation associated with the disease. In an embodiment, the template nucleic acid comprises a promoter sequence. In another embodiment, the template nucleic acid does not comprise a promoter sequence. In an embodiment, the template nucleic acid comprises a splice donor or acceptor. In another embodiment, the template nucleic acid comprises a polyadenylation signal.

Modified Allogeneic Donor HSCs for Transplantation

Transplantation of donor allogeneic HSCs into a subject suffering from an inherited hematologic genetic disease (e.g., Sickle Cell Disease) or malignant disease (e.g., leukemia) would provide a replacement functional hematopoietic system to the recipient patient. If the donor cells are genetically modified to increase HLA matching between a partially matched potential donor and a recipient patient in need of a transplant. In this scenario, potential donors who would normally be excluded as a suitable donor, based on suboptimal HLA matching (e.g., matching between potential donor and recipient patient at 3 out of 6 loci) would be eligible as a donor after gene editing of one or more HLA loci (e.g., increase matching from 3/6 to 4/6, 5/6, or 6/6). However, gene editing of one or more HLA alleles at one or more HLA loci could reduce the mismatching, thus creating a suitable level of HLA matching to be eligible as an HSC donor for the patient in need of HSC transplantation (e.g., 4/6, 5/6, or 6/6 matching at HLA loci). Without the gene editing of the donor HSC to increase matching, the recipient would not have a suitable donor (e.g., 3/6 matching at HLA loci). For treatment, partially matched donors (e.g., 3/6) are identified for the recipient, entered into the database, which then outputs gRNAs that could be used to target deletion of one or more mismatched HLA alleles. The best strategy (gRNAs with lowest off-target profile, highest on-target profile, and if multiplexing, favor targeted allele editing on opposite chromosomes), and most suitable potential donor (e.g., homozygous at HLA matched alleles, greatest degree of matching at miHA, more similar ancestral background) for gene editing would be selected. The efficiency of gene editing would be tested in the donor T cells (prior to modification of donor HSCs, which are in more limited supply compared to peripheral blood T cells). Donor HSCs would be gene edited to increase matching, and then the modified HSCs would be transplanted into the recipient patient. Briefly, the HSCs are collected from the donor, genome-edited ex vivo to delete or disrupt the mismatched HLA, sorted with an immunomagnetic bead strategy (e.g., CliniMACs or Prodigy) to enrich for the HLA allele-negative fraction (e.g., with HLA-allele specific antibody conjugated to magnetic beads for negative selection). The HSCs with reduced mismatching to the recipient would then be infused into the patient. However, if two different alleles at one locus would need to be edited, then another strategy would be allele replacement through an HDR approach. After the HSCs engraft, the HSCs can reconstitute the blood lineages such that the HSC progeny (e.g., blood lineages, e.g., myeloid cells, lymphoid cells, microglia) with a reduced risk of GVHD.

HLA-Modified T Cell Add-Back as Lymphoid Bridge for Immune Reconstitution During HSC Engraftment A subject who is undergoing allogeneic HSC transplantation is at risk for opportunistic infections in the period immediately following transplantation. A subject receives a myeloablative conditioning regimen to prepare for the HSC transplantation, which further depletes T cells that help prevent infection. Immune reconstitution can take several months in the subject. During this time, HSCs from the donor differentiate into T cells, travel to the thymus and are exposed to antigens and begin to reconstitute adaptive immunity.

In a subject who is undergoing allogeneic HSC transplantation, the use of modified T cell add-back in the period immediately following the transplant can provide an adaptive immunity lymphoid bridge. In a non-malignant disease setting, T cells and HSCs of the donor are modified according to the methods, e.g., undergo CRISPR/Cas9-mediated modifications at the to increase matching at HLA loci that are mismatched between donor and recipient. Modification, e.g., CRISPR/Cas9 mediated modifications at HLA loci, renders the donor T cells and HSCs tolerant to potential rejection by the donor autologous immune system. The HLA gene edited T cells dosed in a subject immediately following myeloablative conditioning and prior to allogenic HSC transplant, or co-infused with HSC transplant, or dosed following HSC transplant. These HLA gene editing T cells provide short term immunity against opportunistic infection while the HLA modified HSC transplant is engrafting. The modified T cells used in lymphoid or T cell add-back may have a limited life span (approximately 2 weeks to 60 days to one year) (Westera et al., Blood 2013; 122(13):2205-2212). In the immediate post-transplantation period, these cells could provide protective immunity in a subject. The specific HLA editing events and the cell dose of the add-back T cells could be modified to balance immune protection and Graft vs. Leukemia effect (GVL) in the case were the patient in need of a transplant has blood cancer (e.g., leukemia, lymphoma), and graft versus host disease (a higher risk of GVHD is associated with higher T cell doses) (Montero et al., Biol Blood Marrow Transplant. 2006 December; 12(12):1318-25). The methods described herein can be dosed one, two, three or multiple times, to maintain adaptive immunity and prevent opportunistic infection, until the HLA edited donor HSC cells have reconstituted lymphopoiesis in vivo.

In a subject who is undergoing allogeneic HSC transplantation, the use of HLA-modified erythromyeloid and T cell add-back in the period immediately following the transplant can provide a myeloid and adaptive immunity lymphoid bridge. Donor HSCs are modified according to the methods described herein and differentiated into erythromyeloid and lymphoid progenitor cells ex vivo. The differentiated, HLA edited erythromyeloid and lymphoid cells are dosed in a subject immediately following myeloablative conditioning and prior to allogeneic HSC transplant, or co-infused with HSC transplant, or dosed following HSC transplant. The differentiated HLA modified myeloid and lymphoid cells are dosed together, or are dosed separately, e.g., modified, HLA modified erythromyeloid progenitor cells are dosed in one dosing regimen and modified, HLA modified lymphoid progenitor cells are dosed in an alternative dosing regimen. Administration of HLA modified, differentiated myeloid and lymphoid cells in a subject undergoing HSC transplantation provides a short term erythromyeloid and lymphoid bridge of HLA matched innate and adaptive immune cells. These cells provide short term protection against anemia and short term immunity against opportunistic infection. These cells can have a limited life span. In the immediate post-transplantation period, these cells can improve anemia and provide protective immunity in a subject. The dose of such cells can be modified to balance immune protection and graft versus host disease (a higher risk of GVHD is associated with higher T cell doses) (Montero et al., Biol Blood Marrow Transplant. 2006 December; 12(12):1318-25). The methods described herein can be dosed one, two, three or multiple times, to maintain erythromyeloid and lymphoid cell counts and until the donor HSC cells have reconstituted the myeloid and lymphoid lineage.

Therapeutic Compositions Enriched for Cells with Allele-Specific Genetic Modifications Ex Vivo Disruption (e.g., Knockout) of 1, 2 or 3 HLA-A, HLA-B and/or HLA-DRB1 Alleles in Donor Corneas to Decrease Rates of Corneal Transplant Rejection Corneal transplantation is a common procedure in the United States and worldwide. Every year in the U.S., more than 40,000 patients undergo corneal transplantation. (Eye Bank Association of America 2014 Eye Banking Statistical Report. Available at www.restoresight.org/wp-content/uploads/2015/03/2014_Statistical_Report-FINAL.pdf. Accessed: Jun. 16, 2015). Corneal transplant may be indicated for corneal dystrophies, infections and trauma, which cause opacification of the cornea and vision loss.

About twenty percent of corneal transplant patients reject their corneas, for approximately 6,000-8,000 patients experiencing rejection of a corneal transplant annually in the U.S (Dunn et al., *Cornea* 33(10): 1003-9 (2014)). Patients who experience a rejection event most commonly go on to graft failure, requiring a subsequent corneal transplant.

There are a number of approaches currently being investigated to prevent corneal transplant rejection, including immunosuppression in the eye. However, corneal transplant rejection rates remain high and are often associated with graft failure.

The current disclosure aims to decrease expression of non-matching MHC class I and class II genes, e.g., HLA-A, HLA-B and HLA-DRB1, in order to decrease corneal graft rejection and, ultimately, decrease rates of corneal graft failure. In a mouse model of corneal graft rejection, reduction in the expression of MHC class I antigens has been demonstrated to decrease rates of transplant rejection (Kamiya et al., *Exp Eye Res.* 70(6): 737-43 (2000)). The current methods disrupt (e.g., knock out) non-matching MHC class I genes, which reduces the expression of non-matching MHC class I antigens. The method therefore should reduce the rates of transplant rejection.

The method knocks out 1, 2 or 3 HLA-A, HLA-B, or HLA-DRB1 allele(s) in donor corneas, as follows. The method is identical to the method used to target disruption (e.g., knockout) of HLA-A, HLA-B, or HLA-DRB1 allele(s) in HSCs, except the method is used to target corneal cells, including corneal epithelial cells and corneal stromal cells, e.g., corneal keratocytes.

Disruption (e.g., knockout) of a single HLA allele, for example KO of a single HLA-A, HLA-B or HLA-DRB1, will match the donor to the recipient at 3/6 HLA alleles, with 1/6 donor alleles not being expressed, for an effective 4/6 match regarding foreign antigen recognition. The KO of a single allele will decrease expression of mismatched HLA antigens and decrease risk of corneal transplant rejection.

Disruption (e.g., knockout) of a two HLA alleles (for example KO of an HLA-A allele and an HLA-B allele, an HLA-A allele and a HLA-DRB1 allele, or an HLA-B allele and an HLA-DRB1 allele), will match the donor to the recipient at 3/6 HLA alleles, with 2/6 donor alleles not being expressed, for an effective 5/6 match regarding foreign antigen recognition. The KO of two alleles will decrease expression of mismatched HLA antigens and decrease risk of corneal transplant rejection.

Disruption (e.g., knockout) of a three HLA alleles (for example KO of an HLA-A allele, an HLA-B allele, and an HLA-DRB1 allele), will match the donor to the recipient at 3/6 HLA alleles, with 3/6 donor alleles not being expressed, for an effective 6/6 match regarding foreign antigen recognition. The KO of three alleles will decrease expression of mismatched HLA antigens and decrease risk of corneal transplant rejection.

If a specific HLA allele is associated with higher rates of rejection in corneal transplantation, that HLA allele will be targeted for disruption (e.g., knockout).

The HLA alleles targeted for knock-out are the same as those found in the Example 12: "Knock out of HLA alleles to facilitate matching of HLA genotypes". For example, donor corneas with the HLA-genotype:

| | Donor | | |
|---|---|---|---|
| | HLA Class I | | HLA Class II |
| | HLA-A* | HLA-B* | HLA-DRB1* |
| Allele 1 | 0101g | 0801g | 0301 |
| Allele 2 | 0301g | 0702g | 1501 |

have the most common HLA haplotypes in European population. Knock-out of three HLA alleles, e.g., HLA-A*0301g, HLA-B*0702g, HLA-DRB1*1501, will generate corneal tissue expressing the most common HLA haplotype in individuals of European descent. This tissue would be most likely to match the largest proportion of the European population. The same disruption strategy, e.g., knockout of HLA alleles in donor corneal tissue with the most common haplotypes for a specific population, can be applied to the most common HLA haplotypes for African American, Hispanic, and Asian corneal tissue, as explained in Example 12.

The method can be applied to donor corneas ex vivo. Corneal cells can be modified ex vivo for HLA disruption (e.g., knockout) and transplanted after modification in the donor. Cell types targeted for corneal modification include: corneal epithelial cells, e.g., basal cells, wing cells, surface cells, corneal stromal cells, e.g., keratocytes, fibroblasts, myofibroblasts.

More generally, the systems and methods described herein are useful in the production of therapeutic compositions enriched for (e.g., purified compositions of) cells with allele-specific genetic modifications. An exemplary method for producing enriched populations of cells with allele-specific gene modifications has two general steps: first, a gene editing step in which a population of cells is exposed to or contacted with a CRISPR/Cas9 system capable of associating with and optionally cutting or mutating a single allele of a gene encoding an identifiable gene product, i.e., a gene product that can be detected, whether directly or indirectly. The second step is to identify, collect and/or separate (i.e., to "enrich for") those cells which express the gene product but do not express a variant of the gene product encoded by the targeted allele. Both of these steps is explained more fully below.

Turning first to the gene editing step, a CRISPR/Cas9 system may be configured to associate with a single allele of a gene by incorporating, in a targeting domain of a gRNA molecule, a sequence complementary to a target sequence that is specific to the allele at which editing is desired. The target sequence of the targeted allele may differ from those of non-targeted alleles in any suitable manner that reduces or prevents the association of the gRNA molecule with non-targeted alleles, for instance by means of base-pair differences, insertions, deletions, inversions, duplications, etc. The population of cells are preferably, but not necessarily, exposed to the CRISPR/Cas9 system outside of the body to facilitate the ex-vivo performance of the enrichment step, and may be any cell type or population that is therapeutically useful, for instance an unmanipulated or minimally-manipulated cell fraction from a tissue such as blood or marrow, a purified fraction of cells such as HSCs, or a population that has been purified, treated and/or expanded in vitro. The cells may be taken from a subject into which (or whom) they may be later reintroduced, or may be taken from a donor. Suitable cells and populations of cells are described more generally in the “Target Cells” section below, and means of administering CRISPR/Cas9 systems to such cells or populations are generally explained under “Delivery, Formulations and Routes of Administration”.

As for the enrichment of edited cells, it is facilitated in most (though not all) cases by the detection of the identifiable gene product. In the exemplary embodiments set forth below, the identifiable gene product is a cell surface marker or forms part of a cell surface protein complex, and can be identified in living cells by means of antibody detection, for instance using fluorophore-conjugated antibodies and fluorescence activated cell sorting (FACS). These and other tools are known in the art and are made commercially available by a variety of sources including BD Biosciences (San Jose, CA), Abcam (Cambridge, UK) and others.

In the case of HLA alleles, and other gene products encoding cell surface proteins to which antibodies are available or may be developed, an exemplary FACS-based enrichment process will typically involve contacting a population of cells previously subjected to an allele-specific editing process with two fluorescent antibodies: a first fluorescent antibody that is specifically targeted to a first variant of the identifiable gene product encoded by the allele of the gene targeted in the gene editing step; and a second fluorescent antibody that binds to a second variant of the identifiable gene product encoded by an allele of the gene not targeted in the first step. The second antibody may be specific to the second variant, or it may have broad specificity for multiple variants including the second variant and, optionally, the first variant. During FACS sorting, gates are set for cells that do not express the first variant, identified by low or no fluorescent signal from the first antibody, and cells that do express the second variant, as identified by high signal from the second antibody, and the cells that fall into these gates are collected to form an enriched population of cells with an allele-specific genetic modification.

It should be noted that, in addition to FACS and other flow cytometric detection methods, any other suitable detection method can be used to enrich for edited cells, provided that the method permits detection of gene products encoded by both targeted and non-targeted alleles. As non-limiting examples, conjugated magnetic beads and direct microscopic micromanipulation may both be used to enrich for cells with allele-specific genetic modifications. Detection of non-targeted alleles may be done with a reagent that is specific for a variant encoded by a second, non-targeted allele or that more generally detects multiple or all variants of the gene product. Reagents useful for detecting these gene products can include labeled or tagged antibodies, ligands, agonists, antagonists, aptamers, polynucleotides, polypeptides, etc, that can be detected on or in the cells within the population with sufficient resolution to identify and collect individual cells that express the gene product encoded by non-targeted alleles. As an alternative to direct detection of the gene product, it may be useful to detect a substance or cellular state that is promoted or inhibited by targeted and non-targeted alleles of the gene.

Additionally, while the examples above and throughout the present disclosure focus on deletion or knock-out of the targeted allele, they are readily adaptable to other editing strategies, including those that change the targeted allele to a second allele, provided the second allele encodes a variant of a gene product that is not detected by the first detection antibody or reagent (i.e. the antibody or reagent specific to the unmodified, targeted allele) but are detected by the second antibody or reagent that binds a second variant encoded by a successfully edited allele of the gene.

I. Guide RNA (gRNA) Molecules

A gRNA molecule, as that term is used herein, refers to a nucleic acid that promotes the specific targeting or homing of a gRNA molecule/Cas9 molecule complex to a target nucleic acid. gRNA molecules can be unimolecular (having a single RNA molecule), sometimes referred to herein as “chimeric” gRNAs, or modular (comprising more than one, and typically two, separate RNA molecules). The gRNA molecules provided herein comprise a targeting domain comprising, consisting of, or consisting essentially of a nucleic acid sequence fully or partially complementary to a target nucleic acid sequence in or near the sequences of allelic variants of a specific locus, e.g., HLA-A, HLA-B, HLA-C, HLA-DRB1, HLA-DRB3/4/5, or HLA-DQB1. In certain embodiments, the gRNA molecule further comprises one or more additional domains, including for example a first complementarity domain, a linking domain, a second complementarity domain, a proximal domain, a tail domain, and a 5' extension domain. Each of these domains is discussed in detail below. In certain embodiments, one or more of the domains in the gRNA molecule comprises an amino acid sequence identical to or sharing sequence homology with a naturally occurring sequence, e.g., from *S. pyogenes*, *S. aureus*, or *S. thermophilus*.

Figure 7:
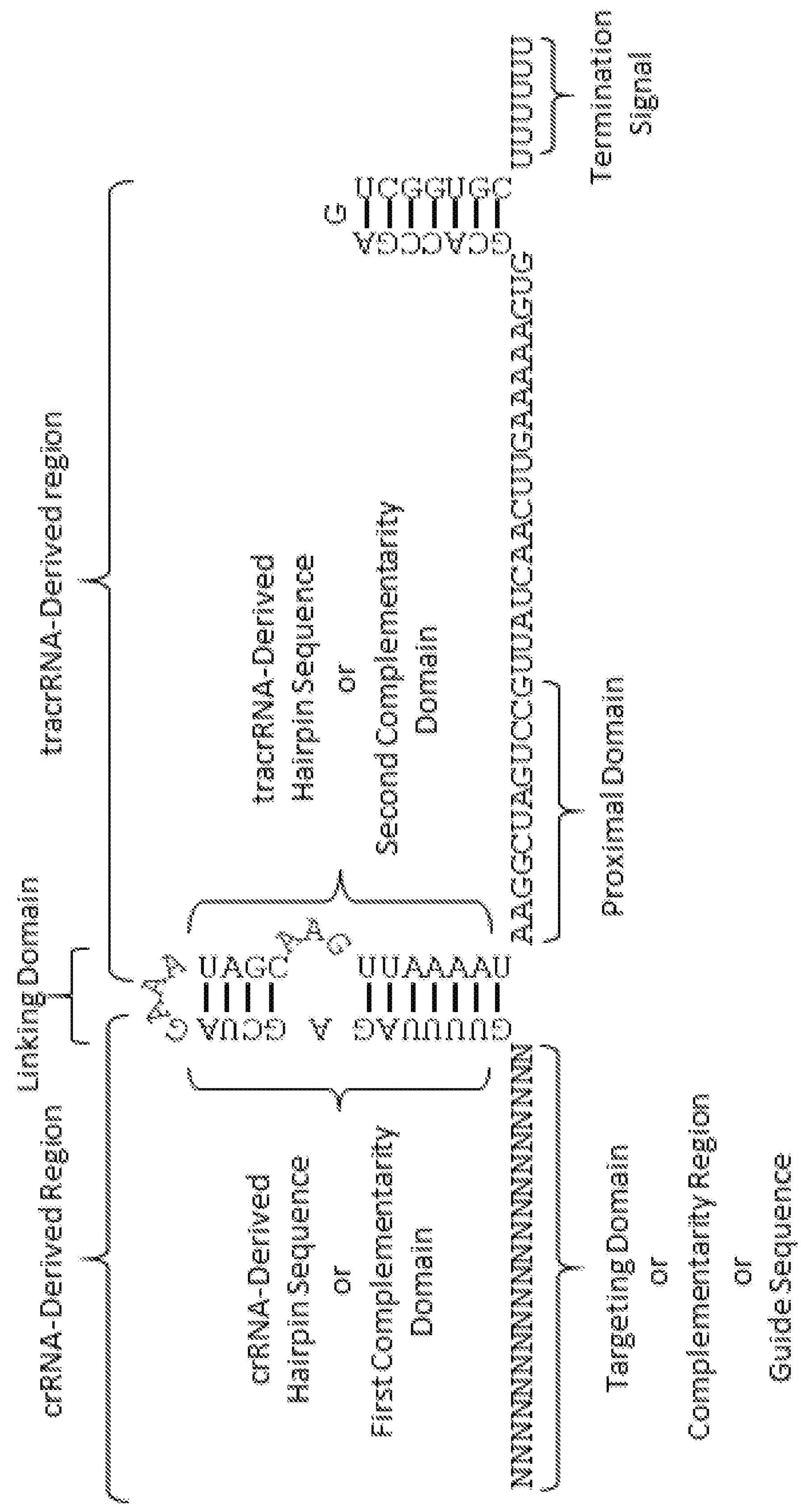
FIG. 7 illustrates gRNA domain nomenclature using an exemplary gRNA sequence (SEQ ID NO:42).

Several exemplary gRNA structures are provided in FIGS. 1A-1I. With regard to the three-dimensional form, or intra- or inter-strand interactions of an active form of a gRNA, regions of high complementarity are sometimes shown as duplexes in FIGS. 1A-1I and other depictions provided herein. FIG. 7 illustrates gRNA domain nomenclature using the gRNA sequence of SEQ ID NO:42, which contains one hairpin loop in the tracrRNA-derived region. In certain embodiments, a gRNA may contain more than one (e.g., two, three, or more) hairpin loops in this region (see, e.g., FIGS. 1H-1I).

In certain embodiments, a unimolecular, or chimeric, gRNA comprises, preferably from 5' to 3': a targeting domain complementary to a target domain in the sequences of allelic variants of a specific locus, e.g., HLA-A, HLA-B, HLA-C, HLA-DRB1, HLA-DRB3/4/5, or HLA-DQB1; a first complementarity domain; a linking domain; a second complementarity domain (which is complementary to the first complementarity domain); a proximal domain; and optionally, a tail domain.

In certain embodiments, a modular gRNA comprises: a first strand comprising, preferably from 5' to 3': a targeting domain complementary to a target domain in the sequences of allelic variants of a specific locus, e.g., HLA-A, HLA-B, HLA-C, HLA-DRB1, HLA-DRB3/4/5, or HLA-DQB1; and a first complementarity domain; and a second strand, comprising, preferably from 5' to 3': optionally, a 5' extension domain; a second complementarity domain: a proximal domain; and optionally, a tail domain.

Targeting Domain

The targeting domain (sometimes referred to alternatively as the guide sequence, or complementarity region) comprises, consists of, or consists essentially of a nucleic acid sequence that is complementary or partially complementary to a nucleic acid sequence in or near the sequences of allelic variants of a specific locus, e.g., HLA-A, HLA-B, HLA-C, HLA-DRB1, HLA-DRB3/4/5, or HLA-DQB1. The nucleic acid sequence in or near the sequences of allelic variants of a specific locus, e.g., HLA-A, HLA-B, HLA-C, HLA-DRB1, HLA-DRB3/4/5, or HLA-DQB1 to which all or a portion of the targeting domain is complementary or partially complementary is referred to herein as the target domain. In certain embodiments, the target domain comprises a target position. In other embodiments, a target position lies outside (i.e., upstream or downstream of) the target domain.

Methods for selecting targeting domains are known in the art (see, e.g., Fu 2014; Sternberg 2014). Examples of suitable targeting domains for use in the methods, compositions, and kits described herein include those set forth in SEQ ID NOs:219-361.

The strand of the target nucleic acid comprising the target domain is referred to herein as the complementary strand because it is complementary to the targeting domain sequence. Since the targeting domain is part of a gRNA molecule, it comprises the base uracil (U) rather than thymine (T); conversely, any DNA molecule encoding the gRNA molecule will comprise thymine rather than uracil. In a targeting domain/target domain pair, the uracil bases in the targeting domain will pair with the adenine bases in the target domain. In certain embodiments, the degree of complementarity between the targeting domain and target domain is sufficient to allow targeting of a Cas9 molecule to the target nucleic acid.

In certain embodiments, the targeting domain comprises a core domain and an optional secondary domain. In certain of these embodiments, the core domain is located 3' to the secondary domain, and in certain of these embodiments the core domain is located at or near the 3' end of the targeting domain. In certain of these embodiments, the core domain consists of or consists essentially of about 8 to about 13 nucleotides at the 3' end of the targeting domain. In certain embodiments, only the core domain is complementary or partially complementary to the corresponding portion of the target domain, and in certain of these embodiments the core domain is fully complementary to the corresponding portion of the target domain. In other embodiments, the secondary domain is also complementary or partially complementary to a portion of the target domain. In certain embodiments, the core domain is complementary or partially complementary to a core domain target in the target domain, while the secondary domain is complementary or partially complementary to a secondary domain target in the target domain. In certain embodiments, the core domain and secondary domain have the same degree of complementarity with their respective corresponding portions of the target domain. In other embodiments, the degree of complementarity between the core domain and its target and the degree of complementarity between the secondary domain and its target may differ. In certain of these embodiments, the core domain may have a higher degree of complementarity for its target than the secondary domain, whereas in other embodiments the secondary domain may have a higher degree of complementarity than the core domain.

In certain embodiments, the targeting domain and/or the core domain within the targeting domain is 3 to 100, 5 to 100, 10 to 100, or 20 to 100 nucleotides in length, and in certain of these embodiments the targeting domain or core domain is 3 to 15, 3 to 20, 5 to 20, 10 to 20, 15 to 20, 5 to 50, 10 to 50, or 20 to 50 nucleotides in length. In certain embodiments, the targeting domain and/or the core domain within the targeting domain is 6, 7, 8, 9, 10, 11, 12, 13, 14, 15, 16, 17, 18, 19, 20, 21, 22, 23, 24, 25, or 26 nucleotides in length. In certain embodiments, the targeting domain and/or the core domain within the targeting domain is 6+/−2, 7+/−2, 8+/−2, 9+/−2, 10+/−2, 10+/−4, 10+/−5, 11+/−2, 12+/−2, 13+/−2, 14+/−2, 15+/−2, or 16+−2, 20+/−5, 30+/−5, 40+/−5, 50+/−5, 60+/−5, 70+/−5, 80+/−5, 90+/−5, or 100+/−5 nucleotides in length.

In certain embodiments wherein the targeting domain includes a core domain, the core domain is 3 to 20 nucleotides in length, and in certain of these embodiments the core domain 5 to 15 or 8 to 13 nucleotides in length. In certain embodiments wherein the targeting domain includes a secondary domain, the secondary domain is 0, 1, 2, 3, 4, 5, 6, 7, 8, 9, 10, 1, 12, 13, 14 or 15 nucleotides in length. In certain embodiments wherein the targeting domain comprises a core domain that is 8 to 13 nucleotides in length, the targeting domain is 26, 25, 24, 23, 22, 21, 20, 19, 18, 17, or 16 nucleotides in length, and the secondary domain is 13 to 18, 12 to 17, 11 to 16, 10 to 15, 9 to 14, 8 to 13, 7 to 12, 6 to 11, 5 to 10, 4 to 9, or 3 to 8 nucleotides in length, respectively.

In certain embodiments, the targeting domain is fully complementary to the target domain. Likewise, where the targeting domain comprises a core domain and/or a secondary domain, in certain embodiments one or both of the core domain and the secondary domain are fully complementary to the corresponding portions of the target domain. In other embodiments, the targeting domain is partially complementary to the target domain, and in certain of these embodiments where the targeting domain comprises a core domain and/or a secondary domain, one or both of the core domain and the secondary domain are partially complementary to the corresponding portions of the target domain. In certain of these embodiments, the nucleic acid sequence of the targeting domain, or the core domain or targeting domain within the targeting domain, is at least 80, 85, 90, or 95% complementary to the target domain or to the corresponding portion of the target domain. In certain embodiments, the targeting domain and/or the core or secondary domains within the targeting domain include one or more nucleotides that are not complementary with the target domain or a portion thereof, and in certain of these embodiments the targeting domain and/or the core or secondary domains within the targeting domain include 1, 2, 3, 4, 5, 6, 7, or 8 nucleotides that are not complementary with the target domain. In certain embodiments, the core domain includes 1, 2, 3, 4, or 5 nucleotides that are not complementary with the corresponding portion of the target domain. In certain embodiments wherein the targeting domain includes one or more nucleotides that are not complementary with the target domain, one or more of said noncomplementary nucleotides are located within five nucleotides of the 5' or 3' end of the targeting domain. In certain of these embodiments, the targeting domain includes 1, 2, 3, 4, or 5 nucleotides within five nucleotides of its 5' end, 3' end, or both its 5' and 3' ends that are not complementary to the target domain. In certain embodiments wherein the targeting domain includes two or more nucleotides that are not complementary to the target domain, two or more of said non-complementary nucleotides are adjacent to one another, and in certain of these embodiments the two or more consecutive non-complementary nucleotides are located within five nucleotides of the 5' or 3' end of the targeting domain. In other embodiments, the two or more consecutive non-complementary nucleotides are both located more than five nucleotides from the 5' and 3' ends of the targeting domain.

In certain embodiments, the targeting domain, core domain, and/or secondary domain do not comprise any modifications. In other embodiments, the targeting domain, core domain, and/or secondary domain, or one or more nucleotides therein, have a modification, including but not limited to the modifications set forth below. In certain embodiments, one or more nucleotides of the targeting domain, core domain, and/or secondary domain may comprise a 2' modification (e.g., a modification at the 2' position on ribose), e.g., a 2-acetylation, e.g., a 2' methylation. In certain embodiments, the backbone of the targeting domain can be modified with a phosphorothioate. In certain embodiments, modifications to one or more nucleotides of the targeting domain, core domain, and/or secondary domain render the targeting domain and/or the gRNA comprising the targeting domain less susceptible to degradation or more bio-compatible, e.g., less immunogenic. In certain embodiments, the targeting domain and/or the core or secondary domains include 1, 2, 3, 4, 5, 6, 7, or 8 or more modifications, and in certain of these embodiments the targeting domain and/or core or secondary domains include 1, 2, 3, or 4 modifications within five nucleotides of their respective 5' ends and/or 1, 2, 3, or 4 modifications within five nucleotides of their respective 3' ends. In certain embodiments, the targeting domain and/or the core or secondary domains comprise modifications at two or more consecutive nucleotides.

In certain embodiments wherein the targeting domain includes core and secondary domains, the core and secondary domains contain the same number of modifications. In certain of these embodiments, both domains are free of modifications. In other embodiments, the core domain includes more modifications than the secondary domain, or vice versa.

In certain embodiments, modifications to one or more nucleotides in the targeting domain, including in the core or secondary domains, are selected to not interfere with targeting efficacy, which can be evaluated by testing a candidate modification using a system as set forth below. gRNAs having a candidate targeting domain having a selected length, sequence, degree of complementarity, or degree of modification can be evaluated using a system as set forth below. The candidate targeting domain can be placed, either alone or with one or more other candidate changes in a gRNA molecule/Cas9 molecule system known to be functional with a selected target, and evaluated.

In certain embodiments, all of the modified nucleotides are complementary to and capable of hybridizing to corresponding nucleotides present in the target domain. In another embodiment, 1, 2, 3, 4, 5, 6, 7, or 8 or more modified nucleotides are not complementary to or capable of hybridizing to corresponding nucleotides present in the target domain.

First and Second Complementarity Domains

The first and second complementarity (sometimes referred to alternatively as the crRNA-derived hairpin sequence and tracrRNA-derived hairpin sequences, respectively) domains are fully or partially complementary to one another. In certain embodiments, the degree of complementarity is sufficient for the two domains to form a duplexed region under at least some physiological conditions. In certain embodiments, the degree of complementarity between the first and second complementarity domains, together with other properties of the gRNA, is sufficient to allow targeting of a Cas9 molecule to a target nucleic acid. Examples of first and second complementary domains are set forth in FIGS. 1A-1G.

In certain embodiments (see, e.g., FIGS. 1A-1B) the first and/or second complementarity domain includes one or more nucleotides that lack complementarity with the corresponding complementarity domain. In certain embodiments, the first and/or second complementarity domain includes 1, 2, 3, 4, 5, or 6 nucleotides that do not complement with the corresponding complementarity domain. For example, the second complementarity domain may contain 1, 2, 3, 4, 5, or 6 nucleotides that do not pair with corresponding nucleotides in the first complementarity domain. In certain embodiments, the nucleotides on the first or second complementarity domain that do not complement with the corresponding complementarity domain loop out from the duplex formed between the first and second complementarity domains. In certain of these embodiments, the unpaired loop-out is located on the second complementarity domain, and in certain of these embodiments the unpaired region begins 1, 2, 3, 4, 5, or 6 nucleotides from the 5' end of the second complementarity domain.

In certain embodiments, the first complementarity domain is 5 to 30, 5 to 25, 7 to 25, 5 to 24, 5 to 23, 7 to 22, 5 to 22, 5 to 21, 5 to 20, 7 to 18, 7 to 15, 9 to 16, or 10 to 14 nucleotides in length, and in certain of these embodiments the first complementarity domain is 5, 6, 7, 8, 9, 10, 11, 12, 13, 14, 15, 16, 17, 18, 19, 20, 21, 22, 23, 24, or 25 nucleotides in length. In certain embodiments, the second complementarity domain is 5 to 27, 7 to 27, 7 to 25, 5 to 24, 5 to 23, 5 to 22, 5 to 21, 7 to 20, 5 to 20, 7 to 18, 7 to 17, 9 to 16, or 10 to 14 nucleotides in length, and in certain of these embodiments the second complementarity domain is 5, 6, 7, 8, 9, 10, 11, 12, 13, 14, 15, 16, 17, 18, 19, 20, 21, 22, 23, 24, 25, or 26 nucleotides in length. In certain embodiments, the first and second complementarity domains are each independently 6+/−2, 7+/−2, 8+/−2, 9+/−2, 10+/−2, 11+/−2, 12+/−2, 13+/−2, 14+/−2, 15+/−2, 16+/−2, 17+/−2, 18+/−2, 19+/−2, or 20+/−2, 21+/−2, 22+/−2, 23+/−2, or 24+/−2 nucleotides in length. In certain embodiments, the second complementarity domain is longer than the first complementarity domain, e.g., 2, 3, 4, 5, or 6 nucleotides longer.

In certain embodiments, the first and/or second complementarity domains each independently comprise three subdomains, which, in the 5' to 3' direction are: a 5' subdomain, a central subdomain, and a 3' subdomain. In certain embodiments, the 5' subdomain and 3' subdomain of the first complementarity domain are fully or partially complementary to the 3' subdomain and 5' subdomain, respectively, of the second complementarity domain.

In certain embodiments, the 5' subdomain of the first complementarity domain is 4 to 9 nucleotides in length, and in certain of these embodiments the 5' domain is 4, 5, 6, 7, 8, or 9 nucleotides in length. In certain embodiments, the 5' subdomain of the second complementarity domain is 3 to 25, 4 to 22, 4 to 18, or 4 to 10 nucleotides in length, and in certain of these embodiments the 5' domain is 3, 4, 5, 6, 7, 8, 9, 10, 11, 12, 13, 14, 15, 16, 17, 18, 19, 20, 21, 22, 23, 24, or 25 nucleotides in length. In certain embodiments, the central subdomain of the first complementarity domain is 1, 2, or 3 nucleotides in length. In certain embodiments, the central subdomain of the second complementarity domain is 1, 2, 3, 4, or 5 nucleotides in length. In certain embodiments, the 3' subdomain of the first complementarity domain is 3 to 25, 4 to 22, 4 to 18, or 4 to 10 nucleotides in length, and in certain of these embodiments the 3' subdomain is 3, 4, 5, 6, 7, 8, 9, 10, 11, 12, 13, 14, 15, 16, 17, 18, 19, 20, 21, 22, 23, 24, or 25 nucleotides in length. In certain embodiments, the 3' subdomain of the second complementarity domain is 4 to 9, e.g., 4, 5, 6, 7, 8, or 9 nucleotides in length.

The first and/or second complementarity domains can share homology with, or be derived from, naturally occurring or reference first and/or second complementarity domain. In certain of these embodiments, the first and/or second complementarity domains have at least 50%, 60%, 70%, 80%, 85%, 90%, or 95% homology with, or differ by no more than 1, 2, 3, 4, 5, or 6 nucleotides from, the naturally occurring or reference first and/or second complementarity domain. In certain of these embodiments, the first and/or second complementarity domains may have at least 50%, 60%, 70%, 80%, 85%, 90%, or 95% homology with homology with a first and/or second complementarity domain from *S. pyogenes* or *S. aureus*.

In certain embodiments, the first and/or second complementarity domains do not comprise any modifications. In other embodiments, the first and/or second complementarity domains or one or more nucleotides therein have a modification, including but not limited to a modification set forth below. In certain embodiments, one or more nucleotides of the first and/or second complementarity domain may comprise a 2' modification (e.g., a modification at the 2' position on ribose), e.g., a 2-acetylation, e.g., a 2' methylation. In certain embodiments, the backbone of the targeting domain can be modified with a phosphorothioate. In certain embodiments, modifications to one or more nucleotides of the first and/or second complementarity domain render the first and/or second complementarity domain and/or the gRNA comprising the first and/or second complementarity less susceptible to degradation or more bio-compatible, e.g., less immunogenic. In certain embodiments, the first and/or second complementarity domains each independently include 1, 2, 3, 4, 5, 6, 7, or 8 or more modifications, and in certain of these embodiments the first and/or second complementarity domains each independently include 1, 2, 3, or 4 modifications within five nucleotides of their respective 5' ends, 3' ends, or both their 5' and 3' ends. In other embodiments, the first and/or second complementarity domains each independently contain no modifications within five nucleotides of their respective 5' ends, 3' ends, or both their 5' and 3' ends. In certain embodiments, one or both of the first and second complementarity domains comprise modifications at two or more consecutive nucleotides.

In certain embodiments, modifications to one or more nucleotides in the first and/or second complementarity domains are selected to not interfere with targeting efficacy, which can be evaluated by testing a candidate modification in the system set forth below. gRNAs having a candidate first or second complementarity domain having a selected length, sequence, degree of complementarity, or degree of modification can be evaluated using a system as set forth below. The candidate complementarity domain can be placed, either alone or with one or more other candidate changes in a gRNA molecule/Cas9 molecule system known to be functional with a selected target, and evaluated.

In certain embodiments, the duplexed region formed by the first and second complementarity domains is, for example, 6, 7, 8, 9, 10, 11, 12, 13, 14, 15, 16, 17, 18, 19, 20, 21, or 22 bp in length, excluding any looped out or unpaired nucleotides.

In certain embodiments, the first and second complementarity domains, when duplexed, comprise 11 paired nucleotides (see, for e.g., gRNA of SEQ ID NO:48). In certain embodiments, the first and second complementarity domains, when duplexed, comprise 15 paired nucleotides (see, e.g., gRNA of SEQ ID NO:50). In certain embodiments, the first and second complementarity domains, when duplexed, comprise 16 paired nucleotides (see, e.g., gRNA of SEQ ID NO:5). In certain embodiments, the first and second complementarity domains, when duplexed, comprise 21 paired nucleotides (see, e.g., gRNA of SEQ ID NO:29).

In certain embodiments, one or more nucleotides are exchanged between the first and second complementarity domains to remove poly-U tracts. For example, nucleotides 23 and 48 or nucleotides 26 and 45 of the gRNA of SEQ ID NO:48 may be exchanged to generate the gRNA of SEQ ID NOs:49 or 31, respectively. Similarly, nucleotides 23 and 39 of the gRNA of SEQ ID NO:29 may be exchanged with nucleotides 50 and 68 to generate the gRNA of SEQ ID NO:30.

Linking Domain

The linking domain is disposed between and serves to link the first and second complementarity domains in a unimolecular or chimeric gRNA. FIGS. 1B-1E provide examples of linking domains. In certain embodiments, part of the linking domain is from a crRNA-derived region, and another part is from a tracrRNA-derived region.

In certain embodiments, the linking domain links the first and second complementarity domains covalently. In certain of these embodiments, the linking domain consists of or comprises a covalent bond. In other embodiments, the linking domain links the first and second complementarity domains non-covalently. In certain embodiments, the linking domain is ten or fewer nucleotides in length, e.g., 1, 2, 3, 4, 5, 6, 7, 8, 9, or 10 nucleotides. In other embodiments, the linking domain is greater than 10 nucleotides in length, e.g., 11, 12, 13, 14, 15, 16, 17, 18, 19, 20, 21, 22, 23, 24, or 25 or more nucleotides. In certain embodiments, the linking domain is 2 to 50, 2 to 40, 2 to 30, 2 to 20, 2 to 10, 2 to 5, 10 to 100, 10 to 90, 10 to 80, 10 to 70, 10 to 60, 10 to 50, 10 to 40, 10 to 30, 10 to 20, 10 to 15, 20 to 100, 20 to 90, 20 to 80, 20 to 70, 20 to 60, 20 to 50, 20 to 40, 20 to 30, or 20 to 25 nucleotides in length. In certain embodiments, the linking domain is 10+/−5, 20+/−5, 20+/−10, 30+/−5, 30+/−10, 40+/−5, 40+/−10, 50+/−5, 50+/−10, 60+/−5, 60+/−10, 70+/−5, 70+/−10, 80+/−5, 80+/−10, 90+/−5, 90+/−10, 100+/−5, or 100+/−10 nucleotides in length.

In certain embodiments, the linking domain shares homology with, or is derived from, a naturally occurring sequence, e.g., the sequence of a tracrRNA that is 5' to the second complementarity domain. In certain embodiments, the linking domain has at least 50%, 60%, 70%, 80%, 90%, or 95% homology with or differs by no more than 1, 2, 3, 4, 5, or 6 nucleotides from a linking domain disclosed herein, e.g., the linking domains of FIGS. 1B-1E.

In certain embodiments, the linking domain does not comprise any modifications. In other embodiments, the linking domain or one or more nucleotides therein have a modification, including but not limited to the modifications set forth below. In certain embodiments, one or more nucleotides of the linking domain may comprise a 2' modification (e.g., a modification at the 2' position on ribose), e.g., a 2-acetylation, e.g., a 2' methylation. In certain embodiments, the backbone of the linking domain can be modified with a phosphorothioate. In certain embodiments, modifications to one or more nucleotides of the linking domain render the linking domain and/or the gRNA comprising the linking domain less susceptible to degradation or more bio-compatible, e.g., less immunogenic. In certain embodiments, the linking domain includes 1, 2, 3, 4, 5, 6, 7, or 8 or more modifications, and in certain of these embodiments the linking domain includes 1, 2, 3, or 4 modifications within five nucleotides of its 5' and/or 3' end. In certain embodiments, the linking domain comprises modifications at two or more consecutive nucleotides.

In certain embodiments, modifications to one or more nucleotides in the linking domain are selected to not interfere with targeting efficacy, which can be evaluated by testing a candidate modification using a system as set forth below. gRNAs having a candidate linking domain having a selected length, sequence, degree of complementarity, or degree of modification can be evaluated in a system as set forth below. The candidate linking domain can be placed, either alone or with one or more other candidate changes in a gRNA molecule/Cas9 molecule system known to be functional with a selected target, and evaluated.

In certain embodiments, the linking domain comprises a duplexed region, typically adjacent to or within 1, 2, or 3 nucleotides of the 3' end of the first complementarity domain and/or the 5' end of the second complementarity domain. In certain of these embodiments, the duplexed region of the linking region is 10+/−5, 15+/−5, 20+/−5, 20+/−10, or 30+/−5 bp in length. In certain embodiments, the duplexed region of the linking domain is 1, 2, 3, 4, 5, 6, 7, 8, 9, 10, 11, 12, 13, 14, or 15 bp in length. In certain embodiments, the sequences forming the duplexed region of the linking domain are fully complementarity. In other embodiments, one or both of the sequences forming the duplexed region contain one or more nucleotides (e.g., 1, 2, 3, 4, 5, 6, 7, or 8 nucleotides) that are not complementary with the other duplex sequence.

5' Extension Domain

In certain embodiments, a modular gRNA as disclosed herein comprises a 5' extension domain, i.e., one or more additional nucleotides 5' to the second complementarity domain (see, e.g., FIG. 1A). In certain embodiments, the 5' extension domain is 2 to 10 or more, 2 to 9, 2 to 8, 2 to 7, 2 to 6, 2 to 5, or 2 to 4 nucleotides in length, and in certain of these embodiments the 5' extension domain is 2, 3, 4, 5, 6, 7, 8, 9, or 10 or more nucleotides in length.

In certain embodiments, the 5' extension domain nucleotides do not comprise modifications, e.g., modifications of the type provided below. However, in certain embodiments, the 5' extension domain comprises one or more modifications, e.g., modifications that it render it less susceptible to degradation or more bio-compatible, e.g., less immunogenic. By way of example, the backbone of the 5' extension domain can be modified with a phosphorothioate, or other modification(s) as set forth below. In certain embodiments, a nucleotide of the 5' extension domain can comprise a 2' modification (e.g., a modification at the 2' position on ribose), e.g., a 2-acetylation, e.g., a 2' methylation, or other modification(s) as set forth below.

In certain embodiments, the 5' extension domain can comprise as many as 1, 2, 3, 4, 5, 6, 7, or 8 modifications. In certain embodiments, the 5' extension domain comprises as many as 1, 2, 3, or 4 modifications within 5 nucleotides of its 5' end, e.g., in a modular gRNA molecule. In certain embodiments, the 5' extension domain comprises as many as 1, 2, 3, or 4 modifications within 5 nucleotides of its 3' end, e.g., in a modular gRNA molecule.

In certain embodiments, the 5' extension domain comprises modifications at two consecutive nucleotides, e.g., two consecutive nucleotides that are within 5 nucleotides of the 5' end of the 5' extension domain, within 5 nucleotides of the 3' end of the 5' extension domain, or more than 5 nucleotides away from one or both ends of the 5' extension domain. In certain embodiments, no two consecutive nucleotides are modified within 5 nucleotides of the 5' end of the 5' extension domain, within 5 nucleotides of the 3' end of the 5' extension domain, or within a region that is more than 5 nucleotides away from one or both ends of the 5' extension domain. In certain embodiments, no nucleotide is modified within 5 nucleotides of the 5' end of the 5' extension domain, within 5 nucleotides of the 3' end of the 5' extension domain, or within a region that is more than 5 nucleotides away from one or both ends of the 5' extension domain.

Modifications in the 5' extension domain can be selected so as to not interfere with gRNA molecule efficacy, which can be evaluated by testing a candidate modification in a system as set forth below. gRNAs having a candidate 5' extension domain having a selected length, sequence, degree of complementarity, or degree of modification, can be evaluated in a system as set forth below. The candidate 5' extension domain can be placed, either alone, or with one or more other candidate changes in a gRNA molecule/Cas9 molecule system known to be functional with a selected target and evaluated.

In certain embodiments, the 5' extension domain has at least 60, 70, 80, 85, 90 or 95% homology with, or differs by no more than 1, 2, 3, 4, 5, or 6 nucleotides from, a reference 5' extension domain, e.g., a naturally occurring, e.g., an *S. pyogenes, S. aureus*, or *S. thermophilus,* 5' extension domain, or a 5' extension domain described herein, e.g., from FIGS. 1A-1G.

Proximal Domain

FIGS. 1A-1G provide examples of proximal domains.

In certain embodiments, the proximal domain is 5 to 20 or more nucleotides in length, e.g., 5, 6, 7, 8, 9, 10, 11, 12, 13, 14, 15, 16, 17, 18, 19, 20, 21, 22, 23, 24, 25, or 26 nucleotides in length. In certain of these embodiments, the proximal domain is 6+/−2, 7+/−2, 8+/−2, 9+/−2, 10+/−2, 11+/−2, 12+/−2, 13+/−2, 14+/−2, 14+/−2, 16+/−2, 17+/−2, 18+/−2, 19+/−2, or 20+/−2 nucleotides in length. In certain embodiments, the proximal domain is 5 to 20, 7, to 18, 9 to 16, or 10 to 14 nucleotides in length.

In certain embodiments, the proximal domain can share homology with or be derived from a naturally occurring proximal domain. In certain of these embodiments, the proximal domain has at least 50%, 60%, 70%, 80%, 85%, 90%, or 95% homology with or differs by no more than 1, 2, 3, 4, 5, or 6 nucleotides from a proximal domain disclosed herein, e.g., an *S. pyogenes, S. aureus*, or *S. thermophilus* proximal domain, including those set forth in FIGS. 1A-1G.

In certain embodiments, the proximal domain does not comprise any modifications. In other embodiments, the proximal domain or one or more nucleotides therein have a modification, including but not limited to the modifications set forth in herein. In certain embodiments, one or more nucleotides of the proximal domain may comprise a 2' modification (e.g., a modification at the 2' position on ribose), e.g., a 2-acetylation, e.g., a 2' methylation. In certain embodiments, the backbone of the proximal domain can be modified with a phosphorothioate. In certain embodiments, modifications to one or more nucleotides of the proximal domain render the proximal domain and/or the gRNA comprising the proximal domain less susceptible to degradation or more bio-compatible, e.g., less immunogenic. In certain embodiments, the proximal domain includes 1, 2, 3, 4, 5, 6, 7, or 8 or more modifications, and in certain of these embodiments the proximal domain includes 1, 2, 3, or 4 modifications within five nucleotides of its 5' and/or 3' end.

In certain embodiments, the proximal domain comprises modifications at two or more consecutive nucleotides.

In certain embodiments, modifications to one or more nucleotides in the proximal domain are selected to not interfere with targeting efficacy, which can be evaluated by testing a candidate modification in a system as set forth below. gRNAs having a candidate proximal domain having a selected length, sequence, degree of complementarity, or degree of modification can be evaluated in a system as set forth below. The candidate proximal domain can be placed, either alone or with one or more other candidate changes in a gRNA molecule/Cas9 molecule system known to be functional with a selected target, and evaluated.

Tail Domain

A broad spectrum of tail domains are suitable for use in the gRNA molecules disclosed herein. FIGS. 1A and 1C-1G provide examples of such tail domains.

In certain embodiments, the tail domain is absent. In other embodiments, the tail domain is 1 to 100 or more nucleotides in length, e.g., 1, 2, 3, 4, 5, 6, 7, 8, 9, 10, 20, 30, 40, 50, 60, 70, 80, 90, or 100 nucleotides in length. In certain embodiments, the tail domain is 1 to 5, 1 to 10, 1 to 15, 1 to 20, 1 to 50, 10 to 100, 20 to 100, 10 to 90, 20 to 90, 10 to 80, 20 to 80, 10 to 70, 20 to 70, 10 to 60, 20 to 60, 10 to 50, 20 to 50, 10 to 40, 20 to 40, 10 to 30, 20 to 30, 20 to 25, 10 to 20, or 10 to 15 nucleotides in length. In certain embodiments, the tail domain is 5+/−5, 10+/−5, 20+/−10, 20+/−5, 25+/−10, 30+/−10, 30+/−5, 40+/−10, 40+/−5, 50+/−10, 50+/−5, 60+/−10, 60+/−5, 70+/−10, 70+/−5, 80+/−10, 80+/−5, 90+/−10, 90+/−5, 100+/−10, or 100+/−5 nucleotides in length.

In certain embodiments, the tail domain can share homology with or be derived from a naturally occurring tail domain or the 5' end of a naturally occurring tail domain. In certain of these embodiments, the proximal domain has at least 50%, 60%, 70%, 80%, 85%, 90%, or 95% homology with or differs by no more than 1, 2, 3, 4, 5, or 6 nucleotides from a naturally occurring tail domain disclosed herein, e.g., an *S. pyogenes, S. aureus*, or *S. thermophilus* tail domain, including those set forth in FIGS. 1A and 1C-1G.

In certain embodiments, the tail domain includes sequences that are complementary to each other and which, under at least some physiological conditions, form a duplexed region. In certain of these embodiments, the tail domain comprises a tail duplex domain which can form a tail duplexed region. In certain embodiments, the tail duplexed region is 3, 4, 5, 6, 7, 8, 9, 10, 11, or 12 bp in length. In certain embodiments, the tail domain comprises a single stranded domain 3' to the tail duplex domain that does not form a duplex. In certain of these embodiments, the single stranded domain is 3 to 10 nucleotides in length, e.g., 3, 4, 5, 6, 7, 8, 9, 10, or 4 to 6 nucleotides in length.

In certain embodiments, the tail domain does not comprise any modifications. In other embodiments, the tail domain or one or more nucleotides therein have a modification, including but not limited to the modifications set forth herein. In certain embodiments, one or more nucleotides of the tail domain may comprise a 2' modification (e.g., a modification at the 2' position on ribose), e.g., a 2-acetylation, e.g., a 2' methylation. In certain embodiments, the backbone of the tail domain can be modified with a phosphorothioate. In certain embodiments, modifications to one or more nucleotides of the tail domain render the tail domain and/or the gRNA comprising the tail domain less susceptible to degradation or more bio-compatible, e.g., less immunogenic. In certain embodiments, the tail domain includes 1, 2, 3, 4, 5, 6, 7, or 8 or more modifications, and in certain of these embodiments the tail domain includes 1, 2, 3, or 4 modifications within five nucleotides of its 5' and/or 3' end. In certain embodiments, the tail domain comprises modifications at two or more consecutive nucleotides.

In certain embodiments, modifications to one or more nucleotides in the tail domain are selected to not interfere with targeting efficacy, which can be evaluated by testing a candidate modification as set forth below. gRNAs having a candidate tail domain having a selected length, sequence, degree of complementarity, or degree of modification can be evaluated using a system as set forth below. The candidate tail domain can be placed, either alone or with one or more other candidate changes in a gRNA molecule/Cas9 molecule system known to be functional with a selected target, and evaluated.

In certain embodiments, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. When a U6 promoter is used for in vivo transcription, these nucleotides may be the sequence UUUUUU. When an H1 promoter is used for transcription, these nucleotides may be the sequence UUUU. When alternate pol-III promoters are used, these nucleotides may be various numbers of uracil bases depending on, e.g., the termination signal of the pol-III promoter, or they may include alternate bases.

In certain embodiments, the proximal and tail domain taken together comprise, consist of, or consist essentially of the sequence set forth in SEQ ID NOs:32, 33, 34, 35, 36, or 37.

In Vivo and In Vitro Transcription of gRNAs

Given that the T7 RNA polymerase requires a G to initiate transcription, the T7 promoter typically has two Gs at its 3' end (e.g., TAATACGACTCACTATAGG the 3' end two Gs are underlined (SEQ ID NO:209)) to ensure transcription of the entire gRNA sequence downstream of the promoter. The consequence, however, is that the transcript that is produced may contain at least one if not both of the Gs from the promoter sequence, which may alter the gRNA specificity or the interaction between the gRNA and the Cas9 protein. To address this concern in cases where the gRNA target sequence starts with a G (e.g., the targeting domain of a gRNA molecule to be prepared by in vitro transcription using a T7 promoter contains the following targeting domain sequence: GTAACGGCAGACTTCTCCTC (SEQ ID NO:206), the T7 promoter sequence encoded in the gRNA PCR template can be modified such that only one of the Gs at the 3' end of the T7 promoter was removed: (modified T7 promoter sequence: TAATACGACTCACTATA (SEQ ID NO:211). Thus a 5' sense primer of the gRNA PCR template can be designed as: CACCGCTAGCTAATACGACTCACTATAGTAACGGCAGACTTCTCCTCGTTTTAGAGCTAG AAATA (SEQ ID NO:207), where the modified T7 promoter sequence is underlined). For gRNA target sequences that don't start with a G (e.g., the targeting domain of a gRNA molecule to be prepared by in vitro transcription using a T7 promoter contains the following targeting domain sequence: AAGGTGAACGTGGATGAAGT (SEQ ID NO:208), the T7 promoter sequence encoded in the gRNA PCR template can be modified such that only one of the Gs at the 3' end of the T7 promoter was removed: (modified T7 promoter sequence: TAATACGACTCACTATAG (SEQ ID NO:210).

A T7 promoter sequence and modified T7 promoter sequence is not limited to the sequences described herein.

For example, T7 promoter sequences (and modifications thereof) can be at least any of the sequences referred to in "Promoters/Catalog/T7" of the Registry of Standard Biological Parts (located at the following address: parts.igem.org/Promoters/Catalog/T7). It is to be understood that the present disclosure encompasses methods where a gRNA disclosed herein is prepared by in vitro transcription from a DNA template that includes a modified T7 promoter as described herein where one or more of the 3' terminal Gs have been removed (e.g., where the sequence TAATACGACTCACTATAG (SEQ ID NO:210) is located immediately upstream of a targeting domain that lacks a Gat it's 5' end or the sequence TAATACGACTCACTATA (SEQ ID NO:211) is located immediately upstream of a targeting domain that has a G at it's 5' end). Other variations on these modified T7 promoters will be recognized by those skilled in the art based on other T7 promoter sequences including at least any of the sequences referred to in "Promoters/Catalog/T7" of the Registry of Standard Biological Parts (located at the following address: parts.igem.org/Promoters/Catalog/T7 and incorporated herein by reference in its entirety).

Exemplary Unimolecular/Chimeric gRNAs

In certain embodiments, a unimolecular or chimeric gRNA as disclosed herein has the structure: 5' [targeting domain]-[first complementarity domain]-[linking domain]-[second complementarity domain]-[proximal domain]-[tail domain]-3', wherein:

the targeting domain comprises a core domain and optionally a secondary domain, and is 10 to 50 nucleotides in length;

the first complementarity domain is 5 to 25 nucleotides in length and, in certain embodiments has at least 50, 60, 70, 80, 85, 90, or 95% homology with a reference first complementarity domain disclosed herein;

the linking domain is 1 to 5 nucleotides in length;

the second complementarity domain is 5 to 27 nucleotides in length and, in certain embodiments has at least 50, 60, 70, 80, 85, 90, or 95% homology with a reference second complementarity domain disclosed herein;

the proximal domain is 5 to 20 nucleotides in length and, in certain embodiments has at least 50, 60, 70, 80, 85, 90, or 95% homology with a reference proximal domain disclosed herein; and the tail domain is absent or a nucleotide sequence is 1 to 50 nucleotides in length and, in certain embodiments has at least 50, 60, 70, 80, 85, 90, or 95% homology with a reference tail domain disclosed herein.

In certain embodiments, a unimolecular gRNA as disclosed herein comprises, preferably from 5' to 3': a targeting domain, e.g., comprising 10-50 nucleotides; a first complementarity domain, e.g., comprising 15, 16, 17, 18, 19, 20, 21, 22, 23, 24, 25, or 26 nucleotides; a linking domain: a second complementarity domain: a proximal domain; and a tail domain, wherein.

(a) the proximal and tail domain, when taken together, comprise at least 15, 18, 20, 25, 30, 31, 35, 40, 45, 49, 50, or 53 nucleotides;

(b) there are at least 15, 18, 20, 25, 30, 31, 35, 40, 45, 49, 50, or 53 nucleotides 3' to the last nucleotide of the second complementarity domain; or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the sequence from (a), (b), and/or (c) has at least 50%, 60%, 70%, 75%, 80%, 85%, 90%, 95%, or 99% homology with the corresponding sequence of a naturally occurring gRNA, or with a gRNA described herein.

In certain embodiments, the proximal and tail domain, when taken together, comprise at least 15, 18, 20, 25, 30, 31, 35, 40, 45, 49, 50, or 53 nucleotides.

In certain embodiments, there are at least 15, 18, 20, 25, 30, 31, 35, 40, 45, 49, 50, or 53 nucleotides 3' to the last nucleotide of the second complementarity domain.

In certain embodiments, there are at least 16, 19, 21, 26, 31, 32, 36, 41, 46, 50, 51, or 54 nucleotides 3' to the last nucleotide of the second complementarity domain that are complementary to the corresponding nucleotides of the first complementarity domain.

In certain embodiments, the targeting domain consists of, consists essentially of, or comprises 16, 17, 18, 19, 20, 21, 22, 23, 24, 25, or 26 nucleotides (e.g., 16, 17, 18, 19, 20, 21, 22, 23, 24, 25, or 26 consecutive nucleotides) complementary or partially complementary to the target domain or a portion thereof, e.g., the targeting domain is 16, 17, 18, 19, 20, 21, 22, 23, 24, 25, or 26 nucleotides in length. In certain of these embodiments, the targeting domain is complementary to the target domain over the entire length of the targeting domain, the entire length of the target domain, or both.

In certain embodiments, a unimolecular or chimeric gRNA molecule disclosed herein (comprising a targeting domain, a first complementary domain, a linking domain, a second complementary domain, a proximal domain and, optionally, a tail domain) comprises the amino acid sequence set forth in SEQ ID NO:42, wherein the targeting domain is listed as 20 Ns (residues 1-20) but may range in length from 16 to 26 nucleotides and wherein the final six residues (residues 97-102) represent a termination signal for the U6 promoter but may be absent or fewer in number. In certain embodiments, the unimolecular, or chimeric, gRNA molecule is a *S. pyogenes* gRNA molecule.

In certain embodiments, a unimolecular or chimeric gRNA molecule disclosed herein (comprising a targeting domain, a first complementary domain, a linking domain, a second complementary domain, a proximal domain and, optionally, a tail domain) comprises the amino acid sequence set forth in SEQ ID NO:38, wherein the targeting domain is listed as 20 Ns (residues 1-20) but may range in length from 16 to 26 nucleotides, and wherein the final six residues (residues 97-102) represent a termination signal for the U6 promoter but may be absent or fewer in number. In certain embodiments, the unimolecular or chimeric gRNA molecule is an *S. aureus* gRNA molecule.

Figure 1H:
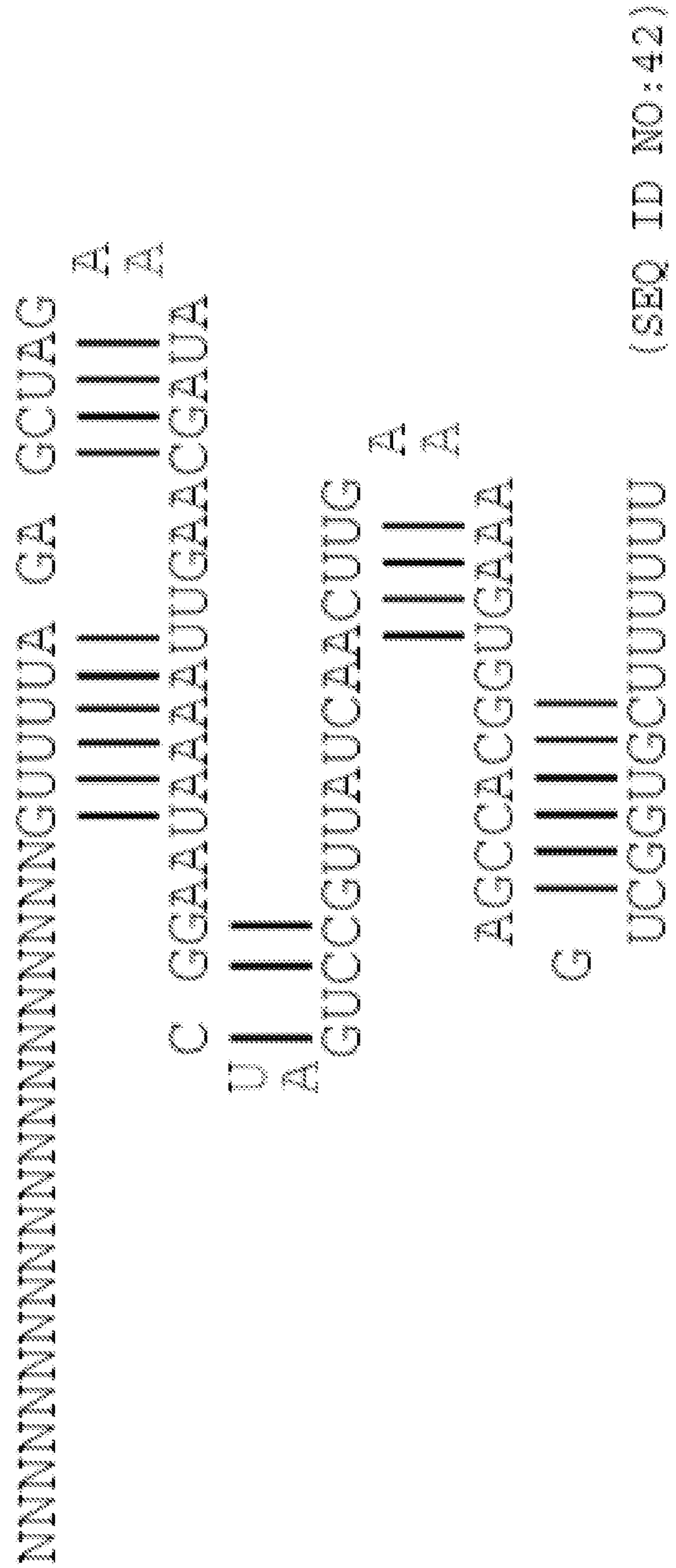

The sequences and structures of exemplary chimeric gRNAs are also shown in FIGS. 1H-1I.

Exemplary Modular gRNAs

In certain embodiments, a modular gRNA disclosed herein comprises: a first strand comprising, preferably from 5' to 3'; a targeting domain, e.g., comprising 15, 16, 17, 18, 19, 20, 21, 22, 23, 24, 25, or 26 nucleotides; a first complementarity domain; and a second strand, comprising, preferably from 5' to 3': optionally a 5' extension domain: a second complementarity domain; a proximal domain; and a tail domain, wherein:

(a) the proximal and tail domain, when taken together, comprise at least 15, 18, 20, 25, 30, 31, 35, 40, 45, 49, 50, or 53 nucleotides;

(b) there are at least 15, 18, 20, 25, 30, 31, 35, 40, 45, 49, 50, or 53 nucleotides 3' to the last nucleotide of the second complementarity domain; or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the sequence from (a), (b), or (c), has at least 60, 75, 80, 85, 90, 95, or 99% homology with the corresponding sequence of a naturally occurring gRNA, or with a gRNA described herein.

In certain embodiments, the proximal and tail domain, when taken together, comprise at least 15, 18, 20, 25, 30, 31, 35, 40, 45, 49, 50, or 53 nucleotides.

In certain embodiments, there are at least 15, 18, 20, 25, 30, 31, 35, 40, 45, 49, 50, or 53 nucleotides 3' to the last nucleotide of the second complementarity domain.

In certain embodiments, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 16, 17, 18, 19, 20, 21, 22, 23, 24, 25, or 26 nucleotides (e.g., 16, 17, 18, 19, 20, 21, 22, 23, 24, 25, or 26 consecutive nucleotides) having complementarity with the target domain, e.g., the targeting domain is 16, 17, 18, 19, 20, 21, 22, 23, 24, 25, or 26 nucleotides in length.

In certain embodiments, the targeting domain consists of, consists essentially of, or comprises 16, 17, 18, 19, 20, 21, 22, 23, 24, 25, or 26 nucleotides (e.g., 16, 17, 18, 19, 20, 21, 22, 23, 24, 25, or 26 consecutive nucleotides) complementary to the target domain or a portion thereof. In certain of these embodiments, the targeting domain is complementary to the target domain over the entire length of the targeting domain, the entire length of the target domain, or both.

In certain embodiments, the targeting domain comprises, consists of, or consists essentially of 16 nucleotides (e.g., 16 consecutive nucleotides) having complementarity with the target domain, e.g., the targeting domain is 16 nucleotides in length. In certain embodiments of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 17 nucleotides (e.g., 17 consecutive nucleotides) having complementarity with the target domain, e.g., the targeting domain is 17 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 18 nucleotides (e.g., 18 consecutive nucleotides) having complementarity with the target domain, e.g., the targeting domain is 18 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 19 nucleotides (e.g., 19 consecutive nucleotides) having complementarity with the target domain, e.g., the targeting domain is 19 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 20 nucleotides (e.g., 20 consecutive nucleotides) having complementarity with the target domain, e.g., the targeting domain is 20 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 21 nucleotides (e.g., 21 consecutive nucleotides) having complementarity with the target domain, e.g., the targeting domain is 21 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 22 nucleotides (e.g., 22 consecutive nucleotides) having complementarity with the target domain, e.g., the targeting domain is 22 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 23 nucleotides (e.g., 23 consecutive nucleotides) having complementarity with the target domain, e.g., the targeting domain is 23 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 24 nucleotides (e.g., 24 consecutive nucleotides) having complementarity with the target domain, e.g., the targeting domain is 24 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 25 nucleotides (e.g., 25 consecutive nucleotides) having complementarity with the target domain, e.g., the targeting domain is 25 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, consists of, or consists essentially of 26 nucleotides (e.g., 26 consecutive nucleotides) having complementarity with the target domain, e.g., the targeting domain is 26 nucleotides in length. In certain of these embodiments, (a) the proximal and tail domain, when taken together, comprise at least 15, 18, 20, 25, 30, 31, 35, 40, 45, 49, 50, or 53 nucleotides; (b) there are at least 15, 18, 20, 25, 30, 31, 35, 40, 45, 49, 50, or 53 nucleotides 3' to the last nucleotide of the second complementarity domain; and/or there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

gRNA Delivery

In certain embodiments of the methods provided herein, the methods comprise delivery of one or more (e.g., two, three, or four) gRNA molecules as described herein. In certain of these embodiments, the gRNA molecules are delivered by intrahepatic injection, intraparenchymal injection into liver, intraparenchymal injection into the lung, intravenous delivery into the portal vein, intravenous injection, intramuscular injection, subcutaneous injection, or inhalation.

II. Methods for Designing gRNAs

Methods for designing gRNAs are described herein, including methods for selecting, designing and validating target domains. Exemplary targeting domains are also provided herein. Targeting Domains discussed herein can be incorporated into the gRNAs described herein.

Methods for selection and validation of target sequences as well as off-target analyses are described, e.g., in Mali et al., 2013 Science 339(6121): 823-826; Hsu et al. Nat Biotechnol, 31(9): 827-32; Fu et al., 2014 Nat Biotechnol, doi: 10.1038/nbt.2808. PubMed PMID: 24463574; Heigwer et al., 2014 Nat Methods 11(2):122-3. doi: 10.1038/nmeth.2812. PubMed PMID: 24481216; Bae et al., 2014 Bioinformatics PubMed PMID: 24463181; Xiao A et al., 2014 Bioinformatics PubMed PMID: 24389662.

For example, a software tool can be used to optimize the choice of gRNA within a user's target sequence, e.g., to minimize total off-target activity across the genome. Off target activity may be other than cleavage. For each possible gRNA choice using *S. pyogenes* Cas9, the tool can identify all off-target sequences (preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA is then ranked according to its total predicted off-target cleavage; the top-ranked gRNAs represent those that are likely to have the greatest on-target and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate gRNA molecules can be evaluated by art-known methods or as described in Section IV herein. Guide RNAs (gRNAs) for use with *S. pyogenes, S. aureus* and *N. meningitidis* Cas9s were identified using a DNA sequence searching algorithm. Guide RNA design was carried out using a custom guide RNA design software based on the public tool cas-offinder (reference: Cas-OFFinder: a fast and versatile algorithm that searches for potential off-target sites of Cas9 RNA-guided endonucleases, Bioinformatics. 2014 Feb. 17. Bae S. Park J, Kim J S. PMID: 24463181). Said custom guide RNA design software scores guides after calculating their genomewide off-target propensity. Typically matches ranging from perfect matches to 7 mismatches are considered for guides ranging in length from 17 to 24. Once the off-target sites are computationally determined, an aggregate score is calculated for each guide and summarized in a tabular output using a web-interface. In addition to identifying potential gRNA sites adjacent to PAM sequences, the software also identifies all PAM adjacent sequences that differ by 1, 2, 3 or more nucleotides from the selected gRNA sites. Genomic DNA sequence for each gene was obtained from the UCSC Genome browser and sequences were screened for repeat elements using the publically available RepeatMasker program. RepeatMasker searches input DNA sequences for repeated elements and regions of low complexity. The output is a detailed annotation of the repeats present in a given query sequence.

Following identification, gRNAs were grouped based on the frequency at which the gRNA target the sequences of allelic variants of a specific locus, e.g., HLA-A, HLA-B, HLA-C, HLA-DRB1, HLA-DRB3/4/5, or HLA-DQB1. "Frequency" refers to the number of the allelic variants the gRNA target over the total number of the allelic variants, e.g., as disclosed in the database described herein, for a specific locus, e.g., HLA-A, HLA-B, HLA-C, HLA-DRB1, HLA-DRB3/4/5, or HLA-DQB1. For example, if a gRNA targets all of the allelic variants in a locus, e.g., HLA-A, HLA-B, HLA-C, HLA-DRB1, HLA-DRB3/4/5, or HLA-DQB1, the gRNA targets the allelic variants of a specific locus at a frequency of 100%.

After that, the RNAs were ranked into tiers based on their distance to the target site, their orthogonality or presence of a 5' G (based on identification of close matches in the human genome containing a relevant PAM, e.g., in the case of *S. pyogenes*, a NGG PAM, in the case of *S. aureus*, NNGRRN (SEQ ID NO:203) (e.g, a NNGRRT (SEQ ID NO:204) or NNGRRV (SEQ ID NO:205)) PAM, and in the case of *N. meningitidis*, a NNNNGATT (SEQ ID NO:212) or NNNNGCTT (SEQ ID NO:213) PAM. Orthogonality refers to the number of sequences in the human genome that contain a minimum number of mismatches to the target sequence. A "high level of orthogonality" or "good orthogonality" may, for example, refer to 20-mer gRNAs that have no identical sequences in the human genome besides the intended target, nor any sequences that contain one or two mismatches in the target sequence. Targeting domains with good orthogonality are selected to minimize off-target DNA cleavage.

As an example, for *S. pyogenes* and *N. meningitidis* targets, 17-mer, or 20-mer gRNAs were designed. As another example, for *S. aureus* targets, 18-mer. 19-mer, 20-mer, 21-mer, 22-mer, 23-mer and 24-mer gRNAs were designed. Targeting domains, disclosed herein, may comprise the 17-mer. The targeting domains of 18 or more nucleotides may comprise the 17-mer. Targeting domains, disclosed herein, may comprises the 18-mer. The targeting domains of 19 or more nucleotides may comprise the 18-mer. Targeting domains, disclosed herein, may comprise the 19-mer. The targeting domains of 20 or more nucleotides may comprise the 19-mer. Targeting domains, disclosed herein, may comprises the 20-mer. The targeting domains of 21 or more nucleotides may comprise the 20-mer. Targeting domains, disclosed herein, may comprise the 21-mer. The targeting domains of 22 or more nucleotides may comprise the 21-mer gRNAs. Targeting domains, disclosed herein, may comprises the 22-mer described. The targeting domains of 23 or more nucleotides may comprise the 22-mer. Targeting domains, disclosed herein, may comprises the 23-mer. The targeting domains of 24 or more nucleotides may comprise the 23-mer. Targeting domains, disclosed herein, may comprises the 24-mer. The targeting domains of 25 or more nucleotides may comprise the 24-mer gRNAs.

As an example, gRNAs were designed for use with *S. pyogenes, S. aureus* and *N. meningitidis* Cas9 enzymes. The gRNAs were identified and ranked into 4 tiers for *S. pyogenes*. The targeting domain to be used with *S. pyogenes* Cas9 enzymes for tier 1 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), (2) a high level of orthogonality, and (3) the presence of 5'G. The targeting domain to be used with *S. pyogenes* Cas9 enzymes for tier 2 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), and (2) a high level of orthogonality. The targeting domain to be used with *S. pyogenes* Cas9 enzymes for tier 3 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), and (2) the presence of 5'G. The targeting domain to be used with *S. pyogenes* Cas9 enzymes for tier 4 gRNA molecules were selected based on distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1).

The gRNAs were identified and ranked into 5 tiers for *S. aureus*, when the relevant PAM was NNGRRT or NNGRRV. The targeting domain to be used with *S. aureus* Cas9 enzymes for tier 1 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), (2) a high level of orthogonality, (3) the presence of 5'G. and (4) PAM is NNGRRT. The targeting domain to be used with *S. aureus* Cas9 enzymes for tier 2 gRNA molecules were selected based on 1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), (2) a high level of orthogonality, and (3) PAM is NNGRRT. The targeting domain to be used with *S. aureus* Cas9 enzymes for tier 3 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), (2) the presence of 5'G, and (3) PAM is NNGRRT. The targeting domain to be used with *S. aureus* Cas9 enzymes for tier 4 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1) and (2) PAM is NNGRRT. The targeting domain to be used with *S. aureus* Cas9 enzymes for tier 4 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1) and (2) PAM is NNGRRV.

The gRNAs were identified and ranked into 4 tiers for *N. meningitidis*. The gRNAs were identified and ranked into 4 tiers for *N. meningitidis*. The targeting domain to be used with *N. meningitidis* Cas9 enzymes for tier 1 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), (2) a high level of orthogonality, and (3) the presence of 5'G. The targeting domain to be used with *N. meningitidis* Cas9 enzymes for tier 2 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), and (2) a high level of orthogonality. The targeting domain to be used with *N. meningitidis* Cas9 enzymes for tier 3 gRNA molecules were selected based on (1) distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1), and (2) the presence of 5'G. The targeting domain to be used with *N. meningitidis* Cas9 enzymes for tier 4 gRNA molecules were selected based on distance to a target site (e.g., targeting the coding sequence of an allelic variant sequence of a specific locus, e.g., HLA-A, HLA-B, HLA-C, HLA-DRB1, HLA-DRB3/4/5, or HLA-DQB1).

In an embodiment, when a single gRNA molecule is used to target a Cas9 nickase to create a single strand break in the coding sequence of an allelic variant sequence, e.g., HLA-A, HLA-B, HLA-C, HLA-DRB1, HLA-DRB3/4/5, or HLA-DQB1.

In an embodiment, when a single gRNA molecule is used to target a Cas9 nuclease to create a double strand break in the coding sequence of an allelic variant sequence, e.g., HLA-A, HLA-B, HLA-C, HLA-DRB1, HLA-DRB3/4/5, or HLA-DQB1.

In an embodiment, dual targeting is used to create two double strand breaks in the coding sequence of an allelic variant sequence, e.g., HLA-A, HLA-B, HLA-C, HLA-DRB1, HLA-DRB3/4/5, or HLA-DQB1. In an embodiment, two gRNAs are used to target either upstream or downstream of a position in the coding sequence of an allelic variant sequence, e.g., HLA-A, HLA-B, HLA-C, HLA-DRB1, HLA-DRB3/4/5, or HLA-DQB1. In an embodiment, a first and a second gRNAs are used to target two Cas9 nucleases to flank, e.g., the first of gRNA is used to target upstream of and the second gRNA is used to target downstream of a position in the coding sequence of an allelic variant sequence, e.g., HLA-A, HLA-B, HLA-C, HLA-DRB1, HLA-DRB3/4/5, or HLA-DQB1.

In an embodiment, dual targeting is used to create a double strand break and a pair of single strand breaks to delete a genomic sequence of an allelic variant sequence, e.g., HLA-A, HLA-B, HLA-C, HLA-DRB1, HLA-DRB3/4/5, or HLA-DQB1. In an embodiment, the first, second and third gRNAs are used to target one Cas9 nuclease and two Cas9 nickases to flank, e.g., the first gRNA that will be used with the Cas9 nuclease is used to target upstream of or downstream of a position in the coding sequence of an allelic variant sequence, e.g., HLA-A, HLA-B, HLA-C, HLA-DRB1, HLA-DRB3/4/5, or HLA-DQB1, and the second and third gRNAs that will be used with the Cas9 nickase pair are used to target the opposite side of the positon in the coding sequence of an allelic variant sequence, e.g., HLA-A, HLA-B, HLA-C, HLA-DRB1, HLA-DRB3/4/5, or HLA-DQB1.

In an embodiment, when four gRNAs (e.g., two pairs) are used to target four Cas9 nickases to create four single strand breaks to delete genomic sequence including the mutation, the first pair and second pair of gRNAs are used to target four Cas9 nickases to flank, e.g., the first pair of gRNAs are used to target upstream of a position in the coding sequence of an allelic variant sequence, e.g., HLA-A, HLA-B, HLA-C, HLA-DRB1, HLA-DRB3/4/5, or HLA-DQB1, and the second pair of gRNAs are used to target downstream of in the coding sequence of an allelic variant sequence, e.g., HLA-A. HLA-B, HLA-C, HLA-DRB1, HLA-DRB3/4/5, or HLA-DQB1.

gRNAs were identified for both single-gRNA nuclease cleavage and for a dual-gRNA paired "nickase" strategy. Criteria for selecting gRNAs and the determination for which gRNAs can be used for which strategy is based on several considerations:

gRNA pairs should be oriented on the DNA such that PAMs are facing out and cutting with the D10A Cas9 nickase will result in 5' overhangs.

An assumption that cleaving with dual nickase pairs will result in deletion of the entire intervening sequence at a reasonable frequency. However, it will also often result in indel mutations at the site of only one of the gRNAs. Candidate pair members can be tested for how efficiently they remove the entire sequence versus just causing indel mutations at the site of one gRNA.

The Targeting Domains discussed herein can be incorporated into the gRNAs described herein.

III. Cas9 Molecules

Cas9 molecules of a variety of species can be used in the methods and compositions described herein. While *S. pyogenes* and *S. aureus* Cas9 molecules are the subject of much of the disclosure herein, Cas9 molecules of, derived from, or based on the Cas9 proteins of other species listed herein can be used as well. These include, for example, Cas9 molecules from Acidovorax *avenae, Actinobacillus pleuropneumoniae, Actinobacillus succinogenes, Actinobacillus suis, Actinomyces* sp., *Cycliphilus denitrificans, Aminomonas paucivorans. Bacillus cereus. Bacillus smithii, Bacillus thuringiensis. Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae.*

Cas9 Domains

Crystal structures have been determined for two different naturally occurring bacterial Cas9 molecules. The crystal structure of *S. pyogenes* Cas9 in its unbound state has been described in Jinek et al.; *Science.* 2014 Mar. 14; 343(6176): 1247997. The crystal structure of *S. pyogenes* Cas9 in complex with a single gRNA has been disclosed in Jiang et al.; *Science.* 2015 Jun. 26; 348(6242):1477-81. The crystal structure of *S. pyogenes* Cas9 in complex with a single gRNA (e.g., a synthetic fusion of crRNA and tracrRNA) and its target DNA has been described in Nishimasu et al., *Cell.* 2014 Feb. 27:156(5):935-49; Anders et al., *Nature.* 2014 Sep. 25; 513(7519):569-73. The crystal structures of *S. aureus* Cas9 in complex with a single guide RNA (sgRNA) and its double-stranded DNA targets has been disclosed in Nishimasu et al., *Cell.* 2015 Aug. 27; 162(5):1113-26

A naturally occurring Cas9 molecule comprises two lobes: a recognition (REC) lobe and a nuclease (NUC) lobe; each of which further comprise domains described herein. Cas9 domains have been described in Jinek et al.; *Science.* 2014 Mar. 14; 343(6176):1247997; Jiang et al., *Science.* 2015 Jun. 26; 348(6242):1477-81: Nishimasu et al., *Cell.* 2014 Feb. 27; 156(5):93549; Anders et al., *Nature.* 2014 Sep. 25:513(7519):569-73; Nishimasu et al., *Cell.* 2015 Aug. 27; 162(5):1113-26. The domain nomenclature and the numbering of the amino acid residues encompassed by each domain used throughout this disclosure is as described previously (Nishimasu et al., *Cell.* 2014 Feb. 27; 156(5): 935-49). The numbering of the amino acid residues is with reference to Cas9 from *S. pyogenes.*

The REC lobe comprises the arginine-rich bridge helix (BH), the REC1 domain, and the REC2 domain. The REC lobe does not share structural similarity with other known proteins, indicating that it is a Cas9-specific functional domain. The BH domain is a long □ helix and arginine rich region and comprises amino acids 60-93 of the sequence of *S. pyogenes* Cas9. The REC1 domain is important for recognition of the repeat:anti-repeat duplex, e.g., of a gRNA or a tracrRNA, and is therefore critical for Cas9 activity by recognizing the target sequence. The REC1 domain comprises two REC1 motifs at amino acids 94 to 179 and 308 to 717 of the sequence of *S. pyogenes* Cas9. These two REC1 domains, though separated by the REC2 domain in the linear primary structure, assemble in the tertiary structure to form the REC1 domain. The REC2 domain, or parts thereof, may also play a role in the recognition of the repeat:anti-repeat duplex. The REC2 domain comprises amino acids 180-307 of the sequence of *S. pyogenes* Cas9.

The NUC lobe comprises the RuvC domain, the HNH domain, and the PAM-interacting (PI) domain. The RuvC domain shares structural similarity to retroviral integrase superfamily members and cleaves a single strand, e.g., the non-complementary strand of the target nucleic acid molecule. The RuvC domain is assembled from the three split RuvC motifs (RuvC I, RuvCII, and RuvCIII, which are often commonly referred to in the art as RuvCI domain, or N-terminal RuvC domain, RuvCII domain, and RuvCIII domain) at amino acids 1-59, 718-769, and 909-1098, respectively, of the sequence of *S. pyogenes* Cas9. Similar to the REC1 domain, the three RuvC motifs are linearly separated by other domains in the primary structure, however in the tertiary structure, the three RuvC motifs assemble and form the RuvC domain. The HNH domain shares structural similarity with HNH endonucleases and cleaves a single strand, e.g., the complementary strand of the target nucleic acid molecule. The HNH domain lies between the RuvC II-III motifs and comprises amino acids 775-908 of the sequence of *S. pyogenes* Cas9. The P1 domain interacts with the PAM of the target nucleic acid molecule, and comprises amino acids 1099-1368 of the sequence of *S. pyogenes* Cas9.

RuvC-Like Domain and HNH-Like Domain

In certain embodiments, a Cas9 molecule or Cas9 polypeptide comprises an HNH-like domain and a RuvC-like domain, and in certain of these embodiments cleavage activity is dependent on the RuvC-like domain and the HNH-like domain. A Cas9 molecule or Cas9 polypeptide can comprise one or more of a RuvC-like domain and an HNH-like domain. In certain embodiments, a Cas9 molecule or Cas9 polypeptide comprises a RuvC-like domain, e.g., a RuvC-like domain described below, and/or an HNH-like domain, e.g., an HNH-like domain described below.

RuvC-Like Domains

In certain embodiments, a RuvC-like domain cleaves a single strand, e.g., the non-complementary strand of the target nucleic acid molecule. The Cas9 molecule or Cas9 polypeptide can include more than one RuvC-like domain (e.g., one, two, three or more RuvC-like domains). In certain embodiments, a RuvC-like domain is at least 5, 6, 7, 8 amino acids in length but not more than 20, 19, 18, 17, 16 or 15 amino acids in length. In certain embodiments, the Cas9 molecule or Cas9 polypeptide comprises an N-terminal RuvC-like domain of about 10 to 20 amino acids, e.g., about 15 amino acids in length.

N-Terminal RuvC-Like Domains

Some naturally occurring Cas9 molecules comprise more than one RuvC-like domain with cleavage being dependent on the N-terminal RuvC-like domain. Accordingly, a Cas9 molecule or Cas9 polypeptide can comprise an N-terminal RuvC-like domain. Exemplary N-terminal RuvC-like domains are described below.

In certain embodiments, a Cas9 molecule or Cas9 polypeptide comprises an N-terminal RuvC-like domain comprising an amino acid sequence of Formula I:

(SEQ ID NO: 20)

$$D\text{-}X_1\text{-}G\text{-}X_2\text{-}X_3\text{-}X_4\text{-}X_5\text{-}G\text{-}X_6\text{-}X_7\text{-}X_8\text{-}X_9,$$

wherein, $X_1$ is selected from I, V, M, L, and T (e.g., selected from I, V, and L);

$X_2$ is selected from T, I, V, S, N, Y, E, and L (e.g., selected from T, V, and I);

$X_3$ is selected from N, S, G, A, D, T, R, M, and F (e.g., A or N);

$X_4$ is selected from S, Y, N, and F (e.g., S);

$X_5$ is selected from V, I, L, C, T, and F (e.g., selected from V, I and L);

$X_6$ is selected from W, F, V, Y, S, and L (e.g., W);

$X_7$ is selected from A, S, C, V, and G (e.g., selected from A and S);

$X_8$ is selected from V, I, L, A, M, and H (e.g., selected from V, I, M and L); and $X_9$ is selected from any amino acid or is absent (e.g., selected from T, V, I, L, Δ, F, S, A, Y, M, and R, or, e.g., selected from T, V, I, L, and Δ).

In certain embodiments, the N-terminal RuvC-like domain differs from a sequence of SEQ ID NO:20 by as many as 1 but no more than 2, 3, 4, or 5 residues.

In certain embodiments, the N-terminal RuvC-like domain is cleavage competent. In other embodiments, the N-terminal RuvC-like domain is cleavage incompetent.

In certain embodiments, a Cas9 molecule or Cas9 polypeptide comprises an N-terminal RuvC-like domain comprising an amino acid sequence of Formula II:

(SEQ ID NO: 21)

$$D\text{-}X_1\text{-}G\text{-}X_2\text{-}X_3\text{-}S\text{-}X_5\text{-}G\text{-}X_6\text{-}X_7\text{-}X_8\text{-}X_9,,$$

wherein $X_1$ is selected from I, V, M, L, and T (e.g., selected from I, V, and L);

$X_2$ is selected from T, I, V, S, N, Y, E, and L (e.g., selected from T, V, and I);

$X_3$ is selected from N, S, G, A, D, T, R, M and F (e.g., A or N);

$X_5$ is selected from V, I, L, C, T, and F (e.g., selected from V, I and L);

$X_6$ is selected from W, F, V, Y, S, and L (e.g., W);

$X_7$ is selected from A, S, C, V, and G (e.g., selected from A and S);

$X_8$ is selected from V, I, L, A, M, and H (e.g., selected from V, I, M and L); and $X_9$ is selected from any amino acid or is absent (e.g., selected from T, V, I, L, Δ, F, S, A, Y, M, and R or selected from e.g., T, V, I, L, and A).

In certain embodiments, the N-terminal RuvC-like domain differs from a sequence of SEQ ID NO:21 by as many as 1 but not more than 2, 3, 4, or 5 residues.

In certain embodiments, the N-terminal RuvC-like domain comprises an amino acid sequence of Formula III:

(SEQ ID NO: 22)

$$D\text{-}I\text{-}G\text{-}X_2\text{-}X_3\text{-}S\text{-}V\text{-}G\text{-}W\text{-}A\text{-}X_8\text{-}X_9,$$

wherein $X_2$ is selected from T, I, V, S, N, Y, E, and L (e.g., selected from T, V, and I);

$X_3$ is selected from N, S, G, A, D, T, R, M, and F (e.g., A or N);

$X_8$ is selected from V, I, L, A, M, and H (e.g., selected from V, I, M and L); and $X_9$ is selected from any amino acid or is absent (e.g., selected from T, V, I, L, Δ, F, S, A, Y, M, and R or selected from e.g., T, V, I, L, and A).

In certain embodiments, the N-terminal RuvC-like domain differs from a sequence of SEQ ID NO:22 by as many as 1 but not more than, 2, 3, 4, or 5 residues.

In certain embodiments, the N-terminal RuvC-like domain comprises an amino acid sequence of Formula IV:

(SEQ ID NO: 23)
D-I-G-T-N-S-V-G-W-A-V-X, wherein

X is a non-polar alkyl amino acid or a hydroxyl amino acid, e.g., X is selected from V, I, L, and T (e.g., the Cas9 molecule can comprise an N-terminal RuvC-like domain shown in FIGS. 2A-2G (depicted as Y)).

In certain embodiments, the N-terminal RuvC-like domain differs from a sequence of SEQ ID NO:23 by as many as 1 but not more than, 2, 3, 4, or 5 residues.

In certain embodiments, the N-terminal RuvC-like domain differs from a sequence of an N-terminal RuvC like domain disclosed herein, e.g., in FIGS. 3A-3B, as many as 1 but no more than 2, 3, 4, or 5 residues. In an embodiment, 1, 2, 3 or all of the highly conserved residues identified in FIGS. 3A-3B are present.

In certain embodiments, the N-terminal RuvC-like domain differs from a sequence of an N-terminal RuvC-like domain disclosed herein, e.g., in FIGS. 4A-4B, as many as 1 but no more than 2, 3, 4, or 5 residues. In an embodiment, 1, 2, or all of the highly conserved residues identified in FIGS. 4A-4B are present.

Additional RuvC-Like Domains

In addition to the N-terminal RuvC-like domain, the Cas9 molecule or Cas9 polypeptide can comprise one or more additional RuvC-like domains. In certain embodiments, the Cas9 molecule or Cas9 polypeptide can comprise two additional RuvC-like domains. Preferably, the additional RuvC-like domain is at least 5 amino acids in length and, e.g., less than 15 amino acids in length, e.g., 5 to 10 amino acids in length, e.g., 8 amino acids in length.

An additional RuvC-like domain can comprise an amino acid sequence of Formula V:

(SEQ ID NO: 15)
I-$X_1$-$X_2$-E-$X_3$-A-R-E wherein, $X_1$ is V or H;

$X_2$ is I, L or V (e.g., I or V); and $X_3$ is M or T.

In certain embodiments, the additional RuvC-like domain comprises an amino acid sequence of Formula VI:

(SEQ ID NO: 16)
I-V-$X_2$-E-M-A-R-E, wherein $X_2$ is 1, L or V (e.g., I or V) (e.g., the Cas9 molecule or Cas9 polypeptide can comprise an additional RuvC-like domain shown in FIG. 2A-2G (depicted as B)).

An additional RuvC-like domain can comprise an amino acid sequence of Formula VII:

(SEQ ID NO: 17)
H-H-A-$X_1$-D-A-$X_2$-$X_3$, wherein $X_1$ is H or L;

$X_2$ is R or V; and $X_3$ is E or V.

In certain embodiments, the additional RuvC-like domain comprises the amino acid sequence: H-H-A-H-D-A-Y-L (SEQ ID NO:18).

In certain embodiments, the additional RuvC-like domain differs from a sequence of SEQ ID NOs:15-18 by as many as 1 but not more than 2, 3, 4, or 5 residues.

In certain embodiments, the sequence flanking the N-terminal RuvC-like domain has the amino acid sequence of Formula VIII:

(SEQ ID NO: 19)
K-$X_1$'-Y-$X_2$'-$X_3$'-$X_4$'-Z-T-D-$X_9$'-Y, wherein $X_1$' is selected from K and P;

$X_2$' is selected from V, L, I, and F (e.g., V, I and L);

$X_3$' is selected from G, A and S (e.g., G);

$X_4$' is selected from L, I, V, and F (e.g., L);

$X_9$' is selected from D, E, N, and Q; and

Z is an N-terminal RuvC-like domain, e.g., as described above, e.g., having 5 to 20 amino acids.

HNH-Like Domains

In an embodiment, an HNH-like domain cleaves a single stranded complementary domain, e.g., a complementary strand of a double stranded nucleic acid molecule. In certain embodiments, an HNH-like domain is at least 15, 20, or 25 amino acids in length but not more than 40, 35, or 30 amino acids in length, e.g., 20 to 35 amino acids in length, e.g., 25 to 30 amino acids in length. Exemplary HNH-like domains are described below.

In an embodiment, a Cas9 molecule or Cas9 polypeptide comprises an HNH-like domain having an amino acid sequence of Formula IX:

(SEQ ID NO: 25)
$X_1$-$X_2$-$X_3$-H-$X_4$-$X_5$-P-$X_6$-$X_7$-$X_8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X_{20}$-$X_{21}$-$X_{22}$-$X_{23}$-N, wherein $X_1$ is selected from D, E, Q and N (e.g., D and E);

$X_2$ is selected from L, I, R, Q, V, M, and K;

$X_3$ is selected from D and E;

$X_4$ is selected from I, V, T, A, and L (e.g., A, I and V);

$X_5$ is selected from V, Y, I, L, F, and W (e.g., V, I and L);

$X_6$ is selected from Q, H, R, K, Y, I, L, F, and W;

$X_7$ is selected from S, A, D, T, and K (e.g., S and A);

$X_8$ is selected from F, L, V, K, Y, M, I, R, A, E, D, and Q (e.g., F);

$X_9$ is selected from L, R, T, I, V, S, C, Y, K, F, and G;

$X_{10}$ is selected from K, Q, Y, T, F, L, W, M, A, E, G, and S;

$X_{11}$ is selected from D, S, N, R, L, and T (e.g., D);

$X_{12}$ is selected from D, N and S;

$X_{13}$ is selected from S, A, T, G, and R (e.g., S);

$X_{14}$ is selected from I, L, F, S, R, Y, Q, W, D, K, and H (e.g., I, L and F);

$X_{15}$ is selected from D, S, I, N, E, A, H, F, L, Q, M, G, Y, and V;

$X_{16}$ is selected from K, L, R, M, T, and F (e.g., L, R and K);

$X_{17}$ is selected from V, L, I, A and T;

$X_{18}$ is selected from L, I, V, and A (e.g., L and I);

$X_{19}$ is selected from T, V, C, E, S, and A (e.g., T and V);

$X_{20}$ is selected from R, F, T, W, E, L, N, C, K, V, S, Q, I, Y, H, and A;

$X_{21}$ is selected from S, P, R, K, N, A, H, Q, G, and L;

$X_{22}$ is selected from D, G, T, N, S, K, A, I, E, L, Q, R, and Y; and $X_{23}$ is selected from K, V, A, E, Y, I, C, L, S, T, G, K, M, D, and F.

In certain embodiments, a HNH-like domain differs from a sequence of SEQ ID NO:25 by at least one but not more than, 2, 3, 4, or 5 residues.

In certain embodiments, the HNH-like domain is cleavage competent. In other embodiments, the HNH-like domain is cleavage incompetent.

In certain embodiments, a Cas9 molecule or Cas9 polypeptide comprises an HNH-like domain comprising an amino acid sequence of Formula X:

(SEQ ID NO: 26)

$X_1$-$X_2$-$X_3$-H-$X_4$-$X_5$-P-$X_6$-S-$X_8$-$X_9$-$X_{10}$-D-D-S-$X_{14}$-$X_{15}$-N-K-V-L-$X_{19}$-$X_{20}$-$X_{21}$-$X_{22}$-$X_{23}$-N, wherein $X_1$ is selected from D and E;

$X_2$ is selected from L, I, R, Q, V, M, and K;

$X_3$ is selected from D and E;

$X_4$ is selected from I, V, T, A, and L (e.g., A, I and V);

$X_5$ is selected from V, Y, I, L, F, and W (e.g., V, I and L);

$X_6$ is selected from Q, H, R, K, Y, I, L, F, and W;

$X_8$ is selected from F, L, V, K, Y, M, I, R, A, E, D, and Q (e.g., F);

$X_9$ is selected from L, R, T, I, V, S, C, Y, K, F, and G;

$X_{10}$ is selected from K, Q, Y, T, F, L, W, M, A, E, G, and S;

$X_{14}$ is selected from I, L, F, S, R, Y, Q, W, D, K and H (e.g., I, L and F);

$X_{15}$ is selected from D, S, I, N, E, A, H, F, L, Q, M, G, Y, and V;

$X_{19}$ is selected from T, V, C, E, S, and A (e.g., T and V);

$X_{20}$ is selected from R, F, T, W, E, L, N, C, K, V, S, Q, I, Y, H, and A;

$X_{21}$ is selected from S, P, R, K, N, A, H, Q, G, and L;

$X_{22}$ is selected from D, G, T, N, S, K, A, I, E, L, Q, R, and Y; and $X_{23}$ is selected from K, V, A, E, Y, I, C, L, S, T, G, K, M, D, and F.

In certain embodiment, the HNH-like domain differs from a sequence of SEQ ID NO:26 by 1, 2, 3, 4, or 5 residues.

In certain embodiments, a Cas9 molecule or Cas9 polypeptide comprises an HNH-like domain comprising an amino acid sequence of Formula XI:

(SEQ ID NO: 27)

$X_1$-V-$X_3$-H-I-V-P-$X_6$-S-$X_8$-$X_9$-$X_{10}$-D-D-S-$X_{14}$-$X_{15}$-N-K-V-L-T-$X_{20}$-$X_{21}$-$X_{22}$-$X_{23}$-N, wherein $X_1$ is selected from D and E;

$X_3$ is selected from D and E;

$X_6$ is selected from Q, H, R, K, Y, I, L, and W;

$X_8$ is selected from F, L, V, K, Y, M, I, R, A, E, D, and Q (e.g., F);

$X_9$ is selected from L, R, T, I, V, S, C, Y, K, F, and G;

$X_{10}$ is selected from K, Q, Y, T, F, L, W, M, A, E, G, and S;

$X_{14}$ is selected from I, L, F, S, R, Y, Q, W, D, K, and H (e.g., I, L and F);

$X_{15}$ is selected from D, S, I, N, E, A, H, F, L, Q, M, G, Y, and V;

$X_{20}$ is selected from R, F, T, W, E, L, N, C, K, V, S, Q, I, Y, H, and A;

$X_{21}$ is selected from S, P, R, K, N, A, H, Q, G, and L;

$X_{22}$ is selected from D, G, T, N, S, K, A, I, E, L, Q, R, and Y; and $X_{23}$ is selected from K, V, A, E, Y, I, C, L, S, T, G, K, M, D, and F.

In certain embodiments, the HNH-like domain differs from a sequence of SEQ ID NO:27 by 1, 2, 3, 4, or 5 residues.

In certain embodiments, a Cas9 molecule or Cas9 polypeptide comprises an HNH-like domain having an amino acid sequence of Formula XII:

(SEQ ID NO: 28)

D-$X_2$-D-H-I-$X_5$-P-Q-$X_7$-F-$X_9$-$X_{10}$-D-$X_{12}$-S-I-D-N-$X_{16}$-V-L-$X_{19}$-$X_{20}$-S-$X_{22}$-$X_{23}$-N, wherein $X_2$ is selected from I and V;

$X_5$ is selected from I and V;

$X_7$ is selected from A and S;

$X_9$ is selected from I and L;

$X_{10}$ is selected from K and T;

$X_{12}$ is selected from D and N;

$X_{16}$ is selected from R, K, and L;

$X_{19}$ is selected from T and V;

$X_{20}$ is selected from S, and R;

$X_{22}$ is selected from K, D, and A; and $X_{23}$ is selected from E, K, G, and N (e.g., the Cas9 molecule or Cas9 polypeptide can comprise an HNH-like domain as described herein).

In an embodiment, the HNH-like domain differs from a sequence of SEQ ID NO:28 by as many as 1 but no more than 2, 3, 4, or 5 residues.

In certain embodiments, a Cas9 molecule or Cas9 polypeptide comprises the amino acid sequence of Formula XIII:

(SEQ ID NO: 24)

L-Y-Y-L-Q-N-G-$X_1$'-D-M-Y-$X_2$'-$X_3$'-$X_4$'-$X_5$'-L-D-I-$X_6$'-$X_7$'-L-S-$X_8$'-Y-Z-N-R-$X_9$'-K-$X_{10}$'-D-$X_{11}$'-V-P, wherein $X_1$' is selected from K and R;

$X_2$' is selected from V and T;

$X_3$' is selected from G and D;

$X_4$' is selected from E, Q and D;

$X_5$' is selected from E and D;

$X_6$' is selected from D, N, and H;

$X_7$' is selected from Y, R, and N;

$X_8$' is selected from Q, D, and N;

$X_9$' is selected from G and E;

$X_{10}$' is selected from S and G;

$X_{11}$' is selected from D and N; and

Z is an HNH-like domain, e.g., as described above.

In certain embodiments, the Cas9 molecule or Cas9 polypeptide comprises an amino acid sequence that differs from a sequence of SEQ ID NO:24 by as many as 1 but not more than 2, 3, 4, or 5 residues.

In certain embodiments, the HNH-like domain differs from a sequence of an HNH-like domain disclosed herein, e.g., in FIGS. 5A-5C, by as many as 1 but not more than 2, 3, 4, or 5 residues. In certain embodiments, 1 or both of the highly conserved residues identified in FIGS. 5A-5C are present.

In certain embodiments, the HNH-like domain differs from a sequence of an HNH-like domain disclosed herein, e.g., in FIGS. 6A-6B, by as many as 1 but not more than 2, 3, 4, or 5 residues. In an embodiment, 1, 2, or all 3 of the highly conserved residues identified in FIGS. 6A-6B are present.

Split Cas9 Molecules and Gene Editing Systems

In some embodiments, the Cas9 fusion molecule comprises a split Cas9 molecule, as described in more detail in WO15/089427 and WO14/018423, the entire contents of each of which are expressly incorporated herein by reference. Split Cas9 molecules are summarized briefly, below.

In an aspect, disclosed herein is a non-naturally occurring or engineered inducible CRISPR enzyme, e.g., Cas9 enzyme, comprising: a first CRISPR enzyme fusion construct attached to a first half of an inducible dimer and a second CRISPR enzyme fusion construct attached to a second half of the inducible dimer, wherein the first CRISPR enzyme fusion construct is operably linked to one or more nuclear localization signals, wherein the second CRISPR enzyme fusion construct is operably linked to one or more nuclear export signals, wherein contact with an inducer energy source brings the first and second halves of the inducible dimer together, wherein bringing the first and second halves of the inducible dimer together allows the first and second CRISPR enzyme fusion constructs to constitute a functional gene editing system.

In another aspect, in the inducible gene editing system, the inducible dimer is or comprises or consists essentially of or consists of an inducible heterodimer. In an aspect, in inducible gene editing system, the first half or a first portion or a first fragment of the inducible heterodimer is or comprises or consists of or consists essentially of an FKBP, optionally FKBP 12. In an aspect, in the inducible gene editing system, the second half or a second portion or a second fragment of the inducible heterodimer is or comprises or consists of or consists essentially of FRB. In one aspect, in the inducible gene editing system, the arrangement of the first CRISPR enzyme fusion construct is or comprises or consists of or consists essentially of N' terminal Cas9 part-FRB-NES. In another aspect, in the inducible gene editing system, the arrangement of the first CRISPR enzyme fusion construct is or comprises or consists of or consists essentially of NES-N' terminal Cas9 part-FRB-NES. In one aspect in the inducible gene editing system, the arrangement of the second CRISPR enzyme fusion construct is or comprises or consists essentially of or consists of C terminal Cas9 part-FKBP-NLS. In another aspect, in the inducible gene editing system, the arrangement of the second CRISPR enzyme fusion construct is or comprises or consists of or consists essentially of NLS-C terminal Cas9 part-FKBP-NLS. In an aspect, in inducible gene editing system there can be a linker that separates the Cas9 part from the half or portion or fragment of the inducible dimer. In an aspect, in the inducible gene editing system, the inducer energy source is or comprises or consists essentially of or consists of rapamycin. In an aspect, in inducible gene editing system, the inducible dimer is an inducible homodimer. In an aspect, in inducible gene editing system, the CRISPR enzyme is Cas9, e.g., SpCas9 or SaCas9. In an aspect in an gene editing system, the Cas9 is split into two parts at any one of the following split points, according or with reference to SpCas9: a split position between 202A/203S; a split position between 255F/256D; a split position between 310E/311I; a split position between 534R/535; a split position between 572E/573C: a split position between 713S/714G: a split position between 1003L/104E; a split position between 1 G54G/1 Q55E; a split position between 11 14N/1115S; a split position between 1152K/1153S; a split position between 1245K, 1246G; or a split between 1098 and 1099. In an aspect, in the inducible gene editing system, one or more functional domains are associated with one or both parts of the Cas9 enzyme, e.g., the functional domains optionally including a transcriptional activator, a transcriptional or a nuclease such as a f'ok I nuclease. In an aspect, in the inducible gene editing system, the functional gene editing system binds to the target sequence and the enzyme is a deadCas9, optionally having a diminished nuclease activity of at least 97%, or 100% (or no more than 3% and advantageously 0%) nuclease activity) as compared with the CRISPR enzyme not having the at least one mutation. In an aspect, in the inducible gene editing system, the deadCas9 (CRISPR enzyme) comprises two or more mutations wherein two or more of DIG, E762, H840, N854, N863, or D986 according to SpCas9 protein or any corresponding ortholog or N580 according to SaCas9 protein are mutated, or the CRISPR enzyme comprises at least one mutation, e.g., wherein at least H840 is mutated. The disclosure further provides, a polynucleotide encoding the inducible gene editing system as herein discussed.

Also disclosed herein is a vector for delivery of the first CRISPR enzyme fusion construct, attached to a first half or portion or fragment of an inducible dimer and operably linked to one or more nuclear localization signals, according as herein discussed. In an aspect, disclosed herein is a vector for delivery of the second CRISPR enzyme fusion construct, attached to a second half or portion or fragment of an inducible dimer and operably linked to one or more nuclear export signals.

Cas9 Activities

In certain embodiments, the Cas9 molecule or Cas9 polypeptide is capable of cleaving a target nucleic acid molecule. Typically wild-type Cas9 molecules cleave both strands of a target nucleic acid molecule. Cas9 molecules and Cas9 polypeptides can be engineered to alter nuclease cleavage (or other properties), e.g., to provide a Cas9 molecule or Cas9 polypeptide which is a nickase, or which lacks the ability to cleave target nucleic acid. A Cas9 molecule or Cas9 polypeptide that is capable of cleaving a target nucleic acid molecule is referred to herein as an eaCas9 (an enzymatically active Cas9) molecule or eaCas9 polypeptide.

In certain embodiments, an eaCas9 molecule or eaCas9 polypeptide comprises one or more of the following enzymatic activities:

a nickase activity, i.e., the ability to cleave a single strand, e.g., the non-complementary strand or the complementary strand, of a nucleic acid molecule;

a double stranded nuclease activity, i.e., the ability to cleave both strands of a double stranded nucleic acid and create a double stranded break, which in an embodiment is the presence of two nickase activities: an endonuclease activity; an exonuclease activity; and a helicase activity, i.e., the ability to unwind the helical structure of a double stranded nucleic acid.

In certain embodiments, an enzymatically active or an eaCas9 molecule or eaCas9 polypeptide cleaves both DNA strands and results in a double stranded break. In certain embodiments, an eaCas9 molecule or eaCas9 polypeptide cleaves only one strand, e.g., the strand to which the gRNA hybridizes to, or the strand complementary to the strand the gRNA hybridizes with. In an embodiment, an eaCas9 molecule or eaCas9 poly peptide comprises cleavage activity associated with an HNH domain. In an embodiment, an eaCas9 molecule or eaCas9 polypeptide comprises cleavage activity associated with a RuvC domain. In an embodiment, an eaCas9 molecule or eaCas9 polypeptide comprises cleavage activity associated with an HNH domain and cleavage activity associated with a RuvC domain. In an embodiment, an eaCas9 molecule or eaCas9 polypeptide comprises an active, or cleavage competent, HNH domain and an inactive, or cleavage incompetent, RuvC domain. In an embodiment, an eaCas9 molecule or eaCas9 polypeptide comprises an inactive, or cleavage incompetent, HNH domain and an active, or cleavage competent, RuvC domain.

Targeting and PAMs

A Cas9 molecule or Cas9 polypeptide can interact with a gRNA molecule and, in concert with the gRNA molecule, localizes to a site which comprises a target domain, and in certain embodiments, a PAM sequence.

In certain embodiments, the ability of an eaCas9 molecule or eaCas9 polypeptide to interact with and cleave a target nucleic acid is PAM sequence dependent. A PAM sequence is a sequence in the target nucleic acid. In an embodiment, cleavage of the target nucleic acid occurs upstream from the PAM sequence. eaCas9 molecules from different bacterial species can recognize different sequence motifs (e.g., PAM sequences). In an embodiment, an eaCas9 molecule of *S. pyogenes* recognizes the sequence motif NGG and directs cleavage of a target nucleic acid sequence 1 to 10, e.g., 3 to 5, bp upstream from that sequence (see, e.g., Mali 2013). In an embodiment, an eaCas9 molecule of *S. thermophilus* recognizes the sequence motif NGGNG (SEQ ID NO:199) and/or NNAGAAW (W=A or T) (SEQ ID NO:200) and directs cleavage of a target nucleic acid sequence 1 to 10, e.g., 3 to 5, bp upstream from these sequences (see, e.g., Horvath 2010; Deveau 2008). In an embodiment, an eaCas9 molecule of *S. mutans* recognizes the sequence motif NGG and/or NAAR (R=A or G) (SEQ ID NO:201) and directs cleavage of a target nucleic acid sequence 1 to 10, e.g., 3 to 5 bp, upstream from this sequence (see, e.g., Deveau 2008). In an embodiment, an eaCas9 molecule of *S. aureus* recognizes the sequence motif NNGRR (R=A or G) (SEQ ID NO:202) and directs cleavage of a target nucleic acid sequence 1 to 10, e.g., 3 to 5, bp upstream from that sequence. In an embodiment, an eaCas9 molecule of *S. aureus* recognizes the sequence motif NNGRRN (R=A or G) (SEQ ID NO:203) and directs cleavage of a target nucleic acid sequence 1 to 10, e.g., 3 to 5, bp upstream from that sequence. In an embodiment, an eaCas9 molecule of *S. aureus* recognizes the sequence motif NNGRRT (R=A or G) (SEQ ID NO:204) and directs cleavage of a target nucleic acid sequence 1 to 10, e.g., 3 to 5, bp upstream from that sequence. In an embodiment, an eaCas9 molecule of *S. aureus* recognizes the sequence motif NNGRRV (R=A or G) (SEQ ID NO:205) and directs cleavage of a target nucleic acid sequence 1 to 10, e.g., 3 to 5, bp upstream from that sequence. The ability of a Cas9 molecule to recognize a PAM sequence can be determined, e.g., using a transformation assay as described previously (Jinek 2012). In the aforementioned embodiments, N can be any nucleotide residue, e.g., any of A, G, C, or T.

As is discussed herein, Cas9 molecules can be engineered to alter the PAM specificity of the Cas9 molecule.

Exemplary naturally occurring Cas9 molecules have been described previously (see, e.g., Chylinski 2013). Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. aureus, S. pyogenes* (e.g., strain SF370, MGAS10270, MGAS10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysgalactiae* (e.g., strain GGS 124), *S. bovis* (e.g., strain ATCC 700338), *S. anginosus* (e.g., strain F0211), *S. agalactiae* (e.g., strain NEM316, A909), *Listeria monocytogenes* (e.g., strain F6854), *Listeria innocua* (*L. innocua*, e.g., strain Clip11262), *Enterococcus italicus* (e.g., strain DSM 15952), or *Enterococcus faecium* (e.g., strain 1,231,408).

In certain embodiments, a Cas9 molecule or Cas9 polypeptide comprises an amino acid sequence: having 60%, 65%, 70%, 75%, 80%, 85%, 90%, 95% 96%, 97%, 98% or 99% homology with; differs at no more than, 2, 5, 10, 15, 20, 30, or 40% of the amino acid residues when compared with; differs by at least 1, 2, 5, 10 or 20 amino acids, but by no more than 100, 80, 70, 60, 50, 40 or 30 amino acids from: or identical to any Cas9 molecule sequence described herein, or to a naturally occurring Cas9 molecule sequence, e.g., a Cas9 molecule from a species listed herein (e.g., SEQ ID NOs:1, 2, 4-6, or 12) or described in Chylinski 2013. In an embodiment, the Cas9 molecule or Cas9 polypeptide comprises one or more of the following activities: a nickase activity; a double stranded cleavage activity (e.g., an endonuclease and/or exonuclease activity); a helicase activity; or the ability, together with a gRNA molecule, to localize to a target nucleic acid.

In certain embodiments, a Cas9 molecule or Cas9 polypeptide comprises any of the amino acid sequence of the consensus sequence of FIGS. 2A-2G, wherein "*" indicates any amino acid found in the corresponding position in the amino acid sequence of a Cas9 molecule of *S. pyogenes, S. thermophilus, S mutans*, or *L. innocua*, and "-" indicates absent. In an embodiment, a Cas9 molecule or Cas9 polypeptide differs from the sequence of the consensus sequence disclosed in FIGS. 2A-2G by at least 1, but no more than 2, 3, 4, 5, 6, 7, 8, 9, or 10 amino acid residues. In certain embodiments, a Cas9 molecule or Cas9 polypeptide comprises the amino acid sequence of SEQ ID NO:2. In other embodiments, a Cas9 molecule or Cas9 polypeptide differs from the sequence of SEQ ID NO:2 by at least 1, but no more than 2, 3, 4, 5, 6, 7, 8, 9, or 10 amino acid residues.

A comparison of the sequence of a number of Cas9 molecules indicate that certain regions are conserved. These are identified below as:

- region 1 (residues 1 to 180, or in the case of region 1' residues 120 to 180)
- region 2 (residues 360 to 480);
- region 3 (residues 660 to 720);
- region 4 (residues 817 to 900); and
- region 5 (residues 900 to 960).

In an embodiment, a Cas9 molecule or Cas9 polypeptide comprises regions 1-5, together with sufficient additional Cas9 molecule sequence to provide a biologically active molecule, e.g., a Cas9 molecule having at least one activity described herein. In an embodiment, each of regions 1-5, independently, have 50%, 60%, 70%, 80%, 85%, 90%, 95%, 96%, 97%, 98% or 99% homology with the corresponding residues of a Cas9 molecule or Cas9 polypeptide described herein, e.g., a sequence from FIGS. 2A-2G.

In an embodiment, a Cas9 molecule or Cas9 polypeptide comprises an amino acid sequence referred to as region 1:

- having 50%, 60%, 70%, 80%, 85%, 90%, 95%, 96%, 97%, 98% or 99% homology with amino acids 1-180 (the numbering is according to the motif sequence in FIG. 2; 52% of residues in the four Cas9 sequences in FIGS. 2A-2G are conserved) of the amino acid sequence of Cas9 of *S. pyogenes;*
- differs by at least 1, 2, 5, 10 or 20 amino acids but by no more than 90, 80, 70, 60, 50, 40 or 30 amino acids from amino acids 1-180 of the amino acid sequence of Cas9 of *S. pyogenes, S. thermophilus, S. mutans*, or *Listeria innocua*; or
- is identical to amino acids 1-180 of the amino acid sequence of Cas9 of *S. pyogenes, S. thermophilus, S. mutans*, or *L. innocua.*

In an embodiment, a Cas9 molecule or Cas9 polypeptide comprises an amino acid sequence referred to as region 1':

- having 55%, 60%, 65%, 70%, 75%, 80%, 85%, 90%, 95%, 96%, 97%, 98% or 99% homology with amino acids 120-180 (55% of residues in the four Cas9 sequences in FIG. 2 are conserved) of the amino acid sequence of Cas9 of *S. pyogenes, S. thermophilus, S. mutans* or *L. innocua;*
- differs by at least 1, 2, or 5 amino acids but by no more than 35, 30, 25, 20 or 10 amino acids from amino acids 120-180 of the amino acid sequence of Cas9 of *S. pyogenes, S. thermophilus, S. mutans*, or *L. innocua*; or
- is identical to amino acids 120-180 of the amino acid sequence of Cas9 of *S. pyogenes, S. thermophilus, S. mutans*, or *L. innocua.*

In an embodiment, a Cas9 molecule or Cas9 polypeptide comprises an amino acid sequence referred to as region 2:

- having 50%, 55%, 60%, 65%, 70%, 75%, 80%, 85%, 90%, 95%, 96%, 97%, 98% or 99% homology with amino acids 360-480 (52% of residues in the four Cas9 sequences in FIG. 2 are conserved) of the amino acid sequence of Cas9 of *S. pyogenes, S. thermophilus. S mutans*, or *L. innocua;*
- differs by at least 1, 2, or 5 amino acids but by no more than 35, 30, 25, 20 or 10 amino acids from amino acids 360-480 of the amino acid sequence of Cas9 of *S. pyogenes, S. thermophilus, S. mutans*, or *L. innocua*: or
- is identical to amino acids 360-480 of the amino acid sequence of Cas9 of *S. pyogenes, S. thermophilus, S. mutans*, or *L. innocua.*

In certain embodiments, a Cas9 molecule or Cas9 polypeptide comprises an amino acid sequence referred to as region 3:

- having 55%, 60%, 65%, 70%, 75%, 80%, 85%, 90%, 95%, 96%, 97%, 98%, or 99% homology with amino acids 660-720 (56% of residues in the four Cas9 sequences in FIG. 2 are conserved) of the amino acid sequence of Cas9 of *S. pyogenes, S. thermophilus, S. mutans* or *L. innocua;*
- differs by at least 1, 2, or 5 amino acids but by no more than 35, 30, 25, 20 or 10 amino acids from amino acids 660-720 of the amino acid sequence of Cas9 of *S. pyogenes, S. thermophilus, S. mutans* or *L. innocua*; or
- is identical to amino acids 660-720 of the amino acid sequence of Cas9 of *S. pyogenes, S. thermophilus, S. mutans* or *L. innocua.*

In an embodiment, a Cas9 molecule or Cas9 polypeptide comprises an amino acid sequence referred to as region 4:

- having 50%, 55%, 60%, 65%, 70%, 75%, 80%, 85%, 90%, 95%, 96%, 97%, 98%, or 99% homology with amino acids 817-900 (55% of residues in the four Cas9 sequences in FIGS. 2A-2G are conserved) of the amino acid sequence of Cas9 of *S. pyogenes, S thermophilus, S. mutans*, or *L. innocua;*
- differs by at least 1, 2, or 5 amino acids but by no more than 35, 30, 25, 20 or 10 amino acids from amino acids 817-900 of the amino acid sequence of Cas9 of *S. pyogenes, S. thermophilus, S. mutans*, or *L. innocua*; or is identical to amino acids 817-900 of the amino acid sequence of Cas9 of *S. pyogenes, S. thermophilus, S. mutans*, or *L. innocua*.

In an embodiment, a Cas9 molecule or Cas9 polypeptide comprises an amino acid sequence referred to as region 5:

having 50%, 55%, 60%, 65%, 70%, 75%, 80%, 85%, 90%, 95%, 96%, 97%, 98%, or 99% homology with amino acids 900-960 (60% of residues in the four Cas9 sequences in FIGS. 2A-2G are conserved) of the amino acid sequence of Cas9 of *S. pyogenes, S. thermophilus, S. mutans*, or *L. innocua;* differs by at least 1, 2, or 5 amino acids but by no more than 35, 30, 25, 20 or 10 amino acids from amino acids 900-960 of the amino acid sequence of Cas9 of *S. pyogenes, S. thermophilus, S. mutans*, or *L. innocua*; or is identical to amino acids 900-960 of the amino acid sequence of Cas9 of *S. pyogenes, S. thermophilus, S. mutans*, or *L. innocua*.

Engineered or Altered Cas9

Cas9 molecules and Cas9 polypeptides described herein can possess any of a number of properties, including nuclease activity (e.g., endonuclease and/or exonuclease activity); helicase activity: the ability to associate functionally with a gRNA molecule; and the ability to target (or localize to) a site on a nucleic acid (e.g., PAM recognition and specificity). In certain embodiments, a Cas9 molecule or Cas9 polypeptide can include all or a subset of these properties. In a typical embodiment, a Cas9 molecule or Cas9 polypeptide has the ability to interact with a gRNA molecule and, in concert with the gRNA molecule, localize to a site in a nucleic acid. Other activities, e.g., PAM specificity, cleavage activity, or helicase activity can vary more widely in Cas9 molecules and Cas9 poly peptides.

Cas9 molecules include engineered Cas9 molecules and engineered Cas9 polypeptides (engineered, as used in this context, means merely that the Cas9 molecule or Cas9 polypeptide differs from a reference sequences, and implies no process or origin limitation). An engineered Cas9 molecule or Cas9 polypeptide can comprise altered enzymatic properties, e.g., altered nuclease activity, (as compared with a naturally occurring or other reference Cas9 molecule) or altered helicase activity. As discussed herein, an engineered Cas9 molecule or Cas9 polypeptide can have nickase activity (as opposed to double strand nuclease activity). In an embodiment an engineered Cas9 molecule or Cas9 polypeptide can have an alteration that alters its size, e.g., a deletion of amino acid sequence that reduces its size, e.g., without significant effect on one or more, or any Cas9 activity. In an embodiment, an engineered Cas9 molecule or Cas9 polypeptide can comprise an alteration that affects PAM recognition. E.g., an engineered Cas9 molecule can be altered to recognize a PAM sequence other than that recognized by the endogenous wild-type PI domain. In an embodiment a Cas9 molecule or Cas9 polypeptide can differ in sequence from a naturally occurring Cas9 molecule but not have significant alteration in one or more Cas9 activities.

Cas9 molecules or Cas9 polypeptides with desired properties can be made in a number of ways, e.g., by alteration of a parental, e.g., naturally occurring, Cas9 molecules or Cas9 polypeptides, to provide an altered Cas9 molecule or Cas9 polypeptide having a desired property. For example, one or more mutations or differences relative to a parental Cas9 molecule, e.g., a naturally occurring or engineered Cas9 molecule, can be introduced. Such mutations and differences comprise: substitutions (e.g., conservative substitutions or substitutions of non-essential amino acids); insertions; or deletions. In an embodiment, a Cas9 molecule or Cas9 polypeptide can comprises one or more mutations or differences, e.g., at least 1, 2, 3, 4, 5, 10, 15, 20, 30, 40 or 50 mutations but less than 200, 100, or 80 mutations relative to a reference, e.g., a parental, Cas9 molecule.

In certain embodiments, a mutation or mutations do not have a substantial effect on a Cas9 activity, e.g. a Cas9 activity described herein. In other embodiments, a mutation or mutations have a substantial effect on a Cas9 activity, e.g. a Cas9 activity described herein.

Non-Cleaving and Modified-Cleavage Cas9

In an embodiment, a Cas9 molecule or Cas9 polypeptide comprises a cleavage property that differs from naturally occurring Cas9 molecules, e.g., that differs from the naturally occurring Cas9 molecule having the closest homology. For example, a Cas9 molecule or Cas9 polypeptide can differ from naturally occurring Cas9 molecules, e.g., a Cas9 molecule of *S. pyogenes*, as follows: its ability to modulate, e.g., decreased or increased, cleavage of a double stranded nucleic acid (endonuclease and/or exonuclease activity), e.g., as compared to a naturally occurring Cas9 molecule (e.g., a Cas9 molecule of *S. pyogenes*); its ability to modulate, e.g., decreased or increased, cleavage of a single strand of a nucleic acid, e.g., a non-complementary strand of a nucleic acid molecule or a complementary strand of a nucleic acid molecule (nickase activity), e.g., as compared to a naturally occurring Cas9 molecule (e.g., a Cas9 molecule of *S. pyogenes*); or the ability to cleave a nucleic acid molecule, e.g., a double stranded or single stranded nucleic acid molecule, can be eliminated.

In certain embodiments, an eaCas9 molecule or eaCas9 polypeptide comprises one or more of the following activities: cleavage activity associated with an N-terminal RuvC-like domain; cleavage activity associated with an HNH-like domain; cleavage activity associated with an HNH-like domain and cleavage activity associated with an N-terminal RuvC-like domain.

In certain embodiments, an eaCas9 molecule or eaCas9 polypeptide comprises an active, or cleavage competent, HNH-like domain (e.g., an HNH-like domain described herein, e.g., SEQ ID NOs:24-28) and an inactive, or cleavage incompetent, N-terminal RuvC-like domain. An exemplary inactive, or cleavage incompetent N-terminal RuvC-like domain can have a mutation of an aspartic acid in an N-terminal RuvC-like domain, e.g., an aspartic acid at position 9 of the consensus sequence disclosed in FIG. 2A-2G or an aspartic acid at position 10 of SEQ ID NO:2, e.g., can be substituted with an alanine. In an embodiment, the eaCas9 molecule or eaCas9 polypeptide differs from wild-type in the N-terminal RuvC-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes, S. aureus*, or *S. thermophilus*. In an embodiment, the reference Cas9 molecule is the naturally occurring Cas9 molecule having the closest sequence identity or homology.

In an embodiment, an eaCas9 molecule or eaCas9 polypeptide comprises an inactive, or cleavage incompetent, HNH domain and an active, or cleavage competent, N-terminal RuvC-like domain (e.g., a RuvC-like domain described herein, e.g., SEQ ID NOs:15-23). Exemplary inactive, or cleavage incompetent HNH-like domains can have a mutation at one or more of: a histidine in an HNH-like domain, e.g., a histidine shown at position 856 of the consensus sequence disclosed in FIGS. 2A-2G, e.g., can be substituted with an alanine; and one or more asparagines in an HNH-like domain. e.g., an asparagine shown at position 870 of the consensus sequence disclosed in FIGS. 2A-2G and/or at position 879 of the consensus sequence disclosed in FIGS. 2A-2G, e.g., can be substituted with an alanine. In an embodiment, the eaCas9 differs from wild-type in the HNH-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes, S. aureus*, or *S. thermophilus*. In an embodiment, the reference Cas9 molecule is the naturally occurring Cas9 molecule having the closest sequence identity or homology.

In certain embodiments, exemplary Cas9 activities comprise one or more of PAM specificity, cleavage activity, and helicase activity. A mutation(s) can be present, e.g., in: one or more RuvC domains, e.g., an N-terminal RuvC domain; an HNH domain; a region outside the RuvC domains and the HNH domain. In an embodiment, a mutation(s) is present in a RuvC domain. In an embodiment, a mutation(s) is present in an HNH domain. In an embodiment, mutations are present in both a RuvC domain and an HNH domain.

Exemplary mutations that may be made in the RuvC domain or HNH domain with reference to the *S. pyogenes* Cas9 sequence include: D10A, E762A, H840A, N854A, N863A and/or D986A. Exemplary mutations that may be made in the RuvC domain with reference to the *S. aureus* Cas9 sequence include N580A (see, e.g., SEQ ID NO: 11).

Whether or not a particular sequence, e.g., a substitution, may affect one or more activity, such as targeting activity, cleavage activity, etc., can be evaluated or predicted, e.g., by evaluating whether the mutation is conservative. In an embodiment, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

In an embodiment, a Cas9 molecule comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of *S. aureus* or *S. pyogenes*, as follows: its ability to modulate, e.g., decreased or increased, cleavage of a double stranded break (endonuclease and/or exonuclease activity), e.g., as compared to a naturally occurring Cas9 molecule (e.g., a Cas9 molecule of *S. aureus* or *S. pyogenes*); its ability to modulate, e.g., decreased or increased, cleavage of a single strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of *S. aureus* or *S. pyogenes*); or the ability to cleave a nucleic acid molecule, e.g., a double stranded or single stranded nucleic acid molecule, can be eliminated. In certain embodiments, the nickase is *S. aureus* Cas9-derived nickase comprising the sequence of SEQ ID NO:10 (D10A) or SEQ ID NO:11 (N580A) (Friedland 2015).

In an embodiment, the altered Cas9 molecule is an eaCas9 molecule comprising one or more of the following activities: cleavage activity associated with a RuvC domain; cleavage activity associated with an HNH domain; cleavage activity associated with an HNH domain and cleavage activity associated with a RuvC domain.

In certain embodiments, the altered Cas9 molecule or Cas9 polypeptide comprises a sequence in which:

the sequence corresponding to the fixed sequence of the consensus sequence disclosed in FIGS. 2A-2G differs at no more than 1, 2, 3, 4, 5, 10, 15, or 20% of the fixed residues in the consensus sequence disclosed in FIGS. 2A-2G; and the sequence corresponding to the residues identified by "*" in the consensus sequence disclosed in FIGS. 2A-2G differs at no more than 1, 2, 3, 4, 5, 10, 15, 20, 25, 30, 35, or 40% of the "*" residues from the corresponding sequence of naturally occurring Cas9 molecule, e.g., an *S. pyogenes, S. thermophilus, S. mutans*, or *L. innocua* Cas9 molecule.

In an embodiment, the altered Cas9 molecule or Cas9 polypeptide is an eaCas9 molecule or eaCas9 polypeptide comprising the amino acid sequence of *S. pyogenes* Cas9 disclosed in FIGS. 2A-2G with one or more amino acids that differ from the sequence of *S. pyogenes* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In an embodiment, the altered Cas9 molecule or Cas9 polypeptide is an eaCas9 molecule or eaCas9 polypeptide comprising the amino acid sequence of *S. thermophilus* Cas9 disclosed in FIGS. 2A-2G with one or more amino acids that differ from the sequence of *S. thermophilus* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In an embodiment, the altered Cas9 molecule or Cas9 polypeptide is an eaCas9 molecule or eaCas9 polypeptide comprising the amino acid sequence of *S. mutans* Cas9 disclosed in FIGS. 2A-2G with one or more amino acids that differ from the sequence of *S. mutans* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In an embodiment, the altered Cas9 molecule or Cas9 poly peptide is an eaCas9 molecule or eaCas9 polypeptide comprising the amino acid sequence of *L. innocua* Cas9 disclosed in FIGS. 2A-2G with one or more amino acids that differ from the sequence of *L. innocua* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In certain embodiments, the altered Cas9 molecule or Cas9 polypeptide, e.g., an eaCas9 molecule or eaCas9 polypeptide, can be a fusion, e.g., of two of more different Cas9 molecules, e.g., of two or more naturally occurring Cas9 molecules of different species. For example, a fragment of a naturally occurring Cas9 molecule of one species can be fused to a fragment of a Cas9 molecule of a second species. As an example, a fragment of a Cas9 molecule of *S. pyogenes* comprising an N-terminal RuvC-like domain can be fused to a fragment of Cas9 molecule of a species other than *S. pyogenes* (e.g., *S. thermophilus*) comprising an HNH-like domain.

Cas9 with Altered or No PAM Recognition

Naturally occurring Cas9 molecules can recognize specific PAM sequences, for example the PAM recognition sequences described above for, e.g., *S. pyogenes, S. thermophilus, S. mutans*, and *S. aureus*.

In certain embodiments, a Cas9 molecule or Cas9 polypeptide has the same PAM specificities as a naturally occurring Cas9 molecule. In other embodiments, a Cas9 molecule or Cas9 polypeptide has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule or Cas9 polypeptide recognizes in order to decrease off-target sites and/or improve specificity; or eliminate a PAM recognition requirement. In certain embodiments, a Cas9 molecule or Cas9 polypeptide can be altered, e.g., to increase length of PAM recognition sequence and/or improve Cas9 specificity to high level of identity (e.g., 98%, 99% or 100% match between gRNA and a PAM sequence), e.g., to decrease off-target sites and/or increase specificity. In certain embodiments, the length of the PAM recognition sequence is at least 4, 5, 6, 7, 8, 9, 10 or 15 amino acids in length. In an embodiment, the Cas9 specificity requires at least 90%, 95%, 96%, 97%, 98%, 99% or more homology between the gRNA and the PAM sequence. Cas9 molecules or Cas9 polypeptides that recognize different PAM sequences and/or have reduced off-target activity can be generated using directed evolution. Exemplary methods and systems that can be used for directed evolution of Cas9 molecules are described (see, e.g., Esvelt 2011). Candidate Cas9 molecules can be evaluated, e.g., by methods described below.

Size-Optimized Cas9

Engineered Cas9 molecules and engineered Cas9 polypeptides described herein include a Cas9 molecule or Cas9 polypeptide comprising a deletion that reduces the size of the molecule while still retaining desired Cas9 properties, e.g., essentially native conformation, Cas9 nuclease activity, and/or target nucleic acid molecule recognition. Provided herein are Cas9 molecules or Cas9 polypeptides comprising one or more deletions and optionally one or more linkers, wherein a linker is disposed between the amino acid residues that flank the deletion. Methods for identifying suitable deletions in a reference Cas9 molecule, methods for generating Cas9 molecules with a deletion and a linker, and methods for using such Cas9 molecules will be apparent to one of ordinary skill in the art upon review of this document.

A Cas9 molecule, e.g., a *S. aureus* or *S. pyogenes* Cas9 molecule, having a deletion is smaller, e.g., has reduced number of amino acids, than the corresponding naturally-occurring Cas9 molecule. The smaller size of the Cas9 molecules allows increased flexibility for delivery methods, and thereby increases utility for genome-editing. A Cas9 molecule can comprise one or more deletions that do not substantially affect or decrease the activity of the resultant Cas9 molecules described herein. Activities that are retained in the Cas9 molecules comprising a deletion as described herein include one or more of the following:

a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which in an embodiment is the presence of two nickase activities: an endonuclease activity; an exonuclease activity; a helicase activity, i.e., the ability to unwind the helical structure of a double stranded nucleic acid; and recognition activity of a nucleic acid molecule, e.g., a target nucleic acid or a gRNA.

Activity of the Cas9 molecules described herein can be assessed using the activity assays described herein or in the art.

Identifying Regions Suitable for Deletion

Suitable regions of Cas9 molecules for deletion can be identified by a variety of methods. Naturally-occurring orthologous Cas9 molecules from various bacterial species can be modeled onto the crystal structure of *S. pyogenes* Cas9 (Nishimasu 2014) to examine the level of conservation across the selected Cas9 orthologs with respect to the three-dimensional conformation of the protein. Less conserved or unconserved regions that are spatially located distant from regions involved in Cas9 activity, e.g., interface with the target nucleic acid molecule and/or gRNA, represent regions or domains are candidates for deletion without substantially affecting or decreasing Cas9 activity.

Nucleic Acids Encoding Cas9 Molecules

Nucleic acids encoding the Cas9 molecules or Cas9 polypeptides, e.g., an eaCas9 molecule or eaCas9 polypeptides are provided herein. Exemplary nucleic acids encoding Cas9 molecules or Cas9 polypeptides have been described previously (see, e.g., Cong 2013; Wang 2013; Mali 2013; Jinek 2012).

In an embodiment, a nucleic acid encoding a Cas9 molecule or Cas9 polypeptide can be a synthetic nucleic acid sequence. For example, the synthetic nucleic acid molecule can be chemically modified, e.g., as described herein. In an embodiment, the Cas9 mRNA has one or more (e.g., all of the following properties: it is capped, polyadenylated, substituted with 5-methylcytidine and/or pseudouridine.

In addition, or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

In addition, or alternatively, a nucleic acid encoding a Cas9 molecule or Cas9 polypeptide may comprise a nuclear localization sequence (NLS). Nuclear localization sequences are known in the art.

An exemplary codon optimized nucleic acid sequence encoding a Cas9 molecule of *S. pyogenes* is set forth in SEQ ID NO:3. The corresponding amino acid sequence of an *S. pyogenes* Cas9 molecule is set forth in SEQ ID NO:2.

Exemplary codon optimized nucleic acid sequences encoding a Cas9 molecule of *S. aureus* are set forth in SEQ ID NOs:7-9. An amino acid sequence of an *S. aureus* Cas9 molecule is set forth in SEQ ID NO:6.

An exemplary codon optimized nucleic acid sequences encoding a Cas9 molecule of *N. meningitidis aureus* are set forth in SEQ ID NOs: 13. The corresponding amino acid sequence of an *N. meningitides* Cas9 molecule is set forth in SEQ ID NO:12.

If any of the above Cas9 sequences are fused with a peptide or polypeptide at the C-terminus, it is understood that the stop codon will be removed.

Other Cas Molecules and Cas Polypeptides

Various types of Cas molecules or Cas polypeptides can be used to practice the methods disclosed herein. In some embodiments Cas molecules of Type II Cas systems are used. In other embodiments, Cas molecules of other Cas systems are used. For example Type I or Type III Cas molecules may be used. Exemplary Cas molecules (and Cas systems) have been described previously (see, e.g. Haft 2005 and Makarova 2011). Exemplary Cas molecules (and Cas systems) are also shown in Table 17.

TABLE 17

Cas Systems

| Gene name‡ | System type or subtype | Name from Haft 2005§ | Structure of encoded protein (PDB accessions)¶ | Families (and superfamily) of encoded protein#** | Representatives |
|---|---|---|---|---|---|
| cas1 | Type I<br>Type II<br>Type III | cas1 | 3GOD, 3LFX and 2YZS | COG1518 | SERP2463, SPy1047 and ygbT |
| cas2 | Type I<br>Type II<br>Type III | cas2 | 2IVY, 2I8E and 3EXC | COG1343 and COG3512 | SERP2462, SPy1048, SPy1723 (N-terminal domain) and ygbF |
| cas3' | Type I‡‡ | cas3 | NA | COG1203 | APE1232 and ygcB |
| cas3" | Subtype I-A<br>Subtype I-B | NA | NA | COG2254 | APE1231 and BH0336 |
| cas4 | Subtype I-A<br>Subtype I-B<br>Subtype I-C<br>Subtype I-D<br>Subtype II-B | cas4 and csa1 | NA | COG1468 | APE1239 and BH0340 |
| cas5 | Subtype I-A<br>Subtype I-B<br>Subtype I-C<br>Subtype I-E | cas5a, cas5d, cas5e, cas5h, cas5p, cas5t and cmx5 | 3KG4 | COG1688 (RAMP) | APE1234, BH0337, devS and ygcI |
| cas6 | Subtype I-A<br>Subtype I-B<br>Subtype I-D<br>Subtype III-A<br>Subtype III-B | cas6 and cmx6 | 3I4H | COG1583 and COG5551 (RAMP) | PF1131 and slr7014 |
| cas6e | Subtype I-E | cse3 | 1WJ9 | (RAMP) | ygcH |
| cas6f | Subtype I-F | csy4 | 2XLJ | (RAMP) | y1727 |
| cas7 | Subtype I-A<br>Subtype I-B<br>Subtype I-C<br>Subtype I-E | csa2, csd2, cse4, csh2, csp1 and cst2 | NA | COG1857 and COG3649 (RAMP) | devR and ygcJ |
| cas8a1 | Subtype I-A‡‡ | cmx1, cst1, csx8, csx13 and CXXC-CXXC | NA | BH0338-like | LA3191§§ and PG2018§§ |
| cas8a2 | Subtype I-A‡‡ | csa4 and csx9 | NA | PH0918 | AF0070, AF1873, MJ0385, PF0637, PH0918 and SSO1401 |
| cas8b | Subtype I-B‡‡ | csh1 and TM1802 | NA | BH0338-like | MTH1090 and TM1802 |
| cas8c | Subtype I-C‡‡ | csd1 and csp2 | NA | BH0338-like | BH0338 |
| cas9 | Type II‡‡ | csn1 and csx12 | NA | COG3513 | FTN_0757 and SPy1046 |
| cas10 | Type III‡‡ | cmr2, csm1 and csx11 | NA | COG1353 | MTH326, Rv2823c§§ and TM1794§§ |
| cas10d | Subtype I-D‡‡ | csc3 | NA | COG1353 | slr7011 |
| csy1 | Subtype I-F‡‡ | csy1 | NA | y1724-like | y1724 |
| csy2 | Subtype I-F | csy2 | NA | (RAMP) | y1725 |
| csy3 | Subtype I-F | csy3 | NA | (RAMP) | y1726 |
| cse1 | Subtype I-E‡‡ | cse1 | NA | YgcL-like | ygcL |
| cse2 | Subtype I-E | cse2 | 2ZCA | YgcK-like | ygcK |
| csc1 | Subtype I-D | csc1 | NA | alr1563-like (RAMP) | alr1563 |
| csc2 | Subtype I-D | csc1 and csc2 | NA | COG1337 (RAMP) | slr7012 |
| csa5 | Subtype I-A | csa5 | NA | AF1870 | AF1870, MJ0380, PF0643 and SSO1398 |
| csn2 | Subtype II-A | csn2 | NA | SPy1049-like | SPy1049 |
| csm2 | Subtype III-A‡‡ | csm2 | NA | COG1421 | MTH1081 and SERP2460 |
| csm3 | Subtype III-A | csc2 and csm3 | NA | COG1337 (RAMP) | MTH1080 and SERP2459 |
| csm4 | Subtype III-A | csm4 | NA | COG1567 (RAMP) | MTH1079 and SERP2458 |
| csm5 | Subtype III-A | csm5 | NA | COG1332 (RAMP) | MTH1078 and SERP2457 |
| csm6 | Subtype III-A | APE2256 and csm6 | 2WTE | COG1517 | APE2256 and SSO1445 |
| cmr1 | Subtype III-B | cmr1 | NA | COG1367 (RAMP) | PF1130 |
| cmr3 | Subtype III-B | cmr3 | NA | COG1769 (RAMP) | PF1128 |

TABLE 17-continued

Cas Systems

| Gene name[‡] | System type or subtype | Name from Haft 2005[§] | Structure of encoded protein (PDB accessions)[¶] | Families (and superfamily) of encoded protein[#]** | Representatives |
|---|---|---|---|---|---|
| cmr4 | Subtype III-B | cmr4 | NA | COG1336 (RAMP) | PF1126 |
| cmr5 | Subtype III-B[‡‡] | cmr5 | 2ZOP and 2OEB | COG3337 | MTH324 and PF1125 |
| cmr6 | Subtype III-B | cmr6 | NA | COG1604 (RAMP) | PF1124 |
| csb1 | Subtype I-U | GSU0053 | NA | (RAMP) | Balac_1306 and GSU0053 |
| csb2 | Subtype I-U[§§] | NA | NA | (RAMP) | Balac_1305 and GSU0054 |
| csb3 | Subtype I-U | NA | NA | (RAMP) | Balac_1303[§§] |
| csx17 | Subtype I-U | NA | NA | NA | Btus_2683 |
| csx14 | Subtype I-U | NA | NA | NA | GSU0052 |
| csx10 | Subtype I-U | csx10 | NA | (RAMP) | Caur_2274 |
| csx16 | Subtype III-U | VVA1548 | NA | NA | VVA1548 |
| csaX | Subtype III-U | csaX | NA | NA | SSO1438 |
| csx3 | Subtype III-U | csx3 | NA | NA | AF1864 |
| csx1 | Subtype III-U | csa3, csx1, csx2, DXTHG, NE0113 and TIGR02710 | 1XMX and 2I71 | COG1517 and COG4006 | MJ1666, NE0113, PF1127 and TM1812 |
| csx15 | Unknown | NA | NA | TTE2665 | TTE2665 |
| csf1 | Type U | csf1 | NA | NA | AFE_1038 |
| csf2 | Type U | csf2 | NA | (RAMP) | AFE_1039 |
| csf3 | Type U | csf3 | NA | (RAMP) | AFE_1040 |
| csf4 | Type U | csf4 | NA | NA | AFE_1037 |

Other Nucleases

The methods and database schemas described herein for selecting and designing gRNA molecules can also be used for other systems, such as Cpf1 systems, transcription activator-like effector nuclease (TALEN) systems, and zinc finger nuclease (ZFN) systems, as would be understood by one of ordinary skill in the art using the teachings disclosed herein. For example, Cpf1 is a single RNA-guided endonuclease of a Class 2 CRISPR-Cas system (see Zetsche et al., 2015, Cell 163, 1-13). Transcription activator-like effector nuclease (TALEN) systems are fusions of TALEs derived from *Xanthomonas* species to a restriction endonuclease, FokI. By modifying amino acid repeats in the TALEs, one of ordinary skill in the art could customize TALEN systems to specifically bind target DNA and introduce cleavage between TAL binding sites. Similarly, zinc finger nuclease systems utilize a FokI nuclease as a DNA-cleavage domain, and specific zinc fingers recognize different nucleotide triplets and dimerize the FolkI nuclease, resulting in the introduction of a double stranded break between the two distinct zinc finger binding sites.

IV. Functional Analysis of Candidate Molecules

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule are described, e.g., in Jinek et al., *SCIENCE* 2012, 337(6096):816-821.

Binding and Cleavage Assay: Testing the Endonuclease Activity of Cas9 Molecule

The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and ~3-6 pmol (~20-40 mCi) [γ-32P]-ATP in 1×T4 polynucleotide kinase reaction buffer at 37° C. for 30 min, in a 50 μL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM MgCl2, 1 mM DTT, 5% glycerol) in a total volume of 9 μl. Reactions are initiated by the addition of 1 μl target DNA (10 nM) and incubated for 1 h at 37° C. Reactions are quenched by the addition of 20 μl of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cas9 molecule.

Binding Assay: Testing the Binding of Cas9 Molecule to Target DNA

Exemplary methods for evaluating the binding of Cas9 molecule to target DNA are described, e.g., in Jinek et al., *SCIENCE* 2012; 337(6096):816-821.

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1×TBE. DNA bands are visualized by UV shadowing, excised, and eluted by soaking gel pieces in DEPC-treated $H_2O$. Eluted DNA is ethanol precipitated and dissolved in DEPC-treated $H_2O$. DNA samples are 5' end labeled with [γ-32P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM $MgCl_2$, 1 mM DTT and 10% glycerol in a total volume of 10 μl. Cas9 protein molecule is programmed with equimolar amounts of pre-annealed gRNA molecule and titrated from 100 pM to 1 μM. Radiolabeled DNA is added to a final concentration of 20 pM. Samples are incubated for 1 h at 37° C. and resolved at 4° C., on an 8% native polyacrylamide gel containing 1×TBE and 5 mM $MgCl_2$. Gels are dried and DNA visualized by phosphorimaging.

Techniques for Measuring Thermostability of Cas9/gRNA Complexes

The thermostability of Cas9-gRNA ribonucleoprotein (RNP) complexes can be detected by differential scanning fluorimetry (DSF) and other techniques. The thermostability of a protein can increase under favorable conditions such as the addition of a binding RNA molecule, e.g., a gRNA. Thus, information regarding the thermostability of a Cas9/gRNA complex is useful for determining whether the complex is stable.

Differential Scanning Fluorimetry (DSF)

DSF is a technique that may be used to measure the thermostability of a protein. The assay can be applied in a number of ways. Exemplary protocols include, but are not limited to, a protocol to determine the desired solution conditions for RNP formation (assay 1, see below), a protocol to test the desired stoichiometric ratio of gRNA:Cas9 protein (assay 2, see below), a protocol to screen for effective gRNA molecules for Cas9 molecules, e.g., wild-type or mutant Cas9 molecules (assay 3, see below), and a protocol to examine RNP formation in the presence of target DNA (assay 4).

Assay 1

To determine the desired solution to form RNP complexes, a 2 μM solution of Cas9 is made in water with 10×SYPRO Orange® (Life Technologies Cat #S-6650) and dispensed into a 384 well plate. An equimolar amount of gRNA diluted in solutions with varied pH and salt is then added. After incubating at room temperature for 10 minutes and centrifugation at 2000 rpm to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Assay 2

The second assay includes mixing various concentrations of gRNA molecules with 2 μM Cas9 in the buffer from assay 1 above and incubating at RT for 10 minutes in a 384 well plate. An equal volume of optimal buffer with 10×SYPRO Orange® (Life Technologies cat #S-6650) is added and the plate is sealed with Microseal® B adhesive (MSB-1001). Following centrifugation at 2000 rpm to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Assay 3

In the third assay, a Cas9 molecule (e.g., a Cas9 protein, e.g., a Cas9 variant protein) of interest is purified. A library of variant gRNA molecules is synthesized and resuspended to a concentration of 20 μM. The Cas9 molecule is incubated with the gRNA molecule at a final concentration of 1 μM each in a predetermined buffer in the presence of 5×SYPRO Orange® (Life Technologies Cat #5-6650). After incubating at room temperature for 10 minutes and centrifugation at 2000 rpm for 2 minutes to remove any bubbles, a Bio-Rad CFX384™ Real-Time System C1000 Touch™ Thermal Cycler with the Bio-Rad CFX Manager software is used to run a gradient from 20° C. to 90° C. with an increase of 1° C. in temperature every 10 seconds.

Assay 4

In the fourth assay, a DSF experiment is performed with the following samples: Cas9 protein alone, Cas9 protein with gRNA, Cas9 protein with gRNA and target DNA, and Cas9 protein with target DNA. The order of mixing components is: reaction solution, Cas9 protein, gRNA, DNA, and SYPRO Orange. The reaction solution contains 10 mM HEPES pH 7.5, 100 mM NaCl, in the absence or presence of MgCl2. Following centrifugation at 2000 rpm for 2 minutes to remove any bubbles, a Bio-Rad CFX384T™ Real-Time System C1000 Touch™ Thermal Cycler with the Bio-Rad CFX Manager software is used to run a gradient from 20° C. to 90° C. with a 1° increase in temperature every 10 seconds.

V. Genome Editing Approaches

Mutations in a gene, e.g., a gene described herein may be corrected using one of the approaches discussed herein. In an embodiment, a mutation in the gene is corrected by homology directed repair (HDR) using an exogenously provided template nucleic acid (see below). In another embodiment, a mutation in the gene is corrected by homology directed repair without using an exogenously provided template nucleic acid (see below).

Also described herein are methods for targeted disruption (e.g., knockout) of one or both alleles of the gene using NHEJ (see below). In another embodiment, methods are provided for targeted knockdown of the gene (see below).

HDR Repair, HDR Mediated Knockin and Template Nucleic Acids

As described herein, nuclease-induced homology directed repair (HDR) can be used to alter a target sequence and correct (e.g., repair or edit) a mutation in the genome. Alteration of the target sequence occurs by homology-directed repair (HDR) with an exogenously provided donor template or template nucleic acid. For example, the donor template or the template nucleic acid provides for alteration of the target sequence. It is contemplated that a plasmid donor can be used as a template for homologous recombination. It is further contemplated that a single stranded donor template can be used as a template for alteration of the target sequence by alternate methods of homology directed repair (e.g., single strand annealing) between the target sequence and the donor template. Donor template-effected alteration of a target sequence depends on cleavage by a Cas9 molecule. Cleavage by Cas9 can comprise a double strand break or two single strand breaks. As described herein, nuclease-induced homology directed repair (HDR) can be used to alter a target sequence and correct (e.g., repair or edit) a mutation in the genome without the use of an exogenously provided donor template or template nucleic acid. Alteration of the target sequence occurs by homology-directed repair (HDR) with endogenous genomic donor sequence. For example, the endogenous genomic donor sequence provides for alteration of the target sequence. It is contemplated that in an embodiment the endogenous genomic donor sequence is located on the same chromosome as the target sequence. It is further contemplated that in another embodiment the endogenous genomic donor sequence is located on a different chromosome from the target sequence. Alteration of a target sequence by endogenous genomic donor sequence depends on cleavage by a Cas9 molecule. Cleavage by Cas9 can comprise a double strand break or two single strand breaks.

Mutations that can be corrected by HDR using a template nucleic acid, or using endogenous genomic donor sequence, include point mutations. In an embodiment, a point mutation can be corrected by either a single double-strand break or two single strand breaks. In an embodiment, a point mutation can be corrected by (1) a single double-strand break, (2) two single strand breaks, (3) two double stranded breaks with a break occurring on each side of the target position, (4) one double stranded break and two single strand breaks with the double strand break and two single strand breaks occurring on each side of the target position (5) four single stranded breaks with a pair of single stranded breaks occurring on each side of the target position, or (6) one single stranded break.

In an embodiment where a single-stranded template nucleic acid is used, the target position can be altered by alternative HDR.

Donor template-effected alteration of a target position depends on cleavage by a Cas9 molecule. Cleavage by Cas9 can comprise a nick, a double strand break, or two single strand breaks, e.g., one on each strand of the target nucleic acid. After introduction of the breaks on the target nucleic acid, resection occurs at the break ends resulting in single stranded overhanging DNA regions.

In canonical HDR, a double-stranded donor template is introduced, comprising homologous sequence to the target nucleic acid that will either be directly incorporated into the target nucleic acid or used as a template to correct the sequence of the target nucleic acid. After resection at the break, repair can progress by different pathways, e.g., by the double Holliday junction model (or double strand break repair, DSBR, pathway) or the synthesis-dependent strand annealing (SDSA) pathway. In the double Holliday junction model, strand invasion by the two single stranded overhangs of the target nucleic acid to the homologous sequences in the donor template occurs, resulting in the formation of an intermediate with two Holliday junctions. The junctions migrate as new DNA is synthesized from the ends of the invading strand to fill the gap resulting from the resection. The end of the newly synthesized DNA is ligated to the resected end, and the junctions are resolved, resulting in the correction of the target nucleic acid, e.g., incorporation of the correct sequence of the donor template at the corresponding target position. Crossover with the donor template may occur upon resolution of the junctions. In the SDSA pathway, only one single stranded overhang invades the donor template and new DNA is synthesized from the end of the invading strand to fill the gap resulting from resection. The newly synthesized DNA then anneals to the remaining single stranded overhang, new DNA is synthesized to fill in the gap, and the strands are ligated to produce the corrected DNA duplex.

In alternative HDR, a single strand donor template, e.g., template nucleic acid, is introduced. A nick, single strand break, or double strand break at the target nucleic acid, for altering a desired target position, is mediated by a Cas9 molecule, e.g., described herein, and resection at the break occurs to reveal single stranded overhangs. Incorporation of the sequence of the template nucleic acid to correct or alter the target position of the target nucleic acid typically occurs by the SDSA pathway, as described above.

Methods of promoting HDR pathways, e.g., canonical HDR or alt-HDR, are described herein in Section VI.

Additional details on template nucleic acids are provided in Section IV entitled "Template nucleic acids" in International Application PCT/US2014/057905.

Mutations in the sequences of allelic variants of a specific locus, e.g., HLA-A, HLA-B, HLA-C, HLA-DRB1, HLA-DRB3/4/5, or HLA-DQB1 that can be corrected (e.g., altered) by HDR with a template nucleic acid or with endogenous genomic donor sequence include. An A1AT sequence can also be inserted into the sequences of allelic variants of a specific locus, e.g., HLA-A, HLA-B, HLA-C, HLA-DRB1, HLA-DRB3/4/5, or HLA-DQB1 by HDR with a template nucleic acid, e.g., a template nucleic acid described herein Double Strand Break Mediated Correction or Knockin In an embodiment, double strand cleavage is effected by a Cas9 molecule having cleavage activity associated with an HNH-like domain and cleavage activity associated with a RuvC-like domain, e.g., an N-terminal RuvC-like domain, e.g., a wild type Cas9. Such embodiments require only a single gRNA.

Single Strand Break Mediated Correction or Knockin

In some embodiments, one single strand break, or nick, is effected by a Cas9 molecule having nickase activity, e.g., a Cas9 nickase as described herein. A nicked target nucleic acid can be a substrate for alt-HDR.

In other embodiments, two single strand breaks, or nicks, are effected by a Cas9 molecule having nickase activity, e.g., cleavage activity associated with an HNH-like domain or cleavage activity associated with an N-terminal RuvC-like domain. Such embodiments usually require two gRNAs, one for placement of each single strand break. In an embodiment, the Cas9 molecule having nickase activity cleaves the strand to which the gRNA hybridizes, but not the strand that is complementary to the strand to which the gRNA hybridizes. In an embodiment, the Cas9 molecule having nickase activity does not cleave the strand to which the gRNA hybridizes, but rather cleaves the strand that is complementary to the strand to which the gRNA hybridizes.

In an embodiment, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HNH activity and will cut on the strand to which the gRNA hybridizes (e.g., the complementary strand, which does not have the NGG PAM on it). In other embodiments, a Cas9 molecule having an H840, e.g., an H840A, mutation can be used as a nickase. H840A inactivates HNH;

therefore, the Cas9 nickase has (only) RuvC activity and cuts on the non-complementary strand (e.g., the strand that has the NGG PAM and whose sequence is identical to the gRNA). In other embodiments, a Cas9 molecule having an N863, e.g., the N863A mutation, mutation can be used as a nickase. N863A inactivates HNH therefore the Cas9 nickase has (only) RuvC activity and cuts on the non-complementary strand (the strand that has the NGG PAM and whose sequence is identical to the gRNA). In other embodiments, a Cas9 molecule having an N580, e.g., the N580A mutation, mutation can be used as a nickase. N580A inactivates HNH therefore the Cas9 nickase has (only) RuvC activity and cuts on the non-complementary strand (the strand that has the NGG PAM and whose sequence is identical to the gRNA). In an embodiment, in which a nickase and two gRNAs are used to position two single strand nicks, one nick is on the + strand and one nick is on the − strand of the target nucleic acid. The PAMs can be outwardly facing. The gRNAs can be selected such that the gRNAs are separated by, from about 0-50, 0-100, or 0-200 nucleotides. In an embodiment, there is no overlap between the target sequences that are complementary to the targeting domains of the two gRNAs. In an embodiment, the gRNAs do not overlap and are separated by as much as 50, 100, or 200 nucleotides. In an embodiment, the use of two gRNAs can increase specificity, e.g., by decreasing off-target binding (Ran et al., Cell 2013; 154(6): 1380-1389).

In an embodiment, a single nick can be used to induce HDR, e.g., alt-HDR. It is contemplated herein that a single nick can be used to increase the ratio of HR to NHEJ at a given cleavage site. In an embodiment, a single strand break is formed in the strand of the target nucleic acid to which the targeting domain of said gRNA is complementary. In another embodiment, a single strand break is formed in the strand of the target nucleic acid other than the strand to which the targeting domain of said gRNA is complementary.

Placement of Double Strand or Single Strand Breaks Relative to the Target Position The double strand break or single strand break in one of the strands should be sufficiently close to target position such that an alteration is produced in the desired region, e.g., correction of a mutation occurs. In an embodiment, the distance is not more than 50, 100, 200, 300, 350 or 400 nucleotides. It is believed that the break should be sufficiently close to target position such that the target position is within the region that is subject to exonuclease-mediated removal during end resection. If the distance between the target position and a break is too great, the mutation or other sequence desired to be altered may not be included in the end resection and, therefore, may not be corrected, as donor sequence, either exogenously provided donor sequence or endogenous genomic donor sequence, in some embodiments is only used to correct sequence within the end resection region.

In an embodiment, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150 or 200 nucleotides of the region desired to be altered, e.g., a mutation. The break, e.g., a double strand or single strand break, can be positioned upstream or downstream of the region desired to be altered, e.g., a mutation. In some embodiments, a break is positioned within the region desired to be altered, e.g., within a region defined by at least two mutant nucleotides. In some embodiments, a break is positioned immediately adjacent to the region desired to be altered, e.g., immediately upstream or downstream of a mutation.

In an embodiment, a single strand break is accompanied by an additional single strand break, positioned by a second gRNA molecule, as discussed below. For example, the targeting domains bind configured such that a cleavage event, e.g., the two single strand breaks, are positioned within 1, 2, 3, 4, 5, 10, 15, 20, 25, 30, 35, 40, 45, 50, 60, 70, 80, 90, 100, 150 or 200 nucleotides of a target position. In an embodiment, the first and second gRNA molecules are configured such, that when guiding a Cas9 nickase, a single strand break will be accompanied by an additional single strand break, positioned by a second gRNA, sufficiently close to one another to result in alteration of the desired region. In an embodiment, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In an embodiment, the two gRNA molecules are configured to position cuts at the same position, or within a few nucleotides of one another, on different strands, e.g., essentially mimicking a double strand break.

In an embodiment, in which a gRNA (unimolecular (or chimeric) or modular gRNA) and Cas9 nuclease induce a double strand break for the purpose of inducing HDR-mediated correction, the cleavage site is between 0-200 bp (e.g., 0-175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In embodiments, one can promote HDR by using nickases to generate a break with overhangs. The single stranded nature of the overhangs can enhance the cell's likelihood of repairing the break by HDR as opposed to, e.g., NHEJ. Specifically, in some embodiments, HDR is promoted by selecting a first gRNA that targets a first nickase to a first target sequence, and a second gRNA that targets a second nickase to a second target sequence which is on the opposite DNA strand from the first target sequence and offset from the first nick.

In an embodiment, the targeting domain of a gRNA molecule is configured to position a cleavage event sufficiently far from a preselected nucleotide, e.g., the nucleotide of a coding region, such that the nucleotide is not altered. In an embodiment, the targeting domain of a gRNA molecule is configured to position an intronic cleavage event sufficiently far from an intron/exon border, or naturally occurring splice signal, to avoid alteration of the exonic sequence or unwanted splicing events. The gRNA molecule may be a first, second, third and/or fourth gRNA molecule, as described herein.

Placement of a First Break and a Second Break Relative to Each Other

In an embodiment, a double strand break can be accompanied by an additional double strand break, positioned by a second gRNA molecule, as is discussed below.

In an embodiment, a double strand break can be accompanied by two additional single strand breaks, positioned by a second gRNA molecule and a third gRNA molecule.

In an embodiment, a first and second single strand breaks can be accompanied by two additional single strand breaks positioned by a third gRNA molecule and a fourth gRNA molecule.

When two or more gRNAs are used to position two or more cleavage events, e.g., double strand or single strand breaks, in a target nucleic acid, it is contemplated that the two or more cleavage events may be made by the same or different Cas9 proteins. For example, when two gRNAs are used to position two double stranded breaks, a single Cas9 nuclease may be used to create both double stranded breaks. When two or more gRNAs are used to position two or more single stranded breaks (nicks), a single Cas9 nickase may be used to create the two or more nicks. When two or more gRNAs are used to position at least one double stranded break and at least one single stranded break, two Cas9 proteins may be used, e.g., one Cas9 nuclease and one Cas9 nickase. It is contemplated that when two or more Cas9 proteins are used that the two or more Cas9 proteins may be delivered sequentially to control specificity of a double stranded versus a single stranded break at the desired position in the target nucleic acid.

In some embodiments, the targeting domain of the first gRNA molecule and the targeting domain of the second gRNA molecules are complementary to opposite strands of the target nucleic acid molecule. In some embodiments, the gRNA molecule and the second gRNA molecule are configured such that the PAMs are oriented outward.

In certain embodiments, two gRNA are selected to direct Cas9-mediated cleavage at two positions that are a preselected distance from each other. In embodiments, the two points of cleavage are on opposite strands of the target nucleic acid. In some embodiments, the two cleavage points form a blunt ended break, and in other embodiments, they are offset so that the DNA ends comprise one or two overhangs (e.g., one or more 5' overhangs and/or one or more 3' overhangs). In some embodiments, each cleavage event is a nick. In embodiments, the nicks are close enough together that they form a break that is recognized by the double stranded break machinery (as opposed to being recognized by, e.g., the SSBr machinery). In embodiments, the nicks are far enough apart that they create an overhang that is a substrate for HDR, i.e., the placement of the breaks mimics a DNA substrate that has experienced some resection. For instance, in some embodiments the nicks are spaced to create an overhang that is a substrate for processive resection. In some embodiments, the two breaks are spaced within 25-65 nucleotides of each other. The two breaks may be, e.g., about 25, 30, 35, 40, 45, 50, 55, 60 or 65 nucleotides of each other. The two breaks may be, e.g., at least about 25, 30, 35, 40, 45, 50, 55, 60 or 65 nucleotides of each other. The two breaks may be, e.g., at most about 30, 35, 40, 45, 50, 55, 60 or 65 nucleotides of each other. In embodiments, the two breaks are about 25-30, 30-35, 35-40, 40-45, 45-50, 50-55, 55-60, or 6065 nucleotides of each other.

In some embodiments, the break that mimics a resected break comprises a 3' overhang (e.g., generated by a DSB and a nick, where the nick leaves a 3' overhang), a 5' overhang (e.g., generated by a DSB and a nick, where the nick leaves a 5' overhang), a 3' and a 5' overhang (e.g., generated by three cuts), two 3' overhangs (e.g., generated by two nicks that are offset from each other), or two 5' overhangs (e.g., generated by two nicks that are offset from each other).

In an embodiment, in which two gRNAs (independently, unimolecular (or chimeric) or modular gRNA) complexing with Cas9 nickases induce two single strand breaks for the purpose of inducing HDR-mediated correction, the closer nick is between 0-200 bp (e.g., 0-175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position and the two nicks will ideally be within 25-65 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp, 45 to 50 bp, 50 to 55 bp, 55 to 60 bp, 60 to 65 bp) and no more than 100 bp away from each other (e.g., no more than 90, 80, 70, 60, 50, 40, 30, 20, 10 or 5 bp away from each other). In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position. In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position. The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are, in embodiments, within 25-65 bp of each other (e.g., between 25 to 55, 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, 20 or 10 bp).

When two gRNAs are used to target Cas9 molecules to breaks, different combinations of Cas9 molecules are envisioned. In some embodiments, a first gRNA is used to target a first Cas9 molecule to a first target position, and a second gRNA is used to target a second Cas9 molecule to a second target position. In some embodiments, the first Cas9 molecule creates a nick on the first strand of the target nucleic acid, and the second Cas9 molecule creates a nick on the opposite strand, resulting in a double stranded break (e.g., a blunt ended cut or a cut with overhangs).

Different combinations of nickases can be chosen to target one single stranded break to one strand and a second single stranded break to the opposite strand. When choosing a combination, one can take into account that there are nickases having one active RuvC-like domain, and nickases having one active HNH domain. In an embodiment, a RuvC-like domain cleaves the non-complementary strand of the target nucleic acid molecule. In an embodiment, an HNH-like domain cleaves a single stranded complementary domain, e.g., a complementary strand of a double stranded nucleic acid molecule. Generally, if both Cas9 molecules have the same active domain (e.g., both have an active RuvC domain or both have an active HNH domain), one will choose two gRNAs that bind to opposite strands of the target. In more detail, in some embodiments, a first gRNA is complementary with a first strand of the target nucleic acid and binds a nickase having an active RuvC-like domain and causes that nickase to cleave the strand that is non-complementary to that first gRNA, i.e., a second strand of the target nucleic acid; and a second gRNA is complementary with a second strand of the target nucleic acid and binds a nickase having an active RuvC-like domain and causes that nickase to cleave the strand that is non-complementary to that second gRNA, i.e., the first strand of the target nucleic acid. Conversely, in some embodiments, a first gRNA is complementary with a first strand of the target nucleic acid and binds a nickase having an active HNH domain and causes that nickase to cleave the strand that is complementary to that first gRNA, i.e., a first strand of the target nucleic acid; and a second gRNA is complementary with a second strand of the target nucleic acid and binds a nickase having an active HNH domain and causes that nickase to cleave the strand that is complementary to that second gRNA, i.e., the second strand of the target nucleic acid. In another arrangement, if one Cas9 molecule has an active RuvC-like domain and the other Cas9 molecule has an active HNH domain, the gRNAs for both Cas9 molecules can be complementary to the same strand of the target nucleic acid, so that the Cas9 molecule with the active RuvC-like domain will cleave the non-complementary strand and the Cas9 molecule with the HNH domain will cleave the complementary strand, resulting in a double stranded break.

Length of the Homology Arms of the Donor Template

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm does not extend into repeated elements. e.g., Alu repeats or LINE repeats.

Exemplary homology arm lengths include at least 50, 100, 250, 500, 750, 1000, 2000, 3000, 4000, or 5000 nucleotides. In some embodiments, the homology arm length is 50-100, 100-250, 250-500, 500-750, 750-1000, 1000-2000, 2000-3000, 3000-4000, or 4000-5000 nucleotides.

Target position, as used herein, refers to a site on a target nucleic acid (e.g., the chromosome) that is modified by a Cas9 molecule-dependent process. For example, the target position can be a modified Cas9 molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides are added. The target position may comprise one or more nucleotides that are altered, e.g., corrected, by a template nucleic acid. In an embodiment, the target position is within a target sequence (e.g., the sequence to which the gRNA binds). In an embodiment, a target position is upstream or downstream of a target sequence (e.g., the sequence to which the gRNA binds).

A template nucleic acid, as that term is used herein, refers to a nucleic acid sequence which can be used in conjunction with a Cas9 molecule and a gRNA molecule to alter the structure of a target position. In an embodiment, the target nucleic acid is modified to have the some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA. In an embodiment, the template nucleic acid is encoded on the same vector backbone, e.g. AAV genome, plasmid DNA, as the Cas9 and gRNA. In an embodiment, the template nucleic acid is excised from a vector backbone in vivo, e.g., it is flanked by gRNA recognition sequences. In an embodiment, the template nucleic acid comprises endogenous genomic sequence In an embodiment, the template nucleic acid alters the structure of the target position by participating in a homology directed repair event. In an embodiment, the template nucleic acid alters the sequence of the target position. In an embodiment, the template nucleic acid results in the incorporation of a modified, or non-naturally occurring base into the target nucleic acid.

Typically, the template sequence undergoes a breakage mediated or catalyzed recombination with the target sequence. In an embodiment, the template nucleic acid includes sequence that corresponds to a site on the target sequence that is cleaved by an eaCas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a gene, e.g., a gene described herein, can be used to alter the structure of a target sequence. The template sequence can be used to alter an unwanted structure, e.g., an unwanted or mutant nucleotide.

A template nucleic acid typically comprises the following components:

[5' homology arm]-[replacement sequence]-[3' homology arm].

The homology arms provide for recombination into the chromosome, thus replacing the undesired element, e.g., a mutation or signature, with the replacement sequence. In an embodiment, the homology arms flank the most distal cleavage sites.

In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, 2000, 3000, 4000, or 5000 nucleotides 5' from the 5' end of the replacement sequence.

In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, 2000, 3000, 4000, or 5000 nucleotides 3' from the 3' end of the replacement sequence.

In an embodiment, to correct a mutation, the homology arms, e.g., the 5' and 3' homology arms, may each comprise about 1000 base pairs (bp) of sequence flanking the most distal gRNAs (e.g., 1000 bp of sequence on either side of the mutation).

It is contemplated herein that one or both homology arms may be shortened to avoid including certain sequence repeat elements, e.g., Alu repeats or LINE elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

It is contemplated herein that template nucleic acids for correcting a mutation may be designed for use as a single-stranded oligonucleotide, e.g., a single-stranded oligodeoxynucleotide (ssODN). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made. In some embodiments, a longer homology arm is made by a method other than chemical synthesis, e.g., by denaturing a long double stranded nucleic acid and purifying one of the strands, e.g., by affinity for a strand-specific sequence anchored to a solid substrate.

In some embodiments alt-HDR proceeds more efficiently when the template nucleic acid has extended homology 5' to the nick (i.e., in the 5' direction of the nicked strand). Accordingly, in some embodiments, the template nucleic acid has a longer homology arm and a shorter homology arm, wherein the longer homology arm can anneal 5' of the nick. In some embodiments, the arm that can anneal 5' to the nick is at least 25, 50, 75, 100, 125, 150, 175, or 200, 300, 400, 500, 600, 700, 800, 900, 1000, 1500, 2000, 3000, 4000, or 5000 nucleotides from the nick or the 5' or 3' end of the replacement sequence. In some embodiments, the arm that can anneal 5' to the nick is at least 10%, 20%, 30%, 40%, or 50% longer than the arm that can anneal 3' to the nick. In some embodiments, the arm that can anneal 5' to the nick is at least 2×, 3×, 4×, or 5× longer than the arm that can anneal 3' to the nick. Depending on whether a ssDNA template can anneal to the intact strand or the nicked strand, the homology arm that anneals 5' to the nick may be at the 5' end of the ssDNA template or the 3' end of the ssDNA template, respectively.

Similarly, in some embodiments, the template nucleic acid has a 5' homology arm, a replacement sequence, and a 3' homology arm, such that the template nucleic acid has extended homology to the 5' of the nick. For example, the 5' homology arm and 3' homology arm may be substantially the same length, but the replacement sequence may extend farther 5' of the nick than 3' of the nick. In some embodiments, the replacement sequence extends at least 10%, 20%, 30%, 40%, 50%, 2×, 3×, 4×, or 5× further to the 5' end of the nick than the 3' end of the nick.

In some embodiments alt-HDR proceeds more efficiently when the template nucleic acid is centered on the nick. Accordingly, in some embodiments, the template nucleic acid has two homology arms that are essentially the same size. For instance, the first homology arm of a template nucleic acid may have a length that is within 10%, 9%, 8%, 7%, 6%, 5%, 4%, 3%, 2%, or 1% of the second homology arm of the template nucleic acid.

Similarly, in some embodiments, the template nucleic acid has a 5' homology arm, a replacement sequence, and a 3' homology arm, such that the template nucleic acid extends substantially the same distance on either side of the nick. For example, the homology arms may have different lengths, but the replacement sequence may be selected to compensate for this. For example, the replacement sequence may extend further 5' from the nick than it does 3' of the nick, but the homology arm 5' of the nick is shorter than the homology arm 3' of the nick, to compensate. The converse is also possible, e.g., that the replacement sequence may extend further 3' from the nick than it does 5' of the nick, but the homology arm 3' of the nick is shorter than the homology arm 5' of the nick, to compensate.

Exemplary Arrangements of Linear Nucleic Acid Template Stems

In an embodiment, the nucleic acid template system is double stranded. In an embodiment, the nucleic acid template system is single stranded. In an embodiment, the nucleic acid template system comprises a single stranded portion and a double stranded portion. In an embodiment, the template nucleic acid comprises about 50 to 100, e.g., 55 to 95, 60 to 90, 65 to 85, or 70 to 80, base pairs, homology on either side of the nick and/or replacement sequence. In an embodiment, the template nucleic acid comprises about 50, 55, 60, 65, 70, 75, 80, 85, 90, 95, or 100 base pairs homology 5' of the nick or replacement sequence. 3' of the nick or replacement sequence, or both 5' and 3' of the nick or replacement sequences.

In an embodiment, the template nucleic acid comprises about 150 to 200, e.g., 155 to 195, 160 to 190, 165 to 185, or 170 to 180, base pairs homology 3' of the nick and/or replacement sequence. In an embodiment, the template nucleic acid comprises about 150, 155, 160, 165, 170, 175, 180, 185, 190, 195, or 200 base pairs homology 3' of the nick or replacement sequence. In an embodiment, the template nucleic acid comprises less than about 100, 90, 80, 70, 60, 50, 40, 30, 20, 15, or 10 base pairs homology 5' of the nick or replacement sequence.

In an embodiment, the template nucleic acid comprises about 150 to 200, e.g., 155 to 195, 160 to 190, 165 to 185, or 170 to 180, base pairs homology 5' of the nick and/or replacement sequence. In an embodiment, the template nucleic acid comprises about 150, 155, 160, 165, 170, 175, 180, 185, 190, 195, or 200 base pairs homology 5' of the nick or replacement sequence. In an embodiment, the template nucleic acid comprises less than about 100, 90, 80, 70, 60, 50, 40, 30, 20, 15, or 10 base pairs homology 3' of the nick or replacement sequence.

Exemplary Template Nucleic Acids

In an embodiment, the template nucleic acid is a single stranded nucleic acid. In another embodiment, the template nucleic acid is a double stranded nucleic acid. In some embodiments, the template nucleic acid comprises a nucleotide sequence, e.g., of one or more nucleotides, that will be added to or will template a change in the target nucleic acid. In other embodiments, the template nucleic acid comprises a nucleotide sequence that may be used to modify the target position. In other embodiments, the template nucleic acid comprises a nucleotide sequence, e.g., of one or more nucleotides, that corresponds to wild type sequence of the target nucleic acid, e.g., of the target position.

The template nucleic acid may comprise a replacement sequence. In some embodiments, the template nucleic acid comprises a 5' homology arm. In other embodiments, the template nucleic acid comprises a 3' homology arm.

In embodiments, the template nucleic acid is linear double stranded DNA. The length may be, e.g., about 150-200 base pairs, e.g., about 150, 160, 170, 180, 190, or 200 base pairs. The length may be, e.g., at least 150, 160, 170, 180, 190, or 200 base pairs. In some embodiments, the length is no greater than 150, 160, 170, 180, 190, or 200 base pairs. In some embodiments, a double stranded template nucleic acid has a length of about 160 base pairs, e.g., about 155-165, 150-170, 140-180, 130-190, 120-200, 110-210, 100-220, 90-230, or 80-240 base pairs.

The template nucleic acid can be linear single stranded DNA. In embodiments, the template nucleic acid is (i) linear single stranded DNA that can anneal to the nicked strand of the target nucleic acid, (ii) linear single stranded DNA that can anneal to the intact strand of the target nucleic acid, (iii) linear single stranded DNA that can anneal to the transcribed strand of the target nucleic acid, (iv) linear single stranded DNA that can anneal to the non-transcribed strand of the target nucleic acid, or more than one of the preceding. The length may be, e.g., about 150-200 nucleotides, e.g., about 150, 160, 170, 180, 190, or 200 nucleotides. The length may be, e.g., at least 150, 160, 170, 180, 190, or 200 nucleotides. In some embodiments, the length is no greater than 150, 160, 170, 180, 190, or 200 nucleotides. In some embodiments, a single stranded template nucleic acid has a length of about 160 nucleotides, e.g., about 155-165, 150-170, 140-180, 130-190, 120-200, 110-210, 100-220, 90-230, or 80-240 nucleotides.

In some embodiments, the template nucleic acid is circular double stranded DNA, e.g., a plasmid. In some embodiments, the template nucleic acid comprises about 500 to 1000 base pairs of homology on either side of the replacement sequence and/or the nick. In some embodiments, the template nucleic acid comprises about 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence.

In some embodiments, the template nucleic acid is an adenovirus vector, e.g., an AAV vector, e.g., a ssDNA molecule of a length and sequence that allows it to be packaged in an AAV capsid. The vector may be, e.g., less than 5 kb and may contain an ITR sequence that promotes packaging into the capsid. The vector may be integration-deficient. In some embodiments, the template nucleic acid comprises about 150 to 1000 nucleotides of homology on either side of the replacement sequence and/or the nick. In some embodiments, the template nucleic acid comprises about 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at least 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at most 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence.

In some embodiments, the template nucleic acid is a lentiviral vector, e.g., an IDLV (integration deficiency lentivirus). In some embodiments, the template nucleic acid comprises about 500 to 100) base pairs of homology on either side of the replacement sequence and/or the nick. In some embodiments, the template nucleic acid comprises about 300, 400, 500, 600, 700, 800, 900, 1000, 1500, or 2000 base pairs of homology 5' of the nick or replacement sequence. 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence.

In an embodiment, the template nucleic acid comprises one or more mutations, e.g., silent mutations, that prevent Cas9 from recognizing and cleaving the template nucleic acid. The template nucleic acid may comprise, e.g., at least 1, 2, 3, 4, 5, 10, 20, or 30 silent mutations relative to the corresponding sequence in the genome of the cell to be altered. In embodiments, the template nucleic acid comprises at most 2, 3, 4, 5, 10, 20, 30, or 50 silent mutations relative to the corresponding sequence in the genome of the cell to be altered. In an embodiment, the cDNA comprises one or more mutations, e.g., silent mutations that prevent Cas9 from recognizing and cleaving the template nucleic acid. The template nucleic acid may comprise, e.g., at least 1, 2, 3, 4, 5, 10, 20, or 30 silent mutations relative to the corresponding sequence in the genome of the cell to be altered. In embodiments, the template nucleic acid comprises at most 2, 3, 4, 5, 10, 20, 30, or 50 silent mutations relative to the corresponding sequence in the genome of the cell to be altered.

In an embodiment, the template nucleic acid alters the structure of the target position by participating in a homology directed repair event. In an embodiment, the template nucleic acid alters the sequence of the target position. In an embodiment, the template nucleic acid results in the incorporation of a modified, or non-naturally occurring base into the target nucleic acid.

Typically, the template sequence undergoes a breakage mediated or catalyzed recombination with the target sequence. In an embodiment, the template nucleic acid includes sequence that corresponds to a site on the target sequence that is cleaved by an eaCas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a noncoding sequence, e.g., an alteration in an exon or in a 5' or 3' non-translated or non-transcribed region. Such alterations include an alteration in a control element, e.g., a promoter, enhancer, and an alteration in a cis-acting or trans-acting control element. A template nucleic acid having homology with a target position can be used to alter the structure of a target sequence. The template sequence can be used to alter an unwanted structure, e.g., an unwanted or mutant nucleotide.

Table 18 below provides exemplary template nucleic acids. In an embodiment, the template nucleic acid includes the 5' homology arm and the 3' homology arm of a row from Table 18. In another embodiment, a 5' homology arm from the first column can be combined with a 3' homology arm from Table 18. In each embodiment, a combination of the 5' and 3' homology arms include a replacement sequence.

TABLE 18

| 5' homology arm (the number of nucleotides from SEQ ID NO: 5'H, beginning at the 3' end of SEQ ID NO: 5'H) | Replacement Sequence: G, A, C or T, or a cDNA sequence described herein, optionally a promoter, further optionally a polyA signal, as described herein | 3' homology arm (the number of nucleotides from SEQ ID NO: 3'H, beginning at the 5' end of SEQ ID NO: 3'H) |
|---|---|---|
| 10 or more | | 10 or more |
| 20 or more | | 20 or more |
| 50 or more | | 50 or more |
| 100 or more | | 100 or more |
| 150 or more | | 150 or more |
| 200 or more | | 200 or more |
| 250 or more | | 250 or more |
| 300 or more | | 300 or more |
| 350 or more | | 350 or more |
| 400 or more | | 400 or more |
| 450 or more | | 450 or more |
| 500 or more | | 500 or more |
| 550 or more | | 550 or more |
| 600 or more | | 600 or more |
| 650 or more | | 650 or more |
| 700 or more | | 700 or more |
| 750 or more | | 750 or more |
| 800 or more | | 800 or more |
| 850 or more | | 850 or more |
| 900 or more | | 900 or more |
| 1000 or more | | 1000 or more |
| 1100 or more | | 1100 or more |
| 1200 or more | | 1200 or more |
| 1300 or more | | 1300 or more |
| 1400 or more | | 1400 or more |
| 1500 or more | | 1500 or more |
| 1600 or more | | 1600 or more |
| 1700 or more | | 1700 or more |
| 1800 or more | | 1800 or more |
| 1900 or more | | 1900 or more |
| 1200 or more | | 1200 or more |
| At least 50 but not long enough to include a repeated element. | | At least 50 but not long enough to include a repeated element. |
| At least 100 but not long enough to include a repeated element. | | At least 100 but not long enough to include a repeated element. |
| At least 150 but not long enough to include a repeated element. | | At least 150 but not long enough to include a repeated element. |
| 5 to 100 nucleotides | | 5 to 100 nucleotides |
| 10 to 150 nucleotides | | 10 to 150 nucleotides |
| 20 to 150 nucleotides | | 20 to 150 nucleotides |
| | Template Construct | |

NHEJ Approaches for Gene Targeting

As described herein, nuclease-induced non-homologous end-joining (NHEJ) can be used to target gene-specific disruption (e.g., knockout). Nuclease-induced NHEJ can also be used to remove (e.g., delete) sequences in a gene of interest.

In an embodiment, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature, however, at a given break site certain indel sequences are favored and are over represented in the population, likely due to small regions of microhomology. The lengths of deletions can vary widely; most commonly in the 1-50 bp range, but they can reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs (e.g., motifs less than or equal to 50 nucleotides in length) as long as the generation of a specific final sequence is not required. If a double-strand break is targeted near to a target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. In this way, DNA segments as large as several hundred kilobases can be deleted. Both of these approaches can be used to delete specific DNA sequences; however, the error-prone nature of NHEJ may still produce indel mutations at the site of repair.

Both double strand cleaving eaCas9 molecules and single strand, or nickase, eaCas9 molecules can be used in the methods and compositions described herein to generate NHEJ-mediated indels. NHEJ-mediated indels targeted to the gene, e.g., a coding region, e.g., an early coding region of a gene, of interest can be used to knockout (i.e., eliminate expression of) a gene of interest. For example, early coding region of a gene of interest includes sequence immediately following a start codon, within a first exon of the coding sequence, or within 500 bp of the start codon (e.g., less than 500, 450, 400, 350, 300, 250, 200, 150, 100 or 50 bp).

Placement of Double Strand or Single Strand Breaks Relative to the Target Position In an embodiment, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In an embodiment, the cleavage site is between 0-30 bp away from the target position (e.g., less than 30, 25, 20, 15, 10, 9, 8, 7, 6, 5, 4, 3, 2 or 1 bp from the target position).

In an embodiment, in which two gRNAs complexing with Cas9 nickases induce two single strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In an embodiment, the gRNAs are configured to position cuts at the same position, or within a few nucleotides of one another, on different strands, essentially mimicking a double strand break. In an embodiment, the closer nick is between 0-30 bp away from the target position (e.g., less than 30, 25, 20, 15, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In an embodiment, the gRNAs are configured to place a single strand break on either side of a nucleotide of the target position.

Both double strand cleaving eaCas9 molecules and single strand, or nickase, eaCas9 molecules can be used in the methods and compositions described herein to generate breaks both sides of a target position. Double strand or paired single strand breaks may be generated on both sides of a target position to remove the nucleic acid sequence between the two cuts (e.g., the region between the two breaks in deleted). In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single strand breaks (i.e., two gRNAs complex with Cas9 nickases) on either side of the target position. In another embodiment, four gRNAs, e.g., independently, unimolecular (or chimeric) or modular gRNA, are configured to generate two pairs of single strand breaks (i.e., two pairs of two gRNAs complex with Cas9 nickases) on either side of the target position. The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

Targeted Knockdown

Unlike CRISPR/Cas-mediated gene knockout, which permanently eliminates expression by mutating the gene at the DNA level, CRISPR/Cas knockdown allows for temporary reduction of gene expression through the use of artificial transcription factors. Mutating key residues in both DNA cleavage domains of the Cas9 protein (e.g. the D10A and H840A mutations) results in the generation of a catalytically inactive Cas9 (eiCas9 which is also known as dead Cas9 or dCas9) molecule. A catalytically inactive Cas9 complexes with a gRNA and localizes to the DNA sequence specified by that gRNA's targeting domain, however, it does not cleave the target DNA. Fusion of the dCas9 to an effector domain, e.g., a transcription repression domain, enables recruitment of the effector to any DNA site specified by the gRNA. Although an enzymatically inactive (eiCas9) Cas9 molecule itself can block transcription when recruited to early regions in the coding sequence, more robust repression can be achieved by fusing a transcriptional repression domain (for example KRAB, SID or ERD) to the Cas9 and recruiting it to the target knockdown position, e.g., within 1000 bp of sequence 3' of the start codon or within 500 bp of a promoter region 5' of the start codon of a gene. It is likely that targeting DNAseI hypersensitive sites (DHSs) of the promoter may yield more efficient gene repression or activation because these regions are more likely to be accessible to the Cas9 protein and are also more likely to harbor sites for endogenous transcription factors. Especially for gene repression, it is contemplated herein that blocking the binding site of an endogenous transcription factor would aid in downregulating gene expression. In an embodiment, one or more eiCas9 molecules may be used to block binding of one or more endogenous transcription factors. In another embodiment, an eiCas9 molecule can be fused to a chromatin modifying protein. Altering chromatin status can result in decreased expression of the target gene. One or more eiCas9 molecules fused to one or more chromatin modifying proteins may be used to alter chromatin status.

In an embodiment, a gRNA molecule can be targeted to a known transcription response elements (e.g., promoters, enhancers, etc.), a known upstream activating sequences (UAS), and/or sequences of unknown or known function that are suspected of being able to control expression of the target DNA.

CRISPR/Cas-mediated gene knockdown can be used to reduce expression of an unwanted allele or transcript. Contemplated herein are scenarios wherein permanent destruction of the gene is not ideal. In these scenarios, site-specific repression may be used to temporarily reduce or eliminate expression. It is also contemplated herein that the off-target effects of a Cas-repressor may be less severe than those of a Cas-nuclease as a nuclease can cleave any DNA sequence and cause mutations whereas a Cas-repressor may only have an effect if it targets the promoter region of an actively transcribed gene. However, while nuclease-mediated knockout is permanent, repression may only persist as long as the Cas-repressor is present in the cells. Once the repressor is no longer present, it is likely that endogenous transcription factors and gene regulatory elements would restore expression to its natural state.

Single-Strand Annealing

Single strand annealing (SSA) is another DNA repair process that repairs a double-strand break between two repeat sequences present in a target nucleic acid. Repeat sequences utilized by the SSA pathway are generally greater than 30 nucleotides in length. Resection at the break ends occurs to reveal repeat sequences on both strands of the target nucleic acid. After resection, single strand overhangs containing the repeat sequences are coated with RPA protein to prevent the repeats sequences from inappropriate annealing, e.g., to themselves. RAD52 binds to and each of the repeat sequences on the overhangs and aligns the sequences to enable the annealing of the complementary repeat sequences. After annealing, the single-strand flaps of the overhangs are cleaved. New DNA synthesis fills in any gaps, and ligation restores the DNA duplex. As a result of the processing, the DNA sequence between the two repeats is deleted. The length of the deletion can depend on many factors including the location of the two repeats utilized, and the pathway or processivity of the resection.

In contrast to HDR pathways. SSA does not require a template nucleic acid to alter or correct a target nucleic acid sequence. Instead, the complementary repeat sequence is utilized.

Other DNA Repair Pathways

SSBR (Single Strand Break Repair)

Single-stranded breaks (SSB) in the genome are repaired by the SSBR pathway, which is a distinct mechanism from the DSB repair mechanisms discussed above. The SSBR pathway has four major stages: SSB detection, DNA end processing, DNA gap filling, and DNA ligation. A more detailed explanation is given in Caldecott, Nature Reviews Genetics 9, 619-631 (August 2008), and a summary is given here.

In the first stage, when a SSB forms, PARP1 and/or PARP2 recognize the break and recruit repair machinery. The binding and activity of PARP1 at DNA breaks is transient and it seems to accelerate SSBr by promoting the focal accumulation or stability of SSBr protein complexes at the lesion. Arguably the most important of these SSBr proteins is XRCC1, which functions as a molecular scaffold that interacts with, stabilizes, and stimulates multiple enzymatic components of the SSBr process including the protein responsible for cleaning the DNA 3' and 5' ends. For instance. XRCC1 interacts with several proteins (DNA polymerase beta, PNK, and three nucleases, APE1, APTX, and APLF) that promote end processing. APE1 has endonuclease activity. APLF exhibits endonuclease and 3' to 5' exonuclease activities. APTX has endonuclease and 3' to 5' exonuclease activity.

This end processing is an important stage of SSBR since the 3'- and/or 5'-termini of most, if not all, SSBs are 'damaged'. End processing generally involves restoring a damaged 3'-end to a hydroxylated state and and/or a damaged 5' end to a phosphate moiety, so that the ends become ligation-competent. Enzymes that can process damaged 3' termini include PNKP, APE1, and TDP1. Enzymes that can process damaged 5' termini include PNKP, DNA polymerase beta, and APTX. LIG3 (DNA ligase III) can also participate in end processing. Once the ends are cleaned, gap filling can occur.

At the DNA gap filling stage, the proteins typically present are PARP1, DNA polymerase beta, XRCC1, FEN1 (flap endonuclease 1), DNA polymerase delta/epsilon, PCNA, and LIG1. There are two ways of gap filling, the short patch repair and the long patch repair. Short patch repair involves the insertion of a single nucleotide that is missing. At some SSBs, "gap filling" might continue displacing two or more nucleotides (displacement of up to 12 bases have been reported). FEN1 is an endonuclease that removes the displaced 5'-residues. Multiple DNA polymerases, including Pol β, are involved in the repair of SSBs, with the choice of DNA polymerase influenced by the source and type of SSB.

In the fourth stage, a DNA ligase such as LIG1 (Ligase I) or LIG3 (Ligase III) catalyzes joining of the ends. Short patch repair uses Ligase III and long patch repair uses Ligase I.

Sometimes, SSBR is replication-coupled. This pathway can involve one or more of CtIP, MRN, ERCC1, and FEN1. Additional factors that may promote SSBR include: aPARP, PARP1, PARP2, PARG, XRCC1, DNA polymerase b, DNA polymerase d, DNA polymerase e, PCNA, LIG1, PNK, PNKP, APE1, APTX, APLF, TDP1, LIG3, FEN1, CtIP, MRN, and ERCC1.

MMR (Mismatch Repair)

Cells contain three excision repair pathways: MMR, BER, and NER. The excision repair pathways have a common feature in that they typically recognize a lesion on one strand of the DNA, then exo/endonucleaseases remove the lesion and leave a 1-30 nucleotide gap that is sub-sequentially filled in by DNA polymerase and finally sealed with ligase. A more complete picture is given in Li, Cell Research (2008) 18:85-98, and a summary is provided here.

Mismatch Repair (MMR) Operates on Mispaired DNA Bases.

The MSH2/6 or MSH2/3 complexes both have ATPases activity that plays an important role in mismatch recognition and the initiation of repair. MSH2/6 preferentially recognizes base-base mismatches and identifies mispairs of 1 or 2 nucleotides, while MSH2/3 preferentially recognizes larger ID mispairs.

hMLH1 heterodimerizes with hPMS2 to form hMutLα which possesses an ATPase activity and is important for multiple steps of MMR. It possesses a PCNA/replication factor C (RFC)-dependent endonuclease activity which plays an important role in 3' nick-directed MMR involving EXO1. (EXO1 is a participant in both HR and MMR.) It regulates termination of mismatch-provoked excision. Ligase I is the relevant ligase for this pathway. Additional factors that may promote MMR include: EXO1, MSH2, MSH3, MSH6, MLH1, PMS2, MLH3, DNA Pol d, RPA, HMGB1, RFC, and DNA ligase I.

Base Excision Repair (BER)

The base excision repair (BER) pathway is active throughout the cell cycle: it is responsible primarily for removing small, non-helix-distorting base lesions from the genome. In contrast, the related Nucleotide Excision Repair pathway (discussed in the next section) repairs bulky helix-distorting lesions. A more detailed explanation is given in Caldecott, Nature Reviews Genetics 9, 619-631 (August 2008), and a summary is given here.

Upon DNA base damage, base excision repair (BER) is initiated and the process can be simplified into five major steps: (a) removal of the damaged DNA base; (b) incision of the subsequent a basic site; (c) clean-up of the DNA ends; (d) insertion of the correct nucleotide into the repair gap; and (e) ligation of the remaining nick in the DNA backbone. These last steps are similar to the SSBR.

In the first step, a damage-specific DNA glycosylase excises the damaged base through cleavage of the N-glycosidic bond linking the base to the sugar phosphate backbone. Then AP endonuclease-1 (APE1) or bifunctional DNA glycosylases with an associated lyase activity incised the phosphodiester backbone to create a DNA single strand break (SSB). The third step of BER involves cleaning-up of the DNA ends. The fourth step in BER is conducted by Pol β that adds a new complementary nucleotide into the repair gap and in the final step XRCC1/Ligase III seals the remaining nick in the DNA backbone. This completes the short-patch BER pathway in which the majority (~80%) of damaged DNA bases are repaired. However, if the 5'-ends in step 3 are resistant to end processing activity, following one nucleotide insertion by Pol β there is then a polymerase switch to the replicative DNA polymerases, Pol δ/ε, which then add ~2-8 more nucleotides into the DNA repair gap. This creates a 5'-flap structure, which is recognized and excised by flap endonuclease-1 (FEN-1) in association with the processivity factor proliferating cell nuclear antigen (PCNA). DNA ligase I then seals the remaining nick in the DNA backbone and completes long-patch BER. Additional factors that may promote the BER pathway include: DNA glycosylase, APE1, Polb, Pold, Pole, XRCC1, Ligase III, FEN-1, PCNA, RECQL4, WRN, MYH, PNKP, and APTX.

Nucleotide Excision Repair (NER)

Nucleotide excision repair (NER) is an important excision mechanism that removes bulky helix-distorting lesions from DNA. Additional details about NER are given in Marteijn et al., Nature Reviews Molecular Cell Biology 15, 465-481 (2014), and a summary is given here. NER a broad pathway encompassing two smaller pathways: global genomic NER (GG-NER) and transcription coupled repair NER (TC-NER). GG-NER and TC-NER use different factors for recognizing DNA damage. However, they utilize the same machinery for lesion incision, repair, and ligation.

Once damage is recognized, the cell removes a short single-stranded DNA segment that contains the lesion. Endonucleases XPF/ERCC1 and XPG (encoded by ERCC5) remove the lesion by cutting the damaged strand on either side of the lesion, resulting in a single-strand gap of 22-30 nucleotides. Next, the cell performs DNA gap filling synthesis and ligation. Involved in this process are: PCNA, RFC, DNA Pol δ, DNA Pol ε or DNA Pol κ, and DNA ligase I or XRCC1/Ligase III. Replicating cells tend to use DNA pol ε and DNA ligase I, while non-replicating cells tend to use DNA Pol δ, DNA Pol κ, and the XRCC1/Ligase III complex to perform the ligation step.

NER can involve the following factors: XPA-G, POLH, XPF, ERCC1, XPA-G, and LIG1. Transcription-coupled NER (TC-NER) can involve the following factors: CSA, CSB, XPB, XPD, XPG, ERCC1, and TTDA. Additional factors that may promote the NER repair pathway include XPA-G, POLH, XPF, ERCC1, XPA-G, LIG1, CSA, CSB, XPA, XPB, XPC, XPD, XPF, XPG, TTDA, UVSSA, USP7, CETN2, RAD23B, UV-DDB, CAK subcomplex, RPA, and PCNA.

Interstrand Crosslink (ICL)

A dedicated pathway called the ICL repair pathway repairs interstrand crosslinks. Interstrand crosslinks, or covalent crosslinks between bases in different DNA strand, can occur during replication or transcription. ICL repair involves the coordination of multiple repair processes, in particular, nucleolytic activity, translesion synthesis (TLS), and HDR. Nucleases are recruited to excise the ICL on either side of the crosslinked bases, while TLS and HDR are coordinated to repair the cut strands. ICL repair can involve the following factors: endonucleases, e.g., XPF and RAD51C, endonucleases such as RAD51, translesion polymerases, e.g., DNA polymerase zeta and Rev1), and the Fanconi anemia (FA) proteins, e.g., FancJ.

Other Pathways

Several other DNA repair pathways exist in mammals.

Translesion synthesis (TLS) is a pathway for repairing a single stranded break left after a defective replication event and involves translesion polymerases, e.g., DNA pol□ and Rev1.

Error-free postreplication repair (PRR) is another pathway for repairing a single stranded break left after a defective replication event.

VI. Target Cells

Cas9 molecules, gRNA molecules (e.g., Cas9 molecule/gRNA molecule complexes), and optionally donor template nucleic acids, can be used to modify cells, e.g., to alter target nucleic acids, in a wide variety of cells.

In an embodiment, a cell is manipulated by editing a target gene, e.g., by knockout of the target gene. In another embodiment, a cell is manipulated by editing a targeting gene, e.g., by correcting a mutation in the target gene. In yet another embodiment, a cell is manipulated by modulating the expression of a target gene, e.g., by knockdown or activation of the target gene. In still another embodiment, a cell is manipulated by introducing a gene, e.g., by knockin of a gene, e.g., in a targeted locus. In an embodiment, the cell is manipulated ex vivo. In another embodiment, the cell is manipulated in vivo.

The Cas9, gRNA, and optionally donor template nucleic acid molecules described herein can be delivered to a target cell. In an embodiment, the target cell is a circulating blood cell, e.g., a reticulocyte, a myeloid progenitor cell, a lymphoid progenitor cell, a hematopoietic stem/progenitor cell, or an endothelial cell. In an embodiment, the target cell is a bone marrow cell (e.g., a myeloid progenitor cell, e.g., a lymphoid progenitor cell, e.g., an erythroid progenitor cell, e.g., a hematopoietic stem/progenitor cell, e.g., an endothelial cell, e.g., a mesenchymal stem cell). In an embodiment, the target cell is a myeloid progenitor cell (e.g. a common myeloid progenitor (CMP) or a granulocyte macrophage progenitor (GMP) cell). In an embodiment, the target cell is a lymphoid progenitor cell, e.g., a common lymphoid progenitor (CLP). In an embodiment, the target cell is an erythroid progenitor cell (e.g. a megakaryocyte erythroid progenitor (MEP) cell). In an embodiment, the target cell is a hematopoietic stein/progenitor cell (e.g. a long term hematopoietic stem/progenitor cell (LT-HSPC), a short term hematopoietic stem/progenitor cell (ST-HSPC), a multipotent progenitor (MPP) cell, a lineage restricted progenitor (LRP) cell). In an embodiment, the target cell is a $CD34^+$ cell, a $CD34^+CD90^+$ cell, a $CD34^+CD38^-$ cell, a $CD34^+CD90^+CD49f^+CD38^-CD45RA^-$ cell, a $CD105^+$ cell, a $CD31^+$, or a $CD133^+$ cell. In an embodiment, the target cell is a an umbilical cord blood $CD34^+$ HSPC, an umbilical cord venous endothelial cell, an umbilical cord arterial endothelial cells, an amniotic fluid $CD34^+$ cell, an amniotic fluid endothelial cell, a placental endothelial cell or a placental hematopoietic $CD34^+$ cell. In an embodiment, the target cell is a mobilized peripheral blood hematopoietic $CD34^+$ cell (after the patient is treated with a mobilization agent, e.g., G-CSF or Plerixafor). In an embodiment, the target cell is a peripheral blood endothelial cell.

In an embodiment, the target cell is manipulated ex vivo and administered to a subject. Sources of target cells for ex vivo manipulation may include, by way of example, the subject's blood, cord blood, or the subject's bone marrow. Sources of target cells for ex vivo manipulation may also include, by way of example, heterologous donor blood, cord blood, or bone marrow.

In an embodiment, a myeloid progenitor cell is removed from the subject, manipulated ex vivo as described above, and the myeloid progenitor cell is returned to the subject. In an embodiment, an erythroid progenitor cell is removed from the subject, manipulated ex vivo as described above, and the erythroid progenitor cell is returned to the subject. In an embodiment, a lymphoid progenitor cell is removed from the subject, manipulated ex vivo as described above, and the lymphoid progenitor cell is returned to the subject. In an embodiment, a multipotent progenitor cell is removed from the subject, manipulated ex vivo as described above, and the hematopoietic stem cell is returned to the subject. In an embodiment, a hematopoietic stem/progenitor cell is removed from the subject, manipulated ex vivo as described above, and the hematopoietic stem/progenitor cell is returned to the subject. In an embodiment, a $CD34^+$ hematopoietic stem cell is removed from the subject, manipulated ex vivo as described above, and the $CD34^+$ hematopoietic stem/progenitor cell is returned to the subject.

A suitable cell can also include a stem cell such as, by way of example, an embryonic stem cell, an induced pluripotent stem cell, a hematopoietic stem cell, an endothelial cell, a hemogenic endothelial cell, and a mesenchymal stem cell. In an embodiment, the cell is an induced pluripotent stem (iPS) cell or a cell derived from an iPS cell, e.g., an iPS cell generated from the subject, modified to induce a mutation and differentiated into a clinically relevant cell such as a myeloid progenitor cell, a lymphoid progenitor cell, an erythroid progenitor cell, a multipotent progenitor cell, or a hematopoietic stem/progenitor cell. A suitable cell can also include an endothelial cell or amniotic cell that is differentiated into a hematopoietic stem cell.

In an embodiment, a viral vector is used to transduce the target cell. In an embodiment, AAV (e.g., AAV6 and AAVDJ) is used to transduce the target cell. In an embodiment, a lentivirus vector or an integration deficient lentivirus vector is used to transduce the target cell. In an embodiment, a ribonucleic acid (e.g., a gRNA molecule and an mRNA encoding a Cas9 molecule) is used to transfect the target cell. In an embodiment, a protein (e.g., a Cas9 molecule) and a ribonucleic acid (e.g., a gRNA molecule) are used to transfect the target cell. In an embodiment, a ribonucleoprotein complex (e.g., a Cas9 molecule/gRNA molecule complex) is used to transfect the target cell. In an embodiment, a deoxyribonucleic acid (e.g., a DNA encoding a gRNA molecule, a Cas9 molecule, or both) is used to transfect the target cells.

Cells produced by the methods described herein may be used immediately. Alternatively, the cells may be frozen (e.g., in liquid nitrogen) and stored for later use. The cells will usually be frozen in 10% dimethylsulfoxide (DMSO), 50% serum, 40% buffered medium, or some other such solution as is commonly used in the art to preserve cells at such freezing temperature and thawed in such a manner as commonly known in the art for thawing frozen cultured cells.

VII. Delivery, Formulations and Routes of Administration

The components, e.g., a Cas9 molecule, gRNA molecule (e.g., a Cas9 molecule/gRNA molecule complex), and a donor template nucleic acid, or all three, can be delivered, formulated, or administered in a variety of forms, see, e.g., Tables 19 and 20. In an embodiment, one Cas9 molecule and two or more (e.g., 2, 3, 4, or more) different gRNA molecules are delivered, e.g., by an AAV vector. In an embodiment, the sequence encoding the Cas9 molecule and the sequence(s) encoding the two or more (e.g., 2, 3, 4, or more) different gRNA molecules are present on the same nucleic acid molecule, e.g., an AAV vector. When a Cas9 or gRNA component is delivered encoded in DNA the DNA will typically include a control region, e.g., comprising a promoter, to effect expression. Useful promoters for Cas9 molecule sequences include, e.g., CMV, SFFV, EFS, EF-1a, PGK, CAG, and CBH promoters. In an embodiment, the promoter is a constitutive promoter. In another embodiment, the promoter is a tissue specific promoter. Useful promoters for gRNAs include H1, EF-1a, U6, and tRNA promoters. Promoters with similar or dissimilar strengths can be selected to tune the expression of components. Sequences encoding a Cas9 molecule can comprise a nuclear localization signal (NLS), e.g., an SV40 NLS. In an embodiment, the sequence encoding a Cas9 molecule comprises at least two nuclear localization signals. In an embodiment, a promoter for a Cas9 molecule or a gRNA molecule can be, independently, inducible, tissue specific, or cell specific.

Table 19 provides examples of how the components can be formulated, delivered, or administered.

TABLE 19

| Elements | | | |
|---|---|---|---|
| Cas9 Molecule(s) | gRNA Molecule(s) | Optional Donor Template Nucleic Acid | Comments |
| DNA | DNA | DNA | In this embodiment, a Cas9 molecule, typically an eaCas9 molecule, and a gRNA are transcribed from DNA. In this embodiment, they are encoded on separate molecules. In this embodiment, the donor template is provided as a separate DNA molecule. |

TABLE 19-continued

<table>
<tr><th colspan="4">Elements</th></tr>
<tr><th>Cas9 Molecule(s)</th><th>gRNA Molecule(s)</th><th>Optional Donor Template Nucleic Acid</th><th>Comments</th></tr>
<tr><td>DNA</td><td colspan="2">DNA</td><td>In this embodiment, a Cas9 molecule, typically an eaCas9 molecule, and a gRNA are transcribed from DNA. In this embodiment, they are encoded on separate molecules. In this embodiment, the donor template is provided on the same DNA molecule that encodes the gRNA.</td></tr>
<tr><td colspan="2">DNA</td><td>DNA</td><td>In this embodiment, a Cas9 molecule, typically an eaCas9 molecule, and a gRNA are transcribed from DNA, here from a single molecule. In this embodiment, the donor template is provided as a separate DNA molecule.</td></tr>
<tr><td>DNA</td><td>DNA</td><td>DNA</td><td>In this embodiment, a Cas9 molecule, typically an eaCas9 molecule, and a gRNA are transcribed from DNA. In this embodiment, they are encoded on separate molecules. In this embodiment, the donor template is provided on the same DNA molecule that encodes the Cas9.</td></tr>
<tr><td>DNA</td><td>RNA</td><td>DNA</td><td>In this embodiment, a Cas9 molecule, typically an eaCas9 molecule, is transcribed from DNA, and a gRNA is provided as in vitro transcribed or synthesized RNA. In this embodiment, the donor template is provided as a separate DNA molecule.</td></tr>
<tr><td>DNA</td><td>RNA</td><td>DNA</td><td>In this embodiment, a Cas9 molecule, typically an eaCas9 molecule, is transcribed from DNA, and a gRNA is provided as in vitro transcribed or synthesized RNA. In this embodiment, the donor template is provided on the same DNA molecule that encodes the Cas9.</td></tr>
<tr><td>mRNA</td><td>RNA</td><td>DNA</td><td>In this embodiment, a Cas9 molecule, typically an eaCas9 molecule, is translated from in vitro transcribed mRNA, and a gRNA is provided as in vitro transcribed or synthesized RNA. In this embodiment, the donor template is provided as a DNA molecule.</td></tr>
<tr><td>mRNA</td><td>DNA</td><td>DNA</td><td>In this embodiment, a Cas9 molecule, typically an eaCas9 molecule, is translated from in vitro transcribed mRNA, and a gRNA is transcribed from DNA. In this embodiment, the donor template is provided as a separate DNA molecule.</td></tr>
<tr><td>mRNA</td><td colspan="2">DNA</td><td>In this embodiment, a Cas9 molecule, typically an eaCas9 molecule, is translated from in vitro transcribed mRNA, and a gRNA is transcribed from DNA. In this embodiment, the donor template is provided on the same DNA molecule that encodes the gRNA.</td></tr>
<tr><td>Protein</td><td>DNA</td><td>DNA</td><td>In this embodiment, a Cas9 molecule, typically an eaCas9 molecule, is provided as a protein, and a gRNA is transcribed from DNA. In this embodiment, the donor template is provided as a separate DNA molecule.</td></tr>
<tr><td>Protein</td><td colspan="2">DNA</td><td>In this embodiment, a Cas9 molecule, typically an eaCas9 molecule, is provided as a protein, and a gRNA is transcribed from DNA. In this embodiment, the donor template is provided on the same DNA molecule that encodes the gRNA.</td></tr>
<tr><td>Protein</td><td>RNA</td><td>DNA</td><td>In this embodiment, an eaCas9 molecule is provided as a protein, and a gRNA is provided as transcribed or synthesized RNA. In this embodiment, the donor template is provided as a DNA molecule.</td></tr>
</table>

Table 20 summarizes various delivery methods for the components of a Cas system, e.g., the Cas9 molecule component and the gRNA molecule component, as described herein.

TABLE 20

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

DNA-Based Delivery of a Cas9 Molecule and or One or More gRNA Molecules

Nucleic acids encoding Cas9 molecules (e.g., eaCas9 molecules), gRNA molecules, a donor template nucleic acid, or any combination (e.g., two or all) thereof, can be administered to subjects or delivered into cells by art-known methods or as described herein. For example, Cas9-encoding and/or gRNA-encoding DNA, as well as donor template nucleic acids can be delivered, e.g., by vectors (e.g., viral or non-viral vectors), non-vector based methods (e.g., using naked DNA or DNA complexes), or a combination thereof.

Nucleic acids encoding Cas9 molecules (e.g., eaCas9 molecules) and/or gRNA molecules can be conjugated to molecules (e.g., N-acetylgalactosamine) promoting uptake by the target cells (e.g., hepatocytes). Donor template molecules can be conjugated to molecules (e.g., N-acetylgalactosamine) promoting uptake by the target cells (e.g., hepatocytes).

In some embodiments, the Cas9- and/or gRNA-encoding DNA is delivered by a vector (e.g., viral vector/virus or plasmid).

Vectors can comprise a sequence that encodes a Cas9 molecule and/or a gRNA molecule.

A vector can also comprise a sequence encoding a signal peptide (e.g., for nuclear localization, nucleolar localization, mitochondrial localization), fused, e.g., to a Cas9 molecule sequence. For example, the vectors can comprise a nuclear localization sequence (e.g., from SV40) fused to the sequence encoding the Cas9 molecule.

One or more regulatory/control elements, e.g., promoters, enhancers, introns, polyadenylation signals, Kozak consensus sequences, and internal ribosome entry sites (IRES), can be included in the vectors. In some embodiments, the promoter is recognized by RNA polymerase II (e.g., a CMV promoter). In other embodiments, the promoter is recognized by RNA polymerase III (e.g., a U6 promoter). In some embodiments, the promoter is a regulated promoter (e.g., inducible promoter). In other embodiments, the promoter is a constitutive promoter. In some embodiments, the promoter is a tissue specific promoter. In some embodiments, the promoter is a viral promoter. In other embodiments, the promoter is a non-viral promoter.

In some embodiments, the vector is a viral vector (e.g., for generation of recombinant viruses). In some embodiments, the virus is a DNA virus (e.g., dsDNA or ssDNA virus). In other embodiments, the virus is an RNA virus (e.g., an ssRNA virus). In some embodiments, the virus infects dividing cells. In other embodiments, the virus infects non-dividing cells. Exemplary viral vectors/viruses include, e.g., retroviruses, lentiviruses, adenovirus, adeno-associated virus (AAV), vaccinia viruses, poxviruses, and herpes simplex viruses.

In some embodiments, the virus infects both dividing and non-dividing cells. In some embodiments, the virus can integrate into the host genome. In some embodiments, the virus is engineered to have reduced immunity, e.g., in human. In some embodiments, the virus is replication-competent. In other embodiments, the virus is replication-defective, e.g., having one or more coding regions for the genes necessary for additional rounds of virion replication and/or packaging replaced with other genes or deleted. In some embodiments, the virus causes transient expression of the Cas9 molecule and/or the gRNA molecule. In other embodiments, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In an embodiment, the viral vector recognizes a specific cell type or tissue. For example, the viral vector can be pseudotyped with a different/alternative viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

Exemplary viral vectors/viruses include, e.g., retroviruses, lentiviruses, adenovirus, adeno-associated virus (AAV), vaccinia viruses, poxviruses, and herpes simplex viruses.

Exemplary viral vectors/viruses include, e.g., retroviruses, lentiviruses, adenovirus, adeno-associated virus (AAV), vaccinia viruses, poxviruses, and herpes simplex viruses.

In some embodiments, the Cas9- and/or gRNA-encoding nucleic acid sequence is delivered by a recombinant retrovirus. In some embodiments, the retrovirus (e.g., Moloney murine leukemia virus) comprises a reverse transcriptase, e.g., that allows integration into the host genome. In some embodiments, the retrovirus is replication-competent. In other embodiments, the retrovirus is replication-defective, e.g., having one of more coding regions for the genes necessary for additional rounds of virion replication and packaging replaced with other genes, or deleted.

In some embodiments, the Cas9- and/or gRNA-encoding nucleic acid sequence is delivered by a recombinant lentivirus. In an embodiment, the donor template nucleic acid is delivered by a recombinant retrovirus. For example, the lentivirus is replication-defective, e.g., does not comprise one or more genes required for viral replication.

In an embodiment, the Cas9- and/or gRNA-encoding nucleic acid sequence is delivered by a recombinant lentivirus. In an embodiment, the donor template nucleic acid is delivered by a recombinant lentivirus. For example, the lentivirus is replication-defective, e.g., does not comprise one or more genes required for viral replication.

In some embodiments, the Cas9- and/or gRNA-encoding nucleic acid sequence is delivered by a recombinant adenovirus. In an embodiment, the donor template nucleic acid is delivered by a recombinant adenovirus. In some embodiments, the adenovirus is engineered to have reduced immunity in human.

In some embodiments, the Cas9- and/or gRNA-encoding nucleic acid sequence is delivered by a recombinant AAV. In an embodiment, the donor template nucleic acid is delivered by a recombinant AAV. In some embodiments, the AAV does not incorporate its genome into that of a host cell, e.g., a target cell as describe herein. In some embodiments, the AAV can incorporate its genome into that of the host cell. In some embodiments, the AAV is a self-complementary adeno-associated virus (scAAV), e.g., a scAAV that packages both strands which anneal together to form double stranded DNA.

In an embodiment, an AAV capsid that can be used in the methods described herein is a capsid sequence from serotype AAV1, AAV2, AAV3, AAV4, AAV5, AAV6, AAV7, AAV8, AAV9, AAV.rh8, AAV.rh10, AAV.rh32/33, AAV.rh43, AAV.rh64R1, or AAV7m8.

In an embodiment, the Cas9- and/or gRNA-encoding DNA is delivered in a re-engineered AAV capsid, e.g., with 50% or greater, e.g., 60% or greater, 70% or greater, 80% or greater, 90% or greater, or 95% or greater, sequence homology with a capsid sequence from serotypes AAV1, AAV2, AAV3, AAV4, AAV5, AAV6, AAV7, AAV8, AAV9, AAV.rh8, AAV.rh10. AAV.rh32/33, AAV.rh43, or AAV.rh64R1.

In an embodiment, the Cas9- and/or gRNA-encoding DNA is delivered by a chimeric AAV capsid. In an embodiment, the donor template nucleic acid is delivered by a chimeric AAV capsid. Exemplary chimeric AAV capsids include, but are not limited to, AAV9i1, AAV2i8, AAV-DJ, AAV2G9, AAV2i8G9, or AAV8G9.

In an embodiment, the AAV is a self-complementary adeno-associated virus (scAAV), e.g., a scAAV that packages both strands which anneal together to form double stranded DNA.

In an embodiment, the Cas9- and/or gRNA-encoding DNA is delivered by a hybrid virus, e.g., a hybrid of one or more of the viruses described herein. In an embodiment, the hybrid virus is hybrid of an AAV (e.g., of any AAV serotype), with a Bocavirus. B19 virus, porcine AAV, goose AAV, feline AAV, canine AAV, or MVM.

A Packaging cell is used to form a virus particle that is capable of infecting a target cell. Such a cell includes a 293 cell, which can package adenovirus, and a ψ2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed, eg. Cas9. For example, an AAV vector used in gene therapy typically only possesses inverted terminal repeat (ITR) sequences from the AAV genome which are required for packaging and gene expression in the host or target cell. The missing viral functions can be supplied in trans by the packaging cell line and/or plasmid containing E2A, E4, and VA genes from adenovirus, and plasmid encoding Rep and Cap genes from AAV, as described in "Triple Transfection Protocol." Henceforth, the viral DNA is packaged in a cell line, which contains a helper plasmid encoding the other AAV genes, namely rep and cap, but lacking ITR sequences. In embodiment, the viral DNA is packaged in a producer cell line, which contains E1A and/or E1B genes from adenovirus. The cell line is also infected with adenovirus as a helper. The helper virus (e.g., adenovirus or HSV) or helper plasmid promotes replication of the AAV vector and expression of AAV genes from the helper plasmid with ITRs. The helper plasmid is not packaged in significant amounts due to a lack of ITR sequences. Contamination with adenovirus can be reduced by, e.g., heat treatment to which adenovirus is more sensitive than AAV.

In an embodiment, the viral vector is a lentivirus vector. In an embodiment, the viral vector is an integrase deficient SIN lentivirus vector. In an embodiment the LV or IDLV are pseudotyped with the VSV-G envelope. Use of self-inactivating (SIN) lentiviral vectors (LVs) to efficiently transduce both dividing and non-dividing cells for gene therapy is described, e.g., in Segal et al., *J Biol Chem.* 2004; 279(15): 14509-14519. The HIV-1-based lentivirus vector is a replication incompetent enveloped retrovirus that contains two copies of the ~10 kb single stranded, positive sense RNA genome. Segregation of the viral genes encoding structural proteins and enzymatic proteins among different plasmids and elimination of certain accessory genes from the RNA genome render the lentivirus vector unable to replicate in transduced cells (Naldini et al., Curr. Opin. Biotechnol. 1998; 9(5):457-463). In an embodiment, the packaging signal is restricted to the transfer vector that encodes the transgene expression cassette (e.g. recipient HLA allele regulated by recipient endogenous HLA promoter), thereby preventing packaging of LV structural and enzymatic encoding genes. To produce virus, the transfer vector containing the transgene can be co-transfected with separate plasmids that encode the viral proteins required for packaging the transgene expression cassette and an envelope protein. In an embodiment, the vesicular stomatitis virus glycoprotein-G [VSV-G]) is used to expand tropism of the virus.

In an embodiment, SIN lentivirus vector is be used to transfer transgenes (e.g., matched HLA alleles) to donor HSPCs. Use of integrating recombinant lentiviruses are being used to genetically modify hematopoietic stem/progenitor cells (HSPCs) ex vivo to treat X-linked Adrenoleukodystophy, Metachromatic Leukodystrophy, and Wiskott-Aldrich Syndrome is described, e.g., in Cartier et al; *Science.* 2009 Nov. 6; 326(5954):818-23; Biffi et al., *Science.* 2013; 341(6148):1233158-1233158; Aiuti et al. *Science.* 2013; 341(6148):1233151-1233151. Use of lentivirus vectors in the clinic for the production of cancer-specific chimeric antigen receptor (CAR)-expressing T lymphocytes to treat leukemia and glioblastoma is described, e.g., in Maude et al, SL, N Engl J Med. 2014; 371(16):1507-1517; and Johnson et al., *Science Translational Medicine.* 2015; 7(275): 275ra22-275ra22.

In an embodiment, Integrase-deficient lentivirus vector (IDLV) is used to deliver donor Cas9, gRNA, and/or donor repair template DNA for delivery of a transgene (e.g., recipient identical HLA allele) for targeted integration and/or knockin of recipient matched HLA transgene, e.g., into the original HLA locus or into a safe harbor locus. IDLVs are able to transduce primary human cells but cannot integrate genetic cargo into the host cell genome. Given the packaging capacity of lentivirus vectors (~10 kb), IDLVs are a useful tool for the delivery of Cas9, gRNAs, and donor repair templates for homology directed repair (HDR)-based genome editing strategies (Kumar et al, Human Gene Therapy. 2001; 12(15):1893-1905). IDLVs have been used to deliver zinc finger nucleases (ZFNs), TAL effector nucleases (TALENs), meganuclease, and donor repair templates for site-specific modification of primary target cells ex vivo and in vivo (Lombardo et al, A. Nature Biotechnology. 2007; 25(11):1298-1306; Joglekar et al, Mol Ther. 2013; 21(9): 1705-1717; Holkers et al, *Nucleic Acids Res.* 2013; 41(5): e63: Rivière et al. Gene Ther. 2014; 21(5):529-532). In an embodiment, the cell is a dividing cell or rapidly dividing cell. In another embodiment, the cell is a quiescent cell or slowly dividing cell (e.g., a long-term HSPC, a neuron, or a hepatocyte).

In an embodiment, the viral vector has the ability of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, a single chain antibody, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In an embodiment, the viral vector achieves cell type specific expression. For example, a tissue-specific promoter can be constructed to restrict expression of the transgene (Cas 9 and gRNA) in only the target cell. The specificity of the vector can also be mediated by microRNA-dependent control of transgene expression. In an embodiment, the viral vector has increased efficiency of fusion of the viral vector and a target cell membrane. For example, a fusion protein such as fusion-competent hemagglutinin (HA) can be incorporated to increase viral uptake into cells. In an embodiment, the viral vector has the ability of nuclear localization. For example, a virus that requires the breakdown of the nuclear envelope (during cell division) and therefore will not infect a non-diving cell can be altered to incorporate a nuclear localization peptide in the matrix protein of the virus thereby enabling the transduction of non-proliferating cells.

In some embodiments, the Cas9- and/or gRNA-encoding DNA is delivered by a non-vector based method (e.g., using naked DNA or DNA complexes). For example, the DNA can be delivered, e.g., by organically modified silica or silicate (Ormosil), electroporation, transient cell compression or squeezing (e.g., as described in Lee, et al., Nano Lett 12: 6322-27), gene gun, sonoporation, magnetofection, lipid-mediated transfection, dendrimers, inorganic nanoparticles, calcium phosphates, or a combination thereof.

In an embodiment, delivery via electroporation comprises mixing the cells with the Cas9- and/or gRNA-encoding DNA in a cartridge, chamber or cuvette and applying one or more electrical impulses of defined duration and amplitude. In an embodiment, delivery via electroporation is performed using a system in which cells are mixed with the Cas9- and/or gRNA-encoding DNA in a vessel connected to a device (eg, a pump) which feeds the mixture into a cartridge, chamber or cuvette wherein one or more electrical impulses of defined duration and amplitude are applied, after which the cells are delivered to a second vessel.

In some embodiments, the Cas9- and/or gRNA-encoding DNA is delivered by a combination of a vector and a non-vector based method. In an embodiment, the donor template nucleic acid is delivered by a combination of a vector and a non-vector based method. For example, virosomes combine liposomes with an inactivated virus (e.g., HIV or influenza virus), which can result in more efficient gene transfer, e.g., in respiratory epithelial cells than either viral or liposomal methods alone.

In an embodiment, the delivery vehicle is a non-viral vector. In an embodiment, the non-viral vector is an inorganic nanoparticle. Exemplary inorganic nanoparticles include, e.g., magnetic nanoparticles (e.g., $Fe_3MnO_2$) or silica. The outer surface of the nanoparticle can be conjugated with a positively charged polymer (e.g., polyethylenimine, polylysine, polyserine) which allows for attachment (e.g., conjugation or entrapment) of payload. In an embodiment, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids for gene transfer are shown below in Table 21.

TABLE 21

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxy-ethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 22

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |

TABLE 22-continued

Polymers Used for Gene Transfer

| Polymer | Abbreviation |
|---|---|
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In an embodiment, the vehicle has targeting modifications to increase target cell update of nanoparticles and liposomes, e.g., cell specific antigens, monoclonal antibodies, single chain antibodies, aptamers, polymers, sugars (e.g., N-acetyl-galactosamine (GalNAc)), and cell penetrating peptides. In an embodiment, the vehicle uses fusogenic and endosome-destabilizing peptides/polymers. In an embodiment, the vehicle undergoes acid-triggered conformational changes (e.g., to accelerate endosomal escape of the cargo). In an embodiment, a stimuli-cleavable polymer is used, e.g., for release in a cellular compartment. For example, disulfide-based cationic polymers that are cleaved in the reducing cellular environment can be used.

In an embodiment, the delivery vehicle is a biological non-viral delivery vehicle. In an embodiment, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In an embodiment, the vehicle is a genetically modified bacteriophage (e.g., engineered phages having large packaging capacity, less immunogenic, containing mammalian plasmid maintenance sequences and having incorporated targeting ligands). In an embodiment, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In an embodiment, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes—subject (i.e., patient) derived membrane-bound nanovesicle (30-100 nm) of endocytic origin (e.g., can be produced from various cell types and can therefore be taken up by cells without the need of for targeting ligands).

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In an embodiment, the nucleic acid molecule is delivered by a different means than one or more of the components of the Cas system. e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein.

Delivery of RNA Encoding a Cas9 Molecule

RNA encoding Cas9 molecules (e.g., eaCas9 molecules or eiCas9 molecules) and/or gRNA molecules, can be delivered into cells, e.g., target cells described herein, by art-known methods or as described herein. For example, Cas9-encoding and/or gRNA-encoding RNA can be delivered, e.g., by microinjection, electroporation, transient cell compression or squeezing (eg, as described in Lee, et al., 2012, *Nano Lett* 12: 6322-27), lipid-mediated transfection, peptide-mediated delivery, or a combination thereof. Cas9-encoding and/or gRNA-encoding RNA can be conjugated to molecules) promoting uptake by the target cells (e.g., target cells described herein).

In an embodiment, delivery via electroporation comprises mixing the cells with the RNA encoding Cas9 molecules (e.g., eaCas9 molecules, eiCas9 molecules or eiCas9 fusion proteins) and/or gRNA molecules, with or without donor template nucleic acid molecules, in a cartridge, chamber or cuvette and applying one or more electrical impulses of defined duration and amplitude. In an embodiment, delivery via electroporation is performed using a system in which cells are mixed with the RNA encoding Cas9 molecules (e.g., eaCas9 molecules, eiCas9 molecules or eiCas9 fusion proteins) and/or gRNA molecules, with or without donor template nucleic acid molecules in a vessel connected to a device (eg, a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells described herein).

Delivery Cas9 Molecule Protein

Cas9 molecules (e.g., eaCas9 molecules or eiCas9 molecules) can be delivered into cells by art-known methods or as described herein. For example, Cas9 protein molecules can be delivered, e.g., by microinjection, electroporation, transient cell compression or squeezing (eg, as described in Lee, et al. 2012; Nano Lett 12: 6322-27), lipid-mediated transfection, peptide-mediated delivery, or a combination thereof. Delivery can be accompanied by DNA encoding a gRNA or by a gRNA. Cas9 protein can be conjugated to molecules promoting uptake by the target cells (e.g., target cells described herein).

In an embodiment, delivery via electroporation comprises mixing the cells with the Cas9 molecules (e.g., eaCas9 molecules, eiCas9 molecules or eiCas9 fusion proteins) and/or gRNA molecules, with or without donor nucleic acid, in a cartridge, chamber or cuvette and applying one or more electrical impulses of defined duration and amplitude. In an embodiment, delivery via electroporation is performed using a system in which cells are mixed with the Cas9 molecules (e.g., eaCas9 molecules, eiCas9 molecules or eiCas9 fusion proteins) and/or gRNA molecules, with or without donor nucleic acid in a vessel connected to a device (eg, a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells described herein).

A Cas9 protein can be combined with a gRNA molecule to form a ribonucleoprotein (RNP) complex to be administered to a subject or delivered into a cell by art-known methods or as described herein. Direct delivery of Cas9/gRNA RNP complex to cells eliminates the needs of expression from nucleic acid (e.g., transfection of plasmids encoding Cas9 and gRNA). It also eliminated unwanted integration of DNA segments derived from nucleic acid delivery (e.g., transfection of plasmids encoding Cas9 and gRNA). Therefore it is an alternative delivery approach which provide rapid action, fast turnover, high rate of on-target modification, reduced off target effect and less toxicity to cells. It can also be utilized to deliver the Cas9/gRNA complex to hard to transfect cells (e.g., hard to transfect primary and pluripotent stem cells). A Cas9/gRNA ribonucleoprotein (RNP) complex usually is formed prior to administration (i.e., pre-formed). When multiple (e.g., more than one) Cas9/gRNA ribonucleoprotein (RNP) complexes are involved, they can be delivered (e.g., administered) simultaneously or sequentially. In an embodiment, a Cas9/gRNA ribonucleoprotein (RNP) complexes can be delivered to cells by electroporation.

Route of Administration

Systemic modes of administration include oral and parenteral routes. Parenteral routes include, by way of example, intravenous, intraarterial, intramuscular, intradermal, subcutaneous, intranasal, and intraperitoneal routes. Components administered systemically may be modified or formulated to target hepatocytes, liver oval cells, macrophages or monocytes.

Local modes of administration include, by way of example, intraparenchymal delivery to the liver, intrahepatic artery infusion and infusion into the portal vein. In an embodiment, significantly smaller amounts of the components (compared with systemic approaches) may exert an effect when administered locally (for example, directly into the liver parenchyma) compared to when administered systemically (for example, intravenously). Local modes of administration can reduce or eliminate the incidence of potentially toxic side effects that may occur when therapeutically effective amounts of a component are administered systemically.

Administration may be provided as a periodic bolus (for example, intravenously) or as continuous infusion from an internal reservoir or from an external reservoir (for example, from an intravenous bag or implantable pump). Components may be administered locally, for example, by continuous release from a sustained release drug delivery device implanted in the liver.

In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Bi-Modal or Differential Delivery of Components

Separate delivery of the components of a Cas system, e.g., the Cas9 molecule component and the gRNA molecule component, and more particularly, delivery of the components by differing modes, can enhance performance, e.g., by improving tissue specificity and safety.

In an embodiment, the Cas9 molecule and the gRNA molecule are delivered by different modes, or as sometimes referred to herein as differential modes. Different or differential modes, as used herein, refer modes of delivery that confer different pharmacodynamic or pharmacokinetic properties on the subject component molecule, e.g., a Cas9 molecule, gRNA molecule, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., adeno associated virus or lentivirus, delivery.

By way of example, the components, e.g., a Cas9 molecule and a gRNA molecule, can be delivered by modes that differ in terms of resulting half-life or persistent of the delivered component the body, or in a particular compartment, tissue or organ. In an embodiment, a gRNA molecule can be delivered by such modes. The Cas9 molecule component can be delivered by a mode that results in less persistence or less exposure to the body or a particular compartment or tissue or organ.

More generally, in an embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In an embodiment, the first pharmacodynamic or pharmacokinetic property, e.g., distribution, persistence or exposure, is more limited than the second pharmacodynamic or pharmacokinetic property.

In an embodiment, the first mode of delivery is selected to optimize, e.g., minimize, a pharmacodynamic or pharmacokinetic property, e.g., distribution, persistence or exposure.

In an embodiment, the second mode of delivery is selected to optimize, e.g., maximize, a pharmacodynamic or pharmacokinetic property, e.g., distribution, persistence or exposure.

In an embodiment, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In an embodiment, the second mode of delivery comprises a relatively transient element, e.g., an RNA or protein.

In an embodiment, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a Cas9 molecule, is delivered in a transient manner, for example as mRNA or as protein, ensuring that the full Cas9 molecule/gRNA molecule complex is only present and active for a short period of time.

Furthermore, the components can be delivered in different molecular form or with different delivery vectors that complement one another to enhance safety and tissue specificity.

Use of differential delivery modes can enhance performance, safety and efficacy. E.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in an embodiment, a first component, e.g., a gRNA molecule is delivered by a first delivery mode that results in a first spatial, e.g., tissue, distribution. A second component, e.g., a Cas9 molecule is delivered by a second delivery mode that results in a second spatial, e.g., tissue, distribution. In an embodiment the first mode comprises a first element selected from a liposome, nanoparticle, e.g., polymeric nanoparticle, and a nucleic acid, e.g., viral vector. The second mode comprises a second element selected from the group. In an embodiment, the first mode of delivery comprises a first targeting element, e.g., a cell specific receptor or an antibody, and the second mode of delivery does not include that element. In embodiment, the second mode of delivery comprises a second targeting element, e.g., a second cell specific receptor or second antibody.

When the Cas9 molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule and the Cas9 molecule are packaged in separated delivery vehicles with distinct but overlapping tissue tropism, the fully functional complex is only be formed in the tissue that is targeted by both vectors.

Ex Vivo Delivery

In some embodiments, components described in Table 19 are introduced into cells which are then introduced into the subject. Methods of introducing the components can include, e.g., any of the delivery methods described in Table 20.

VIII. Modified Nucleosides, Nucleotides, and Nucleic Acids

Modified nucleosides and modified nucleotides can be present in nucleic acids, e.g., particularly gRNA, but also other forms of RNA, e.g., mRNA, RNAi, or siRNA. As described herein, "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:

(i) alteration, e.g., replacement, of one or both of the non-linking phosphate oxygens and/or of one or more of the linking phosphate oxygens in the phosphodiester backbone linkage;

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring nucleobase;

(v) replacement or modification of the ribose-phosphate backbone;

(vi) modification of the 3' end or 5' end of the oligonucleotide, e.g., removal, modification or replacement of a terminal phosphate group or conjugation of a moiety; and (vii) modification of the sugar.

The modifications listed above can be combined to provide modified nucleosides and nucleotides that can have two, three, four, or more modifications. For example, a modified nucleoside or nucleotide can have a modified sugar and a modified nucleobase. In an embodiment, every base of a gRNA is modified, e.g., all bases have a modified phosphate group, e.g., all are phosphorothioate groups. In an embodiment, all, or substantially all, of the phosphate groups of a unimolecular or modular gRNA molecule are replaced with phosphorothioate groups.

In an embodiment, modified nucleotides, e.g., nucleotides having modifications as described herein, can be incorporated into a nucleic acid, e.g., a "modified nucleic acid." In an embodiment, the modified nucleic acids comprise one, two, three or more modified nucleotides. In an embodiment, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are a modified nucleotides.

Unmodified nucleic acids can be prone to degradation by, e.g., cellular nucleases. For example, nucleases can hydrolyze nucleic acid phosphodiester bonds. Accordingly, in one aspect the modified nucleic acids described herein can contain one or more modified nucleosides or nucleotides, e.g., to introduce stability toward nucleases.

In an embodiment, the modified nucleosides, modified nucleotides, and modified nucleic acids described herein can exhibit a reduced innate immune response when introduced into a population of cells, both in vivo and ex vivo. The term "innate immune response" includes a cellular response to exogenous nucleic acids, including single stranded nucleic acids, generally of viral or bacterial origin, which involves the induction of cytokine expression and release, particularly the interferons, and cell death. In an embodiment, the modified nucleosides, modified nucleotides, and modified nucleic acids described herein can disrupt binding of a major groove interacting partner with the nucleic acid. In an embodiment, the modified nucleosides, modified nucleotides, and modified nucleic acids described herein can exhibit a reduced innate immune response when introduced into a population of cells, both in vivo and ex vivo, and also disrupt binding of a major groove interacting partner with the nucleic acid.

Definitions of Chemical Groups

As used herein, "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In an embodiment, aryl groups have from 6 to about 20 carbon atoms.

As used herein, "alkenyl" refers to an aliphatic group containing at least one double bond.

As used herein, "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl.

As used herein, "arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl. 3-phenylpropyl, 9-fluorenyl, benzhydryl, and trityl groups.

As used herein, "cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl.

As used herein, "heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl.

As used herein, "heteroaryl" refers to a monovalent radical of a heteroaromatic ring system. Examples of heteroaryl moieties include, but are not limited to, imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

Phosphate Backbone Modifications

The Phosphate Group

In an embodiment, the phosphate group of a modified nucleotide can be modified by replacing one or more of the oxygens with a different substituent. Further, the modified nucleotide, e.g., modified nucleotide present in a modified nucleic acid, can include the wholesale replacement of an unmodified phosphate moiety with a modified phosphate as described herein. In an embodiment, the modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. In an embodiment, one of the non-bridging phosphate oxygen atoms in the phosphate backbone moiety can be replaced by any of the following groups: sulfur (S), selenium (Se), $BR_3$ (wherein R can be, e.g., hydrogen, alkyl, or aryl), C (e.g., an alkyl group, an aryl group, and the like), H, $NR_2$ (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotide diastereomers. In an embodiment, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

Replacement of the Phosphate Group

The phosphate group can be replaced by non-phosphorus containing connectors. In an embodiment, the charge phosphate group can be replaced by a neutral moiety.

Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Replacement of the Ribophosphate Backbone

Scaffolds that can mimic nucleic acids can also be constructed wherein the phosphate linker and ribose sugar are replaced by nuclease resistant nucleoside or nucleotide surrogates. In an embodiment, the nucleobases can be tethered by a surrogate backbone. Examples can include, without limitation, the morpholino, cyclobutyl, pyrrolidine and peptide nucleic acid (PNA) nucleoside surrogates.

Sugar Modifications

The modified nucleosides and modified nucleotides can include one or more modifications to the sugar group. For example, the 2' hydroxyl group (OH) can be modified or replaced with a number of different "oxy" or "deoxy" substituents. In an embodiment, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom.

Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In an embodiment, the "oxy"-2' hydroxyl group modification can include "locked" nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In an embodiment, the "oxy"-2' hydroxyl group modification can include the methoxyethyl group (MOE), ($OCH_2CH_2OCH_3$, e.g., a PEG derivative).

"Deoxy" modifications can include hydrogen (i.e. deoxyribose sugars, e.g., at the overhang portions of partially ds RNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH_2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the 1' position on the sugar, e.g., alpha-nucleosides. The modified nucleic acids can also include "abasic" sugars, which lack a nucleobase at C-1'. These abasic sugars can also be further modified at one or more of the constituent sugar atoms. The modified nucleic acids can also include one or more sugars that are in the L form, e.g. L-nucleosides.

Generally, RNA includes the sugar group ribose, which is a 5-membered ring having an oxygen. Exemplary modified nucleosides and modified nucleotides can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). In an embodiment, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replaced with α-L-threofuranosyl-(3'→2')).

Modifications on the Nucleobase

The modified nucleosides and modified nucleotides described herein, which can be incorporated into a modified nucleic acid, can include a modified nucleobase. Examples of nucleobases include, but are not limited to, adenine (A), guanine (G), cytosine (C), and uracil (U). These nucleobases can be modified or wholly replaced to provide modified nucleosides and modified nucleotides that can be incorporated into modified nucleic acids. The nucleobase of the nucleotide can be independently selected from a purine, a pyrimidine, a purine or pyrimidine analog. In an embodiment, the nucleobase can include, for example, naturally-occurring and synthetic derivatives of a base.

Uracil

In an embodiment, the modified nucleobase is a modified uracil. Exemplary nucleobases and nucleosides having a modified uracil include without limitation pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine ($ho^5U$), 5-aminoallyl-uridine, 5-halo-uridine (e.g. 5-iodo-uridine or 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s2U$), 5-aminomethyl-2-thio-uridine ($nm^5s2U$), 5-methylaminomethyl-uridine ($mnm^5U$), 5-methylaminomethyl-2-thio-uridine ($mnm^3s2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($\tau mnm^5s2U$), 5-propynyl-uridine, 1-propynyl-pseudouridine, 5-taurinomethyl-uridine ($\tau cm^5U$), 1-taurinomethyl-pseudouridine, 5-taurinomethyl-2-thio-uridine ($\tau m^5s2U$), 1-taurinomethyl-4-thio-pseudouridine, 5-methyl-uridine ($m^5U$, i.e., having the nucleobase deoxythymine), 1-methyl-pseudouridine ($m^1\psi$), 5-methyl-2-thio-uridine ($m^5s2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s2U$), α-thio-uridine, 2'-O-methyl-uridine (Urn), 5,2'-O-dimethyl-uridine ($m^5Um$), 2'-O-methyl-pseudouridine (ψm), 2-thio-2'-O-methyl-uridine (s2Um), 5-methoxycarbonylmethyl-2'-O-methyl-uridine ($mcm^5Um$), 5-carbamoylmethyl-2'-O-methyl-uridine ($ncm^3Um$), 5-carboxymethylaminomethyl-2'-O-methyl-uridine ($cmnm^5Um$), 3,2'-O-methyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

Cytosine

In an embodiment, the modified nucleobase is a modified cytosine. Exemplary nucleobases and nucleosides having a modified cytosine include without limitation 5-aza-cytidine, 6-aza-cytidine, pseudoisocytidine, 3-methyl-cytidine ($m^3C$), N4-acetyl-cytidine (act), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k^2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4{}_2Cm$), 1-thio-cytidine, 2'-F-ara-cytidine, 2'-F-cytidine, and 2'-OH-ara-cytidine.

Adenine

In an embodiment, the modified nucleobase is a modified adenine. Exemplary nucleobases and nucleosides having a modified adenine include without limitation 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenosine, 7-deaza-8-aza-adenosine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenosine ($m^2A$), N6-methyl-adenosine ($m^6A$), 2-methylthio-N6-methyl-adenosine ($ms2m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl)adenosine ($ms2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6{}_2A$), N6-hydroxynorvalylcarbamoyl-adenosine ($hn^6A$), 2-methylthio-N6-hydroxynorvalylcarbamoyl-adenosine ($ms2hn^6A$), N6-acetyl-adenosine ($ac^6A$), 7-methyl-adenosine, 2-methylthio-adenosine, 2-methoxy-adenosine, α-thio-adenosine, 2'-O-methyl-adenosine (Am), $N^6$, 2'-O-dimethyl-adenosine ($m^6$ Am), $N^6$-Methyl-2'-deoxyadenosine, N6,N6, 2'-O-trimethyl-adenosine ($m^6{}_2Am$), 1,2'-O-dimethyl-adenosine ($m^1$ Am), 2'-O-ribosyladenosine (phosphate) (Ar (p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

Guanine

In an embodiment, the modified nucleobase is a modified guanine. Exemplary nucleobases and nucleosides having a modified guanine include without limitation inosine (1), 1-methyl-inosine ($m^1I$), wyosine (imG), methylwyosine (mimG), 4-demethyl-wyosine (imG-14), isowyosine (imG2), wybutosine (yW), peroxyiwybutosine ($o_2yW$), hydroxywybutosine (OHyW), undermodified hydroxywybutosine (OHVW*), 7-deaza-guanosine, queuosine (Q), epoxyqucuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine (m'G), N2-methyl-guanosine ($m^2G$), N2,N2-dimethyl-guanosine ($m^2{}_2G$), N2.7-dimethyl-guanosine ($m^2$,7G), N2, N2, 7-dimethyl-guanosine ($m^2$,2,7G), 8-oxo-guanosine, 7-methyl-8-oxo-guanosine, 1-methyl-6-thio-guanosine, N2-methyl-6-thio-guanosine, N2,N2-dimethyl-O-thio-guanosine, α-thio-guanosine. 2'-O-methyl-guanosine (Gm), N2-methyl-2'-O-methyl-guanosine ($m^2Gm$), N2,N2-dimethyl-2'-O-methyl-guanosine ($m^2{}_2Gm$), 1-methyl-2'-O-methyl-guanosine (m'Gm), N2,7-dimethyl-2'-O-methyl-guanosine ($m^2$,7Gm), 2'-O-methyl-inosine (Im), 1,2'-O-dimethyl-inosine (m'Im), $O^6$-phenyl-2'-deoxyinosine, 2'-O-ribosylguanosine (phosphate) (Gr(p)), 1-thio-guanosine, $O^6$-methyl-guanosine. $O^6$-Methyl-2'-deoxyguanosine, 2'-F-ara-guanosine, and 2'-F-guanosine.

Exemplary Modified gRNAs

In some embodiments, the modified nucleic acids can be modified gRNAs. It is to be understood that any of the gRNAs described herein can be modified in accordance with this section. As discussed herein, transiently expressed or delivered nucleic acids can be prone to degradation by, e.g., cellular nucleases. Accordingly, in one aspect the modified gRNAs described herein can contain one or more modified nucleosides or nucleotides which introduce stability toward nucleases. It is believed that these and other modified gRNAs described herein exhibit enhanced stability with certain cell types (e.g., circulating cells such as T cells) and that this might be responsible for the observed improvements.

For example, as discussed herein, we have seen improvements in ex vivo editing of genes in certain cell types (e.g., T cells) when the 5' end of a gRNA is modified by the inclusion of a eukaryotic mRNA cap structure or cap analog. The present disclosure encompasses the realization that the improvements observed with a 5' capped gRNA can be extended to gRNAs that have been modified in other ways to achieve the same type of structural or functional result (e.g., by the inclusion of modified nucleosides or nucleotides, or when an in vitro transcribed gRNA is modified by treatment with a phosphatase such as calf intestinal alkaline phosphatase to remove the 5' triphosphate group). The modified gRNAs described herein may contain one or more modifications (e.g., modified nucleosides or nucleotides) which introduce stability toward nucleases (e.g., by the inclusion of modified nucleosides or nucleotides and/or a 3' polyA tail).

Thus, in one aspect, methods and compositions discussed herein provide methods and compositions for gene editing of certain cells (e.g., ex vivo gene editing) by using gRNAs which have been modified at or near their 5' end (e.g., within 1-10, 1-5, or 1-2 nucleotides of their 5' end).

In some embodiments, the 5' end of the gRNA molecule lacks a 5' triphosphate group. In some embodiments, the 5' end of the targeting domain lacks a 5' triphosphate group. In some embodiments, the 5' end of the gRNA molecule includes a 5' cap. In some embodiments, the 5' end of the targeting domain includes a 5' cap. In some embodiments, the gRNA molecule lacks a 5' triphosphate group. In some embodiments, the gRNA molecule comprises a targeting domain and the 5' end of the targeting domain lacks a 5' triphosphate group. In some embodiments, gRNA molecule includes a 5' cap. In some embodiments, the gRNA molecule comprises a targeting domain and the 5' end of the targeting domain includes a 5' cap.

In an embodiment, the 5' end of a gRNA is modified by the inclusion of a eukaryotic mRNA cap structure or cap analog (e.g., without limitation a G(5')ppp(5')G cap analog, a m7G(5')ppp(5')G cap analog, or a 3'-O-Me-m7G(5')ppp (5')G anti reverse cap analog (ARCA)). In certain embodiments the 5' cap comprises a modified guanine nucleotide that is linked to the remainder of the gRNA molecule via a 5'-5' triphosphate linkage. In some embodiments, the 5' cap comprises two optionally modified guanine nucleotides that are linked via a 5'-5' triphosphate linkage. In some embodiments, the 5' end of the gRNA molecule has the chemical formula:

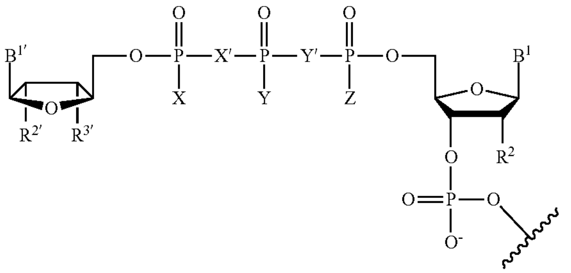

wherein:

each of B1 and B1' is independently

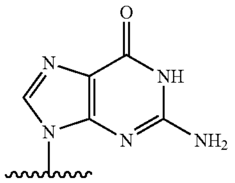

or

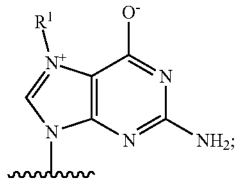

each R1 is independently C1-4 alkyl, optionally substituted by a phenyl or a 6-membered heteroaryl;

each of R2, R2, and R3 is independently H, F, OH, or O-C1-4 alkyl;

each of X, Y, and Z is independently O or S; and each of X' and Y' is independently O or CH2.

In an embodiment, each R1 is independently —CH3, —CH2CH3, or —CH2C6H5.

In an embodiment, R1 is —CH3.

In an embodiment, B1' is

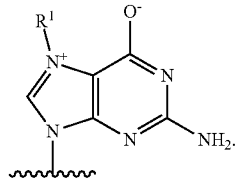

In an embodiment, each of R2, R2', and R3' is independently H, OH, or O—CH3.

In an embodiment, each of X, Y, and Z is O.

In an embodiment, X' and Y' are O.

In an embodiment, the 5' end of the gRNA molecule has the chemical formula:

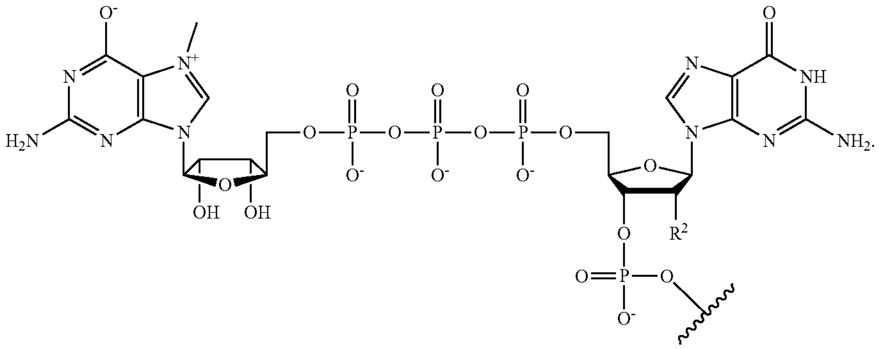

In an embodiment, the 5' end of the gRNA molecule has the chemical formula:

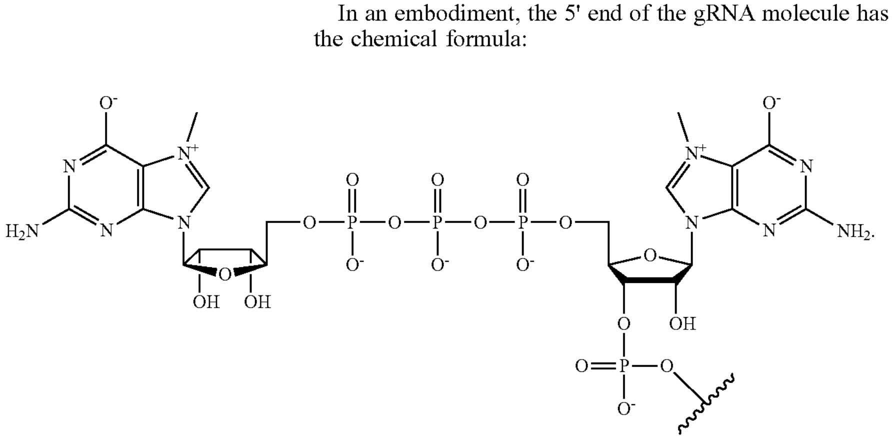

In an embodiment, the 5' end of the gRNA molecule has the chemical formula:

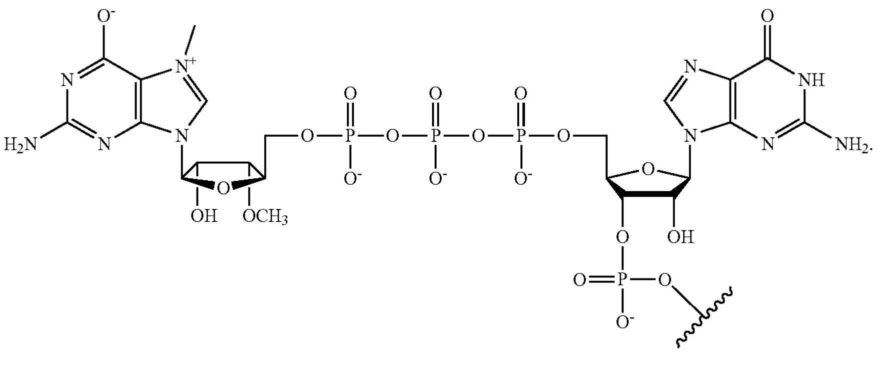

In an embodiment, the 5' end of the gRNA molecule has the chemical formula:

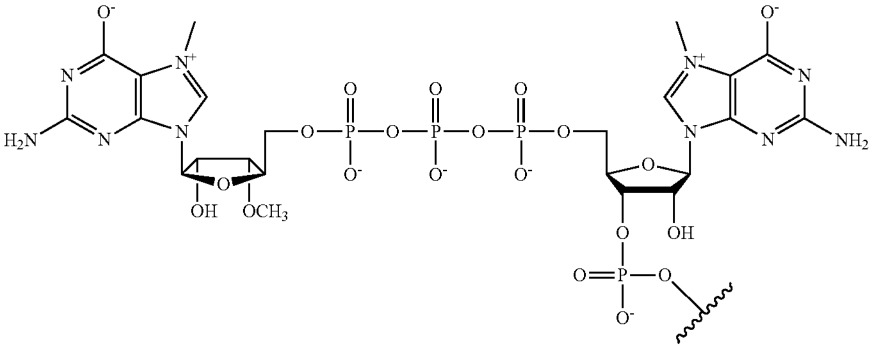

In an embodiment, X is S, and Y and Z are O.

In an embodiment, Y is S, and X and Z are O.

In an embodiment, Z is S, and X and Y are O.

In an embodiment, the phosphorothioate is the Sp diastereomer.

In an embodiment, X' is CH2, and Y' is O.

In an embodiment, X' is O, and Y' is CH2.

In an embodiment, the 5' cap comprises two optionally modified guanine nucleotides that are linked via an optionally modified 5'-5' tetraphosphate linkage.

In an embodiment, the 5' end of the gRNA molecule has the chemical formula:

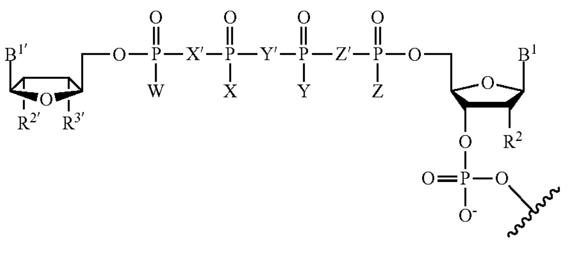

wherein:

each of B1 and B1' is independently

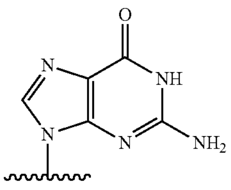 or 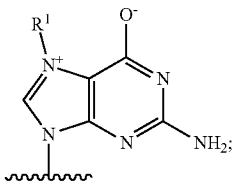

each R1 is independently C1-4 alkyl, optionally substituted by a phenyl or a 6-membered heteroaryl;

each of R2, R2', and R3' is independently H, F, OH, or O—C1-4 alkyl;

each of W, X, Y, and Z is independently O or S; and each of X', Y', and Z' is independently O or CH2.

In an embodiment, each R1 is independently —CH3, —CH2CH3, or —CH2C6H5.

In an embodiment, R1 is —CH3.

In an embodiment, B1' is

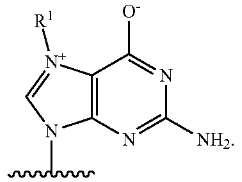

In an embodiment, each of R2, R2' and R3' is independently H, OH, or O—CH3.

In an embodiment, each of W, X, Y, and Z is O.

In an embodiment, each of X', Y', and Z' are O.

In an embodiment, X' is CH2, and Y' and Z' are O.

In an embodiment, Y' is CH2, and X' and Z' are O.

In an embodiment, Z' is CH2, and X' and Y' are O.

In an embodiment, the 5' cap comprises two optionally modified guanine nucleotides that are linked via an optionally modified 5'-5' pentaphosphate linkage.

In an embodiment, the 5' end of the gRNA molecule has the chemical formula:

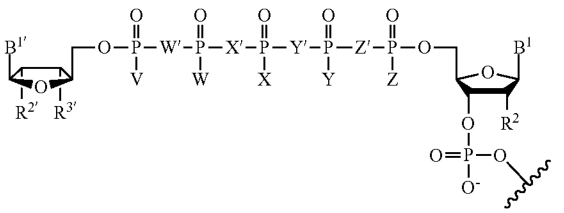

wherein:

each of B1 and B1' is independently

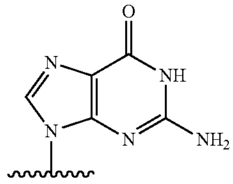

or

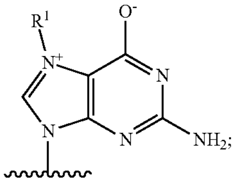

each R1 is independently C1-4 alkyl, optionally substituted by a phenyl or a 6-membered heteroaryl;

each of R2, R2', and R3' is independently H, F, OH, or O—C1-4 alkyl;

each of V, W, X, Y, and Z is independently O or S; and each of W', X', Y', and Z' is independently O or CH2.

In an embodiment, each R1 is independently —CH3, —CH2CH3, or —CH2C6H5.

In an embodiment, R1 is —CH3.

In an embodiment, B1' is

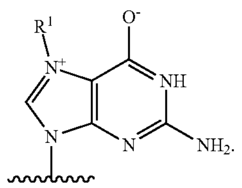

In an embodiment, each of R2, R2', and R3' is independently H, OH, or O—CH3.

In an embodiment, each of V, W, X, Y, and Z is O.

In an embodiment, each of W', X', Y', and Z' is O.

It is to be understood that as used herein, the term "5' cap" encompasses traditional mRNA 5' cap structures but also analogs of these. For example, in addition to the 5' cap structures that are encompassed by the chemical structures shown above, one may use, e.g., tetraphosphate analogs having a methylene-bis(phosphonate) moiety (e.g., see Rydzik, A M et al., (2009) Org Biomol Chem 7(22):4763-76), analogs having a sulfur substitution for a non-bridging oxygen (e.g., see Grudzien-Nogalska, E. et al. (2007) RNA 13(10): 1745-1755), N7-benzylated dinucleoside tetraphosphate analogs (e.g., see Grudzien, E. et al., (2004) RNA 10(9): 1479-1487), or anti-reverse cap analogs (e.g., see U.S. Pat. No. 7,074,596 and Jemielity, J. et al., (2003) RNA 9(9): 1 108-1 122 and Stepinski, J. et al., (2001) RNA 7(10):1486-1495). The present application also encompasses the use of cap analogs with halogen groups instead of OH or OMe (e.g., see U.S. Pat. No. 8,304,529); cap analogs with at least one phosphorothioate (PS) linkage (e.g., see U.S. Pat. No. 8,153,773 and Kowalska, J. et al., (2008) RNA 14(6): 1 1 19-1131); and cap analogs with at least one boranophosphate or phosphoroselenoate linkage (e.g., see U.S. Pat. No. 8,519,110); and alkynyl-derivatized 5' cap analogs (e.g., see U.S. Pat. No. 8,969,545).

In general, the 5' cap can be included during either chemical synthesis or in vitro transcription of the gRNA. In an embodiment, a 5' cap is not used and the gRNA (e.g., an in vitro transcribed gRNA) is instead modified by treatment with a phosphatase (e.g., calf intestinal alkaline phosphatase) to remove the 5' triphosphate group.

Methods and compositions discussed herein also provide methods and compositions for gene editing by using gRNAs which comprise a 3' polyA tail. Such gRNAs may, for example, be prepared by adding a polyA tail to a gRNA molecule precursor using a polyadenosine polymerase following in vitro transcription of the gRNA molecule precursor. For example, in one embodiment, a poly A tail may be added enzymatically using a polymerase such as *E. coli* polyA polymerase (E-PAP). gRNAs including a poly A tail may also be prepared by in vitro transcription from a DNA template. In one embodiment, a polyA tail of defined length is encoded on a DNA template and transcribed with the gRNA via an RNA polymerase (such as T7 RNA polymerase). gRNAs with a polyA tail may also be prepared by ligating a polyA oligonucleotide to a gRNA molecule precursor following in vitro transcription using an RNA ligase or a DNA ligase with or without a splinted DNA oligonucleotide complementary to the gRNA molecule precursor and the poly A oligonucleotide. For example, in one embodiment, a polyA tail of defined length is synthesized as a synthetic oligonucleotide and ligated on the 3' end of the gRNA with either an RNA ligase or a DNA ligase with or without a splinted DNA oligonucleotide complementary to the guide RNA and the polyA oligonucleotide. gRNAs including the polyA tail may also be prepared synthetically, in one or several pieces that are ligated together by either an RNA ligase or a DNA ligase with or without one or more splinted DNA oligonucleotides.

In some embodiments, the polyA tail is comprised of fewer than 50 adenine nucleotides, for example, fewer than 45 adenine nucleotides, fewer than 40 adenine nucleotides, fewer than 35 adenine nucleotides, fewer than 30 adenine nucleotides, fewer than 25 adenine nucleotides or fewer than 20 adenine nucleotides. In some embodiments the polyA tail is comprised of between 5 and 50 adenine nucleotides, for example between 5 and 40 adenine nucleotides, between 5 and 30 adenine nucleotides, between 10 and 50 adenine nucleotides, or between 15 and 25 adenine nucleotides. In some embodiments, the polyA tail is comprised of about 20 adenine nucleotides.

Methods and compositions discussed herein also provide methods and compositions for gene editing (e.g., ex vivo gene editing) by using gRNAs which include one or more modified nucleosides or nucleotides that are described herein.

While some of the exemplary modifications discussed in this section may be included at any position within the gRNA sequence, in some embodiments, a gRNA comprises a modification at or near its 5' end (e.g., within 1-10, 1-5, or 1-2 nucleotides of its 5' end). In some embodiments, a gRNA comprises a modification at or near its 3' end (e.g., within 1-10, 1-5, or 1-2 nucleotides of its 3' end). In some embodiments, a gRNA comprises both a modification at or near its 5' end and a modification at or near its 3' end. For example, in some embodiments, a gRNA molecule (e.g., an in vitro transcribed gRNA) comprises a targeting domain which is complementary with a target domain from a gene expressed in a eukaryotic cell, wherein the gRNA molecule is modified at its 5' end and comprises a 3' polyA tail. The gRNA molecule may, for example, lack a 5' triphosphate group (e.g., the 5' end of the targeting domain lacks a 5' triphosphate group). In an embodiment, a gRNA (e.g., an in vitro transcribed gRNA) is modified by treatment with a phosphatase (e.g., calf intestinal alkaline phosphatase) to remove the 5' triphosphate group and comprises a 3' polyA tail as described herein. The gRNA molecule may alternatively include a 5' cap (e.g., the 5' end of the targeting domain includes a 5' cap). In an embodiment, a gRNA (e.g., an in vitro transcribed gRNA) contains both a 5' cap structure or cap analog and a 3' polyA tail as described herein. In some embodiments, the 5' cap comprises a modified guanine nucleotide that is linked to the remainder of the gRNA molecule via a 5'-5' triphosphate linkage. In some embodiments, the 5' cap comprises two optionally modified guanine nucleotides that are linked via an optionally modified 5'-5' triphosphate linkage (e.g., as described above). In some embodiments the polyA tail is comprised of between 5 and 50 adenine nucleotides, for example between 5 and 40 adenine nucleotides, between 5 and 30 adenine nucleotides, between 10 and 50 adenine nucleotides, between 15 and 25 adenine nucleotides, fewer than 30 adenine nucleotides, fewer than 25 adenine nucleotides or about 20 adenine nucleotides.

In yet other embodiments, the present disclosure provides a gRNA molecule comprising a targeting domain which is complementary with a target domain from a gene expressed in a eukaryotic cell, wherein the gRNA molecule comprises a 3' polyA tail which is comprised of fewer than 30 adenine nucleotides (e.g., fewer than 25 adenine nucleotides, between 15 and 25 adenine nucleotides, or about 20 adenine nucleotides). In some embodiments, these gRNA molecules are further modified at their 5' end (e.g., the gRNA molecule is modified by treatment with a phosphatase to remove the 5' triphosphate group or modified to include a 5' cap as described herein).

In some embodiments, gRNAs can be modified at a 3' terminal U ribose. For example, the two terminal hydroxyl groups of the U ribose can be oxidized to aldehyde groups and a concomitant opening of the ribose ring to afford a modified nucleoside as shown below:

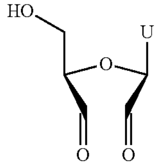

wherein "U" can be an unmodified or modified uridine.

In another embodiment, the 3' terminal U can be modified with a 2'3' cyclic phosphate as shown below:

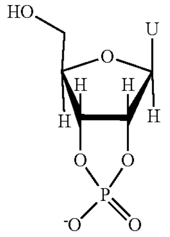

wherein "U" can be an unmodified or modified uridine.

In some embodiments, the gRNA molecules may contain 3' nucleotides which can be stabilized against degradation, e.g., by incorporating one or more of the modified nucleotides described herein. In this embodiment, e.g., uridines can be replaced with modified uridines, e.g., 5-(2-amino)propyl uridine, and 5-bromo uridine, or with any of the modified uridines described herein; adenosines, cytidines and guanosines can be replaced with modified adenosines, cytidines and guanosines, e.g., with modifications at the 8-position, e.g., 8-bromo guanosine, or with any of the modified adenosines, cytidines or guanosines described herein.

In some embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., $NH_2$; alkylamino, dialkylamino, heterocyclylamino, arylamino, diarylamino, heteroarylamino, diheteroarylamino, or amino acid); or cyano (—CN). In some embodiments, the phosphate backbone can be modified as described herein, e.g., with a phosphothioate group. In some embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

In some embodiments, a gRNA can include "locked" nucleic acids (LNA) in which the 2' OH-group can be connected, e.g., by a C1-6 alkylene or C1-6 heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclylamino, arylamino, diarylamino, heteroarylamino, or diheteroarylamino, ethylenediamine, or polyamino) and aminoalkoxy or $O(CH_2)_n$-amino (wherein amino can be, e.g., $NH_2$; alkylamino, dialkylamino, heterocyclylamino, arylamino, diarylamino, heteroarylamino, or diheteroarylamino, ethylenediamine, or polyamino).

In some embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNA molecules include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In an embodiment, a gRNA comprises a 4'-S, 4'-Se or a 4'-C-aminomethyl-2'-O-Me modification.

In some embodiments, deaza nucleotides, e.g., 7-deaza-adenosine, can be incorporated into the gRNA. In some embodiments, O- and N-alkylated nucleotides, e.g., N6-methyl adenosine, can be incorporated into the gRNA. In some embodiments, one or more or all of the nucleotides in a gRNA molecule are deoxynucleotides.

miRNA Binding Sites microRNAs (or miRNAs) are naturally occurring cellular 19-25 nucleotide long noncoding RNAs. They bind to nucleic acid molecules having an appropriate miRNA binding site, e.g., in the 3' UTR of an mRNA, and down-regulate gene expression. Down regulation is either by reducing nucleic acid molecule stability or by inhibiting translation. An RNA species disclosed herein, e.g., an mRNA encoding Cas9 can comprise an miRNA binding site, e.g., in its 3'UTR. The miRNA binding site can be selected to promote down regulation of expression is a selected cell type. By way of example, the incorporation of a binding site for miR-122, a microRNA abundant in liver, can inhibit the expression of the gene of interest in the liver.

IX. gRNA Identification System and Database

Described herein are systems, methods and computer readable medium for identifying gRNAs for editing alleles using CRISPR/Cas9 systems. Further described herein are systems, methods and computer readable medium for implementing or creating a database schema for identifying gRNAs for editing alleles using CRISPR/Cas9 systems. The gRNA identification system allows a user (e.g., a medical practitioner or professional, a clinical coordinator, a physician, or an allele sequencing laboratory technician) to identify gRNAs suitable for editing a particular allele. As described herein, a user may want to edit an allele to increase the number of allele matches between a targeted transplant recipient and a targeted transplant donor. The gRNA identification system receives data related to alleles from a recipient and alleles from a potential donor, and identifies the mismatched alleles from the input. Then, the gRNA identification system queries a database to generate a list of gRNAs suitable for editing the alleles from the potential donor. The list of gRNAs is ranked based on one or more criteria. The gRNA identification system also includes implementing a database schema that comprises various tables storing data related to, for example, alleles, gRNAs, haplotypes, and ancestry information.

A database is constructed to store every HLA allelic variant recorded to date. Records of these HLA allelic variants are publicly available, see for example: (hla.alleles.org/alleles/index.html, Robinson J. Halliwell J A, Hayhurst J H, Flicek P. Parham P, Marsh SGE, The IPD and IMGT/HLA database: allele variant databases, Nucleic Acids Research (2015) 43:D423-431). The database may be updated as the record of the HLA allelic variants is updated. Using this data set, gRNA sequences that target specific single alleles that may be present at one of the MHC loci (HLA-A, -B, -C, DRB1, -DRB3/4/5, and -DQB1) are designed. Using publicly available databases (National Marrow Donor Program: bioinformatics.bethematchclinical.org/HLA-Resources/Haplotype-Frequencies/High-Resolution-HLA-Alleles-and-Haplotypes-in-the-US-Population/; bioinformatics.bethematchclinical.org/HLA-Resources/Haplotype-Frequencies/Jewish-High-Resolution-Haplotype-Frequencies/), the database also cross-references individual alleles and haplotypes to alleles and haplotypes that are commonly present and specific to persons of different ancestral backgrounds (i.e., ancestries, races, ethnic background) of human subjects within which these individual alleles are identified. In an example embodiment, the database may include the following number of allelic variants or more (as the number of variants identified increase over time with new patients; the current number of allelic variants per locus are listed to provide an example of the high degree of polymorphisms at the MHC loci); HLA-A (3.094 alleles), HLA-B (3,865 alleles), HLA-C (2,618 alleles), HLA-DRB1 (1,719 alleles), HLA-DRB3/4/5 (95 alleles), HLA-DQB1 (777 alleles). For these alleles (and likely more as the number will increase), at least 106,234 gRNAs may be included in this database. In an example embodiment, the length of the targeting domain of a gRNA to be used with an *S. pyogenes* Cas9 is 17 or 20 nucleotides. In an example embodiment, the length of the targeting domain of a gRNA to be used with an *S. aureus* Cas9 is 20 or 24 nucleotides. In another embodiment, the length of the targeting domain of a gRNA to be used is 15, 16, 17, 18, 19, 20, 21, 22, 23, 24, 25, 26, 27, 28, 29, or 30 nucleotides. In the database, allele frequencies and common haplotypes detected in European American (e.g., Caucasian). African American, Asian (including Pacific Islander), Hispanic (e.g., Latino) populations and persons of Jewish ancestry may also be included.

Using the database, gRNAs that are highly specific to single alleles out of thousands of allelic variants, if any, can be selected, and the off-target effect (whether the allele-specific gRNAs could potentially mis-target on other alleles at other genomic loci within the human chromosome sequences) can be identified. Additionally, the database can identify gRNAs that target individual HLA loci (e.g., HLA-A) without allelic specificity that would support bi-allelic disruption with the same gRNA. In an example embodiment, the allelic variants, gRNAs, and ancestry data from the database may be linked to publicly available national and international cord blood and bone marrow donor hematopoietic stem/progenitor cell registries, in order to cross-reference and identify mismatched, partially matched, or haploidentical HSPC donors. The mismatched, partially matched, or haploidentical HSPC donor cells can be edited with CRISPR/Cas9 technology to alter the HLA genotype such that the donor cells subsequently match the recipient subject in need of an allogeneic HSPC transplant for disease treatment but for whom no matched donor could be identified without editing mismatched or partially matched donor cells.

The user (e.g., a medical practitioner or professional, a clinical coordinator, a physician, or an allele sequencing laboratory technician) provides the HLA typing, for example, DNA sequencing of both HLA haplotypes, of a targeted transplant recipient's MHC loci in order to identify the specific allelic variants associated with the recipient's full haplotype. The complete HLA haplotype information may be entered into cord blood and bone marrow stem cell registries in order to search for a potential donor that has the highest degree of HLA matching (the highest number of matched alleles on both chromosomal copies) from public or private stem cell donor databases. Based on the available donors with the highest degree of matching to the transplant recipient located from the public/private databases, the user or the system can determine the alleles that need to be edited in order to increase the level of HLA matching. Once edited, the donor cells have the potential to meet the criteria for allogeneic HSCT and have a reduced likelihood and/or severity of GVHD occurrence. The gRNA identification system described herein allows a user to find gRNAs that can edit specific alleles without targeting other alleles that are present in the donor's genomic DNA. The gRNA identification system generates a list of gRNAs that can be used to edit an allele. The user can use one or more of the gRNAs on the list to disrupt or knockout the unmatched alleles, and then knock in or replace the unmatched alleles with recipient-specific alleles in the donor cells.

If two potential donors have a similar level of MHC matching (e.g., 4/6) and either can be selected for correction of a mismatched MHC allele to improve matching between donor and recipient (e.g., to 5/6 match), then the user can cross-reference the most common minor histocompatibility antigens (miHAgs) in the ancestry database that are MHC restricted. MiHAgs are well-known in the art. See, for example, Spierings et al., PLOS Genetics, 3(6):1108-1119, 2007; Spierings, Tissue Antigens, 84:347-360, 2014; and Spierings et al., Biol. Blood Marrow Transplant, 19:1244-1253, 2013). The user can use the ancestry database to cross-reference the potential "corrected" MHC haplotypes with the miHAgs that are restricted to the potentially "corrected" MHC antigens (e.g., donor miHAgs that can be restricted by "corrected" MHC receptors present in the donor cells, thereby leading to Host versus Graft rejection). As these miHAgs are differentially present among ancestral groups, cross-referencing the two potential donors with miHAgs in ancestral groups allows the user to select the better MHC allele to correct and to select the more suitable donor. In this example, when the user is faced with the option of selecting one of two alleles to correct, the user can use the information in the ancestry database of the gRNA identification system to make an informed decision on which donor to select for MHC correction based on: 1) the more common MHC locus found in the ancestral group of the transplant recipient and 2) the miHAgs that are not MHC restricted across the donor/recipient mismatched MHC. This is relevant in that genetic differences between donors and recipients at the miHAgs also impact outcome of allogeneic HSCT. The degree of predicted minor histocompatibility antigen mismatch has been shown to correlate with less favorable clinical outcome, especially in the context of nonablative alloHSCT (Larsen et al., *Biol Blood Marrow Transplant* (2010), 16(10:1370-81). Thus, cross referencing both donor MHC haplotypes with the ancestry database that indicates the MHC haplotypes that are restricted to miHAgs common in specific ancestral groups can further improve the outcome of an allo-HSCT.

Using a publicly available data set that includes HLA allelic variants recorded to date (hla.alleles.org), a database was built and established to contain gRNA sequences that are designed for individual alleles which have been reported for HLA-A, -B, -C, DRB1, -DRB3/4/5, and -DQB1 loci and cross-references every allele to the ancestry of human subjects within which these individual alleles are represented (Marsh, S. G. E. (2015), Nomenclature for factors of the HLA system, update March 2015. Tissue Antigens. doi: 10.1111/tan.12581; Maiers M, et al. Hum. Immunol. 2007; 68(9):779-788) (see "gRNA" and "example" sections for allele-specific gRNA examples and for detailed database design). The following numbers of allelic variants (e.g., the total number of alleles discovered to date. Additional alleles may be added as new variants are identified) were included within the database: HLA-A (3,094 alleles), HLA-B (3,865 alleles), HLA-C (2,618 alleles), HLA-DRB1 (1,719 alleles), HLA-DRB3/4/5 (95 alleles), HLA-DQB1 (777 alleles). Using the database, gRNAs, if any, that are specific to one out of thousands of allelic variants that are represented in the database can be selected. In addition, the database described herein can identify and tier gRNAs that target individual HLA loci without allelic specificity that would allow for bi-allelic disruption with one or more gRNAs. Allelic variants, gRNAs, and ancestry can be linked to current cord blood and bone marrow donor registries for cross-referencing and identifying partially matched donors that could be later modified with CRISPR-Cas9 in order to create a more fully matched donor for allo-HSCT in recipient subjects.

Guide RNAs (gRNAs) for use with *S. pyogenes*, *S. aureus*, and *N. meningitidis* Cas9 molecules can be identified using a DNA sequence searching algorithm. Guide RNA (gRNA) design is carried out using a custom guide RNA design software based on the public tool cas-offinder (Bae et al. (2014) Bioinformatics 30(10): 1473-5). The custom gRNA design software scores gRNAs after calculating their genome-wide off-target propensity. Typically matches ranging from perfect matches to 7 mismatches are considered for guides ranging in length from 17 to 24. Once the off-target sites are computationally determined, an aggregate score is calculated for each guide and summarized in a tabular output using a web-interface. In addition to identifying potential gRNA sites adjacent to PAM sequences, the software also identifies all PAM adjacent sequences through the entire genomic sequence of each MHC locus that differ by 1, 2, 3 or more nucleotides from the selected gRNA sites. Genomic DNA sequence for each gene was obtained from the UCSC Genome browser and sequences were screened for repeat elements using the publically available RepeatMasker program. RepeatMasker searches input DNA sequences for repeated elements and regions of low complexity. The output is a detailed annotation of the repeats present in a given query sequence.

After identifying gRNAs that target the MHC allele of interest for gene editing, gRNAs are further tiered based on the following criteria: 1) distance to the target site, 2) presence of a 5' G, and 3) based on orthogonality score, or identification of near matches in the human genome containing a relevant PAM (e.g., in the case of *S. pyogenes*, a NGG PAM, in the case of *S. aureus*, a NNGRRT or NNGRRV PAM, and in the case of *N. meningitidis*, a NNNNGATT or NNNNGCTT PAM). Orthogonality refers to the number of sequences in the human genome that contain a minimum number of mismatches to the target sequence. A "high level of orthogonality" or "good orthogonality" may, for example, refer to 20-mer gRNAs that have no identical sequences in the human genome besides the intended target, nor any sequences that contain one or two mismatches in the target sequence. Targeting domains with good orthogonality are selected to minimize off-target DNA cleavage.

Accordingly, an exemplary embodiments of the gRNA identification system described herein allow for a user to search for gRNAs that target a single allele that will not target other alleles, for example at six HLA loci. The gRNA identification system can also be used for querying specific alleles, by changing the query input to a specific allele identifier. Exemplary embodiments provide a system and method for identifying gRNAs for editing alleles. Exemplary embodiments also provide a non-transitory computer readable medium and a system for implementing a database schema for the gRNA identification system.

A non-transitory computer readable storage medium stores instructions for execution by a processing device for implementing the database schema described below. A system for implementing a database schema includes a processor, and a memory storing the database schema described below. A non-transitory computer readable medium stores instructions for execution by a processing device, where execution of the instructions causes the processing device to create a database in accordance with the database schema described below.

The database schema includes an allele table that stores data related to major HLA alleles and a gRNA table that stores data related to gRNAs. The database schema further includes an allele-gRNA-relation table that stores relationships between records of the allele table and records of the gRNA table, where the allele table has a one-to-many relationship with the allele-gRNA-relation table, and the gRNA table has a one-to-many relationship with the allele-gRNA-relation table. The database schema also includes a haplotype table that stores data related to haplotypes, where the allele table has a one-to-many relationship with the haplotype table. The database schema also includes a haplotype-frequency table that stores data related to frequency of a haplotype occurring within a plurality of ancestries, where the haplotype table has a one-to-one relationship with the haplotype-frequency table. An ancestry table storing data related to ancestry is also included in the database schema.

The database schema also includes an ancestry-haplotype-relation table that stores relationships between records of the haplotype-frequency table and records of the ancestry table, where the haplotype-frequency table has one-to-many relationship with the ancestry-haplotype-relation table and the ancestry table has a one-to-many relationship with the ancestry-haplotype-relation table. The database schema further includes an allele frequency table that stores data related to frequency of an allele occurring within a plurality of ancestries, where the allele table has a one-to-one relationship with the allele frequency table. The database schema also includes an allele-ancestry-relation table that stores relationships between records of the allele frequency table and records of the ancestry table, where the allele frequency table has a one-to-many relationship with the allele-ancestry-relation table and the ancestry table has a one-to-many relationship with the allele-ancestry-relation table.

The database may also include a minor-antigens table that stores data related to minor histocompatibility antigens, and a major-minor-restriction table that stores data related to HLA restrictions to minor histocompatibility antigens. The minor-antigen table has a one-to-many relationship to the major-minor-restriction table, and the allele table has a one-to-many relationship with the major-minor-restriction table.

The allele table includes an allele id key, an allele attribute, a gene name attribute, and an allele sequence attribute. The gRNA table includes a gRNA id key, a Cas variant attribute, a gRNA sequence (with PAM) attribute, a gRNA sequence (without PAM) attribute, a strand attribute, an orthogonality score attribute, and an off-target list information attribute. The allele-guide-relation table includes a relation id key, an allele id attribute that corresponds to an allele id key of the allele table, and a gRNA id attribute that corresponds to a gRNA id key of the gRNA table. The haplotype table includes a haplotype id key, a HLA-A allele attribute, a HLA-B allele attribute, a HLA-C allele attribute, a HLA-DRB1 locus attribute, a HLA-DRB3/DRB4/DRB5 locus attribute, and a HLA-DQB1 allele locus attribute.

The haplotype-frequency table includes a haplotype frequency id key, a haplotype id attribute that corresponds to a haplotype id key of the haplotype table, an attribute for frequency of occurrence of a haplotype in European ancestry group, an attribute for rank of a haplotype occurrence in European ancestry group, an attribute for frequency of occurrence of a haplotype in African American ancestry group, an attribute for rank of a haplotype occurrence in African American ancestry group, an attribute for frequency of occurrence of a haplotype in Asian ancestry group, an attribute for rank of a haplotype occurrence in Asian ancestry group, an attribute for frequency of occurrence of a haplotype in Hispanic ancestry group, an attribute for rank of a haplotype occurrence in Hispanic ancestry group, an attribute for frequency of occurrence of a haplotype in Jewish ancestry group, and an attribute for rank of a haplotype occurrence in Jewish ancestry group.

The allele-frequency table comprises an allele frequency id key, an allele id attribute corresponds to an allele id key of the allele table, an attribute for frequency of occurrence of an allele in European ancestry group, an attribute for rank of an allele occurrence in European ancestry group, an attribute for frequency of occurrence of an allele in African American ancestry group, an attribute for rank of an allele occurrence in African American ancestry group, an attribute for frequency of occurrence of an allele in Asian ancestry group, an attribute for rank of an allele occurrence in Asian ancestry group, an attribute for frequency of occurrence of an allele in Hispanic ancestry group, an attribute for rank of an allele occurrence in Hispanic ancestry group, an attribute for frequency of occurrence of an allele in Jewish ancestry group, and an attribute for rank of an allele occurrence in Jewish ancestry group.

The allele-frequency table has an identifying relationship with the allele table and is entirely dependent on the allele table. The haplotype-frequency table has an identifying relationship with the haplotype table and is entirely dependent on the haplotype table.

A system for identifying gRNAs for editing one or more alleles includes a processor, and a memory storing instructions that when executed causes the processor to implement the method described below. The method may also be performed in a computational system for identifying gRNAs for editing one or more alleles.

The method includes receiving, via an interface of the computational system, a listing of a first plurality of alleles of a targeted transplant recipient, and receiving, via the interface of the computational system, a listing of a second plurality of alleles of a targeted transplant donor. The method continues by processing the listings of the first and second pluralities of alleles to identify one or more mismatched alleles between the first plurality of alleles and the second plurality of alleles, and querying a database to determine whether one or more gRNAs are suitable for editing the one or more mismatched alleles of the second plurality of alleles. In response to determining that one or more gRNAs from the database are suitable to edit the one or more mismatched alleles, a list of gRNAs is generated that identifies the one or more gRNAs found to be suitable. The list of gRNAs is ranked, and displayed.

The method may also include displaying the DNA sequence for each of the first plurality of alleles. The database stores a number indicating a likelihood of an allele occurring in a racial group. The method may also include displaying a frequency of occurrence of each of the first plurality of alleles within an ancestry. The method may further include displaying a restriction relationship between each of the first plurality of alleles and a minor histocompatibility antigen. The first plurality of alleles may be the maternally inherited major HLA haplotype of the targeted transplant recipient, and the second plurality of alleles may be the maternally inherited major HLA haplotype of the targeted transplant donor. The listing of the first plurality of alleles comprises one allele, two alleles, three alleles, four alleles, five alleles, six alleles, seven alleles, or eight alleles. The listing of the second plurality of alleles comprises one allele, two alleles, three alleles, four alleles, five alleles, six alleles, seven alleles, or eight alleles.

The list of gRNAs identifies one gRNA for editing one mismatched allele. The list of gRNAs may identify more than one gRNA for editing more than one mismatched alleles. The list of gRNAs may identify one gRNA for editing more than one mismatched alleles.

A gRNA from the list of gRNAs is capable of editing a mismatched allele from the second plurality of alleles of the targeted transplant donor to increase the number of matching alleles between the first plurality of alleles and the second plurality of alleles. A gRNA from the list of gRNAs is capable of editing the one or more mismatched alleles to reduce the likelihood of Graft-versus-host disease (GVHD) occurring in the targeted transplant recipient.

Figure 24:
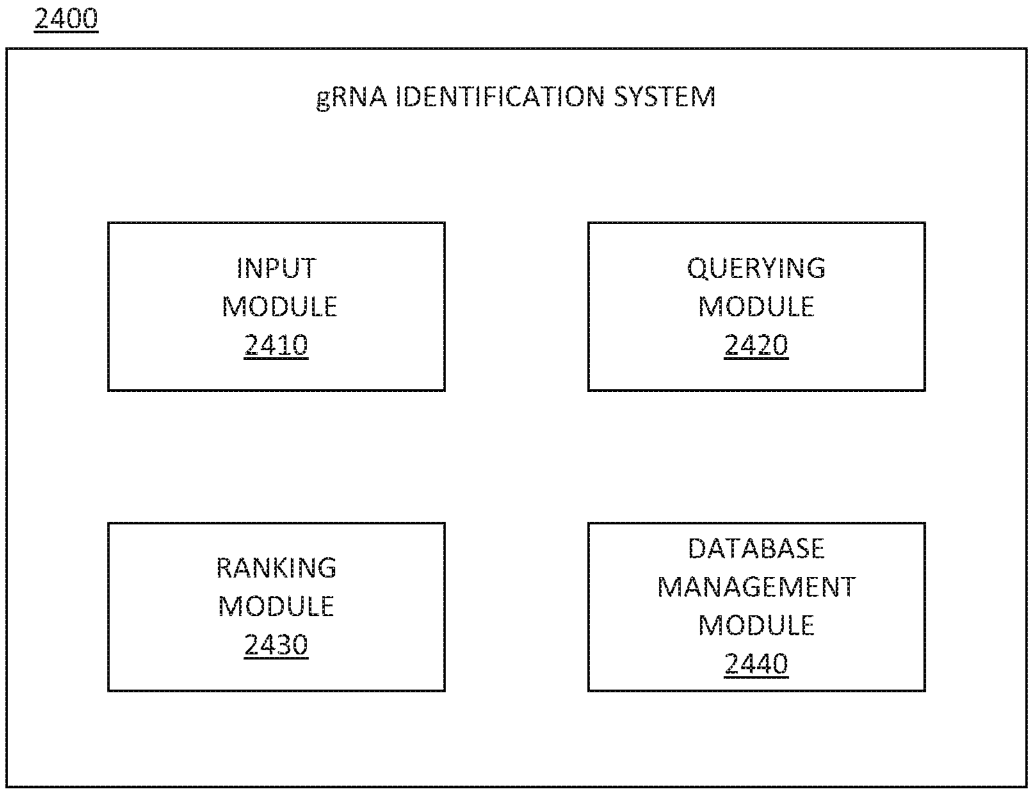
FIG. 24 is a block diagram showing a gRNA identification system implemented in modules, according to an exemplary embodiment.

FIG. 24 is a block diagram showing a gRNA identification system 2400 implemented in modules, according to an example embodiment. The modules may be implemented in device 1010 shown in FIG. 33. The modules include an input module 2410, a querying module 2420, a ranking module 2430, and a database management module 2440. The modules may include various circuits, circuitry and one or more software components, programs, applications, or other units of code base or instructions configured to be executed by one or more processors included in device 1010. In other embodiments, one or more of modules 2410, 2420, 2430, 2440 may be included in server 1020, while other of the modules 2410, 2420, 2430, 2440 are provided in the device 1010 or as part of database management system 1040. Although modules 2410, 2420, 2430, and 2440 are shown as distinct modules in FIG. 24, it should be understood that modules 2410, 2420, 2430, and 2440 may be implemented as fewer or more modules than illustrated. It should be understood that any of modules 2410, 2420, 2430, and 2440 may communicate with one or more components included in system 3300 (FIG. 33), such as device 3310, server 3320, database management system 3340 or database(s) 3350.

The input module 2410 may be configured to manage and analyze input received from an interface associated with a device, for example, device 3310. The input can include a listing of a first group of alleles of a targeted transplant recipient and a listing of a second group of alleles of a targeted transplant donor. The input may also include information related to haplotypes of the targeted transplant recipient and/or the targeted transplant donor, ancestry information of the targeted transplant recipient and/or the targeted transplant donor. The input module 2410 may also be configured to identify one or more mismatched alleles between the alleles of the targeted transplant recipient and the alleles of the targeted transplant donor.

The querying module 2420 may be configured to analyze the input and mismatched alleles, and query a database to determine whether one or more gRNAs in the database are suitable for editing a mismatched allele. The querying module 2420 may also be configured to generate a list of gRNAs from the database that are suitable for editing the one or more mismatched alleles that were identified.

The ranking module 2430 may be configured to analyze a list of gRNAs and rank the list based on various criteria. For example, the individual gRNAs in the list of gRNAs may be ranked based upon their respective off-target effects on non-targeted alleles. The database management module 2440 may be configured to access and manage a database storing information related to alleles, haplotypes, gRNAs, ancestry, and other information.

Figure 25:
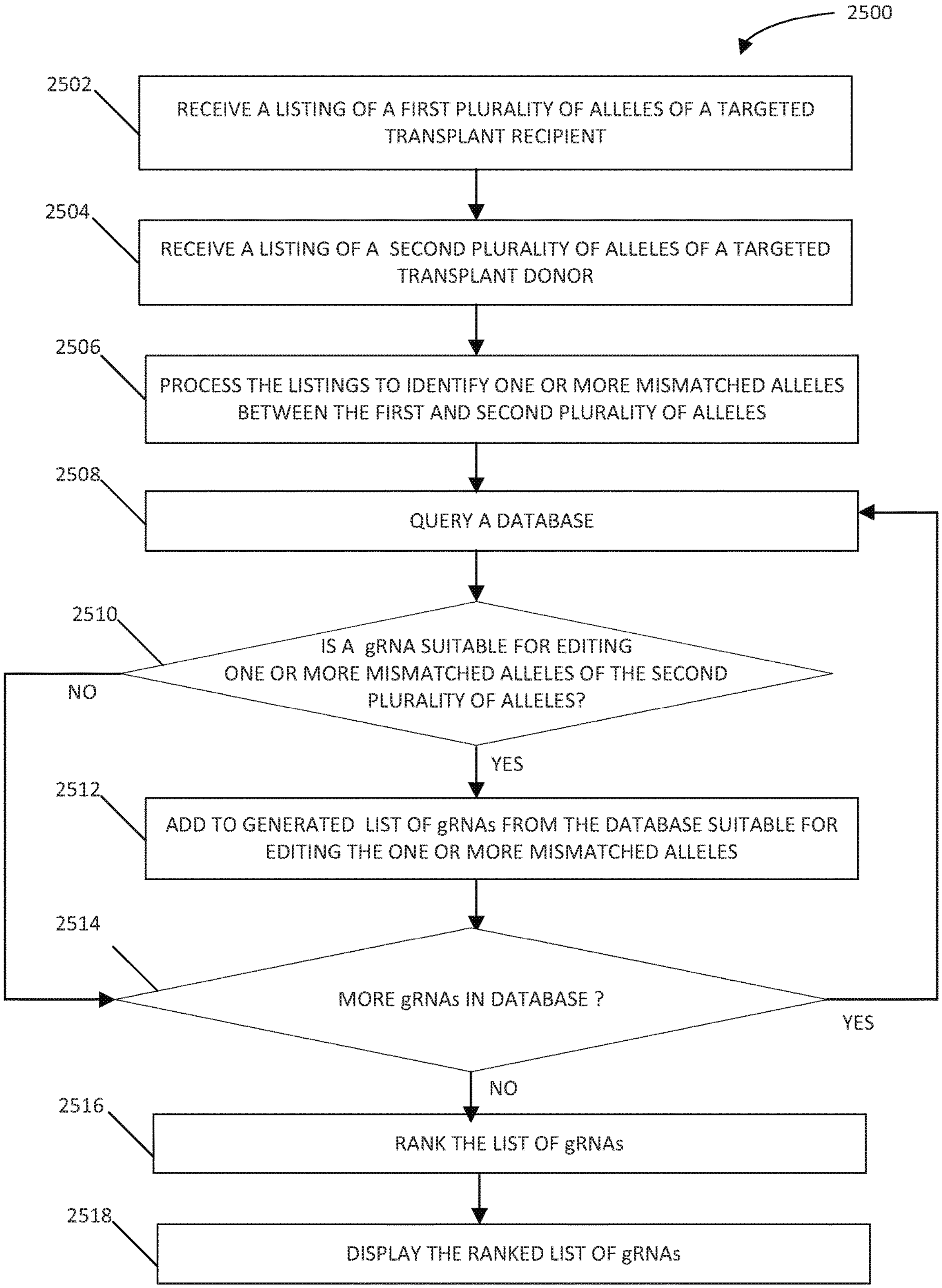
FIG. 25 is a flowchart showing an exemplary method for identifying gRNAs for editing alleles, according to an exemplary embodiment.

FIG. 25 is a flowchart showing an exemplary method 2500 for identifying gRNAs for editing alleles, according to an example embodiment. The method 2500 may be performed using the modules in the gRNA identification system 2400 shown in FIG. 24. The exemplary method 2500 begins, at step 2502, with the input module 2410 receiving a listing of a first group of alleles of a targeted transplant recipient. In an example embodiment, the first group of alleles may be the maternally inherited major HLA haplotype of the targeted transplant recipient, or the paternally inherited major HLA haplotype of the targeted transplant recipient. A haplotype, as used herein, refers to a group of alleles for different HLA genes.

At step 2504 the input module 2410 receives a listing of a second group of alleles of a targeted transplant donor. In an example embodiment, the second group of alleles may be the maternally inherited major HLA haplotype (e.g., the group of MHC loci comprising HLA-A/-B/-DRB1 on one chromosome), or the paternally inherited major HLA haplotype (e.g., the group of MHC loci comprising HLA-A/-B/-DRB1 on the other chromosome) to be targeted for gene editing the potential HSC donor. The type of information received as input for the transplant recipient dictates the type of information received as input for the transplant donor, and vice-versa.

In some embodiments, the input module 2410 may receive input related to ancestry information of the transplant recipient and the donor, gender, and age information of the transplant recipient and the donor.

The exemplary method 2500 proceeds to step 2506, where the input module 2410 processes the received input to identify one or more mismatched alleles between the first group of alleles and the second group of alleles. A mismatched allele may be identified based on a comparison of each of the alleles from the first group of alleles and the second group of alleles. A mismatched allele, as used herein, refers to an allele from the transplant donor that is different from the corresponding allele of the transplant recipient. In some embodiments, there may be one mismatched allele. In other embodiments, there may be multiple mismatched alleles. The input module 2410 may store a record of the identified mismatched alleles for further processing.

At step 2508, the querying module 2420 queries a database to determine whether a gRNA from the database is suitable for editing the one or more mismatched alleles of the transplant donor. In an example embodiment, the database may be implemented according to database schemas 2700 and 2700' described in relation to FIGS. 27A, 27B and 27C which are described further below. The database can store information related to alleles and gRNAs. As described above, the gRNA identification system aids in identifying gRNAs that are suitable for the editing of one or more alleles of the transplant donor so that the donor alleles can match the alleles of the transplant recipient. At step 2510, the querying module 2420 determines whether the gRNA is suitable for editing one or more mismatched alleles of the transplant donor. If the gRNA is suitable, it is added to a generated list of suitable gRNAs in step 2512. If there are more gRNAs in the database (step 2514), the process iterates and the database is queried with respect to each gRNA in the database to determine whether the gRNA is suitable for the editing of one or more alleles of the transplant donor so that the donor alleles can match the alleles of the transplant recipient. Any suitable gRNAs that are identified are added to the generated list. In some embodiments, multiple gRNAs may be available to edit the mismatched donor allele. In other embodiments, one or no gRNAs may be available to edit the mismatched donor allele. In an example embodiment, if there is more than one mismatched allele, the querying module 2420 first identifies a gRNA that can edit all of the mismatched alleles. Then, the querying module 2420 identifies a gRNA that can edit at least one of the mismatched alleles. In this manner, the gRNA identification system 2400 may be present efficient gRNA options to a user, when one gRNA can be used to edit all of the mismatched alleles, rather than needing multiple gRNAs to edit all of the mismatched alleles. When all suitable gRNAs have been added to the generated list, the ranking module 2430 ranks the list of gRNAs based on certain criteria at step 2516. For example, the gRNAs may be ranked based on their off-target effects, or the lack thereof, on non-targeted alleles. The ranking process is described further below with respect to FIG. 26.

Figure 33:
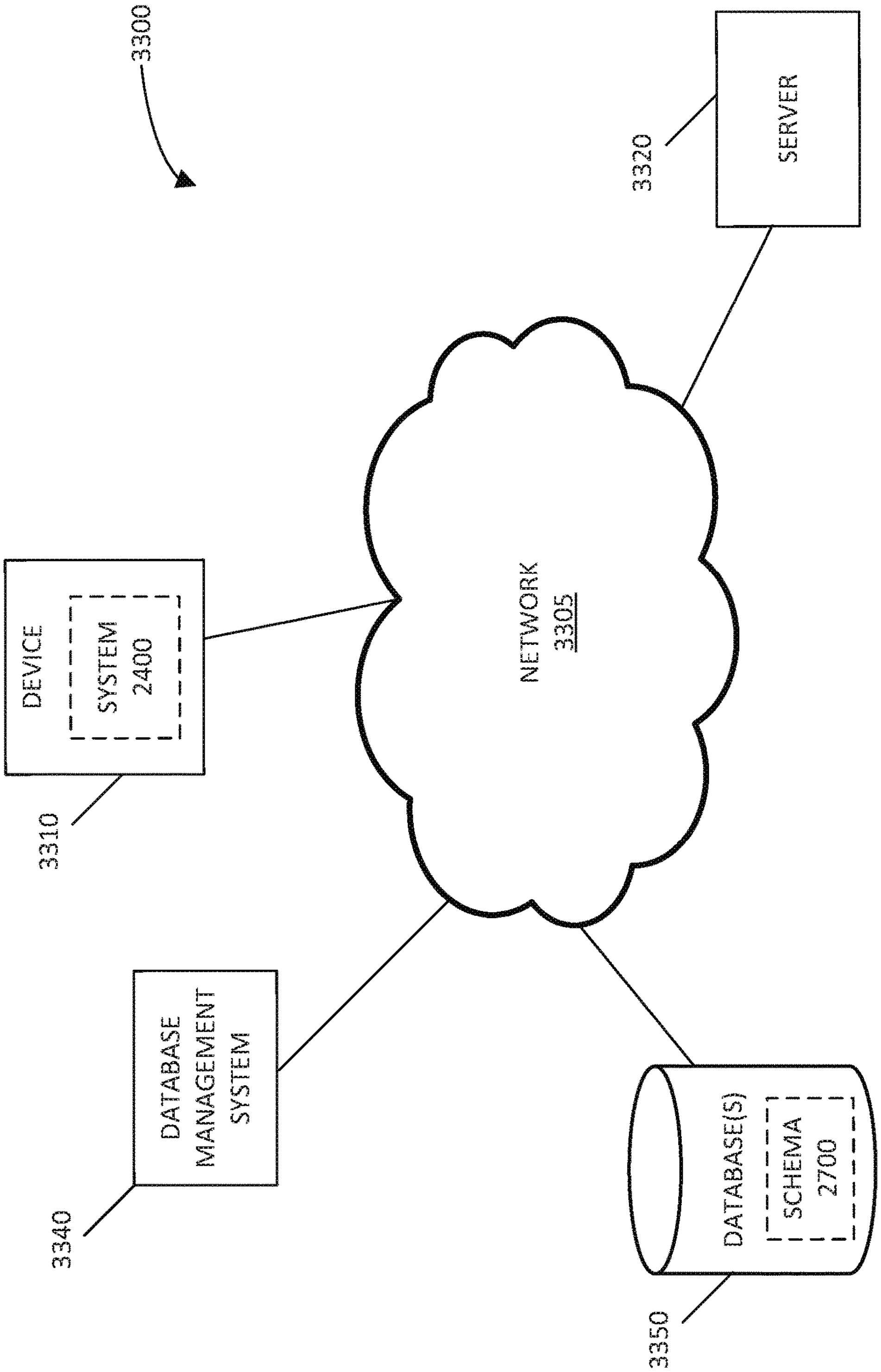
FIG. 33 illustrates a network diagram depicting a system for implementing the gRNA identification system, according to an example embodiment.

At step 2518, the ranked list of suitable gRNAs is displayed to a user via a display device, for example, visual display device 3418 described in relation to FIG. 33. In an example embodiment, the DNA sequence for each of the recipient's alleles is also displayed. In another example embodiment, the occurrence frequency of each of the recipient's alleles (the first group of alleles) within an ancestry is displayed. In another example embodiment, the miHAgs restricted by the recipient's MHC and donor's MHC is displayed.

In a non-limiting example, there may be one (single or singular) mismatched allele between the recipient (first group of alleles) and the donor (second group of alleles). The gRNA identification system, in this case, may identify one gRNA to edit the one mismatched allele. In another non-limiting example, there may be more than one mismatched alleles between the recipient (first group of alleles) and the donor (second group of alleles). The gRNA identification system, in this case, may identify multiple gRNAs to edit the multiple mismatched alleles. In this example, the mismatched alleles may be sequential or nonsequential. In another non-limiting example, there may be more than one mismatched alleles between the recipient (first group of alleles) and the donor (second group of alleles). The gRNA identification system, in this case, may identify one (single or singular) gRNA to edit the multiple mismatched alleles. In this example, the mismatched alleles may be sequential or nonsequential.

Figure 26:
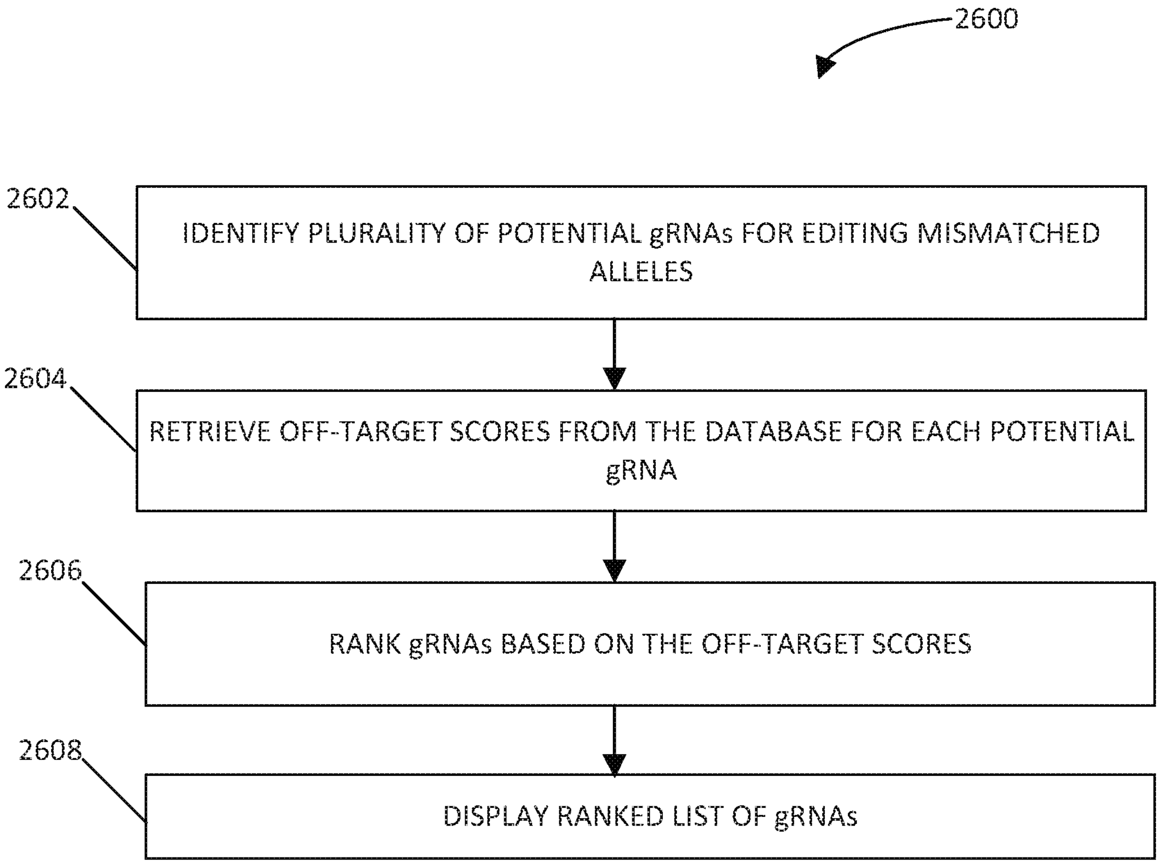
FIG. 26 is a flowchart showing an exemplary method for ranking gRNAs, according to an exemplary embodiment.

FIG. 26 is a flowchart showing an exemplary method 2600 for ranking gRNAs, according to an example embodiment. The method 2600 begins at step 2602 with the gRNA identification system 2400 having identified potential gRNAs suitable for editing mismatched alleles (as described in relation to FIG. 25). At step 2604, the ranking module 2430 retrieves previously determined off-target scores based on mismatch, insertions/deletions (indels), chromatin state, etc. from the database for each potential gRNA. At step 2606, the ranking module 2430 ranks the gRNAs based on the retrieved off-target scores such as mismatch, insertions/deletions (indels), chromatin information, etc. The ranked list of gRNAs is displayed to a user via a display device in step 2608, for example, visual display device 3418 described in relation to FIG. 34.

In an exemplary embodiment, the ranking module 2430 determines an off-target score based on mismatch, insertions/deletions (indels), chromatin information, etc. for each of the gRNAs stored in the database. This score is associated with the gRNA and stored so it can be retrieved during the ranking process. The ranking module 2430 ranks the list of gRNAs based on the off-target score or other factors associated with the gRNA stored in the database. In some embodiments, the off-target score is generated by aligning a gRNA sequence with the human genome, and determining a mismatch between the human genome and the gRNA sequence.

For example, the gRNA identification system can be used to optimize the choice of gRNA within a user's target sequence, to minimize total off-target activity across the genome. In an example embodiment, the algorithm for determining off-target scores allows for variations in protospacer-adjacent motif (PAM) sequences recognized by Cas9, in addition to the number of mismatches. For example, the degeneracy in PAM recognition by Cas9 may be accounted for when determining potential off-target sites. In the case of *S. pyogenes* Cas9, the example algorithm first compiles all the 23-bp DNA sequences composed of 20-bp sequences corresponding to the sgRNA sequence of interest and the 5'-NRG-3' PAM sequences. The example algorithm then compares all the compiled sequences with the query sequence and counts the number of mismatched bases in the 20-bp sgRNA sequence. See Bae S., Park J. & Kim J.-S. Cas-OFFinder: A fast and versatile algorithm that searches for potential off-target sites of Cas9 RNA-guided endonucleases. Bioinformatics 30, 1473-1475 (2014).

In another embodiment, the off-target score may be determined by taking into account chromatin state of the human genome. See cheetah.bioch.virginia.edu/AdliLab/CROP-IT/about.html.

In yet another embodiment, the sequence may be scanned for possible CRISPR guides (e.g., 20 nucleotides followed by a PAM sequence: NGG) and scanned for possible off-target matches throughout the selected genome. For example, the off-target score may be computed by taking into account total number of mismatches, a mismatch absolute position (to accommodate for the relatively high disturbance of mismatches falling close to the PAM site), and mean pairwise distance between mismatches (to account for the steric affect of closely neighboring mismatches in disrupting guide-DNA interaction). See crispr.mit.edu/about.

In another example embodiment, the process for determining the off-target score tests for specificity by using Bowtie 2 (an existing genome indexing program provided by Johns Hopkins University) to map the identified gRNA sequence to the rest of the organisms chromosomal DNA. If the gRNA can be mapped to another sequence, then it has an off-target. In an example embodiment, the off-target score calculation may also take into consideration a number of mismatches allowed in the off-targets in the first 6 bases at the 5' end of the sequence. In yet another example embodiment, the off-target score calculation may also take into account a tolerated edit distance to the target sequence (that is, the number of mismatches and indels allowed in the off-targets). See www.e-crisp.org/E-CRISP/aboutpage.html.

A user can utilize the gRNA identification system described herein to evaluate a partially HLA matched donor for a prospective recipient patient who requires hematopoietic stem cell transplantation. The user can use available bone marrow and cord blood databases to identify potential partially-matched donor or screen individuals biologically related to the transplant recipient. The user may choose a donor from several potential donors with a high number of alleles matching at MHC loci. Donors of similar ethnic ancestries/origins is preferred because persons of different ethnic ancestries/origins have different frequencies of miHAgs that are MHC restricted. If there are several potential donors in the same ancestry, then the user can use the gRNA identification system described herein to find frequencies of MHC, and the donor miHAgs would be sequenced in order to select the donor with the most similar miHAg profiles (for example, ten miHAg loci). If a donor has miHAgs that are restricted by the "corrected" MHC (according to the recipient's MHC), then this donor cannot be selected.

Figure 27A:
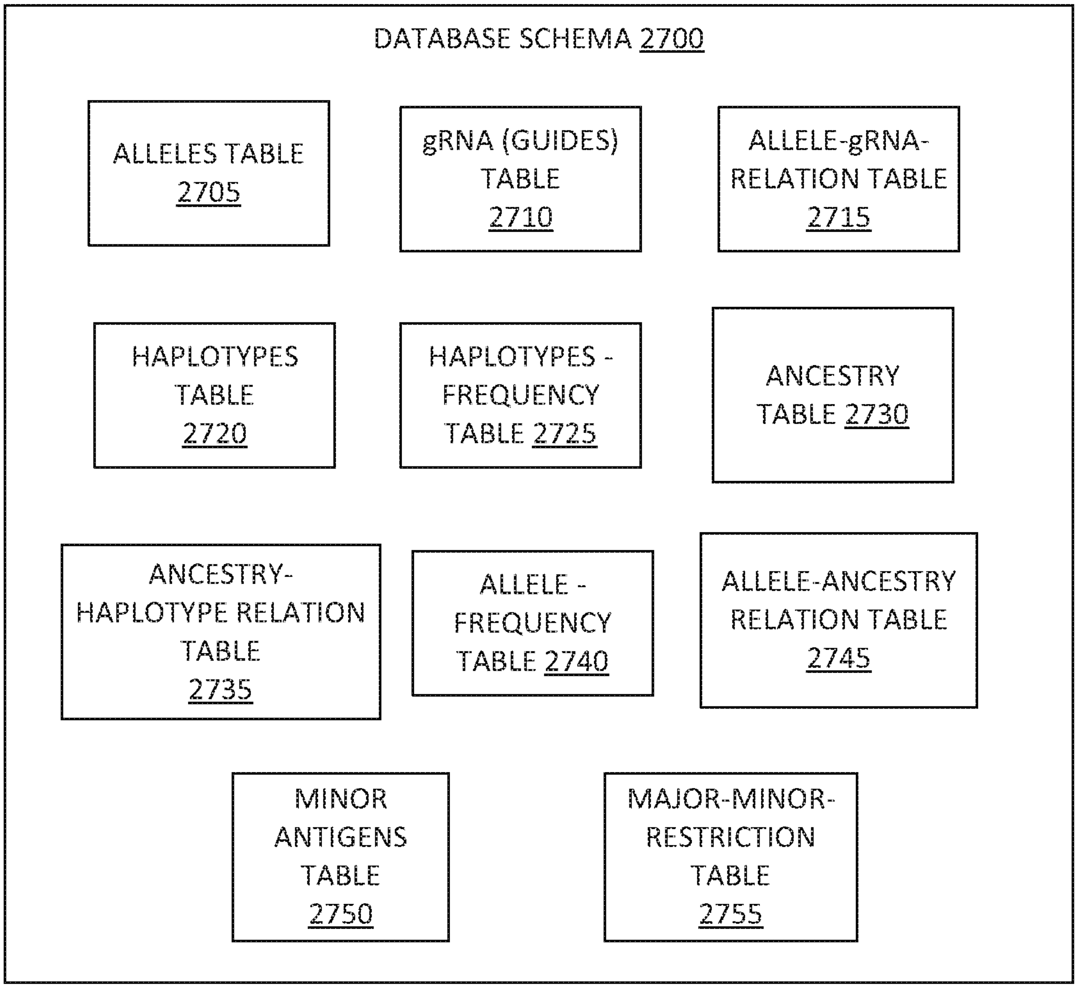
FIG. 27A illustrates an exemplary database schema at a high level for the gRNA identification system, according to an exemplary embodiment.

FIG. 27A illustrates an exemplary database schema 2700 for the gRNA identification system, according to an example embodiment. The exemplary database schema 2700 includes an allele table 2705, a gRNA table 2710, an allele-gRNA-relation table 2715, a haplotype table 2720, a haplotype-frequency table 2725, an ancestry table 2730, an ancestry-haplotype-relation table 2735, an allele-frequency table 2740, and an allele-ancestry-relation table 2745. In some embodiments, the exemplary database schema 2700 also includes a minor-antigens table 2750 and a major-minor-restriction table 2755. Even though the exemplary database schema 2700 is shown as including 11 tables in FIG. 27A, it should be understood that the database schema 2700 can include fewer or more number of tables.

Figure 27B:
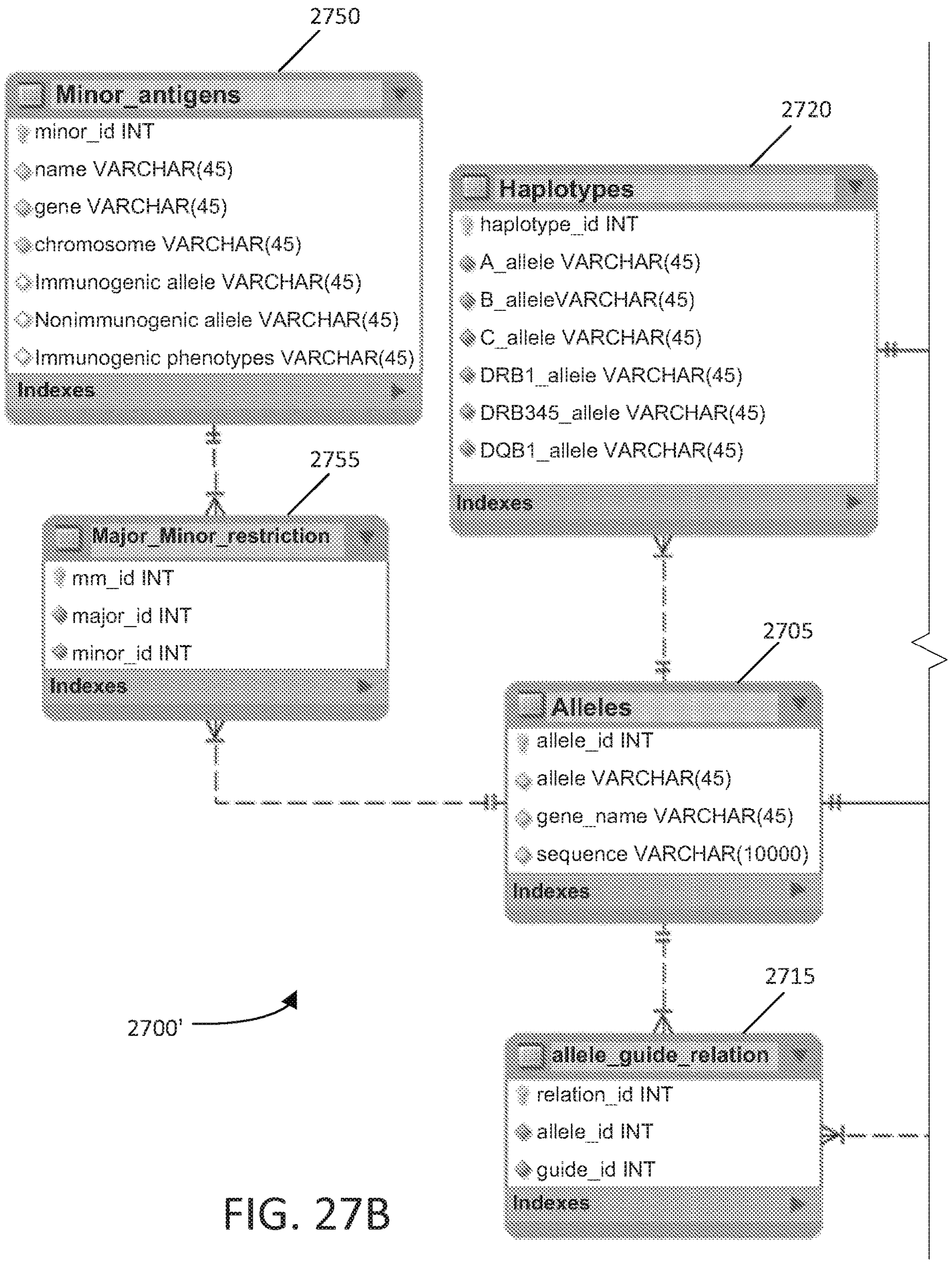
FIG. 27B illustrates an exemplary database schema in detail for the gRNA identification system, according to an exemplary embodiment.
Figure 27C:
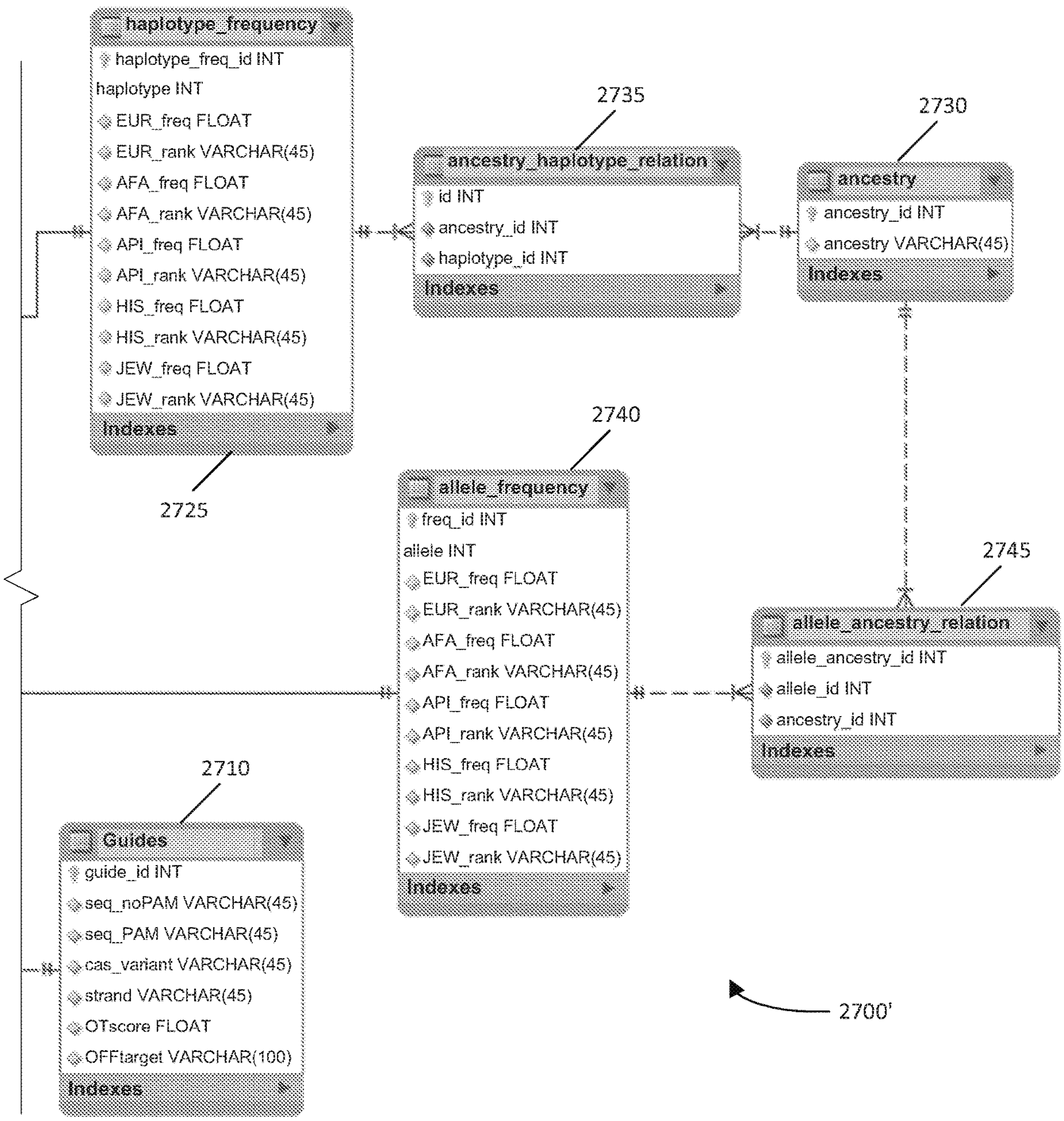
FIG. 27C illustrates an exemplary database schema in detail for the gRNA identification system, according to an exemplary embodiment.

FIGS. 27B and 27C illustrate an exemplary database schema 2700' in detail for the gRNA identification system, according to an example embodiment. The exemplary database schema 2700' is illustrated using MySQL. Each of the tables in the database schema include a key and one or more attributes. The exemplary database schema 2700' includes an allele table 2705, a gRNA table 2710, an allele-gRNA-relation table 2715, a haplotype table 2720, a haplotype-frequency table 2725, an ancestry table 2730, an ancestry-haplotype-relation table 2735, an allele-frequency table 2740, and an allele-ancestry-relation table 2745. In some embodiments, the exemplary database schema 2700 also includes a minor-antigens table 2750 and a major-minor-restriction table 2755. Even though the exemplary database schema 2700 is shown as including 11 tables in FIGS. 27B and 27C, it should be understood that the database schema 2700 can include fewer or more number of tables.

In an example embodiment, the gRNA (Guides) table contains gRNA ID, gRNA target sequence without the Protospacer Adjacent Motif (PAM), gRNA target sequence with the PAM, Cas variant type (some gRNAs are specific for *S. pyogenes* or *S. aureus* and contain the targeting domain length specific for these Cas9 variants), the genomic DNA strand to which the targeting gRNA is directed and binds to (e.g., + or − strand), orthogonality score (weighted sum of off-target hit-score in the human genome), and off-target counts (the number of times that the gRNA targets or hits on other genomic loci not identified as the targeted locus with different number of mismatches or indels). An example allele table contains the following categories and related data: allele ID, allele identifier (HLA nomenclature), gene (locus) name, and allele sequence. An example allele-frequency table contains the frequency record ID, allele identifier, frequencies and rank in the European American (Caucasian), African American, Asian, Hispanic, and Jewish populations as annotated in the NBMP databases (National Marrow Donor Program: bioinformatics.bethematchclinical.org/HLA-Resources/Haplotype-Frequencies/High-Resolution-HLA-Alleles-and-Haplotypes-in-the-US-Population/; bioinformatics.bethematchclinical.org/HLA-Resources/Haplotype-Frequencies/Jewish-High-Resolution-Haplotype-Frequencies/).

The allele table 2705 stores data related to major HLA alleles. In an example embodiment, the allele table 2705 is populated using data from a publicly available HLA allele database (found at hla.alleles.org/alleles/text_index.htm). In some embodiments, the allele table 2705 stores data related HLA allelic variants' sequences. The allele table 2705 includes an allele id key, an allele attribute, a gene name attribute, and an allele sequence attribute.

The gRNA table 2710 stores data related to gRNAs. In some embodiments, the gRNAs are designed to edit an allele as described above. In one embodiment the gRNA table 2710 includes a gRNA id key, a gRNA type attribute, a gRNA sequence with Protospacer Adjacent Motif (PAM) attribute, a gRNA sequence (without PAM) attribute, a strand attribute, an orthogonality score attribute, and an off-target list information attribute.

The allele-gRNA-relation table 2715 stores relationships between records of the allele table 2705 and records of the gRNA table 2710. In the exemplary database schema 2700, the allele table 2705 has a one-to-many relationship with the allele-gRNA-relation table 2715. The gRNA table 2710 has a one-to-many relationship with the allele-gRNA-relation table 2715. In one embodiment the allele-guide-relation table includes a relation id key, an allele id attribute that corresponds to an allele id key of the allele table, a gRNA id attribute that correspond to a gRNA id key of the gRNA table.

The haplotype table 2720 stores data related to haplotypes. A haplotype is a group of genes or alleles that was inherited together from a single parent. The allele table 2705 has a one-to-many relationship with the haplotype table. The haplotype table 2720 includes a haplotype id key, a HLA-A allele attribute, a HLA-B allele attribute, a HLA-C allele attribute, a HLA-DRB1 locus attribute, a HLA-DRB3/DRB4/DRB5 locus attribute, a HLA-DQB1 allele locus attribute.

The haplotype-frequency table 2725 stores data related to frequency of a haplotype occurring within an ancestry. The haplotype table 2720 has a one-to-one relationship with the haplotype-frequency table 2725. In one embodiment, the haplotype-frequency table 2725 includes a haplotype frequency id key, a haplotype id attribute that corresponds to a haplotype id key of the haplotype table 2720, an attribute for frequency of occurrence of a haplotype in European ancestry group, and an attribute for rank of a haplotype occurrence in European ancestry group. The haplotype-frequency table 2725 may also include an attribute for frequency of occurrence of a haplotype in African American ancestry group, an attribute for rank of a haplotype occurrence in African American ancestry group, an attribute for frequency of occurrence of a haplotype in Asian ancestry group, an attribute for rank of a haplotype occurrence in Asian ancestry group, an attribute for frequency of occurrence of a haplotype in Hispanic ancestry group, an attribute for rank of a haplotype occurrence in Hispanic ancestry group, an attribute for frequency of occurrence of a haplotype in Jewish ancestry group, and an attribute for rank of a haplotype occurrence in Jewish ancestry group. The haplotype-frequency table 2725 has an identifying relationship with the haplotype table 2720 and is entirely dependent on the haplotype table 2720.

The ancestry table 2730 stores data related to multiple ethnic ancestries or origins. In an example embodiment, the ancestry table 2730 stores data related to European ancestry group, African American ancestry group, Asian ancestry group. Hispanic ancestry group, and Jewish ancestry group. The ancestry origin table 2730 may include an ancestry id key, and an ancestry name attribute.

The ancestry-haplotype-relation table 2735 stores relationships between records of the haplotype-frequency table 2725 and records of the ancestry table 2730. The haplotype-frequency table 2725 has a one-to-many relationship with the ancestry-haplotype-relation table 2735. The ancestry table 2730 has a one-to-many relationship with the ancestry-haplotype-relation table 2735. In one embodiment, the ancestry-haplotype-relation table 2735 includes an id key, an ancestry id attribute that corresponds to the ancestry id key of the ancestry table 2730, and a haplotype id attribute that corresponds to a haplotype id key of the haplotype-frequency table 2725.

The allele-frequency table 2740 stores data related to frequency of an allele occurring within an ancestry. The allele table 2705 has a one-to-one relationship with the allele frequency table. In one embodiment, the allele-frequency table 2740 includes an allele frequency id key, an allele attribute corresponds to an allele ID of the allele table, an attribute for frequency of occurrence of an allele in European ancestry group, an attribute for rank of an allele occurrence in European ancestry group, an attribute for frequency of occurrence of an allele in African American ancestry group, an attribute for rank of an allele occurrence in African American ancestry group, an attribute for frequency of occurrence of an allele in Asian ancestry group, an attribute for rank of an allele occurrence in Asian ancestry group, an attribute for frequency of occurrence of an allele in Hispanic ancestry group, an attribute for rank of an allele occurrence in Hispanic ancestry group, an attribute for frequency of occurrence of an allele in Jewish ancestry group, and an attribute for rank of an allele occurrence in Jewish ancestry group. The allele-frequency table 2740 has an identifying relationship with the allele table 2705 and is entirely dependent on the allele table 2705.

The allele-ancestry-relation table 2745 stores relationships between records of the allele-frequency table 2740 and records of the ancestry table 2730. The allele-frequency table 2740 has a one-to-many relationship with the allele-ancestry-relation table 2745. The ancestry table 2730 has a one-to-many relationship with the allele-ancestry-relation table 2745. In one embodiment the allele-ancestry-relation table 2745 includes an allele-ancestry id key, an allele id attribute that corresponds to the allele id key of the allele-frequency table 2740, and an ancestry id attribute that correspond to the ancestry id key of the ancestry table 2730.

The minor-antigens table 2750 stores data related to minor histocompatibility antigens (miHAgs). In one embodiment the minor-antigens tables 2750 includes a miHAgs id key, a miHAg name attribute, a miHAg gene attribute, a chromosome attribute, an Immunogenic allele attribute, an Nonimmunogenic allele attribute, and an Immunogenic phenotypes attribute.

The major-minor-restriction table 2755 stores data related to HLA restrictions to miHAgs. The minor-antigen table 2750 has a one-to-many relationship to the major-minor-restriction table 2755. The allele table 2705 has a one-to-many relationship with the major-minor-restriction table 2755. In one embodiment the major-minor-restriction table 2755 includes a major-minor id key, a major id attribute that corresponds to the allele id key of the allele table 2705, and a minor id attribute that corresponds to the miHAg id key of the minor-antigens table 2750.

Even though each of the tables 2705, 2710, 2715, 2720, 2725, 2730, 2735, 2740, 2745, 2750, and 2755 is described as having a particular key and particular attributes, it should be understood that each of the tables may be configured to have a different key or different number of keys, and/or different attributes or different number of attributes.

Tables 1-12 show exemplary data that may be stored in one or more tables of the database schema 2700 or 2700' described in connection with FIGS. 27A, 27B, 27C, for example, the haplotype table 2720 and/or the haplotype frequency table 2725.

Figure 28A:
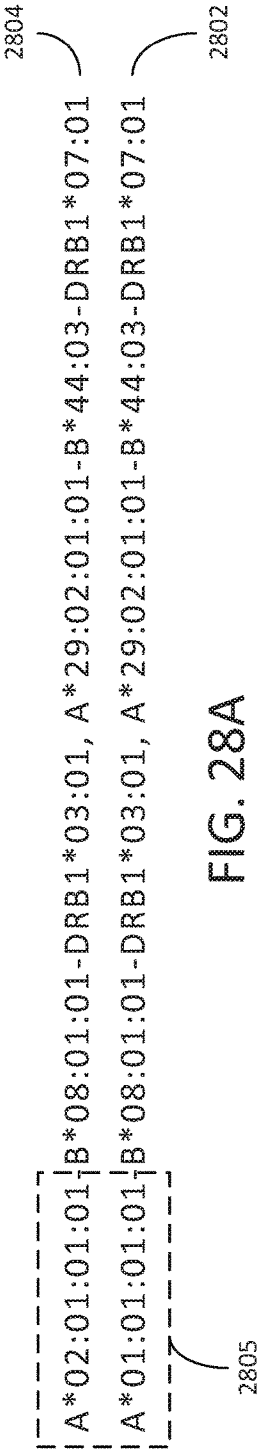
FIG. 28A illustrates an exemplary allele inputs to the gRNA identification system, according to an exemplary embodiment.

FIG. 28A illustrates an exemplary allele input to the gRNA identification system, according to an example embodiment. The first group of alleles, that is, the alleles of the targeted transplant recipient, may be alleles 2802. The second group of alleles, that is, the alleles of the targeted transplant donor, may be alleles 2804. As can be seen in FIG. 28A, a mismatch between the alleles 2802 and alleles 2804 exists, which is shown by box 2805. As shown, the donor allele A*02:01:01:01 does not match the recipient allele A*01:01:01:01. The gRNA identification system can be used to identify gRNAs that can edit this mismatched donor allele to match it to the recipient allele. This example input/scenario may be referred to as "knocking out a single allele." As described above, the gRNA identification system may identify one gRNA for knocking out the single allele.

Figure 28B:
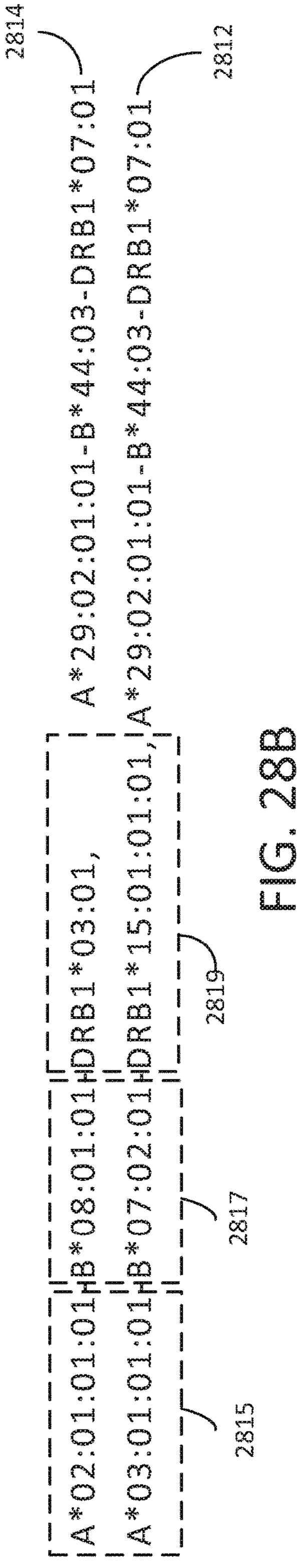
FIG. 28B illustrates an exemplary allele inputs to the gRNA identification system, according to an exemplary embodiment.

FIG. 28B illustrates an exemplary allele input to the gRNA identification system, according to an example embodiment. In this example, the first group of alleles, that is the alleles of the recipient, may be alleles 2812. The second group of alleles, that is, the alleles of the targeted transplant donor, may be alleles 2814. As can be seen in FIG. 28B, multiple mismatches between the alleles 2802 and alleles 2804 exist, which are shown by boxes 2815, 2817, and 2819. As shown, the donor alleles A*02:01:01:01-B*08:01:01-DRB1*03:01 do not match the recipient alleles A*03:01:01:01-B*07:02:01-DRB1*15:01:01:01. The gRNA identification system can be used to identify gRNAs that can edit these mismatched donor alleles to match it to the recipient alleles. This example input/scenario may be referred to as "knocking out multiple alleles." As described above, the gRNA identification system may identify a single gRNA or multiple gRNAs for knocking out multiple alleles.

Figure 28C:
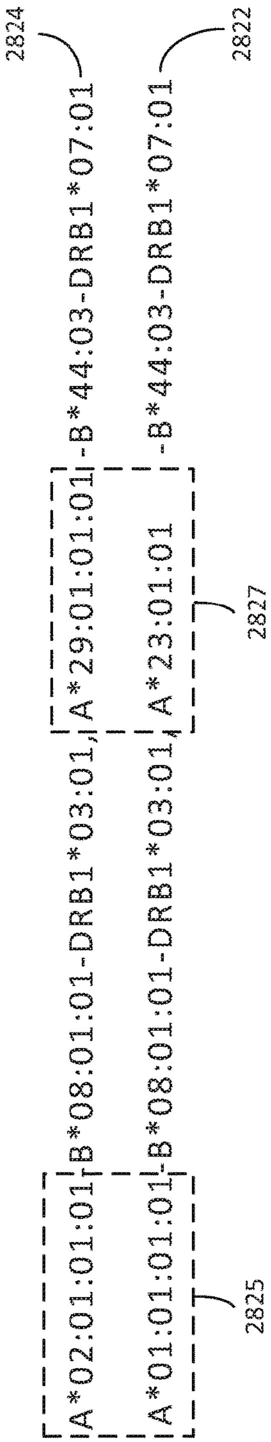
FIG. 28C illustrates an exemplary allele inputs to the gRNA identification system, according to an exemplary embodiment.

FIG. 28C illustrates an exemplary allele input to the gRNA identification system, according to an example embodiment. In this example, the first group of alleles, that is the alleles of the recipient, may be alleles 2822. The second group of alleles, that is, the alleles of the targeted transplant donor, may be alleles 2824. As can be seen in FIG. 28C, multiple mismatches between the alleles 2802 and alleles 2804 exist, which are shown by boxes 2825 and 2827. As shown, the donor alleles A*02:01:01:01 and A*29:02:01:01 do not match the recipient alleles A*01:01:01:01 and A*23:01:01. The gRNA identification system can be used to identify gRNAs that can edit these mismatched donor alleles to match it to the recipient alleles. This example input/scenario may be referred to as "biallelic disruption." As described above, the gRNA identification system may be used to identify a single gRNA or multiple gRNAs for biallelic disruption.

In this manner, the gRNA identification system is capable of receiving donor alleles and recipient alleles that have a singular mismatched allele (FIG. 28A), multiple sequential mismatched alleles (FIG. 28B), or multiple nonsequential mismatched alleles (FIG. 28C).

FIG. 29 illustrates an exemplary query or input 2900 for the gRNA identification system, and an exemplary gRNA list 2950 as an output of the gRNA identification system, according to an example embodiment. As described above, a user may input or enter a query including a group of alleles for a donor and a group of alleles for a recipient/patient. As described above, the gRNA identification system outputs a list of gRNAs that are suitable for editing one or more mismatched alleles of the donor alleles. As shown in FIG. 29, the user enters query 2900, and the gRNA identification system generates gRNA list 2950 as the output. Based on the query, the gRNA identification system targets the mismatched alleles and excludes the matched alleles when determining suitable gRNAs for gene editing. In this example, the gRNA identification system targets A*02:01:01:01 and A*29:02:01:01 as they are the mismatched alleles between the donor and the patient, and the alleles B*08:01:01, DRB1*03:01:01:01. B*44:03:01 and DRB1*07:01:01:01 are excluded since they match between the donor and the patient alleles. As shown in FIG. 29, an off-target score (2910) is displayed for each of the gRNAs, and the list is ranked based on the off-target score. The gRNA sequence (2905) is also displayed. In addition, the type of Cas9 molecule to be used with each gRNA is displayed as "type" (2915). "sa" refers to a Cas9 molecule from *S. aureus*, and "spy" refers to a Cas9 molecule from *S. pyogenes*. The strand to which each listed gRNA binds is also displayed as − strand or + strand (2920).

As described above, the gRNA identification system may provide other outputs in addition to a list of gRNAs suitable for editing mismatched alleles. FIG. 30 illustrates an exemplary table 3000 showing allele sequences as an output of the gRNA identification system, according to an example embodiment. The allele sequence may be of the one or more alleles of the recipient or the donor or both.

FIG. 31A illustrates an exemplary table 3100 showing haplotype frequency as an output of the gRNA identification system, according to an example embodiment. The haplotype frequency of occurrence is shown based on ancestry. FIG. 31B illustrates an exemplary table 3150 showing allele frequency as an output of the gRNA identification system, according to an example embodiment. The allele frequency of occurrence is shown based on ancestry. FIG. 32 illustrates an exemplary table 3200 showing minor histocompatibility antigens (miHAgs) restriction in view of major histocompatibility complex (MHC) as an output of the gRNA identification system.

In an exemplary use of the database and the gRNA identification system, a user may enter a query with limited HLA genotype information of a donor. For example, the limited HLA genotype information may include information for the allele group and the specific HLA protein. In another example, the limited HLA genotype information may include information for the allele group, the specific HLA protein, and the synonymous DNA substitution within the coding region. In the limited HLA genotype information, the user may not include information showing the differences in a non-coding region.

If such limited HLA genotype information is provided in a query to the database, the gRNA identification system may provide as search results sequences of all subtypes of target alleles for further research such as alignment. In another example, the gRNA identification system may provide as search results number or percentage of subtypes of a target allele that have on-target or off-target sites for a specific guide, which may indicate how likely this gRNA may edit the unknown target HLA subtype in a donor. In yet another example, the gRNA identification system may provide as search results number or percentage of subtypes of an excluded allele that has on-target or off-target sites for a specific gRNA, that may indicate how likely this gRNA may have off-target effect in unknown excluded HLA subtype in the donor.

FIG. 33 illustrates a network diagram depicting a system 3300 for implementing the gRNA identification system, according to an example embodiment. The system 3300 can include a network 3305, device 3310, server 3320, database management system 3340, and database(s) 3350. Each of components 3310, 3320, 3340, and 3350 is in communication with the network 3305.

In an example embodiment, one or more portions of network 3305 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

The device 3310 may comprise, but is not limited to, work stations, computers, general purpose computers, Internet appliances, hand-held devices, wireless devices, portable devices, wearable computers, cellular or mobile phones, portable digital assistants (PDAs), smart phones, tablets, ultrabooks, netbooks, laptops, desktops, multi-processor systems, microprocessor-based or programmable consumer electronics, mini-computers, and the like. The device 3310 can include one or more components described in relation to computing device 3400 shown in FIG. 34.

The device 3310 may connect to network 3305 via a wired or wireless connection. The device 3310 may include one or more applications or software systems such as, but not limited to, a web browser application, a database management system, and a gRNA identification system described herein.

In an example embodiment, the device 3310 may perform all the functionalities described herein. In other embodiments, the gRNA identification system may be included on the device 3310, and the server 3320 performs the functionalities described herein. In yet another embodiment, the device 3310 may perform some of the functionalities, and the server 3320 performs the other functionalities described herein.

Each of the server 3320, database management system 3340, and the database(s) 3350 is connected to the network 3305 via a wired connection. Alternatively, one or more of the server 3320, database management system 3340, and the database(s) 3350 may be connected to the network 3305 via a wireless connection. The server 3320 comprises one or more computers or processors configured to communicate with the device 3310, database management system 3340, and database(s) 3350 via network 3305. The server 3320 hosts one or more applications or websites accessed by the device 3310 and/or facilitates access to the content of database(s) 3350. The database management system 3340 comprises one or more computers or processors configured to facilitate access to the content of databases(s) 3350. Database(s) 3350 comprise one or more storage devices for storing data and/or instructions (or code) for use by the device 3310 or the server 3320. Database(s) 3350 may also store data according to the database schema 2700 or 2700' described in connection with FIGS. 27A, 27B, and 27C. The database management system 3340, the database(s) 3350, and/or the server 3320, may be located at one or more geographically distributed locations from each other or from the device 3310. Alternatively, the database(s) 3350 may be included within the server 3320.

Figure 34:
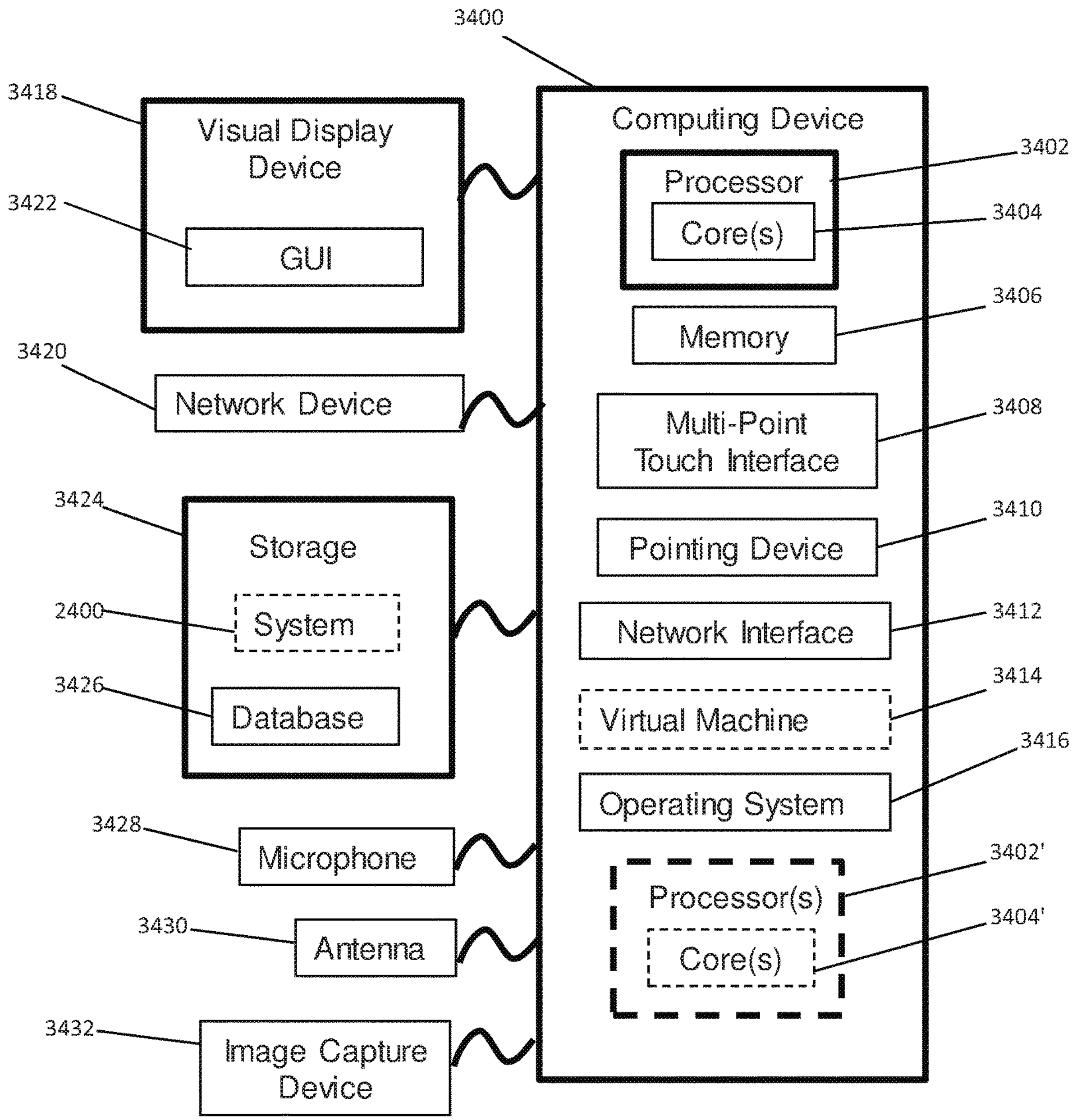
FIG. 34 is a block diagram of an exemplary computing device that can be used to implement exemplary embodiments of the gRNA identification system described herein.

FIG. 34 is a block diagram of an exemplary computing device 3400 that may be used to implement exemplary embodiments of the gRNA identification system 2400 described herein. The computing device 3400 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 3406 included in the computing device 3400 may store computer-readable and computer-executable instructions or software for implementing exemplary embodiments of the gRNA identification system 2400. The computing device 3400 also includes configurable and/or programmable processor 3402 and associated core 3404, and optionally, one or more additional configurable and/or programmable processor(s) 3402' and associated core(s) 3404' (for example, in the case of computer systems having multiple processors/cores), for executing computer-readable and computer-executable instructions or software stored in the memory 3406 and other programs for controlling system hardware. Processor 3402 and processor(s) 3402' may each be a single core processor or multiple core (3404 and 3404') processor.

Virtualization may be employed in the computing device 3400 so that infrastructure and resources in the computing device may be shared dynamically. A virtual machine 3414 may be provided to handle a process running on multiple processors so that the process appears to be using only one computing resource rather than multiple computing resources. Multiple virtual machines may also be used with one processor.

Memory 3406 may include a computer system memory or random access memory, such as DRAM, SRAM, EDO RAM, and the like. Memory 3406 may include other types of memory as well, or combinations thereof.

A user may interact with the computing device 3400 through a visual display device 3418, such as a computer monitor, which may display one or more graphical user interfaces 3422 that may be provided in accordance with exemplary embodiments. The computing device 3400 may include other I/O devices for receiving input from a user, for example, a keyboard or any suitable multi-point touch interface 3408, a pointing device 3410 (e.g., a mouse), a microphone 3428, and/or an image capturing device 3432 (e.g., a camera or scanner). The multi-point touch interface 3408 (e.g., keyboard, pin pad, scanner, touch-screen, etc.) and the pointing device 3410 (e.g., mouse, stylus pen, etc.) may be coupled to the visual display device 3418. The computing device 3400 may include other suitable conventional I/O peripherals.

The computing device 3400 may also include one or more storage devices 3424, such as a hard-drive, CD-ROM, or other computer readable media, for storing data and computer-readable instructions and/or software that implement exemplary embodiments of the gRNA identification system 2400 described herein. Exemplary storage device 3424 may also store one or more databases for storing any suitable information required to implement exemplary embodiments. For example, exemplary storage device 3424 can store one or more databases 3426 for storing information, such as allele sequences, gRNA sequences, haplotypes, ancestry information, miHAgs information, MHC information off-target scores, and/or any other information to be used by embodiments of the system 2400 and database schemas 2700, 2700'. The databases may be updated manually or automatically at any suitable time to add, delete, and/or update one or more items in the databases.

The computing device 3400 can include a network interface 3412 configured to interface via one or more network devices 3420 with one or more networks, for example, Local Area Network (LAN). Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing device 3400 can include one or more antennas 3430 to facilitate wireless communication (e.g., via the network interface) between the computing device 3400 and a network. The network interface 3412 may include a built-in network adapter, network interface card, PCMCIA network card, card bus network adapter, wireless network adapter. USB network adapter, modem or any other device suitable for interfacing the computing device 3400 to any type of network capable of communication and performing the operations described herein. Moreover, the computing device 3400 may be any computer system, such as a workstation, desktop computer, server, laptop, handheld computer, tablet computer (e.g., the iPad™ tablet computer), mobile computing or communication device (e.g., the iPhone™ communication device), point-of sale terminal, internal corporate devices, or other form of computing or telecommunications device that is capable of communication and that has sufficient processor power and memory capacity to perform the operations described herein.

The computing device 3400 may run any operating system 3416, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 3416 may be run in native mode or emulated mode. In an exemplary embodiment, the operating system 3416 may be run on one or more cloud machine instances.

The following description is presented to enable any person skilled in the art to create and use a computer system configuration and related method and article of manufacture to identify gRNAs for alleles. While the database schema described herein is exemplified for identifying gRNAs for use with a CRISPR/Cas9 molecule, it will be readily apparent to any person skilled in the art that the database schema and gRNA identification methods described herein may be used to identify and select sequences that can be used with other nucleases (e.g., TALEN, Cpf1, and zinc finger nucleases). Various modifications to the example embodiments will be readily apparent to those skilled in the art, and the generic principles defined herein may be applied to other embodiments and applications without departing from the spirit and scope of the invention. Moreover, in the following description, numerous details are set forth for the purpose of explanation. However, one of ordinary skill in the art will realize that the invention may be practiced without the use of these specific details. In other instances, well-known structures and processes are shown in block diagram form in order not to obscure the description of the invention with unnecessary detail. Thus, the present disclosure is not intended to be limited to the embodiments shown, but is to be accorded the widest scope consistent with the principles and features disclosed herein.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components or method steps, those elements, components or steps may be replaced with a single element, component or step. Likewise, a single element, component or step may be replaced with multiple elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other embodiments, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

EXAMPLES

The following Examples are merely illustrative and are not intended to limit the scope or content of the invention in any way.

Example 1: Cloning and Initial Screening of gRNAs

The suitability of candidate gRNAs can be evaluated as described in this example. Although described for a chimeric gRNA, the approach can also be used to evaluate modular gRNAs.

Cloning gRNAs into Vectors

For each gRNA, a pair of overlapping oligonucleotides is designed and obtained. Oligonucleotides are annealed and ligated into a digested vector backbone containing an upstream U6 promoter and the remaining sequence of a long chimeric gRNA. Plasmid is sequence-verified and prepped to generate sufficient amounts of transfection-quality DNA. Alternate promoters may be used to drive in vivo transcription (e.g. H1 promoter) or for in vitro transcription (e.g., a T7 promoter).

Cloning gRNAs in Linear dsDNA Molecule (STITCHR)

For each gRNA, a single oligonucleotide is designed and obtained. The U6 promoter and the gRNA scaffold (e.g. including everything except the targeting domain, e.g., including sequences derived from the crRNA and tracrRNA, e.g., including a first complementarity domain; a linking domain; a second complementarity domain; a proximal domain; and a tail domain) are separately PCR amplified and purified as dsDNA molecules. The gRNA-specific oligonucleotide is used in a PCR reaction to stitch together the U6 and the gRNA scaffold, linked by the targeting domain specified in the oligonucleotide. Resulting dsDNA molecule (STITCHR product) is purified for transfection. Alternate promoters may be used to drive in vivo transcription (e.g., H1 promoter) or for in vitro transcription (e.g., T7 promoter). Any gRNA scaffold may be used to create gRNAs compatible with Cas9s from any bacterial species.

Initial gRNA Screen

Each gRNA to be tested is transfected, along with a plasmid expressing Cas9 and a small amount of a GFP-expressing plasmid into human cells. In preliminary experiments, these cells can be immortalized human cell lines such as 293T, K562, or U2OS. Alternatively, primary human cells may be used. In this case, cells may be relevant to the eventual therapeutic cell target (for example, an erythroid cell). The use of primary cells similar to the potential therapeutic target cell population may provide important information on gene targeting rates in the context of endogenous chromatin and gene expression.

Transfection may be performed using lipid transfection (such as Lipofectamine or Fugene) or by electroporation (such as Lonza Nucleofection™). Following transfection, GFP expression can be determined either by fluorescence microscopy or by flow cytometry to confirm consistent and high levels of transfection. These preliminary transfections can comprise different gRNAs and different targeting approaches (17-mers, 20-mers, nuclease, dual-nickase, etc.) to determine which gRNAs/combinations of gRNAs give the greatest activity.

Efficiency of cleavage with each gRNA may be assessed by measuring NHEJ-induced indel formation at the target locus by a T7E1-type assay or by sequencing. Alternatively, other mismatch-sensitive enzymes, such as Cell/Surveyor nuclease, may also be used.

For the T7E1 assay, PCR amplicons are approximately 500-700 bp with the intended cut site placed asymmetrically in the amplicon. Following amplification, purification and size-verification of PCR products, DNA is denatured and re-hybridized by heating to 95° C. and then slowly cooling. Hybridized PCR products are then digested with T7 Endonuclease I (or other mismatch-sensitive enzyme) that recognizes and cleaves non-perfectly matched DNA. If indels are present in the original template DNA, when the amplicons are denatured and re-annealed, this results in the hybridization of DNA strands harboring different indels and therefore lead to double-stranded DNA that is not perfectly matched. Digestion products may be visualized by gel electrophoresis or by capillary electrophoresis. The fraction of DNA that is cleaved (density of cleavage products divided by the density of cleaved and uncleaved) may be used to estimate a percent NHEJ using the following equation: %

NHEJ=(1−(1−fraction cleaved)$^{1/2}$). The T7E1 assay is sensitive down to about 2-5% NHEJ.

Sequencing may be used instead of, or in addition to, the T7E1 assay. For Sanger sequencing, purified PCR amplicons are cloned into a plasmid backbone, transformed, miniprepped and sequenced with a single primer. Sanger sequencing may be used for determining the exact nature of indels after determining the NHEJ rate by T7E1.

Sequencing may also be performed using next generation sequencing techniques. When using next generation sequencing, amplicons may be 300-500 bp with the intended cut site placed asymmetrically. Following PCR, next generation sequencing adapters and barcodes (for example illumina multiplex adapters and indexes) may be added to the ends of the amplicon, e.g., for use in high throughput sequencing (for example on an Illumina MiSeq). This method allows for detection of very low NHEJ rates.

Example 2: Assessment of Gene Targeting by NHEJ

The gRNAs that induce the greatest levels of NHEJ in initial tests can be selected for further evaluation of gene targeting efficiency. In this case, cells are derived from disease subjects and, therefore, harbor the relevant mutation.

Following transfection (usually 2-3 days post-transfection) genomic DNA may be isolated from a bulk population of transfected cells and PCR may be used to amplify the target region. Following PCR, gene targeting efficiency to generate the desired mutations (either knockout of a target gene or removal of a target sequence motif) may be determined by sequencing. For Sanger sequencing, PCR amplicons may be 500-700 bp long. For next generation sequencing, PCR amplicons may be 300-500 bp long. If the goal is to knockout gene function, sequencing may be used to assess what percent of alleles have undergone NHEJ-induced indels that result in a frameshift or large deletion or insertion that would be expected to destroy gene function. If the goal is to remove a specific sequence motif, sequencing may be used to assess what percent of alleles have undergone NHEJ-induced deletions that span this sequence.

Example 3: Assessment of Gene Targeting by HDR

The gRNAs that induce the greatest levels of NHEJ in initial tests can be selected for further evaluation of gene targeting efficiency. In this case, cells are derived from disease subjects and, therefore, harbor the relevant mutation.

Following transfection (usually 2-3 days post-transfection) genomic DNA may be isolated from a bulk population of transfected cells and PCR may be used to amplify the target region. Following PCR, gene targeting efficiency can be determined by several methods.

Determination of gene targeting frequency involves measuring the percentage of alleles that have undergone homologous directed repair (HDR) with the exogenously provided donor template or endogenous genomic donor sequence and which therefore have incorporated the desired correction. If the desired HDR event creates or destroys a restriction enzyme site, the frequency of gene targeting may be determined by a RFLP assay. If no restriction site is created or destroyed, sequencing may be used to determine gene targeting frequency. If a RFLP assay is used, sequencing may still be used to verify the desired HDR event and ensure that no other mutations are present. If an exogenously provided donor template is employed, at least one of the primers is placed in the endogenous gene sequence outside of the region included in the homology arms, which prevents amplification of donor template still present in the cells. Therefore, the length of the homology arms present in the donor template may affect the length of the PCR amplicon. PCR amplicons can either span the entire donor region (both primers placed outside the homology arms) or they can span only part of the donor region and a single junction between donor and endogenous DNA (one internal and one external primer). If the amplicons span less than the entire donor region, two different PCRs should be used to amplify, and sequence both the 5' and the 3' junction.

If the PCR amplicon is short (less than 600 bp) it is possible to use next generation sequencing. Following PCR, next generation sequencing adapters and barcodes (for example Illumina multiplex adapters and indexes) may be added to the ends of the amplicon, e.g., for use in high throughput sequencing (for example on an Illumina MiSeq). This method allows for detection of very low gene targeting rates.

If the PCR amplicon is too long for next generation sequencing, Sanger sequencing can be performed. For Sanger sequencing, purified PCR amplicons will be cloned into a plasmid backbone (for example, TOPO cloned using the LifeTech Zero Blunt® TOPO® cloning kit), transformed, miniprepped and sequenced.

The same or similar assays described above can be used to measure the percentage of alleles that have undergone HDR with endogenous genomic donor sequence and which therefore have incorporated the desired correction.

Example 4: Testing *S. aureus* Cas9 gRNAs Targeted to the CCR5 Locus

Transplantation of autologous CD34$^+$ hematopoietic stem/progenitor cells (HSPCs) that have been genetically modified to prevent expression of the wild-type CCR5 gene product prevents entry of the HIV virus HSPC progeny that are normally susceptible to HIV infection (e.g., macrophages and CD4 T-lymphocytes). Clinically, transplantation of HSPCs that contain a genetic mutation in the coding sequence for the CCR5 chemokine receptor has been shown to control HIV infection long-term (Hütter et. al, New England Journal Of Medicine, 2009; 360(7):692-698). Genome editing with the CRISPR/Cas9 platform precisely alters endogenous gene targets, e.g., by creating an indel at the targeted cut site that can lead to inhibition of gene expression at the edited locus. In this Example, genome editing with eleven *S. aureus* Cas9 gRNAs that were selected (Table 23) based on the criterion described in Section II (Methods for Designing gRNAs).

Figure 8:
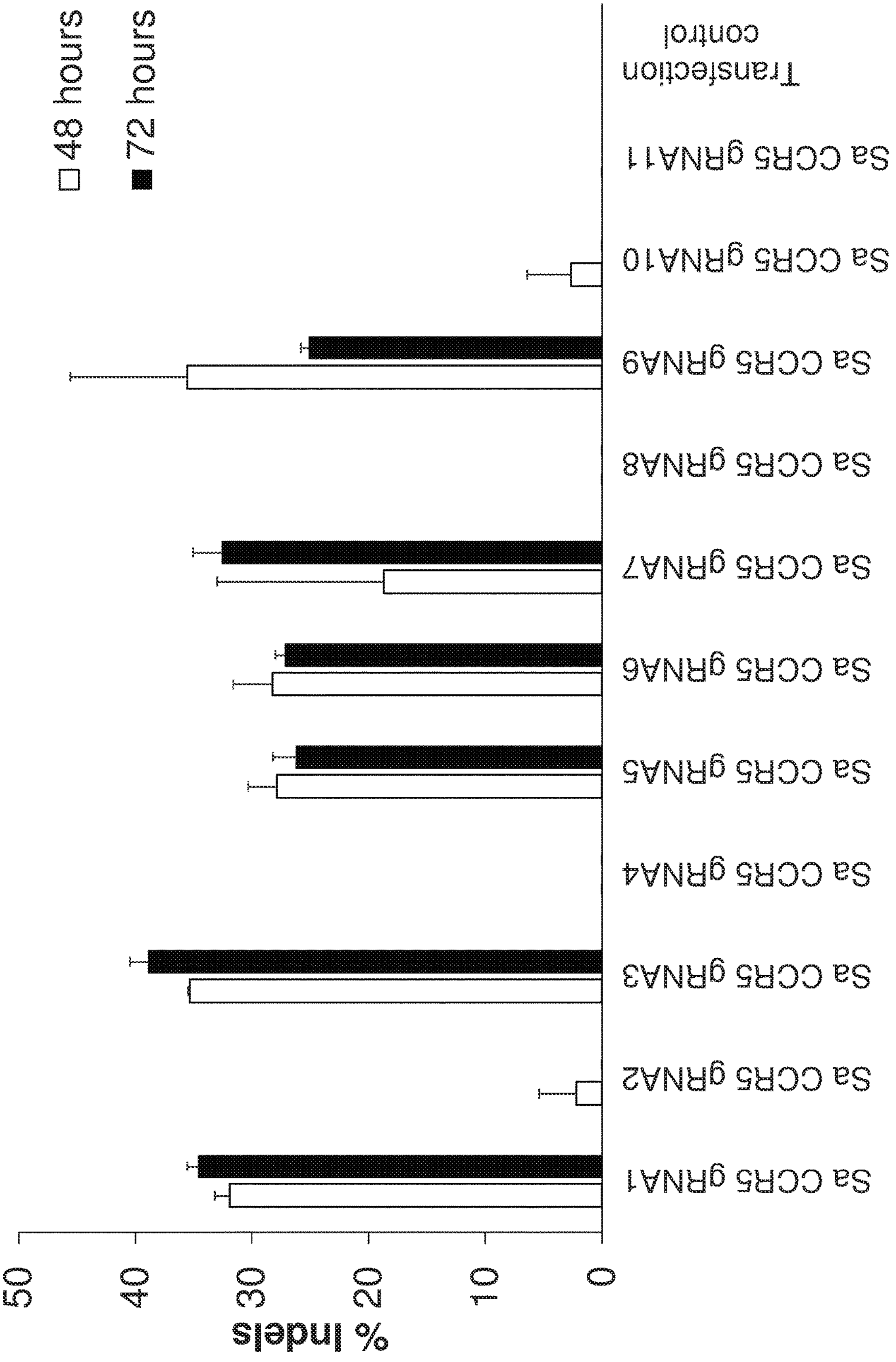
FIG. 8 depicts the detection of indels at the CCR5 locus after delivery of *S. aureus* gRNA and *S. aureus* Cas9.

Human 293FT cells (Life Technologies) were transfected (Lipofectamine™, per the manufacturer's instructions) with plasmid DNA encoding *S. aureus* Cas9 and oligonucleotides encoding different *S. aureus* gRNAs that are transcribed in the target cells from the U6 promoter. Genomic DNA was isolated at 48 and 72 hour time points relative to transfection, CCR5 locus PCRs performed on gDNA, and the indels were analysis by T7E1 endonuclease assay. Values shown are the mean+/−s.d, of 2 technical replicates (FIG. 8). In order to detect indels at the CCR5 locus, T7E1 assays were performed on CCR5 locus-specific PCR products that were amplified from genomic DNA samples from transfected and then percentage of indels detected at the CCR5 locus was calculated. Up to 40% indels were detected in cells that contacted the *S. aureus* CCR5 gRNAs and *S. aureus* Cas9 plasmid DNA.

TABLE 23

| S. aureus gRNA Name Designation | S. aureus gRNA Target Sequence | SEQ ID NO |
|---|---|---|
| CCR5_Sa1 | GCC UAU AAA AUA GAG CCC UGU C | 351 |
| CCR5_Sa2 | AUA CAG UCA GUA UCA AUU CUG G | 352 |
| CCR5_Sa3 | GUG GUG ACA AGU GUG AUC AC | 353 |
| CCR5_Sa4 | CCA UAC AGU CAG UAU CAA UUC UGG | 354 |
| CCR5_Sa5 | AAG CCU AUA AAA UAG AGC CCU GUC | 355 |
| CCR5_Sa6 | UGG GGU GGU GAC AAG UGU GAU CAC | 356 |
| CCR5_Sa7 | GGG UGG UGA CAA GUG UGA UCA C | 357 |
| CCR5_Sa8 | GGU GAC AAG UGU GAU CAC | 358 |
| CCR5_Sa9 | GCC UUU UGC AGU UUA UCA GGA U | 359 |
| CCR5_Sa10 | GCU CUA UUU UAU AGG CUU CUU CUC | 360 |
| CCR5_Sa11 | GCU CUU CAG CCU UUU GCA GUU UAU | 361 |

*S. aureus* Cas9 gRNA target sequences

Example 5: Modification of gRNA by Addition of 5' Cap and 3' Poly-A Tail Increases Genome Editing at Target Genetic Loci and Improves CD34$^+$ Cell Viability and Survival During virus-host co-evolution, viral RNA capping that mimics capping of mRNA evolved to allow viral RNA to escape detection from the cell's innate immune system (Delcroy et al., 2012, Nature Reviews Microbiology, 10:51-45). Toll-like receptors in hematopoietic stem/progenitor cells sense the presence of foreign single and double stranded RNA that can lead to innate immune response, cell senescence, and programmed cell death (Kajaste-Rudnitski and Naldini, 2015, Human Gene Therapy, 26:201-209). Results from initial experiments showed that human hematopoietic stem/progenitor cells electroporated with unmodified target specific gRNA and Cas9 mRNA led to reduced cell survival, proliferation potential, multipotency (e.g., loss of erythroid differentiation potential and skewed myeloid differentiation potential) compared to cells electroporated with GFP mRNA alone. In order to address this issue, it was hypothesized that cell senescence and apoptosis was due to the target cell sensing of foreign nucleic acid and induction of an innate immune response and subsequent induction of programmed cell death and loss of proliferative and differentiation potential.

Toward optimization of genome editing in hematopoietic/stem progenitor cells and to test this hypothesis, human CD34$^+$ cells from mobilized peripheral blood and bone marrow were electroporated (using the Maxcyte device) with *S. pyogenes* Cas9 mRNA co-delivered with HBB (HBB-8 gRNA; SEQ ID NO: 217) or AAVS1 (gRNA AAVS1-1; SEQ ID NO: 218) targeted gRNA in vitro transcribed with or without the addition of a 5' cap and 3' poly-A tail.

Figure 11:
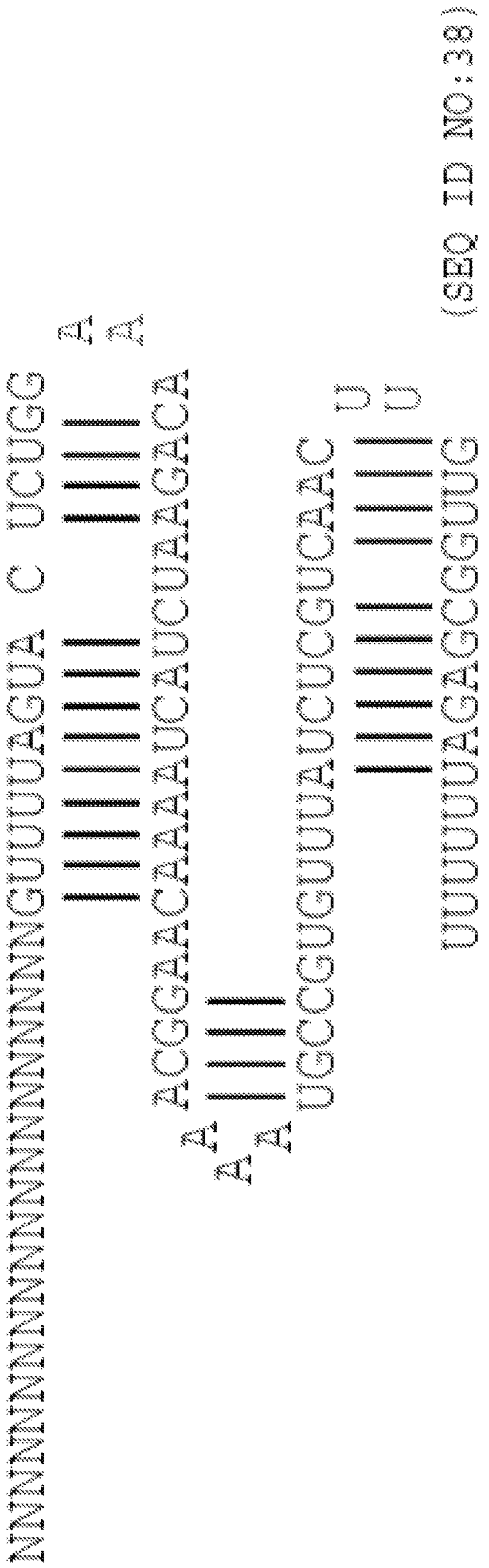
FIG. 11 depicts representative flow cytometry data showing maintenance of viable (propidium iodide negative) human CD34+ cells after electroporation with capped and tailed AAVS1 gRNA and Cas9 mRNA.
Figure 2D:
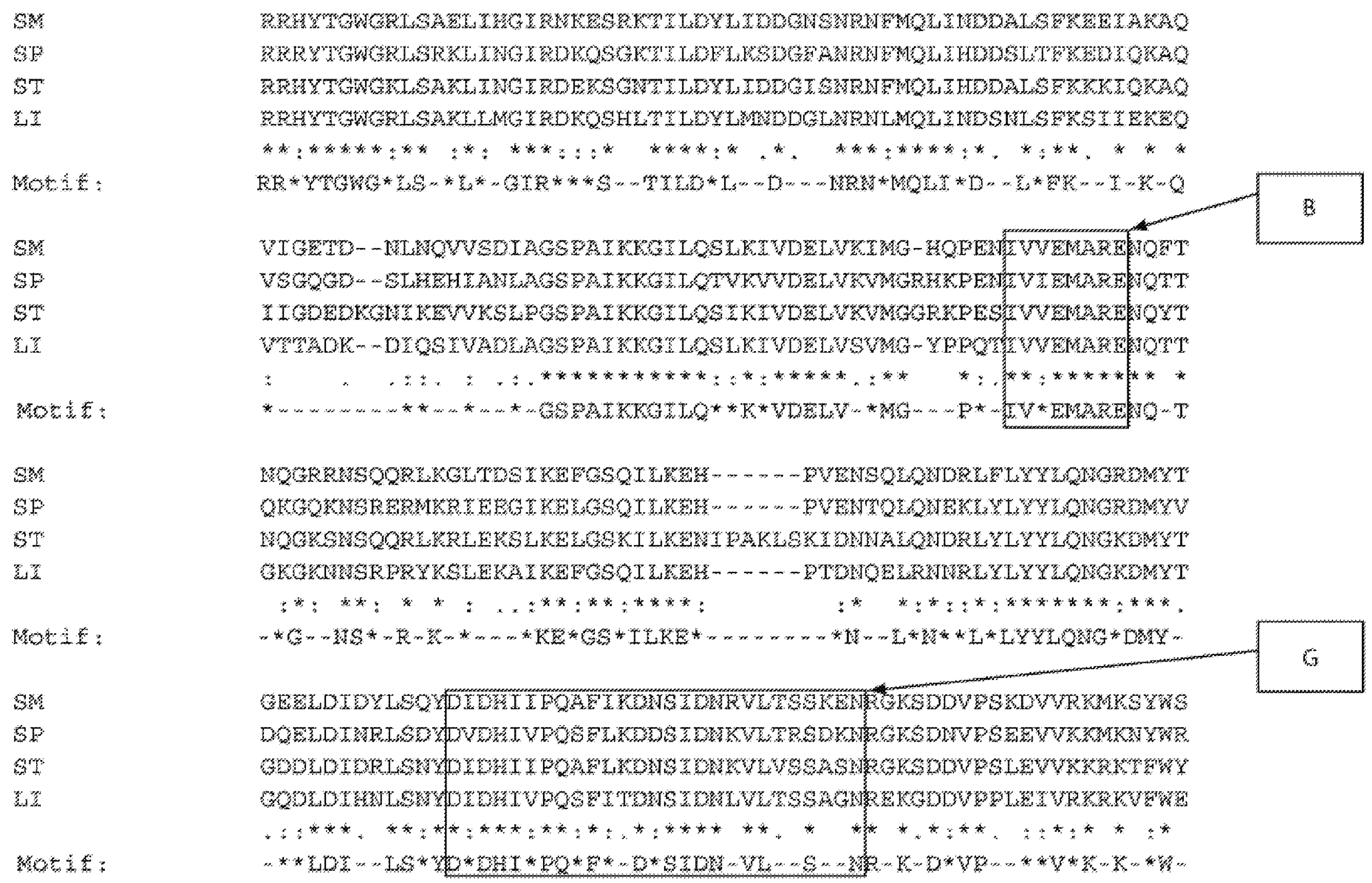
Figure 9:
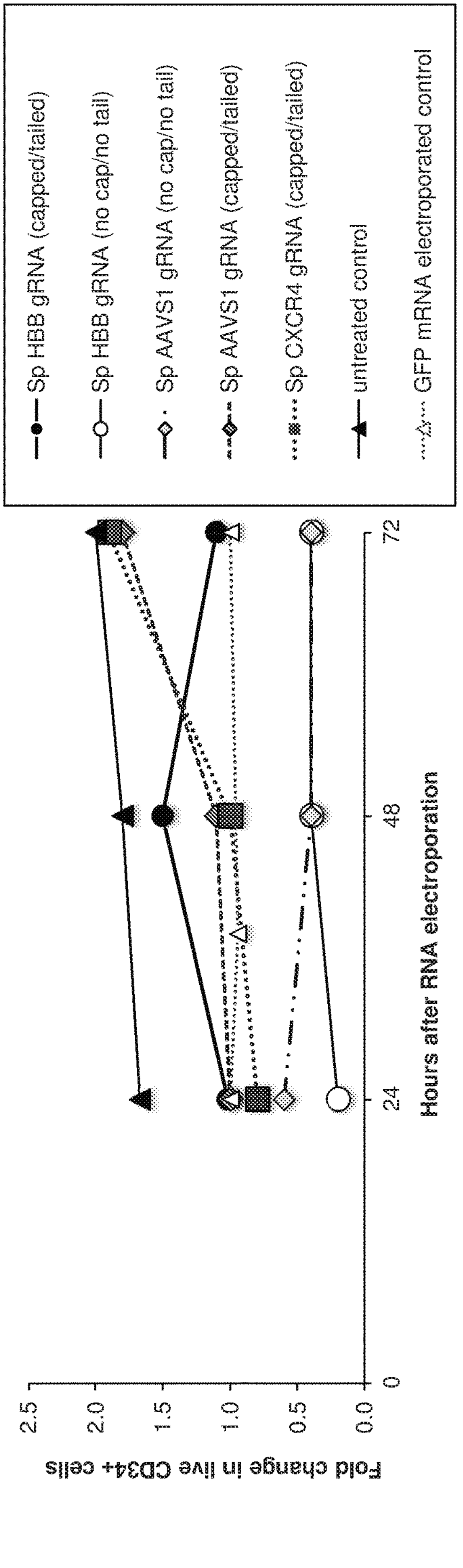
FIG. 9 depicts the kinetics of $CD34^+$ cell number increase after electroporation with the indicated uncapped/untailed gRNAs or capped/tailed gRNAs with paired Cas9 mRNA (either *S. pyogenes* (Sp) or *S. aureus* Sa Cas9).
Figure 10:
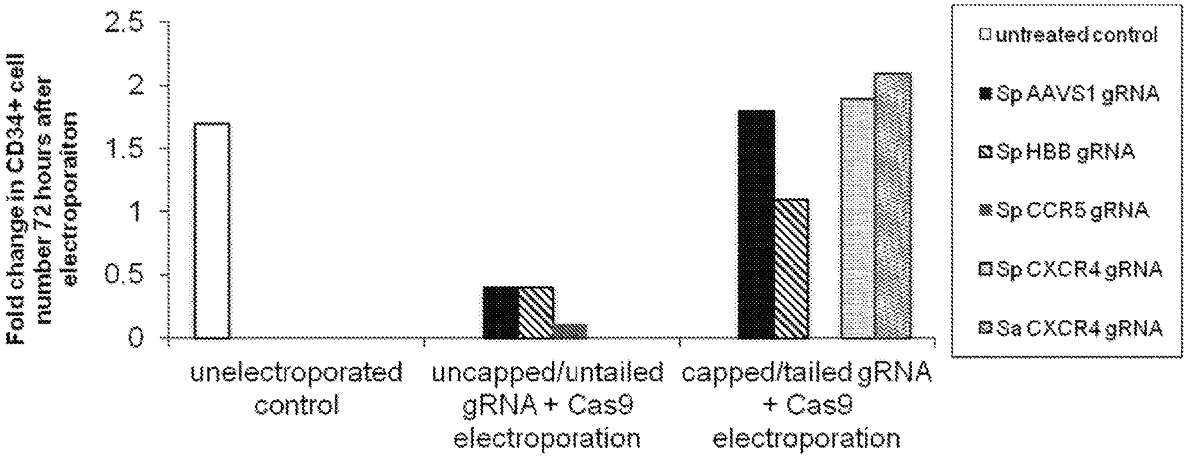
FIG. 10 depicts the fold change in total live $CD34^+$ cells 72 hours after electroporation with the indicated uncapped/untailed gRNAs or capped/tailed gRNAs with paired Cas9 mRNA (either *S. pyogenes* (Sp) or *S. aureus* Sa Cas9).
Figure 11:
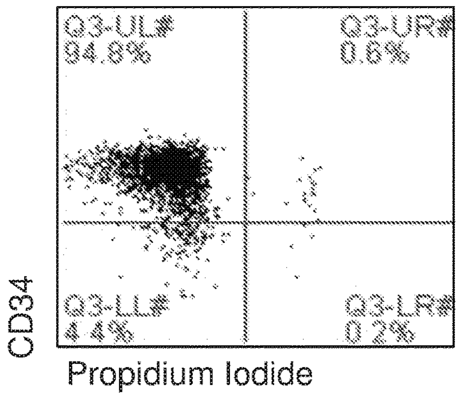

As shown in FIGS. 9-11, electroporation of capped and tailed gRNAs increased human CD34$^+$ cell survival and viability. CD34+ cells were electroporated with the indicated uncapped/untailed gRNAs or capped/tailed gRNAs with paired Cas9 mRNA (either *S. pyogenes* (Sp) or *S. aureus* (Sa) Cas9). Control samples include: cells that were electroporated with GFP mRNA alone or were not electroporated but were cultured for the indicated time frame.

Human CD34$^+$ cells that were electroporated with Cas9 paired with a single uncapped and untailed HBB or AAVS1 gRNA exhibited decreased proliferation potential over 3 days in culture compared to cells that were electroporated with the same gRNA sequence that was in vitro transcribed to have a 5' cap and a 3' polyA tail (FIG. 9). Other capped and tailed gRNAs (targeted to HBB (HBB-8 gRNA; SEQ ID NO: 217), AAVS1 (AAVS1-1 gRNA: SEQ ID NO: 218), CXCR4 (CXCR4-231 gRNA; SEQ ID NO: 214), and CCR5 (CCR5-U43 gRNA; SEQ ID NO: 216) loci) delivered with Cas9 mRNA did not negatively impact HSPC viability, proliferation, or multipotency, as determined by comparison of the fold increase in number of total live CD34$^+$ cells over three days after delivery. Importantly, there was no difference in the proliferative potential of CD34$^+$ cells contacted with capped and tailed gRNA and Cas9 mRNA compared to cells contacted with GFP mRNA or cells that were untreated. Analysis of cell viability (by co-staining with either 7-aminoactinomycin D or propidium iodide with AnnexinV antibody followed by flow cytometry analysis) at seventy-two hours after contacting Cas9 mRNA and gRNAs indicated that cells that contacted capped and tailed gRNAs expanded in culture and maintained viability while HSPCs that contacted uncapped and tailed gRNAs exhibited a decrease in viable cell number (FIG. 10). Viable cells (propidium iodide negative) that contacted capped and tailed gRNAs also maintained expression of the CD34 cell surface marker (FIG. 11).

As shown in FIGS. 12,13, 14A-14C, 15A and 15B, electroporation of Cas9 mRNA and capped and tailed gRNA supported efficient editing in human CD34 cells and their progeny.

Figure 12:
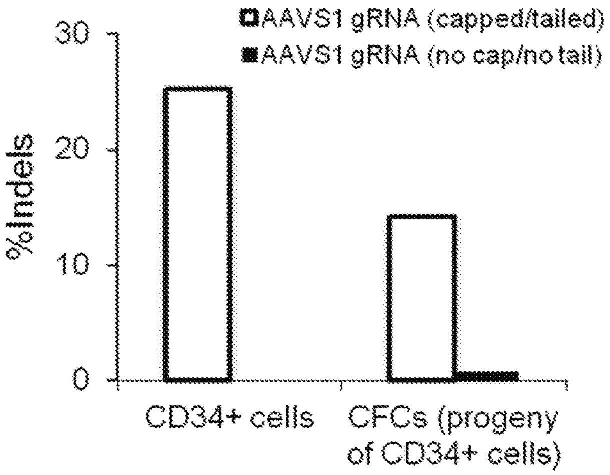
FIG. 12 depicts the percentage of insertions/deletions (indels) detected in $CD34^+$ cells and their hematopoietic colony forming cell (CFC) progeny at the targeted AAVS1 locus after delivery of Cas9 mRNA with capped and tailed AAVS1 gRNA compared to uncapped and untailed AAVS1 gRNA.
Figure 13:
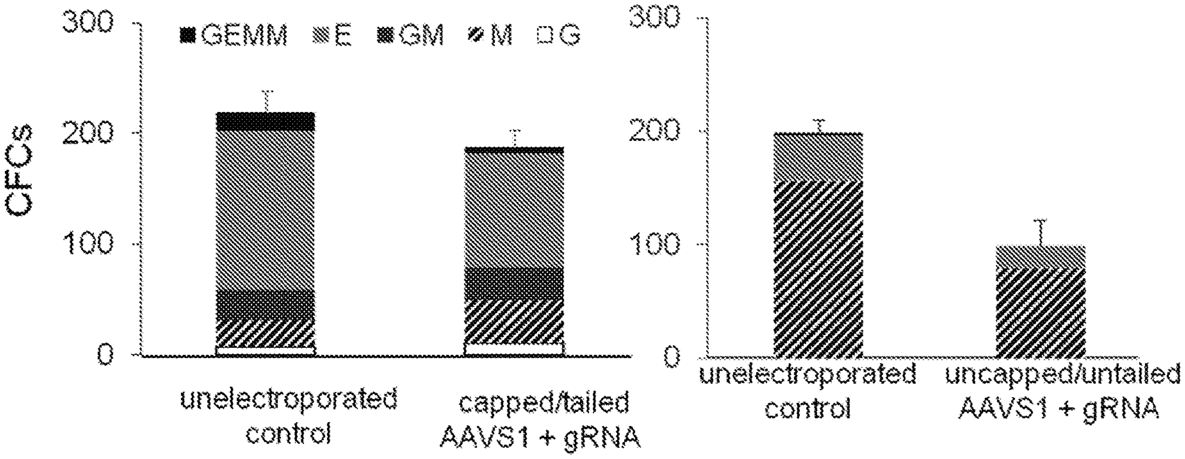
FIG. 13 depicts the maintenance of hematopoietic colony forming potential (CFCs) in CD34+ cells after editing with capped/tailed AAVS1 gRNA. Note loss of CFC potential for cells electroporated with uncapped/untailed AAVS1 gRNA.

In addition to the improved survival, target cells that contacted capped and tailed AAVS1 specific gRNA also exhibited a higher percentage of on-target genome editing (% indels) compared to cells that contacted Cas9 mRNA and uncapped/untailed gRNAs (FIG. 12). In addition, a higher level of targeted editing was detected in the progeny of CD34$^+$ cells that contacted Cas9 mRNA with capped/tailed gRNA compared to the progeny of CD34$^+$ cells that contacted Cas9 mRNA with uncapped/untailed gRNA (FIG. 12. CFCs). Delivery of uncapped/untailed gRNA also reduced the ex vivo hematopoietic potential of CD34$^+$ cells, as determined in colony forming cell (CFC) assays. Cells that contacted uncapped an untailed gRNAs with Cas9 mRNA exhibited a loss in total colony forming potential (e.g., potency) and a reduction in the diversity of colony subtype (e.g. loss of erythroid and progenitor potential and skewing toward myeloid macrophage phenotype in progeny) (FIG. 13). In contrast, cells that contacted capped and tailed gRNAs maintained CFC potential both with respect to the total number of colonies differentiated from the CD34+ cells and with respect to colony diversity (detected of mixed hematopoietic colonies [GEMMs] and erythroid colonies [E]).

Figure 14A:
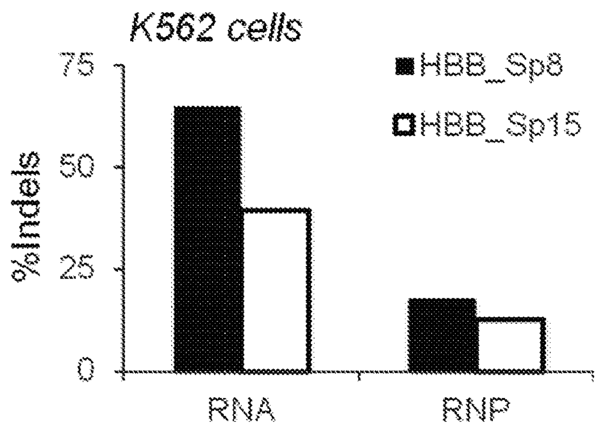
FIG. 14A depicts efficient targeted locus editing (% indels) in the K562 erythroleukemia cell line, a human erythroleukemia cell line has similar properties to HSPCs, after delivery of capped and tailed HBB gRNA with *S. pyogenes* Cas9 mRNA or ribonucleoprotein (RNP).

Next, capped and tailed HBB specific gRNAs were co-delivered with either Cas9 mRNA or complexed with Cas9 ribonucleoprotein (RNP) and then electroporated into K562 cells, a erythroleukemia cell line that been shown to mimic certain characteristics of HSPCs. Co-delivery of capped and tailed gRNA with Cas9 mRNA or RNP led to high level of genome editing at the HBB locus, as determined by T7E1 assay analysis of HBB locus PCR products (FIG. 14A). Next, 3 different capped and tailed gRNAs (targeting the HBB, AAVS1, and CXCR4 loci) were co-delivered with *S.*

Figure 14B:
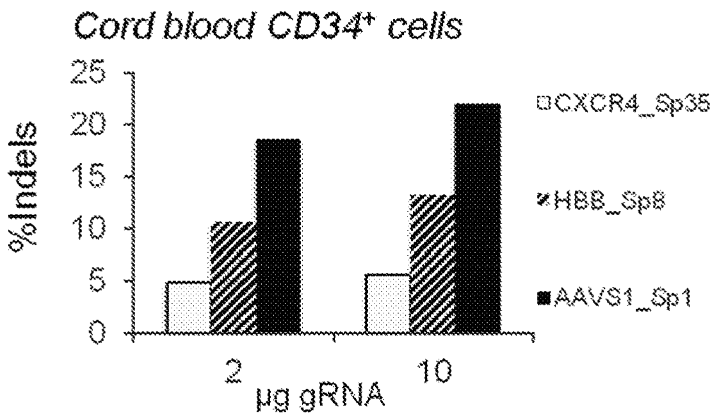
FIG. 14B depicts Cas9-mediated/capped and tailed gRNA mediated editing (% indels) at the indicated target genetic loci (AAVS1, HBB, CXCR4) in human cord blood $CD34^+$ cells. Right: CFC potential of cord blood CD34+ cells after electroporation with Cas9 mRNA and capped and tailed HBB-8 (SEQ ID NO: 217) (unelectroporated control or cells electroporated with 2 or 10 μg HBB gRNAs). Cells were electroporated with Cas9 mRNA and 2 or 10 μg of gRNA.
Figure 14C:
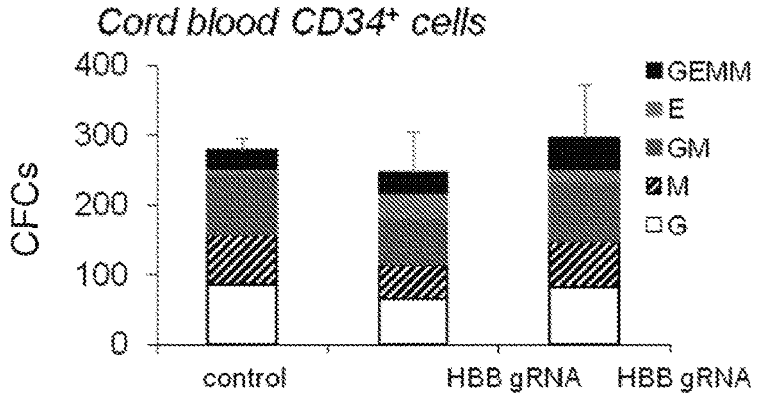
FIG. 14C depicts CFC assays for cells electroporated with 2 μg or 10 μg of capped/tailed HBB gRNA. CFCs: colony forming cells, GEMM: mixed hematopoietic colony granulocyte-erythrocyte-macrophage-monocyte. E: erythrocyte colony, GM: granulocyte-macrophage colong, G: granulocyte colony.
Figure 15A:
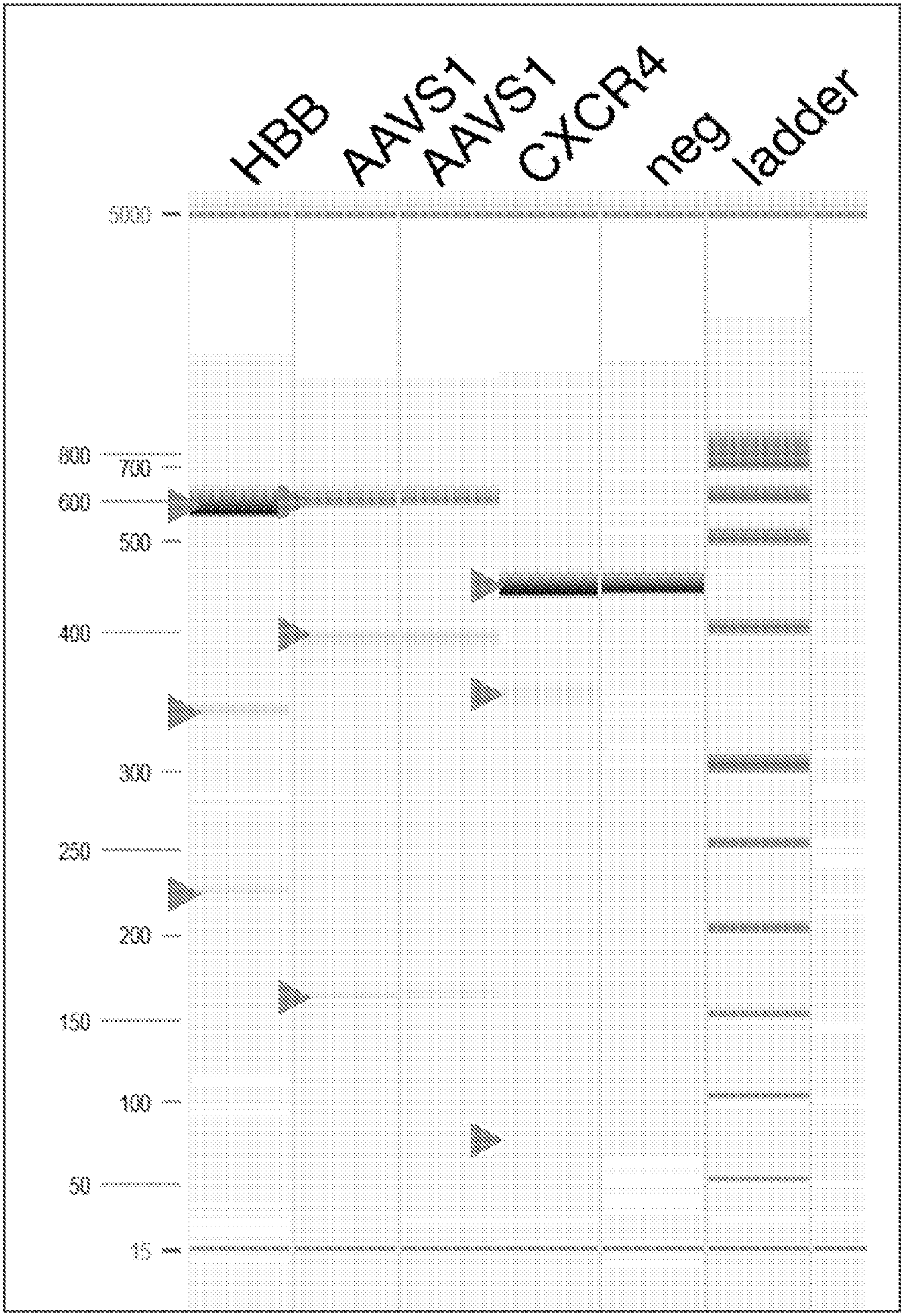
FIG. 15A depicts a representative gel image showing cleavage at the indicated loci (T7E1 analysis) in cord blood $CD34^+$ cells at 72 hours after delivery of capped and tailed AAVS1, HBB, or CXCR4 gRNA and *S. pyogenes* Cas9 mRNA. The example gel corresponds to the summary data shown in FIG. 14B.
Figure 15B:
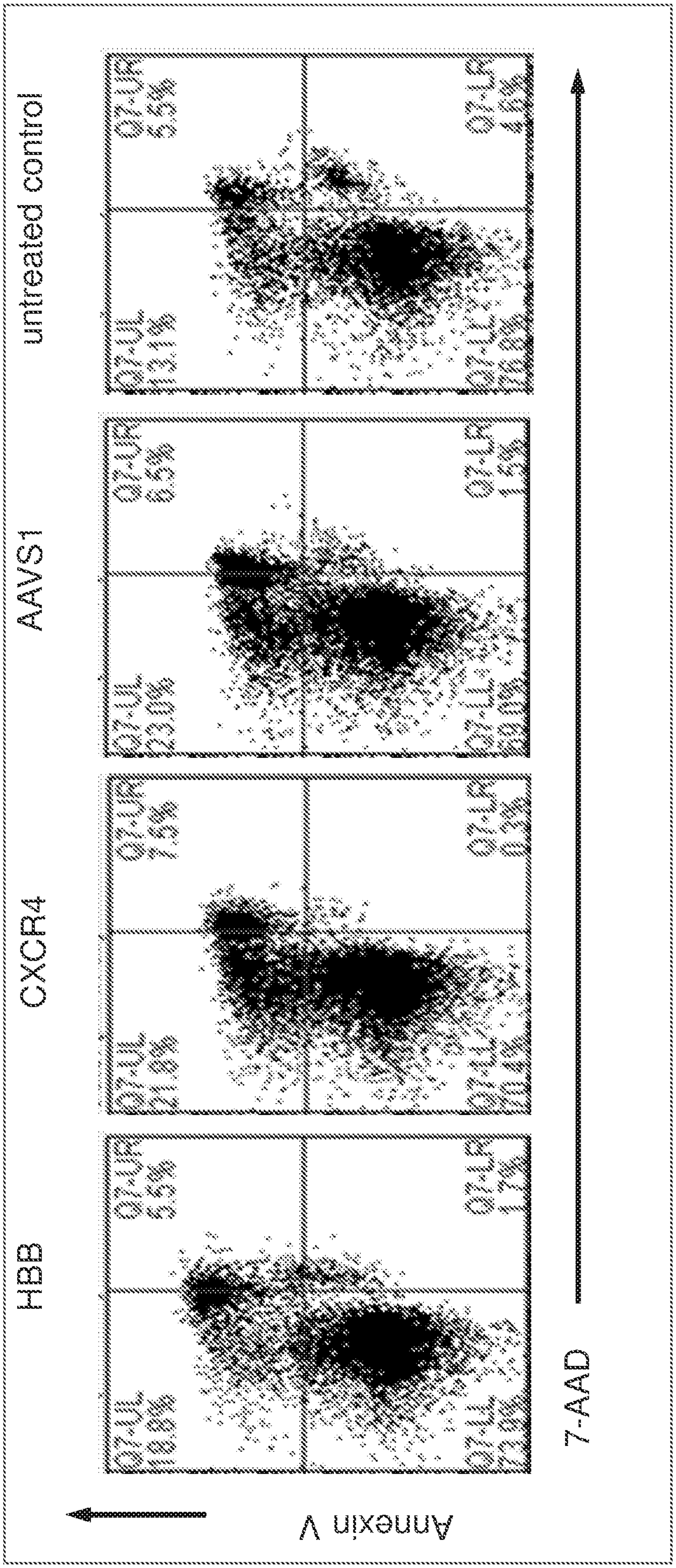
FIG. 15B depicts cell viability in CB $CD34^+$ cells 48 hours after delivery of Cas9 mRNA and indicated gRNAs as determined by co-staining with 7-AAD and Annexin V and flow cytometry analysis.

*pyogenes* Cas9 mRNA into $CD34^+$ cells isolated from umbilical cord blood (CB). Here, different amounts of gRNA (2 or 10 μg gRNA plus 10 stg of *S. pyogenes* Cas9 mRNA) were electroporated into the cells and the percentages of genome editing evaluated at target loci by T7E1 assay analysis of locus PCR products. In contrast, no cleavage was detected at the HBB locus in the genomic DNA from CB $CD34^+$ cells that were electroporated with uncapped and untailed HBB gRNA with Cas9 mRNA. The results indicated that CB $CD34^+$ cells electroporated with Cas9 mRNA and capped and tailed gRNAs maintained proliferative potential and colony forming potential. Five to 20% indels were detected at target loci and the amount of capped and tailed gRNA co-delivered with the Cas9 mRNA did not impact the percentage of targeted editing (FIG. 14B). A representative gel image of the indicated locus specific PCR products after T7E1 assay was performed shows cleavage at the targeted loci in CB $CD34^+$ cells 72 hours after delivery of capped and tailed locus-specific gRNAs (AAVS1, HBB, and CXCR4 gRNAs) co-delivered with *S. pyogenes* Cas9 mRNA by electroporation (Maxcyte device) (FIG. 15A). Importantly, there was no difference in the viability of the cells electroporated with capped and tailed AAVS1-specific gRNA, HBB-specific gRNA, or CXCR4-specific gRNA co-delivered with *S. pyogenes* Cas9 mRNA compared to cells that did not contact Cas9 mRNA or gRNA (i.e., untreated control). Live cells are indicated by negative staining for 7-AAD and AnnexinV as determined by flow cytometry analysis (bottom left quadrants of flow cytometry plots. FIG. 15B). CB $CD34^+$ cells electroporated with capped and tailed AAVS1 specific gRNA, HBB-specific gRNA, or CXCR4-specific gRNA co-delivered with *S. pyogenes* Cas9 mRNA maintained ex vivo hematopoietic colony forming potential as determined by CFC assays. The representation ex vivo hematopoietic potential in CFC assays for cells that contacted HBB-specific gRNA and Cas9 is shown in the FIG. 14C.

Example 6: Targeting Cas9/gRNA to Disrupt Single HLA-A Allele in Donor Cells and Replacement of HLA-A Allele with Recipient Allele In this example, an African American recipient subject requires HSCT. The recipient's HLA typing is conducted by conventional methods (e.g., DNA sequencing) and then compared to available donor genotypes in marrow and cord blood donor registries. A fully matched donor cannot be identified in the National Bone Marrow Program registry, the National Cord Blood Program registry, or other stem cell or cord blood registries. However, a partially matched umbilical cord blood European American (Caucasian) donor has been identified, in which 5 of the 6 alleles at the genetic loci that are required for cord blood (CB) matching to meet the requirements for allo-UCT (i.e., HLA-A, HLA-B, HLA-DRB1) (FIGS. 16A-16B). In order to increase the level of matching between the potential donor and recipient, Cas9 and one or more gRNA specific for the A*02:01:01:01 allele is delivered to the donor cord blood HSPCs or targeted disruption of that specific allele (monoallelic gene editing). One or more potentially modified (e.g., capped/tailed) gRNAs are selected from the top tier gRNAs that were generated for the specific HLA-A allele that is to be disrupted (Table 24). After disruption of the allele with Cas9/gRNA, T7E1 assay and DNA sequencing analysis verify disruption of the allele. The HLA-$A^{lo}$, e.g., HLA-$A^{+/-}$ e.g., HLA-A*02:01:01:01 negative cells (e.g., cells in which the HLA-A*02:01:01:01 monoallelic disruption is successful) are purified by sorting. The mismatched recipient HLA-A allele (e.g., A*01:01:01:01) DNA sequence (e.g., cDNA, FIGS. 17A-17B) is generated, cloned into a lentivirus vector. The endogenous promoter sequence that regulates this allele in the recipient cells is sequenced and also cloned into the lentivirus vector upstream of the A*01:01:01:01 cDNA sequence. This HLA-A transgene expression cassette (e.g, HLA promoter regulating matched HLA allele) is then packaged into lentivirus vector particles. The sorted donor HLA-$A^{lo}$, e.g., HLA-$A^{+/-}$ e.g., HLA-A*02:01:01:01 negative cells are contacted with lentivirus vector particles for gene transfer of the A*01:01:01:01 transgene expression cassette into the cells. The transduced cells are then sorted based on increased expression of HLA-A on the cell surface (compared to untransduced HLA-$A^{lo}$ cells). After HLA-A monoallelic gene replacement, the HLA modified cord blood donor HSPCs match 6 of 6 HLA loci with the recipient subject. The matched donor cord blood HSPCs are transplanted into the recipient subject according to conventional cord blood transplant clinical protocols.

TABLE 24

Guide RNAs for Cas9 targeted disruption of single HLA-A allele A*02:01:01:01 (monoallelic disruption at single genetic locus). HLA-A*02:01:01:01

| gRNA sequence (-PAM) | gRNA type (Cas9 type, length) | Strand |
|---|---|---|
| GAGUGAGAGCCCGCCCAGGU (SEQ ID NO: 219) | sa20 | - |
| GCACUGUCACUGCUUGCAGC (SEQ ID NO: 220) | sa20 | - |
| GACGGCUCCCAUCUCAGGGU (SEQ ID NO: 221) | sa20 | - |
| GUAGCUCCCUCCUUUUCUAU (SEQ ID NO: 222) | sa20 | - |
| GAAGAGCUCAGAUAGAAAAG (SEQ ID NO: 223) | sa20 | + |
| GAAGACGGCUCCCAUCUCAGGGUG (SEQ ID NO: 224) | sa24 | - |
| GAGAGUAGCUCCCUCCUUUUCUAU (SEQ ID NO: 225) | sa24 | - |
| GUGAGAGCCCGCCCAGGUCUGGGU (SEQ ID NO: 226) | sa24 | - |
| GGGCUGGGAAGACGGCUCCCAUCU (SEQ ID NO: 227) | sa24 | - |
| GGAAGACGGCUCCCAUCUCAGGGU (SEQ ID NO: 228) | sa24 | - |
| GAGAACCGGCCUCGCUC (SEQ ID NO: 229) | spy17 | - |
| GAGAGCCCGCCCAGGUC (SEQ ID NO: 230) | spy17 | - |
| GGAGUGAGAGCCCGCCC (SEQ ID NO: 231) | spy17 | - |
| GCUCAGAUAGAAAAGGA (SEQ ID NO: 232) | spy17 | + |
| GCUCCCAUCUCAGGGUG (SEQ ID NO: 233) | spy17 | - |

TABLE 24-continued

| Guide RNAs for Cas9 targeted disruption of single HLA-A allele A*02:01:01:01 (monoallelic disruption at single genetic locus). HLA-A*02:01:01:01 | | |
|---|---|---|
| gRNA sequence (-PAM) | gRNA type (Cas9 type, length) | Strand |
| GGGCGGGCUCUCACUCCAUG (SEQ ID NO: 234) | spy20 | + |
| GUGAGAGCCCGCCCAGGUCU (SEQ ID NO: 235) | spy20 | - |
| GGGAAGACGGCUCCCAUCUC (SEQ ID NO: 236) | spy20 | - |
| GGCUCCCAUCUCAGGGUGAG (SEQ ID NO: 237) | spy20 | - |
| GGAAGACGGCUCCCAUCUCA (SEQ ID NO: 238) | spy20 | - |

Abbreviations: sa: *S. aureus* gRNA, spy: *S. pyogenes* gRNA.

Example 7: Targeting Cas9/gRNA to Biallelic Disruption of the HLA-A Gene in Donor Cells and Replacement of Two Donor Mismatched HLA-A Alleles with Recipient Subject Identical HLA-A Alleles In this example, a Hispanic (Latino) recipient subject requires HSCT. The recipient's HLA typing is conducted by conventional methods (e.g., DNA sequencing) and then compared to available donor genotypes in marrow and cord blood donor registries. A fully matched donor cannot be identified in the National Bone Marrow Program registry, the National Cord Blood Program registry, or other stem cell or cord blood registries. However, a partially matched umbilical cord blood European American (Caucasian) donor has been identified, in which 4 of the 6 alleles at the genetic loci that are required for cord blood (CB) matching to meet the requirements for allo-UCT (i.e., HLA-A, HLA-B, HLA-DRB1) (FIGS. 18A-18B). In order to increase the level of matching between the potential donor and recipient, Cas9 and one or more gRNAs that target the HLA-A locus (e.g., targets common sequence to both HLA-A alleles in the donor cells) are delivered to the donor cord blood donor HSPCs for targeted disruption of the gene (biallelic gene editing). One or more gRNAs (potentially modified gRNAs, e.g., capped/tailed) are selected from the top tier gRNAs that were generated for the HLA-A alleles to be disrupted at the locus (Table 25). After biallelic disruption of the locus with Cas9/gRNA, T7E1 assay and DNA sequencing analysis verify disruption of the allele. HLA-A$^{-/-}$, e.g., HLA-A*02:01:01:01 and A*29:02:01:01 negative cells (e.g., cells in which the biallelic disruption is successful) are purified by sorting. The DNA sequences) (e.g., cDNAs) of the recipient subject identical HLA-A alleles that were not initially present in the donor cells (e.g., A*01:01:01:01 and A*23:01:01 are generated and cloned into a lentivirus vector. The endogenous promoter sequence that regulates these alleles in the recipient subject cells are sequenced and also cloned into a lentivirus vector or vectors upstream of the A*01:01:01:01 and A*23:01:01 cDNA sequences, with each promoter regulating the allele, that corresponds to the promoter/allele combination in the subject cells. The HLA-A transgene expression cassettes are packaged into lentivirus vector particles. The sorted donor HLA-A$^{-/-}$ cells, e.g., HLA-A*02:01:01:01 and A*29:02:01:01 negative cells (e.g., cells in which the biallelic disruption is successful) are contacted with lentivirus vector particles for gene transfer of both the A*01:01:01:01 and A*23:01:01 transgene expression cassettes into the recipient cells. The transduced cells are then sorted based on increased expression of HLA-A on the cell surface (compared to untransduced HLA-A$^{-/-}$ cells). After HLA-A biallelic gene replacement, the HLA modified cord blood donor HSPCs match 6 of 6 HLA loci with the recipient subject. The matched donor cord blood HSPCs are transplanted into the recipient subject according to conventional cord blood transplant clinical protocols.

TABLE 25

| gRNAs for Cas9 targeted biallelic disruption at the HLA-A locus for disruption of alleles A*02:01:01:01 and A*29:02:01. HLA-A*02:01:01:01 and HLA-A*29:02:01:01 | | |
|---|---|---|
| gRNA sequence (-PAM) | gRNA type (Cas9 type, length) | Strand |
| GCACUGUCACUGCUUGCAGC (SEQ ID NO: 239) | sa20 | - |
| GACGGCUCCCAUCUCAGGGU (SEQ ID NO: 240) | sa20 | - |
| GUAGCUCCCUCCUUUUCUAU (SEQ ID NO: 241) | sa20 | - |
| GAAGAGCUCAGAUAGAAAAG (SEQ ID NO: 242) | sa20 | + |
| GAGCCCGCCCAGGUCUGGGU (SEQ ID NO: 243) | sa20 | - |
| GAAGACGGCUCCCAUCUCAGGGUG (SEQ ID NO: 244) | sa24 | - |
| GAGAGUAGCUCCCUCCUUUUCUAU (SEQ ID NO: 245) | sa24 | - |
| GGGCUGGGAAGACGGCUCCCAUCU (SEQ ID NO: 246) | sa24 | - |
| GGAAGACGGCUCCCAUCUCAGGGU (SEQ ID NO: 247) | sa24 | - |
| GGGCACUGUCACUGCUUGCAGCCU (SEQ ID NO: 248) | sa24 | - |
| AAGACGGCUCCCAUCUC (SEQ ID NO: 249) | spy17 | - |
| GAGAACCGGCCUCGCUC (SEQ ID NO: 250) | spy17 | - |
| AGCUCAGAUAGAAAAGG (SEQ ID NO: 251) | spy17 | + |
| GCUCAGAUAGAAAAGGA (SEQ ID NO: 252) | spy17 | + |
| GCUCCCAUCUCAGGGUG (SEQ ID NO: 253) | spy17 | - |
| CGGCUCCCAUCUCAGGGUGA (SEQ ID NO: 254) | spy20 | - |
| GGGAAGACGGCUCCCAUCUC (SEQ ID NO: 255) | spy20 | - |

TABLE 25-continued gRNAs for Cas9 targeted biallelic disruption at the HLA-A locus for disruption of alleles A*02:01:01:01 and A*29:02:01. HLA-A*02:01:01:01 and HLA-A*29:02:01:01

| gRNA sequence (-PAM) | gRNA type (Cas9 type, length) | Strand |
|---|---|---|
| GGCUCCCAUCUCAGGGUGAG (SEQ ID NO: 256) | spy20 | - |
| GGAAGACGGCUCCCAUCUCA (SEQ ID NO: 257) | spy20 | - |
| GCAAGCAGUGACAGUGCCCA (SEQ ID NO: 258) | spy20 | + |

Abbreviations: sa: *S. aureus* gRNA, spy: *S. pyogenes* gRNA.

Example 8: Targeting Cas9 and gRNAs for Multiplex Genome Editing by Disruption of Mismatched HLA Haplotype and Gene Replacement of One Copy Each of HLA-A, HLA-B, and HLA-DRB1

In this example, a Hispanic (Latino) recipient subject requires HSCT. The recipient's HLA typing is conducted by conventional methods (e.g., DNA sequencing) and then compared to available donor genotypes in marrow and cord blood donor registries. A fully matched donor cannot be identified in the National Bone Marrow Program registry, the National Cord Bloord Program Registry, or other stem cell or cord blood registries. However, a haploidentical umbilical cord blood European American (Caucasian) donor has been identified, in which 3 of the 6 alleles at the genetic loci (e.g., haploidentical) that are required for cord blood (CB) matching to meet the requirements for allo-UCT (i.e., HLA-A, HLA-B, HLA-DRB1) (FIGS. 18A-18B). In order to increase the level of matching between the potential donor and recipient subject. Cas9 and a multiple gRNAs (e.g, potentially modified gRNAs, e.g., capped/tailed gRNAs) that target the alleles in the unmatched haplotype in the donor HSPCs (e.g., A*02:01:01:01, B*08:01:01, and DRB1*03:01:01) are delivered to the donor cord blood HSPCs for targeted monoallelic disruption at multiple genetic loci (e.g., multiplex gene editing, e.g., HLA-A, HLA-B, HLA-DRB1). One or more potentially modified gRNAs (e.g., capped/tailed gRNAs) are selected from the top tier gRNAs that were generated for the HLA-A, HLA-B, and HLA-DRB1 donor specific alleles (that do not match with the recipient) to be disrupted at those specific genetic loci (Table 26). After targeted monoallelic disruption of the genetic loci with Cas9/gRNA, T7E1 assay and DNA sequencing analysis verify disruption of the alleles. HLA-$A^{+/-}$, e.g., HLA-A*02:01:01:01 negative; HLA-$B^{+/-}$, e.g., B*08:01:01 negative; and HLA-$DRB1^{+/-}$, e.g., DRB1*03:01:01:01 negative cells (e.g., cells in which the monoallelic disruption are successful at three loci) are purified by sorting. The mismatched recipient subject HLA-A alleles that were not initially present in the haploidentical donor cells (e.g., A*03:01:01:01 B*07:02:01, DRB1*15:01:01:01) are sequenced and the DNA sequences (e.g., cDNAs) are then cloned into a lentivirus vector or vectors upstream of their endogenous promoter also determined by sequencing the DNA proximal to those alleles in the recipient subject cells. The HLA-A, -B-, and -DRB1 transgene expression cassettes are packaged into lentivirus vector particles. The sorted donor HLA-$A^{+/-}$ HLA-$B^{+/-}$, HLA-$DRB1^{+/-}$ cells, e.g., (e.g., cells in which the multiplex monoallelic disruption of HLA-A, -B, -DRB1 is successful) are contacted with lentivirus vector particles for gene transfer of HLA-A, -B, B, and -DRB1 transgene expression cassettes into the recipient cells. The transduced cells are then sorted based on increased expression of HLA-A, -B, and -DRB1 on the cell surface (compared to untransduced HLA-$A^{+/-}$ HLA-$B^{+/-}$, HLA-$DRB1^{+/-}$ cells). After HLA-A, -B, and -DRB1 gene replacement, the HLA modified cord blood donor HSPCs match 6 of 6 HLA loci with the recipient subject. The matched donor cord blood HSPCs are transplanted into the recipient subject according to conventional cord blood transplant clinical protocols.

TABLE 26 gRNAs for Cas9 targeted haplotype disruption at the (a) HLA-A, (b) HLA-B, and (c) HLA-DRB1 genetic loci for disruption of alleles A*02:01:01:01, B*08:01:01, and DRB1*03:01:01:01.

| gRNA sequence (-PAM) | gRNA type (Cas9 type and length) | Strand |
|---|---|---|
| (a) HLA-A*02:01:01:01 | | |
| GAGUGAGAGCCCGCCCAGGU (SEQ ID NO: 259) | sa20 | - |
| GCACUGUCACUGCUUGCAGC (SEQ ID NO: 260) | sa20 | - |
| GACGGCUCCCAUCUCAGGGU (SEQ ID NO: 261) | sa20 | - |
| GUAGCUCCCUCCUUUUCUAU (SEQ ID NO: 262) | sa20 | - |
| GAAGAGCUCAGAUAGAAAAG (SEQ ID NO: 263) | sa20 | + |
| GAAGACGGCUCCCAUCUCAGGGUG (SEQ ID NO: 264) | sa24 | - |
| GAGAGUAGCUCCCUCCUUUUCUAU (SEQ ID NO: 265) | sa24 | - |
| GUGAGAGCCCGCCCAGGUCUGGGU (SEQ ID NO: 266) | sa24 | - |
| GGGCUGGGAAGACGGCUCCCAUCU (SEQ ID NO: 267) | sa24 | - |
| GGAAGACGGCUCCCAUCUCAGGGU (SEQ ID NO: 268) | sa24 | - |
| GAGAACCGGCCUCGCUC (SEQ ID NO: 269) | spy17 | - |
| GAGAGCCCGCCCAGGUC (SEQ ID NO: 270) | spy17 | - |
| GGAGUGAGAGCCCGCCC (SEQ ID NO: 271) | spy17 | - |
| GCUCAGAUAGAAAAGGA (SEQ ID NO: 272) | spy17 | + |
| GCUCCCAUCUCAGGGUG (SEQ ID NO: 273) | spy17 | - |
| GGGCGGGCUCUCACUCCAUG (SEQ ID NO: 274) | spy20 | + |

TABLE 26-continued gRNAs for Cas9 targeted haplotype disruption at the (a) HLA-A, (b) HLA-B, and (c) HLA-DRB1 genetic loci for disruption of alleles A*02:01:01:01, B*08:01:01, and DRB1*03:01:01:01.

| gRNA sequence (-PAM) | gRNA type (Cas9 type and length) | Strand |
|---|---|---|
| GUGAGAGCCCGCCCAGGUCU (SEQ ID NO: 275) | spy20 | - |
| GGGAAGACGGCUCCCAUCUC (SEQ ID NO: 276) | spy20 | - |
| GGCUCCCAUCUCAGGGUGAG (SEQ ID NO: 277) | spy20 | - |
| GGAAGACGGCUCCCAUCUCA (SEQ ID NO: 278) | spy20 | - |
| (b) HLA-B*08:01:01 | | |
| GCACUGUCGCUGCACGCAGC (SEQ ID NO: 279) | sa20 | - |
| GACGGCUCCCAUCUCAGGGU (SEQ ID NO: 280) | sa20 | - |
| GAGCCGGCCCAGGUCUCGGU (SEQ ID NO: 281) | sa20 | - |
| GUAGCUCCCUCCUUUUCCAC (SEQ ID NO: 282) | sa20 | - |
| GAAGAGCUCAGGUGGAAAAG (SEQ ID NO: 283) | sa20 | + |
| GAAGACGGCUCCCAUCUCAGGGUG (SEQ ID NO: 284) | sa24 | - |
| GCGGCUACUACAACCAGAGCGAGG (SEQ ID NO: 285) | sa24 | + |
| GUGGGAGCCGGCCCAGGUCUCGGU (SEQ ID NO: 286) | sa24 | - |
| GGAAGACGGCUCCCAUCUCAGGGU (SEQ ID NO: 287) | sa24 | - |
| GGACUGGGAAGACGGCUCCCAUCU (SEQ ID NO: 288) | sa24 | - |
| GAGACCCGGCCUCGCUC (SEQ ID NO: 289) | spy17 | - |
| GUGCAGCGACAGUGCCC (SEQ ID NO: 290) | spy17 | + |
| GGAGCCGGCCCAGGUCU (SEQ ID NO: 291) | spy17 | - |
| GCUCCCAUCUCAGGGUG (SEQ ID NO: 292) | spy17 | - |
| GCUCAGGUGGAAAAGGA (SEQ ID NO: 293) | spy17 | + |
| GGGAAGACGGCUCCCAUCUC (SEQ ID NO: 294) | spy20 | - |
| GCGUGCAGCGACAGUGCCCA (SEQ ID NO: 295) | spy20 | + |
| GGCUCCCAUCUCAGGGUGAG (SEQ ID NO: 296) | spy20 | - |
| GGAAGACGGCUCCCAUCUCA (SEQ ID NO: 297) | spy20 | - |
| GGGCCGGCUCCCACUCCAUG (SEQ ID NO: 298) | spy20 | + |
| (c) HLA-DRB1*03:01:01:01 | | |
| GAUGGACUCGCCGCUGCACU (SEQ ID NO: 299) | sa20 | - |
| GGGACACCAGACCACGUUUC (SEQ ID NO: 300) | sa20 | + |
| GGACACCAGACCACGUUUCU (SEQ ID NO: 301) | sa20 | + |
| GACUUCAGCCAAGAGGAUUC (SEQ ID NO: 302) | sa20 | + |
| GAAUCCUCUUGGCUGAAGUC (SEQ ID NO: 303) | sa20 | - |
| GCUGGGGACACCAGACCACGUUUC (SEQ ID NO: 304) | sa24 | + |
| GACAAGCCCUCUCACAGUGGAAUG (SEQ ID NO: 305) | sa24 | + |
| GAAAGGACACUCUGGACUUCAGCC (SEQ ID NO: 306) | sa24 | + |
| UUAGGAUGGACUCGCCGCUGCACU (SEQ ID NO: 307) | sa24 | - |
| UCAGGAAUCCUCUUGGCUGAAGUC (SEQ ID NO: 308) | sa24 | - |
| GCGGCGAGUCCAUCCUA (SEQ ID NO: 309) | spy17 | + |
| GAGUACUCCAAGAAACG (SEQ ID NO: 310) | spy17 | - |
| CACCAGACCACGUUUCU (SEQ ID NO: 311) | spy17 | + |
| CUCCAAGAAACGUGGUC (SEQ ID NO: 312) | spy17 | - |
| AAUCAGAAAGGACACUC (SEQ ID NO: 313) | spy17 | + |
| GUAGAGUACUCCAAGAAACG (SEQ ID NO: 314) | spy20 | - |
| GCAGCGGCGAGUCCAUCCUA (SEQ ID NO: 315) | spy20 | + |
| GUACUCCAAGAAACGUGGUC (SEQ ID NO: 316) | spy20 | - |
| GGACACCAGACCACGUUUCU (SEQ ID NO: 317) | spy20 | + |
| GCUCUCCAUUCCACUGUGAG (SEQ ID NO: 318) | spy20 | - |

In Examples 9-11 below, human umbilical cord blood mononuclear cells (MNCs) from several donors were HLA typed by amplification of genomic DNA followed by DNA sequence-based typing and/or sequence-specific primers/probes (Kashi Clinical Laboratories, Portland, OR). Primary human cells, cord bloodMNCs from three HSC donors were HLA typed as described above and a 4-digit typing report was generated for the HLA-A, HLA-B and HLA-DRB1 alleles (Table 27). Samples were paired as partially-matched donor and recipient based on the highest allele matching number. For each putative donor and recipient pair, mismatched alleles were identified, such that editing of those loci would reduce the number of allelic mismatches between potential donor and recipient. The database was used to search for appropriate gRNAs for use in editing targeted loci in an allele-specific manner. The 4 out of 8 digits (2 out of 4 fields) for HLA typing could be any subtype of the indicated allele (e.g., HLA-A 02:01 could be HLA-A 02:01:01:01). The database was searched for gRNAs that match to the on-target site for all subtypes of the target allele. The search was tailored such that the identified gRNAs would not target any subtypes of the other HLA alleles in the donor cells (e.g., HLA-B, HLA-DRB1). The database also provided the count/percentage of subtypes of the target allele with on-target specificity for each identified gRNA. In this process, if user would target multiple alleles at the same time, the database would first search for gRNAs with on-target sites in all target loci, and gRNAs with on-target in the other alleles were avoided. After obtaining identifying appropriate gRNAs, the database also provides sequences for subtypes of all donor alleles to be used as reference. On-/off-target sites of gRNAs identified in the previous step are searched against these donor allele subtype sequences. The final step in gRNA selection includes gRNA selection based on the data from the first steps (higher count/percentage of target allele subtypes, lower off-target count/percentage in excluded alleles, lower off-target effect in the whole genome, etc.).

TABLE 27

HLA typing results of four stem cell donors for assessment of putative donor and recipient pairs for gene editing to improve matching for HSC transplantation.

| # Patient ID | Lab ID number/ Sample Type (Lab ID) | HLA Class I A* | | HLA Class I B* | | HLA Class II DRB1* | |
|---|---|---|---|---|---|---|---|
| 1 | 160202008HLA/ Cells | 01:01 | 26:01 | 07:02 | 57:01 | 15:01 | 16:01 |
| 2 | 160202009HLA/ Cells | 01:01 | 01:01 | 07:02 | 57:01 | 01:01 | 13:05 |
| 3 | 160202010HLA/ Cells | 01:01 | 02:01 | 07:02 | 51:01 | 04:02 | 15:01 |

Example 9: Targeting Cas9 and gRNAs for Genome Editing by Disruption of Mismatched HLA-A Allele (HLA-A 26:01) in Primary Human T-Lymphocytes To increase the level of matching between a potential donor have an unsuitable level of HLA matching at 6 alleles to a recipient (3 loci, 3/6 mismatched HLA alleles) targeted allele-specific gene editing was performed using Cas9 and specifically-identified gRNAs using the database described herein. As a result, the level of HLA matching between cells from the mismatched donor (Table 27, Patient 1) were made suitable (by reducing HLA mismatch to 2/6 mismatched HLA alleles) for transfer to a potential recipient patient (Table 27, Patient 2) through gene disruption (Table 28).

TABLE 28

HLA genotypes of primary human HSCs from potential allogeneic donor and recipient pair before and after gene editing strategy 1 to increase matching of Patient 1 donor HSC genotype to Patient 2 recipient genotype.

Before gene editing

| Patient 1 (DONOR) Gene | Allele 1 | Allele 2 | Patient 2 (RECIPIENT) Gene | Allele 1 | Allele 2 | Mismatched HLA Before Editing |
|---|---|---|---|---|---|---|
| HLA-A | 01:01 | 26:01 | HLA-A | 01:01 | 01:01 | 3/6 |
| HLA-B | 07:02 | 57:01 | HLA-B | 07:02 | 57:01 | |
| HLA-DRB1 | 15:01 | 16:01 | HLA-DRB1 | 01:01 | 13:05 | |

After gene editing

| Patient 1 (DONOR) Gene | Allele 1 | Allele 2 | Patient 2 (RECIPIENT) Gene | Allele 1 | Allele 2 | Mismatched HLA After Editing |
|---|---|---|---|---|---|---|
| HLA-A | 01:01 | | HLA-A | 01:01 | 01:01 | 2/6 |
| HLA-B | 07:02 | 57:01 | HLA-B | 07:02 | 57:01 | |
| HLA-DRB1 | 15:01 | 16:01 | HLA-DRB1 | 01:01 | 13:05 | |

Patient 1 (donor) mismatched with Patient 2 (recipient) at 3 out of 6 typed HLA alleles (HLA-A, HLA-B, and HLA-DRB1: Table 28). Targeted disruption of the HLA-A 26:01 would reduce HLA mismatching between the potential donor (Patient 1) and recipient (Patient 2). Therefore, gRNAs were identified and selected from the database having a predicted high on-target specificity for allele HLA-A 26:01 combined with a predicted low off-target specificity at the other HLA alleles present in the donor (Table 29). The gRNAs were in vitro transcribed from PCR templates and engineered to have 5' and 3' end modifications (e.g., modification such as 5' ARCA cap and 3' polyA [20A] tail), which were previously shown to improve T lymphocyte and HSC viability after treatment with Cas9 protein complexed to the modified gRNAs (RNPs), while maintaining high degree of gene editing in these types of primary blood cells.

Figure 19A:
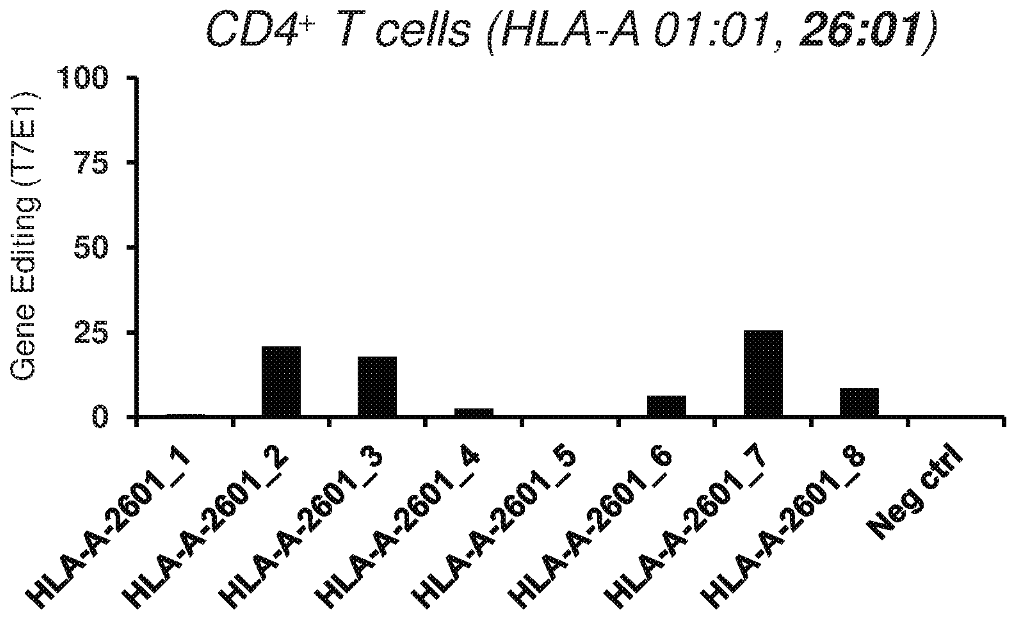
FIG. 19A shows total gene editing frequency (as detected by T7E1 endonuclease analysis) in primary $CD4^+$ T lymphocytes from a human umbilical cord blood HSC donor that has been HLA typed after electroporation of *S. pyogenes* Cas9 protein complexed to different HLA-A 26:01 allele-specific modified gRNA molecules comprising a 5'-ARCA cap and a 3' polyA [20A] tail. The targeted allele at the HLA-A locus is indicated in bold at the top of the chart.
Figure 19B:
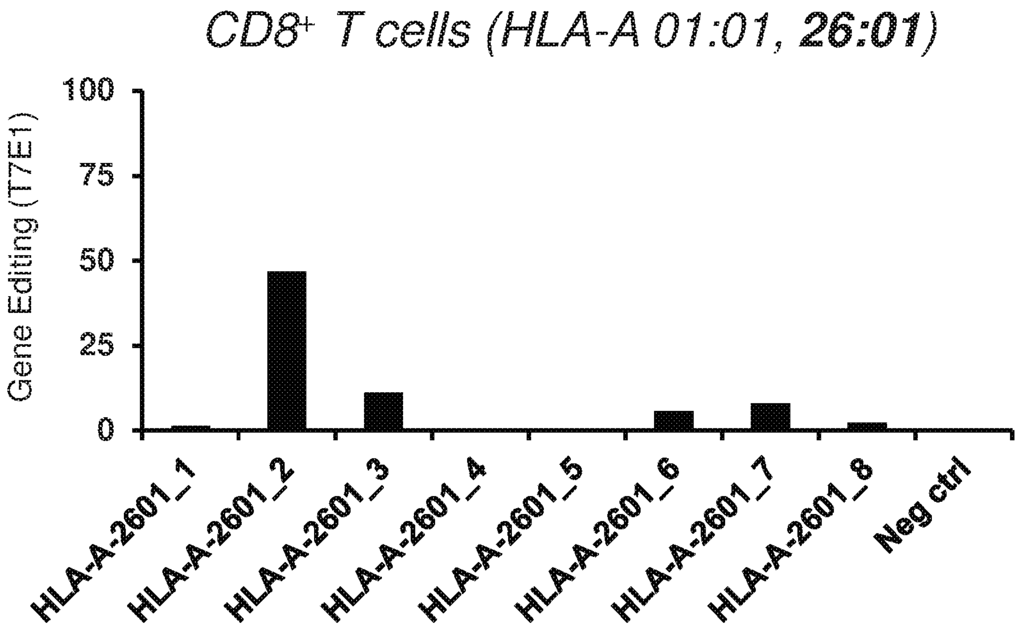
FIG. 19B shows total gene editing frequency (as detected by T7E1 endonuclease analysis) in primary $CD8^+$ T lymphocytes from a human umbilical cord blood HSC donor that has been HLA typed after electroporation of *S. pyogenes* Cas9 protein complexed to different HLA-A 26:01 allele-specific modified gRNA molecules comprising a 5'-ARCA cap and a 3' polyA [20A] tail.

To evaluate allele-specific gene editing in donor cells, primary T lymphocytes ($CD4^+$ and $CD8^+$ T cells) were isolated from the cord blood (CB) unit and the gRNAs listed in Table 29 were screened in these cells. Briefly, the modified HLA-A 26:01 allele specific gRNAs were precomplexed with *S. pyogenes* Cas9 protein to yield RNPs which were electroporated into donor T lymphocytes (Amaxa Nucleofector). Genomic DNA was isolated from the cells 3-4 days after RNP delivery, and the HLA-A locus was PCR amplified from extracted gDNA. Gene editing was evaluated using the T7E1 endonuclease assay analysis to identify the most effective gRNA for allele specific editing of A*26:01 (FIG. 19A-19B). HLA-A 26:01_2 gRNA had the highest level of on-target activity, as compared to the other gRNAs tested, in primary human hematopoietic cells from Patient 1. In summary, this example shows allele-targeted gene disruption of an HLA gene in primary human blood cells.

TABLE 29

| S. pyogenes gRNAs targeted to HLA-A 26:01 | | | | | | | | | |
|---|---|---|---|---|---|---|---|---|---|
| S. pyogenes gRNAs targeted to HLA-A 26:01 | | | | Off-target in other HLA alleles present in donor at MHC locus | | | | | |
| gRNA ID | Size | guide (DNA sequence) | % in A*26:01 | A*01:01 | A*26:01 | B*07:02 | B*57:01 | DRB1* 15:01 | DRB1* 16:01 |
| HLA-A2601_1 | 20 | ACGGTTCTCACAC CATCCAG (SEQ ID NO: 319) | 100 | (3, 1) (2, 69) | (0, 38) | (3, 1) (2, 46) | (3, 22) | 0 | 0 |
| HLA-A2601_2 | 20 | CACACCATCCAG AGGATGTA (SEQ ID NO: 320) | 100 | 0 | (0, 38) | 0 | 0 | 0 | 0 |
| HLA-A2601_3 | 20 | CCGGAACACACG GAATGTGA (SEQ ID NO: 321) | 97.4 | (3, 70) | (0, 38) | 0 | (4, 22) | 0 | 0 |
| HLA-A2601_4 | 20 | TGCGGAGCCACT CCACGCAC (SEQ ID NO: 322) | 97.4 | (3, 3) (2, 66) (5, 1) | (0, 37) | 0 | (1, 1) (0, 21) | 0 | 0 |
| HLA-A2601_5 | 17 | ACCATCCAGAGG ATGTA (SEQ ID NO: 323) | 100 | (3, 1) (2, 69) | (0, 38) | (3, 1) (2, 46) | (3, 22) | 0 | 0 |
| HLA-A2601_6 | 17 | GTTCTCACACCAT CCAG (SEQ ID NO: 324) | 100 | 0 | (0, 38) | 0 | 0 | 0 | 0 |
| HLA-A2601_7 | 17 | GAACACACGGAA TGTGA (SEQ ID NO: 325) | 97.4 | (3, 70) | (0, 38) | 0 | (4, 22) | 0 | 0 |
| HLA-A2601_8 | 17 | GGAGCCACTCCA CGCAC (SEQ IDD NO: 326) | 97.4 | (3, 3) (2, 66) (5, 1) | (0, 37) | 0 | (1, 1) (0, 21) | 0 | 0 |

Example 10: Targeting Cas9 and gRNAs for Multiplex Genome Editing by Disruption of Mismatched HLA-B Allele (HLA-B 51:01) and HLA-DRB1 (04:02) in Primary Human T-Lymphocytes To increase the level of matching between a potential donor having an unsuitable level of HLA matching at 6 alleles to a recipient (3 loci, 4/6 mismatched HLA alleles), multiplex gene disruption of mismatched alleles HLA-B 51:01 and HLA-DRB1 04:02 (Table 30) was performed using Cas9 and specifically-identified gRNAs using the database described herein. As a result, the level of HLA matching between cells from the mismatched donor (Table 30, Patient 3) were made suitable (reducing HLA mismatch to 2/6 mismatched HLA alleles) for transfer to a potential recipient patient (Table 30, Patient 2).

TABLE 30

Multiplex HLA (MHC Class I and Class II) gene editing of primary human HSCs from potential allogeneic donor and recipient pair to increase matching of donor HSCs (Patient 3) to recipient (Patient 2).

| Before gene editing | | | | | | |
|---|---|---|---|---|---|---|
| DONOR (Patient 3) | | | RECIPIENT (Patient 2) | | | Mismatched HLA |
| Gene | Allele 1 | Allele 2 | Gene | Allele 1 | Allele 2 | before editing |
| HLA-A | 01:01 | 02:01 | HLA-A | 01:01 | 26:01 | 3/6 |
| HLA-B | 07:02 | 51:01 | HLA-B | 07:02 | 57:01 | |
| HLA-DRB1 | 04:02 | 15:01 | HLA-DRB1 | 15:01 | 16:01 | |

| After gene editing | | | | | | |
|---|---|---|---|---|---|---|
| DONOR (Patient 3) | | | RECIPIENT (Patient 2) | | | Mismatched HLA after |
| Gene | Allele 1 | Allele 2 | Gene | Allele 1 | Allele 2 | editing |
| HLA-A | 01:01 | 02:01 | HLA-A | 01:01 | 26:01 | 1/6 |
| HLA-B | 07:02 | | HLA-B | 07:02 | 57:01 | |
| HLA-DRB1 | | 15:01 | HLA-DRB1 | 15:01 | 16:01 | |

Patient 3 (donor) is mismatched with Patient 2 (recipient) at 3 out of 6 typed HLA alleles (HLA-A, HLA-B, and HLA-DRB1, Table 30). Targeted disruption of HLA-B 51:01 and HLA-DRB1 04:02 would reduce HLA mismatching between the potential donor (Patient 3) and recipient (Patient 2). Therefore, gRNAs were identified and selected from the database having a predicted high on-target specificity for allele HLA-B 51:01 and for HLA-DRB1 04:02 (Tables 31 and 32) combined with a predicted low off-target specificity at the other the other HLA alleles present in the donor (Table 30). The gRNAs were in vitro transcribed from PCR templates and were engineered to have 5' and 3' end modifications (e.g., 5' ARCA cap and 3' polyA [20A] tail) previously shown to improve HSC viability after treatment with Cas9 protein complexed to the modified gRNAs (RNPs) while maintaining high degree of gene editing.

TABLE 31

*S. pyogenes* gRNAs targeted to HLA-B 51:01

| *S. pyogenes* gRNAs targeted to HLA-B 51:01 | | | | Off-targets in other HLA alleles present in donor at MHC locus | | | | | |
|---|---|---|---|---|---|---|---|---|---|
| gRNA ID | Size | guide (DNA sequence) | % in B*5101 | A*01:01 | A*02:01 | B*07:02 | B*51:01 | DRB1* 04:02 | DRB1* 15:01 |
| HLA-B-5101_1 | 20 | CCTCGCTCTGG TTGTAGTAG (SEQ ID NO: 327) | 100 | 0 | 0 | 0 | (0, 54) | 0 | 0 |
| HLA-B-5101_2 | 20 | CGTCTGCCAAG TGTGAGACC (SEQ ID NO: 328) | 98.2 | 0 | (5, 2) (6, 116) | (6, 45) | (1, 1) (0, 53) | 0 | 0 |
| HLA-B-5101_3 | 20 | CTCTCGGTAAG TCTGTGTGT (SEQ ID NO: 329) | 98.2 | (3, 67) (4, 3) | (3, 116) (4, 3) | (3, 47) | (0, 54) | 0 | 0 |
| HLA-B-5101_4 | 20 | GCGAGGCCGG GTCTCACACT (SEQ ID NO: 330) | 98.2 | 0 | 0 | 0 | (1, 1) (0, 53) | 0 | 0 |
| HLA-B-5101_5 | 17 | CGCTCTGGTTG TAGTAG (SEQ ID NO: 331) | 100 | 0 | (5, 1) | 0 | (0, 54) (5, 1) | 0 | 0 |
| HLA-B-5101_6 | 17 | AGGCCGGGTCT CACACT (SEQ ID NO: 332) | 98.2 | 0 | 0 | 0 | (1, 1) (0, 53) | 0 | 0 |
| HLA-B-5101_7 | 17 | CTTACCGAGAG AACCTG (SEQ ID NO: 333) | 98.2 | (3,2) (2, 68) | (3, 115) (5, 1) (4, 4) | (2, 47) | (0, 54) | 0 | 0 |
| HLA-B-5101_8 | 17 | CGATCCGCAGG TTCTCT (SEQ ID NO: 334) | 98.2 | (5,2) (4, 68) | (5, 116) | (3, 47) | (1, 1) (0, 53) | 0 | 0 |

TABLE 32

*S. pyogenes* gRNAs targeted to HLA-DRB1 04:02

| *S. pyogenes* gRNAs targeted to HLA-DRB1 04:02 | | | | Off-targets in other HLA alleles present in donor at MHC locus | | | | | |
|---|---|---|---|---|---|---|---|---|---|
| gRNA ID | Size | guide (DNA sequence) | % in DRB1 *04:02 | A*01:01 | A*02:01 | B*07:02 | B*51:01 | DRB1* 04:02 | DRB1* 15:01 |
| HLA_DRB1-0402_1 | 20 | AGGACATCCTGG AAGACGAG (SEQ ID NO: 335) | 100 | 0 | 0 | 0 | 0 | (0, 3) | (4, 27) (5, 2) |
| HLA_DRB1-0402_2 | 20 | GGAAGACGAGCG GGCCGCGG (SEQ ID NO: 336) | 100 | 0 | 0 | 0 | 0 | (0, 3) | (4, 27) (5, 2) |
| HLA_DRB1-0402_3 | 20 | CCTGGAAGACGA GCGGGCCG (SEQ ID NO: 337) | 100 | 0 | 0 | 0 | 0 | (0, 3) | (4, 27) (5, 2) |

TABLE 32-continued

| S. pyogenes gRNAs targeted to HLA-DRB1 04:02 | | | | | | | | | | |
|---|---|---|---|---|---|---|---|---|---|---|
| *S. pyogenes* gRNAs targeted to HLA-DRB1 04:02 | | | | Off-targets in other HLA alleles present in donor at MHC locus | | | | | | |
| gRNA ID | Size | guide (DNA sequence) | % in DRB1 *04:02 | A*01:01 | A*02:01 | B*07:02 | B*51:01 | DRB1* 04:02 | DRB1* 15:01 |
| HLA_DRB1-0402_4 | 20 | CCGCGGCCCGCTC GTCTTCC (SEQ ID NO: 338) | 100 | (6, 1) | 0 | 0 | 0 | (0, 3) | (4, 27) (5, 2) |
| HLA_DRB1-0402_5 | 17 | GGAAGACGAGCG GGCCG (SEQ ID NO: 339) | 100 | 0 | 0 | 0 | 0 | (0, 3) | (4, 27) (5, 2) |
| HLA_DRB1-0402_6 | 17 | ACATCCTGGAAG ACGAG (SEQ ID NO: 340) | 100 | 0 | 0 | 0 | 0 | (0, 3) | (4, 28) (5, 6) |
| HLA_DRB1-0402_7 | 17 | CATCCTGGAAGAC GAGC (SEQ ID NO: 341) | 100 | 0 | 0 | 0 | 0 | (0, 3) | (4, 28) (5, 1) |
| HLA_DRB1-0402_8 | 17 | CGGCCCGCTCGTC TTCC (SEQ ID NO: 342) | 100 | 0 | 0 | 0 | 0 | (0, 3) | (4, 27) (5, 2) |

Figure 20A:
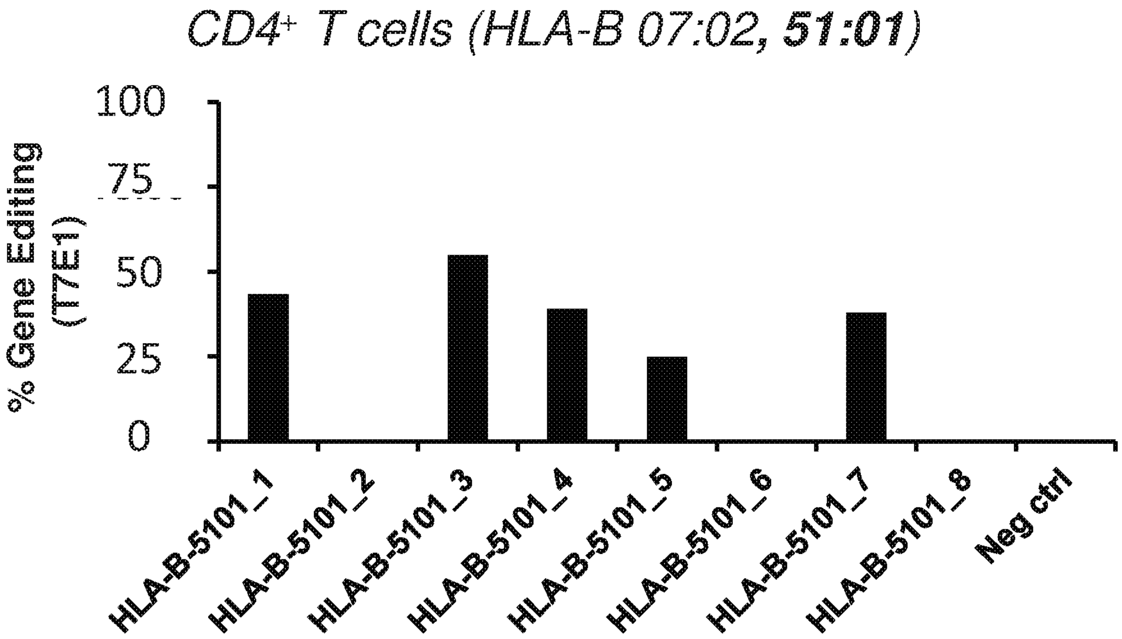
FIG. 20A shows total gene editing frequency (as detected by T7E1 endonuclease analysis) in primary $CD4^+$ T lymphocytes after electroporation of *S. pyogenes* Cas9 protein complexed to different HLA-B 07:02:01 allele-specific modified gRNA molecules comprising a 5'-ARCA cap and a 3' polyA [20A] tail. The targeted allele at the HLA-B locus is indicated in bold at the top of the chart.
Figure 20B:
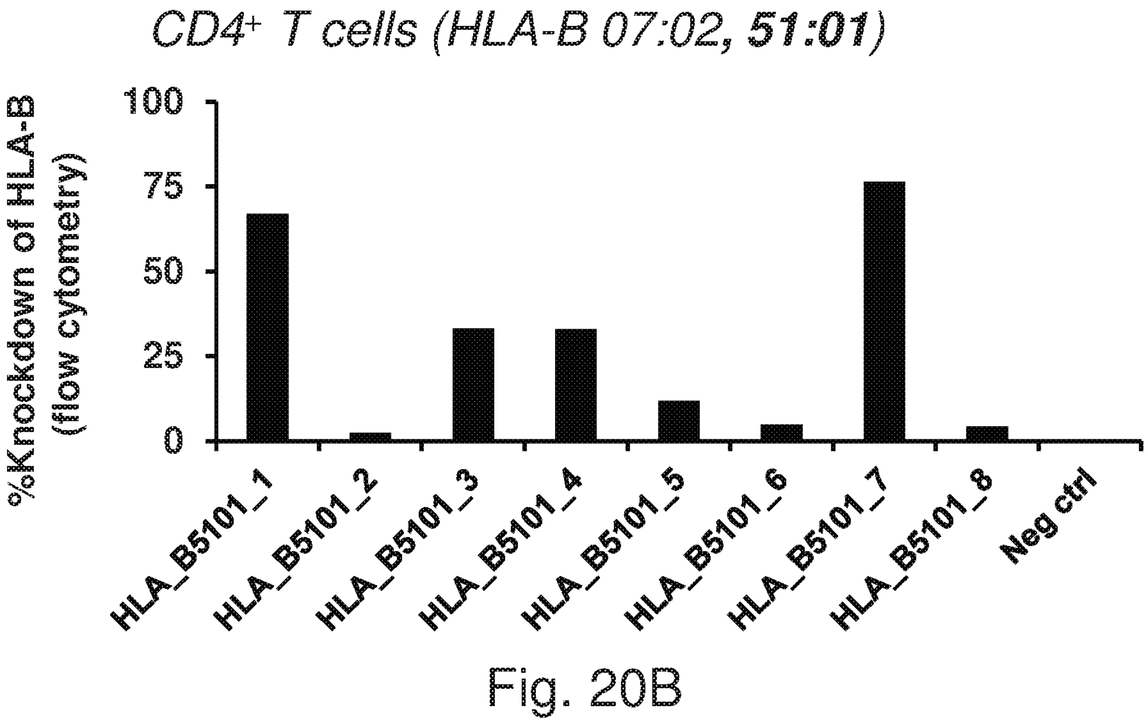
FIG. 20B shows total knockdown of HLA-B protein expression in primary $CD4^+$ T lymphocytes as determined by flow cytometry analysis after electroporation of *S. pyogenes* Cas9 protein complexed to different HLA-B 07:02 allele-specific modified gRNA molecules comprising a 5'-ARCA cap and a 3' polyA [20A] tail. The targeted allele at the HLA-B locus is indicated in bold at the top of the chart. Percent knockdown of HLA-B expression was calculated by the following formula: (% HLA-$B^+$ in neg control−% HLA-B in experimental sample)/% HLA-B+ in neg control. For example for HLA-B_5101: ((98.9% HLA-$B^+$−32.8% HLA-B*)/98.9% HLA-B*)=66.8% knockdown of HLA-B.
Figure 20C:
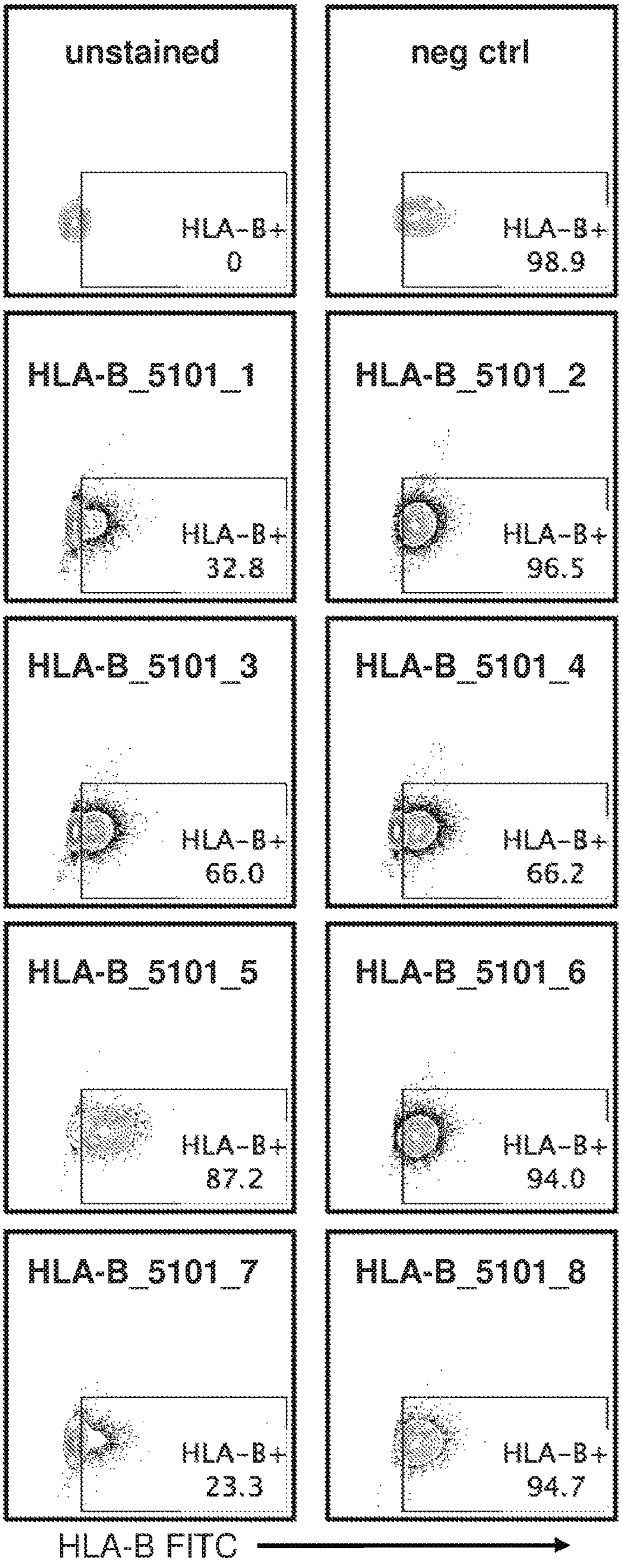
FIG. 20C shows flow cytometry analysis to detect protein expression of HLA-B in primary $CD4^+$ T lymphocytes after electroporation of *S. pyogenes* Cas9 protein complexed to different HLA-B 07:02 allele-specific modified gRNA molecules comprising a 5'-ARCA cap and a 3' polyA [20A] tail using an HLA-B 07:02 allele-specific antibody. To compare cell surface expression of HLA-B, untreated control (unedited) cells from the same donor (neg control) for which close to 100% of the cells are expected to express HLA-B, and cells from the same donor that were not stained with fluorophore conjugated HLA-B antibody (and therefore would be 0% HLA-$B^+$ (no antibody)) were used to set the gate for HLA-B+ cells (top 2 panels). The cells treated with Cas9 RNPs with the indicated gRNAs are shown at top of each flow cytometry dotplot.
Figure 21:
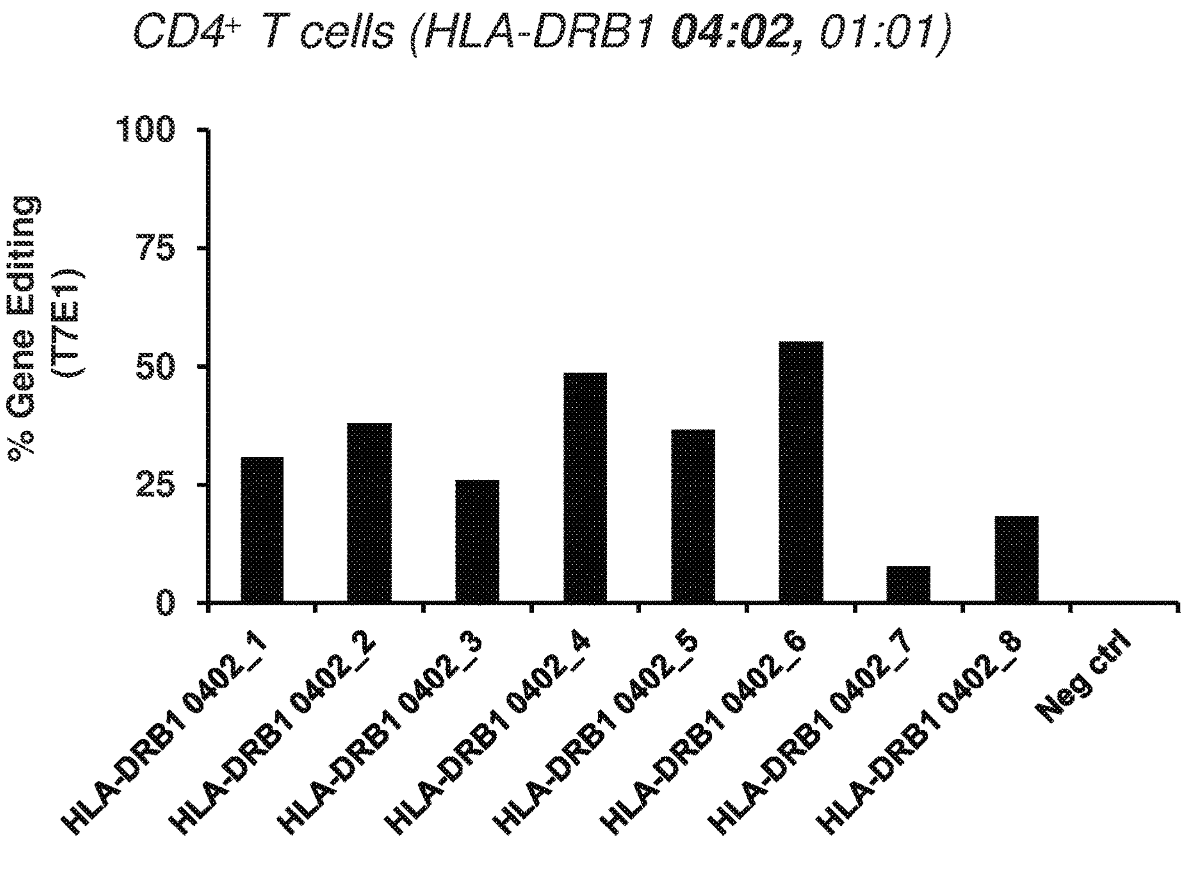
FIG. 21 shows total gene editing frequency (as detected by T7E1 endonuclease analysis) in primary $CD4^+$ T lymphocytes after electroporation of *S. pyogenes* Cas9 protein complexed to different HLA-DRB1 04:02 allele-specific modified gRNA molecules comprising a 5'-ARCA cap and a 3' polyA [20A] tail. The targeted allele at the HLA-Alocus is indicated in bold at the top of the chart.

To evaluate allele-specific gene editing in donor cells, primary T lymphocytes ($CD4^+$ T cells) were isolated from the CB unit and the gRNAs listed in Tables 31 and 32 were screened in these cells. Briefly, the modified HLA-B 51:01 and HLA-DRB1 04:02 allele-specific gRNAs (Tables 31 and 32) were precomplexed with *S. pyogenes* Cas9 protein to yield RNPs which were electroporated into donor T lymphocytes (Amaxa Nucleofector). Genomic DNA was isolated from the cells 3-4 days after RNP delivery, and the HLA-A locus PCR amplified from extracted gDNA. Gene editing was evaluated using the T7E1 endonuclease assay analysis to identify, the most effective gRNA at allele specific editing of B*51:01 (FIG. 20A). T-cells electroporated with Cas9 RNP exhibited high viability (>80%) after editing and were expanded in culture. Edited cells were also evaluated by flow cytometry analysis in order to quantify decreased HLA-B protein expression (anti-human HLA-B-FITC) at the surface of the cells that was the result of the gene disruption (FIGS. 20B and 20C). gRNAs that supported high levels of gene disruption as determined using the T7E1 endonuclease assay also exhibit high percentage loss or reduction in cell surface expression of HLA-B. For example, HLA-B 5101_1 gRNA supported 43% gene disruption and 67% knockdown of HLA-B expression. Cells co-stained with HLA-B allele specific antibody and MHC Class I (AlexaFluor 647 conjugated anti-human HLA-A, -B, -C, Biolegend Catalog #311416) could be subdivided into 2 fractions: cells that were HLA-$B^{low/-}$ and MHC Class $I^+$ and cells that were HLA-$B^+$/MHC Class $I^+$. This distinction between the two populations in their relative expression of MHC Class I cell surface antigens would support isolation through FACS or immunomagnetic sorting to obtain a purified population of cells that lack allele-specific expression of one HLA gene but maintain all other Class I cell surface antigens. In the same cells, modified (capped and tailed) HLA-DRB1 04:02 targeting gRNA were complexed to *S. pyogenes* Cas9 protein (RNPs) and electroporated into the cells to evaluate allele specific gene disruption of MHC Class II genes. T7E1 analysis of gDNA extracted from these cells revealed substantial allele-specific disruption of DRB1 04:02 in primary human T lymphocytes (FIG. 21). In summary, this example shows allele-specific knockdown of multiple HLA genes in primary human blood cells.

Example 11: Targeting Cas9 and gRNAs for Multiplex Genome Editing by Disruption of Mismatched HLA-A Allele (HLA-A 02:01) and HLA-DRB1 (04:02) in Primary Human T Lymphocytes and HSCs To increase the level of matching between a potential donor having an unsuitable level of HLA matching at 6 alleles to a recipient (3 loci, 4/6 mismatched HLA alleles), multiplex gene disruption of mismatched alleles of HLA-A 02:01 and HLA-DRB1 04:02 (Table 33) was performed using Cas9 and specifically-identified gRNAs using the database described herein. As a result, the level of HLA matching between cells from the mismatched donor (Table 33, Patient 3) were made suitable (by reducing HLA mismatch to 2/6 mismatched HLA alleles) for transfer to a potential recipient patient (Table 33, Patient 1).

TABLE 33

| HLA typing of primary human HSCs from potential allogeneic donor and recipient pair to increase matching of donor HSCs to recipient | | | | | | |
|---|---|---|---|---|---|---|
| Before gene editing | | | | | | |
| Donor (Patient 3) | | | Recipient (Patient 1) | | | Mismatched HLA |
| Gene | Allele 1 | Allele 2 | Gene | Allele 1 | Allele 2 | before editing |
| HLA-A | 01:01 | 02:01 | HLA-A | 01:01 | 01:01 | 4/6 |
| HLA-B | 07:02 | 51:01 | HLA-B | 07:02 | 57:01 | |
| HLA-DRB1 | 04:02 | 15:01 | HLA-DRB1 | 01:01 | 13:05 | |

TABLE 33-continued

| HLA typing of primary human HSCs from potential allogeneic donor and recipient pair to increase matching of donor HSCs to recipient | | | | | | |
|---|---|---|---|---|---|---|
| After gene editing | | | | | | |
| Donor (Patient 3) | | | Recipient (Patient 1) | | | Mismatched HLA |
| Gene | Allele 1 | Allele 2 | Gene | Allele 1 | Allele 2 | after editing |
| HLA-A | 01:01 | | HLA-A | 01:01 | 26:01 | 2/6 |
| HLA-B | 07:02 | 51:01 | HLA-B | 07:02 | 57:01 | |
| HLA-DRB1 | | 15:01 | HLA-DRB1 | 01:01 | 16:01 | |

Patient 3 (donor) mismatched with Patient 1 (recipient) at 4 out of 6 typed HLA alleles (HLA-A, HLA-B, and HLA-DRB1). Targeted disruption of HLA-A 02:01 and HLA-DRB1 04:02 would reduce HLA mismatching between HSC donor (Patient 3 and recipient (Patient 1). Therefore, gRNAs were identified and selected from the database having a predicted high on-target specificity for allele HLA-A 02:01 and for HLA-DRB1 04:02 combined with a predicted low off-target specificity at the other HLA alleles present in the donor (Tables 34 and 32). The gRNAs were in vitro transcribed from PCR templates and were engineered to have 5' and 3' end modifications (e.g., 5' ARCA cap and 3' polyA [20A] tail) previously shown to improve HSC viability after treatment with Cas9 protein complexed to the modified gRNAs (RNPs) while maintaining high degree of gene editing.

TABLE 34

| *S. pyogenes* gRNAs targeted to HLA-A 02:01 | | | | | | | | | |
|---|---|---|---|---|---|---|---|---|---|
| gRNA ID | Size | guide (DNA sequence) | % in A*02:01 | A*01:01 | A*02:01 | B*07:02 | B*51:01 | DRB1 *04:02 | DRB1* 15:01 |
| HLA-A 0201_1 | 20 | ACTCCACGC ACGTGCCCTC C (SEQ ID NO: 343) | 99.2 | (3, 1) (4, 67) (5,2) | (0, 117) (1,2) | (2, 45) (3, 2) | (2, 50) (3, 4) | 0 | 0 |
| HLA-A 0201_2 | 20 | CTACCTGGA GGGCACGTG CG (SEQ ID NO: 344) | 99.1 | (1, 1) (2, 67) (3,2) | (0, 118) (1,1) | (2, 46) (3, 1) | (2, 50) (3, 4) | 0 | 0 |
| HLA-A 0201_3 | 20 | GTGGACCTG GGGACCCTG CG (SEQ ID NO: 345) | 98.3 | (2, 68) (3, 2) | (0, 117) (1,2) | (5, 47) | 0 | 0 | 0 |
| HLA-A 0201_4 | 20 | CCACTCACA GACTCACCG AG (SEQ ID NO: 346) | 97.5 | 0 | (0, 116) (1,2) | 0 | (6, 51) | 0 | (6,5) |
| HLA-A 0201_5 | 17 | GCACGTGCC CTCCAGGT (SEQ ID NO: 347) | 98.3 | 0 | (0, 118) (1, 1) | (2, 46) (3, 1) (5, 1) | (2, 50) (3, 4) | 0 | 0 |
| HLA-A 0201_6 | 17 | AGGGCACGT GCGTGGAG (SEQ ID NO: 348) | 98.3 | (2, 1) (3, 66) (4, 2) | (0, 118) (1, 1) | (2, 45) (3, 2) | (2, 52) (3, 2) | 0 | 0 |
| HLA-A 0201_7 | 17 | CCTGGAGGG CACGTGCG (SEQ ID NO: 349) | 98.3 | (1, 1) (2, 67) (3, 2) | (0, 118) (1, 1) | (2, 46) (3, 1) | (2, 50) (3, 4) | 0 | 0 |
| HLA-A 0201_8 | 17 | CTCACAGAC TCACCGAG (SEQ ID NO: 350) | 97.5 | 0 | (0, 116) | 0 (1,2) | 0 | 0 | 0 |

Figure 22A:
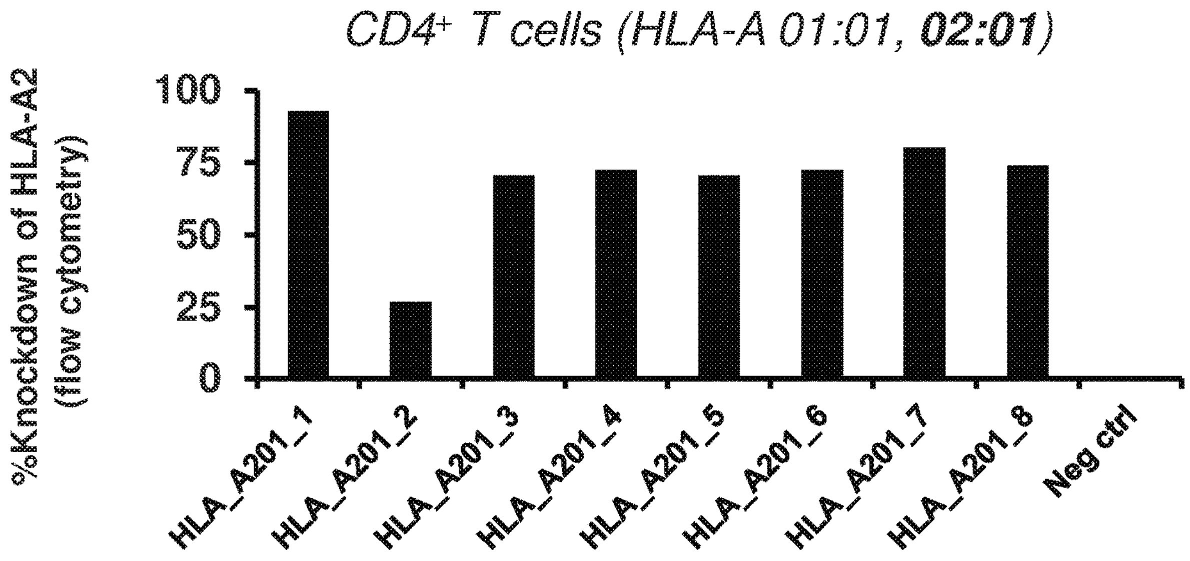
FIG. 22A shows total gene editing frequency (as detected by DNA sequencing analysis) in primary $CD4^+$ T lymphocytes after electroporation of *S. pyogenes* Cas9 protein complexed to different HLA-A 26:01 allele-specific modified gRNA molecules comprising a 5'-ARCA cap and a 3' polyA [20A] tail. The targeted allele (HLA-A2) at the HLA-A locus is indicated in bold at the top of the chart. Percent knockdown of HLA-A2 expression was calculated by the following formula: (% HLA-$A0201^+$ in neg control-% HLA-A2 in experimental sample)/% HLA-$A2^+$ in neg control. For example for HLA-A201_1: ((96.1% HLA-$A2^+$−6.85% HLA-$A2^+$)/96.1% HLA-$A2^+$)=92.9% knockdown of HLA-A2.
Figure 22B:
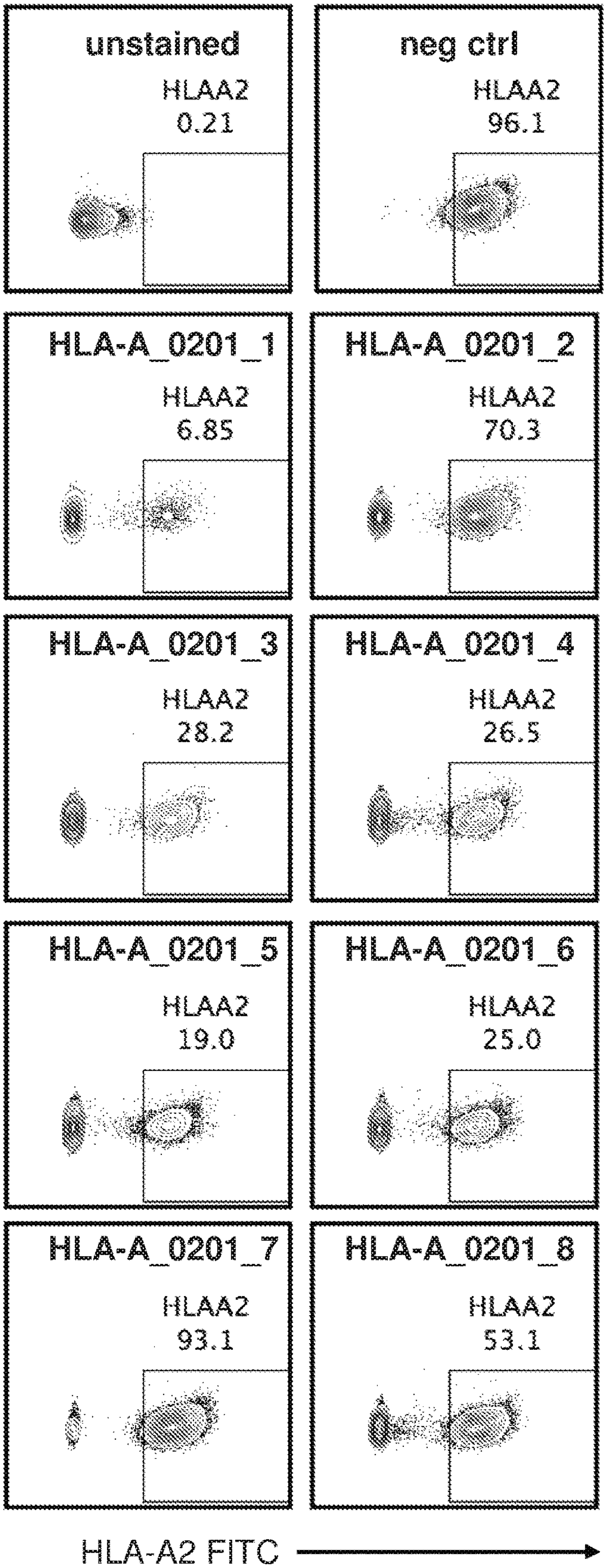
FIG. 22B shows flow cytometry analysis of HLA-A2 allele protein expression in primary $CD4^+$ T lymphocytes after electroporation of *S. pyogenes* Cas9 protein complexed to different HLA-A2 allele-specific modified gRNA molecules comprising a 5'-ARCA cap and a 3' polyA [20A] tail. To compare cell surface expression of HLA-A0201, untreated control (unedited) cells from the same donor (neg control) for which close to 100% of the cells are expected to express HLA-A2 and cells from the same donor that were not stained with fluorophore conjugated HLA-A2 antibody (and therefore would be 0% HLA-$A2^+$ (no antibody)) were used to set the gate for HLA-$A2^+$ cells (top 2 panels).
Figure 23:
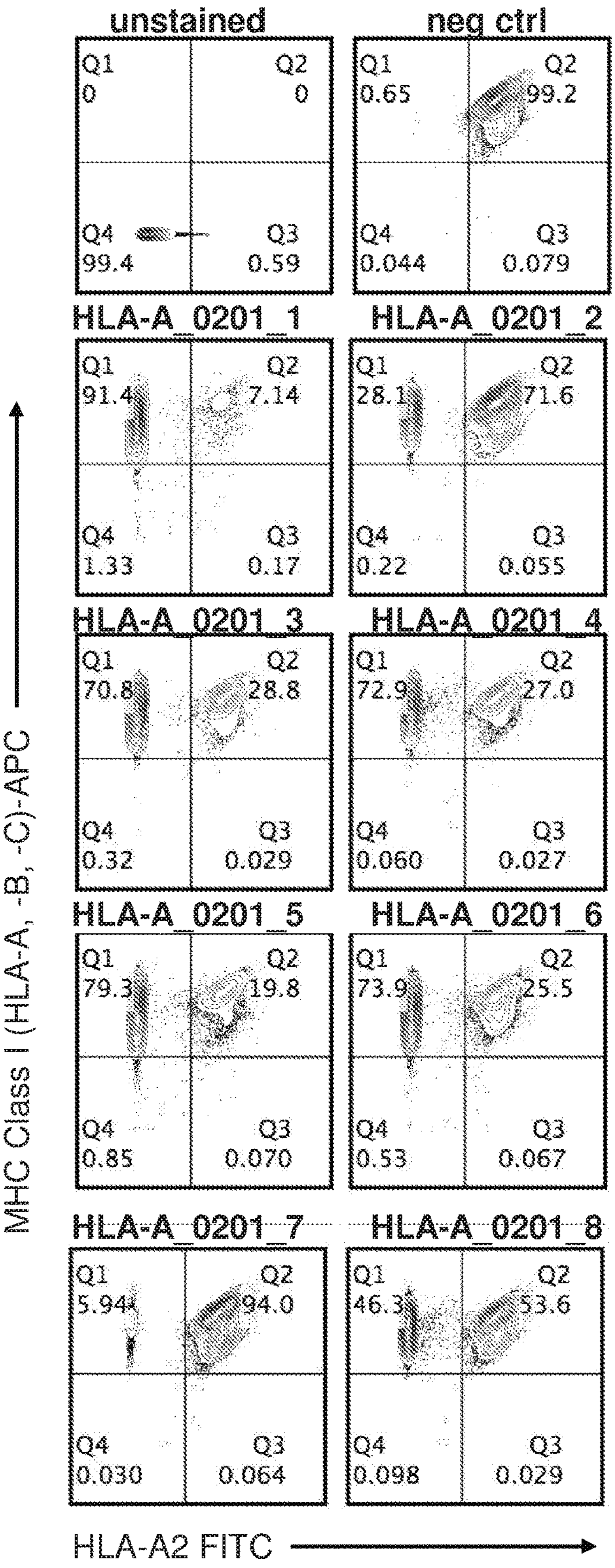
FIG. 23 shows flow cytometry analysis of HLA-A2 allele and total MHC Class 1 (not allele specific, detects common epitope of HLA-A, -B, -C) protein expression in primary $CD4^+$ T lymphocytes after electroporation of *S. pyogenes* Cas9 protein complexed to different HLA-A2 allele-specific modified gRNA molecules comprising a 5'-ARCA cap and a 3' polyA [20A] tail. Cells that were double positive for MHC Class I and HLA-A2 (which fall into Quadrant [Q] 2 or Q2 of flow cytometry plots (e.g., 7.14% of cells that were treated with HLA-A_0201_1 RNP) maintained both ClassI and HLA-A2 allele specific gene expression. Cells that were single positive for MHC Class I but negative for HLA-A2 (which fall into Q1 of flow cytometry plots (e.g., 91.4% of cells that were treated with HLA-A_0201_1 RNP) maintained MHC Class I antigens except for the HLA-A2 allele (e.g., lost protein expression of HLA-A2 after gene editing targeting that allele).

To evaluate allele-specific gene editing in donor cells, primary T lymphocytes ($CD4^+$ T cells) were isolated from the CB unit and the gRNAs listed in Table 34 were screened in these cells. Briefly, the modified HLA-A 02:01 and HLA-DRB1 04:02 allele specific gRNAs were precomplexed with *S. pyogenes* Cas9 protein to yield RNPs which were electroporated into donor T lymphocytes (Amaxa Nucleofector). Genomic DNA was isolated from the cells 3-4 days after RNP delivery, and the HLA-A locus PCR amplified from gDNA. Gene editing was evaluated by T7E1 endonuclease assay analysis (FIG. 22A) and by flow cytometry analysis with an HLA-A2 allele specific antibody (FITC conjugated anti-human HLA-A2, Biolegend catalog #343303) (FIG. 22B) in order to identify the most effective gRNA at allele specific editing of A*02:0. Flow cytometry analysis revealed up to 92% reduction in HLA-A2 protein expression on the surface of viable human T cells (FIG. 22B). This shows that the A*02:01 allele targeted gRNAs targeting the HLA-A locus are specific for the HLA-A2 allele. Cells co-stained with HLA-A2 allele specific antibody and MHC Class I (AlexaFluor 647 conjugated anti-human HLA-A, -B, -C, Biolegend Catalog #311416) could be subdivided into 2 fractions: cells that were HLA-$A2^-$ (knockdown of allele-specific gene expression) and MHC Class $I^+$ and cells that were HLA-$A2^+$ MHC Class $I^+$. This distinction between the two populations in their relative expression of MHC Class I cell surface antigens would support isolation through FACS or immunomagnetic sorting to obtain a purified population of cells that lack allele-specific expression of one HLA gene but maintain all other MHC Class I cell surface antigens (FIG. 23). On-target allele-specific editing was also conducted in T lymphocytes targeting DRB1*04:02 alleles with the same results shown in FIG. 21C. Cells co-stained with HLA-A2 allele specific antibody and MHC Class I (HLA-A, -B, -C) could be subdivided into 2 fractions: cells that were HLA-$A2^-$ and MHC Class $I^+$ and cells that were HLA-$A2^+$/MHC Class $I^+$. This distinction between the two populations in their relative expression of MHC Class I cell surface antigens would support isolation through FACS or immunomagnetic sorting to obtain a purified population of cells that lack allele-specific expression of one HLA gene, but maintain all other Class I cell surface antigens. In summary, this example shows allele-specific knockdown of multiple HLA genes in primary human blood cells.

Example 12: Knock Out of HLA Alleles to Facilitate Matching of HLA Genotypes

To decrease the likelihood of rejection of a transplanted HLA-mismatched allogeneic cell (e.g., an HSC), a recipient subject requiring transplantation is HLA typed (e.g., HLA-A, HLA-B and HLA-DRB1 polymorphisms are determined) at the 6 HLA alleles (2 alleles each at HLA-A, HLA-B and HLA-DRB1). Ideally, the recipient genotype is matched with a donor having the same 6/6 HLA alleles since a 6/6 HLA allele match is associated with a reduced risk of developing GVHD after transplantation. If no donor having a 6/6 allele match is available (e.g., from a bone marrow or cord blood HSC donor registry, or a related family member), but partially-matched donors having a 5/6, 4/6, 3/6 or 2/6 HLA allele match are available, the methods described herein may be used to reduce mismatching between the partially matched donor and recipient. As necessary, a single allele or multiple alleles (two, three, four, five, or six alleles) may be disrupted using the gene editing methods described herein to reduce the risk of developing GVHD an/or the severity of disease in the transplantation recipient. In all instances describing HLA allelic matching between a donor and a recipient in the examples below, the numerator indicates the number of matched alleles and the denominator indicates the number of expressed alleles.

The methods described herein may be used to modify donor blood cells (e.g., HSCs and T cells) to generate immune-compatible blood cells. For example, the methods may be used to disrupt (e.g., knockout) 1, 2 or 3 HLA alleles in a donor HSC to generate a cells matching HLA genotypes most frequently present in particular populations. For example, the most common 10 haplotypes for four ethnic groups in North America are listed in Tables 35-38 (see, e.g., National Marrow Donor Program HLA haplotype frequency data, available at bioinformatics.bethematchclinical.org/hla-resources/haplotype-frequencies/; Burdett et al., *Hum. Immunol.* 64 (10 Suppl): S6 (2003)).

TABLE 35

Most common 10 HLA-A, HLA-B and HLA-DRB1 haplotypes for individuals with European ancestry in the United States.

| HLA-A | HLA-B | HLA-DRB1 | European rank |
|---|---|---|---|
| 0101g | 0801g | 0301 | 1 |
| 0301g | 0702g | 1501 | 2 |
| 0201g | 4402g | 0401 | 3 |
| 0201g | 0702g | 1501 | 4 |
| 2902 | 4403 | 0701 | 5 |
| 0201g | 1501g | 0401 | 6 |
| 0101g | 5701 | 0701 | 7 |
| 0301g | 3501g | 0101 | 8 |
| 0201g | 4001g | 1302 | 9 |
| 3001 | 1302 | 0701 | 10 |

TABLE 36

Most common 10 HLA-A, HLA-B and HLA-DRB1 haplotypes for individuals with African American ancestry in the United States.

| HLA-A | HLA-B | HLA-DRB1 | African American rank |
|---|---|---|---|
| 3001 | 4201 | 0302 | 1 |
| 0101g | 0801g | 0301 | 2 |
| 6801g | 5802 | 1201g | 3 |
| 6802 | 1510 | 0301 | 4 |
| 3303 | 5301 | 0804 | 5 |
| 3601 | 5301 | 1101 | 6 |
| 0301g | 0702g | 1501 | 7 |
| 3402 | 4403 | 1503 | 8 |
| 2902 | 4403 | 0701 | 9 |
| 3001 | 4201 | 0302 | 10 |

TABLE 37

Most common 10 HLA-A, HLA-B and HLA-DRB1 haplotypes for individuals with Asian ancestry in the United States.

| HLA-A | HLA-B | HLA-DRB1 | Asian rank |
|---|---|---|---|
| 3303 | 5801g | 0301 | 1 |
| 0207g | 4601 | 0901 | 2 |
| 3303 | 4403 | 0701 | 3 |
| 3001 | 1302 | 0701 | 4 |

TABLE 37-continued

| Most common 10 HLA-A, HLA-B and HLA-DRB1 haplotypes for individuals with Asian ancestry in the United States. | | | |
|---|---|---|---|
| HLA-A | HLA-B | HLA-DRB1 | Asian rank |
| 3303 | 5801g | 1302 | 5 |
| 1101g | 1502 | 1202 | 6 |
| 2402g | 5201g | 1502 | 7 |
| 0101g | 5701 | 0701 | 8 |
| 3303 | 4403 | 1302 | 9 |
| 0101g | 3701 | 1001 | 10 |

TABLE 38

| Most common 10 HLA-A, HLA-B and HLA-DRB1 haplotypes for individuals with Hispanic/Latino ancestry in the United States: | | | |
|---|---|---|---|
| HLA-A | HLA-B | HLA-DRB1 | Hispanic rank |
| 2902 | 4403 | 0701 | 1 |
| 0101g | 0801g | 0301 | 2 |
| 0301g | 0702g | 1501 | 3 |
| 3002 | 1801g | 0301 | 4 |
| 3301 | 1402 | 0102 | 5 |
| 6803 | 3905 | 0407 | 6 |
| 2301g | 4403 | 0701 | 7 |
| 2402g | 3906 | 1406 | 8 |
| 0201g | 0702g | 1501 | 9 |
| 0206 | 3905 | 0407 | 10 |

For donors having a 3/6 HLA allele match to a recipient, a single HLA allele, 2 HLA alleles, or 3 HLA alleles can be disrupted to increase the degree of HLA matching, e.g., to increase HLA matching to 4/6, 5/6 or 6/6 allele match, respectively.

As indicated below, the methods described herein can be applied to any donor cell that is matched at 3/6 HLA alleles to a recipient. For example, when a donor and recipient have the HLA genotype listed below (Table 39), where the donor HLA genotype includes two most common European American haplotypes and the recipient has a haplotype match at allele 1 and any non-matching haplotype at allele 2, the methods described herein may be used to increase the degree of HLA matching by:

(a) Disruption (e.g., knockout) of a single allele (e.g., HLA-A*0301g, HLA-B*0702, HLA-DRB1*1501) to generate a 4/6 match.

(b) Multiplex disruption (e.g., knockout) of 2 alleles (e.g., HLA-A*0301g and HLA-B*0702g, HLA-A*0301g and HLA-DRB1*1501, HLA-B*0702g and HLA-DRB1*1501) to generate a 5/6 HLA match.

(c) Multiplex disruption (e.g., knockout) of 3 alleles (e.g., HLA-A*0301g, HLA-B*0702g. and HLA-DRB1*1501) to generate a 6/6 HLA match.

TABLE 39

| | Donor | | | Recipient | | |
|---|---|---|---|---|---|---|
| | HLA Class I | | HLA Class II | HLA Class I | | HLA Class II |
| | HLA-A* | HLA-B* | HLA-A* | HLA-A* | HLA-B* | HLA-DRB1* |
| Allele 1 | 0101g | 0801g | 0301 | 0101g | 0801g | 0301 |
| Allele 2 | 0301g | 0702g | 1501 | Any non-matching allele, e.g., 2402 | Any non-matching allele, e.g., 3502 | Any non-matching allele, e.g., 1104 |

For example, when a donor and recipient have the HLA genotype listed below (Table 40), where the donor HLA genotype includes two most common African American haplotypes and the recipient has a haplotype match at allele 1 and any non-matching haplotype at allele 2, the methods described herein may be used to increase the degree of HLA matching by:

(a) Disruption (e.g., knockout) of a single allele (e.g., HLA-A*0101g, HLA-B*0801g or HLA-DRB1*0301) to generate a 4/6 HLA match.
(b) Multiplex disruption (e.g., knockout) of 2 alleles (e.g., HLA-A*0101g and HLA-B*0801g, HLA-A*0101g and HLA-DRB1*0301, HLA-B*0801g and HLA-DRB1*0301) to generate a 5/6 HLA match.
(c) Multiplex disruption (e.g., knockout) of 3 alleles (e.g., HLA-A*0101g, HLA-B*0801g, and HLA-DRB1*0301) to generate a 6/6 HLA match.

TABLE 40

| | Donor | | | Recipient | | |
|---|---|---|---|---|---|---|
| | HLA Class I | | HLA Class II | HLA Class I | | HLA Class II |
| | HLA-A* | HLA-B* | HLA-A* | HLA-A* | HLA-B* | HLA-DRB1* |
| Allele 1 | 3001 | 4201 | 0302 | 3001 | 4201 | 0302 |
| Allele 2 | 0101g | 0801g | 0301 | Any non-matching allele, e.g. 2402g | Any non-matching allele, e.g. 3543g | Any non-matching allele, e.g. 0407 |

For example, when a donor and recipient have the HLA genotype listed below (Table 41), where the donor HLA genotype includes two most common Asian haplotypes and the recipient has a haplotype match at allele 1 and any non-matching haplotype at allele 2, the methods described herein may be used to increase the degree of HLA matching by:

(a) Disruption (e.g., knockout) of a single allele (e.g., HLA-A*0207g, HLA-B*4601 or HLA-DRB1*0901) to generate a 4/6 HLA match.
(b) Multiplex disruption (e.g., knockout) of 2 alleles (e.g., HLA-A*0207g and HLA-B*4601, HLA-A*0207g and HLA-DRB1*0901, HLA-B*4601 and HLA-DRB1*0901) to generate a 5/6 HLA match.
(c) Multiplex disruption (e.g., knockout) of 3 alleles (e.g., HLA-A*0207g, HLA-B*4601, and HLA-DRB1*0901) to generate a 6/6 HLA match.

TABLE 41

| | Donor | | | Recipient | | |
|---|---|---|---|---|---|---|
| | HLA Class I | | HLA Class II | HLA Class I | | HLA Class II |
| | HLA-A* | HLA-B* | HLA-A* | HLA-A* | HLA-B* | HLA-DRB1* |
| Allele 1 | 3303 | 5801g | 0301 | 3303 | 5801g | 0301 |
| Allele 2 | 0207g | 4601 | 0901 | Any non-matching allele, e.g., 1101g | Any non-matching allele, e.g., 5201g | Any non-matching allele, e.g., 1501 |

For example, when a donor and recipient have the HLA genotype listed below (Table 42), where the donor HLA genotype includes two most common Hispanic/Latino haplotypes and the recipient has a haplotype match at allele 1 and any non-matching haplotype at allele 2, the methods described herein may be used to increase the degree of HLA matching by:

(a) Disruption (e.g., knockout) of a single allele (e.g., HLA-A*0101g, HLA-B*0801g or HLA-DRB1*0301) to generate a 4/6 HLA match.

(b) Multiplex disruption (e.g., knockout) of 2 alleles (e.g., HLA-A*0101g and HLA-B*0801g, HLA-A*0101g and HLA-DRB1*0301, HLA-B*0801g and HLA-DRB1*0301) to generate a 5/6 HLA match.

(c) Multiplex disruption (e.g., knockout) of 3 alleles (e.g., HLA-A*0207g, HLA-B*4601, and HLA-DRB1*0301) to generate a 6/6 HLA match.

TABLE 42

| | Donor | | | Recipient | | |
|---|---|---|---|---|---|---|
| | HLA Class I | | HLA Class II | HLA Class I | | HLA Class II |
| | HLA-A* | HLA-B* | HLA-A* | HLA-A* | HLA-B* | HLA-DRB1* |
| Allele 1 | 2902 | 4403 | 0701 | 2902 | 4403 | 0701 |
| Allele 2 | 0101g | 0801g | 0301 | Any non-matching allele, e.g., 3102 | Any non-matching allele, e.g., 3501g | Any non-matching allele, e.g., 0407 |

As indicated below, the methods described herein can be applied to any donor cell that is matched at 4/6 HLA alleles to a recipient. For example, when a donor and recipient have the HLA genotype listed below (Table 43), where the donor HLA genotype includes two most common Hispanic/Latino haplotypes and the recipient has a haplotype match at allele 1 and any non-matching haplotype at allele 2 (e.g., at HLA-A), the methods described herein may be used to increase the degree of HLA matching by:

(a) Disruption (e.g., knockout) of a single allele (e.g., HLA-B*0801g or HLA-DRB1*0301) to generate a 5/6 HLA match.

(b) TMultiplex disruption (e.g., knockout) of 2 alleles (e.g., HLA-B*0801g and HLA-DRB1*0301) to generate a 6/6 HLA match.

TABLE 43

| | Donor | | | Recipient | | |
|---|---|---|---|---|---|---|
| | HLA Class I | | HLA Class II | HLA Class I | | HLA Class II |
| | HLA-A* | HLA-B* | HLA-A* | HLA-A* | HLA-B* | HLA-DRB1* |
| Allele 1 | 2902 | 4403 | 0701 | 2902 | 4403 | 0701 |
| Allele 2 | 0101g | 0801g | 0301 | 0101g | 1402 | 0405 |

As indicated below, the methods described herein can be applied to any donor cell that is matched at 5/6 HLA alleles to a recipient. For example, when a donor and recipient have the HLA genotype listed below (Table 44), where the donor HLA genotype includes two most common Hispanic/Latino haplotypes and the recipient has a haplotype match at allele 1 and any haplotype that matches at two of three HLA loci at allele 2, the methods described herein may be used to increase the degree of HLA matching by:

(a) Disruption (e.g., knockout) of a single allele (e.g., HLA-DRB1*0301) to generate a 6/6 HLA match.

TABLE 44

| | Donor | | | Recipient | | |
|---|---|---|---|---|---|---|
| | HLA Class I | | HLA Class II | HLA Class I | | HLA Class II |
| | HLA-A* | HLA-B* | HLA-A* | HLA-A* | HLA-B* | HLA-DRB1* |
| Allele 1 | 2902 | 4403 | 0701 | 2902 | 4403 | 0701 |
| Allele 2 | 0101g | 0801g | 0301 | Any non-matching allele, e.g., 0101g | Any non-matching allele, e.g., 0801g | Any non-matching allele, e.g., 1303 |

Example 16: Gene Disruption (e.g., Knockout) of HLA Alleles to Facilitate Matching of HLA Genotypes that are Most Likely to be Unmatched in Minority or Underrepresented Populations The following text and tables describe the knockout of 1, 2 or 3 HLA alleles in donor cells that to generate an improved HLA match in the most commonly unmatched HLA haplotypes in recipients requiring donor tissue or HSCT.

For example, the following HLA haplotypes are common in individuals of Asian descent and uncommon in any other subjects in the United States National Marrow Donor Program (NMDP) (Table 45). Therefore, a recipient of Asian ancestry and/or any of the following haplotypes may not find a 6/6 HLA match within the NMDP.

TABLE 45

HLA haplotypes that are common in individuals of Asian descent and uncommon in general donor pool of the NMDP

| HLA Class I | | HLA Class II |
|---|---|---|
| HLA-A* | HLA-B* | HLA-DRB1* |
| 2 | 46 | 09:01 |
| 33 | 44 | 13:02 |
| 11 | 75 | 12:02 |
| 24 | 35 | 12:02 |
| 2 | 46 | 08:03 |
| 11 | 62 | 04:06 |
| 24 | 54 | 04:05 |
| 24 | 38 | 15:02 |
| 24 | 75 | 12:02 |
| 11 | 46 | 09:01 |
| 2 | 13 | 12:02 |

For example, the following HLA haplotypes are common in individuals of African American descent and uncommon in any other subjects in the United States National Marrow Donor Program (NMDP) (Table 0.46). Therefore, a recipient of African American ancestry and/or any of the following haplotypes may not find a 6/6 match within the NMDP.

TABLE 46

HLA haplotypes that are common in individuals of African American descent and uncommon in general donor pool of the NMDP

| HLA Class I | | HLA Class II |
|---|---|---|
| HLA-A* | HLA-B* | HLA-DRB1* |
| 68 | 58 | 1201 |
| 36 | 53 | 1101 |
| 34 | 44 | 1503 |
| 30 | 42 | 0804 |

TABLE 46-continued

HLA haplotypes that are common in individuals of African American descent and uncommon in general donor pool of the NMDP

| HLA Class I | | HLA Class II |
|---|---|---|
| HLA-A* | HLA-B* | HLA-DRB1* |
| 30 | 57 | 1301 |
| 68 | 53 | 1503 |

For example, the following HLA haplotypes are common in individuals of Hispanic/Latino descent and uncommon in any other subjects in the United States National marrow donor program (NMDP) (Table 47). Therefore, a recipient with Hispanic/Latino ancestry and/or any of the following haplotypes may not find a 6/6 match within the NMDP.

TABLE 47

HLA haplotypes that are common in individuals of Hispanic descent and uncommon in general donor pool of the NMDP

| HLA Class I | | HLA Class II |
|---|---|---|
| HLA-A* | HLA-B* | HLA-DRB1* |
| 2 | 35 | 0802 |
| 68 | 39 | 0407 |
| 2 | 39 | 0407 |
| 24 | 39 | 1406 |
| 2 | 35 | 0407 |
| 2 | 62 | 0802 |
| 31 | 35 | 0802 |
| 24 | 35 | 0407 |
| 24 | 61 | 0802 |

The HLA haplotypes listed in Tables 45, 46 and 47 are common within specific populations but are uncommon in the donor pool, especially in the Caucasian individual donor pool, which comprises the large majority of the United States National Marrow Donor Program (NMDP). A recipient having a haplotype listed in Tables 56, 57 or 58 is less likely to find a 6/6 match in the NMDP. The methods described herein may be used for the disruption (e.g., knockout) of one, two or three HLA alleles in a donor cell to improve HLA matching for recipients, including and especially those with HLA haplotypes listed in Tables 45, 46 and 47.

Tables 48-50 describe examples of the appropriate HLA-gene disruption (e.g., knock-out) strategies for donor cells that can be applied to the most commonly unmatched minority haplotypes (e.g., the haplotypes listed in Tables 45, 46, and 47). In Tables 48-50, for each of the most common haplotypes in minority populations (who are underrepresented in the donor pool and are thus at risk for not finding an ideal 6/6 HLA match), the most common haplotype matches are suggested, wherein gene disruption (e.g., knock-out) of a single HLA locus in a donor cell will improve HLA matching.

TABLE 48

For Asian Recipient:

| Example | Allele | Recipient haplotype A | Recipient haplotype B | Recipient haplotype DRB1 | Nth most common haplotype in recipient group | Disruption (e.g., knock out) of HLA_on allele 2 | Donor haplotype A | Donor haplotype B | Donor haplotype DRB1 | Nth Most Frequent allele in NMDP Registry Asian | AFA | CAU | HIS |
|---|---|---|---|---|---|---|---|---|---|---|---|---|---|
| | 1 | 3001 | 1302 | 701 | 4 | | 3001 | 1302 | 701 | | | 10 | |
| 1 | 2 | 2 | 46 | 0901 | 3 | HLA-B | 2 | 62 | 0901 | 35 | 1351 | 257 | 442 |
| 2 | 2 | 2 | 46 | 0901 | 3 | HLA-B | 2 | 51 | 0901 | 53 | 679 | 265 | 423 |
| 3 | 2 | 2 | 46 | 0901 | 3 | HLA-B | 2 | 60 | 0901 | 19 | 1625 | 322 | 1660 |
| 4 | 2 | 2 | 46 | 0901 | 3 | HLA-B | 2 | 7 | 0901 | 1159 | 344 | 353 | 982 |
| 5 | 2 | 2 | 46 | 0901 | 3 | HLA-B | 2 | 44 | 0901 | 1353 | 1485 | 537 | 331 |
| 6 | 2 | 33 | 44 | 1302 | 5 | HLA-DRB1 | 33 | 44 | 0102 | | 1171 | 889 | |
| 7 | 2 | 33 | 44 | 1302 | 5 | HLA-DRB1 | 33 | 44 | 0701 | | 440 | 1023 | |
| 8 | 2 | 33 | 44 | 1302 | 5 | HLA-DRB1 | 33 | 44 | 1503 | | 324 | 11884 | |
| 9 | 2 | 11 | 75 | 1202 | 9 | HLA-DRB1 | 11 | 75 | 1502 | 692 | 6066 | 5855 | 17589 |
| 10 | 2 | 11 | 75 | 1202 | 9 | HLA-DRB1 | 11 | 75 | 0901 | 228 | 18040 | 8520 | 17598 |
| 11 | 2 | 11 | 75 | 1202 | 9 | HLA-DRB1 | 11 | 75 | 1501 | 51 | 6689 | 16385 | 4740 |
| 12 | 2 | 11 | 75 | 1202 | 9 | HLA-A | 2 | 75 | 1202 | 30 | 4233 | 7386 | 4105 |
| 13 | 2 | 11 | 75 | 1202 | 9 | HLA-A | 24 | 75 | 1202 | 18 | 4411 | 7615 | 3425 |
| 14 | 2 | 11 | 75 | 1202 | 9 | HLA-A | 74 | 75 | 1202 | 3311 | 2889 | 28016 | 28169 |
| 15 | 2 | 24 | 35 | 1202 | 11 | HLA-A | 2 | 35 | 1202 | 481 | 4388 | 5771 | 14775 |
| 16 | 2 | 24 | 35 | 1202 | 11 | HLA-DRB1 | 24 | 35 | 1104 | 84 | 670 | 25 | 12 |
| 17 | 2 | 24 | 35 | 1202 | 11 | HLA-DRB1 | 24 | 35 | 0103 | 3573 | 1159 | 146 | 689 |
| 18 | 2 | 24 | 35 | 1202 | 11 | HLA-DRB1 | 24 | 35 | 1401 | 317 | 1144 | 167 | 184 |
| 19 | 2 | 24 | 35 | 1202 | 11 | HLA-DRB1 | 24 | 35 | 0101 | 620 | 908 | 179 | 496 |
| 20 | 2 | 24 | 35 | 1202 | 11 | HLA-DRB1 | 24 | 35 | 1202 | 11 | 554 | 4308 | 2171 |
| 21 | 2 | 24 | 35 | 1202 | 11 | HLA-B | 24 | 62 | 1202 | 100 | 3786 | 5038 | 2488 |
| 22 | 2 | 24 | 35 | 1202 | 11 | HLA-B | 24 | 27 | 1202 | 210 | 18924 | 7567 | 5083 |
| 23 | 2 | 24 | 35 | 1202 | 11 | HLA-B | 24 | 75 | 1202 | 18 | 4411 | 7615 | 3425 |
| 24 | 2 | 24 | 35 | 1202 | 11 | HLA-B | 24 | 13 | 1202 | 108 | 18812 | 8609 | 9014 |
| 25 | 2 | 2 | 46 | 0803 | 12 | HLA-B | 2 | 51 | 0803 | 263 | 2501 | 347 | 827 |
| 26 | 2 | 2 | 46 | 0803 | 12 | HLA-B | 2 | 38 | 0803 | 89 | 14962 | 3782 | 14824 |
| 27 | 2 | 2 | 46 | 0803 | 12 | HLA-B | 2 | 46 | 0803 | 12 | 11738 | 4401 | 5619 |

TABLE 49

For African American Recipient:

| Example | Allele | Recipient haplotype A | Recipient haplotype B | Recipient haplotype DRB1 | Nth most common haplotype in recipient group | Disruption (e.g., knock out) of HLA_on allele 2: | Donor haplotype A | Donor haplotype B | Donor haplotype DRB1 | Nth Most Frequent allele in NMDP Registry Asian | AFA | CAU | HIS |
|---|---|---|---|---|---|---|---|---|---|---|---|---|---|
| | 1 | 0101g | 0801g | 301 | 2 | N/A | 0101g | 0801g | 301 | 40 | 2 | 1 | 2 |
| 29 | 2 | 36 | 53 | 1101 | 6 | HLA-DRB1 | 36 | 53 | 0301 | 9169 | 240 | 12182 | 3646 |
| 30 | 2 | 36 | 53 | 1101 | 6 | HLA-DRB1 | 36 | 53 | 0804 | 24834 | 192 | 12184 | 4206 |
| 31 | 2 | 36 | 53 | 1101 | 6 | HLA-DRB1 | 36 | 53 | 1101 | 4434 | 6 | 3758 | 431 |
| 32 | 2 | 36 | 53 | 1101 | 6 | HLA-DRB1 | 36 | 53 | 1503 | 24833 | 123 | 9287 | 1396 |
| 33 | 2 | 34 | 44 | 1503 | 7 | HLA-DRB1 | 34 | 44 | 1302 | 2886 | 366 | 12047 | 1365 |
| 34 | 2 | 34 | 44 | 1503 | 7 | HLA-DRB1 | 34 | 44 | 0701 | 1832 | 656 | 3866 | 1782 |
| 35 | 2 | 34 | 44 | 1503 | 7 | HLA-DRB1 | 34 | 44 | 1301 | 6439 | 1364 | 3654 | 12872 |
| 36 | 2 | 34 | 44 | 1503 | 7 | HLA-B | 34 | 53 | 1503 | 24221 | 49 | 7996 | 1572 |
| 37 | 2 | 30 | 42 | 0804 | 7 | HLA-B | 30 | 35 | 0804 | 20439 | 948 | 2604 | 21750 |
| 38 | 2 | 30 | 42 | 0804 | 7 | HLA-B | 30 | 53 | 0804 | 7587 | 62 | 5635 | 1419 |
| 39 | 2 | 30 | 42 | 0804 | 7 | HLA-DRB1 | 30 | 42 | 0302 | 2148 | 1 | 1353 | 62 |
| 40 | 2 | 30 | 57 | 1301 | 15 | HLA-DRB1 | 30 | 57 | 0701 | 2029 | 232 | 854 | 1651 |
| 41 | 2 | 30 | 57 | 1301 | 15 | HLA-DRB1 | 30 | 57 | 1503 | 20944 | 100 | 5094 | 1524 |
| 42 | 2 | 30 | 57 | 1301 | 15 | HLA-B | 30 | 13 | 1301 | 594 | 2367 | 1041 | 946 |
| 43 | 2 | 30 | 57 | 1301 | 15 | HLA-B | 30 | 58 | 1301 | 3798 | 478 | 6477 | 1158 |
| 44 | 2 | 30 | 57 | 1301 | 15 | HLA-A | 1 | 57 | 1301 | 452 | 1004 | 140 | 672 |
| 45 | 2 | 68 | 53 | 1503 | 20 | HLA-DRB1 | 68 | 53 | 1501 | 26442 | 2181 | 1903 | 2341 |
| 46 | 2 | 68 | 53 | 1503 | 20 | HLA-DRB1 | 68 | 53 | 1302 | 1998 | 54 | 185 | 120 |
| 47 | 2 | 68 | 53 | 1503 | 20 | HLA-DRB1 | 68 | 53 | 1303 | 11416 | 38 | 4379 | 867 |
| 48 | 2 | 68 | 53 | 1503 | 20 | HLA-B | 68 | 7 | 1503 | 5433 | 24 | 7199 | 365 |

TABLE 50

| For Hispanic Recipient: | | | | | | | | | | | | | |
|---|---|---|---|---|---|---|---|---|---|---|---|---|---|
| | | Recipient haplotype | | | Nth most common haplotype in recipient | Disruption (e.g., knock out) of HLA_on | Donor haplotype | | | Nth Most Frequent allele in NMDP Registry | | | |
| | Allele | A | B | DRB1 | group | allele 2: | A | B | DRB1 | Asian | AFA | CAU | HIS |
| | 1 | 2902 | 4403 | 701 | 1 | | 2902 | 4403 | 701 | 1307 | 9 | 5 | 1 |
| 50 | 2 | 2 | 35 | 0802 | 3 | HLA-DRB1 | 2 | 62 | 0802 | 642 | 3771 | 1194 | 14 |
| 51 | 2 | 2 | 35 | 0802 | 3 | HLA-DRB1 | 2 | 39 | 0802 | 273 | 1981 | 1620 | 41 |
| 52 | 2 | 2 | 35 | 0802 | 3 | HLA-DRB1 | 2 | 61 | 0802 | 201 | 2971 | 2146 | 22 |
| 53 | 2 | 68 | 39 | 0407 | 5 | HLA-B | 68 | 35 | 0407 | 5184 | 1810 | 1357 | 31 |
| 54 | 2 | 2 | 39 | 0407 | 6 | HLA-DRB1 | 2 | 39 | 0101 | 1793 | 1329 | 235 | 576 |
| 55 | 2 | 24 | 39 | 1406 | 8 | HLA-A | 2 | 39 | 1406 | 2087 | 4227 | 3406 | 51 |
| 56 | 2 | 2 | 35 | 0407 | 10 | HLA-A | 24 | 35 | 0407 | 2307 | 723 | 1167 | 18 |
| 57 | 2 | 2 | 62 | 0802 | 14 | HLA-B | 2 | 35 | 0802 | 278 | 1161 | 952 | 3 |
| 58 | 2 | 31 | 35 | 0802 | 16 | HLA-A | 2 | 35 | 0802 | 278 | 1161 | 952 | 3 |
| 59 | 2 | 24 | 35 | 0407 | 18 | HLA-A | 2 | 35 | 0407 | 945 | 882 | 862 | 10 |
| 60 | 2 | 24 | 61 | 0802 | 19 | HLA-B | 24 | 39 | 0802 | 1446 | 3425 | 2947 | 82 |
| 61 | 2 | 24 | 61 | 0802 | 19 | HLA-A | 2 | 61 | 0802 | 201 | 2971 | 2146 | 22 |

By selecting commonly represented haplotypes for modification, e.g., by gene disruption (e.g., knockout) of 1, 2, or 3 HLA allele(s)), the likelihood of matching underrepresented recipients is increased. An alternative NMDP-based database can be created to facilitate determination of the most appropriate HLA modifications, e.g., by gene disruption (e.g., knockout) of 1, 2 or 3 HLA allele(s), that can be used for transplantation in the greatest quantity of recipients. The methods and donor cells will be chosen based on availability of donor tissue, recipient haplotype, and predicted efficacy of a specific HLA knockout.

For example, where an African American recipient having the genotype HLA-A68, HLA-B53, HLA-DRB1-1503; HLA-A0101g, HLA-B0801g, HLA-DRB1*0301 requires an HSCT, a caucasian donor with the genotype HLA-A68, HLA-B53, HLA-DRB1*1302; HLA-A0101g, HLA-B0801g, HLA-DRB1-0301 is likely to be available because these haplotypes are the 185th and 1st most common haplotypes, respectively, in the caucasian donor pool. Gene disruption (e.g., knockout) of the mismatched HLA-DRB1*1302 allele in donor cells using the methods described herein will generate an effective 6/6 HLA match. Alternatively, if gene disruption at a HLA-B locus is more desirable (e.g., because of increased survival rates or lower incidence of GVHD), a different donor may be selected. Ex vivo HLA-B7 gene disruption (e.g., knockout) in donor HSCs with the genotype HLA-A68, HLA-B7, HLA-DQ-1503; HLA-0101g, HLA-0801g, HLA-DQ-0301 may be used, as these haplotypes are the 24th and 2nd most common haplotypes, respectively, in the African American donor pool.

The NMDP database, or any organ donor database, can be mined for common HLA haplotypes that, if disrupted (e.g., knocked out) at one or more HLA loci (e.g., HLA-A, HLA-B or HLA-DRB1), will provide matched donor cells for the greatest population. Alternatively, the NMDP database, or any organ donor database, can be mined for common HLA haplotypes that, if disrupted (e.g., knocked out) at a single HLA locus (e.g., HLA-A, HLA-B or HLA-DRB1), will provide matched donor cells for recipients most unlikely to find matching donor tissue or HSCs.

For example, in a recipient with who is found to have a match at 3/6 HLA alleles, the methods described herein can be used to:

(a) Disrupt (e.g., knockout) a single HLA allele (e.g., HLA-A, HLA-B or HLA-DRB1) of the donor cell to produce an HLA match of the donor to the recipient at 3/6 HLA alleles (with 1/6 donor alleles not being expressed), for an effective 4/6 match regarding foreign antigen recognition). Disruption of a single HLA donor allele will effectively create a 4/6 match which may decrease the risk of developing and/or severity of GVHD in the recipient.

(b) Disrupt (e.g., knockout) two HLA alleles (e.g., an HLA-A allele and an HLA-B allele, an HLA-A allele and a HLA-DRB1 allele, or an HLA-B allele and an HLA-DRB1 allele) of the donor cell to produce an HLA match of the donor to the recipient at 3/6 HLA alleles (with 2/6 donor alleles not being expressed), for an effective 5/6 match regarding foreign antigen recognition. Disruption of a two HLA donor alleles will effectively create a 5/6 match which may decrease the risk of developing and/or severity of GVHD in the recipient.

(c) Disrupt (e.g., knockout) three HLA alleles (e.g., an HLA-A allele, an HLA-B allele, and an HLA-DRB1 allele) of the donor cell to produce an HLA match of the donor to the recipient at 3/6 HLA alleles (with 3/6 donor alleles not being expressed), for an effective 6/6 match regarding foreign antigen recognition. Disruption of a three HLA donor alleles will effectively create a 6/6 match which may decrease the risk of developing and/or severity of GVHD in the recipient.

For example, in a recipient with who is found to have a match at 4/6 HLA alleles, the methods described herein can be used to:

(a) Disrupt (e.g., knockout) a single HLA allele (e.g., HLA-A, HLA-B or HLA-DRB1) of the donor cell to produce an HLA match of the donor to the recipient at 4/6 HLA alleles (with 1/6 donor alleles not being expressed), for an effective 5/6 match regarding foreign antigen recognition). Disruption of a single HLA donor allele will effectively create a 5/6 match which may decrease the risk of developing and/or severity of GVHD in the recipient.

(b) Disrupt (e.g., knockout) two HLA alleles (e.g., an HLA-A allele and an HLA-B allele, an HLA-A allele and a HLA-DRB1 allele, or an HLA-B allele and an HLA-DRB1 allele) of the donor cell to produce an HLA match of the donor to the recipient at 4/6 HLA alleles (with 2/6 donor alleles not being expressed), for an effective 6/6 match regarding foreign antigen recognition. Disruption of a two HLA donor alleles will effectively create a 6/6 match which may decrease the risk of developing and/or severity of GVHD in the recipient.

For example, if a recipient has the genotype HLA-A2 HLA-B46 HLA-DRB1 0901: HLA-A33 HLA-B44 HLA-DRB1*1302 and a donor is found with the genotype HLA-A2 HLA-B62 HLA-DRB1 0901: HLA-A33 HLA-B58 HLA-DRB1*1302, 4/6 HLA alleles match between the donor and recipient. Disruption (e.g., knock out) of HLA-B62 in the donor cell creates 4/6 matched alleles, one non-expressed (null) allele, and 1 mismatched allele. In such a situation, the effective HLA match is 5/6 which may, decrease the risk of developing and/or severity of GVHD in the recipient, as compared to a 4/6 HLA match.

For example, in a recipient with who is found to have a match at 5/6 HLA alleles, the methods described herein can be used to:

(c) Disrupt (e.g., knockout) a single HLA allele (e.g., HLA-A, HLA-B or HLA-DRB1) of the donor cell to produce an HLA match of the donor to the recipient at 5/6 HLA alleles (with 1/6 donor alleles not being expressed), for an effective 6/6 match regarding foreign antigen recognition). Disruption of a single HLA donor allele will effectively create a 6/6 match which may decrease the risk of developing and/or severity of GVHD in the recipient.

For example, if a recipient has the haplotype HLA-A2 HLA-B46 HLA-DR0901: HLA-A33 HLA-B44 HLA-DR1302 and a donor is found with the haplotype HLA-A2 HLA-B62 HLA-DR0901: HLA-A33 HLA-B44 HLA-DR1302, 5/6 HLA alleles match between the donor and recipient. Disruption (e.g., knock out) of HLA-B62 in the donor cell creates 5/6 matched alleles and one non-expressed (null) allele. In such a situation, the effective HLA match is 6/6 which may decrease the risk of developing and/or severity of GVHD in the recipient, as compared to a 5/6 HLA match.

For example, an Asian recipient with the genotype HLA-A*3001 2, HLA-B*1302 46, HLA-DRB1*701 0901 can receive a donor HSC transplantation from a donor with the following genotype: HLA-A*3001 2, HLA-B*1302 62, HLA-DRB1*701 0901, following ex vivo disruption (e.g., knock-out) of HLA-B62 in the donor cell. The donor cell will have the genotype HLA-A*3001 2, HLA-B*1302/–, HLA-DRB1*701 0901, for an effective 6/6 match with recipient genotype HLA-A*3001 2, HLA-B*1302 46, HLA-DRB1*701 0901. Donor HSCs with the haplotype HLA-A*3001, HLA-B*1302, HLA-DRB1*701 are the 10th most frequent HLA haplotype in those of caucasian descent available in the NMDP. Donor HSCs with the haplotype HLA-A2, HLA-B62, and HLA-DRB1-0901 are the 62nd most frequent HLA haplotype in those of caucasian descent available in the NMDP. Therefore, a donor genotype of HLA-A*3001 2, HLA-B*1302 62, HLA-DRB1*701 0901 is likely to be available for donation to a recipient.

For example, an Asian recipient with the genotype HLA-A*3001, HLA-B*1302, HLA-DRB1*701; HLA-A2, HLA-B46, HLA-DRB1-0901 can receive a donor HSC transplantation from a donor with the following genotype: HLA-A*3001, HLA-B*1302, HLA-DRB1*701; HLA-A2, HLA-B60, HLA-DRB1-0901, following ex vivo disruption (e.g., knock-out) of HLA-B in the donor cell. The donor cell will have the genotype HLA-A*3001, HLA-B*1302, HLA-DRB1*701; HLA-A2. HLA-B–, HLA-DRB1-0901, for an effective 6/6 match with recipient genotype HLA-A*3001, HLA-B*1302, HLA-DRB1*701; HLA-A2, HLA-B46, HLA-DRB1-0901. Donor HSCs with the haplotype HLA-A*3001, HLA-B*1302, HLA-DRB1*701 are the 10th most frequent HLA haplotype in those of caucasian descent available in the NMDP. Donor HSCs with the haplotype HLA-A2, HLA-B60, and HLA-DRB1-0901 are the 19th most frequent HLA haplotype in those of Asian descent available in the NMDP. Therefore, a donor genotype of HLA-A*3001, HLA-B*1302, HLA-DRB1*701; HLA-A2, HLA-B60, HLA-DRB1-0901 is likely to be available for donation to a recipient.

For example, an African American recipient with the genotype:

| Allele | A | B | DRB1 |
|---|---|---|---|
| 1 | 0101g | 0801g | 301 |
| 2 | 36 | 53 | 1101 |

can receive a donor HSC transplantation from a donor with the following genotype:

| Allele | A | B | DRB1 |
|---|---|---|---|
| 1 | 0101g | 0801g | 301 |
| 2 | 36 | 53 | 0804 |

following ex vivo disruption (e.g., knock-out) of HLA-DRB1*0804 in the donor cell. The donor cell will have the genotype:

| Allele | A | B | DRB1 |
|---|---|---|---|
| 1 | 0101g | 0801g | 301 |
| 2 | 36 | 53 | null |

for an effective 6/6 match with recipient genotype.

For example, an African American recipient with the genotype:

| Allele | A | B | DRB1 |
|---|---|---|---|
| 1 | 0101g | 0801g | 301 |
| 2 | 68 | 53 | 1503 |

can receive a donor HSC transplantation from a donor with the following genotype:

| Allele | A | B | DRB1 |
|---|---|---|---|
| 1 | 0101g | 0801g | 301 |
| 2 | 68 | 7 | 1503 |

following ex vivo disruption (e.g., knock-out) of HLA-DRB1*1503 in the donor cell. The donor cell will have the genotype:

| Allele | A | B | DRB1 |
|---|---|---|---|
| 1 | 0101g | 0801g | 301 |
| 2 | 36 | 53 | null |

for an effective 6/6 match with recipient genotype.

For example, a Hispanic/Latino recipient with the genotype:

| Allele | A | B | DRB1 |
|---|---|---|---|
| 1 | 2902 | 4403 | 701 |
| 2 | 2 | 35 | 0802 |

can receive a donor HSC transplantation from a donor with the following genotype:

| Allele | A | B | DRB1 |
|---|---|---|---|
| 1 | 2902 | 4403 | 701 |
| 2 | 2 | 62 | 0802 |

following ex vivo disruption (e.g., knock-out) of HLA-62 in the donor cell. The donor cell will have the genotype:

| Allele | A | B | DRB1 |
|---|---|---|---|
| 1 | 2902 | 4403 | 701 |
| 2 | 2 | null | 0802 |

for an effective 6/6 match with recipient genotype.

For example, a Hispanic/Latino recipient with the genotype:

| Allele | A | B | DRB1 |
|---|---|---|---|
| 1 | 2902 | 4403 | 701 |
| 2 | 68 | 39 | 0407 |

can receive a donor HSC transplantation from a donor with the following genotype:

| Allele | A | B | DRB1 |
|---|---|---|---|
| 1 | 2902 | 4403 | 701 |
| 2 | 68 | 35 | 0407 |

following ex vivo disruption (e.g., knock-out) of HLA-B*35 in the donor cell. The donor cell will have the genotype:

| Allele | A | B | DRB1 |
|---|---|---|---|
| 1 | 2902 | 4403 | 701 |
| 2 | 2 | null | 0802 |

for an effective 6/6 match with recipient genotype.

For example, a Hispanic recipient with the genotype:

| Allele | A | B | DRB1 |
|---|---|---|---|
| 1 | 2902 | 4403 | 701 |
| 2 | 24 | 39 | 1406 |

can receive a donor HSC transplantation from a donor with the following genotype:

| Allele | A | B | DRB1 |
|---|---|---|---|
| 1 | 2902 | 4403 | 701 |
| 2 | 2 | 39 | 1406 |

following ex vivo disruption (e.g., knock-out) of HLA-A*2 in the donor cell. The donor cell will have the genotype:

| Allele | A | B | DRB1 |
|---|---|---|---|
| 1 | 2902 | 4403 | 701 |
| 2 | null | 39 | 1406 |

for an effective 6/6 match with recipient genotype.

For example, a Hispanic recipient with the genotype:

| Allele | A | B | DRB1 |
|---|---|---|---|
| 1 | 2902 | 4403 | 701 |
| 2 | 2 | 35 | 0407 |

can receive a donor HSC transplantation from a donor with the following genotype:

| Allele | A | B | DRB1 |
|---|---|---|---|
| 1 | 2902 | 4403 | 701 |
| 2 | 24 | 35 | 0407 |

following ex vivo disruption (e.g., knock-out) of HLA-A*24 in the donor cell. The donor cell will have the genotype:

| Allele | A | B | DRB1 |
|---|---|---|---|
| 1 | 2902 | 4403 | 701 |
| 2 | null | 35 | 0407 |

for an effective 6/6 match with recipient genotype.

For example, a Hispanic recipient with the genotype:

| Allele | A | B | DRB1 |
|---|---|---|---|
| 1 | 2902 | 4403 | 701 |
| 2 | 2 | 62 | 0802 |

can receive a donor HSC transplantation from a donor with the following genotype:

| Allele | A | B | DRB1 |
|---|---|---|---|
| 1 | 2902 | 4403 | 701 |
| 2 | 2 | 35 | 0802 |

following ex vivo disruption (e.g., knock-out) of HLA-B*35 in the donor cell. The donor cell will have the genotype:

| Allele | A | B | DRB1 |
|---|---|---|---|
| 1 | 2902 | 4403 | 701 |
| 2 | 2 | null | 0802 |

for an effective 6/6 match with recipient genotype.

The method described herein may also be used to ex vivo disrupt (e.g., knock-out) at least one (e.g., one, two, three, four, five or six) HLA allele (e.g., HLA-A, HLA-B and HLA-DRB1 alleles) in cells (e.g., HSCs) from a number of different donors and pooling the donor cells (prior to or after gene disruption), to create donor cells having one or more matched HLA alleles to a particular recipient (e.g., a HLA-A$^{-/common\ allele}$, HLA-B$^{-/common\ allele}$, HLA-DR$^{-/common\ allele}$ genotype). These cells may be developed for the most common HLA (e.g., HLA-A, HLA-B, HLA-DR) genotypes and maintained for use in one or more recipients.

One of ordinary skill will readily ascertain that these methods can also be used to disrupt (e.g., knockout) other HLA-loci (e.g., HLA-C and HLA-DQ). For example, in a recipient with a specific HLA haplotype who has an 8/10 HLA match with a donor, a relevant non-matching donor allele can be knocked out to effectively render the donor-recipient match a 9/10. For example: disruption (e.g., knock-out) of a single HLA-DQ allele in donor tissue that is haplotype matched at HLA-A, HLA-B, HLA-C and HLA-DR but was unmatched at a single HLA-DQ alleles can be performed to generate an effective 9/10 haplotype match, which would effectively render a 10/10 donor-recipient HLA match since the mismatched HLA-DQ allele would not be expressed.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An in vitro or ex vivo method of reducing the cell surface expression of a protein encoded by a first allele of an endogenous human leukocyte antigen (HLA) gene in a blood cell, the method comprising:

contacting the blood cell with a first allele-specific gRNA molecule and a Cas9 molecule, wherein the blood cell is isolated from a first subject having a first haplotype at the endogenous HLA gene, wherein the first allele-specific gRNA molecule comprises a targeting domain which is complementary to a target domain in the HLA gene, wherein the allele-specific gRNA molecule and the Cas9 molecule associate with and mediate a knock-out or knock-down of expression of the first allele of the endogenous HLA gene, and wherein the first allele-specific gRNA molecule and the Cas9 molecule associate with a single allele of the HLA gene, thereby reducing the cell surface expression of the protein encoded by the first allele of the endogenous HLA gene.

2. The method of claim 1, further comprising contacting the blood cell with a second gRNA molecule.

3. The method of claim 2, wherein the second gRNA molecule targets a gene selected from the group consisting of HBB, BCL11a, HBA1, HBA2, ATRX, RPS19, FANCA, FANCB, FANCC, FANCD1, FANCD2, FANCE, FANCF, FANCG, FANCI, FANCJ, FANCL, FANCM, FANCN, FANCP, RAD51C, PKLR, IFNG, SEC23B, ANK1, SPTB, SPTA, SLC4A1, EPB42, EPO, CSF2, CSF3, VWF, F7, F8, F9, F2, F5, F7, F10, F11, F12, F13A1, F13B, PROC, PROS1, SERPINC1, FGA, FGB, FGG, PROZ, PLG, PLAT, PLAU, F3, TFPI, PAI, HCF2, IDUA, IDS, GALNS, ARSB, SGSH, NAGLU, HGSNAT, GALNS, IL2RG, ADA, IL7R, CD247, RAG1, RAG2, DCLRE1C, PTPRC, JAK3, RMRP, FOXP3, STAT1, ICOS, TNFRSF13B, CD19, TNFRSF13C, CD20, CD81, CCR5, CXCR4, RFX5, RFX5, RFXAP, MHC2TA, RFXB, TAP1, TAP2, TAPBP, VPS45, HAX1, ELANE, NCF1, CYBB, CYBA, NCF2, NCF4, PRF1, HPLH, WAS, LYST, AK2, BTK, TNFSF5, AICDA, CD40, UNG, GBA, MPL, MAN2B1, LIPA, GYS2, G6PC, G6PT1/SLC37A4, GAA, AGL, GBE1, PYGM, PYGL, PFKM, PHKA2, PHKB, PGAM2, GH1, TG, INS, GCG, FXN, LCAT, APOA1, IGF1, AGA, UOX, IDUA, IDS, GALNS, ARSB, SGSH, NAGLU, ARSA, ABCD1, GLA, HPRT, ADA, GALC, ASAH1, PPT1, TPP1, NPC1, NPC2, SMPD1, SMPD1, JAK2, TET2, EPOR, EPOR, PIGA, C5, C3, IL6, IL1A, IL1B, IL2, IL3, IL7, IL9, IL12, IL17, IL18, IL4, IL10, IL11, IL35, IL26, IL13, IL23, IL27, IFNG, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, CX3CL1, CXCR1, CXCR2, CXCR3, CXCR4, CXCR5, CCR1, CCR2, CCR3, CCR4, CCR5, CCR6, CCR7, CCR8, CCR9, CCR10, CCR11, CX3CR1, DARC, C1INH, EGF, VEGF, IFNA1, IFNA2, IFNB1, TNF, ABL1, BCL2, BCL11A, BCL11B, BCR, BMI1, BRD2, CCND1, CCND2, CDX2, ETV6, JAK2, JUND, KLF6, LCK, LMO1, LMO2, LYL1, MLL, MLLT10, MTCP1, MYC, NFKB2, NOTCH1, NUP98, OLIG2, PBX1, PICALM, RAP1GDS1, RUNX1, STIL, TAL1, TAL2, NKAIN2, TCF3, TCL1A, TLX1, TLX3, FAS, BID, CD152, PCDCD1, CBLB, PTPN6, CD19, PARP1, CD223, CD272, CD200R1, TIGIT, LAIR1, PTGER2, PTGER4, CD16, PDCD1, HAVCR2, CD40, WAS, WT1, and CHK1.

4. The method of claim 1, wherein the gRNA molecule is a modified gRNA molecule comprising a 5'-end modification and/or a 3'-end modification.

5. The method of claim 4, wherein the 5'-end modification is a 5'-end cap structure and the 3'-end modification is a 3'-end poly-A tail.

6. The method of claim 5, wherein the 5'-end cap structure is a 3'-O-Me-m7G(5')ppp(5')G anti reverse cap analog (ARCA).

7. The method of claim 1, further comprising selecting the first allele-specific gRNA molecule using a database schema.

8. The method of claim 7, wherein the step of selecting the first allele-specific gRNA molecule using a database schema comprises:

receiving, via an interface of a computational system, a listing of a first plurality of alleles of the endogenous HLA gene of a first subject;

receiving, via the interface of the computational system, a listing of a second plurality of alleles of the endogenous HLA gene of a second subject;

processing the listings of the first and the second pluralities of alleles to identify one or more mismatched alleles between the first plurality of alleles and the second plurality of alleles;

querying a database to determine whether one or more gRNA molecules are suitable for editing the one or more mismatched alleles of the second plurality of alleles;

generating a list of gRNA molecules that identifies the one or more gRNA molecules found to be suitable;

ranking the list of gRNA molecules; and displaying the ranked list of gRNA molecules.

9. The method of claim 1, wherein the blood cell is selected from the group consisting of a circulating blood cell, a mobilized blood cell, a bone marrow cell, a myeloid progenitor cell, a lymphoid progenitor cell, a lymphoid cell, a multipotent progenitor cell, or a lineage restricted progenitor cell.

10. The method of claim 1, wherein the HLA gene is selected from the group consisting of HLA-A, HLA-B, HLA-C, HLA-DRB1, HLA-DRB3/4/5, HLA-DQ, and HLA-DP.

11. The method of claim 1, wherein the Cas9 molecule is an enzymatically active Cas9 molecule (eaCas9) which generates a single-strand break or a double-strand break in the endogenous HLA gene.

12. The method of claim 1, wherein the Cas9 molecule is selected from the group consisting of wild-type Cas9, a Cas9 nickase, a dead Cas9 (dCas9), a split Cas9, and an inducible Cas9.

13. The method of claim 1, wherein the Cas9 molecule is selected from the group consisting of:

(i) a Cas9 molecule comprising N-terminal RuvC-like domain cleavage activity, and lacking HNH-like domain cleavage activity;

(ii) a Cas9 molecule comprising an amino acid mutation at an amino acid position corresponding to amino acid position N863 of *Streptococcus pyogenes* Cas9;

(iii) a Cas9 molecule comprising HNH-like domain cleavage activity, and lacking N-terminal RuvC-like domain cleavage activity; and (iv) a Cas9 molecule comprising an amino acid mutation at an amino acid position corresponding to amino acid position D10 of *Streptococcus pyogenes* Cas9.

14. The method of claim 1, wherein the Cas9 molecule is a Cas9 polypeptide or a nucleic acid encoding the Cas9 polypeptide.

15. The method of claim 1, wherein the Cas9 molecule is a Cas9 polypeptide, and wherein the gRNA molecule and the Cas9 polypeptide are associated in a ribonucleotide complex prior to the contacting the blood cell.

16. The method of claim 1, further comprising contacting the blood cell with a template nucleic acid.

17. The method of claim 16, wherein the template nucleic acid is a single stranded oligodeoxynucleotide (ssODN).

18. The method of claim 1, further comprising contacting the blood cell with a transgene, wherein the contacting occurs under conditions that allow the transgene to integrate into the genome of the blood cell.

19. The method of claim 18, wherein the transgene is a gene encoding a human leukocyte antigen (HLA) gene, a chemotherapy selection marker, a cell surface antigen, or a suicide gene; wherein the HLA gene is identical to an HLA gene of a recipient of the blood cell.

20. The method of claim 18, wherein the transgene is an HLA gene or a fragment thereof.

21. The method of claim 20, wherein the HLA gene is selected from the group consisting of HLA-A, HLA-B, HLA-C, HLA-DRB1, HLA-DRB3/4/5, HLA-DQ, and HLA-DP.

22. The method of claim 1, further comprising contacting the blood cell with an enzymatically inactive Cas9 (eiCas9) molecule.

23. The method of claim 22, wherein the eiCas9 is fused to a transcriptional repressor or a transcriptional activator.

24. The method of claim 1, wherein the blood cell is part of a population of cells.

25. The method of claim 24, wherein the amount of blood cell in the population of cells that comprise a reduced cell surface expression of the protein encoded by the first allele of the endogenous HLA gene is identified by using an antibody specific to the first allele of the endogenous HLA gene.

26. The method of claim 1, further comprising transferring the blood cell to a second subject after the contacting step, wherein the second subject has a second haplotype at the endogenous HLA gene.

27. The method of claim 26, further comprising administration of a T cell add-back to the second subject after the transferring step.

* * * * *